(12) United States Patent
Falb et al.

(10) Patent No.: US 10,273,489 B2
(45) Date of Patent: *Apr. 30, 2019

(54) BACTERIA ENGINEERED TO TREAT DISEASES THAT BENEFIT FROM REDUCED GUT INFLAMMATION AND/OR TIGHTENED GUT MUCOSAL BARRIER

(71) Applicant: Synlogic Operating Company, Inc., Cambridge, MA (US)

(72) Inventors: Dean Falb, Sherborn, MA (US); Vincent M. Isabella, Cambridge, MA (US); Jonathan W. Kotula, Somerville, MA (US); Paul F. Miller, Salem, CT (US)

(73) Assignee: Synlogic Operating Company, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/301,230

(22) PCT Filed: Mar. 2, 2016

(86) PCT No.: PCT/US2016/020530
§ 371 (c)(1),
(2) Date: Sep. 30, 2016

(87) PCT Pub. No.: WO2016/141108
PCT Pub. Date: Sep. 9, 2016

(65) Prior Publication Data
US 2017/0128499 A1    May 11, 2017

Related U.S. Application Data

(63) Continuation-in-part of application No. 14/998,376, filed on Dec. 22, 2015.

(60) Provisional application No. 62/127,097, filed on Mar. 2, 2015, provisional application No. 62/127,131, filed on Mar. 2, 2015, provisional application No. 62/184,770, filed on Jun. 25, 2015, provisional application No. 62/248,814, filed on Oct. 30, 2015, provisional application No. 62/248,825, filed on Oct. 30, 2015, provisional application No. 62/248,805, filed on Oct. 30, 2015, provisional application No. 62/256,042, filed on Nov. 16, 2015, provisional application No. 62/256,044, filed on Nov. 16, 2015, provisional application No. 62/256,048, filed on Nov. 16, 2015, provisional application No. 62/291,461, filed on Feb. 4, 2016, provisional application No. 62/291,470, filed on Feb. 4, 2016, provisional application No. 62/291,468, filed on Feb. 4, 2016.

(51) Int. Cl.
| | | |
|---|---|---|
| C12N 1/20 | (2006.01) |
| A23L 33/135 | (2016.01) |
| C12N 15/70 | (2006.01) |
| C12N 9/02 | (2006.01) |
| C12N 9/12 | (2006.01) |
| A61K 35/741 | (2015.01) |
| A61K 38/20 | (2006.01) |
| A61K 38/26 | (2006.01) |
| A61K 38/44 | (2006.01) |
| A61K 31/19 | (2006.01) |
| A61K 31/198 | (2006.01) |
| A61K 35/00 | (2006.01) |

(52) U.S. Cl.
CPC ............. *C12N 15/70* (2013.01); *A61K 31/19* (2013.01); *A61K 31/198* (2013.01); *A61K 35/741* (2013.01); *A61K 38/20* (2013.01); *A61K 38/2013* (2013.01); *A61K 38/2066* (2013.01); *A61K 38/26* (2013.01); *A61K 38/446* (2013.01); *C12N 9/001* (2013.01); *C12N 9/1217* (2013.01); *C12Y 103/08001* (2013.01); *C12Y 115/01001* (2013.01); *C12Y 207/02007* (2013.01); *A61K 2035/115* (2013.01); *Y02A 50/401* (2018.01); *Y02A 50/414* (2018.01); *Y02A 50/473* (2018.01)

(58) Field of Classification Search
None
See application file for complete search history.

(56) References Cited

U.S. PATENT DOCUMENTS

| | | |
|---|---|---|
| 5,589,168 A | 12/1996 | Allen et al. |
| 5,989,463 A | 11/1999 | Tracy et al. |
| 6,203,797 B1 | 3/2001 | Perry |
| 6,835,376 B1 | 12/2004 | Neeser et al. |
| 7,731,976 B2 | 6/2010 | Cobb et al. |
| 9,487,764 B2 | 11/2016 | Falb et al. |

(Continued)

FOREIGN PATENT DOCUMENTS

| | | |
|---|---|---|
| EP | 1 383 897 B1 | 6/2006 |
| EP | 2 344 626 B1 | 3/2017 |

(Continued)

OTHER PUBLICATIONS

Eckburg et al., Diversity of the Human Intestinal Microbial Flora Science vol. 308 Jun. 10, 2005 1635-1638.*

(Continued)

*Primary Examiner* — Maria G Leavitt
(74) *Attorney, Agent, or Firm* — Finnegan, Henderson, Farabow, Garrett & Dunner, LLP; Chang B. Hong

(57) ABSTRACT

Genetically engineered bacteria, pharmaceutical compositions thereof, and methods of treating or preventing autoimmune disorders, inhibiting inflammatory mechanisms in the gut, and/or tightening gut mucosal barrier function are disclosed.

6 Claims, 79 Drawing Sheets

Specification includes a Sequence Listing.

(56) References Cited

U.S. PATENT DOCUMENTS

| | | | |
|---|---|---|---|
| 2015/0139940 A1* | 5/2015 | Bermudez Humaran | .................... C12N 15/746 424/85.2 |
| 2016/0177274 A1* | 6/2016 | Falb | .................... C12R 1/19 424/93.2 |
| 2016/0206666 A1 | 7/2016 | Falb et al. | |
| 2016/0340665 A1 | 11/2016 | Falb et al. | |
| 2017/0014457 A1 | 1/2017 | Falb et al. | |
| 2017/0067065 A1 | 3/2017 | Falb et al. | |
| 2017/0137789 A9 | 5/2017 | Falb et al. | |
| 2017/0253862 A1 | 9/2017 | Falb et al. | |

FOREIGN PATENT DOCUMENTS

| | | |
|---|---|---|
| WO | WO 2006/079790 A2 | 8/2006 |
| WO | WO 2013/175358 A1 | 11/2013 |
| WO | WO 2014/093852 A1 | 6/2014 |
| WO | WO 20141138324 A1 | 9/2014 |
| WO | WO 2016/106343 A1 | 6/2016 |

OTHER PUBLICATIONS

Sat et al The *Escherichia coli* n1azE'F Suicide Nlodule Mediates Thyrnineless Death Journal of Bacterjology, Mar. 2003, p. J 803--1807.*

Levanon et al., Effect of Oxygen on the *Escherichia coli* ArCA and FNR Regulation Systems and Metabolic Responses; Biotechnology and Bioengineering 2005, pp. 556-564.*

Unden et al Control of FNR Function of *Escherichia coli* by O2 and Reducing Conditions J. Mol. Microbiol. Biotechnol. (2002) 4(3): 263-268.*

Gardlik et al Recombinant Probiotic Therapy in Experimental Colitis in Mice Folia Biologica (Praha) 58, 238-245 (2012).*

Pohlmann et al. Improving health from the inside Use of engineered intestinal microorganisms as in situ cytokine delivery system Bioengineered 4:3, 172-179; May/Jun. 2013.*

Aboulnaga, E-H. et al. (2013) "Effect of an Oxygen-Tolerant Bifurcating Butyryl Coenzyme A Dehydrogenase/Electron-Transferring Flavoprotein Complex from *Clostridium difficile* on Butyrate Production in *Escherichia coli*" *J Cacteriol*, 195(16):3704-3713.

Ahmad, Z.A. et al. (2012) "scFv Antibody: Principles and Clinical Application" *Clin Dev Immunol*, 2012:980250 (15 pages).

Albiniak, A.M. et al. (2013) "High-level secretion of a recombinant protein to the culture medium with a *Bacillus subtilis* twin-arginine translocation system in *Escherichia coli*" *FEBS J*, 280:3810-3821.

Altenhoefer et al. (Apr. 9, 2004) "The probiotic *Escherichia coli* strain Nissle 1917 Interferes with invasion of human intestinal epithelial cells by different enteroinvasive bacterial pathogens" *FEMS Immunol Med Microbiol*, 40(3):223-229.

Andersen, P.S. et al. (Apr. 1995) "Uracil uptake in *Escherichia coli*K-12: isolation of uraA mutants and cloning of the gene" *J Bacteriol*, 177(8):2008-2013.

Archer, E.J. et al. (Oct. 2012) "Engineered *E. coli* That Detect and Respond to Gut Inflammation through Nitric Oxide Sensing" *ACS Synthetic Biology*, 1(10):451-457.

Arpaia, N. et al. (Nov. 2013) "Metabolites produced by commensal bacteria promote peripheral regulatory T-cell generation" *Nature*, doi:10.1038/nature12726 (6 pages). Final publication in 504(7480):451-455.

Arrieta et al. (Sep. 30, 2015) "Early infancy microbial and metabolic alterations affect risk of childhood asthma" *Sci Transl Med.* 7(307):307ra152 (16 pages).

Arthur et al. (Oct. 5, 2012) "Intestinal inflammation targets cancer-inducing activity of the rnicrobiota" *Science*, 338(6103):120-123. NIH Public Access Author Manuscript; available in PMC May 6, 2013 (11 pages).

Atarashi, K. et al. (Jan. 2011) "Induction of colonic regulatory T cells by indigenous *Clostridium* species" *Science*, 331(6015):337-341. NIH Public Access Author Manuscript; available in PMC Mar. 28, 2014 (10 pages).

Brophy, J.A.N. et al. (May 2014) "Principles of genetic circuit design" *Nature Methods*, 11(5):508-520. NIH Public Access Author Manuscript; available in PMC Nov. 13, 2014 (30 pages).

Callura et al. (Sep. 7, 2010) "Tracking, tuning, and terminating microbial physiology using synthetic riboregulators" *Proc Natl Acad Sci USA*, 107(36):15898-15903.

Castiglione et al. (Sep. 2009) "The transcription factor DNR from *Pseudomonas aeruginosa* specifically requires nitric oxide and heam for the activation of a target promoter in *Escherichia coli*" *Microbiology*, 155(Pt 9):2838-2844.

Clarkson et al. (1971) "Diaminopimelic Acid and Lysine Auxotrophs of *Pseudomonas aeruginosa* 8602" *J Gen Microbiol*, 66:161-169.

Cohen, L.B. et al. (Jun. 2014) "Biologic therapies in inflammatory bowel disease" *Transl Res*, 163(6):533-556.

Collinson, I. et al. (2015) "Channel crossing: how are proteins shipped across the bacterial plasma membrane?" *Philos Trans R Soc B*, 370:20150025 [online]. Retrieved from: http://rstb.royalsocietypublishing.org/, on Jun. 16, 2016 (13 pages).

Costa, T.R.D. et al. (2015) "Secretion systems in Gram-negative bacteria: structural and mechanistic insights" *Nat Rev Microbiol*, 13(6):343-359.

Cuevas-Ramos et al. (Jun. 22, 2010) "*Escherichia coli* induces DNA damage in vivo and triggers genomic instability in mammalian cells" *Proc Natl Acad Sci USA*, 107(25):11537-11542.

Davis-Richardson, A.G. and E.W. Triplett (Jul. 2015) "A model for the role of gut bacteria in the development of autoimmunity for type 1 diabetes" *Diabetologia*, 58(7):1386-1393.

Dinleyici et al. (Nov. 2014) "*Saccharomyces boulardii* CNCM I-745 in different clinical conditions" *Expert Opin Biol Ther*, 14(11):1593-1609.

Dunn, A.K. et al. (Jul. 2010) "The alternative oxidase (AOX) gene in *Vibrio fischeri* is controlled by NsrR and upregulated in response to nitric oxide" *Mol Microbiol*, 77(1):44-55. NIH Public Access Author Manuscript; available in PMC Jun. 14, 2013 (24 pages).

Fasano, A. and T. Shea-Donohue (Sep. 2005) "Mechanisms of disease: the role of intestinal barrier function in the pathogenesis of gastrointestinal autoimmune diseases" *Nat Clin Pract Gastroenterol Hepatol*, 2(9):416-422.

Fasano, A. (Feb. 2012) "Leaky gut and autoimmune diseases" *Clin Rev Allergy Immunol*, 42(1):71-78.

Frenzel, A. et al. (Jul. 2013) "Expression of recombinant antibodies" *Front Immunol*, 4:217 (20 pages).

Furusawa, Y. et al. (2013) "Commensal microbe-derived butyrate induces the differentiation of colonic regylatory T cells" *Nature*, doi:10.1088/nature12721 (7 pages). Final publication in 504:446-450.

Gardner et al. (2000) "Construction of a genetic toggle switch in *Escherichia coli*" *Nature*, 403:339-342.

Gerdes et al. (Oct. 2006) "Essential genes on metabolic maps" *Curr Opin Biotechnol*, 17(5):448-456.

Gerlach, R.G. and M. Hensel (2007) "Protein secretion systems and adhesins: The molecular armory of Gram-negative pathogens" *Int J Med Microbiol*, 297:401-415.

Ghishan, F.K. and P.R. Kiela (Jun. 2014) "Epithelial transport in inflammatory bowel diseases" *Inflamm Bowel Dis*, 20(6):1099-1109. NIH Public Access Author Manuscript; available in PMC Jun. 1, 2015 (22 pages).

Giardina, G. et al. (2008) "NO sensing in Pseudomonas aeruginosa: Structure of the Transcriptional Regulator DNR" *J Mol Biol*, 378:1002-1015.

Giardina, G. et al. (Oct. 2009) "A dramatic conformational rearrangement is necessary for the activation of DNR from *Pseudomonas aeruginosa*. Crystal structure of wild-type DNR" *Proteins*, 77(1):174-180.

Hamer, H.M. et al. (Jan. 2008) "Review article: the role of butyrate on colonic function" *Aliment Pharmacol Ther*, 27(2):104-119.

(56) References Cited

OTHER PUBLICATIONS

Hetzel, M. et al. (2003) "Acryloyl-CoA reductase from *Clostridium propionicum*. An enzyme complex of propionyl-CoA dehydrogenase and electron-transferring flavoprotien" *Eur J Biochem*, 270:902-910.

Hristodorov, D. et al. (Sep./Oct. 2014) "Recombinant H22(scFv) blocks CD64 and prevents the capture of anti-TNF monoclonal antibody, A potantral strategy to enhance anti-TNF therapy" *mAbs*, 6(5):1283-1289.

Ianiro, G. et al. (Oct. 2014) "Fecal microbiota transplantation in inflammatory bowel disease: beyond the excitement" *Medicine*, 93(19):e97 (11 pages).

International Patent Application No. PCT/US2015/067435, filed Dec. 22, 2015, by Massachusetts Institute of Technology: International Search Report and Written Opinion, dated Jun. 13, 2016.

International Patent Application No. PCT/US2016/020530, filed Mar. 2, 2016, by Synlogic, Inc.: International Search Report and Written Opinion, dated Jun. 24, 2016.

Isabella, V.M. et al. (2009; online Nov. 6, 2008) "Functional analysis of NsrR, a nitric oxide-sensing Rrf2 repressor in *Neisseria gonorrhoeae*" *Mol Microbiol*, 71(1):227-239.

Karlinsey, J. et al. (Sep. 2012) "The NsrR Regulon in Nitrosative Stress Resistance of *Salmonella enterica* serovar Typhimurium" *Mol Microbiol*, 85(6):1179-1193. NIH Public Access Author Manuscript; available in PMC Sep. 1, 2013 (24 pages).

Keates, A.C. et al. (2008) "TransKingdom RNA interference: a bacterial approach to challenges in RNAi therapy and delivery" *Biotechnol Genet Eng Rev*, 25:113-128.

Kleman, G.L. and W.R. Strohl (Nov. 1994) "Acetate metabolism by *Escherichia coli* in high-cell-density fermentation" *Appl Environ Microbiol*, 60(11):3952-3958.

Kobayashi, H. et al. (Jun. 2004) "Programmable cells: Interfacing natural and engineered networks" *PNAS*, 101(22):8414-8419.

Kotula, J.W. et al. (Apr. 2014) "Programmable bacteria detect and record an environmental signal in the mammalian gut" *PNAS*, 111(13):4838-4843, with Supporting Information (11 pages).

Lerner, A. and, Matthias (Jun. 2015) "Changes in intestinal tight junction permeability associated with industrial food additives explain the rising incidence of autoimmune disease" *Autoimmun Rev*, 14(6):479-489.

Lerner, A. and T. Matthias (Nov. 2015) "Rheumatoid arthritis-celiac disease relationship: Joints get that gut feeling" *Autoimmun Rev*, 14(11):1038-1047.

Lopez, G. and J.C. Anderson (Dec. 2015) "Synthetic Auxotrophs with Ligand-Dependent Essential Genes for a BL21(DE3) Biosafety Strain" *ACS Synthetic Biology*, 4(12):1279-1286.

Meadow, P. and E. Work (1959) "Biosynthesis of diaminopimelic acid and lysine in *Escherichia coli*" *Biochem J*, 72(3):396-400.

Mizoguchi, A. (2012) "Animal models of inflammatory bowel disease" *Prog Mol Biol Transl Sci*, 105:263-320.

Nielsen, O.H. (Mar. 2014) "New strategies for treatment of inflammatory bowel disease" *Front Med*, 1:3 (5 pages).

Nougayrede et al. (Aug. 11, 2006) "*Escherichia coli* induces DNA double-strand breaks in eukaryotic cells" *Science*, 313(5788):848-851.

Olier et al. (Nov.-Dec. 2012) "Genotoxicity of *Escherichia coli* Nissle 1917 strain cannot be dissociated from its probiotic activity" *Gut Microbes*, 3(6):501-509.

Paun, A. and J.S. Danska (Oct. 10, 2015) "Immuno-ecology: how the microbiome regulates tolerance and autoimmunity" *Curr Opin Immunol*, 37:34-39.

Pugsley, A.P. (Mar. 1993) "The complete general secretory pathway in gram-negative bacteria" *Microbiol Rev*, 57(1):50-108.

Purcell, O. et al. (2013) "Towards a whole-cell modeling approach for synthetic biology" *Chaos*, 23(2):025112 (8 pages).

Ragsdale, S.W. (Mar. 2008) "Enzymology of the Wood-Ljungdahl Pathway of Acetogenesis" *Ann NY Acad Sci*, 1125:129-136. NIH Public Access Author Manuscript; availabie in PMC Feb. 16, 2011 (15 pages).

Reeves, A.Z. et al. (Apr. 2015) "Engineering *E. coli* into a protein delivery system for mammalian cells" *ACS Synth Biol*, Just Accepted Manuscript, DOI: 10.1021/acssynbio.5b00002 [online]. Retrieved from: http://pubs.acs.org, on Apr. 20, 2015 (26 pages). Final publication in vol. 5, pp. 644-654.

Reister et al. (Oct. 10, 2014) "Complete genome sequence of the Gram-negative probiotic *Escherichia coli* strain Nissle 1917" *J Biotechnol*, 187:106-107.

Rembacken et al. (Aug. 21, 1999) "Non-pathogenic *Escherichia coli* versus mesalazine for the treatment of ulcerative colitis: a randomised trial" *Lancet*, 354(9179):635-639.

Rigel, N.W. and Braunstein (2008) "A new twist on an old pathway—accessory secretion systems" *Mol Microbiol*, 69(2):291-302.

Roquet, N. et al. (May 2014) "Digital and analog gene circuits for biotechnology" *Biotechnol J*, 9(5):597-608. NIH Public Access Author Manuscript: available in PMC May 1, 2015 (22 pages).

Saier Jr., M.H. (2006) "Protein Secretion and Membrane Insertion Systems in Gram-Negative Bacteria" *J Membrane Biol*, 214:75-90.

Sanz, Y. and A. Moya-Pérez (2014) "Microbiota, inflammation and obesity" *Adv Exp Med Biol*; 817:291-317.

Sanz, Y. et al. (Jan. 2015) "Understanding the role of gut microbiome in metabolic disease risk" *Pediatr Res*, 77(1-2)236-244.

Sat et al. (Mar. 2003) "The *Escherichia coli* mazEF suicide module mediates thymineless death" *J Bacteriol*, 185(6):1803-1807.

Schiel-Bengelsdorf, B. and P. Dürre (2012) "Pathway engineering and synthetic biology using acetogens" *FEBS Letters*, 586:2191-2198.

Schreiber, K. et al. (Jun. 2007) "The Anaerobic Regulatory Network Required for *Pseudomonas aeruginosa* Nitrate Respiration" *J Bacteriol*, 189(11):4310-4314.

Schultz (Jul. 2008) "Clinical use of *E. coli* Nissle 1917 in inflammatory bowel disease" *Inflamm Bowel Dis*, 14(7):1012-1018.

Selmer, T. et al. (2002) "Propionate CoA-transferase from Clostridium propionicum Cloning of the gene and identification of gluatamate 324 at the active site" *Eur J Biochem*, 269:372-380.

Simpson, H.L. et al. (2014) "IBD: microbiota manipulation through diet and modified bacteria" *Dig Dis*, 32(Suppl 1):18-25.

Siuti, P. et al. (May 8, 2014) "Engineering genetic circuits that compute and remember" *Nature Protocols*, 9(6):1292-1300.

Smith, P.M. et al. (Aug. 2013) "The microbial metabolites, short-chain fatty acids, regulate colonic $T_{reg}$ cell homeostasis" *Science*, 341(6145):569-573.

Sonnenborn and Schulze (2009) "The non-pathogenic *Escherichia coli* strain Nissle 1917—features of a versatile probiotic" *Microbial Ecology in Health and Disease*, 21:122-158.

Spiro, S. (2006) "Nitric oxide-sensing mechanisms in *Escherichia coli*" *Biochem Soc Trans*, 34(1):200-202.

Stanley, S.A. et al. (Oct. 2003) "Acute infection and macrophage subversion by *Mycobacterium tuberculosis* require a specialized secretion system" *PNAS*, 100(22):13001-13006.

Steidler, L. et al. (Jul. 1, 2003) "Biological containment of genetically modified *Lactococcus lactis* for intestinal delivery of human interleukin 10" *Nat Biotechnol*, 21:785-789.

Tseng, H-C. and K.L.J. Prather (Oct. 2012) "Controlled biosynthesis of odd-chain fuels and chemicals via engineered modular metabolic pathways" *PNAS*, 109(44):17925-17980, with Supporting Information (11 pages).

Ukena et al. (Dec. 12, 2007) "Probiotic *Escherichia coli* Nissle 1917 inhibits leaky gut by enhancing mucosal integrity" *PLoS One*, 2(12):e1308. [online] DOI:10.1371/journal.pone.0001308 (11 pages).

Van Der Meer, J.R. and S. Belkin (Jul. 2010) "Where microbiology meets microengineering: design and applications of reporter bacteria" *Nat Rev Microbiol*, 8(7):511-522.

Vine, C.E. and J.A. Cole (2011) "Unresolved sources, sinks, and pathways for the recovery of enteric bacteria from nitrosative stress" *FEMS Microbiol Lett*, 325:99-107.

Wen, L. et al. (Oct. 2008) "Innate immunity and intestinal microbiota in the development of Type 1 diabetes" *Nature*, 455(7216):1109-1113. HHS Public Access Author Manuscript; available in PMC Apr. 23, 2009 (13 pages).

Wright et al. (Mar. 20, 2015) "GeneGuard: A modular plasmid system designed for biosafety" *ACS Synth Biol*, 4(3):307-316.

(56) References Cited

OTHER PUBLICATIONS

Xiao. B. et al. (May 2014) "Nanoparucles with surface antibody against CD98 and carrying CD98 small interfering RNA reduce colitis in mice" *Gastroenterology*, 146(5):1289-1300. NIH Public Access Author Manuscript; available in PMC May 1, 2015 (27 pages).
Yazbeck, R. et al. (Apr. 2009) "Growth factor based therapies and intestinal disease: is glucagon-like peptide-2 the new way forward?" *Cytokine Growth Factor Rev*, 20(2):175-184.
Zhang and Lin (2009) "DEG 5.0, a database of essential genes in both prokaryotes and eukaryotes" *Nucl Acids Res*, 37(suppl. 1):D455-D458.
U.S. Appl. No. 62/263,329, filed Dec. 4, 2015, by Kotula et al.
U.S. Appl. No. 62/183,935, filed Jun. 24, 2015, by Kotula et al.
U.S. Appl. No. 62/277,654, filed Jan. 12, 2016, by Kotula et al.
U.S. Appl. No. 15/164,828, filed May 25, 2016, by Falb et al.
U.S. Appl. No. 15/260,319, filed Sep. 6, 2016, by Falb et al.
Akawi, L. et al. (2015) "Engineering *Escherichia coli* for high-level production of propionate" *J Ind Microbiol Biotechnol*, 42:1057-1072.
Baek, J-M. et al. (2013) "Butyrate Production in Engineered *Escherichia coli* With Synthetic Scaffolds" *Biotechnol Bioeng*, 110:2790-2794.
Bansal, T. et al. (Jan. 2010) "The bacterial signal indole increases epithelial-cell tight-junction resistance and attenuates indicators of inflammation" *PNAS*, 107(1):228-233.
Becker, S. et al. (Aug. 1996) "$O_2$ as the Regulatory Signal for FNR-Dependent Gene Regulation in *Escherichia coli*" *J Bacteriol*, 178(15):4515-4521.
Braat, H. et al. (2006) "A Phase I Trial With Transgenic Bacteria Expressing Interleukin-10 in Crohn's Disease" *Clin Gastroenterol Hepatol*, 4:754-759.
Duan, F. and J.C. March (Sep. 2008) "Interrupting *Vibrio cholerae* Infection of Human Epithelial Cells With Engineered Commensal Bacterial Signaling" *Biotechnol Bioeng*, 101:128-134.
Duan, F. et al. (Dec. 2008) "Secretion of Insulinotropic Proteins by Commensal Bacteria: Rewiring the Gut to Treat Diabetes" *Applied and Environmental Microbiology*, 74(23):7437-7437.
Gardlik, R. et al. (2012) "Recombinant Probiotic Therapy in Experimental Colitis in Mice" *Folia Biological (Praha)*, 58:238-245.
Huibregtse, I.L. et al. (2012) "Genetically Modified *Lactococcus lactis* for Delivery of Human Interleukin-10 to Dendritic Cells" *Gastroenterol Res Pract*, vol. 2012, Article ID 639291 (7 pages).
International Patent Application No. PCT/US2016/050836, filed Sep. 8, 2016, by Falb, Dean: International Search Report and Written Opinion, dated Mar. 15, 2017.
Macia, L. et al. (Apr. 2015) "Metabolite-sensing receptors GPR43 and GPR109A facilitate dietary fibre-induced gut homeostasis through regulation of the inflammasome" *Nature Communications*, 6:6734, DOI: 10.1038.ncomms7734 (15 pages).
Mengesha, A. et al. (2006) "Development of a flexible and potent hypoxiainducible promoter for tumor-targeted gene expression in attenuated salmonella" *Cancer Biology & Therapy*, 5(9):1120-1128.
Piñero-Lambea, C. et al. (2015) "Engineered bacteria as therapeutic agents" *Curr Opin Biotechnol*, 35:94-102.
Pöhlmann, C. et al. (2013) "Improving health from the inside" *Bioengineered*, 4(3):172-179.
Rao, S. et al. (Aug. 2005) "Toward a live microbial microbicide for HIV: Commensal bacteria secreting an HIV fusion inhibitor peptide" *PNAS*, 102(34):11993-11998.
Romasi, E.F. and J. Lee (2013) "Development of Indole-3-Acetic Acid-Producing *Escherichia coli* by Functional Expression of IpdC, AspC, and Iad1" *J Microbiol Biotechnol*, 23(12):1726-1736.
Schumann, S. et al. (2012) "Dextran Sodium Sulfate-Induced Inflammation Alters the Expression of Proteins by Intestinal *Escherichia coli* Strains in a Gnotobiotic Mouse Model" *Appl Environ Microbiol*, 78(5):1513-1522.
Seo, E-j. et al. (2012) "Construction of recombinant *E. coli* Nissle 1917 (EcN) strains for the expression and secretion of defensins" *Intl J Med Microbiol*, 302:276-287.
Shen, T. et al. (2012) "Improved Production of Tryptophan in Genetically Engineered *Escherichia coli* with TktA and PpsA Overexpression" *J Biomed Biotechnol*, vol. 2012, Article ID 605219 (8 pages).
Sleator, R.D. and C. Hill (2009) "Rational Design of Improved Pharmabiotics" *J Biomed Biotechnol*, vol. 2009, Article ID 275287 (7 pages).
Strauch, K.L. et al. (Feb. 1985) "Oxygen Regulation in *Salmonella typhimurium*" *J Baceriol*, 161(2):673-680.
Thorburn, A.N. et al. (Jun. 2015) "Evidence that asthma is a developmental origin disease influenced by maternal diet and bacterial metabolites" *Nature Communications*, 6:7320, DOI: 10.1038/ncomms8320 (13 pages).
Unden, G. et al. (2002) "Control of FNR Function of *Escherichia coli* by $O_2$ and Reducing Conditions" *J Mol Microbiol Biotechnol*, 4(3):263-268.
Westendorf, A.M. et al. (2005) "Intestinal immunity of *Escherichia coli* NISSLE 1917: a safe carrier for therapeutic molecules" *FEMS Immunol Med Microbiol*, 43:373-384.
Whelan, R.A. et al. (Oct. 2014) "A Transgenic Probiotic Secreting a Parasite Immunomodulator for Site-Directed Treatment of Gut Inflammation" *Molecular Therapy*, 22(10):1730-1740.
U.S. Appl. No. 15/301,324, filed Sep. 30, 2016, by Falb.

\* cited by examiner

Logic031 – pBR322/*bcd*-butyrate cassette
Logic046 – pBR322/*ter*-butyrate cassette

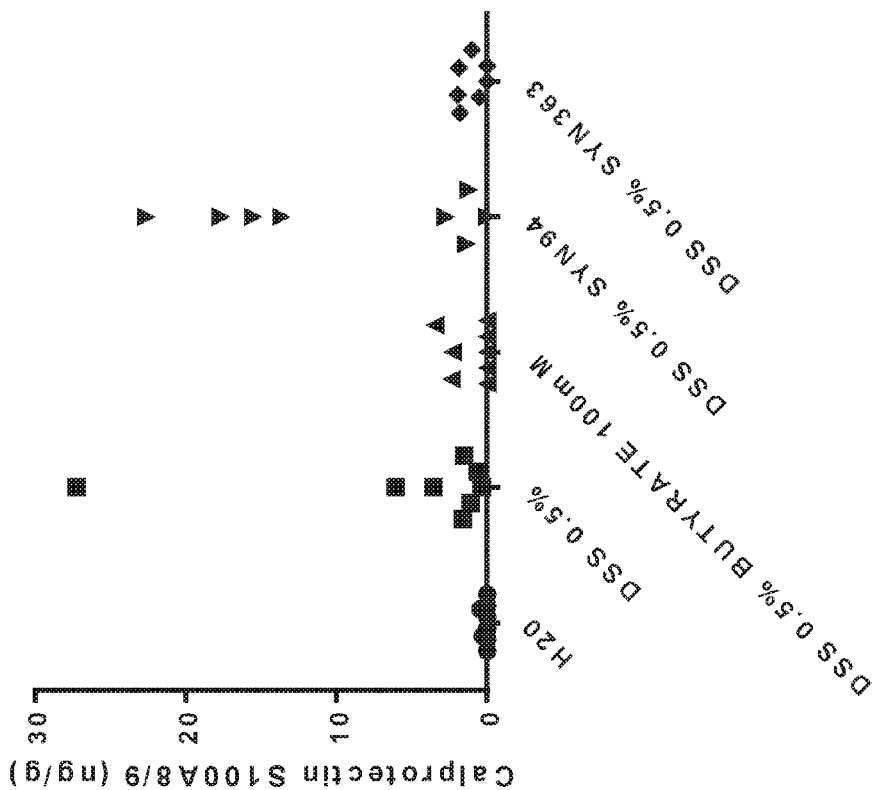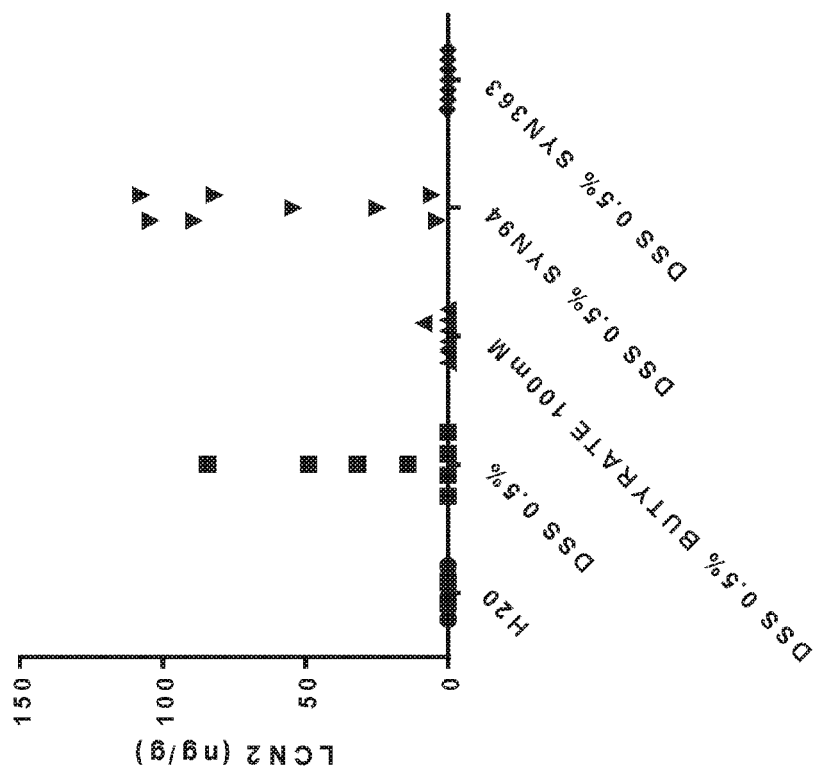
Fig. 27

| Gene | argA | cysE | glnA | glyA | hisB | ilvA | leuB | lysA | metA |
|---|---|---|---|---|---|---|---|---|---|
| AA Auxotroph | Arginine | Cysteine | Glutamine | Glycine | Histidine | Isoleucine | Leucine | Lysine | Methionine |
| Pre-Gavage | | | | | | | | | |
| 24 hours | | | | | | | | | |
| 48 hours | | | | | | | | | |

| Gene | pheA | proA | serA | thrC | trpC | tyrA | ilvD | thyA | uraA | flhD |
|---|---|---|---|---|---|---|---|---|---|---|
| AA Auxotroph | Phenylalanine | Proline | Serine | Threonine | Tryptophan | Tyrosine | Valine/Isoleucine/Leucine | Thiamine | Uracil | FlhD |
| Pre-Gavage | | | | | | | | | | |
| 24 hours | | | | | | | | | | |
| 48 hours | | | | | | | | | | |

Present
Absent

Fig. 56

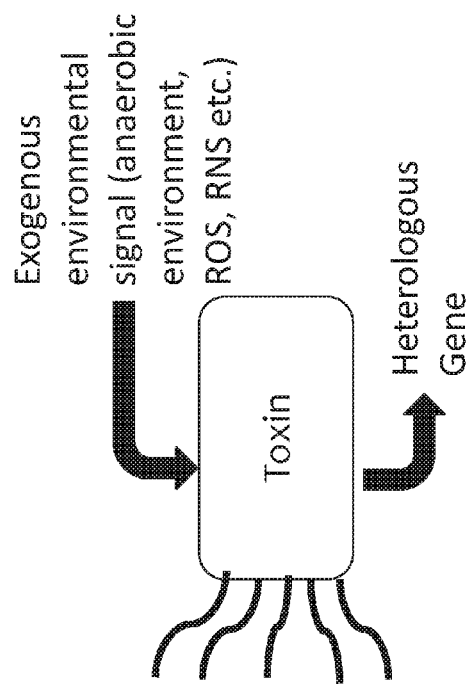
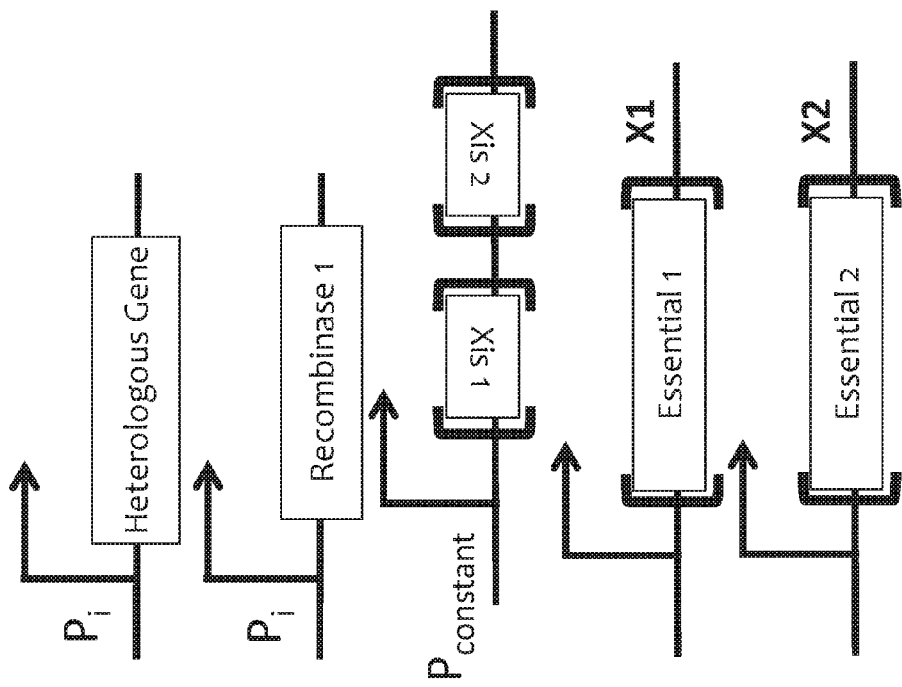
Fig. 64

Wild-type clbA (SEQ ID NO: 82)

```
caaatatcacatatcttaacatatcaataaacacagtaaagtttcatgtaaaaacatcaaac
ataaatacaagctcggaatacgattcacgctatacacattgctaacaggaatgagattatcta
aatgaggattgatatattaattggacatactagttttttcatcaaccagtagagataacttc
cttcactactctcaatgaggaagaataaaacgctatgatcagtttcatttgtagtgataaag
aactctatatttaagccgtatcctgtcaaaacagcactaaaagatatcaacctgatgtctc
attacaatcatgcaattagtacgtgcaaatatgcaaaccattatagttttttcctcagttg
gcaaaaagatttttttaaccttcccatactatagatacagtagccgttgctattagttctc
actgcgagctggtgtgtcgatattgaacaaataagagattagacaactcttatctgaatatcag
tcagcatttttttactccacaggaagctactaacatagtttcacttcctcgttatgaaggtcaa
ttacttttttgaaaatgtgattgtattgaattcattaacaataaaaactaacttcaaaatatagagg
ctttaggactgattgtatttctctcaatgaaatctcatttcatttctgcattagcctctccactc
ttcacctgttttattctctcaatgaactattgagctattccctgcagtccccaacttatcaccgactatc
atcaccccctaaaataactattgagctattccctgcagtccccaacttatcaccgactatc
agctaattcattcgtcaaatgggcagaattgaatcgccacggataatctagacacttctgagcc
gtcgataatattgatttcatattccgtcgtgtgtaagtatcccgcataatcgtgccattca
catttag
``` clbA knockout (SEQ ID NO: 83)

```
ggatggggaaacatggataagttcaaagaaaaacccgttatctctgctgaaagacaagt
attgcgcatgctggcacaaggtgatgagtactctcaaatatcacataatctaacatatcaata
aacacagtaaagtttcatgtgaaaaatgagattgaaaacatacaagctcgaatacgaatcacg
ctatacacattgctaacaggagattattctaaatgaggattgaTGTAGGCTGGAGCTGC
TTCGAAGTTCCTATACTTCTAGAGAATAGGAACTTCGGAATAGGAACTTCGAATAGAACTA
AGGAGGATATTCATATGtcgtcaaatgggcagaattgaatcgccacggataatctagacacttc
tgagccgtcgataatattgatttcatattccgtcggtgg
```

Fig. 73

BACTERIA ENGINEERED TO TREAT DISEASES THAT BENEFIT FROM REDUCED GUT INFLAMMATION AND/OR TIGHTENED GUT MUCOSAL BARRIER

This is a national stage application under 35 U.S.C. § 371 of International Application No. PCT/US2016/020530, filed Mar. 2, 2016, which designated the U.S. and which claims the benefit of U.S. Provisional Application No. 62/127,097, filed Mar. 2, 2015; U.S. Provisional Application No. 62/248,814, filed Oct. 30, 2015; U.S. Provisional Application No. 62/256,042, filed Nov. 16, 2015; U.S. Provisional Application No. 62/291,461, filed Feb. 4, 2016; U.S. Provisional Application No. 62/127,131, filed Mar. 2, 2015; U.S. Provisional Application No. 62/248,825, filed Oct. 30, 2015; U.S. Provisional Application No. 62/256,044, filed Nov. 16, 2015; U.S. Provisional Application No. 62/291,470, filed Feb. 4, 2016; U.S. Provisional Application No. 62/184,770, filed Jun. 25, 2015; U.S. Provisional Application No. 62/248,805, filed Oct. 30, 2015; U.S. Provisional Application No. 62/256,048, filed Nov. 16, 2015; U.S. Provisional Application No. 62/291,468, filed Feb. 4, 2016; U.S. application Ser. No. 14/998,376, filed Dec. 22, 2015, all of which are incorporated herein by reference.

This disclosure relates to compositions and therapeutic methods for inhibiting inflammatory mechanisms in the gut, restoring and tightening gut mucosal barrier function, and/or treating and preventing autoimmune disorders. In certain aspects, the disclosure relates to genetically engineered bacteria that are capable of reducing inflammation in the gut and/or enhancing gut barrier function. In some embodiments, the genetically engineered bacteria are capable of reducing gut inflammation and/or enhancing gut barrier function, thereby ameliorating or preventing an autoimmune disorder. In some aspects, the compositions and methods disclosed herein may be used for treating or preventing autoimmune disorders as well as diseases and conditions associated with gut inflammation and/or compromised gut barrier function, e.g., diarrheal diseases, inflammatory bowel diseases, and related diseases.

Inflammatory bowel diseases (IBDs) are a group of diseases characterized by significant local inflammation in the gastrointestinal tract typically driven by T cells and activated macrophages and by compromised function of the epithelial barrier that separates the luminal contents of the gut from the host circulatory system (Ghishan et al., 2014). IBD pathogenesis is linked to both genetic and environmental factors and may be caused by altered interactions between gut microbes and the intestinal immune system. Current approaches to treat IBD are focused on therapeutics that modulate the immune system and suppress inflammation. These therapies include steroids, such as prednisone, and tumor necrosis factor (TNF) inhibitors, such as Humira® (Cohen et al., 2014). Drawbacks from this approach are associated with systemic immunosuppression, which includes greater susceptibility to infectious disease and cancer.

Other approaches have focused on treating compromised barrier function by supplying the short-chain fatty acid butyrate via enemas. Recently, several groups have demonstrated the importance of short-chain fatty acid production by commensal bacteria in regulating the immune system in the gut (Smith et al., 2013), showing that butyrate plays a direct role in inducing the differentiation of regulatory T cells and suppressing immune responses associated with inflammation in IBD (Atarashi et al., 2011; Furusawa et al., 2013). Butyrate is normally produced by microbial fermentation of dietary fiber and plays a central role in maintaining colonic epithelial cell homeostasis and barrier function (Hamer et al., 2008). Studies with butyrate enemas have shown some benefit to patients, but this treatment is not practical for long term therapy. More recently, patients with IBD have been treated with fecal transfer from healthy patients with some success (Ianiro et al., 2014). This success illustrates the central role that gut microbes play in disease pathology and suggests that certain microbial functions are associated with ameliorating the IBD disease process. However, this approach raises safety concerns over the transmission of infectious disease from the donor to the recipient. Moreover, the nature of this treatment has a negative stigma and thus is unlikely to be widely accepted.

Compromised gut barrier function also plays a central role in autoimmune diseases pathogenesis (Lerner et al., 2015a; Lerner et al., 2015b; Fasano et al., 2005; Fasano, 2012). A single layer of epithelial cells separates the gut lumen from the immune cells in the body. The epithelium is regulated by intercellular tight junctions and controls the equilibrium between tolerance and immunity to nonself-antigens (Fasano et al., 2005). Disrupting the epithelial layer can lead to pathological exposure of the highly immunoreactive subepithelium to the vast number of foreign antigens in the lumen (Lerner et al., 2015a) resulting in increased susceptibility to and both intestinal and extraintestinal autoimmune disorders can occur" (Fasano et al., 2005). Some foreign antigens are postulated to resemble self-antigens and can induce epitope-specific cross-reactivity that accelerates the progression of a pre-existing autoimmune disease or initiates an autoimmune disease (Fasano, 2012). Rheumatoid arthritis and celiac disease, for example, are autoimmune disorders that are thought to involve increased intestinal permeability (Lerner et al., 2015b). In individuals who are genetically susceptible to autoimmune disorders, dysregulation of intercellular tight junctions can lead to disease onset (Fasano, 2012). In fact, the loss of protective function of mucosal barriers that interact with the environment is necessary for autoimmunity to develop (Lerner et al., 2015a).

Changes in gut microbes can alter the host immune response (Paun et al., 2015; Sanz et al., 2014; Sanz et al., 2015; Wen et al., 2008). For example, in children with high genetic risk for type 1 diabetes, there are significant differences in the gut microbiome between children who develop autoimmunity for the disease and those who remain healthy (Richardson et al., 2015). Others have shown that gut bacteria are a potential therapeutic target in the prevention of asthma and exhibit strong immunomodulatory capacity . . . in lung inflammation (Arrieta et al., 2015). Thus, enhancing barrier function and reducing inflammation in the gastrointestinal tract are potential therapeutic mechanisms for the treatment or prevention of autoimmune disorders.

Recently there has been an effort to engineer microbes that produce anti-inflammatory molecules, such as IL-10, and administer them orally to a patient in order to deliver the therapeutic directly to the site of inflammation in the gut. The advantage of this approach is that it avoids systemic administration of immunosuppressive drugs and delivers the therapeutic directly to the gastrointestinal tract. However, while these engineered microbes have shown efficacy in some pre-clinical models, efficacy in patients has not been observed. One reason for the lack of success in treating patients is that the viability and stability of the microbes are compromised due to the constitutive production of large amounts of non-native proteins, e.g., human interleukin. Thus, there remains a great need for additional therapies to reduce gut inflammation, enhance gut barrier function, and/or treat autoimmune disorders, and that avoid undesirable side effects.

The genetically engineered bacteria disclosed herein are capable of producing therapeutic anti-inflammation and/or gut barrier enhancer molecules. The genetically engineered bacteria are functionally silent until they reach an inducing environment, e.g., a mammalian gut, wherein expression of the therapeutic molecule is induced. In certain embodiments, the genetically engineered bacteria are naturally non-pathogenic and may be introduced into the gut in order to reduce gut inflammation and/or enhance gut barrier function and may thereby further ameliorate or prevent an autoimmune disorder. In certain embodiments, the anti-inflammation and/or gut barrier enhancer molecule is stably produced by the genetically engineered bacteria, and/or the genetically engineered bacteria are stably maintained in vivo and/or in vitro. The invention also provides pharmaceutical compositions comprising the genetically engineered bacteria, and methods of treating diseases that benefit from reduced gut inflammation and/or tightened gut mucosal barrier function, e.g., an inflammatory bowel disease or an autoimmune disorder.

In some embodiments, the genetically engineered bacteria of the invention produce one or more therapeutic molecule(s) under the control of one or more promoters induced by an environmental condition, e.g., an environmental condition found in the mammalian gut, such as an inflammatory condition or a low oxygen condition. Thus, in some embodiments, the genetically engineered bacteria of the invention produce one or more therapeutic molecule(s) under the control of an oxygen level-dependent promoter, a reactive oxygen species (ROS)-dependent promoter, or a reactive nitrogen species (RNS)-dependent promoter, and a corresponding transcription factor. In some embodiments, the therapeutic molecule is butyrate; in an inducing environment, the butyrate biosynthetic gene cassette is activated, and butyrate is produced. Local production of butyrate induces the differentiation of regulatory T cells in the gut and/or promotes the barrier function of colonic epithelial cells. The genetically engineered bacteria of the invention produce their therapeutic effect only in inducing environments such as the gut, thereby lowering the safety issues associated with systemic exposure.

BRIEF DESCRIPTION OF THE FIGURES

FIG. 27 depicts levels of mouse lipocalin 2 and calprotectin quantified by ELISA using the fecal samples in an in vivo model of IBD. SYN363 reduces inflammation and/or protects gut barrier function as compared to control SYN94.

FIG. 56 depicts a table illustrating the survival of various amino acid auxotrophs in the mouse gut, as detected 24 hours and 48 hours post-gavage. These auxotrophs were generated using BW25113, a non-Nissle strain of *E. coli*.

FIG. 58 also depicts another non-limiting embodiment of the disclosure, wherein the expression of an essential gene not found in the recombinant bacteria is activated by an exogenous environmental signal. In the absence of arabinose, the AraC transcription factor adopts a conformation that represses transcription of the essential gene under the control of the araBAD promoter and the bacterial cell cannot survive. In the presence of arabinose, the AraC transcription factor undergoes a conformational change that allows it to bind to and activate the araBAD promoter, which induces expression of the essential gene and maintains viability of the bacterial cell.

FIG. 64 depicts another non-limiting embodiment of the disclosure, where an exogenous environmental condition, e.g., low-oxygen conditions, or one or more environmental signals activates expression of a heterologous gene and at least one recombinase from an inducible promoter or inducible promoters. The recombinase then flips at least one excision enzyme into an activated conformation. The at least one excision enzyme then excises one or more essential genes, leading to senescence, and eventual cell death. The natural kinetics of the recombinase and excision genes cause a time delay, the kinetics of which can be altered and optimized depending on the number and choice of essential genes to be excised, allowing cell death to occur within a matter of hours or days. The presence of multiple nested recombinases can be used to further control the timing of cell death.

FIG. 73 depicts exemplary sequences of a wild-type clbA construct and a clbA knockout construct.

DESCRIPTION OF EMBODIMENTS

Figure 1A:
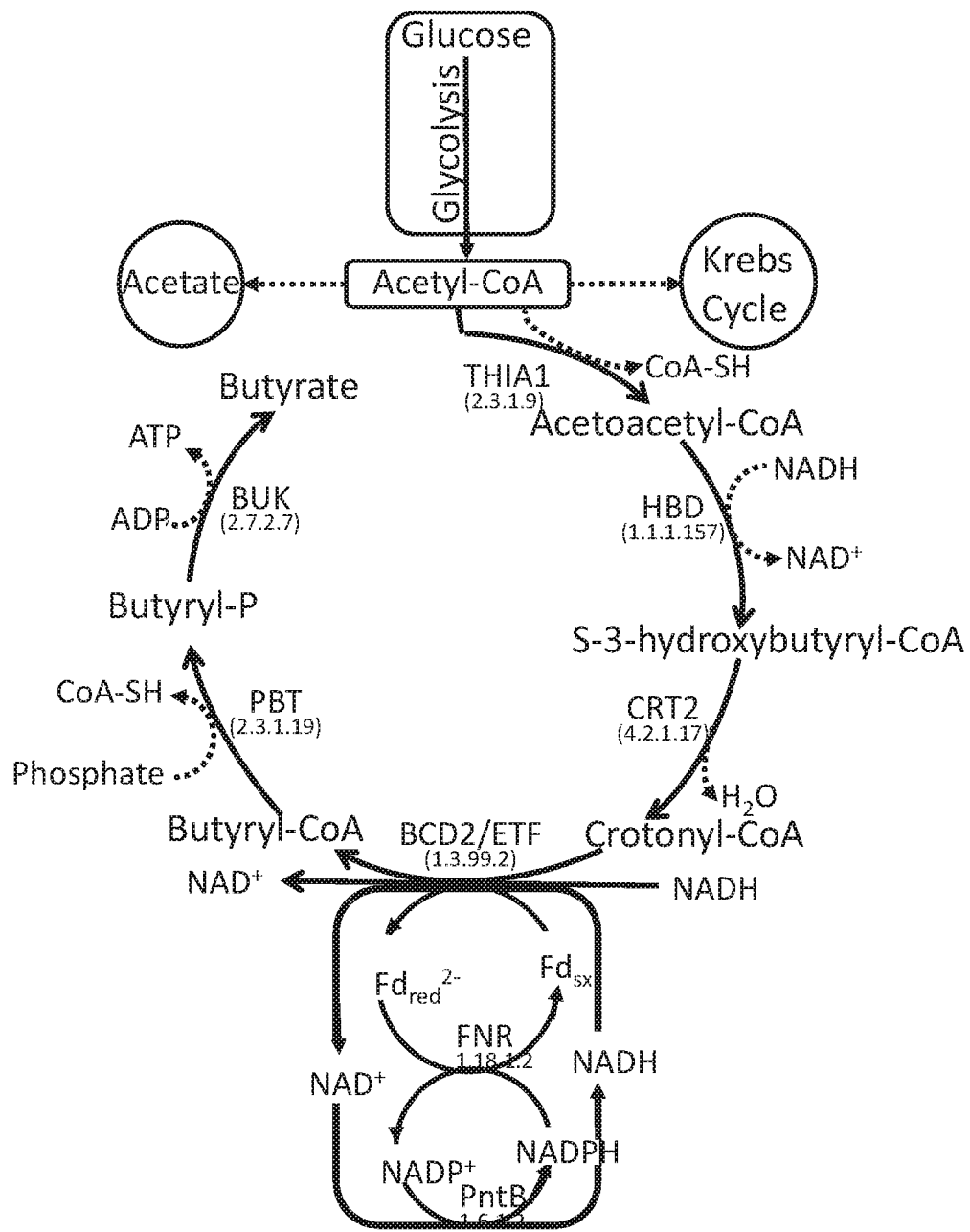
FIG. 1 depicts a schematic of the eight-gene pathway from *C. difficile* for butyrate production. pLogic031 comprises the eight-gene pathway from *C. difficile*, bcd2-etfB3-etfA3-thiA1-hbd-crt2-pbt-buk, synthesized under the control of Tet-inducible promoters (pBR322 backbone). pLogic046 replaces the BCD/EFT complex, a potential rate-limiting step, with single gene from *Treponema denticola*, ter (trans-enoyl-2-reductase), and comprises ter-thiA1-hbd-crt2-pbt-buk.
Figure 1B:
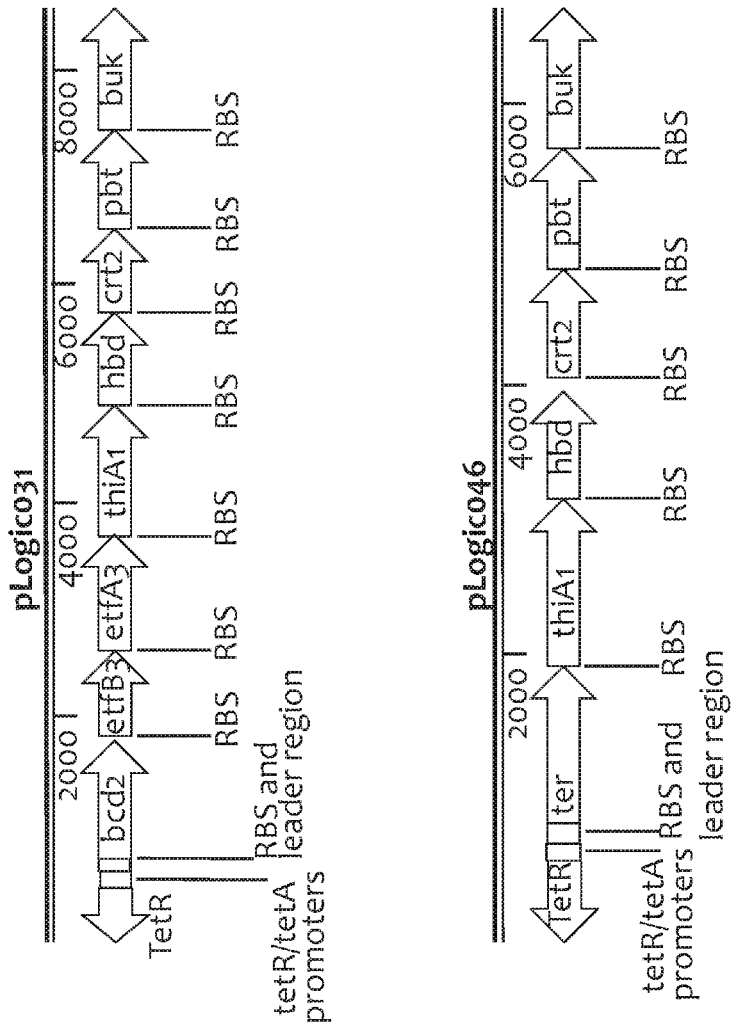

The present disclosure includes genetically engineered bacteria, pharmaceutical compositions thereof, and methods of reducing gut inflammation, enhancing gut barrier function, and/or treating or preventing autoimmune disorders. In some embodiments, the genetically engineered bacteria comprise at least one non-native gene and/or gene cassette for producing a non-native anti-inflammation and/or gut barrier function enhancer molecule(s). The at least one gene and/or gene cassette is further operably linked to a regulatory region that is controlled by a transcription factor that is capable of sensing an inducing condition, e.g., a low-oxygen environment, the presence of ROS, or the presence of RNS. The genetically engineered bacteria are capable of producing the anti-inflammation and/or gut barrier function enhancer molecule(s) in inducing environments, e.g., in the gut. Thus, the genetically engineered bacteria and pharmaceutical compositions comprising those bacteria may be used to treat or prevent autoimmune disorders and/or diseases or conditions associated with gut inflammation and/or compromised gut barrier function, including IBD.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, "diseases and conditions associated with gut inflammation and/or compromised gut barrier function" include, but are not limited to, inflammatory bowel diseases, diarrheal diseases, and related diseases. "Inflammatory bowel diseases" and "IBD" are used interchangeably herein to refer to a group of diseases associated with gut inflammation, which include, but are not limited to, Crohn's disease, ulcerative colitis, collagenous colitis, lymphocytic colitis, diversion colitis, Behcet's disease, and indeterminate colitis. As used herein, "diarrheal diseases" include, but are not limited to, acute watery diarrhea, e.g., cholera; acute bloody diarrhea, e.g., dysentery; and persistent diarrhea. As used herein, related diseases include, but are not limited to, short bowel syndrome, ulcerative proctitis, proctosigmoiditis, left-sided colitis, pancolitis, and fulminant colitis.

Symptoms associated with the aforementioned diseases and conditions include, but are not limited to, one or more of diarrhea, bloody stool, mouth sores, perianal disease, abdominal pain, abdominal cramping, fever, fatigue, weight loss, iron deficiency, anemia, appetite loss, weight loss, anorexia, delayed growth, delayed pubertal development, inflammation of the skin, inflammation of the eyes, inflammation of the joints, inflammation of the liver, and inflammation of the bile ducts.

A disease or condition associated with gut inflammation and/or compromised gut barrier function may be an autoimmune disorder. A disease or condition associated with gut inflammation and/or compromised gut barrier function may be co-morbid with an autoimmune disorder. As used herein, "autoimmune disorders" include, but are not limited to, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hemolytic anemia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, Castleman disease, celiac disease, Chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, Coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile idiopathic arthritis, juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (systemic lupus erythematosus), chronic Lyme disease, Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, type 1 diabetes, asthma, ulcerative colitis, undifferentiated connective tissue disease (UCTD), uveitis, vasculitis, vesiculobullous dermatosis, vitiligo, and Wegener's granulomatosis.

As used herein, "anti-inflammation molecules" and/or "gut barrier function enhancer molecules" include, but are not limited to, short-chain fatty acids, butyrate, propionate, acetate, IL-2, IL-22, superoxide dismutase (SOD), kynurenine, GLP-2, GLP-1, IL-10, IL-27, TGF-β1, TGF-β2, N-acylphosphatidylethanolamines (NAPEs), elafin (also called peptidase inhibitor 3 and SKALP), trefoil factor, melatonin, $PGD_2$, and kynurenic acid, as well as other molecules disclosed herein. Such molecules may also include compounds that inhibit pro-inflammatory molecules, e.g., a single-chain variable fragment (scFv), antisense RNA, siRNA, or shRNA that neutralizes TNF-α, IFN-γ, IL-1β, IL-6, IL-8, IL-17, and/or chemokines, e.g., CXCL-8 and CCL2. A molecule may be primarily anti-inflammatory, e.g., IL-10, or primarily gut barrier function enhancing, e.g., GLP-2. A molecule may be both anti-inflammatory and gut barrier function enhancing. An anti-inflammation and/or gut barrier function enhancer molecule may be encoded by a single gene, e.g., elafin is encoded by the PI3 gene. Alternatively, an anti-inflammation and/or gut barrier function enhancer molecule may be synthesized by a biosynthetic pathway requiring multiple genes, e.g., butyrate. These molecules may also be referred to as therapeutic molecules.

As used herein, the term "gene" or "gene sequene" is meant to refer to a nucleic acid sequence encoding any of the anti-inflammatory and gut barrier function enhancing molecules described herein, e.g., IL-2, IL-22, superoxide dismutase (SOD), kynurenine, GLP-2, GLP-1, IL-10, IL-27, TGF-β1, TGF-β2, N-acylphosphatidylethanolamines (NAPEs), elafin, and trefoil factor, as well as others. The nucleic acid sequence may comprise the entire gene sequence or a partial gene sequence encoding a functional molecule. The nucleic acid sequence may be a natural sequence or a synthetic sequence. The nucleic acid sequence may comprise a native or wild-type sequence or may comprise a modified sequence having one or more insertions, deletions, substitutions, or other modifications, for example, the nucleic acid sequence may be codon-optimized.

As used herein, a "gene cassette" or "operon" encoding a biosynthetic pathway refers to the two or more genes that are required to produce an anti-inflammation and/or gut barrier function enhancer molecule, e.g., butyrate, propionate, and acetate. In addition to encoding a set of genes capable of producing said molecule, the gene cassette or operon may also comprise additional transcription and translation elements, e.g., a ribosome binding site.

As used herein, "butyrogenic gene cassette" and "butyrate biosynthesis gene cassette" are used interchangeably to refer to a set of genes capable of producing butyrate in a biosynthetic pathway. Unmodified bacteria that are capable of producing butyrate via an endogenous butyrate biosynthesis pathway include, but are not limited to, *Clostridium, Peptoclostridium, Fusobacterium, Butyrivibrio, Eubacterium*, and *Treponema*, and these endogenous butyrate biosynthesis pathways may be a source of genes for the genetically engineered bacteria of the invention. The genetically engineered bacteria of the invention may comprise butyrate biosynthesis genes from a different species, strain, or substrain of bacteria, or a combination of butyrate biosynthesis genes from different species, strains, and/or substrains of bacteria. A butyrogenic gene cassette may comprise, for example, the eight genes of the butyrate production pathway from *Peptoclostridium difficile* (also called *Clostridium difficile*): bcd2, etfB3, etfA3, thiA1, hbd, crt2, pbt, and buk, which encode butyryl-CoA dehydrogenase subunit, electron transfer flavoprotein subunit beta, electron transfer flavoprotein subunit alpha, acetyl-CoA C-acetyltransferase, 3-hydroxybutyryl-CoA dehydrogenase, crotonase, phosphate butyryltransferase, and butyrate kinase, respectively (Aboulnaga et al., 2013). One or more of the butyrate biosynthesis genes may be functionally replaced or modified, e.g., codon optimized. *Peptoclostridium difficile* strain 630 and strain 1296 are both capable of producing butyrate, but comprise different nucleic acid sequences for etfA3, thiA1, hbd, crt2, pbt, and buk. A butyrogenic gene cassette may comprise bcd2, etfB3, etfA3, and thiA1 from *Peptoclostridium difficile* strain 630, and hbd, crt2, pbt, and buk from *Peptoclostridium difficile* strain 1296. Alternatively, a single gene from *Treponema denticola* (ter, encoding trans-2-enoynl-CoA reductase) is capable of functionally replacing all three of the bcd2, etfB3, and etfA3 genes from *Peptoclostridium difficile*. Thus, a butyrogenic gene cassette may comprise thiA1, hbd, crt2, pbt, and buk from *Peptoclostridium difficile* and ter from *Treponema denticola*. Alternatively, addition of the tesB gene from *Escherichia Coli* is capable of functionally replacing pbt and buk genes from *Peptoclostridium difficile*. Thus, a butyrogenic gene cassette may comprise thiA1, hbd, and crt2 from *Peptoclostridium difficile*, ter from *Treponema denticola*, and tesB from *Escherichia Coli*, for example, thiA1 from *Peptoclostridium difficile* strain 630, hbd and crt2 from *Peptoclostridium difficile* strain 1296, ter from *Treponema denticola* and tesB from *Escherichia Coli*. The butyrogenic gene cassette may comprise genes for the aerobic biosynthesis of butyrate and/or genes for the anaerobic or microaerobic biosynthesis of butyrate. One or more of the butyrate biosynthesis genes may be functionally replaced or modified, e.g., codon optimized. Exemplary butyrate gene cassettes are shown in FIGS. 1, 3, 4, 5, 6, 7, and 8.

Figure 9:
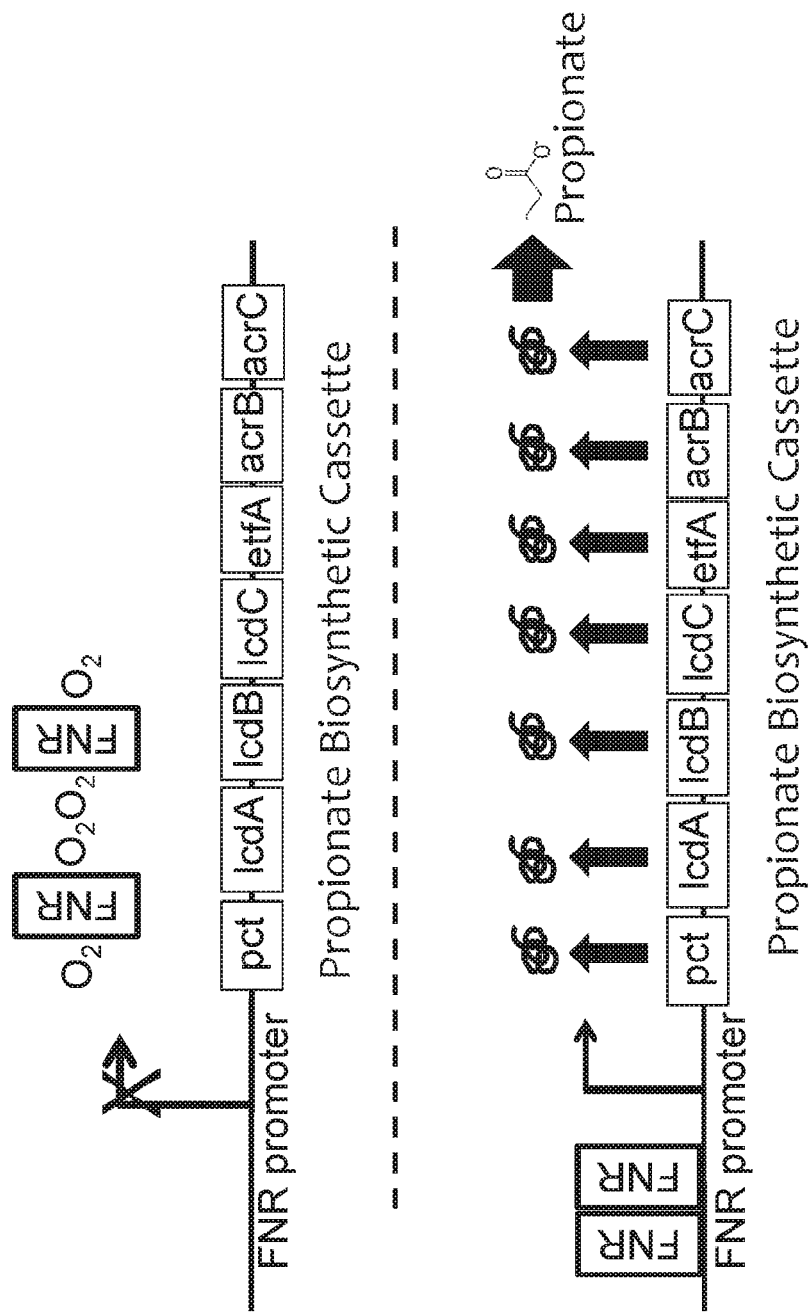
FIG. 9 depicts the gene organization of an exemplary recombinant bacterium of the invention and its induction under low-oxygen conditions. In the upper panel, relatively low propionate production under aerobic conditions in which oxygen ($O_2$) prevents (indicated by "X") FNR (grey boxed "FNR") from dimerizing and activating the FNR-responsive promoter ("FNR promoter"). Therefore, none of the propionate biosynthesis enzymes (pct, lcdA, lcdB, lcdC, etfA, acrB, acrC; black boxes) is expressed. In the lower panel, increased propionate production under low-oxygen conditions due to FNR dimerizing (two grey boxed "FNR"s), binding to the FNR-responsive promoter, and inducing expression of the propionate biosynthesis enzymes, which leads to the production of propionate.
Figure 10:
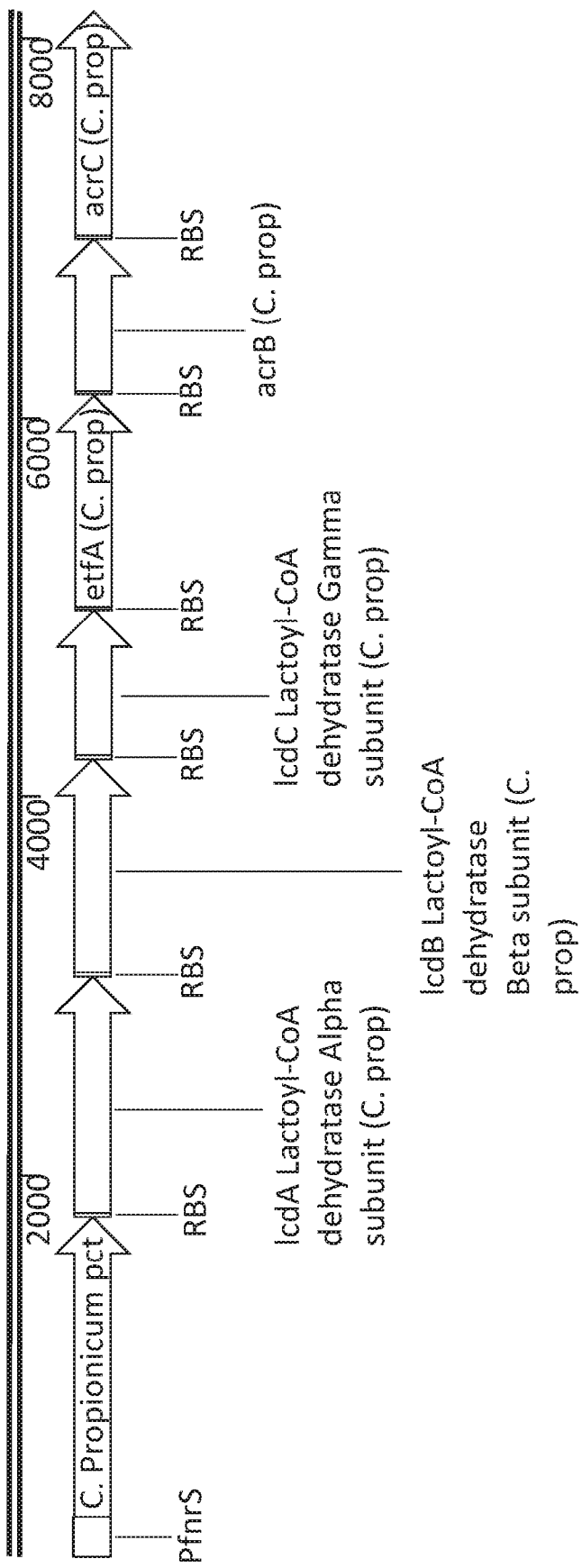
FIG. 10 depicts an exemplary propionate biosynthesis gene cassette.
Figure 11:
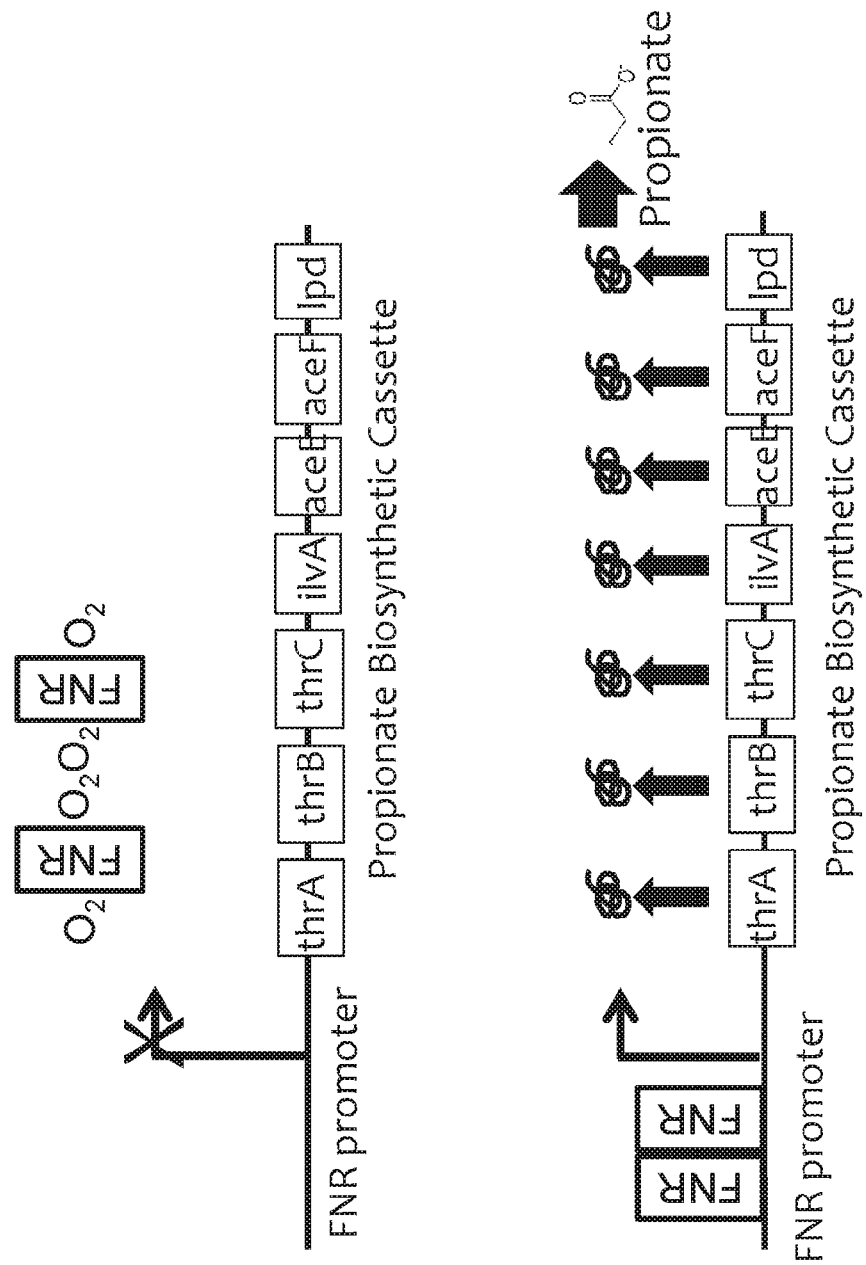
FIG. 11 depicts the gene organization of an exemplary recombinant bacterium of the invention and its induction under low-oxygen conditions. In the upper panel, relatively low propionate production under aerobic conditions in which oxygen ($O_2$) prevents (indicated by "X") FNR (grey boxed "FNR") from dimerizing and activating the FNR-responsive promoter ("FNR promoter"). Therefore, none of the propionate biosynthesis enzymes (thrA, thrB, thrC, ilvA, aceE, aceF, lpd; black boxes) is expressed. In the lower panel, increased propionate production under low-oxygen conditions due to FNR dimerizing (two grey boxed "FNR"s), binding to the FNR-responsive promoter, and inducing expression of the propionate biosynthesis enzymes, which leads to the production of propionate.
Figure 12:
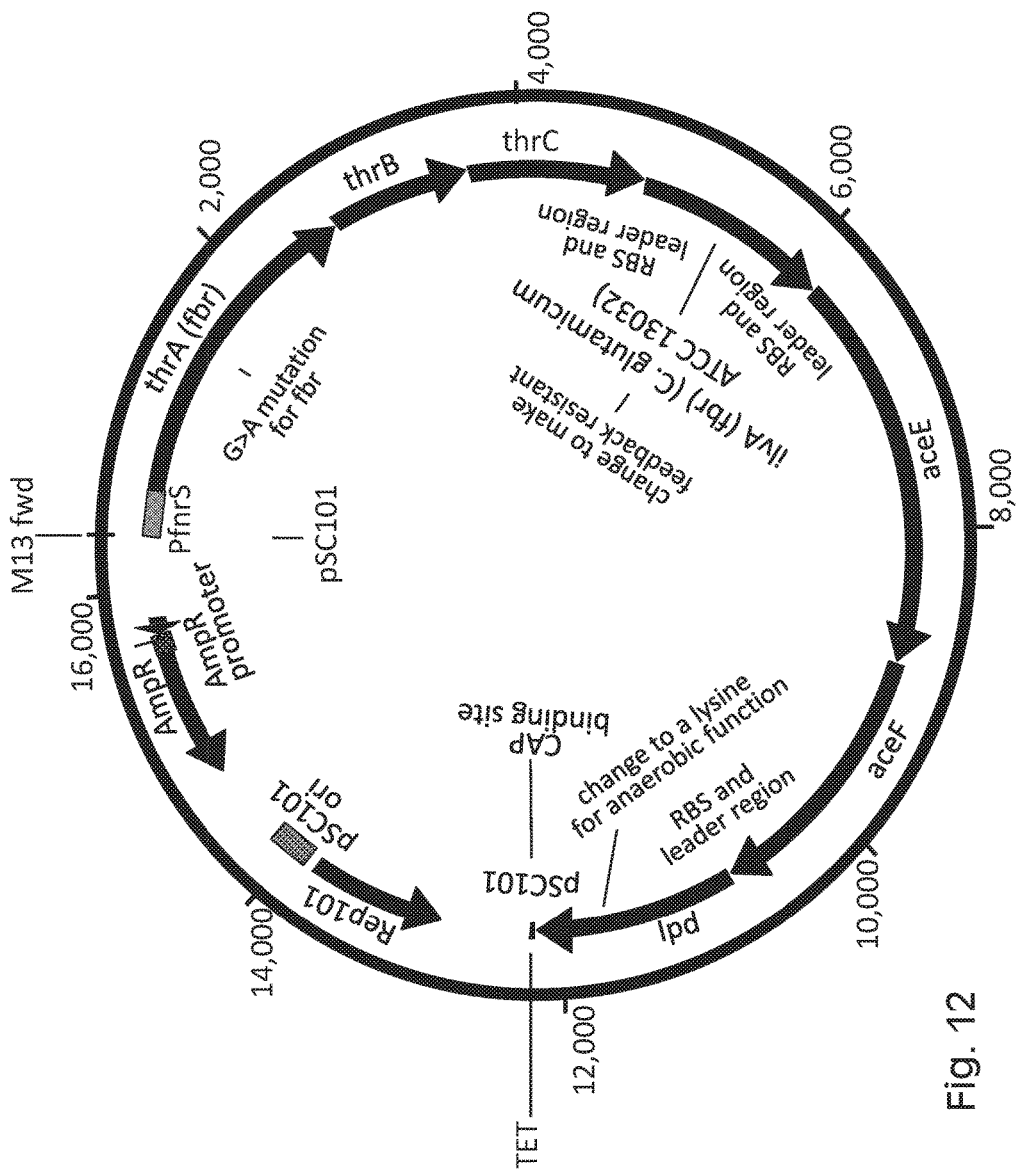
FIG. 12 depicts an exemplary propionate biosynthesis gene cassette.
Figure 13:
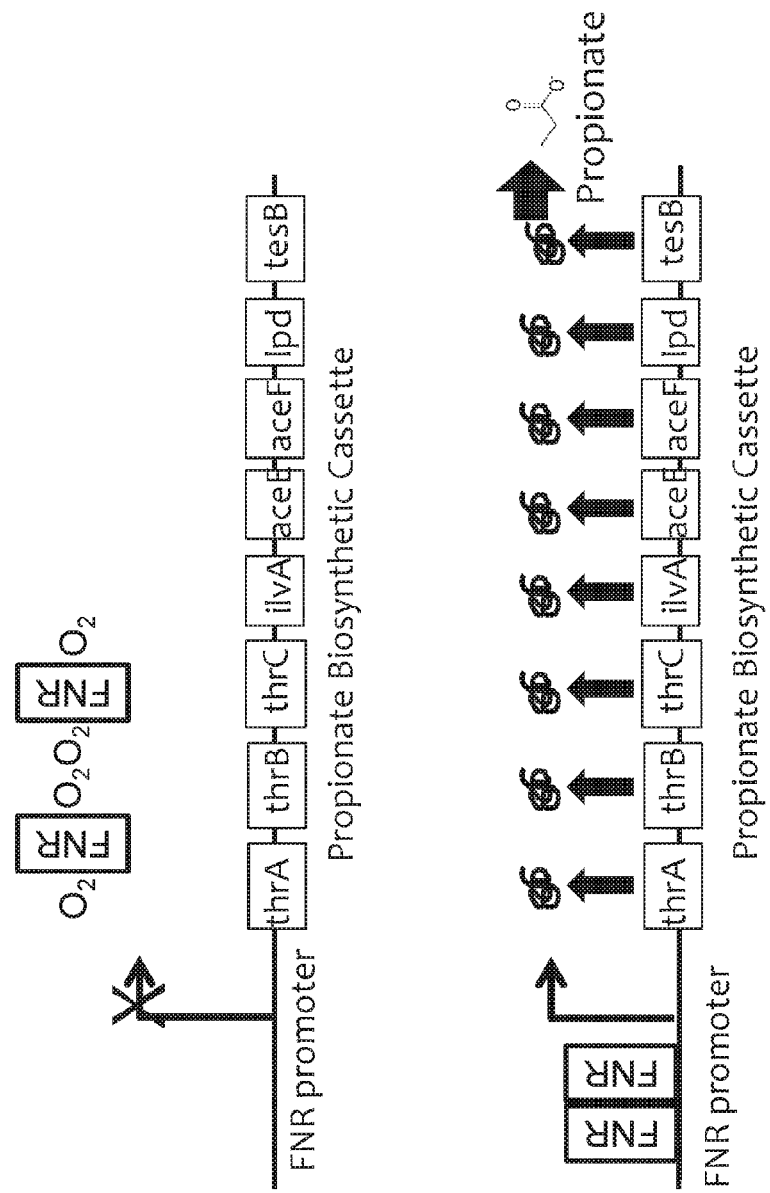
FIG. 13 depicts the gene organization of an exemplary recombinant bacterium of the invention and its induction under low-oxygen conditions. In the upper panel, relatively low propionate production under aerobic conditions in which oxygen ($O_2$) prevents (indicated by "X") FNR (grey boxed "FNR") from dimerizing and activating the FNR-responsive promoter ("FNR promoter"). Therefore, none of the propionate biosynthesis enzymes (thrA, thrB, thrC, ilvA, aceE, aceF, lpd, tesB; black boxes) is expressed. In the lower panel, increased propionate production under low-oxygen conditions due to FNR dimerizing (two grey boxed "FNR"s), binding to the FNR-responsive promoter, and inducing expression of the propionate biosynthesis enzymes, which leads to the production of propionate.
Figure 14:
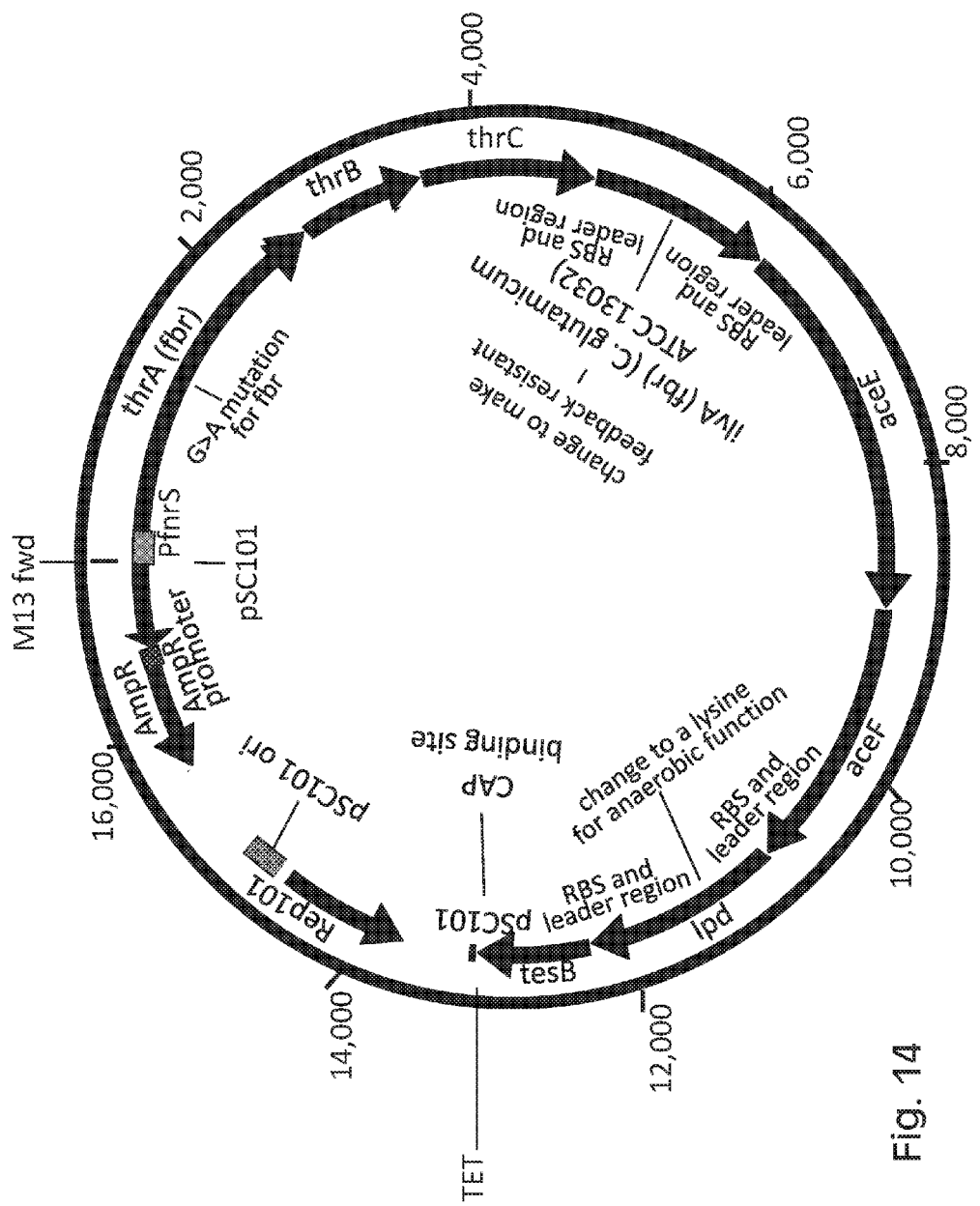
FIG. 14 depicts an exemplary propionate biosynthesis gene cassette.

As used herein, "propionate gene cassette" and "propionate biosynthesis gene cassette" refer to a set of genes capable of producing propionate in a biosynthetic pathway. Unmodified bacteria that are capable of producing propionate via an endogenous propionate biosynthesis pathway include, but are not limited to, *Clostridium propionicum*, *Megasphaera elsdenii*, and *Prevotella ruminicola*, and these endogenous propionate biosynthesis pathways may be a source of genes for the genetically engineered bacteria of the invention. The genetically engineered bacteria of the invention may comprise propionate biosynthesis genes from a different species, strain, or substrain of bacteria, or a combination of propionate biosynthesis genes from different species, strains, and/or substrains of bacteria. In some embodiments, the propionate gene cassette comprises acrylate pathway propionate biosynthesis genes, e.g., pct, lcdA, lcdB, lcdC, etfA, acrB, and acrC, which encode propionate CoA-transferase, lactoyl-CoA dehydratase A, lactoyl-CoA dehydratase B, lactoyl-CoA dehydratase C, electron transfer flavoprotein subunit A, acryloyl-CoA reductase B, and acryloyl-CoA reductase C, respectively (Hetzel et al., 2003, Selmer et al., 2002). In alternate embodiments, the propionate gene cassette comprises pyruvate pathway propionate biosynthesis genes (see, e.g., Tseng et al., 2012), e.g., thrA$^{fbr}$, thrB, thrC, ilvA$^{fbr}$, aceE, aceF, and lpd, which encode homoserine dehydrogenase 1, homoserine kinase, L-threonine synthase, L-threonine dehydratase, pyruvate dehydrogenase, dihydrolipoamide acetyltransferase, and dihydrolipoyl dehydrogenase, respectively. In some embodiments, the propionate gene cassette further comprises tesB, which encodes acyl-CoA thioesterase. The propionate gene cassette may comprise genes for the aerobic biosynthesis of propionate and/or genes for the anaerobic or microaerobic biosynthesis of propionate. One or more of the proprionate biosynthesis genes may be functionally replaced or modified, e.g., codon optimized. Exemplary propionic gene cassettes are shown in FIGS. 9, 11, and 13.

As used herein, "acetate gene cassette" and "acetate biosynthesis gene cassette" refers to a set of genes capable of producing acetate in a biosynthetic pathway. Bacteria synthesize acetate from a number of carbon and energy sources, including a variety of substrates such as cellulose, lignin, and inorganic gases, and utilize different biosynthetic mechanisms and genes, which are known in the art (Ragsdale, 2008). Unmodified bacteria that are capable of producing acetate via an endogenous acetate biosynthesis pathway may be a source of acetate biosynthesis genes for the genetically engineered bacteria of the invention. The genetically engineered bacteria of the invention may comprise acetate biosynthesis genes from a different species, strain, or substrain of bacteria, or a combination of acetate biosynthesis genes from different species, strains, and/or substrains of bacteria. *Escherichia coli* are capable of consuming glucose and oxygen to produce acetate and carbon dioxide during aerobic growth (Kleman et al., 1994). Several bacteria, such as *Acetitomaculum*, *Acetoanaerobium*, *Acetohalobium*, *Acetonema*, *Balutia*, *Butyribacterium*, *Clostridium*, *Moorella*, *Oxobacter*, *Sporomusa*, and *Thermoacetogenium*, are acetogenic anaerobes that are capable of converting CO or $CO_2+H_2$ into acetate, e.g., using the Wood-Ljungdahl pathway (Schiel-Bengelsdorf et al, 2012). Genes in the Wood-Ljungdahl pathway for various bacterial species are known in the art. The acetate gene cassette may comprise genes for the aerobic biosynthesis of acetate and/or genes for the anaerobic or microaerobic biosynthesis of acetate. One or more of the acetate biosynthesis genes may be functionally replaced or modified, e.g., codon optimized. Examples of acetate gene cassettes are described herein.

Each gene sequence and/or gene cassette may be present on a plasmid or bacterial chromosome. In embodiments in which the engineered bacteria comprise one or more gene sequence(s) and one or more gene cassettes, the gene sequence(s) may be present on one or more plasmids and the gene cassette(s) may be present in the bacterial chromosome, and vice versa. In addition, multiple copies of any gene, gene cassette, or regulatory region may be present in the bacterium, wherein one or more copies of the gene, gene cassette, or regulatory region may be mutated or otherwise altered as described herein. In some embodiments, the genetically engineered bacteria are engineered to comprise multiple copies of the same gene, gene cassette, or regulatory region in order to enhance copy number. In some embodiments, the genetically engineered bacteria are engineered to comprise multiple different components of a gene cassette performing multiple different functions. In some embodiments, the genetically engineered bacteria are engineered to comprise one or more copies of different genes, gene cassettes, or regulatory regions to produce engineered bacteria that express more than one therapeutic molecule and/or perform more than one function.

Each gene or gene cassette may be operably linked to an inducible promoter, e.g., an FNR-responsive promoter, an ROS-responsive promoter, and/or an RNS-responsive promoter. An "inducible promoter" refers to a regulatory region that is operably linked to one or more genes, wherein expression of the gene(s) is increased in the presence of an inducer of said regulatory region.

As used herein, a "directly inducible promoter" refers to a regulatory region, wherein the regulatory region is operably linked to a gene or a gene cassette encoding a biosynthetic pathway for producing an anti-inflammation and/or gut barrier function enhancer molecule, e.g. butyrate. In the presence of an inducer of said regulatory region, an anti-inflammation and/or gut barrier function enhancer molecule is expressed. An "indirectly inducible promoter" refers to a regulatory system comprising two or more regulatory regions, for example, a first regulatory region that is operably linked to a gene encoding a first molecule, e.g., a transcription factor, which is capable of regulating a second regulatory region that is operably linked to a gene or a gene cassette encoding a biosynthetic pathway for producing an anti-inflammation and/or gut barrier function enhancer molecule, e.g. butyrate (or other anti-inflammation and/or gut barrier function enhancer molecule). In the presence of an inducer of the first regulatory region, the second regulatory region may be activated or repressed, thereby activating or repressing production of butyrate (or other anti-inflammation and/or gut barrier function enhancer molecule). Both a directly inducible promoter and an indirectly inducible promoter are encompassed by "inducible promoter."

As used herein, "operably linked" refers to a nucleic acid sequence, e.g., a gene or gene cassette for producing an anti-inflammation and/or gut barrier enhancer molecule, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

As used herein, "exogenous environmental conditions" refer to settings or circumstances under which the promoter described herein is directly or indirectly induced. The phrase "exogenous environmental conditions" is meant to refer to the environmental conditions external to the bacteria, but endogenous or native to a mammalian subject. Thus, "exogenous" and "endogenous" may be used interchangeably to refer to environmental conditions in which the environmental conditions are endogenous to a mammalian body, but external or exogenous to a bacterial cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, the exogenous environmental condition is an environment in which ROS is present. In some embodiments, the exogenous environmental condition is an environment in which RNS is present.

In some embodiments, the exogenous environmental conditions are low-oxygen or anaerobic conditions such as the environment of the mammalian gut. In some embodiments, exogenous environmental conditions refer to the presence of molecules or metabolites that are specific to the mammalian gut in a healthy or disease state, e.g., propionate. In some embodiments, the gene or gene cassette for producing a therapeutic molecule is operably linked to an oxygen level-dependent promoter. Bacteria have evolved transcription factors that are capable of sensing oxygen levels. Different signaling pathways may be triggered by different oxygen levels and occur with different kinetics. As used herein, an "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

In some embodiments, the gene or gene cassette for producing a therapeutic molecule is operably linked to an oxygen level-dependent regulatory region such that the therapeutic molecule is expressed in low-oxygen, microaerobic, or anaerobic conditions. For example, the oxygen level-dependent regulatory region is operably linked to a butyrogenic or other gene cassette or gene sequence(s) (e.g., any of the genes described herein); in low-oxygen conditions, the oxygen level-dependent regulatory region is activated by a corresponding oxygen level-sensing transcription factor, thereby driving expression of the butyrogenic or other gene cassette or gene sequence(s). Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003), and non-limiting examples are shown in Table 1.

TABLE 1

Examples of transcription factors and responsive genes and regulatory regions

| Transcription Factor | Examples of responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC |

As used herein, "reactive nitrogen species" and "RNS" are used interchangeably to refer to highly active molecules, ions, and/or radicals derived from molecular nitrogen. RNS can cause deleterious cellular effects such as nitrosative stress. RNS include, but are not limited to, nitric oxide (NO.), peroxynitrite or peroxynitrite anion (ONOO$^-$), nitrogen dioxide (.NO$_2$), dinitrogen trioxide (N$_2$O$_3$), peroxynitrous acid (ONOOH), and nitroperoxycarbonate (ONOOCO$_2^-$) (unpaired electrons denoted by .). Bacteria have evolved transcription factors that are capable of sensing RNS levels. Different RNS signaling pathways are triggered by different RNS levels and occur with different kinetics.

As used herein, "RNS-inducible regulatory region" refers to a nucleic acid sequence to which one or more RNS-sensing transcription factors is capable of binding, wherein the binding and/or activation of the corresponding transcription factor activates downstream gene expression; in the presence of RNS, the transcription factor binds to and/or activates the regulatory region. In some embodiments, the RNS-inducible regulatory region comprises a promoter sequence. In some embodiments, the transcription factor senses RNS and subsequently binds to the RNS-inducible regulatory region, thereby activating downstream gene expression. In alternate embodiments, the transcription factor is bound to the RNS-inducible regulatory region in the absence of RNS; in the presence of RNS, the transcription factor undergoes a conformational change, thereby activating downstream gene expression. The RNS-inducible regulatory region may be operatively linked to a gene or gene cassette, e.g., a butyrogenic or other gene cassette or gene sequence(s), e.g., any of the genes described herein. For example, in the presence of RNS, a transcription factor senses RNS and activates a corresponding RNS-inducible regulatory region, thereby driving expression of an operatively linked gene sequence or gene cassette. Thus, RNS induces expression of the gene or gene cassette.

As used herein, "RNS-derepressible regulatory region" refers to a nucleic acid sequence to which one or more RNS-sensing transcription factors is capable of binding, wherein the binding of the corresponding transcription factor represses downstream gene expression; in the presence of RNS, the transcription factor does not bind to and does not repress the regulatory region. In some embodiments, the RNS-derepressible regulatory region comprises a promoter sequence. The RNS-derepressible regulatory region may be operatively linked to a gene or gene cassette, e.g., a butyrogenic or other gene cassette or gene sequence(s). For example, in the presence of RNS, a transcription factor senses RNS and no longer binds to and/or represses the regulatory region, thereby derepressing an operatively linked gene sequence or gene cassette. Thus, RNS derepresses expression of the gene or gene cassette.

As used herein, "RNS-repressible regulatory region" refers to a nucleic acid sequence to which one or more RNS-sensing transcription factors is capable of binding, wherein the binding of the corresponding transcription factor represses downstream gene expression; in the presence of RNS, the transcription factor binds to and represses the regulatory region. In some embodiments, the RNS-repressible regulatory region comprises a promoter sequence. In some embodiments, the transcription factor that senses RNS is capable of binding to a regulatory region that overlaps with part of the promoter sequence. In alternate embodiments, the transcription factor that senses RNS is capable of binding to a regulatory region that is upstream or downstream of the promoter sequence. The RNS-repressible regulatory region may be operatively linked to a gene sequence or gene cassette. For example, in the presence of RNS, a transcription factor senses RNS and binds to a corresponding RNS-repressible regulatory region, thereby blocking expression of an operatively linked gene sequence or gene cassette. Thus, RNS represses expression of the gene or gene cassette.

As used herein, a "RNS-responsive regulatory region" refers to a RNS-inducible regulatory region, a RNS-repressible regulatory region, and/or a RNS-derepressible regulatory region. In some embodiments, the RNS-responsive regulatory region comprises a promoter sequence. Each regulatory region is capable of binding at least one corresponding RNS-sensing transcription factor. Examples of transcription factors that sense RNS and their corresponding RNS-responsive genes, promoters, and/or regulatory regions include, but are not limited to, those shown in Table 2.

TABLE 2

Examples of RNS-sensing transcription factors and RNS-responsive genes

| RNS-sensing transcription factor: | Primarily capable of sensing: | Examples of responsive genes, promoters, and/or regulatory regions: |
|---|---|---|
| NsrR | NO | norB, aniA, nsrR, hmpA, ytfE, ygbA, hcp, hcr, nrfA, aox |
| NorR | NO | norVW, norR |
| DNR | NO | norCB, nir, nor, nos |

As used herein, "reactive oxygen species" and "ROS" are used interchangeably to refer to highly active molecules, ions, and/or radicals derived from molecular oxygen. ROS can be produced as byproducts of aerobic respiration or metal-catalyzed oxidation and may cause deleterious cellular effects such as oxidative damage. ROS include, but are not limited to, hydrogen peroxide ($H_2O_2$), organic peroxide (ROOH), hydroxyl ion ($OH^-$), hydroxyl radical (.OH), superoxide or superoxide anion ($.O_2^-$), singlet oxygen ($^1O_2$), ozone ($O_3$), carbonate radical, peroxide or peroxyl radical ($.O_2^{-2}$), hypochlorous acid (HOCl), hypochlorite ion ($OCl^-$), sodium hypochlorite (NaOCl), nitric oxide (NO.), and peroxynitrite or peroxynitrite anion ($ONOO^-$) (unpaired electrons denoted by .). Bacteria have evolved transcription factors that are capable of sensing ROS levels. Different ROS signaling pathways are triggered by different ROS levels and occur with different kinetics (Marinho et al., 2014).

As used herein, "ROS-inducible regulatory region" refers to a nucleic acid sequence to which one or more ROS-sensing transcription factors is capable of binding, wherein the binding and/or activation of the corresponding transcription factor activates downstream gene expression; in the presence of ROS, the transcription factor binds to and/or activates the regulatory region. In some embodiments, the ROS-inducible regulatory region comprises a promoter sequence. In some embodiments, the transcription factor senses ROS and subsequently binds to the ROS-inducible regulatory region, thereby activating downstream gene expression. In alternate embodiments, the transcription factor is bound to the ROS-inducible regulatory region in the absence of ROS; in the presence of ROS, the transcription factor undergoes a conformational change, thereby activating downstream gene expression. The ROS-inducible regulatory region may be operatively linked to a gene sequence or gene cassette, e.g., a butyrogenic gene cassette. For example, in the presence of ROS, a transcription factor, e.g., OxyR, senses ROS and activates a corresponding ROS-inducible regulatory region, thereby driving expression of an operatively linked gene sequence or gene cassette. Thus, ROS induces expression of the gene or gene cassette.

As used herein, "ROS-derepressible regulatory region" refers to a nucleic acid sequence to which one or more ROS-sensing transcription factors is capable of binding, wherein the binding of the corresponding transcription factor represses downstream gene expression; in the presence of ROS, the transcription factor does not bind to and does not repress the regulatory region. In some embodiments, the ROS-derepressible regulatory region comprises a promoter sequence. The ROS-derepressible regulatory region may be operatively linked to a gene or gene cassette, e.g., a butyrogenic or other gene cassette or gene sequence(s) described herein. For example, in the presence of ROS, a transcription factor, e.g., OhrR, senses ROS and no longer binds to and/or represses the regulatory region, thereby derepressing an operatively linked gene sequence or gene cassette. Thus, ROS derepresses expression of the gene or gene cassette.

As used herein, "ROS-repressible regulatory region" refers to a nucleic acid sequence to which one or more ROS-sensing transcription factors is capable of binding, wherein the binding of the corresponding transcription factor represses downstream gene expression; in the presence of ROS, the transcription factor binds to and represses the regulatory region. In some embodiments, the ROS-repressible regulatory region comprises a promoter sequence. In some embodiments, the transcription factor that senses ROS is capable of binding to a regulatory region that overlaps with part of the promoter sequence. In alternate embodiments, the transcription factor that senses ROS is capable of binding to a regulatory region that is upstream or downstream of the promoter sequence. The ROS-repressible regulatory region may be operatively linked to a gene sequence or gene cassette. For example, in the presence of ROS, a transcription factor, e.g., PerR, senses ROS and binds to a corresponding ROS-repressible regulatory region, thereby blocking expression of an operatively linked gene sequence or gene cassette. Thus, ROS represses expression of the gene or gene cassette.

As used herein, a "ROS-responsive regulatory region" refers to a ROS-inducible regulatory region, a ROS-repressible regulatory region, and/or a ROS-derepressible regulatory region. In some embodiments, the ROS-responsive regulatory region comprises a promoter sequence. Each regulatory region is capable of binding at least one corresponding ROS-sensing transcription factor. Examples of transcription factors that sense ROS and their corresponding ROS-responsive genes, promoters, and/or regulatory regions include, but are not limited to, those shown in Table 3.

TABLE 3

Examples of ROS-sensing transcription factors and ROS-responsive genes

| ROS-sensing transcription factor: | Primarily capable of sensing: | Examples of responsive genes, promoters, and/or regulatory regions: |
|---|---|---|
| OxyR | $H_2O_2$ | ahpC; ahpF; dps; dsbG; fhuF; flu; fur; gor; grxA; hemH; katG; oxyS; sufA; sufB; sufC; sufD; sufE; sufS; trxC; uxuA; yaaA; yaeH; yaiA; ybjM; ydcH; ydeN; ygaQ; yljA; ytfK |
| PerR | $H_2O_2$ | katA; ahpCF; mrgA; zoaA; fur; hemAXCDBL; srfA |
| OhrR | Organic peroxides NaOCl | ohrA |
| SoxR | $\cdot O_2^-$ NO$\cdot$ (also capable of sensing $H_2O_2$) | soxS |
| RosR | $H_2O_2$ | rbtT; tnp16a; rluC1; tnp5a; mscL; tnp2d; phoD; tnp15b; pstA; tnp5b; xylC; gabD1; rluC2; cgtS9; azlC; narKGHJI; rosR |

As used herein, a "tunable regulatory region" refers to a nucleic acid sequence under direct or indirect control of a transcription factor and which is capable of activating, repressing, derepressing, or otherwise controlling gene expression relative to levels of an inducer. In some embodiments, the tunable regulatory region comprises a promoter sequence. The inducer may be RNS, or other inducer described herein, and the tunable regulatory region may be a RNS-responsive regulatory region or other responsive regulatory region described herein. The tunable regulatory region may be operatively linked to a gene sequence(s) or gene cassette, e.g., a butyrogenic or other gene cassette or gene sequence(s). For example, in one specific embodiment, the tunable regulatory region is a RNS-derepressible regulatory region, and when RNS is present, a RNS-sensing transcription factor no longer binds to and/or represses the regulatory region, thereby permitting expression of the operatively linked gene or gene cassette. In this instance, the tunable regulatory region derepresses gene or gene cassette expression relative to RNS levels. Each gene or gene cassette may be operatively linked to a tunable regulatory region that is directly or indirectly controlled by a transcription factor that is capable of sensing at least one RNS.

As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in gene cassette. In some embodiments, "non-native" refers to two or more nucleic acid sequences that are not found in the same relationship to each other in nature. The non-native nucleic acid sequence may be present on a plasmid or chromosome. In addition, multiple copies of any regulatory region, promoter, gene, and/or gene cassette may be present in the bacterium, wherein one or more copies of the regulatory region, promoter, gene, and/or gene cassette may be mutated or otherwise altered as described herein. In some embodiments, the genetically engineered bacteria are engineered to comprise multiple copies of the same regulatory region, promoter, gene, and/or gene cassette in order to enhance copy number or to comprise multiple different components of a gene cassette performing multiple different functions or to comprise one or more copies of different regulatory regions, promoters, genes, and/or gene cassette to produce engineered bacteria that express more than one therapeutic molecule and/or perform more than one function.

In some embodiments, the genetically engineered bacteria of the invention comprise a gene cassette that is operably linked to a directly or indirectly inducible promoter that is not associated with said gene cassette in nature, e.g., a FNR-responsive promoter operably linked to a butyrogenic gene cassette.

"Constitutive promoter" refers to a promoter that is capable of facilitating continuous transcription of a coding sequence or gene under its control and/or to which it is operably linked. Constitutive promoters and functional variants are well known in the art and include, but are not limited to, BBa_J23100, a constitutive Escherichia coli $\sigma^S$ promoter (e.g., an osmY promoter (International Genetically Engineered Machine (iGEM) Registry of Standard Biological Parts Name BBa_J45992; BBa_J45993)), a constitutive Escherichia coli $\sigma^{32}$ promoter (e.g., htpG heat shock promoter (BBa_J45504)), a constitutive Escherichia coli $\sigma^{70}$ promoter (e.g., lacq promoter (BBa_J54200; BBa_J56015), E. coli CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive Bacillus subtilis $\sigma^A$ promoter (e.g., promoter veg (BBa_K143013), promoter 43 (BBa_K143013), $P_{liaG}$ (BBa_K823000), $P_{lepA}$ (BBa_K823002), $P_{veg}$ (BBa_K823003)), a constitutive Bacillus subtilis $\sigma^B$ promoter (e.g., promoter ctc (BBa_K143010), promoter gsiB (BBa_K143011)), a Salmonella promoter (e.g., Pspv2 from Salmonella (BBa_K112706), Pspv from Salmonella (BBa_K112707)), a bacteriophage T7 promoter (e.g., T7 promoter (BBa_I712074; BBa_I719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), and a bacteriophage SP6 promoter (e.g., SP6 promoter (BBa_J64998)).

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

"Non-pathogenic bacteria" refer to bacteria that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria are commensal bacteria, which are present in the indigenous microbiota of the gut. Examples of non-pathogenic bacteria include, but are not limited to Bacillus, Bacteroides, Bifidobacterium, Brevibacteria, Clostridium, Enterococcus, Escherichia, Lactobacillus, Lactococcus, Saccharomyces, and Staphylococcus, e.g., Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis, and Saccharomyces boulardii (Sonnenborn et al., 2009; Dinleyici et al., 2014; U.S. Pat. Nos. 6,835,376; 6,203,797; 5,589,168; 7,731,976). Non-pathogenic bacteria also include commensal bacteria, which are present in the indigenous microbiota of the gut. Naturally pathogenic bacteria may be genetically engineered to reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic. Examples of probiotic bacteria include, but are not limited to, Bifidobacteria, Escherichia, Lactobacillus, and Saccharomyces, e.g., Bifidobacterium bifidum, Enterococcus faecium, Escherichia coli, Escherichia coli strain Nissle, Lactobacillus acidophilus, Lactobacillus bulgaricus, Lactobacillus paracasei, Lactobacillus plantarum, and Saccharomyces boulardii (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, "stably maintained", "stably expressed" or "stable" bacterium is used to refer to a bacterial host cell carrying non-native genetic material, e.g., a butyrogenic or other gene cassette or gene sequence(s), which is incorporated into the host genome or propagated on a self-replicating extra-chromosomal plasmid, such that the non-native genetic material is retained, expressed, and/or propagated. The stable bacterium is capable of survival and/or growth in vitro, e.g., in medium, and/or in vivo, e.g., in the gut. For example, the stable bacterium may be a genetically modified bacterium comprising a butyrogenic or other gene cassette or gene sequence(s), in which the plasmid or chromosome carrying the butyrogenic or other gene cassette or gene sequence(s) is stably maintained in the host cell, such that the gene cassette or gene sequence(s) can be expressed in the host cell, and the host cell is capable of survival and/or growth in vitro and/or in vivo. In some embodiments, copy number affects the stability of expression of the non-native genetic material. In some embodiments, copy number affects the level of expression of the non-native genetic material.

As used herein, the term "treat" and its cognates refer to an amelioration of a disease or disorder, or at least one discernible symptom thereof. In another embodiment, "treat" refers to an amelioration of at least one measurable physical parameter, not necessarily discernible by the patient. In another embodiment, "treat" refers to inhibiting the progression of a disease or disorder, either physically (e.g., stabilization of a discernible symptom), physiologically (e.g., stabilization of a physical parameter), or both. In another embodiment, "treat" refers to slowing the progression or reversing the progression of a disease or disorder. As used herein, "prevent" and its cognates refer to delaying the onset or reducing the risk of acquiring a given disease or disorder.

Those in need of treatment may include individuals already having a particular medical disorder, as well as those at risk of having, or who may ultimately acquire the disorder. The need for treatment is assessed, for example, by the presence of one or more risk factors associated with the development of a disorder, the presence or progression of a disorder, or likely receptiveness to treatment of a subject having the disorder. Treating autoimmune disorders and/or diseases and conditions associated with gut inflammation and/or compromised gut barrier function may encompass reducing or eliminating excess inflammation and/or associated symptoms, and does not necessarily encompass the elimination of the underlying disease or disorder. In some instances, the "initial colonization of the newborn intestine is particularly relevant to the proper development of the host's immune and metabolic functions and to determine disease risk in early and later life" (Sanz et al., 2015). In some embodiments, early intervention (e.g., prenatal, perinatal, neonatal) using the genetically engineered bacteria of the invention may be sufficient to prevent or delay the onset of the disease or disorder.

As used herein a "pharmaceutical composition" refers to a preparation of genetically engineered bacteria of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., inflammation, diarrhea. A therapeutically effective amount may, for example, be sufficient to treat, prevent, reduce the severity, delay the onset, and/or reduce the risk of occurrence of one or more symptoms of an autoimmune disorder and/or a disease or condition associated with gut inflammation and/or compromised gut barrier function. A therapeutically effective amount, as well as a therapeutically effective frequency of administration, can be determined by methods known in the art and discussed below.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Bacteria

The genetically engineered bacteria of the invention are capable of producing a one or more non-native anti-inflammation and/or gut barrier function enhancer molecule(s). In some embodiments, the genetically engineered bacteria are naturally non-pathogenic bacteria. In some embodiments, the genetically engineered bacteria are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. In some embodiments, non-pathogenic bacteria are Gram-negative bacteria. In some embodiments, non-pathogenic bacteria are Gram-positive bacteria. Exemplary bacteria include, but are not limited to *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis, Saccharomyces boulardii, Clostridium* clusters IV and XIVa of *Firmicutes* (including species of *Eubacterium*), *Roseburia, Faecalibacterium, Enterobacter, Faecalibacterium prausnitzii, Clostridium difficile, Subdoligranulum, Clostridium sporogenes, Campylobacter jejuni, Clostridium saccharolyticum, Klebsiella, Citrobacter, Pseudobutyrivibrio*, and *Ruminococcus*. In certain embodiments, the genetically engineered bacteria are selected from the group consisting of *Bacteroides fragilis, Bacteroides thetaiotaomicron, Bacteroides subtilis, Bifidobacterium bifidum, Bifidobacterium infantis, Bifidobacterium lactis, Clostridium butyricum, Escherichia coli* Nissle, *Lactobacillus acidophilus, Lactobacillus plantarum, Lactobacillus reuteri*, and *Lactococcus lactis*. In some embodiments, the genetically engineered bacterium is a Gram-positive bacterium, e.g., *Clostridium*, that is naturally capable of producing high levels of butyrate. In some embodiments, the genetically engineered bacterium is selected from the group consisting of *C. butyricum* ZJUCB, *C. butyricum* S21, *C. thermobutyricum* ATCC 49875, *C. beijerinckii, C. populeti* ATCC 35295, *C. tyrobutyricum* JM1, *C. tyrobutyricum* C/P 1-776, *C. tyrobutyricum* ATCC 25755, *C. tyrobutyricum* CNRZ 596, and *C. tyrobutyricum* ZJU 8235. In some embodiments, the genetically engineered bacterium is *C. butyricum* CBM588, a probiotic bacterium that is highly amenable to protein secretion and has demonstrated efficacy in treating IBD (Kanai et al., 2015). In some embodiments, the genetically engineered bacterium is *Bacillus*, a probiotic bacterium that is highly genetically tractable and has been a popular chassis for industrial protein production; in some embodiments, the bacterium has highly active secretion and/or no toxic byproducts (Cutting, 2011).

In some embodiments, the genetically engineered bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reinter et al., 2014, emphasis added). Genomic sequencing confirmed that *E. coli* Nissle lacks prominent virulence factors (e.g., *E. coli* α-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and is not uropathogenic. (Sonnenborn et al., 2009). As early as in 1917, *E. coli* Nissle was packaged into medicinal capsules, called Mutaflor, for therapeutic use. *E. coli* Nissle has since been used to treat ulcerative colitis in humans in vivo (Rembacken et al., 1999), to treat inflammatory bowel disease, Crohn's disease, and pouchitis in humans in vivo (Schultz, 2008), and to inhibit enteroinvasive *Salmonella, Legionella, Yersinia*, and *Shigella* in vitro (Altenhoefer et al., 2004). It is commonly accepted that *E. coli* Nissle's therapeutic efficacy and safety have convincingly been proven (Ukena et al., 2007). In some embodiments, the genetically engineered bacteria are *E. coli* Nissle and are naturally capable of promoting tight junctions and gut barrier function. In some embodiments, the genetically engineered bacteria are *E. coli* and are highly amenable to recombinant protein technologies.

One of ordinary skill in the art would appreciate that the genetic modifications disclosed herein may be adapted for other species, strains, and subtypes of bacteria. It is known, for example, that the clostridial butyrogenic pathway genes are widespread in the genome-sequenced clostridia and related species (Aboulnaga et al., 2013). Furthermore, genes from one or more different species of bacteria can be introduced into one another, e.g., the butyrogenic genes from *Peptoclostridium difficile* have been expressed in *Escherichia coli* (Aboulnaga et al., 2013).

Unmodified *E. coli* Nissle and the genetically engineered bacteria of the invention may be destroyed, e.g., by defense factors in the gut or blood serum (Sonnenborn et al., 2009) or by activation of a kill switch, several hours or days after administration. Thus, the genetically engineered bacteria may require continued administration. Residence time in vivo may be calculated for the genetically engineered bacteria. In some embodiments, the residence time is calculated for a human subject.

Anti-inflammation and/or Gut Barrier Function Enhancer Molecules

The genetically engineered bacteria comprise one or more gene sequence(s) and/or gene cassette(s) for producing a non-native anti-inflammation and/or gut barrier function enhancer molecule. In some embodiments, the genetically engineered bacteria comprise one or more gene sequence(s) for producing a non-native anti-inflammation and/or gut barrier function enhancer molecule. For example, the genetically engineered bacteria may comprise two or more gene sequence(s) for producing a non-native anti-inflammation and/or gut barrier function enhancer molecule. In some embodiments, the two or more gene sequences are multiple copies of the same gene. In some embodiments, the two or more gene sequences are sequences encoding different genes. In some embodiments, the two or more gene sequences are sequences encoding multiple copies of one or more different genes. In some embodiments, the genetically engineered bacteria comprise one or more gene cassette(s) for producing a non-native anti-inflammation and/or gut barrier function enhancer molecule. For example, the genetically engineered bacteria may comprise two or more gene cassette(s) for producing a non-native anti-inflammation and/or gut barrier function enhancer molecule. In some embodiments, the two or more gene cassettes are multiple copies of the same gene cassette. In some embodiments, the two or more gene cassettes are different gene cassettes for producing either the same or different anti-inflammation and/or gut barrier function enhancer molecule(s). In some embodiments, the two or more gene cassettes are gene cassettes for producing multiple copies of one or more different anti-inflammation and/or gut barrier function enhancer molecule(s). In some embodiments, the anti-inflammation and/or gut barrier function enhancer molecule is selected from the group consisting of a short-chain fatty acid, butyrate, propionate, acetate, IL-2, IL-22, superoxide dismutase (SOD), GLP-2, GLP-1, IL-10, IL-27, TGF-β1, TGF-β2, N-acylphosphatidylethanolamines (NAPES), elafin (also known as peptidase inhibitor 3 or SKALP), trefoil factor, melatonin, PGD$_2$, kynurenic acid, and kynurenine. A molecule may be primarily anti-inflammatory, e.g., IL-10, or primarily gut barrier function enhancing, e.g., GLP-2. Alternatively, a molecule may be both anti-inflammatory and gut barrier function enhancing.

In some embodiments, the genetically engineered bacteria of the invention express one or more anti-inflammation and/or gut barrier function enhancer molecule(s) that is encoded by a single gene, e.g., the molecule is elafin and encoded by the PI3 gene, or the molecule is interleukin-10 and encoded by the IL10 gene. In alternate embodiments, the genetically engineered bacteria of the invention encode one or more an anti-inflammation and/or gut barrier function enhancer molecule(s), e.g., butyrate, that is synthesized by a biosynthetic pathway requiring multiple genes.

Figure 51:
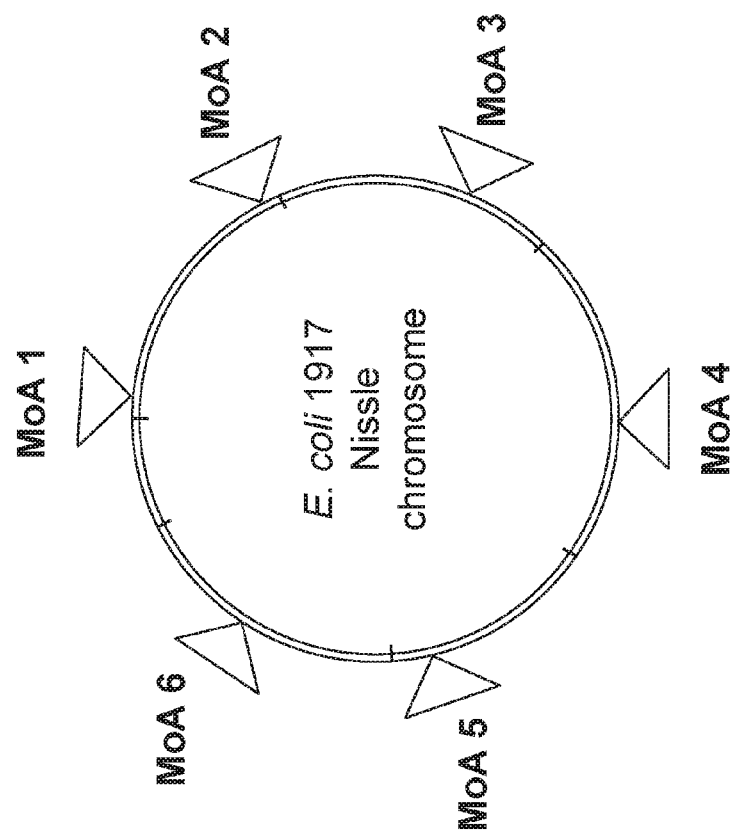
FIG. 51 depicts an exemplary schematic of the *E. coli* 1917 Nissle chromosome comprising multiple mechanisms of action (MoAs).
Figure 52:
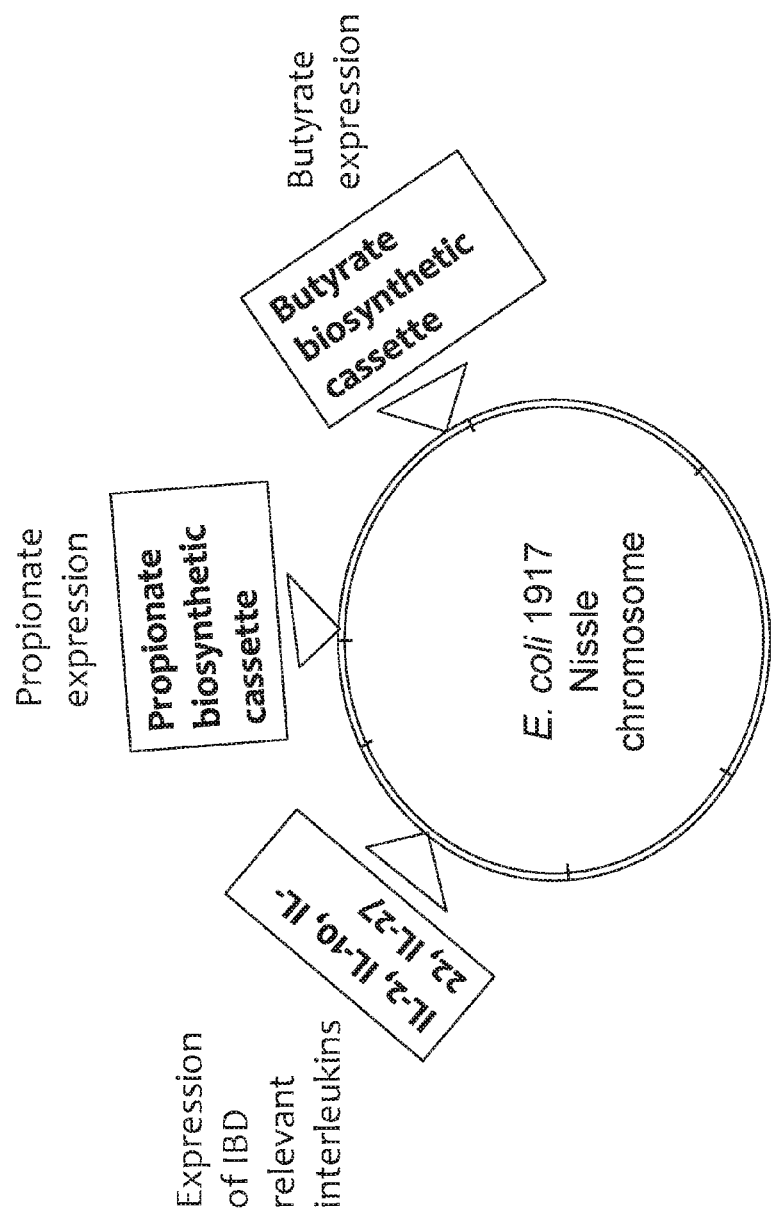
FIG. 52 depicts an exemplary schematic of the *E. coli* 1917 Nissle chromosome comprising multiple mechanisms of action for producing IL-2, IL-10, IL-22, IL-27, propionate, and butyrate.
Figure 53:
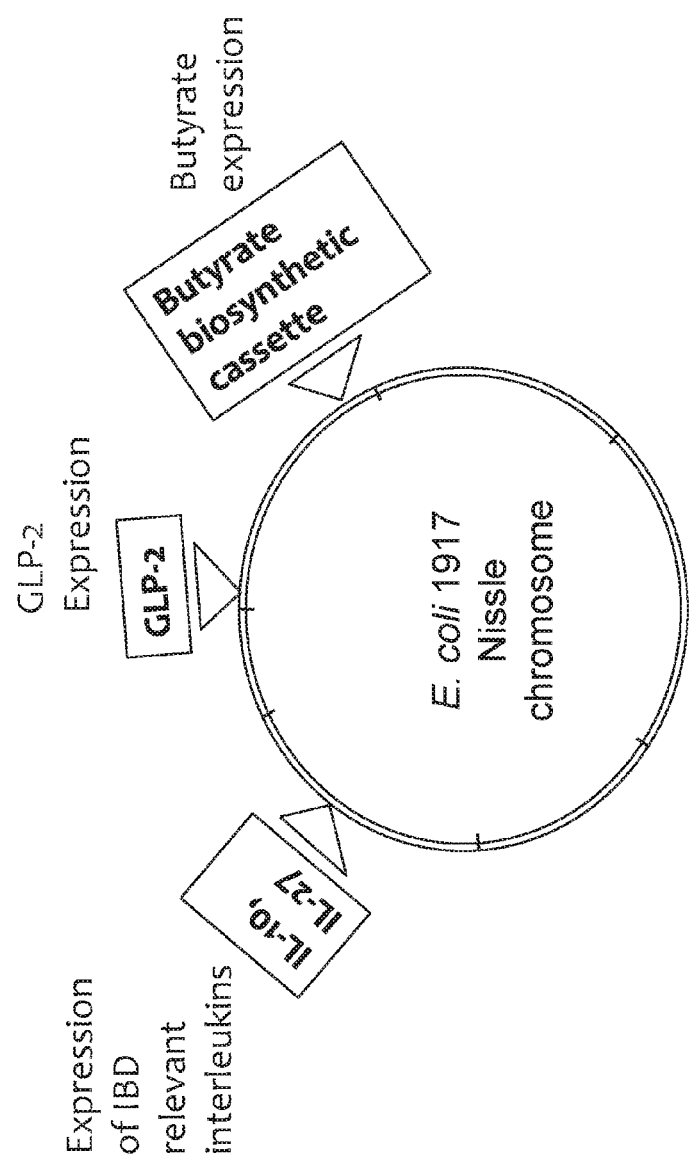
FIG. 53 depicts an exemplary schematic of the *E. coli* 1917 Nissle chromosome comprising multiple mechanisms of action for producing IL-10, IL-27, GLP-2, and butyrate.
Figure 54:
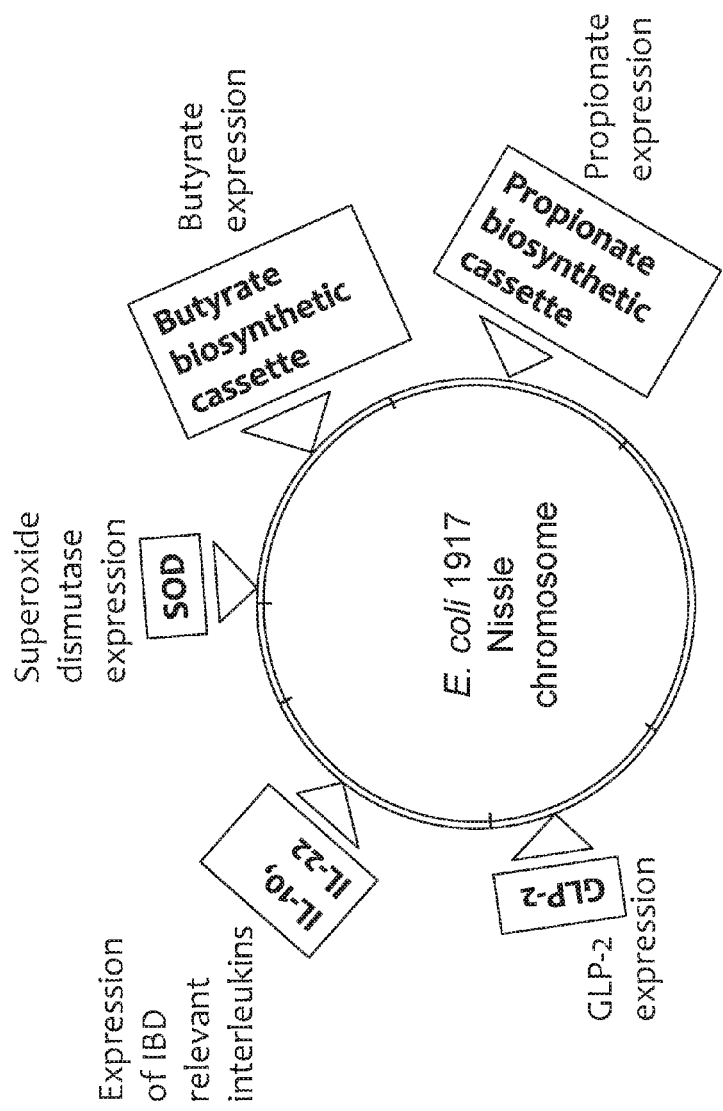
FIG. 54 depicts an exemplary schematic of the *E. coli* 1917 Nissle chromosome comprising multiple mechanisms of action for producing GLP-2, IL-10, IL-22, SOD, butyrate, and propionate.
Figure 55:
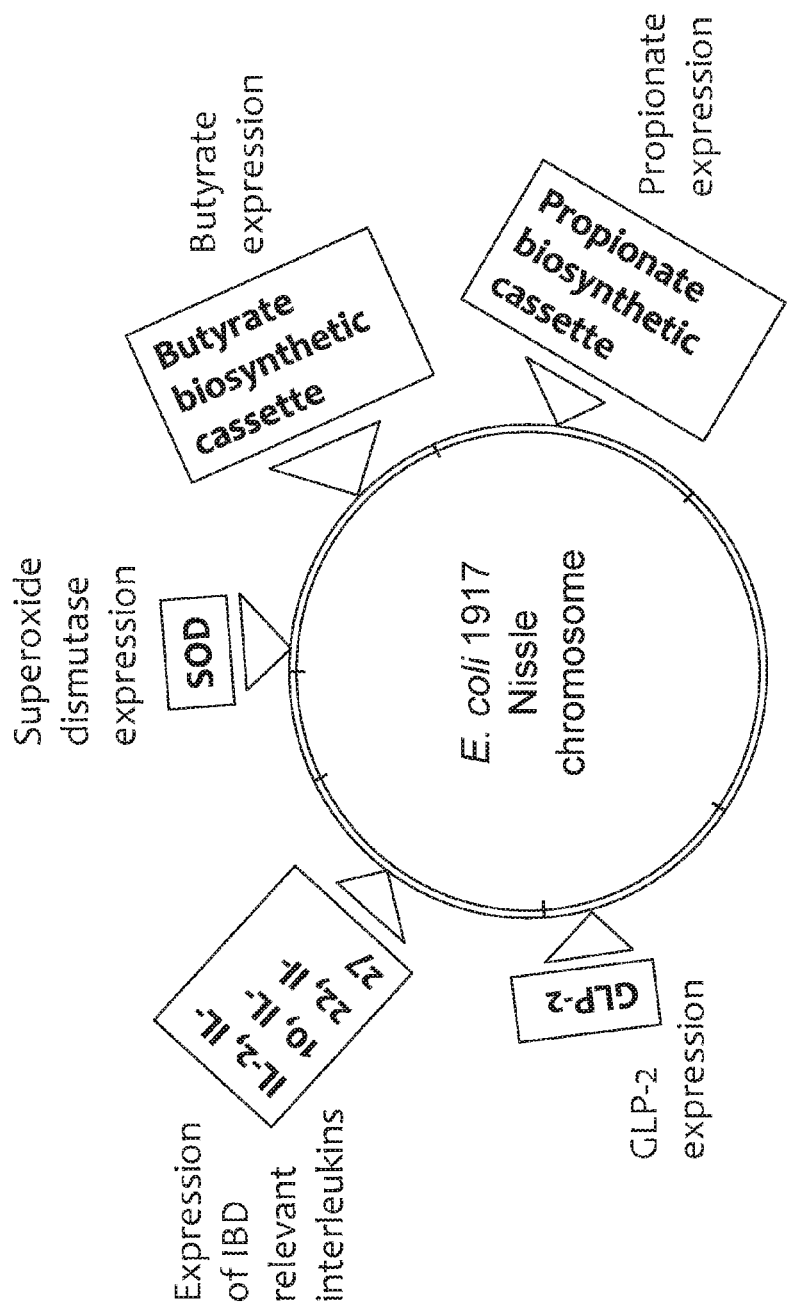
FIG. 55 depicts an exemplary schematic of the *E. coli* 1917 Nissle chromosome comprising multiple mechanisms of action for producing GLP-2, IL-2, IL-10, IL-22, IL-27, SOD, butyrate, and propionate.

The one or more gene sequence(s) and/or gene cassette(s) may be expressed on a high-copy plasmid, a low-copy plasmid, or a chromosome. In some embodiments, expression from the plasmid may be useful for increasing expression of the anti-inflammation and/or gut barrier function enhancer molecule(s). In some embodiments, expression from the chromosome may be useful for increasing stability of expression of the anti-inflammation and/or gut barrier function enhancer molecule(s). In some embodiments, the gene Sequence(s) or gene cassette(s) for producing the anti-inflammation and/or gut barrier function enhancer molecule(s) is integrated into the bacterial chromosome at one or more integration sites in the genetically engineered bacteria. For example, one or more copies of the butyrate biosynthesis gene cassette may be integrated into the bacterial chromosome. In some embodiments, the gene sequence(s) or gene cassette(s) for producing the anti-inflammation and/or gut barrier function enhancer molecule(s) is expressed from a plasmid in the genetically engineered bacteria. In some embodiments, the gene sequence(s) or gene cassette(s) for producing the anti-inflammation and/or gut barrier function enhancer molecule(s) is inserted into the bacterial genome at one or more of the following insertion sites in *E. coli* Nissle: malE/K, araC/BAD, lacZ, thyA, malP/T. Any suitable insertion site may be used (see, e.g., FIG. 51 for exemplary insertion sites). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon.

In some embodiments, the genetically engineered bacteria of the invention comprise one or more butyrogenic gene cassette(s) and are capable of producing butyrate. The genetically engineered bacteria may include any suitable set of butyrogenic genes (see, e.g., Table 4). Unmodified bacteria comprising butyrate biosynthesis genes are known and include, but are not limited to, *Peptoclostridium, Clostridium, Fusobacterium, Butyrivibrio, Eubacterium*, and *Treponema*, and these endogenous butyrate biosynthesis pathways may be a source of genes for the genetically engineered bacteria of the invention. In some embodiments, the genetically engineered bacteria of the invention comprise butyrate biosynthesis genes from a different species, strain, or substrain of bacteria. In some embodiments, the genetically engineered bacteria comprise the eight genes of the butyrate biosynthesis pathway from *Peptoclostridium difficile*, e.g., *Peptoclostridium difficile* strain 630: bcd2, etfB3, etfA3, thiA1, hbd, crt2, pbt, and buk (Aboulnaga et al., 2013), and are capable of producing butyrate under inducing conditions. *Peptoclostridium difficile* strain 630 and strain 1296 are both capable of producing butyrate, but comprise different nucleic acid sequences for etfA3, thiA1, hbd, crt2, pbt, and buk. In some embodiments, the genetically engineered bacteria comprise a combination of butyrogenic genes from different species, strains, and/or substrains of bacteria, and are capable of producing butyrate under inducing conditions. For example, in some embodiments, the genetically engineered bacteria comprise bcd2, etfB3, etfA3, and thiA1 from *Peptoclostridium difficile* strain 630, and hbd, crt2, pbt, and buk from *Peptoclostridium difficile* strain 1296.

The gene products of the bcd2, etfA3, and etfB3 genes in *Clostridium difficile* form a complex that converts crotonyl-CoA to butyryl-CoA, which may function as an oxygen-dependent co-oxidant. In some embodiments, because the genetically engineered bacteria of the invention are designed to produce butyrate in a microaerobic or oxygen-limited environment, e.g., the mammalian gut, oxygen dependence could have a negative effect on butyrate production in the gut. It has been shown that a single gene from *Treponema denticola* (ter, encoding trans-2-enoynl-CoA reductase) can functionally replace this three-gene complex in an oxygen-independent manner. In some embodiments, the genetically engineered bacteria comprise a ter gene, e.g., from *Treponema denticola*, which can functionally replace all three of the bcd2, etfB3, and etfA3 genes, e.g., from *Peptoclostridium difficile*. In this embodiment, the genetically engineered bacteria comprise thiA1, hbd, crt2, pbt, and buk, e.g., from *Peptoclostridium difficile*, and ter, e.g., from *Treponema denticola*, and are capable of producing butyrate in low-oxygen conditions (see, e.g., Table 4). In some embodiments, the genetically engineered bacteria comprise genes for aerobic butyrate biosynthesis and/or genes for anaerobic or microaerobic butyrate biosynthesis. In some embodiments, the genetically engineered bacteria of the invention comprise thiA1, hbd, crt2, pbt, and buk, e.g., from *Peptoclostridium difficile*; ter, e.g., from *Treponema denticola*; one or more of bcd2, etfB3, and etfA3, e.g., from *Peptoclostridium difficile*; and produce butyrate under inducing conditions. Alternatively, the tesB gene from *Escherichia coli* is capable of functionally replacing pbt and buk genes from *Peptoclostridium difficile*. Thus, in some embodiments, a butyrogenic gene cassette may comprise thiA1, hbd and crt2 from *Peptoclostridium difficile*, ter from *Treponema denticola* and tesB from *E. coli*. In some embodiments, one or more of the butyrate biosynthesis genes may be functionally replaced or modified, e.g., codon optimized. In some embodiments, the butyrogenic gene cassette comprises genes for the aerobic biosynthesis of butyrate and/or genes for the anaerobic or microaerobic biosynthesis of butyrate. In some embodiments, one or more of the butyrate biosynthesis genes is functionally replaced, modified, and/or mutated in order to enhance stability and/or increase butyrate production in low-oxygen conditions. In some embodiments, the local production of butyrate induces the differentiation of regulatory T cells in the gut and/or promotes the barrier function of colonic epithelial cells. Exemplary butyrate gene cassettes are shown in FIGS. 1, 3, 4, 5, 6, 7, and 8.

In some embodiments, the genetically engineered bacteria are capable of expressing the butyrate biosynthesis cassette and producing butyrate under inducing conditions. The genes may be codon-optimized, and translational and transcriptional elements may be added. Table 4 depicts the nucleic acid sequences of exemplary genes in the butyrate biosynthesis gene cassette.

In some embodiments, the genetically engineered bacteria comprise the nucleic acid sequence of any one of SEQ ID NOs: 1-10 or a functional fragment thereof. In some embodiments, the genetically engineered bacteria comprise a nucleic acid sequence that, but for the redundancy of the genetic code, encodes the same polypeptide as any one of SEQ ID NOs: 1-10 or a functional fragment thereof. In some embodiments, the genetically engineered bacteria comprise a nucleic acid sequence that encodes a polypeptide of any one of SEQ ID NOs: 11-20 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of any one of SEQ ID NOs: 1-10 or a functional fragment thereof. In some embodiments, genetically engineered bacteria comprise a nucleic acid that is at least about 80%, at least about 85%, at least about 90%, at least about 95%, or at least about 99% homologous to the nucleic acid sequence that encodes a polypeptide of any one of SEQ ID NOs: 11-20 or a functional fragment thereof.

TABLE 4

| Gene sequence | 0123456789012345678901234567890123456789 |
| --- | --- |
| bcd2 (SEQ ID NO: 1) | ATGGATTTAAATTCTAAAAAATATCAGATGCTTAAAGAGCTATATGTAAG<br>CTTCGCTGAAAATGAAGTTAAACCTTTAGCAACAGAACTTGATGAAGAAG<br>AAAGATTTCCTTATGAAACAGTGGAAAAAATGGCAAAAGCAGGAATGATG<br>GGTATACCATATCCAAAAGAATATGGTGGAGAAGGTGGAGACACTGTAGG<br>ATATATAATGGCAGTTGAAGAATTGTCTAGAGTTTGTGGTACTACAGGAG<br>TTATATTATCAGCTCATACATCTCTTGGCTCATGGCCTATATATCAATAT<br>GGTAATGAAGAACAAAAACAAAAATTCTTAAGACCACTAGCAAGTGGAGA<br>AAAATTAGGAGCATTTGGTCTTACTGAGCCTAATGCTGGTACAGATGCGT<br>CTGGCCAACAAACAACTGCTGTTTTAGACGGGGATGAATACATACTTAAT<br>GGCTCAAAAATATTTATAACAAACGCAATAGCTGGTGACATATATGTAGT<br>AATGGCAATGACTGATAAATCTAAGGGGAACAAAGGAATATCAGCATTTA<br>TAGTTGAAAAAGGAACTCCTGGGTTTAGCTTTGGAGTTAAAGAAAAGAAA<br>ATGGGTATAAGAGGTTCAGCTACGAGTGAATTAATATTTGAGGATTGCAG<br>AATACCTAAAGAAAATTTACTTGGAAAAGAAGGTCAAGGATTTAAGATAG<br>CAATGTCTACTCTTGATGGTGGTAGAATTGGTATAGCTGCACAAGCTTTA<br>GGTTTAGCACAAGGTGCTCTTGATGAAACTGTTAAATATGTAAAAGAAAG<br>AGTACAATTTGGTAGACCATTATCAAAATTCCAAAATACACAATTCCAAT<br>TAGCTGATATGGAAGTTAAGGTACAAGCGGCTAGACACCTTGTATATCAA<br>GCAGCTATAAATAAAGACTTAGGAAAACCTTATGGAGTAGAAGCAGCAAT<br>GGCAAAATTATTTGCAGCTGAAACAGCTATGGAAGTTACTACAAAAGCTG<br>TACAACTTCATGGAGGATATGGATACACTCGTGACTATCCAGTAGAAAGA<br>ATGATGAGAGATGCTAAGATAACTGAAATATATGAAGGAACTAGTGAAGT<br>TCAAAGAATGGTTATTTCAGGAAAACTATTAAAATAG |
| etfB3 (SEQ ID NO: 2) | ATGAATATAGTCGTTTGTATAAAACAAGTTCCAGATACAACAGAAGTTAA<br>ACTAGATCCTAATACAGGTACTTTAATTAGAGATGGAGTACCAAGTATAA<br>TAAACCCTGATGATAAAGCAGGTTTAGAAGAAGCTATAAAATTAAAAGAA |

TABLE 4-continued

| Gene sequence | 0123456789012345678901234567890123456789 |
|---|---|
| | GAAATGGGTGCTCATGTAACTGTTATAACAATGGGACCTCCTCAAGCAGA
TATGGCTTTAAAAGAAGCTTTAGCAATGGGTGCAGATAGAGGTATATTAT
TAACAGATAGAGCATTTGCGGGTGCTGATACTTGGGCAACTTCATCAGCA
TTAGCAGGAGCATTAAAAAATATAGATTTTGATATTATAATAGCTGGAAG
ACAGGCGATAGATGGAGATACTGCACAAGTTGGACCTCAAATAGCTGAAC
ATTTAAATCTTCCATCAATAACATATGCTGAAGAAATAAAAACTGAAGGT
GAATATGTATTAGTAAAAAGACAATTTGAAGATTGTTGCCATGACTTAAA
AGTTAAAATGCCATGCCTTATAACAACTCTTAAAGATATGAACACACCAA
GATACATGAAAGTTGGAAGAATATATGATGCTTTCGAAAATGATGTAGTA
GAAACATGGACTGTAAAAGATATAGAAGTTGACCCTTCTAATTTAGGTCT
TAAAGGTTCTCCAACTAGTGTATTTAAATCATTTACAAAATCAGTTAAAC
CAGCTGGTACAATATACAATGAAGATGCGAAAACATCAGCTGGAATTATC
ATAGATAAATTAAAAGAGAAGTATATCATATAA |
| etfA3
(SEQ ID NO: 3) | ATGGGTAACGTTTTAGTAGTAATAGAACAAAGAGAAAATGTAATTCAAAC
TGTTTCTTTAGAATTACTAGGAAAGGCTACAGAAATAGCAAAAGATTATG
ATACAAAAGTTTCTGCATTACTTTTAGGTAGTAAGGTAGAAGGTTTAATA
GATACATTAGCACACTATGGTGCAGATGAGGTAATAGTAGTAGATGATGA
AGCTTTAGCAGTGTATACAACTGAACCATATACAAAAGCAGCTTATGAAG
CAATAAAAGCAGCTGACCCTATAGTTGTATTATTTGGTGCAACTTCAATA
GGTAGAGATTTAGCGCCTAGAGTTTCTGCTAGAATACATACAGGTCTTAC
TGCTGACTGTACAGGTCTTGCAGTAGCTGAAGATACAAAATTATTATTAA
TGACAAGACCTGCCTTTGGTGGAAATATAATGGCAACAATAGTTTGTAAA
GATTTCAGACCTCAAATGTCTACAGTTAGACCAGGGGTTATGAAGAAAA
TGAACCTGATGAAACTAAAGAAGCTGTAATTAACCGTTTCAAGGTAGAAT
TTAATGATGCTGATAAATTAGTTCAAGTTGTACAAGTAATAAAAGAAGCT
AAAAAACAAGTTAAAATAGAAGATGCTAAGATATTAGTTTCTGCTGGACG
TGGAATGGGTGGAAAAGAAAACTTAGACATACTTTATGAATTAGCTGAAA
TTATAGGTGGAGAAGTTTCTGGTTCTCGTGCCACTATAGATGCAGGTTGG
TTAGATAAAGCAAGACAAGTTGGTCAAACTGGTAAAACTGTAAGACCAGA
CCTTTATATAGCATGTGGTATATCTGGAGCAATACAACATATAGCTGGTA
TGGAAGATGCTGAGTTTATAGTTGCTATAAATAAAAATCCAGAAGCTCCA
ATATTTAAATATGCTGATGTTGGTATAGTTGGAGATGTTCATAAAGTGCT
TCCAGAACTTATCAGTCAGTTAAGTGTTGCAAAAGAAAAAGGTGAAGTTT
TAGCTAACTAA |
| thiA1
(SEQ ID NO: 4) | ATGAGAGAAGTAGTAATTGCCAGTGCAGCTAGAACAGCAGTAGGAAGTTT
TGGAGGAGCATTTAAATCAGTTTCAGCGGTAGAGTTAGGGGTAACAGCAG
CTAAAGAAGCTATAAAAAGAGCTAACATAACTCCAGATATGATAGATGAA
TCTCTTTTAGGGGGAGTACTTACAGCAGGTCTTGGACAAAATATAGCAAG
ACAAATAGCATTAGGAGCAGGAATACCAGTAGAAAACCAGCTATGACTA
TAAATATAGTTTGTGGTTCTGGATTAAGATCTGTTTCAATGGCATCTCAA
CTTATAGCATTAGGTGATGCTGATATAATGTTAGTTGGTGGAGCTGAAAA
CATGAGTATGTCTCCTTATTTAGTACCAAGTGCGAGATATGGTGCAAGAA
TGGGTGATGCTGCTTTTGTTGATTCAATGATAAAAGATGGATTATCAGAC
ATATTTAATAACTATCACATGGGTATTACTGCTGAAAACATAGCAGAGCA
ATGGAATATAACTAGAGAAGAACAAGATGAATTAGCTCTTGCAAGTCAAA
ATAAAGCTGAAAAAGCTCAAGCTGAAGGAAAATTTGATGAAGAAATAGTT
CCTGTTGTTATAAAAGGAAGAAAGGTGACACTGTAGTAGATAAAGATGA
ATATATTAAGCCTGGCACTACAATGGAGAAACTTGCTAAGTTAAGACCTG
CATTTAAAAAAGATGGAACAGTTACTGCTGGTAATGCATCAGGAATAAAT
GATGGTGCTGCTATGTTAGTAGTAATGGCTAAAGAAAAAGCTGAAGAACT
AGGAATAGAGCCTCTTGCAACTATAGTTTCTTATGGAACAGCTGGTGTTG
ACCCTAAAATAATGGGATATGGACCAGTTCCAGCAACTAAAAAAGCTTTA
GAAGCTGCTAATATGACTATTGAAGATATAGATTTAGTTGAAGCTAATGA
GGCATTTGCTGCCCAATCTGTAGCTGTAATAAGAGACTTAAATATAGATA
TGAATAAAGTTAATGTTAATGGTGGAGCAATAGCTATAGGACATCCAATA
GGATGCTCAGGAGCAAGAATACTTACTACACTTTTATATGAAATGAAGAG
AAGAGATGCTAAAACTGGTCTTGCTACACTTTGTATAGGCGGTGGAATGG
GAACTACTTTAATAGTTAAGAGATAG |
| hbd
(SEQ ID NO: 5) | ATGAAATTAGCTGTAATAGGTAGTGGAACTATGGGAAGTGGTATTGTACA
AACTTTTGCAAGTTGTGGACATGATGTATGTTTAAAGAGTAGAACTCAAG
GTGCTATAGATAAATGTTTAGCTTTATTAGATAAAAATTTAACTAAGTTA
GTTACTAAGGGAAAAATGGATGAAGCTACAAAAGCAGAAATATTAAGTCA
TGTTAGTTCAACTACTAATTATGAAGATTTAAAAGATATGGATTTAATAA
TAGAAGCATCTGTAGAAGACATGAATATAAAGAAAGATGTTTTCAAGTTA
CTAGATGAATTATGTAAAGAAGATACTATCTTGGCAACAAATACTTCATC
ATTATCTATAACAGAAATAGCTTCTTCTACTAAGCGCCCAGATAAAGTTA
TAGGAATGCATTTCTTTAATCCAGTTCCTATGATGAAATTAGTTGAAGTT
ATAAGTGGTCAGTTAACATCAAAAGTTACTTTTGATACAGTATTTGAATT
ATCTAAGAGTATCAATAAAGTACCAGTAGATGTATCTGAATCTCCTGGAT
TTGTAGTAAATAGAACTTATACCTATGATAAATGAAGCTGTTGGTATA
TATGCAGATGGTGTTGCAAGTAAAGAAGAAATAGATGAAGCTATGAAATT
AGGAGCAAACCATCCAATGGGACCACTAGCATTAGGTGATTTAATCGGAT
TAGATGTTGTTTTAGCTATAATGAACGTTTTATATACTGAATTTGGAGAT TABLE 4-continued

| Gene sequence | 0123456789012345678901234567890123456789 |
|---|---|
| | ACTAAATATAGACCTCATCCACTTTTAGCTAAAATGGTTAGAGCTATCA |
| | ATTAGGAAGAAAAACTAAGATAGGATTCTATGATTATAATAAATAA |
| crt2 (SEQ ID NO: 6) | ATGAGTACAAGTGATGTTAAAGTTTATGAGAATGTAGCTGTTGAAGTAGA |
| | TGGAAATATATGTACAGTGAAAATGAATAGACCTAAAGCCCTTAATGCAA |
| | TAAATTCAAAGACTTTAGAAGAACTTTATGAAGTATTTGTAGATATTAAT |
| | AATGATGAAACTATTGATGTTGTAATATTGACAGGGGAAGGAAAGGCATT |
| | TGTAGCTGGAGCAGATATTGCATACATGAAAGATTTAGATGCTGTAGCTG |
| | CTAAAGATTTTAGTATCTTAGGAGCAAAAGCTTTTGGAGAAATAGAAAAT |
| | AGTAAAAAAGTAGTGATAGCTGCTGTAAACGGATTTGCTTTAGGTGGAGG |
| | ATGTGAACTTGCAATGGCATGTGATATAAGAATTGCATCTGCTAAAGCTA |
| | AATTTGGTCAGCCAGAAGTAACTCTTGGAATAACTCCAGGATATGGAGGA |
| | ACTCAAAGGCTTACAAGATTGGTTGGAATGGCAAAAGCAAAAGAATTAAT |
| | CTTTACAGGTCAAGTTATAAAAGCTGATGAAGCTGAAAAAATAGGGCTAG |
| | TAAATAGAGTCGTTGAGCCAGACATTTTAATAGAAGAAGTTGAGAAATTA |
| | GCTAAGATAATAGCTAAAAATGCTCAGCTTGCAGTTAGATACTCTAAAGA |
| | AGCAATACAACTTGGTGCTCAAACTGATATAAATACTGGAATAGATATAG |
| | AATCTAATTTATTTGGTCTTTGTTTTTCAACTAAAGACCAAAAAGAAGGA |
| | ATGTCAGCTTTCGTTGAAAAGAGAGAAGCTAACTTTATAAAAGGGTAA |
| pbt (SEQ ID NO: 7) | ATGAGAAGTTTTGAAGAAGTAATTAAGTTTGCAAAAGAAAGAGGACCTAA |
| | AACTATATCAGTAGCATGTTGCCAAGATAAAGAAGTTTTAATGGCAGTTG |
| | AAATGGCTAGAAAAGAAAAAATAGCAAATGCCATTTTAGTAGGAGATATA |
| | GAAAAGACTAAAGAAATTGCAAAAAGCATAGACATGGATATCGAAAATTA |
| | TGAACTGATAGATATAAAAGATTTAGCAGAAGCATCTCTAAAATCTGTTG |
| | AATTAGTTTCACAAGGAAAAGCCGACATGGTAATGAAAGGCTTAGTTAGAC |
| | ACATCAATAATACTAAAAGCAGTTTTAAATAAAGAAGTAGGTCTTAGAAC |
| | TGGAAATGTATTAAGTCACGTAGCAGTATTTGATGTAGAGGGATATGATA |
| | GATTATTTTTCGTAACTGACGCAGCTATGAACTTAGCTCCTGATACAAAT |
| | ACTAAAAAGCAAATCATAGAAAATGCTTGCACAGTAGCACATTCATTAGA |
| | TATAAGTGAACCAAAAGTTGCTGCAATATGCGCAAAAGAAAAAGTAAATC |
| | CAAAAATGAAAGATACAGTTGAAGCTAAAGAACTAGAAGAAATGTATGAA |
| | AGAGGAGAAATCAAAGGTTGTATGGTTGGTGGGCCTTTTGCAATTGATAA |
| | TGCAGTATCTTTAGAAGCAGCTAAACATAAAGGTATAAATCATCCTGTAG |
| | CAGGACGAGCTGATATATTATTAGCCCCAGATATTGAAGGTGGTAACATA |
| | TTATATAAAGCTTTGGTATTCTTCTCAAAATCAAAAAATGCAGGAGTTAT |
| | AGTTGGGGCTAAAGCACCAATAATATTAACTTCTAGAGCAGACAGTGAAG |
| | AAACTAAACTAAACTCAATAGCTTTAGGTGTTTTAATGGCAGCAAAGGCA |
| | TAA |
| buk (SEQ ID NO: 8) | ATGAGCAAAATATTTAAAATCTTAACAATAAATCCTGGTTCGACATCAAC |
| | TAAAATAGCTGTATTTGATAATGAGGATTTAGTATTTGAAAAAACTTTAA |
| | GACATTCTTCAGAAGAAATAGGAAAATATGAGAAGGTGTCTGACCAATTT |
| | GAATTTCGTAAACAAGTAATAGAAGAAGCTCTAAAAGAAGGTGGAGTAAA |
| | AACATCTGAATTAGATGCTGTAGTAGGTAGAGGAGGACTTCTTAAACCTA |
| | TAAAAGGTGGTACTTATTCAGTAAGTGCTGCTATGATTGAAGATTTAAAA |
| | GTGGGAGTTTTAGGAGAACACGCTTCAAACCTAGGTGGAATAATAGCAAA |
| | ACAAATAGGTGAAGAAGTAAATGTTCCTTCATACATAGTAGACCCTGTTG |
| | TTGTAGATGAATTAGAAGATGTTGCTAGAATTTCTGGTATGCCTGAAATA |
| | AGTAGAGCAAGTGTAGTACATGCTTTAAATCAAAAGGCAATAGCAAGAAG |
| | ATATGCTAGAGAAATAAACAAGAAATATGAAGATATAAATCTTATAGTTG |
| | CACACATGGGTGGAGGAGTTTCTGTTGGAGCTCATAAAAATGGTAAAATA |
| | GTAGATGTTGCAAACGCATTAGATGGAGAAGGACCTTTCTCTCCAGAAAG |
| | AAGTGGTGGACTACCAGTAGGTGCATTAGTAAAAATGTGCTTTAGTGGAA |
| | AATATACTCAAGATGAAATTAAAAAGAAAATAAAAGGTAATGCGGACTA |
| | GTTGCATACTTAAACACTAATGATGCTAGAGAAGTTGAAGAAAGAATTGA |
| | AGCTGGTGATGAAAAAGCTAAATTAGTATATGAAGCTATGGCATATCAAA |
| | TCTCTAAAGAAATAGGAGCTAGTGCTGCAGTTCTTAAGGGAGATGTAAAA |
| | GCAATATTATTAACTGGTGGAATCGCATATTCAAAAATGTTTACAGAAAT |
| | GATTGCAGATAGAGTTAAATTTATAGCAGATGTAAAAGTTTATCCAGGTG |
| | AAGATGAAATGATTGCATTAGCTCAAGGTGGACTTAGAGTTTTAACTGGT |
| | GAAGAAGAGGCTCAAGTTTATGATAACTAA |
| ter (SEQ ID NO: 9) | ATGATCGTAAAACCTATGGTACGCAACAATATCTGCCTGAACGCCCATCC |
| | TCAGGGCTGCAAGAAGGGAGTGGAAGATCAGATTGAATATACCAAGAAAC |
| | GCATTACCGCAGAAGTCAAAGCTGGCGCAAAAGCTCCAAAAAACGTTCTG |
| | GTGCTTGGCTGCTCAAATGGTTACGGCCTGGCGAGCCGCATTACTGCTGC |
| | GTTCGGATACGGGGCTGCGACCATCGGCGTGTCCTTTGAAAAAGCGGGTT |
| | CAGAAACCAAATATGGTACACCGGGATGGTACAATAATTTGGCATTTGAT |
| | GAAGCGGCAAACGCGAGGGTCTTTATAGCGTGACGATCGACGGCGATGC |
| | GTTTTCAGACGAGATCAAGGCCCAGGTAATTGAGGAAGCCAAAAAAAAAG |
| | GTATCAAATTTGATCTGATCGTATACAGCTTGGCCAGCCCAGTACGTACT |
| | GATCCTGATACAGGTATCATGCACAAAAGCGTTTTGAAACCCTTTGGAAA |
| | AACGTTCACAGGCAAAACAGTAGATCCGTTTACTGGCGAGCTGAAGGAAA |
| | TCTCCGCGGAACCAGCAAATGACGAGGAAGCAGCCGCCACTGTTAAAGTT |
| | ATGGGGGGTGAAGATTGGGAACGTTGGATTAAGCAGCTGTCGAAGGAAGG |
| | CCTCTTAGAAGAAGGCTGTATTACCTTGGCCTATAGTTATATTGGCCCTG |

TABLE 4-continued

| Gene sequence | 0123456789012345678901234567890123456789 |
|---|---|
| | AAGCTACCCAAGCTTTGTACCGTAAAGGCACAATCGGCAAGGCCAAAGAA<br>CACCTGGAGGCCACAGCACACCGTCTCAACAAAGAGAACCCGTCAATCCG<br>TGCCTTCGTGAGCGTGAATAAAGGCCTGGTAACCCGCGCAAGCGCCGTAA<br>TCCCGGTAATCCCTCTGTATCTCGCCAGCTTGTTCAAAGTAATGAAAGAG<br>AAGGGCAATCATGAAGGTTGTATTGAACAGATCACGCGTCTGTACGCCGA<br>GCGCCTGTACCGTAAAGATGGTACAATTCCAGTTGATGAGGAAAATCGCA<br>TTCGCATTGATGATTGGGAGTTAGAAGAAGACGTCCAGAAAGCGGTATCC<br>GCGTTGATGGAGAAAGTCACGGGTGAAAACGCAGAATCTCTCACTGACTT<br>AGCGGGGTACCGCCATGATTTCTTAGCTAGTAACGGCTTTGATGTAGAAG<br>GTATTAATTATGAAGCGGAAGTTGAACGCTTCGACCGTATCTGA |
| tesB<br>(SEQ ID NO: 10) | ATGAGTCAGGCGCTAAAAAATTTACTGACATTGTTAAATCTGGAAAAAAT<br>TGAGGAAGGACTCTTTCGCGGCCAGAGTGAAGATTTAGGTTTACGCCAGG<br>TGTTTGGCGGCCAGGTCGTGGGTCAGGCCTTGTATGCTGCAAAAGAGACC<br>GTCCCTGAAGAGCGGCTGGTACATTCGTTTCACAGCTACTTTCTTCGCCC<br>TGGCGATAGTAAGAAGCCGATTATTTATGATGTCGAAACGCTGCGTGACG<br>GTAACAGCTTCAGCGCCCGCCGGGTTGCTGCTATTCAAAACGGCAAACCG<br>ATTTTTTATATGACTGCCTCTTTCCAGGCACCAGAAGCGGGTTTCGAACA<br>TCAAAAACAATGCCGTCCGCGCCAGCGCCTGATGGCCTCCCTTCGGAAA<br>CGCAAATCGCCCAATCGCTGGCGCACCTGCTGCCGCCAGTGCTGAAAGAT<br>AAATTCATCTGCGATCGTCCGCTGGAAGTCCGTCCGGTGGAGTTTCATAA<br>CCCACTGAAAGGTCACGTCGCAGAACCACATCGTCAGGTGTGGATCCGCG<br>CAAATGGTAGCGTGCCGGATGACCTGCGCGTTCATCAGTATCTGCTCGGT<br>TACGCTTCTGATCTTAACTTCCTGCCGGTAGCTCTACAGCCGCACGGCAT<br>CGGTTTTCTCGAACCGGGGATTCAGATTGCCACCATTGACCATTCCATGT<br>GGTTCCATCGCCCGTTTAATTTGAATGAATGGCTGCTGTATAGCGTGGAG<br>AGCACCTCGGCGTCCAGCGCACGTGGCTTTGTGCGCGGTGAGTTTTATAC<br>CCAAGACGGCGTACTGGTTGCCTCGACCGTTCAGGAAGGGGTGATGCGTA<br>ATCACAATTAA |

TABLE 5

| Amino acid sequence | 0123456789012345678901234567890123456789 |
|---|---|
| bcd2<br>(SEQ ID NO: 11) | MDLNSKKYQMLKELYVSFAENEVKPLATELDEEERFPYETVEKMAKAGMM<br>GIPYPKEYGGEGGDTVGYIMAVEELSRVCGTTGVILSAHTSLGSWPIYQY<br>GNEEQKQKFLRPLASGEKLGAFGLTEPNAGTDASGQQTTAVLDGDEYILN<br>GSKIFITNAIAGDIYVVMAMTDKSKGNKGISAFIVEKGTPGFSFGVKEKK<br>MGIRGSATSELIFEDCRIPKENLLGKEGQGFKIAMSTLDGGRIGIAAQAL<br>GLAQGALDETVKYVKERVQFGRPLSKFQNTQFQLADMEVKVQAARHLVYQ<br>AAINKDLGKPYGVEAAMAKLFAAETAMEVTTKAVQLHGGYGYTRDYPVER<br>MMRDAKITEIYEGTSEVQRMVISGKLLK |
| etfB3<br>(SEQ ID NO: 12) | MNIVVCIKQVPDTTEVKLDPNTGTLIRDGVPSIINPDDKAGLEEAIKLKE<br>EMGAHVTVITMGPPQADMALKEALAMGADRGILLTDRAFAGADTWATSSA<br>LAGALKNIDFDIIIAGRQAIDGDTAQVGPQIAEHLNLPSITYAEEIKTEG<br>EYVLVKRQFEDCCHDLKVKMPCLITTLKDMNTPRYMKVGRIYDAFENDVV<br>ETWTVKDIEVDPSNLGLKGSPTSVFKSFTKSVKPAGTIYNEDAKTSAGII<br>IDKLKEKYII |
| etfA3<br>(SEQ ID NO: 13) | MGNVLVVIEQRENVIQTVSLELLGKATEIAKDYDTKVSALLLGSKVEGLI<br>DTLAHYGADEVIVVDDEALAVYTTEPYTKAAYEAIKAADPIVVLFGATSI<br>GRDLAPRVSARIHTGLTADCTGLAVAEDTKLLLMTRPAFGGNIMATIVCK<br>DFRPQMSTVRPGVMKKNEPDETKEAVINRFKVEFNDADKLVQVQVIKEA<br>KKQVKIEDAKILVSAGRGMGGKENLDILYELAEIIGGEVSGSRATIDAGW<br>LDKARQVGQTGKTVRPDLYIACGISGAIQHIAGMEDAEFIVAINKNPEAP<br>IFKYADVGIVGDVHKVLPELISQLSVAKEKGEVLAN |
| thiA1<br>(SEQ ID NO: 14) | MREVVIASAARTAVGSFGGAFKSVSAVELGVTAAKEAIKRANITPDMIDE<br>SLLGGVLTAGLGQNIARQIALGAGIPVEKPAMTINIVCGSGLRSVSMASQ<br>LIALGDADIMLVGGAENMSMSPYLVPSARYGARMGDAAFVDSMIKDGLSD<br>IFNNYHMGITAENIAEQWNITREEQDELALASQNKAEKAQAEGKFDEEIV<br>PVVIKGRKGDTVVDKDEYIKPGTTMEKLAKLRPAFKKDGTVTAGNASGIN<br>DGAAMLVVMAKEKAEELGIEPLATIVSYGTAGVDPKIMGYGPVPATKKAL<br>EAANMTIEDIDLVEANEAFAAQSVAVIRDLNIDMNKVNVNGGAIAIGHPI<br>GCSGARILTTLLYEMKRRDAKTGLATLCIGGGMGTTLIVKR |
| hbd<br>(SEQ ID NO: 15) | MKLAVIGSGTMGSGIVQTFASCGHDVCLKSRTQGAIDKCLALLDKNLTKL<br>VTKGKMDEATKAEILSHVSSTTNYEDLKDMDLIIEASVEDMNIKKDVFKL<br>LDELCKEDTILATNTSSLSITEIASSTKRPDKVIGMHFFNPVPMMKLVEV<br>ISGQLTSKVTFDTVFELSKSINKVPVDVSESPGFVVNRILIPMINEAVGI<br>YADGVASKEEIDEAMKLGANHPMGPLALGDIGLDVVLAIMNVLYTEFGD<br>TKYRPHPLLAKMVRANQLGRKTKIGFYDYNK |

TABLE 5-continued

| Amino acid sequence | 0123456789012345678901234567890123456789 |
|---|---|
| crt2 (SEQ ID NO: 16) | MSTSDVKVYENVAVEVDGNICTVKMNRPKALNAINSKTLEELYEVFVDIN NDETIDVVILTGEGKAFVAGADIAYMKDLDAVAAKDFSILGAKAFGEIEN SKKVVIAAVNGFALGGGCELAMACDIRIASAKAKFGQPEVTLGITPGYGG TQRLTRLVGMAKAKELIFTGQVIKADEAEKIGLVNRVVEPDILIEEVEKL AKIIAKNAQLAVRYSKEAIQLGAQTDINTGIDIESNLFGLCFSTKDQKEG MSAFVEKREANFIKG |
| pbt (SEQ ID NO: 17) | MRSFEEVIKFAKERGPKTISVACCQDKEVLMAVEMARKEKIANAILVGDI EKTKEIAKSIDMDIENYELIDIKDLAEASLKSVELVSQGKADMVMKGLVD TSIILKAVLNKEVGLRTGNVLSHVAVFDVEGYDRLFFVTDAAMNLAPDTN TKKQIIENACTVAHSLDISEPKVAAICAKEKVNPKMKDTVEAKELEEMYE RGEIKGCMVGGPFAIDNAVSLEAAKHKGINHPVAGRADILLAPDIEGGNI LYKALVFFSKSKNAGVIVGAKAPIILTSRADSEETKLNSIALGVLMAAKA |
| buk (SEQ ID NO: 18) | MSKIFKILTINPGSTSTKIAVFDNEDLVFEKTLRHSSEEIGKYEKVSDQF EFRKQVIEEALKEGGVKTSELDAVVGRGGLLKPIKGGTYSVSAAMIEDLK VGVLGEHASNLGGIIAKQIGEEVNVPSYIVDPVVVDELEDVARISGMPEI SRASVVHALNQKAIARRYAREINKKYEDINLIVAHMGGGVSVGAHKNGKI VDVANALDGEGPFSPERSGGLPVGALVKMCFSGKYTQDEIKKKIKGNGGL VAYLNTNDAREVEERIEAGDEKAKLVYEAMAYQISKEIGASAAVLKGDVK A1LLTGGIAYSKMFTEMIADRVKFIADVKVYPGEDEMIALAQGGLRVLTG EEEAQVYDN |
| ter (SEQ ID NO: 19) | MIVKPMVRNNICLNAHPQGCKKGVEDQIEYTKKRITAEVKAGAKAPKNVL VLGCSNGYGLASRITAAFGYGAATIGVSFEKAGSETKYGTPGWYNNLAFD EAAKREGLYSVTIDGDAFSDEIKAQVIEEAKKKGIKFDLIVYSLASPVRT DPDTGIMHKSVLKPFGKTFTGKTVDPFTGELKEISAEPANDEEAAATVKV MGGEDWERWIKQLSKEGLLEEGCITLAYSYIGPEATQALYRKGTIGKAKE HLEATAHRLNKENPSIRAFVSVNKGLVTRASAVIPVIPLYLASLFKVMKE KGNHEGCIEQITRLYAERLYRKDGTIPVDEENRIRIDDWELEEDVQKAVS ALMEKVTGENAESLTDLAGYRHDFLASNGFDVEGINYEAEVERFDRI |
| tesB (SEQ ID NO: 20) | MSQALKNLLTLLNLEKIEEGLFRGQSEDLGLRQVFGGQVVGQALYAAKET VPEERLVHSFHSYFLRPGDSKKPIIYDVETLRDGNSFSARRVAAIQNGKP IFYMTASFQAPEAGFEHQKTMPSAPAPDGLPSETQIAQSLAHLLPPVLKD KFICDRPLEVRPVEFHNPLKGHVAEPHRQVWIRANGSVPDDLRVHQYLLG YASDLNFLPVALQPHGIGFLEPGIQIATIDHSMWFHRPFNLNEWLLYSVE STSASSARGFVRGEFYIQDGVLVASTVQEGVMRNHN |

In some embodiments, the genetically engineered bacteria of the invention comprise a propionate gene cassette and are capable of producing propionate. The genetically engineered bacteria may express any suitable set of propionate biosynthesis genes (see, e.g., Table 6). Unmodified bacteria that are capable of producing propionate via an endogenous propionate biosynthesis pathway include, but are not limited to, *Clostridium propionicum, Megasphaera elsdenii,* and *Prevotella ruminicola*, and these endogenous propionate biosynthesis pathways may be a source of genes for the genetically engineered bacteria of the invention. In some embodiments, the genetically engineered bacteria of the invention comprise propionate biosynthesis genes from a different species, strain, or substrain of bacteria. In some embodiments, the genetically engineered bacteria comprise the genes pct, lcd, and acr from *Clostridium propionicum*. In some embodiments, the genetically engineered bacteria comprise acrylate pathway genes for propionate biosynthesis, e.g., pct, lcdA, lcdB, lcdC, etfA, acrB, and acrC. In alternate embodiments, the genetically engineered bacteria comprise pyruvate pathway genes for propionate biosynthesis, e.g., thrA$^{fbr}$, thrB, thrC, ilvA$^{fbr}$, aceE, aceF, and lpd, and optionally further comprise tesB. The genes may be codon-optimized, and translational and transcriptional elements may be added. Table 6 depicts the nucleic acid sequences of exemplary genes in the propionate biosynthesis gene cassette.

In some embodiments, the genetically engineered bacteria comprise the nucleic acid sequence of any one of SEQ ID NOs: 21-34 and 10 or a functional fragment thereof. In some embodiments, the genetically engineered bacteria comprise a nucleic acid sequence that encodes a polypeptide of any one of SEQ ID NOs: 35-48 and 20 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of any one of SEQ ID NOs: 21-34 and 10 or a functional fragment thereof. In some embodiments, genetically engineered bacteria comprise a nucleic acid that is at least about 80%, at least about 85%, at least about 90%, at least about 95%, or at least about 99% homologous to the nucleic acid sequence that encodes a polypeptide of any one of SEQ ID NOs: 35-48 and 20 or a functional fragment thereof.

TABLE 6

| Gene sequence | 0123456789012345678901234567890123456789 |
|---|---|
| pct SEQ ID NO: 21 | ATGCGCAAAGTGCCGATTATCACGGCTGACGAGGCCGCAAAACTGATCAA<br>GGACGGCGACACCGTGACAACTAGCGGCTTTGTGGGTAACGCGATCCCTG<br>AGGCCCTTGACCGTGCAGTCGAAAAGCGTTTCCTGGAAACGGGCGAACCG<br>AAGAACATTACTTATGTATATTGCGGCAGTCAGGGCAATCGCGACGGTCG<br>TGGCGCAGAACATTTCGCGCATGAAGGCCTGCTGAAACGTTATATCGCTG<br>GCCATTGGGCGACCGTCCCGGCGTTAGGGAAAATGGCCATGGAGAATAAA<br>ATGGAGGCCTACAATGTCTCTCAGGGCGCCTTGTGTCATCTCTTTCGCGA<br>TATTGCGAGCCATAAACCGGGTGTGTTCACGAAAGTAGGAATCGGCACCT<br>TCATTGATCCACGTAACGGTGGTGGGAAGGTCAACGATATTACCAAGGAA<br>GATATCGTAGAACTGGTGGAAATTAAAGGGCAGGAATACCTGTTTTATCC<br>GGCGTTCCCGATCCATGTCGCGCTGATTCGTGGCACCTATGCGGACGAGA<br>GTGGTAACATCACCTTTGAAAAAGAGGTAGCGCCTTTGGAAGGGACTTCT<br>GTCTGTCAAGCGGTGAAGAACTCGGGTGGCATTGTCGTGGTTCAGGTTGA<br>GCGTGTCGTCAAAGCAGGCACGCTGGATCCGCGCCATGTGAAAGTTCCGG<br>GTATCTATGTAGATTACGTAGTCGTCGCGGATCCGGAGGACCATCAACAG<br>TCCCTTGACTGCGAATATGATCCTGCCCTTAGTGGAGAGCACCGTCGTCC<br>GGAGGTGGTGGGTGAACCACTGCCTTTATCCGCGAAGAAAGTCATCGGCC<br>GCCGTGGCGCGATTGAGCTCGAGAAAGACGTTGCAGTGAACCTTGGGGTA<br>GGTGCACCTGAGTATGTGGCCTCCGTGGCCGATGAAGAAGGCATTGTGGA<br>TTTTATGACTCTCACAGCGGAGTCCGGCGCTATCGGTGGCGTTCCAGCCG<br>GCGGTGTTCGCTTTGGGGCGAGCTACAATGCTGACGCCTTGATCGACCAG<br>GGCTACCAATTTGATTATTACGACGGTGGGGGTCTGGATCTTTGTTACCT<br>GGGTTTAGCTGAATGCGACGAAAAGGGTAATATCAATGTTAGCCGCTTCG<br>GTCCTCGTATCGCTGGGTGCGGCGGATTCATTAACATTACCCAAAACACG<br>CCGAAAGTCTTCTTTTGTGGGACCTTTACAGCCGGGGGGCTGAAAGTGAA<br>AATTGAAGATGGTAAGGTGATTATCGTTCAGGAAGGGAAACAGAAGAAAT<br>TCCTTAAGGCAGTGGAGCAAATCACCTTTAATGGAGACGTGGCCTTAGCG<br>AACAAGCAACAAGTTACCTACATCACGGAGCGTTGCGTCTTCCTCCTCAA<br>AGAAGACGGTTTACACCTTTCGGAAATCGCGCCAGGCATCGATCTGCAGA<br>CCCAGATTTTGGATGTTATGGACTTTGCCCCGATCATTGATCGTGACGCA<br>AACGGGCAGATTAAACTGATGGACGCGGCGTTATTCGCAGAAGGGCTGAT<br>GGGCTTGAAAGAAATGAAGTCTTAA |
| lcdA SEQ ID NO: 22 | ATGAGCTTAACCCAAGGCATGAAAGCTAAACAACTGTTAGCATACTTTCA<br>GGGTAAAGCCGATCAGGATGCACGTGAAGCGAAAGCCCGCGGTGAGCTGG<br>TCTGCTGGTCGGCGTCAGTCGCGCCGCCGGAATTTTGCGTAACAATGGGC<br>ATTGCCATGATCTACCCGGAGACTCATGCAGCGGGCATCGGTGCCCGCAA<br>AGGTGCGATGGACATGCTGGAAGTTGCGGACCGCAAAGGCTACAACGTGG<br>ATTGTTGTTCCTACGCCGTGTAAATATGGGTTACATGGAATGTTTAAAA<br>GAAGCCGCCATCACGGGCGTCAAGCCGGAAGTTTTGGTTAATTCCCCTGC<br>TGCTGACGTTCCGCTTCCCGATTTGGTGATTACGTGTAATAATATCTGTA<br>ACACGCTGCTGAAATGGTACGAAAACTTAGCAGCAGAACTCGATATTCCT<br>TGCATCGTGATCGACGTACCGTTTAATCATACCATGCCGATTCCGGAATA<br>TGCCAAGGCCTACATCGCGGACCAGTTCCGCAATGCAATTTCTCAGCTGG<br>AAGTTATTTGTGGCCGTCCGTTCGATTGGAAGAAATTTAAGGAGGTCAAA<br>GATCAGACCCAGCGTAGCGTATACCACTGGAACCGCATTGCCGAGATGGC<br>GAAATACAAGCCTAGCCCGCTGAACGGCTTCGATCTGTTCAATTACATGG<br>CGTTAATCGTGGCGTGCCGCAGCCTGGATTATGCAGAAATTACCTTTAAA<br>GCGTTCGCGGACGAATTAGAAGAGAATTTGAAGGCGGGTATCTACGCCTT<br>TAAAGGTGCGGAAAAAACGCGCTTTCAATGGGAAGGTATCGCGGTGTGGC<br>CACATTTAGGTCACACGTTTAAATCTATGAAGAATCTGAATTCGATTATG<br>ACCGGTACGGCATACCCCGCCCTTTGGGACCTGCACTATGACGCTAACGA<br>CGAATCTATGCACTCTATGGCTGAAGCGTACACCCGTATTTATATTAATA<br>CTTGTCTGCAGAACAAAGTAGAGGTCCTGCTTGGGATCATGGAAAAAGGC<br>CAGGTGGATGGTACCGTATATCATCTGAATCGCAGCTGCAAACTGATGAG<br>TTTCCTGAACGTGGAAACGGCTGAAATTATTAAAGAGAAGAACGGTCTTC<br>CTTACGTCTCCATTGATGGCGATCAGACCGATCCTCGCGTTTTTTCTCCG<br>GCCCAGTTTGATACCCGTGTTCAGGCCCTGGTTGAGATGATGGAGGCCAA<br>TATGGCGGCAGCGGAATAA |
| lcdB SEQ ID NO: 23 | ATGTCACGCGTGGAGGCAATCCTGTCGCAGCTGAAAGATGTCGCCGCGAA<br>TCCGAAAAAAGCCATGGATGACTATAAAGCTGAAACAGGTAAGGGCGCGG<br>TTGGTATCATGCCGATCTACAGCCCCGAAGAAATGGTACACGCCGCTGGC<br>TATTTGCCGATGGGAATCTGGGCGCCCAGGGCAAAACGATTAGTAAAGC<br>GCGCACCTATCTGCCTGCTTTTGCCTGCAGCGTAATGCAGCAGGTTATGG<br>AATTACAGTGCGAGGGCGCTATGATGACCTGTCCGCAGTTATTTTTAGC<br>GTACCGTGCGACACTCTCAAATGTCTTAGCCAGAAATGGAAAGGTACGTC<br>CCCAGTGATTGTATTTACGCATCCGCAGAACCGCGGATTAGAAGCGGCGA<br>ACCAATTCTTGGTTACCGAGTATGAACTGGTAAAAGCACAACTGGAATCA<br>GTTCTGGGTGTGAAATTTCAAACGCCGCCTGGAAATTCGATTGCAAT<br>TTATAACGAGAATCGTGCCGTGATGCGTGAGTTCGTGAAAGTGGCAGCGG<br>ACTATCCTCAAGTCATTGACGCAGTGAGCCGCCACGCGGTTTTAAAGCG<br>CGCCAGTTTATGCTTAAGGAAAAACATACCGCACTTGTGAAAGAACTGAT<br>CGCTGAGATTAAGCAACGCCAGTCCAGCCGTGGGACGGAAAAAGGTTG<br>TAGTGACGGGCATTCTGTTGGAACCGAATGAGTTATTAGATATCTTTAAT<br>GAGTTTAAGATCGCGATTGTTGATGATGATTTAGCGCAGGAAAGCCGTCA<br>GATCCGTGTTGACGTTCTGGACGGAGAAGGCGGACCGCTCTACCGTATGG |

TABLE 6-continued

| Gene sequence | 012345678901234567890123456789012345678901234567890123456789 |
|---|---|
| | CTAAAGCGTGGCAGCAAATGTATGGCTGCTCGCTGGCAACCGACACCAAG |
| | AAGGGTCGCGGCCGTATGTTAATTAACAAAACGATTCAGACCGGTGCGGA |
| | CGCTATCGTAGTTGCAATGATGAAGTTTTGCGACCCAGAAGAATGGGATT |
| | ATCCGGTAATGTACCGTGAATTTGAAGAAAAAGGGGTCAAATCACTTATG |
| | ATTGAGGTGGATCAGGAAGTATCGTCTTTCGAACAGATTAAAACCCGTCT |
| | GCAGTCATTCGTCGAAATGCTTTAA |
| lcdC SEQ ID NO: 24 | ATGTATACCTTGGGGATTGATGTCGGTTCTGCCTCTAGTAAAGCGGTGAT |
| | TCTGAAAGATGGAAAAGATATTGTCGCTGCCGAGGTTGTCCAAGTCGGTA |
| | CCGGCTCCTCGGGTCCCCAACGCGCACTGGACAAAGCCTTTGAAGTCTCT |
| | GGCTTAAAAAAGGAAGACATCAGCTACACAGTAGCTACGGGCTATGGGCG |
| | CTTCAATTTTAGCGACGCGGATAAACAGATTTCGGAAATTAGCTGTCATG |
| | CCAAAGGCATTTATTTCTTAGTACCAACTGCGCGCACTATTATTGACATT |
| | GGCGGCCAAGATGCGAAAGCCATCCGCCTGGACGACAAGGGGGGTATTAA |
| | GCAATTCTTCATGAATGATAAATGCGCGGCGGGCACGGGGCGTTTCCTGG |
| | AAGTCATGGCTCGCTACTTGAAACCACCCTGGATGAAATGGCTGAACTG |
| | GATGAACAGGCGACTGACACCGCTCCCATTTCAAGCACCTGCACGGTTTT |
| | CGCCGAAAGCGAAGTAATTAGCCAATTGAGCAATGGTGTCTCACGCAACA |
| | ACATCATTAAAGGTGTCCATCTGAGCGTTGCGTCACGTGCGTGGTCTG |
| | GCGTATCGCGGCGGTTTGGAGAAAGATGTTGTTATGACAGGTGGCGTGGC |
| | AAAAAATGCAGGGGTGGTGCGCGCGGTGGCGGGCGTTCTGAAGACCGATG |
| | TTATCGTTGCTCCGAATCCTCAGACGACCGGTGCACTGGGGGCAGCGCTG |
| | TATGCTTATGAGGCCGCCCAGAAGAAGTA |
| etfA SEQ ID NO: 25 | ATGGCCTTCAATAGCGCAGATATTAATTCTTTCCGCGATATTTGGGTGTT |
| | TTGTGAACAGCGTGAGGGCAAACTGATTAACACCGATTTCGAATTAATTA |
| | GCGAAGGTCGTAAACTGGCTGACGAACGCGGAAGCAAACTGGTTGGAATT |
| | TGCTGGGGCACGAAGTTGAAGAAATCGCAAAAGAATTAGGCGGCTATGG |
| | TGCGGACAAGGTAATTGTGTGCGATCATCCGGAACTTAAATTTTACACTA |
| | CGGATGCTTATGCCAAAGTTTTATGTGACGTCGTGATGGAAGAGAAACCG |
| | GAGGTAATTTTGATCGGTGCCACCAACATTGGCCGTGATCTCGGACCGCG |
| | TTGTGCTGCACGCTTGCACACGGGGCTGACGGCTGATTGCACGCACCTGG |
| | ATATTGATATGAATAAATATGTGGACTTTCTTAGCACCAGTAGCACCTTG |
| | GATATCTCGTCGATGACTTTCCCTATGGAAGATACAAACCTTAAAATGAC |
| | GCGCCCTGCATTTGGCGGACATCTGATGGCAACGATCATTTGTCCACGCT |
| | TCCGTCCCTGTATGAGCACAGTGCGCCCCGGAGTGATGAAGAAAGCGGAG |
| | TTCTCGCAGGAGATGGCGCAAGCATGTCAAGTAGTGACCCGTCACGTAAA |
| | TTTGTCGGATGAAGACCTTAAAACTAAAGTAATTAATATCGTGAAGGAAA |
| | CGAAAAAGATTGTGGATCTGATCGGCGCAGAAATTATTGTGTCAGTTGGT |
| | CGTGGTATCTCGAAAGATGTCCAAGGTGGAATTGCACTGGCTGAAAAACT |
| | TGCGGACGCATTTGGTAACGGTGTCGTGGCGGCTCGCGCGCAGTGATTG |
| | ATTCCGGCTGGTTACCTGCGGATCATCAGGTTGGACAAACCGGTAAGACC |
| | GTGCACCCGAAAGTCTACGTGGCGCTGGGTATTAGTGGGGCTATCCAGCA |
| | TAAGGCTGGGATGCAAGACTCTGAACTGATCATTGCCGTCAACAAAGACG |
| | AAAACGGCGCCTATCTTCGACTGCGCCGATTATGGCATCACCGGTGATTTA |
| | TTTAAAATCGTACCGATGATGATCGACGCGATCAAAGAGGGTAAAAACGC |
| | ATGA |
| acrB SEQ ID NO: 26 | ATGCGCATCTATGTGTGTGTGAAACAAGTCCCAGATACGAGCGGCAAGGT |
| | GGCCGTTAACCCTGATGGGACCCTTAACCGTGCCTCAATGGCAGCGATTA |
| | TTAACCCGGACGATATGTCCGCGATCGAACAGGCATTAAAACTGAAAGAT |
| | GAAACCGGATGCCAGGTTACGGCGCTTACGATGGGTCCTCCTCCTGCCGA |
| | GGGCATGTTGCGCGAAATTATTGCAATGGGGGCCGACGATGGTGTGCTGA |
| | TTTCGGCCCGTGAATTTGGGGGGTCCGATACCTTCGCAACCAGTCAAATT |
| | ATTAGCGCGGCAATCCATAAATTAGGCTTAAGCAATGAAGACATGATCTT |
| | TTGCGGTCGTCAGGCCATTGACGGTGATACGGCCCAAGTCGGCCCTCAAA |
| | TTGCCGAAAAACTGAGCATCCCACAGGTAACCTATGCGCAGGAATCAAA |
| | AAATCTGGTGATTTAGTGCTGGTGAAGCGTATGTTGGAGGATGGTTATAT |
| | GATGATCGAAGTCGAAACTCCATGTCTGATTACCTGCATTCAGGATAAAG |
| | CGGTAAAACCACGTTACATGACTCTCAACGGTATTATGGAATGCTACTCC |
| | AAGCCGCTCCTCGTTCTCGATTACGAAGCACTGAAAGATGAACCGCTGAT |
| | CGAACTTGATACCATTGGGCTTAAAGGCTCCCCGACGAATATCTTTAAAT |
| | CGTTTACGCCGCCTCAGAAAGGCGTTGGTGTCATGCTCCAAGGCACCGAT |
| | AAGGAAAAAGTCGAGGATCTGGTGGATAAGCTGATGCAGAAACATGTCAT |
| | CTAA |
| acrC SEQ ID NO: 27 | ATGTTCTTACTGAAGATTAAAAAAGAACGTATGAAACGCATGGACTTTAG |
| | TTTAACGCGTGAACAGGAGATGTTAAAAAAACTGGCGCGTCAGTTTGCTG |
| | AGATCGAGCTGGAACCGGTGGCCGAAGAGATTGATCGTGAGCACGTTTTT |
| | CCTGCAGAAAACTTTAAGAAGATGGCGGAAATTGGCTTAACCGGCATTGG |
| | TATCCCGAAAGAATTTGGTGGCTCCGGTGGAGGCACCCTGGAGAAGGTCA |
| | TTGCCGTGTCAGAATTCGGCAAAAAGTGTATGGCCTCAGCTTCCATTTTA |
| | AGCATTCATCTTATCGCGCCGCAGGCAATCTACAAATATGGGACCAAAGA |
| | ACAGAAAGAGACGTACCTGCCGCGTCTTACCAAAGGTGTGAACTGGGCG |
| | CCTTTGCGCTGACAGAACCAAACGCCGGAAGCGATGCCGGCGCGGTAAAA |
| | ACGACCGCGATTCTGGACAGCCAGACAAACGAGTACGTGCTGAATGCAC |
| | CAAATGCTTTATCAGCGGGGGCGGGCGCGGGTGTTCTTGTAATTTTTG |

TABLE 6-continued

| Gene sequence | 0123456789012345678901234567890123456789 |
|---|---|
| | CGCTTACTGAACCGAAAAAAGGTCTGAAAGGGATGAGCGCGATTATCGTG |
| | GAGAAAGGGACCCCGGGCTTCAGCATCGGCAAGGTGGAGAGCAAGATGGG |
| | GATCGCAGGTTCGGAAACCGCGGAACTTATCTTCGAAGATTGTCGCGTTC |
| | CGGCTGCCAACCTTTTAGGTAAAGAAGGCAAAGGCTTTAAAATTGCTATG |
| | GAAGCCCTGGATGGCGCCCGTATTGGCGTGGGCGCTCAAGCAATCGGAAT |
| | TGCCGAGGGGGCGATCGACCTGAGTGTGAAGTACGTTCACGAGCGCATTC |
| | AATTTGGTAAACCGATCGCGAATCTGCAGGGAATTCAATGGTATATCGCG |
| | GATATGGCGACCAAAACCGCCGCGGCACGCGCACTTGTTGAGTTTGCAGC |
| | GTATCTTGAAGACGCGGGTAAACCGTTCACAAAGGAATCTGCTATGTGCA |
| | AGCTGAACGCCTCCGAAAACGCGCGTTTTGTGACAAATTTAGCTCTGCAG |
| | ATTCACGGGGGTTACGGTTATATGAAAGATTATCCGTTAGAGCGTATGTA |
| | TCGCGATGCTAAGATTACGGAAATTTACGAGGGGACATCAGAAATCCATA |
| | AGGTGGTGATTGCGCGTGAAGTAATGAAACGCTAA |
| thrA$^{fbr}$ SEQ ID NO: 28 | ATGCGAGTGTTGAAGTTCGGCGGTACATCAGTGGCAAATGCAGAACGTTT |
| | TCTGCGTGTTGCCGATATTCTGGAAAGCAATGCCAGGCAGGGGCAGGTGG |
| | CCACCGTCCTCTCTGCCCCCGCCAAAATCACCAACCACCTGGTGGCGATG |
| | ATTGAAAAAACCATTAGCGGCCAGGATGCTTTACCCAATATCAGCGATGC |
| | CGAACGTATTTTTGCCGAACTTTTGACGGGACTCGCCGCCGCCCAGCCGG |
| | GGTTCCCGCTGGCGCAATTGAAAACTTTCGTCGATCAGGAATTTGCCCAA |
| | ATAAAACATGTCCTGCATGGCATTAGTTTGTTGGGGCAGTGCCCGGATAG |
| | CATCAACGCTGCGCTGATTTGCCGTGGCGAGAAAATGTCGATCGCCATTA |
| | TGGCCGGCGTATTAGAAGCGCGCGGTCACAACGTTACTGTTATCGATCCG |
| | GTCGAAAAACTGCTGGCAGTGGGGCATTACCTCGAATCTACCGTCGATAT |
| | TGCTGAGTCCACCCGCCGTATTGCGGCAAGCCGCATTCCGGCTGATCACA |
| | TGGTGCTGATGGCAGGTTTCACCGCCGGTAATGAAAAAGGCGAACTGGTG |
| | GTGCTTGGACGCAACGGTTCCGACTACTCTGCTGCGGTGCTGGCTGCCTG |
| | TTTACGCGCCGATTGTTGCGAGATTTGGACGGACGTTGACGGGGTCTATA |
| | CCTGCGACCCGCGTCAGGTGCCCGATGCGAGGTTGTTGAAGTCGATGTCC |
| | TACCAGGAAGCGATGGAGCTTTCCTACTTCGGCGCTAAAGTTCTTCACCC |
| | CCGCACCATTACCCCCATCGCCCAGTTCCAGATCCCTTGCCTGATTAAAA |
| | ATACCGGAAATCCTCAAGCACCAGGTACGCTCATTGGTGCCAGCCGTGAT |
| | GAAGACGAATTACCGGTCAAGGGCATTTCCAATCTGAATAACATGGCAAT |
| | GTTCAGCGTTTCTGGTCCGGGGATGAAAGGGATGGTCGGCATGGCGGCGC |
| | GCGTCTTTGCAGCGATGTCACGCGCCCGTATTTCCGTGGTGCTGATTACG |
| | CAATCATCTTCCGAATACAGCATCAGTTTCTGCGTTCCACAAAGCGACTG |
| | TGTGCGAGCTGAACGGGCAATGCAGGAAGAGTTCTACCTGGAACTGAAAG |
| | AAGGCTTACTGGAGCCGCTGGCAGTGACGGAACGGCTGGCCATTATCTCG |
| | GTGGTAGGTGATGGTATGCGCACCTTGCGTGGGATCTCGGCGAAATTCTT |
| | TGCCGCACTGGCCCGCGCCAATATCAACATTGTCGCCATTGCTCAGAGAT |
| | CTTCTGAACGCTCAATCTCTGTCGTGGTAAATAACGATGATGCGACCACT |
| | GGCGTGCGCGTTACTCATCAGATGCTGTTCAATACCGATCAGGTTATCGA |
| | AGTGTTTGTGATTGGCGTCGGTGGCGTTGGCGGTGCGCTGCTGGAGCAAC |
| | TGAAGCGTCAGCAAAGCTGGCTGAAGAATAAACATATCGACTTACGTGTC |
| | TGCGGTGTTGCCAACTCGAAGGCTCTGCTCACCAATGTACATGGCCTTAA |
| | TCTGGAAAACTGGCAGGAAGAACTGGCGCAAGCCAAAGAGCCGTTTAATC |
| | TCGGGCGCTTAATTCGCCTCGTGAAAGAATATCATCTGCTGAACCGGTC |
| | ATTGTTGACTGCACTTCCAGCCAGGCAGTGGCGGATCAATATGCCGACTT |
| | CCTGCGCGAAGGTTTCCACGTTGTCACGCCGAACAAAAAGGCCAACACCT |
| | CGTCGATGGATTACTACCATCAGTTGCGTTATGCGGCGGAAAAATCGCGG |
| | CGTAAATTCCTCTATGACACCAACGTTGGGGCTGGATTACCGGTTATTGA |
| | GAACCTGCAAAATCTGCTCAATGCAGGTGATGAATTGATGAAGTTCTCCG |
| | GCATTCTTTCTGGTTCGCTTTCTTATATCTTCGGCAAGTTAGACGAAGGC |
| | ATGAGTTTCTCCGAGGCGACCACGCTGGCGCGGGAAATGGGTTATACCGA |
| | ACCGGACCCGCGAGATGATCTTTCTGGTATGGATGTGGCGCGTAAACTAT |
| | TGATTCTCGCTCGTGAAACGGGACGTGAACTGGAGCTGGCGGATATTGAA |
| | ATTGAACCTGTGCTGCCCGCAGAGTTTAACGCCGAGGGTGATGTTGCCGC |
| | TTTTATGGCGAATCTGTCACAACTCGACGATCTCTTTGCCGCGCGCGTGG |
| | CGAAGGCCCGTGATGAAGGAAAAGTTTTGCGCTATGTTGGCAATATTGAT |
| | GAAGATGGCGTCTGCCGCGTGAAGATTGCCGAAGTGGATGGTAATGATCC |
| | GCTGTTCAAAGTGAAAAATGGCGAAAACGCCCTGGCCTTCTATAGCCACT |
| | ATTATCAGCCGCTGCCGTTGGTACTGCGCGGATATGGTGCGGGCAATGAC |
| | GTTACAGCTGCCGGTGTCTTTGCTGATCTGCTACGTACCCTCTCATGGAA |
| | GTTAGGAGTCTGA |
| thrB SEQ ID NO: 29 | ATGGTTAAAGTTTATGCCCCGGCTTCCAGTGCCAATATGAGCGTCGGGTT |
| | TGATGTGCTCGGGGCGGCGGTGACACCTGTTGATGGTGCATTGCTCGGAG |
| | ATGTAGTCACGGTTGAGGCGGCAGAGACATTCAGTCTCAACAACCTCGGA |
| | CGCTTTGCCGATAAGCTGCCGTCAGAACCACGGGAAAATATCGTTTATCA |
| | GTGCTGGGAGCGTTTTTGCCAGGAACTGGGTAAGCAAATTCCAGTGGCGA |
| | TGACCCTGGAAAAGAATATGCCGATCGGTTCGGGCTTAGGCTCCAGTGCC |
| | TGTTCGGTGGTCGCGGCGCTGATGGCGATGAATGAACACTGCGGCAAGCC |
| | GCTTAATGACACTCGTTTGCTGGCTTTGATGGGCGAGCTGGAAGGCCGTA |
| | TCTCCGGCAGCATTCATTACGACAACGTGGCACCGTGTTTTCTCGGTGGT |
| | ATGCAGTTGATGATCGAAGAAAACGACATCATCAGCCAGCAAGTGCCAGG |
| | GTTTGATGAGTGGCTGTGGGTGCTGGCGTATCCGGGGATTAAAGTCTCGA |
| | CGGCAGAAGCCAGGGCTATTTTACCGGCGCAGTATCGCCGCCAGGATTGC |

TABLE 6-continued

| Gene sequence | 0123456789012345678901234567890123456789 |
|---|---|
| | ATTGCGCACGGGCGACATCTGGCAGGCTTCATTCACGCCTGCTATTCCCG<br>TCAGCCTGAGCTTGCCGCGAAGCTGATGAAAGATGTTATCGCTGAACCCT<br>ACCGTGAACGGTTACTGCCAGGCTTCCGGCAGGCGCGGCAGGCGGTCGCG<br>GAAATCGGCGCGGTAGCGAGCGGTATCTCCGGCTCCGGCCCGACCTTGTT<br>CGCTCTGTGTGACAAGCCGGAAACCGCCCAGCGCGTTGCCGACTGGTTGG<br>GTAAGAACTACCTGCAAAATCAGGAAGGTTTTGTTCATATTTGCCGGCTG<br>GATACGGCGGGCGCACGAGTACTGGAAAACTAA |
| thrC<br>SEQ ID NO: 30 | ATGAAACTCTACAATCTGAAAGATCACAACGAGCAGGTCAGCTTTGCGCA<br>AGCCGTAACCCAGGGGTTGGGCAAAAATCAGGGGCTGTTTTTTCCGCACG<br>ACCTGCCGGAATTCAGCCTGACTGAAATTGATGAGATGCTGAAGCTGGAT<br>TTTGTCACCCGCAGTGCGAAGATCCTCTCGGCGTTTATTGGTGATGAAAT<br>CCCACAGGAAATCCTGGAAGAGCGCGTGCGCGCGGCGTTTGCCTTCCCGG<br>CTCCGGTCGCCAATGTTGAAAGCGATGTCGGTTGTCTGGAATTGTTCCAC<br>GGGCCAACGCTGGCATTTAAAGATTTCGGCGGTCGCTTTATGGCACAAAT<br>GCTGACCCATATTGCGGGTGATAAGCCAGTGACCATTCTGACCGCGACCT<br>CCGGTGATACCGGAGCGGCAGTGGCTCATGCTTTCTACGGTTTACCGAAT<br>GTGAAAGTGGTTATCCTCTATCCACGAGGCAAAATCAGTCCACTGCAAGA<br>AAAACTGTTCTGTACATTGGGCGGCAATATCGAAACTGTTGCCATCGACG<br>GCGATTTCGATGCCTGTCAGGCGCTGGTGAAGCAGGCGTTTGATGATGAA<br>GAACTGAAAGTGGCGCTAGGGTTAAACTCGGCTAACTCGATTAACATCAG<br>CCGTTTGCTGGCGCAGATTTGCTACTACTTTGAAGCTGTTGCGCAGCTGC<br>CGCAGGAGACGCGCAACCAGCTGGTTGTCTCGGTGCAAGCGGAAACTTC<br>GGCGATTTGACGGCGGGTCTGCTGGCGAAGTCACTCGGTCTGCCGGTGAA<br>ACGTTTTATTGCTGCGACCAACGTGAACGATACCGTGCCACGTTTCCTGC<br>ACGACGGTCAGTGGTCACCCAAAGCGACTCAGGCGACGTTATCCAACGCG<br>ATGGACGTGAGTCAGCCGAACAACTGGCCGCGTGTGGAAGAGTTGTTCCG<br>CCGCAAAATCTGGCAACTGAAAGAGCTGGGTTATGCAGCCGTGGATGATG<br>AAACCACGCAACAGACAATGCGTGAGTTAAAAGAACTGGGCTACACTTCG<br>GAGCCGCACGCTGCCGTAGCTTATCGTGCGCTGCGTGATCAGTTGAATCC<br>AGGCGAATATGGCTTGTTCCTCGGCACCGCGCATCCGGCGAAATTTAAAG<br>AGAGCGTGGAAGCGATTCTCGGTGAAACGTTGGATCTGCCAAAAGAGCTG<br>GCAGAACGTGCTGATTTACCCTTGCTTTCACATAATCTGCCCGCCGATTT<br>TGCTGCGTTGCGTAAATTGATGATGAATCATCAGTAA |
| ilvA$^{fbr}$<br>SEQ ID NO: 31 | ATGAGTGAAACATACGTGTCTGAGAAAAGTCCAGGAGTGATGGCTAGCGG<br>AGCGGAGCTGATTCGTGCCGCCGACATTCAAACGGCGCAGGCACGAATTT<br>CCTCCGTCATTGCACCAACTCCATTGCAGTATTGCCCTCGTCTTTCTGAG<br>GAAACCGGAGCGGAAATCTACCTTAAGCGTGAGGATCTGCAGGATGTTCG<br>TTCCTACAAGATCCGCGGTGCGCTGAACTCTGGAGCGCAGCTCACCCAAG<br>AGCAGCGCGATGCAGGTATCGTTGCCGCATCTGCAGGTAACCATGCCCAG<br>GGCGTGGCCTATGTGTGCAAGTCCTTGGGCGTTCAGGGACGCATCTATGT<br>TCCTGTGCAGACTCCAAAGCAAAAGCGTGACCGCATCATGGTTCACGGCG<br>GAGAGTTTGTCTCCTTGGTGGTCACTGGCAATAACTTCGACGAAGCATCG<br>GCTGCAGCGCATGAAGATGCAGAGCGCACCGGCGCAACGCTGATCGAGCC<br>TTTCGATGCTCGCAACACCGTCATCGGTCAGGGCACCGTGGCTGCTGAGA<br>TCTTGTCGCAGCTGACTTCCATGGGCAAGAGTGCAGATCACGTGATGGTT<br>CCAGTCGGCGGTGGCGGACTTCTTGCAGGTGTGGTCAGCTACATGGCTGA<br>TATGGCACCTCGCACTGCGATCGTTGGTATCGAACCAGCGGGAGCAGCAT<br>CCATGCAGGCTGCATTGCACAATGGTGGACCAATCACTTTGGAGACTGTT<br>GATCCCTTTGTGGACGGCGCAGCAGTCAAACGTGTCGGAGATCTCAACTA<br>CACCATCGTGGAGAAGAACCAGGGTCGCGTGCACATGATGAGCGCGACCG<br>AGGGCGCTGTGTGTACTGAGATGCTCGATCTTTACCAAAACGAAGGCATC<br>ATCGCGGAGCCTGCTGGCGCGCTGTCTATCGCTGGGTTGAAGGAAATGTC<br>CTTTGCACCTGGTTCTGCAGTGGTGTGCATCATCTCTGGTGGCAACAACG<br>ATGTGCTGCGTTATGCGGAAATCGCTGAGCGCTCCTTGGTGCACCGCGGT<br>TTGAAGCACTACTTCTTGGTGAACTTCCCGCAAAAGCCTGGTCAGTTGCG<br>TCACTTCCTGGAAGATATCCTGGGACCGGATGATGACATCACGCTGTTTG<br>AGTACCTCAAGCGCAACAACCGTGAGACCGGTACTGCGTTGGTGGGTATT<br>CACTTGAGTGAAGCATCAGGATTCTTTGCTGGAACGTATGGAGGA<br>ATCGGCAATTGATTCCCGTCGCCTCGAGCCGGGCACCCCTGAGTACGAAT<br>ACTTGACCTAA |
| aceE<br>SEQ ID NO: 32 | ATGTCAGAACGTTTCCCAAATGACGTGGATCCGATCGAAACTCGCGACTG<br>GCTCCAGGCGATCGAATCGGTCATCCGTGAAGAAGGTGTTGAGCGTGCTC<br>AGTATCTGATCGACCAACTGCTTGCTGAAGCCCGCAAAGGCGGTGTAAAC<br>GTAGCCGCAGGCACAGGTATCAGCAACTACATCAACACCATCCCCGTTGA<br>AGAACAACCGGAGTATCCGGGTAATCTGGAACTGGAACGCCGTATTCGTT<br>CAGCTATCCGCTGGAACGCCATCATGACGGTGCTGCGTGCGTCGAAAAAA<br>GACCTCGAACTGGGCGGCCATATGGCGTCCTTCCAGTCTTCCGCAACCAT<br>TTATGATGTGTGCTTTAACCACTTCTTCCGTGCACGCAACGAGCAGGATG<br>GCGGCGACCTGGTTTACTTCCAGGGCCACATCTCCCCGGGCGTGTACGCT<br>CGTGCTTTCCTGGAAGGTCGTCTGACTCAGGAGCAGCTGGATAACTTCCG<br>TCAGGAAGTTCACGGCAATGGCCTCTCTTCCTATCCGCACCCGAAACTGA<br>TGCCGGAATTCTGGCAGTTCCCGACCGTATCTATGGGTCTGGGTCCGATT<br>GGTGCTATTTACCAGGCTAAATTCCTGAAATATCTGGAACACCGTGGCCT<br>GAAAGATACCTCTAAACAAACCGTTTACGCGTTCCTCGGTGACGGTGAAA |

TABLE 6-continued

| Gene sequence | 0123456789012345678901234567890123456789 |
|---|---|
| | TGGACGAACCGGAATCCAAAGGTGCGATCACCATCGCTACCCGTGAAAAA |
| | CTGGATAACCTGGTCTTCGTTATCAACTGTAACCTGCAGCGTCTTGACGG |
| | CCCGGTCACCGGTAACGGCAAGATCATCAACGAACTGGAAGGCATCTTCG |
| | AAGGTGCTGGCTGGAACGTGATCAAAGTGATGTGGGGTAGCCGTTGGGAT |
| | GAACTGCTGCGTAAGGATACCAGCGGTAAACTGATCCAGCTGATGAACGA |
| | AACCGTTGACGGCGACTACCAGACCTTCAAATCGAAAGATGGTGCGTACG |
| | TTCGTGAACACTTCTTCGGTAAATATCCTGAAACCGCAGCACTGGTTGCA |
| | GACTGGACTGACGAGCAGATCTGGGCACTGAACCGTGGTGGTCACGATCC |
| | GAAGAAAATCTACGCTGCATTCAAGAAAGCGCAGGAAACCAAAGGCAAAG |
| | CGACAGTAATCCTTGCTCATACCATTAAAGGTTACGGCATGGGCGACGCG |
| | GCTGAAGGTAAAAACATCGCGCACCAGGTTAAGAAAATGAACATGGACGG |
| | TGTGCGTCATATCCGCGACCGTTTCAATGTGCCGGTGTCTGATGCAGATA |
| | TCGAAAAACTGCCGTACATCACCTTCCCGGAAGGTTCTGAAGAGCATACC |
| | TATCTGCACGCTCAGCGTCAGAAACTGCACGGTTATCTGCCAAGCCGTCA |
| | GCCGAACTTCACCGAGAAGCTTGAGCTGCCGAGCCTGCAAGACTTCGGCG |
| | CGCTGTTGGAAGAGCAGAGCAAAGAGATCTCTACCACTATCGCTTTCGTT |
| | CGTGCTCTGAACGTGATGCTGAAGAACAAGTCGATCAAAGATCGTCTGGT |
| | ACCGATCATCGCCGACGAAGCGCGTACTTTCGGTATGGAAGGTCTGTTCC |
| | GTCAGATTGGTATTTACAGCCCGAACGGTCAGCAGTACACCCCGCAGGAC |
| | CGCGAGCAGGTTGCTTACTATAAAGAAGACGAGAAAGGTCAGATTCTGCA |
| | GGAAGGGATCAACGAGCTGGGCGCAGGTTGTTCCTGGCTGGCAGCGGCGA |
| | CCTCTTACAGCACCAACAATCTGCCGATGATCCCGTTCTACATCTATTAC |
| | TCGATGTTCGGCTTCCAGCGTATTGGCGATCTGTGCTGGGCGGCTGGCGA |
| | CCAGCAAGCGCGTGGCTTCCTGATCGGCGGTACTTCCGGTCGTACCACCC |
| | TGAACGGCGAAGGTCTGCAGCACGAAGATGGTCACAGCCACATTCAGTCG |
| | CTGACTATCCCGAACTGTATCTCTTACGACCCGGCTTACGCTTACGAAGT |
| | TGCTGTCATCATGCATGACGGTCTGGAGCGTATGTACGGTGAAAAACAAG |
| | AGAACGTTTACTACTACATCACTACGCTGAACGAAAACTACCACATGCCG |
| | GCAATGCCGGAAGGTGCTGAGGAAGGTATCCGTAAAGGTATCTACAAACT |
| | CGAAACTATTGAAGGTAGCAAAGGTAAAGTTCAGCTGCTCGGCTCCGGTT |
| | CTATCCTGCGTCACGTCCGTGAAGCAGCTGAGATCCTGGCGAAAGATTAC |
| | GGCGTAGGTTCTGACGTTTATAGCGTGACCTCCTTCACCGAGCTGGCGCG |
| | TGATGGTCAGGATTGTGAACGCTGGAACATGCTGCACCCGCTGGAAACTC |
| | CGCGCGTTCCGTATATCGCTCAGGTGATGAACGACGCTCCGGCAGTGGCA |
| | TCTACCGACTATATGAAACTGTTCGCTGAGCAGGTCCGTACTTACGTACC |
| | GGCTGACGACTACCGCGTACTGGGTACTGATGGCTTCGGTCGTTCCGACA |
| | GCCGTGAGAACCTGCGTCACCACTTCGAAGTTGATGCTTCTTATGTCGTG |
| | GTTGCGCGCTGGGCGAACTGGCTAAACGTGGCGAAATCGATAAGAAAGT |
| | GGTTGCTGACGCAATCGCCAAATTCAACATCGATGCAGATAAAGTTAACC |
| | CGCGTCTGGCGTAA |
| aceF SEQ ID NO: 33 | ATGGCTATCGAAATCAAAGTACCGGACATCGGGGCTGATGAAGTTGAAAT |
| | CACCGAGATCCTGGTCAAAGTGGGCGACAAAGTTGAAGCCGACAGTCTG |
| | TGATCACCGTAGAAGGCGACAAAGCCTCTATGGAAGTTCCGTCTCCGCAG |
| | GCGGGTATCGTTAAAGAGATCAAAGTCTCTGTTGGCGATAAAACCCAGAC |
| | CGGCGCACTGATTATGATTTTCGATTCCGCCGACGGTGCAGCAGACGCTG |
| | CACCTGCTCAGGCAGAAGAGAAGAAAGAAGCAGCTCCGGCAGCAGCACCA |
| | GCGGCTGCGGCGGCAAAAGACGTTAACGTTCCGGATATCGGCAGCGACGA |
| | AGTTGAAGTGACCGAAATCCTGGTGAAAGTTGGCGATAAAGTTGAAGCTG |
| | AACAGTCGCTGATCACCGTAGAAGGCGACAAGGCTTCTATGGAAGTTCCG |
| | GCTCCGTTTGCTGGCACCGTGAAAGAGATCAAAGTGAACGTGGGTGACAA |
| | AGTGTCTACCGGCTCGCTGATTATGGTCTTCGAAGTCGCGGGTGAAGCAG |
| | GCGCGGCAGCTCCGGCCGCTAAACAGGAAGCAGCTCCGGCAGCGGCCCCT |
| | GCACCAGCGGCTGGCGTGAAAGAAGTTAACGTTCCGGATATCGGCGGTGA |
| | CGAAGTTGAAGTGACTGAAGTGATGGTGAAAGTGGGCGACAAAGTTGCCG |
| | CTGAACAGTCACTGATCACCGTAGAAGGCGACAAAGCTTCTATGGAAGTT |
| | CCGGCGCCGTTTGCAGGCGTCGTGAAGGAACTGAAAGTCAACGTTGGCGA |
| | TAAAGTGAAAACTGGCTCGCTGATTATGATCTTCGAAGTTGAAGGCGCAG |
| | CGCCTGCGGCAGCTCCTGCGAAACAGGAAGCGGCAGCGCCGGCACCGGCA |
| | GCAAAAGCTGAAGCCCCCGGCAGCAGCACCAGCTGCGAAAGCGGAAGGCAA |
| | ATCTGAATTTGCTGAAAACGACGCTTATGTTCACGCGACTCCGCTGATCC |
| | GCCGTCTGGCACGCGAGTTTGGTGTTAACCTTGCGAAAGTGAAGGGCACT |
| | GGCCGTAAAGGTCGTATCCTGCGCGAAGACGTTCAGGCTTACGTGAAAGA |
| | AGCTATCAAACGTGCAGAAGCAGCTCCGGCAGCGACTGGCGGTGGTATCC |
| | CTGGCATGCTGCCGTGGCCGAAGGTGGACTTCAGCAAGTTTGGTGAAATC |
| | GAAGAAGTGGAACTGGGCCGCATCCAGAAAATCTCTGGTGCGAACCTGAG |
| | CCGTAACTGGGTAATGATCCCGCATGTTACTCACTTCGACAAAACCGATA |
| | TCACCGAGTTGGAAGCGTTCCGTAAACAGCAGAACGAAGAAGCGGCGAAA |
| | CGTAAGCTGGATGTGAAGATCACCCCGGTTGTCTTCATCATGAAAGCCGT |
| | TGCTGCAGCTCTTGAGCAGATGCCTCGCTTCAATAGTTCGCTGTCGGAAG |
| | ACGGTCAGCGTCTGACCCTGAAGAAATACATCAACATCGGTGTGGCGGTG |
| | GATACCCCGAACGGTCTGGTTGTTCCGGTATTCAAAGACGTCAACAAGAA |
| | AGGCATCATCGAGCTGTCTCGCGAGCTGATGACTATTTCTAAGAAAGCGC |
| | GTGACGGTAAGCTGACTGCGGGCGAAATGCAGGGCGGTTGCTTCACCATC |
| | TCCAGCATCGGCGGCCTGGGTACTACCCACTTCGCGCCGATTGTGAACGC |
| | GCCGGAAGTGGCTATCCTCGGCGTTTCCAAGTCCGCGATGGAGCCGGTGT |
| | GGAATGGTAAAGAGTTCGTGCCGCGTCTGATGCTGCCGATTTCTCTCTCC |

TABLE 6-continued

| Gene sequence | 0123456789012345678901234567890123456789 |
|---|---|
| | TTCGACCACCGCGTGATCGACGGTGCTGATGGTGCCCGTTTCATTACCAT CATTAACAACACGCTGTCTGACATTCGCCGTCTGGTGATGTAA |
| lpd SEQ ID NO: 34 | ATGAGTACTGAAATCAAAACTCAGGTCGTGGTACTTGGGGCAGGCCCCGC AGGTTACTCCGCTGCCTTCCGTTGCGCTGATTTAGGTCTGGAAACCGTAA TCGTAGAACGTTACAACACCCTTGGCGGTGTTTGCCTGAACGTCGGCTGT ATCCCTTCTAAAGCACTGCTGCACGTAGCAAAAGTTATCGAAGAAGCCAA AGCGCTGGCTGAACACGGTATCGTCTTCGGCGAACCGAAAACCGATATCG ACAAGATTCGTACCTGGAAAGAGAAAGTGATCAATCAGCTGACCGGTGGT CTGGCTGGTATGGCGAAAGGCCGCAAAGTCAAAGTGGTCAACGGTCTGGG TAAATTCACCGGGGCTAACACCCTGGAAGTTAAGGTGAGAACGGCAAAA CCGTGATCAACTTCGACAACGCGATCATTGCAGCGGGTTCTCGCCCGATC CAACTGCCGTTTATTCCGCATGAAGATCCGCGTATCTGGGACTCCACTGA CGCGCTGGAACTGAAAGAAGTACCAGAACGCCTGCTGGTAATGGGTGGCG GTATCATCGGTCTGGAAATGGGCACCGTTTACCACGCGCTGGGTTCACAG ATTGACGTGGTTGAAATGTTCGACCAGGTTATCCCGGCAGCTGACAAAGA CATCGTTAAAGTCTTCACCAAGCGTATCAGCAAGAAATTCAACCTGATGC TGGAAACCAAAGTTACCGCCGTTGAAGCGAAAGAAGACGGCATTTATGTG ACGATGGAAGGCAAAAAAGCACCCGCTGAACGCAGCGTTACGACGCCGT GCTGGTAGCGATTGGTCGTGTGCCGAACGGTAAAAACCTCGACGCAGGCA AGCAGGCGTGGAAGTTGACGACCGTGGTTTCATCCGCGTTGACAAACAG CTGCGTACCAACGTACCGCACATCTTTGCTATCGGCGATATCGTCGGTCA ACCGATGCTGGCACACAAAGGTGTTCACGAAGGTCACGTTGCCGCTGAAG TTATCGCCGGTAAGAAACACTACTTCGATCCGAAAGTTATCCCGTCCATC GCCTATACCAAACCAGAAGTTGCATGGGTGGGTCTGACTGAGAAAGAAGC GAAAGAGAAAGGCATCAGCTATGAAACCGCCACCTTCCCGTGGGCTGCTT CTGGTCGTGCTATCGCTTCCGACTGCGCAGACGGTATGACCAAGCTGATT TTCGACAAGAATCTCACCGTGTGATCGGTGGTGCGATTGTCGGTACTAA CGGCGGCGAGCTGCTGGGTGAAATCGGCCTGGCAATCGAAATGGGTTGTG ATGCTGAAGACATCGCACTGACCATCCACGCGCACCCGACTCTGCACGAG TCTGTGGGCCTGGCGGCAGAAGTGTTCGAAGGTAGCATTACCGACCTGCC GAACCCGAAAGCGAAGAAGAAGTAA |
| tesB SEQ ID NO: 10 | ATGAGTCAGGCGCTAAAAAATTTACTGACATTGTTAAATCTGGAAAAAAT TGAGGAAGGACTCTTTCGCGGCCAGAGTGAAGATTTAGGTTTACGCCAGG TGTTTGGCGGCCAGGTCGTGGGTCAGGCCTTGTATGCTGCAAAAGAGACC GTCCCTGAAGAGCGGCTGGTACATTCGTTTCACAGCTACTTTCTTCGCCC TGGCGATAGTAAGAAGCCGATTATTTATGATGTCGAAACGCTGCGTGACG GTAACAGCTTCAGCGCCCGCCGGGTTGCTGCTATTCAAACGGCAAACCG ATTTTTTATATGACTGCCTCTTTCCAGGCACCAGAAGCGGGTTTCGAACA TCAAAAAACAATGCCGTCCGCGCCAGCGCCTGATGGCCTCCCTTCGGAAA CGCAAATCGCCCAATCGCTGGCGCACCTGCTGCCGCCAGTGCTGAAAGAT AAATTCATCTGCGATCGTCCGCTGGAAGTCCGTCCGGTGGAGTTTCATAA CCCACTGAAAGGTCACGTCGCAGAACCACATCGTCAGGTGTGGATCGCG CAAATGGTAGCGTGCCGGATGACCTGCGCGTTCATCAGTATCTGCTCGGT TACGCTTCTGATCTTAACTTCCTGCCGGTAGCTCTACAGCCGCACGGCAT CGGTTTTCTCGAACCGGGGATTCAGATTGCCACCATTGACCATTCCATGT GGTTCCATCGCCCGTTTAATTTGAATGAATGGCTGCTGTATAGCGTGGAG AGCACCTCGGCGTCCAGCGCACGTGGCTTTGTGCGCGGTGAGTTTTATAC CCAAGACGGCGTACTGGTTGCCTCGACCGTTCAGGAAGGGGTGATGCGTA ATCACAATTAA |

TABLE 7

| Amino acid sequence | 0123456789012345678901234567890123456789 |
|---|---|
| pct SEQ ID NO: 35 | MRKVPIITADEAAKLIKDGDTVTTSGFVGNAIPEALDRAVEKRFLETGEP KNITYVYCGSQGNRDGRGAEHFAHEGLLKRYIAGHWATVPALGKMAMENK MEAYNVSQGALCHLFRDIASHKPGVFTKVGIGTFIDPRNGGGKVNDITKE DIVELVEIKGQEYLFYPAFPIHVALIRGTYADESGNITFEKEVAPLEGTS VCQAVKNSGGIVVVQVERVVKAGTLDPRHVKVPGIYVDYVVVADPEDHQQ SLDCEYDPALSGEHRRPEVVGEPLPLSAKKVIGRRGAIELEKDVAVNLGV GAPEYVASVADEEGIVDFMTLTAESGAIGGVPAGGVRFGASYNADALIDQ GYQFDYYDGGGLDLCYLGLAECDEKGNINVSRFGPRIAGCGGFINITQNT PKVFFCGTFTAGGLKVKIEDGKVIIVQEGKQKKFLKAVEQITFNGDVALA NKQQVTYITERCVFLLKEDGLHLSEIAPGIDLQTQILDVMDFAPIIDRDA NGQIKLMDAALFAEGLMGLKEMKS |
| lcdA SEQ ID NO: 36 | MSLIQGMKAKQLLAYFQGKADQDAREAKARGELVCWSASVAPPEFCVTMG IAMIYPETHAAGIGARKGAMDMLEVADRKGYNVDCCSYGRVNMGYMECLK EAAITGVKPEVLVNSPAADVPLPDLVITCNNICNTLLKWYENLAAELDIP CIVIDVPFNHTMPIPEYAKAYIADQFRNAISQLEVICGRPFDWKKFKEVK DQTQRSVYHWNRIAEMAKYKPSPLNGFDLFNYMALIVACRSLDYAEITFK |

TABLE 7-continued

| Amino acid sequence | 0123456789012345678901234567890123456789 |
|---|---|
| | AFADELEENLKAGIYAFKGAEKTRFQWEGIAVWPHLGHTFKSMKNLNSIM<br>TGTAYPALWDLHYDANDESMHSMAEAYTRIYINTCLQNKVEVLLGIMEKG<br>QVDGTVYHLNRSCKLMSFLNVETAEIIKEKNGLPYVSIDGDQTDPRVFSP<br>AQFDTRVQALVEMMEANMAAAE |
| lcdB<br>SEQ ID NO: 37 | MSRVEAILSQLKDVAANPKKAMDDYKAETGKGAVGIMPIYSPEEMVHAAG<br>YLPMGIWGAQGKTISKARTYLPAFACSVMQQVMELQCEGAYDDLSAVIFS<br>VPCDTLKCLSQKWKGTSPVIVFTHPQNRGLEAANQFLVTEYELVKAQLES<br>VLGVKISNAALENSIAIYNENRAVMREFVKVAADYPQVIDAVSRHAVFKA<br>RQFMLKEKHTALVKELIAEIKATPVQPWDGKKVVVTGILLEPNELLDIFN<br>EFKIAIVDDDLAQESRQIRVDVLDGEGGPLYRMAKAWQQMYGCSLATDTK<br>KGRGRMLINKTIQTGADAIVVAMMKFCDPEEWDYPVMYREFEEKGVKSLM<br>IEVDQEVSSFEQIKTRLQSFVEML |
| lcdC<br>SEQ ID NO: 38 | MYTLGIDVGSASSKAVILKDGKDIVAAEVVQVGTGSSGPQRALDKAFEVS<br>GLKKEDISYTVATGYGRFNFSDADKQISEISCHAKGIYFLVPTARTIIDI<br>GGQDAKAIRLDDKGGIKQFFMNDKCAAGTGRFLEVMARVLETTLDEMAEL<br>DEQATDTAPISSTCTVFAESEVISQLSNGVSRNNIIKGVHLSVASRACGL<br>AYRGGLEKDVVMTGGVAKNAGVVRAVAGVLKTDVIVAPNPQTTGALGAAL<br>YAYEAAQKK |
| etfA<br>SEQ ID NO: 39 | MAFNSADINSFRDIWVFCEQREGKLINTDFELISEGRKLADERGSKLVGI<br>LLGHEVEEIAKELGGYGADKVIVCDHPELKFYTTDAYAKVLCDVVMEEKP<br>EVILIGATNIGRDLGPRCAARLHTGLTADCTHLDIDMNKYVDFLSTSSTL<br>DISSMTFPMEDTNLKMTRPAFGGHLMATIICPRFRPCMSTVRPGVMKKAE<br>FSQEMAQACQVVTRHVNLSDEDLKTKVININVKETKKIVDLIGAEIIVSVG<br>RGISKDVQGGIALAEKLADAFGNGVVGGSRAVIDSGWLPADHQVGQTGKT<br>VHPKVYVALGISGAIQHKAGMQDSELIIAVNKDETAPIFDCADYGITGDL<br>FKIVPMMIDAIKEGKNA |
| acrB<br>SEQ ID NO: 40 | MRIYVCVKQVPDTSGKVAVNPDGTLNRASMAAIINPDDMSAIEQALKLKD<br>ETGCQVTALTMGPPPAEGMLREIIAMGADDGVLISAREFGGSDTFATSQI<br>ISAAIHKLGLSNEDMIFCGRQAIDGDTAQVGPQIAEKLSIPQVTYGAGIK<br>KSGDLVLVKRMLEDGYMMIEVETPCLITCIQDKAVKPRYMTLNGIMECYS<br>KPLLVLDYEALKDEPLIELDTIGLKGSPTNIFKSFTPPQKGVGVMLQGTD<br>KEKVEDLVDKLMQKHVI |
| acrC<br>SEQ ID NO: 41 | MFLLKIKKERMKRMDFSLTREQEMLKKLARQFAEIELEPVAEEIDREHVF<br>PAENFKKMAEIGLTGIGIPKEFGGSGGGTLEKVIAVSEFGKKCMASASIL<br>SIHLIAPQAIYKYGTKEQKETYLPRLTKGGELGAFALTEPNAGSDAGAVK<br>TTAILDSQTNEYVLNGTKCFISGGGRAGVLVIFALTEPKKGLKGMSAIIV<br>EKGTPGFSIGKVESKMGIAGSETAELIFEDCRVPAANLLGKEGKGFKIAM<br>EALDGARIGVGAQAIGIAEGAIDLSVKYVHERIQFGKPIANLQGIQWYIA<br>DMATKTAAARALVEFAAYLEDAGKPFTKESAMCKLNASENARFVTNLALQ<br>IHGGYGYMKDYPLERMYRDAKITEIYEGTSEIHKVVIAREVMKR |
| thrA<sup>fbr</sup><br>SEQ ID NO: 42 | MRVLKFGGTSVANAERFLRVADILESNARQGQVATVLSAPAKITNHLVAM<br>IEKTISGQDALPNISDAERIFAELLTGLAAAQPGFPLAQLKTFVDQEFAQ<br>IKHVLHGISLLGQCPDSINAALICRGEKMSIAIMAGVLEARGHNVTVIDP<br>VEKLLAVGHYLESTVDIAESTRRIAASRIPADHMVLMAGFTAGNEKGELV<br>VLGRNGSDYSAAVLAACLRADCCEIWTDVDGVYTCDPRQVPDARLLKSMS<br>YQEAMELSYFGAKVLHPRTITPIAQFQIPCLIKNTGNPQAPGTLIGASRD<br>EDELPVKGISNLNNMAMFSVSGPGMKGMVGMAARVFAAMSRARISVVLIT<br>QSSSEYSISFCVPQSDCVRAERAMQEEFYLELKEGLLEPLAVTERLAIIS<br>VVGDGMRTLRGISAKFFAALARANINIVAIAQRSSERSISVVVNNDDATT<br>GVRVTHQMLFNTDQVIEVFVIGVGGVGGALLEQLKRQQSWLKNKHIDLRV<br>CGVANSKALLTNVHGLNLENWQEELAQAKEPFNLGRLIRLVKEYHLLNPV<br>IVDCTSSQAVADQYADFLREGFHVVTPNKKANTSSMDYYHQLRYAAEKSR<br>RKFLYDTNVGAGLPVIENLQNLLNAGDELMKFSGILSGSLSYIFGKLDEG<br>MSFSEATTLAREMGYTEPDPRDDLSGMDVARKLLILARETGRELELADIE<br>IEPVLPAEFNAEGDVAAFMANLSQLDDLFAARVAKARDEGKVLRYVGNID<br>EDGVCRVKIAEVDGNDPLFKVKNGENALAFYSHYYQPLPLVLRGYGAGND<br>VTAAGVFADLLRTLSWKLGV |
| thrB<br>SEQ ID NO: 43 | MVKVYAPASSANMSVGFDVLGAAVTPVDGALLGDVVTVEAAETFSLNNLG<br>RFADKLPSEPRENIVYQCWERFCQELGKQIPVAMTLEKNMPIGSGLGSSA<br>CSVVAALMAMNEHCGKPLNDTRLLALMGELEGRISGSIHYDNVAPCFLGG<br>MQLMIEENDIISQQVPGFDEWLWVLAYPGIKVSTAEARAILPAQYRRQDC<br>IAHGRHLAGFIHACYSRQPELAAKLMKDVIAEPYRERLLPGFRQARQAVA<br>EIGAVASGISGSGPTLFALCDKPETAQRVADWLGKNYLQNQEGFVHICRL<br>DTAGARVLEN |
| thrC<br>SEQ ID NO: 44 | MKLYNLKDHNEQVSFAQAVTQGLGKNQGLFFPHDLPEFSLTEIDEMLKLD<br>FVTRSAKILSAFIGDEIPQEILEERVRAAFAPPAPVANVESDVGCLELFH<br>GPTLAFKDFGGRFMAQMLTHIAGDKPVTILTATSGDTGAAVAHAFYGLPN<br>VKVVILYPRGKISPLQEKLFCTLGGNIETVAIDGDFDACQALVKQAFDDE<br>ELKVALGLNSANSINISRLLAQICYYFEAVAQLPQETRNQLVVSVPSGNF |

TABLE 7-continued

| Amino acid sequence | 0123456789012345678901234567890123456789 |
|---|---|
| | GDLTAGLLAKSLGLPVKRFIAATNVNDTVPRFLHDGQWSPKATQATLSNA<br>MDVSQPNNWPRVEELFRRKIWQLKELGYAAVDDETTQQTMRELKELGYTS<br>EPHAAVAYRALRDQLNPGEYGLFLGTAHPAKFKESVEAILGETLDLPKEL<br>AERADLPLLSHNLPADFAALRKLMMNHQ |
| ilvA$^{fbr}$<br>SEQ ID NO: 45 | MSETYVSEKSPGVMASGAELIRAADIQTAQARISSVIAPTPLQYCPRLSE<br>ETGAEIYLKREDLQDVRSYKIRGALNSGAQLTQEQRDAGIVAASAGNHAQ<br>GVAYVCKSLGVQGRIYVPVQTPKQKRDRIMVHGGEFVSLVVTGNNFDEAS<br>AAAHEDAERTGATLIEPFDARNTVIGQGTVAAEILSQLTSMGKSADHVMV<br>PVGGGGLLAGVVSYMADMAPRTAIVGIEPAGAASMQAALHNGGPITLETV<br>DPFVDGAAVKRVGDLNYTIVEKNQGRVHMMSATEGAVCTEMLDLYQNEGI<br>IAEPAGALSIAGLKEMSFAPGSAVVCIISGGNNDVLRYAEIAERSLVHRG<br>LKHYFLVNFPQKPGQLRHFLEDILGPDDDITLFEYLKRNNRETGTALVGI<br>HLSEASGLDSLLERMEESAIDSRRLEPGTPEYEYLT |
| aceE<br>SEQ ID NO: 46 | MSERFPNDVDPIETRDWLQAIESVIREEGVERAQYLIDQLLAEARKGGVN<br>VAAGTGISNYINTIPVEEQPEYPGNLELERRIRSAIRWNAIMTVLRASKK<br>DLELGGHMASFQSSATIYDVCFNHFFRARNEQDGGDLVYFQGHISPGVYA<br>RAFLEGRLTQEQLDNFRQEVHGNGLSSYPHPKLMPEFWQFPTVSMGLGPI<br>GAIYQAKFLKYLEHRGLKDTSKQTVYAFLGDGEMDEPESKGAITIATREK<br>LDNLVFVINCNLQRLDGPVTGNGKIINELEGIFEGAGWNVIKVMWGSRWD<br>ELLRKDTSGKLIQLMNETVDGDYQTFKSKDGAYVREHFFGKYPETAALVA<br>DWTDEQIWALNRGGHDPKKIYAAFKKAQETKGKATVILAHTIKGYGMGDA<br>AEGKNIAHQVKKMNMDGVRHIRDRFNVPVSDADIEKLPYITFPEGSEEHT<br>YLHAQRQKLHGYLPSRQPNFTEKLELPSLQDFGALLEEQSKEISTTIAFV<br>RALNVMLKNKSIKDRLVPIIADEARTFGMEGLFRQIGIYSPNGQQYTPQD<br>REQVAYYKEDEKGQILQEGINELGAGCSWLAAATSYSTNNLPMIPFYIYY<br>SMFGFQRIGDLCWAAGDQQARGFLIGGTSGRTTLNGEGLQHEDGHSHIQS<br>LIIPNCISYDPAYAYEVAVIMHDGLERMYGEKQENVYYITTLNENYHMP<br>AMPEGAEEGIRKGIYKLETIEGSKGKVQLLGSGSILRHVREAAEILAKDY<br>GVGSDVYSVTSFTELARDGQDCERWNMLHPLETPRVPYIAQVMNDAPAVA<br>STDYMKLFAEQVRTYVPADDYRVLGTDGFGRSDSRENLRHHFEVDASYVV<br>VAALGELAKRGEIDKKVVADAIAKFNIDADKVNPRLA |
| aceF<br>SEQ ID NO: 47 | MAIEIKVPDIGADEVEITEILVKVGDKVEAEQSLITVEGDKASMEVPSPQ<br>AGIVKEIKVSVGDKTQTGALIMIFDSADGAADAAPAQAEEKKEAAPAAAP<br>AAAAAKDVNVPDIGSDEVEVTEILVKVGDKVEAEQSLITVEGDKASMEVP<br>APFAGTVKEIKVNVGDKVSIGSLIMVFEVAGEAGAAAPAAKQEAAPAAAP<br>APAAGVKEVNVPDIGGDEVEVTEVMVKVGDKVAAEQSLITVEGDKASMEV<br>PAPFAGVVKELKVNVGDKVKTGSLIMIFEVEGAAPAAAPAKQEAAPAPA<br>AKAEAPAAAPAAKAEGKSEFAENDAYVHATPLIRRLAREFGVNLAKVKGT<br>GRKGRILREDVQAYVKEAIKRAEAAPAATGGGIPGMLPWPKVDFSKFGEI<br>EEVELGRIQKISGANLSRNWVMIPHVTHFDKTDITELEAFRKQQNEEAAK<br>RKLDVKITPVVFIMKAVAAALEQMPRFNSSLSEDGQRLTLKKYINIGVAV<br>DTPNGLVVPVFKDVNKKGIIELSRELMTISKKARDGKLTAGEMQGGCFTI<br>SSIGGLGTTHFAPIVNAPEVAILGVSKSAMEPVWNGKEFVPRLMLPISLS<br>FDHRVIDGADGARFITIINNTLSDIRRLVM |
| lpd<br>SEQ ID NO: 48 | MSTEIKTQVVVLGAGPAGYSAAFRCADLGLETVIVERYNTLGGVCLNVGC<br>IPSKALLHVAKVIEEAKALAEHGIVFGEPKTDIDKIRTWKEKVINQLTGG<br>LAGMAKGRKVKVVNGLGKFTGANTLEVEGENGKTVINFDNAIIAAGSRPI<br>QLPFIPHEDPRIWDSTDALELKEVPERLLVMGGGIIGLEMGTVYHALGSQ<br>IDVVEMFDQVIPAADKDIVKVFTKRISKKFNLMLETKVTAVEAKEDGIYV<br>TMEGKKAPAEPQRYDAVLVAIGRVPNGKNLDAGKAGVEVDDRGFIRVDKQ<br>LRTNVPHIFAIGDIVGQPMLAHKGVHEGHVAAEVIAGKKHYFDPKVIPSI<br>AYTKPEVAWVGLTEKEAKEKGISYETATFPWAASGRAIASDCADGMTKLI<br>FDKESHRVIGGAIVGTNGGELLGEIGLAIEMGCDAEDIALTIHAHPTLHE<br>SVGLAAEVFEGSITDLPNPKAKKK |
| tesB<br>SEQ ID NO: 20 | MSQALKNLLTLLNLEKIEEGLFRGQSEDLGLRQVFGGQVVGQALYAAKET<br>VPEERLVHSFHSYFLRPGDSKKPIIYDVETLRDGNSFSARRVAAIQNGKP<br>IFYMTASFQAPEAGFEHQKTMPSAPAPDGLPSETQIAQSLAHLLPPVLKD<br>KFICDRPLEVRPVEFHNPLKGHVAEPHRQVWIRANGSVPDDLRVHQYLLG<br>YASDLNFLPVALQPHGIGFLEPGIQIATIDHSMWFHRPFNLNEWLLYSVE<br>STSASSARGFVRGEFYTQDGVLVASTVQEGVMRNHN |

In some embodiments, one or more of the propionate biosynthesis genes is a synthetic propionate biosynthesis gene. In some embodiments, one or more of the propionate biosynthesis genes is an *E. coli* propionate biosynthesis gene. In some embodiments, one or more of the propionate biosynthesis genes is a *C. glutamicum* propionate biosynthesis gene. In some embodiments, one or more of the propionate biosynthesis genes is a *C. propionicum* propionate biosynthesis gene. The propionate gene cassette may comprise genes for the aerobic biosynthesis of propionate and/or genes for the anaerobic or microaerobic biosynthesis of propionate. One or more of the propionate biosynthesis genes may be functionally replaced or modified, e.g., codon optimized. In some embodiments, the genetically engineered bacteria comprise a combination of propionate biosynthesis genes from different species, strains, and/or substrains of bacteria, and are capable of producing propionate under inducing conditions. In some embodiments, one or more of the propionate biosynthesis genes is functionally replaced, modified, and/or mutated in order to enhance stability and/or increase propionate production under inducing conditions. In some embodiments, the genetically engineered bacteria are capable of expressing the propionate biosynthesis cassette and producing propionate under inducing conditions.

In some embodiments, the genetically engineered bacteria of the invention comprise an acetate gene cassette and are capable of producing acetate. The genetically engineered bacteria may include any suitable set of acetate biosynthesis genes. Unmodified bacteria comprising acetate biosynthesis genes are known in the art and are capable of consuming various substrates to produce acetate under aerobic and/or anaerobic conditions (see, e.g., Ragsdale, 2008), and these endogenous acetate biosynthesis pathways may be a source of genes for the genetically engineered bacteria of the invention. In some embodiments, the genetically engineered bacteria of the invention comprise acetate biosynthesis genes from a different species, strain, or substrain of bacteria. In some embodiments, the native acetate biosynthesis genes in the genetically engineered bacteria are enhanced. In some embodiments, the genetically engineered bacteria comprise aerobic acetate biosynthesis genes, e.g., from *Escherichia coli*. In some embodiments, the genetically engineered bacteria comprise anaerobic acetate biosynthesis genes, e.g., from *Acetitomaculum, Acetoanaerobium, Acetohalobium, Acetonema, Balutia, Butyribacterium, Clostridium, Moorella, Oxobacter, Sporomusa*, and/or *Thermoacetogenium*. The genetically engineered bacteria may comprise genes for aerobic acetate biosynthesis or genes for anaerobic or microaerobic acetate biosynthesis. In some embodiments, the genetically engineered bacteria comprise both aerobic and anaerobic or microaerobic acetate biosynthesis genes. In some embodiments, the genetically engineered bacteria comprise a combination of acetate biosynthesis genes from different species, strains, and/or substrains of bacteria, and are capable of producing acetate. In some embodiments, one or more of the acetate biosynthesis genes is functionally replaced, modified, and/or mutated in order to enhance stability and/or acetate production. In some embodiments, the genetically engineered bacteria are capable of expressing the acetate biosynthesis cassette and producing acetate under inducing conditions. In some embodiments, the genetically engineered bacteria are capable of producing an alternate short-chain fatty acid.

In some embodiments, the genetically engineered bacteria of the invention are capable of producing IL-10. Interleukin-10 (IL-10) is a class 2 cytokine, a category which includes cytokines, interferons, and interferon-like molecules, such as IL-19, IL-20, IL-22, IL-24, IL-26, IL-28A, IL-28B, IL-29, IFN-α, IFN-β, IFN-δ, IFN-ε, IFN-κ, IFN-τ, IFN-ω, and limitin. IL-10 is an anti-inflammatory cytokine that signals through two receptors, IL-10R1 and IL-10R2. Deficiencies in IL-10 and/or its receptors are associated with IBD and intestinal sensitivity (Nielsen, 2014). Bacteria expressing IL-10 or protease inhibitors may ameliorate conditions such as Crohn's disease and ulcerative colitis (Simpson et al., 2014). The genetically engineered bacteria may comprise any suitable gene encoding IL-10, e.g., human IL-10. In some embodiments, the gene encoding IL-10 is modified and/or mutated, e.g., to enhance stability, increase IL-10 production, and/or increase anti-inflammatory potency under inducing conditions. In some embodiments, the genetically engineered bacteria are capable of producing IL-10 under inducing conditions, e.g., under a condition(s) associated with inflammation. In some embodiments, the genetically engineered bacteria are capable of producing IL-10 in low-oxygen conditions. In some embodiments, the genetically engineered bacteria comprise a nucleic acid sequence that encodes IL-10. In some embodiments, the genetically engineered bacteria comprise a nucleic acid sequence comprising SEQ ID NO: 49 or a functional fragment thereof. In some embodiments, genetically engineered bacteria comprise a nucleic acid sequence that is at least about 80%, at least about 85%, at least about 90%, at least about 95%, or at least about 99% homologous to a nucleic acid sequence comprising SEQ ID NO: 49 or a functional fragment thereof.

```
IL-10 (SEQ ID NO: 49):
ATG AGC CCC GGA CAG GGA ACT CAA AGC GAG AAC AGC

TGC ACA CAT TTT CCA GGTAAT CTT CCA AAT ATG CTT

CGT GAC TTG CGT GAC GCT TTC TCT CGCGTG AAA ACC

TTT TTT CAG ATG AAG GAT CAG TTA GAT AAT CTG CTG

CTG AAA GAA TCG CTT CTTGAG GAC TTC AAG GGA TAT

CTG GGA TGT CAG GCG TTATCT GAG ATG ATT CAG TTT

TAT TTG GAA GAA GTT ATG CCC CAG GCT GAG AAT CAA

GAC CCT GAC ATC AAA GCGCAT GTG AAT AGC CTG GGC

GAG AAT CTGAAG ACA CTG CGC CTG CGT CTT CGC CGC

TGT CAC CGT TTT CTG CCT TGC GAA AAT AAG AGT AAG

GCC GTT GAG CAA GTG AAAAAT GCT TTC AAC AAG

TTACAA GAA AAA GGG ATT TAC AAA GCT ATG TCT GAG

TTT GAC ATT TTC ATT AAT TAC ATT GAG GCC TAC ATG

ACT ATG AAG ATT CGC AAT
```

In some embodiments, the genetically engineered bacteria are capable of producing IL-2. Interleukin 2 (IL-2) mediates autoimmunity by preserving health of regulatory T cells (Treg). Treg cells, including those expressing Foxp3, typically suppress effector T cells that are active against self-antigens, and in doing so, can dampen autoimmune activity. IL-2 functions as a cytokine to enhance Treg cell differentiation and activity while diminished IL-2 activity can promote autoimmunity events. IL-2 is generated by activated CD4+ T cells, and by other immune mediators including activated CD8+ T cells, activated dendritic cells, natural killer cells, and NK T cells. IL-2 binds to IL-2R, which is composed of three chains including CD25, CD122, and CD132. IL-2 promotes growth of Treg cells in the thymus, while preserving their function and activity in systemic circulation. Treg cell activity plays an intricate role in the IBD setting, with murine studies suggesting a protective role in disease pathogenesis. In some embodiments, the genetically engineered bacteria comprise a nucleic acid sequence encoding SEQ ID NO: 50 or a functional fragment thereof. In some embodiments, genetically engineered bacteria comprise a nucleic acid sequence that is at least about 80%, at least about 85%, at least about 90%, at least about 95%, or at least about 99% homologous to a nucleic acid sequence encoding SEQ ID NO: 50 or a functional fragment thereof. In some embodiments, the genetically engineered bacteria are capable of producing IL-2 under inducing conditions, e.g., under a condition(s) associated with inflammation. In some embodiments, the genetically engineered bacteria are capable of producing IL-2 in low-oxygen conditions.

SEQ ID NO: 50
```
MAPTSSSTKK TQLQLEHLLL DLQMILNGIN NYKNPKLTRM

LTFKFYMPKK ATELKHLQCL EEELKPLEEV LNLAQSKNFH

LRPRDLISNI NVIVLELKGS ETTFMCEYAD ETATIVEFLN

RWITFCQSII SILT
```

In some embodiments, the genetically engineered bacteria are capable of producing IL-22. Interleukin 22 (IL-22) cytokine can be produced by dendritic cells, lymphoid tissue inducer-like cells, natural killer cells and expressed on adaptive lymphocytes. Through initiation of Jak-STAT signaling pathways, IL-22 expression can trigger expression of antimicrobial compounds as well as a range of cell growth related pathways, both of which enhance tissue repair mechanisms. IL-22 is critical in promoting intestinal barrier fidelity and healing, while modulating inflammatory states. Murine models have demonstrated improved intestinal inflammation states following administration of Il-22. Additionally, IL-22 activates STAT3 signaling to promote enhanced mucus production to preserve barrier function. IL-22's association with IBD susceptibility genes may modulate phenotypic expression of disease as well. In some embodiments, the genetically engineered bacteria comprise a nucleic acid sequence encoding SEQ ID NO: 51 or a functional fragment thereof. In some embodiments, genetically engineered bacteria comprise a nucleic acid sequence that is at least about 80%, at least about 85%, at least about 90%, at least about 95%, or at least about 99% homologous to a nucleic acid sequence encoding SEQ ID NO: 51 or a functional fragment thereof. In some embodiments, the genetically engineered bacteria are capable of producing IL-22 under inducing conditions, e.g., under a condition(s) associated with inflammation. In some embodiments, the genetically engineered bacteria are capable of producing IL-22 in low-oxygen conditions.

SEQ ID NO: 51
```
MAALQKSVSS FLMGTLATSC LLLLALLVQG GAAAPISSHC

RLDKSNFQQP YITNRTFMLA KEASLADNNT DVRLIGEKLF

HGVSMSERCY LMKQVLNFTL EEVLFPQSDR FQPYMQEVVP

FLARLSNRLS TCHIEGDDLH IQRNVQKLKD TVKKLGESGE

IKAIGELDLL FMSLRNACI
```

In some embodiments, the genetically engineered bacteria are capable of producing IL-27. Interleukin 27 (IL-27) cytokine is predominately expressed by activated antigen presenting cells, while IL-27 receptor is found on a range of cells including T cells, NK cells, among others. In particular, IL-27 suppresses development of pro-inflammatory T helper 17 (Th17) cells, which play a critical role in IBD pathogenesis. Further, IL-27 can promote differentiation of IL-10 producing Tr1 cells and enhance IL-10 output, both of which have anti-inflammatory effects. IL-27 has protective effects on epithelial barrier function via activation of MAPK and STAT signaling within intestinal epithelial cells. Additionally, IL-27 enhances production of antibacterial proteins that curb bacterial growth. Improvement in barrier function and reduction in bacterial growth suggest a favorable role for IL-27 in IBD pathogenesis. In some embodiments, the genetically engineered bacteria comprise a nucleic acid sequence encoding SEQ ID NO: 52 or a functional fragment thereof. In some embodiments, genetically engineered bacteria comprise a nucleic acid sequence that is at least about 80%, at least about 85%, at least about 90%, at least about 95%, or at least about 99% homologous to a nucleic acid sequence encoding SEQ ID NO: 52 or a functional fragment thereof. In some embodiments, the genetically engineered bacteria are capable of producing IL-27 under inducing conditions, e.g., under a condition(s) associated with inflammation. In some embodiments, the genetically engineered bacteria are capable of producing IL-27 in low-oxygen conditions.

SEQ ID NO: 52
```
MGQTAGDLGW RLSLLLLPLL LVQAGVWGFP RPPGRPQLSL

QELRREFTVS LHLARKLLSE VRGQAHRFAE SHLPGVNLYL

LPLGEQLPDV SLTFQAWRRL SDPERLCFIS TTLQPFHALL

GGLGTQGRWT NMERMQLWAM RLDLRDLQRH LRFQVLAAGF

NLPEEEEEEE EEEEEERKGL LPGALGSALQ GPAQVSWPQL

LSTYRLLHSL ELVLSRAVRE LLLLSKAGHS VWPLGFPTLS

PQP
```

In some embodiments, the genetically engineered bacteria of the invention are capable of producing SOD. Increased ROS levels contribute to pathophysiology of inflammatory bowel disease. Increased ROS levels may lead to enhanced expression of vascular cell adhesion molecule 1 (VCAM-1), which can facilitate translocation of inflammatory mediators to disease affected tissue, and result in a greater degree of inflammatory burden. Antioxidant systems including superoxide dismutase (SOD) can function to mitigate overall ROS burden. However, studies indicate that the expression of SOD in the setting of IBD may be compromised, e.g., produced at lower levels in IBD, thus allowing disease pathology to proceed. Further studies have shown that supplementation with SOD to rats within a colitis model is associated with reduced colonic lipid peroxidation and endothelial VCAM-1 expression as well as overall improvement in inflammatory environment. Thus, in some embodiments, the genetically engineered bacteria comprise a nucleic acid sequence encoding SEQ ID NO: 52 or a functional fragment thereof. In some embodiments, genetically engineered bacteria comprise a nucleic acid sequence that is at least about 80%, at least about 85%, at least about 90%, at least about 95%, or at least about 99% homologous to a nucleic acid sequence encoding SEQ ID NO: 53 or a functional fragment thereof. In some embodiments, the genetically engineered bacteria are capable of producing SOD under inducing conditions, e.g., under a condition(s) associated with inflammation. In some embodiments, the genetically engineered bacteria are capable of producing SOD in low-oxygen conditions.

SEQ ID NO: 53
```
MATKAVCVLK GDGPVQGIIN FEQKESNGPV KVWGSIKGLT

EGLHGFHVHE FGDNTAGCTS AGPHFNPLSR KHGGPKDEER

HVGDLGNVTA DKDGVADVSI EDSVISLSGD HCIIGRTLVV

HEKADDLGKG GNEESTKTGN AGSRLACGVI GIAQ
```

In some embodiments, the genetically engineered bacteria are capable of producing GLP-2 or proglucagon. Glucagon-like peptide 2 (GLP-2) is produced by intestinal endocrine cells and stimulates intestinal growth and enhances gut barrier function. GLP-2 administration has therapeutic potential in treating IBD, short bowel syndrome, and small bowel enteritis (Yazbeck et al., 2009). The genetically engineered bacteria may comprise any suitable gene encoding GLP-2 or proglucagon, e.g., human GLP-2 or proglucagon. In some embodiments, a protease inhibitor, e.g., an inhibitor of dipeptidyl peptidase, is also administered to decrease GLP-2 degradation. In some embodiments, the genetically engineered bacteria express a degradation resistant GLP-2 analog, e.g., Teduglutide (Yazbeck et al., 2009). In some embodiments, the gene encoding GLP-2 or proglucagon is modified and/or mutated, e.g., to enhance stability, increase GLP-2 production, and/or increase gut barrier enhancing potency under inducing conditions. In some embodiments, the genetically engineered bacteria of the invention are capable of producing GLP-2 or proglucagon under inducing conditions. GLP-2 administration in a murine model of IBD is associated with reduced mucosal damage and inflammation, as well as a reduction in inflammatory mediators, such as TNF-α and IFN-γ. Further, GLP-2 supplementation may also lead to reduced mucosal myeloperoxidase in colitis/ileitis models. In some embodiments, the genetically engineered bacteria comprise a nucleic acid sequence encoding SEQ ID NO: 54 or a functional fragment thereof. In some embodiments, genetically engineered bacteria comprise a nucleic acid sequence that is at least about 80%, at least about 85%, at least about 90%, at least about 95%, or at least about 99% homologous to a nucleic acid sequence encoding SEQ ID NO: 54 or a functional fragment thereof. In some embodiments, the genetically engineered bacteria are capable of producing GLP-2 under inducing conditions, e.g., under a condition(s) associated with inflammation. In some embodiments, the genetically engineered bacteria are capable of producing GLP-2 in low-oxygen conditions.

SEQ ID NO: 54
HADGSFSDEMNTILDNLAARDFINWLIQTKITD

In some embodiments, the genetically engineered bacteria are capable of producing kynurenine. Kynurenine is a metabolite produced in the first, rate-limiting step of tryptophan catabolism. This step involves the conversion of tryptophan to kynurenine, and may be catalyzed by the ubiquitously-expressed enzyme indoleamine 2,3-dioxygenase (IDO-1), or by tryptophan dioxygenase (TDO), an enzyme which is primarily localized to the liver (Alvarado et al., 2015). Biopsies from human patients with IBD show elevated levels of IDO-1 expression compared to biopsies from healthy individuals, particularly near sites of ulceration (Ferdinande et al., 2008; Wolf et al., 2004). IDO-1 enzyme expression is similarly upregulated in trinitrobenzene sulfonic acid-and dextran sodium sulfate-induced mouse models of IBD; inhibition of IDO-1 significantly augments the inflammatory response caused by each inducer (Ciorba et al., 2010; Gurtner et al., 2003; Matteoli et al., 2010). Kynurenine has also been shown to directly induce apoptosis in neutrophils (El-Zaatari et al., 2014). Together, these observations suggest that IDO-1 and kynurenine play a role in limiting inflammation. The genetically engineered bacteria may comprise any suitable gene for producing kynurenine. In some embodiments, the genetically engineered bacteria may comprise a gene or gene cassette for producing a tryptophan transporter, a gene or gene cassette for producing IDO-1, and a gene or gene cassette for producing TDO. In some embodiments, the gene for producing kynurenine is modified and/or mutated, e.g., to enhance stability, increase kynurenine production, and/or increase anti-inflammatory potency under inducing conditions. In some embodiments, the engineered bacteria have enhanced uptake or import of tryptophan, e.g., comprise a transporter or other mechanism for increasing the uptake of tryptophan into the bacterial cell. In some embodiments, the genetically engineered bacteria are capable of producing kynurenine under inducing conditions, e.g., under a condition(s) associated with inflammation. In some embodiments, the genetically engineered bacteria are capable of producing kynurenine in low-oxygen conditions.

In some embodiments, the genetically engineered bacteria are capable of producing kynurenic acid. Kynurenic acid is produced from the irreversible transamination of kynurenine in a reaction catalyzed by the enzyme kynurenine-oxoglutarate transaminase. Kynurenic acid acts as an antagonist of ionotropic glutamate receptors (Turski et al., 2013). While glutamate is known to be a major excitatory neurotransmitter in the central nervous system, there is now evidence to suggest an additional role for glutamate in the peripheral nervous system. For example, the activation of NMDA glutamate receptors in the major nerve supply to the GI tract (i.e., the myenteric plexus) leads to an increase in gut motility (Forrest et al., 2003), but rats treated with kynurenic acid exhibit decreased gut motility and inflammation in the early phase of acute colitis (Varga et al., 2010). Thus, the elevated levels of kynurenic acid reported in IBD patients may represent a compensatory response to the increased activation of enteric neurons (Forrest et al., 2003). The genetically engineered bacteria may comprise any suitable gene for producing kynurenic acid. In some embodiments, the gene for producing kynurenic acid is modified and/or mutated, e.g., to enhance stability, increase kynurenic acid production, and/or increase anti-inflammatory potency under inducing conditions. In some embodiments, the genetically engineered bacteria are capable of producing kynurenic acid under inducing conditions, e.g., under a condition(s) associated with inflammation. In some embodiments, the genetically engineered bacteria are capable of producing kynurenic acid in low-oxygen conditions.

In some embodiments, the genetically engineered bacteria are capable of producing IL-19, IL-20, and/or IL-24. In some embodiments, the genetically engineered bacteria are capable of producing IL-19, IL-20, and/or IL-24 under inducing conditions, e.g., under a condition(s) associated with inflammation. In some embodiments, the genetically engineered bacteria are capable of producing IL-19, IL-20 and/or IL-24 in low-oxygen conditions.

In some embodiments, the genetically engineered bacteria of the invention are capable of producing a molecule that is capable of inhibiting a pro-inflammatory molecule. The genetically engineered bacteria may express any suitable inhibitory molecule, e.g., a single-chain variable fragment (scFv), antisense RNA, siRNA, or shRNA, that is capable of neutralizing one or more pro-inflammatory molecules, e.g., TNF, IFN-γ, IL-1β, IL-6, IL-8, IL-17, IL-18, IL-21, IL-23, IL-26, IL-32, Arachidonic acid, prostaglandins (e.g., $PGE_2$), $PGI_2$, serotonin, thromboxanes (e.g., $TXA_2$), leukotrienes (e.g., $LTB_4$), hepoxillin $A_3$, or chemokines (Keates et al., 2008; Ahmad et al., 2012). The genetically engineered bacteria may inhibit one or more pro-inflammatory molecules, e.g., TNF, IL-17. In some embodiments, the genetically engineered bacteria are capable of modulating one or more molecule(s) shown in Table 8. In some embodiments, the genetically engineered bacteria are capable of inhibiting, removing, degrading, and/or metabolizing one or more inflammatory molecules.

an enzyme that is capable of degrading an inflammatory molecule. For example, the genetically engineered bacteria of the invention are capable of expressing a gene cassette for producing butyrate, as well as a molecule or biosynthetic

TABLE 8

| Metabolites | Related bacteria | Potential biological functions |
|---|---|---|
| Bile acids: cholate, hyocholate, deoxycholate, chenodeoxycholate, a-muricholate, b-muricholate, w-muricholate, taurocholate, glycocholate, taurochenoxycholate, glycochenodeoxycholate, taurocholate, tauro-a-muricholate, tauro-b-muricholate, lithocholate, ursodeoxycholate, hyodeoxycholate, glycodeoxylcholate | *Lactobacillus, Bifidobacteria, Enterobacter, Bacteroides, Clostridium* | Absorb dietary fats and lipid-soluble vitamins, facilitate lipid absorption, maintain intestinal barrier function, signal systemic endocrine functions to regulate triglycerides, cholesterol, glucose and energy homeostasis. |
| Choline metabolites: methylamine, dimethylamine, trimethylamine, trimethylamine-N-oxide, dimethylglycine, betaine | *Faecalibacterium prausnitzii, Bifidobacterium* | Modulate lipid metabolism and glucose homeostasis. Involved in nonalcoholic fatty liver disease, dietary induced obesity, diabetes, and cardiovascular disease. |
| Phenolic, benzoyl, and phenyl derivatives: benzoic acid, hippuric acid, 2-hydroxyhippuric acid, 2-hydroxybenzoic acid, 3-hydroxyhippuric acid, 3-hydroxybenzoic acid, 4 hydroxybenzoic acid, 3hydroxyphenylpropionate, 4-hydroxyphenylpropionate, 3-hydroxycinnamate, 4-methylphenol, tyrosine, phenylalanine, 4-cresol, 4-cresyl sulfate, 4-cresyl glucuronide, 4-hydroxyphenylacetate | *Clostridium difficile, F. prausnitzii, Bifidobacterium, Subdoligranulum, Lactobacillus* | Detoxification of xenobiotics; indicate gut microbial composition and activity; utilize polyphenols. Urinary hippuric acid may be a biomarker of hypertension and obesity in humans. Urinary 4-hydroxyphenylacetate, 4-cresol, and phenylacetate are elevated in colorectal cancer. Urinary 4-cresyl sulfate is elevated in children with severe autism. |
| Indole derivatives: N-acetyltryptophan, indoleacetate, indoleacetylglycine (IAG), indole, indoxyl sulfate, indole-3-propionate, melatonin, melatonin 6-sulfate, serotonin, 5-hydroxyindole | *Clostridium sporogenes, E. coli* | Protect against stress-induced lesions in the GI tract; modulate expression of proinflammatory genes, increase expression of anti-inflammatory genes, strengthen epithelial cell barrier properties. Implicated in GI pathologies, brain-gut axis, and a few neurological conditions. |
| Vitamins: vitamin K, vitamin B12, biotin, folate, thiamine, riboflavin, pyridoxine | *Bifidobacterium* | Provide complementary endogenous sources of vitamins, strengthen immune function, exert epigenetic effects to regulate cell proliferation. |
| Polyamines: putrescine, cadaverine, spermidine, spermine | *Campylobacter jejuni, Clostridium saccharolyticum* | Exert genotoxic effects on the host, anti-inflammatory and antitumoral effects. Potential tumor markers. |
| Lipids: conjugated fatty acids, LPS, peptidoglycan, acylglycerols, sphingomyelin, cholesterol, phosphatidylcholines, phosphoethanolamines, triglycerides | *Bifidobacterium, Roseburia, Lactobacillus, Klebsiella, Enterobacter, Citrobacter, Clostridium* | Impact intestinal permeability, activate intestinebrain-liver neural axis to regulate glucose homeostasis; LPS induces chronic systemic inflammation; conjugated fatty acids improve hyperinsulinemia, enhance the immune system and alter lipoprotein profiles. |
| Others: D-lactate, formate, methanol, ethanol, succinate, lysine, glucose, urea, a-ketoisovalerate, creatine, creatinine, endocannabinoids, 2-arachidonoylglycerol (2-AG), N-arachidonoylethanolamide, LPS | *Bacteroides, Pseudobutyrivibrio, Ruminococcus, Faecalibacterium* | Direct or indirect synthesis or utilization of compounds or modulation of linked pathways including endocannabinoid system. |

In some embodiments, the genetically engineered bacteria are capable of producing an anti-inflammation and/or gut barrier enhancer molecule and further producing a molecule that is capable of inhibiting an inflammatory molecule. In some embodiments, the genetically engineered bacteria of the invention are capable of producing an anti-inflammation and/or gut barrier enhancer molecule and further producing pathway for inhibiting, removing, degrading, and/or metabolizing an inflammatory molecule, e.g., $PGE_2$.

RNA interference (RNAi) is a post-transcriptional gene silencing mechanism in plants and animals. RNAi is activated when microRNA (miRNA), double-stranded RNA (dsRNA), or short hairpin RNA (shRNA) is processed into short interfering RNA (siRNA) duplexes (Keates et al., 2008). RNAi can be "activated in vitro and in vivo by non-pathogenic bacteria engineered to manufacture and deliver shRNA to target cells" such as mammalian cells (Keates et al., 2008). In some embodiments, the genetically engineered bacteria of the invention induce RNAi-mediated gene silencing of one or more pro-inflammatory molecules in low-oxygen conditions. In some embodiments, the genetically engineered bacteria produce siRNA targeting TNF in low-oxygen conditions.

Single-chain variable fragments (scFv) are "widely used antibody fragments . . . produced in prokaryotes" (Frenzel et al., 2013). scFv lacks the constant domain of a traditional antibody and expresses the antigen-binding domain as a single peptide. Bacteria such as *Escherichia coli* are capable of producing scFv that target pro-inflammatory cytokines, e.g., TNF (Hristodorov et al., 2014). In some embodiments, the genetically engineered bacteria of the invention express a binding protein for neutralizing one or more pro-inflammatory molecules in low-oxygen conditions. In some embodiments, the genetically engineered bacteria produce scFv targeting TNF in low-oxygen conditions. In some embodiments, the genetically engineered bacteria produce both scFv and siRNA targeting one or more pro-inflammatory molecules in low-oxygen conditions (see, e.g., Xiao et al., 2014).

One of skill in the art would appreciate that additional genes and gene cassettes capable of producing anti-inflammation and/or gut barrier function enhancer molecules are known in the art and may be expressed by the genetically engineered bacteria of the invention. In some embodiments, the gene or gene cassette for producing a therapeutic molecule also comprises additional transcription and translation elements, e.g., a ribosome binding site, to enhance expression of the therapeutic molecule.

In some embodiments, the genetically engineered bacteria produce two or more anti-inflammation and/or gut barrier function enhancer molecules. In certain embodiments, the two or more molecules behave synergistically to reduce gut inflammation and/or enhance gut barrier function. In some embodiments, the genetically engineered bacteria express at least one anti-inflammation molecule and at least one gut barrier function enhancer molecule. In certain embodiments, the genetically engineered bacteria express IL-10 and GLP-2. In alternate embodiments, the genetically engineered bacteria express IL-10 and butyrate.

In some embodiments, the genetically engineered bacteria are capable of producing IL-2, IL-10, IL-22, IL-27, propionate, and butyrate. In some embodiments, the genetically engineered bacteria are capable of producing IL-10, IL-27, GLP-2, and butyrate. In some embodiments, the genetically engineered bacteria are capable of producing GLP-2, IL-10, IL-22, SOD, butyrate, and propionate. In some embodiments, the genetically engineered bacteria are capable of GLP-2, IL-2, IL-10, IL-22, IL-27, SOD, butyrate, and propionate. Any suitable combination of therapeutic molecules may be produced by the genetically engineered bacteria.

Inducible Regulatory Regions
Oxygen Level-dependent Regulation

The genetically engineered bacteria of the invention comprise a promoter that is directly or indirectly induced by exogenous environmental conditions. In some embodiments, a gene or gene cassette for producing an anti-inflammation and/or gut barrier function enhancer molecule is operably linked to an oxygen level-dependent promoter or regulatory region comprising said promoter. In some embodiments, the gene or gene cassette is operably linked to an oxygen level-dependent promoter such that the therapeutic molecule is expressed in low-oxygen, microaerobic, or anaerobic conditions. For example, in low-oxygen conditions, the oxygen level-dependent promoter is activated by a corresponding oxygen level-sensing transcription factor, thereby driving production of the therapeutic molecule.

In certain embodiments, the genetically engineered bacteria comprise a gene or a gene cassette for producing an anti-inflammation and/or gut barrier function enhancer molecule expressed under the control of a fumarate and nitrate reductase regulator (FNR)-responsive promoter, an anaerobic regulation of arginine deiminiase and nitrate reduction (ANR)-responsive promoter, or a dissimilatory nitrate respiration regulator (DNR)-responsive promoter, which are capable of being regulated by the transcription factors FNR, ANR, or DNR, respectively.

In certain embodiments, the genetically engineered bacteria comprise a FNR-responsive promoter. In *E. coli*, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. In some embodiments, multiple distinct FNR nucleic acid sequences are inserted in the genetically engineered bacteria.

In alternate embodiments, the promoter is an alternate oxygen level-dependent promoter, e.g., DNR (Trunk et al., 2010) or ANR (Ray et al., 1997). In *P. aeruginosa*, the anaerobic regulation of ANR is "required for the expression of physiological functions which are inducible under oxygen-limiting or anaerobic conditions" (Sawers, 1991; Winteler et al., 1996). *P. aeruginosa* ANR is homologous with *E. coli* FNR, and "the consensus FNR site (TTGAT----ATCAA) was recognized efficiently by ANR and FNR" (Winteler et al., 1996). Like FNR, in the anaerobic state, ANR activates numerous genes responsible for adapting to anaerobic growth. In the aerobic state, ANR is inactive. *Pseudomonas fluorescens, Pseudomonas putida, Pseudomonas syringae*, and *Pseudomonas mendocina* all have functional analogs of ANR (Zimmermann et al., 1991). Promoters that are regulated by ANR are known in the art, e.g., the promoter of the arcDABC operon (see, e.g., Hasegawa et al., 1998).

The FNR family also includes the dissimilatory nitrate respiration regulator (DNR) (Arai et al., 1995), a transcription factor which is required in conjunction with ANR for "anaerobic nitrate respiration of *Pseudomonas aeruginosa*" (Hasegawa et al., 1998). For certain genes, the FNR-binding motifs "are probably recognized only by DNR" (Hasegawa et al., 1998). In some embodiments, gene expression is further optimized by methods known in the art, e.g., by optimizing ribosomal binding sites and/or increasing mRNA stability.

FNR promoter sequences are known in the art, and any suitable FNR promoter sequence(s) may be used in the genetically engineered bacteria of the invention. Any suitable FNR promoter(s) may be combined with any suitable gene or gene cassette for producing an anti-inflammation and/or gut barrier function enhancer molecule. Non-limiting FNR promoter sequences are provided in Table 9. In some embodiments, the genetically engineered bacteria of the invention comprise one or more of: SEQ ID NO: 55, SEQ ID NO: 56, nirB1 promoter (SEQ ID NO: 57), nirB2 promoter (SEQ ID NO: 58), nirB3 promoter (SEQ ID NO: 59), ydfZ promoter (SEQ ID NO: 60), nirB promoter fused to a strong ribosome binding site (SEQ ID NO: 61), ydfZ promoter fused to a strong ribosome binding site (SEQ ID NO: 62), fnrS, an anaerobically induced small RNA gene (fnrS1 promoter SEQ ID NO: 63 or fnrS2 promoter SEQ ID NO: 64), nirB promoter fused to a crp binding site (SEQ ID NO: 65), and fnrS fused to a crp binding site (SEQ ID NO: 66). In some embodiments, genetically engineered bacteria comprise a nucleic acid sequence that is at least about 80%, at least about 85%, at least about 90%, at least about 95%, or at least about 99% homologous to the DNA sequence of SEQ ID NO: 55, 56, 57, 58, 59, 60, 61, 62, 63, 64, 65, or 66, or a functional fragment thereof.

TABLE 9

| FNR-responsive regulatory region | 12345678901234567890123456789012345678901234567890 |
|---|---|
| SEQ ID NO: 55 | ATCCCCATCACTCTTGATGGAGATCAATTCCCCAAGCTGCTAGAGCGTTA<br>CCTTGCCCTTAAACATTAGCAATGTCGATTTATCAGAGGGCCGACAGGCT<br>CCCACAGGAGAAAACCG |
| SEQ ID NO: 56 | CTCTTGATCGTTATCAATTCCCACGCTGTTTCAGAGCGTTACCTTGCCCT<br>TAAACATTAGCAATGTCGATTTATCAGAGGGCCGACAGGCTCCCACAGGA<br>GAAAACCG |
| nirB1<br>SEQ ID NO: 57 | GTCAGCATAACACCCTGACCTCTCATTAATTGTTCATGCCGGGCGGCACT<br>ATCGTCGTCCGGCCTTTTCCTCTCTTACTCTGCTACGTACATCTATTTCT<br>ATAAATCCGTTCAATTTGTCTGTTTTTTGCACAAACATGAAATATCAGAC<br>AATTCCGTGACTTAAGAAAATTTATACAAATCAGCAATATACCCCTTAAG<br>GAGTATATAAAGGTGAATTTGATTTACATCAATAAGCGGGGTTGCTGAAT<br>CGTTAAGGTAGGCGGTAATAG<u>AAAAGAAATCGAGGCAAAA</u> |
| nirB2<br>SEQ ID NO: 58 | CGGCCCGATCGTTGAACATAGCGGTCCGCAGGCGGCACTGCTTACAGCAA<br>ACGGTCTGTACGCTGTCGTCTTTGTGATGTGCTTCCTGTTAGGTTTCGTC<br>AGCCGTCACCGTCAGCATAACACCCTGACCTCTCATTAATTGCTCATGCC<br>GGACGGCACTATCGTCGTCCGGCCTTTTCCTCTCTTCCCCCGCTACGTGC<br>ATCTATTTCTATAAACCCGCTCATTTTGTCTATTTTTTGCACAAACATGA<br>AATATCAGACAATTCCGTGACTTAAGAAAATTTATACAAATCAGCAATAT<br>ACCCATTAAGGAGTATATAAAGGTGAATTTGATTTACATCAATAAGCGGG<br>GTTGCTGAATCGTTAAGGTAGGCGGTAATAGAAAAGAAATCGAGGCAAAA<br>atgtttgtttaactttaagaaggagatatacat |
| nirB3<br>SEQ ID NO: 59 | GTCAGCATAACACCCTGACCTCTCATTAATTGCTCATGCCGGACGGCACT<br>ATCGTCGTCCGGCCTTTTCCTCTCTTCCCCCGCTACGTGCATCTATTTCT<br>ATAAACCCGCTCATTTTGTCTATTTTTTGCACAAACATGAAATATCAGAC<br>AATTCCGTGACTTAAGAAAATTTATACAAATCAGCAATATACCCATTAAG<br>GAGTATATAAAGGTGAATTTGATTTACATCAATAAGCGGGGTTGCTGAAT<br>CGTTAAGGTAGGCGGTAATAGAAAAGAAATCGAGGCAAAA |
| ydfZ<br>SEQ ID NO: 60 | ATTTCCTCTCATCCCATCCGGGGTGAGAGTCTTTTCCCCCGACTTATGGC<br>TCATGCATGCATCAAAAAAGATGTGAGCTTGATCAAAAACAAAAAATATT<br>TCACTCGACAGGAGTATTTATATTGCGCCCGTTACGTGGGCTTCGACTGT<br>AAATC<u>AGAAAGGAGAAAACACCT</u> |
| nirB + RBS<br>SEQ ID NO: 61 | GTCAGCATAACACCCTGACCTCTCATTAATTGTTCATGCCGGGCGGCACT<br>ATCGTCGTCCGGCCTTTTCCTCTCTTACTCTGCTACGTACATCTATTTCT<br>ATAAATCCGTTCAATTTGTCTGTTTTTTGCACAAACATGAAATATCAGAC<br>AATTCCGTGACTTAAGAAAATTTATACAAATCAGCAATATACCCCTTAAG<br>GAGTATATAAAGGTGAATTTGATTTACATCAATAAGCGGGGTTGCTGAAT<br>CGTTAAGGATCC<u>CTCTAGAAATAATTTTGTTTAACTTTAAGAAGGAGATA<br>TACAT</u> |
| ydfZ + RBS<br>SEQ ID NO: 62 | CATTTCCTCTCATCCCATCCGGGGTGAGAGTCTTTTCCCCCGACTTATGG<br>CTCATGCATGCATCAAAAAAGATGTGAGCTTGATCAAAAACAAAAAATAT<br>TTCACTCGACAGGAGTATTTATATTGCGCCCGGATCC<u>CTCTAGAAATAAT<br>TTTGTTTAACTTTAAGAAGGAGATATACAT</u> |
| fnrS1<br>SEQ ID NO: 63 | AGTTGTTCTTATTGGTGGTGTTGCTTTATGGTTGCATCGTAGTAAATGGT<br>TGTAACAAAAGCAATTTTTCCGGCTGTCTGTATACAAAAACGCCGTAAAG<br>TTTGAGCGAAGTCAATAAACTCTCTACCCATTCAGGGCAATATCTCTCTT<br>GGATCC<u>CTCTAGAAATAATTTTGTTTAACTTTAAGAAGGAGATATACAT</u> |
| fnrS2<br>SEQ ID NO: 64 | AGTTGTTCTTATTGGTGGTGTTGCTTTATGGTTGCATCGTAGTAAATGGT<br>TGTAACAAAAGCAATTTTTCCGGCTGTCTGTATACAAAAACGCCGCAAAG<br>TTTGAGCGAAGTCAATAAACTCTCTACCCATTCAGGGCAATATCTCTCTT<br><u>GGATCCAAAGTGAACTCTAGAAATAATTTTGTTTAACTTTAAGAAGGAGA<br>TATACAT</u> |
| nirB + crp<br>SEQ ID NO: 65 | TCGTCTTTGTGATGTGCTTCCTGTTAGGTTTCGTCAGCCGTCACCGTCAG<br>CATAACACCCTGACCTCTCATTAATTGCTCATGCCGGACGGCACTATCGT<br>CGTCCGGCCTTTTCCTCTCTTCCCCCGCTACGTGCATCTATTTCTATAAA<br>CCCGCTCATTTTGTCTATTTTTTGCACAAACATGAAATATCAGACAATTC<br>CGTGACTTAAGAAAATTTATACAAATCAGCAATATACCCATTAAGGAGTA<br>TATAAAGGTGAATTTGATTTACATCAATAAGCGGGGTTGCTGAATCGTTA |

TABLE 9-continued

| FNR-responsive regulatory region | 123456789012345678901234567890123456789012345678 90 |
|---|---|
| | AGGTAGaaatgtgatctagttcacatttGCGGTAATAGAAAAGAAATCGA GGCAAAAatgtttgtttaactttaagaaggagatatacat |
| fnrS + crp SEQ ID NO: 66 | AGTTGTTCTTATTGGTGGTGTTGCTTTATGGTTGCATCGTAGTAAATGGT TGTAACAAAAGCAATTTTTCCGGCTGTCTGTATACAAAAACGCCGCAAAG TTTGAGCGAAGTCAATAAACTCTCTACCCATTCAGGGCAATATCTCTCaa atgtgatctagttcacatttttgtttaactttaagaaggagatatacat |

In other embodiments, the gene or gene cassette for producing an anti-inflammation and/or gut barrier function enhancer molecule is expressed under the control of an oxygen level-dependent promoter fused to a binding site for a transcriptional activator, e.g., CRP. CRP (cyclic AMP receptor protein or catabolite activator protein or CAP) plays a major regulatory role in bacteria by repressing genes responsible for the uptake, metabolism, and assimilation of less favorable carbon sources when rapidly metabolizable carbohydrates, such as glucose, are present (Wu et al., 2015). This preference for glucose has been termed glucose repression, as well as carbon catabolite repression (Deutscher, 2008; Görke and Stülke, 2008). In some embodiments, the gene or gene cassette for producing an anti-inflammation and/or gut barrier function enhancer molecule is controlled by an oxygen level-dependent promoter fused to a CRP binding site. In some embodiments, the gene or gene cassette for producing an anti-inflammation and/or gut barrier function enhancer molecule is controlled by a FNR promoter fused to a CRP binding site. In these embodiments, cyclic AMP binds to CRP when no glucose is present in the environment. This binding causes a conformational change in CRP, and allows CRP to bind tightly to its binding site. CRP binding then activates transcription of the gene or gene cassette by recruiting RNA polymerase to the FNR promoter via direct protein-protein interactions. In the presence of glucose, cyclic AMP does not bind to CRP and transcription of the gene or gene cassette for producing an anti-inflammation and/or gut barrier function enhancer molecule is repressed. In some embodiments, an oxygen level-dependent promoter (e.g., an FNR promoter) fused to a binding site for a transcriptional activator is used to ensure that the gene or gene cassette for producing an anti-inflammation and/or gut barrier function enhancer molecule is not expressed under anaerobic conditions when sufficient amounts of glucose are present, e.g., by adding glucose to growth media in vitro.

In some embodiments, the genetically engineered bacteria comprise an oxygen level-dependent promoter from a different species, strain, or substrain of bacteria. In some embodiments, the genetically engineered bacteria comprise an oxygen level-sensing transcription factor, e.g., FNR, ANR or DNR, from a different species, strain, or substrain of bacteria. In some embodiments, the genetically engineered bacteria comprise an oxygen level-sensing transcription factor and corresponding promoter from a different species, strain, or substrain of bacteria. The heterologous oxygen level-dependent transcription factor and/or promoter may increase the production of the anti-inflammation and/or gut barrier enhancer molecule in low-oxygen conditions, as compared to the native transcription factor and promoter in the bacteria under the same conditions. In certain embodiments, the non-native oxygen level-dependent transcription factor is a FNR protein from *N. gonorrhoeae* (see, e.g., Isabella et al., 2011). In some embodiments, the corresponding wild-type transcription factor is deleted or mutated to reduce or eliminate wild-type activity. In alternate embodiments, the corresponding wild-type transcription factor is left intact and retains wild-type activity. In some embodiments, the heterologous transcription factor minimizes or eliminates off-target effects on endogenous regulatory regions and genes in the genetically engineered bacteria.

In some embodiments, the genetically engineered bacteria comprise a wild-type gene encoding an oxygen level-dependent transcription factor, such as FNR, ANR or DNR, and a corresponding promoter that is mutated relative to the wild-type promoter from bacteria of the same subtype. The mutated promoter increases the production of an anti-inflammation and/or gut barrier enhancer molecule in low-oxygen conditions, as compared to the wild-type promoter under the same conditions. In some embodiments, the genetically engineered bacteria comprise a wild-type oxygen level-dependent promoter, e.g., a FNR-, ANR- or DNR-responsive promoter, and a corresponding transcription factor that is mutated relative to the wild-type transcription factor from bacteria of the same subtype. The mutant transcription factor increases the expression of the anti-inflammation and/or gut barrier enhancer molecule in low-oxygen conditions, as compared to the wild-type transcription factor under the same conditions. In certain embodiments, the mutant oxygen level-dependent transcription factor is a FNR protein comprising amino acid substitutions that enhance dimerization and FNR activity (see, e.g., Moore et al., 2006). In some embodiments, both the oxygen level-sensing transcription factor and corresponding promoter are mutated relative to the wild-type sequences from bacteria of the same subtype in order to increase expression of the anti-inflammation and/or gut barrier enhancer molecule in low-oxygen conditions.

In some embodiments, the genetically engineered bacteria of the invention comprise a gene encoding an oxygen level-sensing transcription factor, e.g., FNR, ANR or DNR, that is controlled by its native promoter, an inducible promoter, a promoter that is stronger than the native promoter, e.g., a GlnRS promoter, a P(Bla) promoter, or a constitutive promoter. In some instances, it may be advantageous to express the oxygen level-dependent transcription factor under the control of an inducible promoter in order to enhance expression stability. In some embodiments, expression of the oxygen level-dependent transcription factor is controlled by a different promoter than the promoter that controls expression of the therapeutic molecule. In some embodiments, expression of the oxygen level-dependent transcription factor is controlled by the same promoter that controls expression of the therapeutic molecule. In some embodiments, the oxygen level-dependent transcription factor and therapeutic molecule are divergently transcribed from a promoter region.

In some embodiments, the genetically engineered bacteria of the invention comprise multiple copies of the endogenous gene encoding the oxygen level-sensing transcription factor, e.g., the fnr gene. In some embodiments, the gene encoding the oxygen level-sensing transcription factor is present on a plasmid. In some embodiments, the gene encoding the oxygen level-sensing transcription factor and the gene or gene cassette for producing the therapeutic molecule are present on different plasmids. In some embodiments, the gene encoding the oxygen level-sensing transcription factor and the gene or gene cassette for producing the therapeutic molecule are present on the same plasmid. In some embodiments, the gene encoding the oxygen level-sensing transcription factor is present on a chromosome. In some embodiments, the gene encoding the oxygen level-sensing transcription factor and the gene or gene cassette for producing the therapeutic molecule are present on different chromosomes. In some embodiments, the gene encoding the oxygen level-sensing transcription factor and the gene or gene cassette for producing the therapeutic molecule are present on the same chromosome.

In some embodiments, the gene or gene cassette for producing the anti-inflammation and/or gut barrier function enhancer molecule is present on a plasmid and operably linked to a promoter that is induced by low-oxygen conditions. In some embodiments, the gene or gene cassette for producing the anti-inflammation and/or gut barrier function enhancer molecule is present in the chromosome and operably linked to a promoter that is induced by low-oxygen conditions. In some embodiments, the gene or gene cassette for producing the anti-inflammation and/or gut barrier function enhancer molecule is present on a chromosome and operably linked to a promoter that is induced by exposure to tetracycline. In some embodiments, the gene or gene cassette for producing the anti-inflammation and/or gut barrier function enhancer molecule is present on a plasmid and operably linked to a promoter that is induced by exposure to tetracycline. In some embodiments, expression is further optimized by methods known in the art, e.g., by optimizing ribosomal binding sites, manipulating transcriptional regulators, and/or increasing mRNA stability.

In some embodiments, the genetically engineered bacteria comprise a stably maintained plasmid or chromosome carrying the gene(s) or gene cassette(s) capable of producing an anti-inflammation and/or gut barrier function enhancer molecule, such that the gene(s) or gene cassette(s) can be expressed in the host cell, and the host cell is capable of survival and/or growth in vitro, e.g., in medium, and/or in vivo, e.g., in the gut. In some embodiments, a bacterium may comprise multiple copies of the gene or gene cassette for producing the anti-inflammation and/or gut barrier function enhance molecule. In some embodiments, the gene or gene cassette is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, the gene or gene cassette is expressed on a high-copy plasmid. In some embodiments, the high-copy plasmid may be useful for increasing gene or gene cassette expression. In some embodiments, gene or gene cassette is expressed on a chromosome.

In some embodiments, the genetically engineered bacteria may comprise multiple copies of the gene(s) or gene cassette(s) capable of producing an anti-inflammation and/or gut barrier function enhancer molecule. In some embodiments, the gene(s) or gene cassette(s) capable of producing an anti-inflammation and/or gut barrier function enhancer molecule is present on a plasmid and operably linked to an oxygen level-dependent promoter. In some embodiments, the gene(s) or gene cassette(s) capable of producing an anti-inflammation and/or gut barrier function enhancer molecule is present in a chromosome and operably linked to an oxygen level-dependent promoter.

In some embodiments, the genetically engineered bacteria of the invention produce at least one anti-inflammation and/or gut barrier enhancer molecule in low-oxygen conditions to reduce local gut inflammation by at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold as compared to unmodified bacteria of the same subtype under the same conditions. Inflammation may be measured by methods known in the art, e.g., counting disease lesions using endoscopy; detecting T regulatory cell differentiation in peripheral blood, e.g., by fluorescence activated sorting; measuring T regulatory cell levels; measuring cytokine levels; measuring areas of mucosal damage; assaying inflammatory biomarkers, e.g., by qPCR; PCR arrays; transcription factor phosphorylation assays; immunoassays; and/or cytokine assay kits (Mesoscale, Cayman Chemical, Qiagen).

In some embodiments, the genetically engineered bacteria produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more of an anti-inflammation and/or gut barrier enhancer molecule in low-oxygen conditions than unmodified bacteria of the same subtype under the same conditions. Certain unmodified bacteria will not have detectable levels of the anti-inflammation and/or gut barrier enhancer molecule. In embodiments using genetically modified forms of these bacteria, the anti-inflammation and/or gut barrier enhancer molecule will be detectable in low-oxygen conditions.

In certain embodiments, the anti-inflammation and/or gut barrier enhancer molecule is butyrate. Methods of measuring butyrate levels, e.g., by mass spectrometry, gas chromatography, high-performance liquid chromatography (HPLC), are known in the art (see, e.g., Aboulnaga et al., 2013). In some embodiments, butyrate is measured as butyrate level/bacteria optical density (OD). In some embodiments, measuring the activity and/or expression of one or more gene products in the butyrogenic gene cassette serves as a proxy measurement for butyrate production. In some embodiments, the bacterial cells of the invention are harvested and lysed to measure butyrate production. In alternate embodiments, butyrate production is measured in the bacterial cell medium. In some embodiments, the genetically engineered bacteria produce at least about 1 nM/OD, at least about 10 nM/OD, at least about 100 nM/OD, at least about 500 nM/OD, at least about 1 µM/OD, at least about 10 µM/OD, at least about 100 µM/OD, at least about 500 µM/OD, at least about 1 mM/OD, at least about 2 mM/OD, at least about 3 mM/OD, at least about 5 mM/OD, at least about 10 mM/OD, at least about 20 mM/OD, at least about 30 mM/OD, or at least about 50 mM/OD of butyrate in low-oxygen conditions.

In certain embodiments, the anti-inflammation and/or gut barrier enhancer molecule is propionate. Methods of measuring propionate levels, e.g., by mass spectrometry, gas chromatography, high-performance liquid chromatography (HPLC), are known in the art (see, e.g., Hillman, 1978; Lukovac et al., 2014). In some embodiments, measuring the activity and/or expression of one or more gene products in the propionate gene cassette serves as a proxy measurement for propionate production. In some embodiments, the bacterial cells of the invention are harvested and lysed to measure propionate production. In alternate embodiments, propionate production is measured in the bacterial cell medium. In some embodiments, the genetically engineered bacteria produce at least about 1 µM, at least about 10 µM, at least about 100 µM, at least about 500 µM, at least about 1 mM, at least about 2 mM, at least about 3 mM, at least about 5 mM, at least about 10 mM, at least about 15 mM, at least about 20 mM, at least about 30 mM, at least about 40 mM, or at least about 50 mM of propionate in low-oxygen conditions.

RNS-dependent Regulation

In some embodiments, the genetically engineered bacteria of the invention comprise a tunable regulatory region that is directly or indirectly controlled by a transcription factor that is capable of sensing at least one reactive nitrogen species. The tunable regulatory region is operatively linked to a gene or gene cassette capable of directly or indirectly driving the expression of an anti-inflammation and/or gut barrier function enhancer molecule, thus controlling expression of the molecule relative to RNS levels. For example, the tunable regulatory region is a RNS-inducible regulatory region, and the molecule is butyrate; when RNS is present, e.g., in an inflamed tissue, a RNS-sensing transcription factor binds to and/or activates the regulatory region and drives expression of the butyrogenic gene cassette, thereby producing butyrate, which exerts anti-inflammation and/or gut barrier enhancing effects. Subsequently, when inflammation is ameliorated, RNS levels are reduced, and butyrate production is decreased or eliminated.

In some embodiments, the tunable regulatory region is a RNS-inducible regulatory region; in the presence of RNS, a transcription factor senses RNS and activates the RNS-inducible regulatory region, thereby driving expression of an operatively linked gene or gene cassette. In some embodiments, the transcription factor senses RNS and subsequently binds to the RNS-inducible regulatory region, thereby activating downstream gene expression. In alternate embodiments, the transcription factor is bound to the RNS-inducible regulatory region in the absence of RNS; when the transcription factor senses RNS, it undergoes a conformational change, thereby inducing downstream gene expression.

In some embodiments, the tunable regulatory region is a RNS-inducible regulatory region, and the transcription factor that senses RNS is NorR. NorR "is an NO-responsive transcriptional activator that regulates expression of the norVW genes encoding flavorubredoxin and an associated flavoprotein, which reduce NO to nitrous oxide" (Spiro 2006). The genetically engineered bacteria of the invention may comprise any suitable RNS-responsive regulatory region from a gene that is activated by NorR. Genes that are capable of being activated by NorR are known in the art (see, e.g., Spiro, 2006; Vine et al., 2011; Karlinsey et al., 2012; Table 1). In certain embodiments, the genetically engineered bacteria of the invention comprise a RNS-inducible regulatory region from norVW that is operatively linked to a gene or gene cassette, e.g., a butyrogenic gene cassette. In the presence of RNS, a NorR transcription factor senses RNS and activates to the norVW regulatory region, thereby driving expression of the operatively linked butyrogenic gene cassette and producing butyrate.

In some embodiments, the tunable regulatory region is a RNS-inducible regulatory region, and the transcription factor that senses RNS is DNR. DNR (dissimilatory nitrate respiration regulator) "promotes the expression of the nir, the nor and the nos genes" in the presence of nitric oxide (Castiglione et al., 2009). The genetically engineered bacteria of the invention may comprise any suitable RNS-responsive regulatory region from a gene that is activated by DNR. Genes that are capable of being activated by DNR are known in the art (see, e.g., Castiglione et al., 2009; Giardina et al., 2008). In certain embodiments, the genetically engineered bacteria of the invention comprise a RNS-inducible regulatory region from norCB that is operatively linked to a gene or gene cassette, e.g., a butyrogenic gene cassette. In the presence of RNS, a DNR transcription factor senses RNS and activates to the norCB regulatory region, thereby driving expression of the operatively linked butyrogenic gene cassette and producing butyrate. In some embodiments, the DNR is *Pseudomonas aeruginosa* DNR.

In some embodiments, the tunable regulatory region is a RNS-derepressible regulatory region, and binding of a corresponding transcription factor represses downstream gene expression; in the presence of RNS, the transcription factor no longer binds to the regulatory region, thereby derepressing the operatively linked gene or gene cassette.

In some embodiments, the tunable regulatory region is a RNS-derepressible regulatory region, and the transcription factor that senses RNS is NsrR. NsrR is "an Rrf2-type transcriptional repressor [that] can sense NO and control the expression of genes responsible for NO metabolism" (Isabella et al., 2009). The genetically engineered bacteria of the invention may comprise any suitable RNS-responsive regulatory region from a gene that is repressed by NsrR. In some embodiments, the NsrR is *Neisseria gonorrhoeae* NsrR. Genes that are capable of being repressed by NsrR are known in the art (see, e.g., Isabella et al., 2009; Dunn et al., 2010; Table 1). In certain embodiments, the genetically engineered bacteria of the invention comprise a RNS-derepressible regulatory region from norB that is operatively linked to a gene or gene cassette, e.g., a butyrogenic gene cassette. In the presence of RNS, an NsrR transcription factor senses RNS and no longer binds to the norB regulatory region, thereby derepressing the operatively linked butyrogenic gene cassette and producing butyrate.

In some embodiments, it is advantageous for the genetically engineered bacteria to express a RNS-sensing transcription factor that does not regulate the expression of a significant number of native genes in the bacteria. In some embodiments, the genetically engineered bacterium of the invention expresses a RNS-sensing transcription factor from a different species, strain, or substrain of bacteria, wherein the transcription factor does not bind to regulatory sequences in the genetically engineered bacterium of the invention. In some embodiments, the genetically engineered bacterium of the invention is *Escherichia coli*, and the RNS-sensing transcription factor is NsrR, e.g., from is *Neisseria gonorrhoeae*, wherein the *Escherichia coli* does not comprise binding sites for said NsrR. In some embodiments, the heterologous transcription factor minimizes or eliminates off-target effects on endogenous regulatory regions and genes in the genetically engineered bacteria.

In some embodiments, the tunable regulatory region is a RNS-repressible regulatory region, and binding of a corresponding transcription factor represses downstream gene expression; in the presence of RNS, the transcription factor senses RNS and binds to the RNS-repressible regulatory region, thereby repressing expression of the operatively linked gene or gene cassette. In some embodiments, the RNS-sensing transcription factor is capable of binding to a regulatory region that overlaps with part of the promoter sequence. In alternate embodiments, the RNS-sensing transcription factor is capable of binding to a regulatory region that is upstream or downstream of the promoter sequence.

In these embodiments, the genetically engineered bacteria may comprise a two repressor activation regulatory circuit, which is used to express an anti-inflammation and/or gut barrier function enhancer molecule. The two repressor activation regulatory circuit comprises a first RNS-sensing repressor and a second repressor, which is operatively linked to a gene or gene cassette, e.g., a butyrogenic gene cassette. In one aspect of these embodiments, the RNS-sensing repressor inhibits transcription of the second repressor, which inhibits the transcription of the gene or gene cassette. Examples of second repressors useful in these embodiments include, but are not limited to, TetR, C1, and LexA. In the absence of binding by the first repressor (which occurs in the absence of RNS), the second repressor is transcribed, which represses expression of the gene or gene cassette, e.g., a butyrogenic gene cassette. In the presence of binding by the first repressor (which occurs in the presence of RNS), expression of the second repressor is repressed, and the gene or gene cassette, e.g., a butyrogenic gene cassette, is expressed.

A RNS-responsive transcription factor may induce, derepress, or repress gene expression depending upon the regulatory region sequence used in the genetically engineered bacteria. One or more types of RNS-sensing transcription factors and corresponding regulatory region sequences may be present in genetically engineered bacteria. In some embodiments, the genetically engineered bacteria comprise one type of RNS-sensing transcription factor, e.g., NsrR, and one corresponding regulatory region sequence, e.g., from norB. In some embodiments, the genetically engineered bacteria comprise one type of RNS-sensing transcription factor, e.g., NsrR, and two or more different corresponding regulatory region sequences, e.g., from norB and aniA. In some embodiments, the genetically engineered bacteria comprise two or more types of RNS-sensing transcription factors, e.g., NsrR and NorR, and two or more corresponding regulatory region sequences, e.g., from norB and norR, respectively. One RNS-responsive regulatory region may be capable of binding more than one transcription factor. In some embodiments, the genetically engineered bacteria comprise two or more types of RNS-sensing transcription factors and one corresponding regulatory region sequence. Nucleic acid sequences of several RNS-regulated regulatory regions are known in the art (see, e.g., Spiro, 2006; Isabella et al., 2009; Dunn et al., 2010; Vine et al., 2011; Karlinsey et al., 2012).

In some embodiments, the genetically engineered bacteria of the invention comprise a gene encoding a RNS-sensing transcription factor, e.g., the nsrR gene, that is controlled by its native promoter, an inducible promoter, a promoter that is stronger than the native promoter, e.g., the GlnRS promoter or the P(Bla) promoter, or a constitutive promoter. In some instances, it may be advantageous to express the RNS-sensing transcription factor under the control of an inducible promoter in order to enhance expression stability. In some embodiments, expression of the RNS-sensing transcription factor is controlled by a different promoter than the promoter that controls expression of the therapeutic molecule. In some embodiments, expression of the RNS-sensing transcription factor is controlled by the same promoter that controls expression of the therapeutic molecule. In some embodiments, the RNS-sensing transcription factor and therapeutic molecule are divergently transcribed from a promoter region.

In some embodiments, the genetically engineered bacteria of the invention comprise a gene for a RNS-sensing transcription factor from a different species, strain, or substrain of bacteria. In some embodiments, the genetically engineered bacteria comprise a RNS-responsive regulatory region from a different species, strain, or substrain of bacteria. In some embodiments, the genetically engineered bacteria comprise a RNS-sensing transcription factor and corresponding RNS-responsive regulatory region from a different species, strain, or substrain of bacteria. The heterologous RNS-sensing transcription factor and regulatory region may increase the transcription of genes operatively linked to said regulatory region in the presence of RNS, as compared to the native transcription factor and regulatory region from bacteria of the same subtype under the same conditions.

In some embodiments, the genetically engineered bacteria comprise a RNS-sensing transcription factor, NsrR, and corresponding regulatory region, nsrR, from *Neisseria gonorrhoeae*. In some embodiments, the native RNS-sensing transcription factor, e.g., NsrR, is left intact and retains wild-type activity. In alternate embodiments, the native RNS-sensing transcription factor, e.g., NsrR, is deleted or mutated to reduce or eliminate wild-type activity.

In some embodiments, the genetically engineered bacteria of the invention comprise multiple copies of the endogenous gene encoding the RNS-sensing transcription factor, e.g., the nsrR gene. In some embodiments, the gene encoding the RNS-sensing transcription factor is present on a plasmid. In some embodiments, the gene encoding the RNS-sensing transcription factor and the gene or gene cassette for producing the therapeutic molecule are present on different plasmids. In some embodiments, the gene encoding the RNS-sensing transcription factor and the gene or gene cassette for producing the therapeutic molecule are present on the same plasmid. In some embodiments, the gene encoding the RNS-sensing transcription factor is present on a chromosome. In some embodiments, the gene encoding the RNS-sensing transcription factor and the gene or gene cassette for producing the therapeutic molecule are present on different chromosomes. In some embodiments, the gene encoding the RNS-sensing transcription factor and the gene or gene cassette for producing the therapeutic molecule are present on the same chromosome.

In some embodiments, the genetically engineered bacteria comprise a wild-type gene encoding a RNS-sensing transcription factor, e.g., the NsrR gene, and a corresponding regulatory region, e.g., a norB regulatory region, that is mutated relative to the wild-type regulatory region from bacteria of the same subtype. The mutated regulatory region increases the expression of the anti-inflammation and/or gut barrier enhancer molecule in the presence of RNS, as compared to the wild-type regulatory region under the same conditions. In some embodiments, the genetically engineered bacteria comprise a wild-type RNS-responsive regulatory region, e.g., the norB regulatory region, and a corresponding transcription factor, e.g., NsrR, that is mutated relative to the wild-type transcription factor from bacteria of the same subtype. The mutant transcription factor increases the expression of the anti-inflammation and/or gut barrier enhancer molecule in the presence of RNS, as compared to the wild-type transcription factor under the same conditions. In some embodiments, both the RNS-sensing transcription factor and corresponding regulatory region are mutated relative to the wild-type sequences from bacteria of the same subtype in order to increase expression of the anti-inflammation and/or gut barrier enhancer molecule in the presence of RNS.

Nucleic acid sequences of exemplary RNS-regulated constructs comprising a gene encoding NsrR and a norB promoter are shown in Table 10 and Table 11. Table 10 depicts the nucleic acid sequence of an exemplary RNS-regulated construct comprising a gene encoding nsrR, a regulatory region of norB, and a butyrogenic gene cassette (pLogic031-nsrR-norB-butyrate construct; SEQ ID NO: 67). The sequence encoding NsrR is underlined and bolded, and the NsrR binding site, i.e., a regulatory region of norB is boxed. Table 11 depicts the nucleic acid sequence of an exemplary RNS-regulated construct comprising a gene encoding nsrR, a regulatory region of norB, and a butyrogenic gene cassette (pLogic046-nsrR-norB-butyrate construct; SEQ ID NO: 68). The sequence encoding NsrR is underlined and bolded, and the NsrR binding site, i.e., a regulatory region of norB is boxed. Nucleic acid sequences of tetracycline-regulated constructs comprising a tet promoter are shown in Table 12 and Table 13. Table 12 depicts the nucleic acid sequence of an exemplary tetracycline-regulated construct comprising a tet promoter and a butyrogenic gene cassette (pLogic031-tet-butyrate construct; SEQ ID NO: 69). The sequence encoding TetR is underlined, and the overlapping tetR/tetA promoters are boxed. Table 13 depicts the nucleic acid sequence of an exemplary tetracycline-regulated construct comprising a tet promoter and a butyrogenic gene cassette (pLogic046-tet-butyrate construct; SEQ ID NO: 70). The sequence encoding TetR is underlined, and the overlapping tetR/tetA promoters are boxed. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 67, 68, 69, or 70, or a functional fragment thereof.

TABLE 10

Nucleotide sequences of pLogic031-nsrR-norB-butyrate construct (SEQ ID NO: 67)
ttattatcgcaccgcaatcgggattttcgattcataaagcaggtcgtaggtcggcttgtt gagcaggtcttgcagcgtgaaaccgtccagatacgtgaaaaacgacttcattgcaccgcc gagtatgcccgtcagccggcaggacggcgtaatcaggcattcgttgttcgggcccataca ctcgaccagctgcatcggttcgaggtggcggacgaccgcgccgatattgatgcgttcggg cggcgcggccagcctcagcccgccgcctttccgcgtacgctgtgcaagaacccgcctttt gaccagcgcggtaaccactttcatcaaatggcttttggaaatgccgtaggtcgaggcgat ggtggcgatattgaccagcgcgtcgtcgttgacggcggtgtagatgaggacgcgcagccc gtagtcggtatgttgggtcagatacatacaacctccttagtacatgcaaaattatttcta gagcaacatacgagccggaagcataaagtgtaaagcctggggtgcctaatgagttgagtt gaggaattataacaggaagaaatattcctcatacgcttgtaattcctctatggttgttga caattaatcatcggctcgtataatg tataacattcatattttgtgaattttaaa ctctag aaataattttgtttaacttaagaaggagatatacatatggatttaaattctaaaaata tcagatgcttaaagagctatatgtaagcttcgctgaaaatgaagttaaacctttagcaac agaacttgatgaagaagaaagatttccttatgaaacagtggaaaaatggcaaaagcagg aatgatgggtataccatatccaaaagaatatggtggagaaggtggagacactgtaggata tataatggcagttgaagaattgtctagagtttgtggtactacaggagttatattatcagc tcatacatctcttggctcatggcctatatatcaatatggtaatgaagaacaaaaacaaaa attcttaagaccactagcaagtggagaaaaattaggagcatttggtcttactgagcctaa tgctggtacagatgcgtctggccaacaaacaactgctgttttagacggggatgaatacat acttaatggctcaaaaatatttataacaaacgcaatagctggtgacatatatgtagtaat ggcaatgactgataaatctaaggggaacaaaggaatatcagcatttatagttgaaaagg aactcctgggtttagctttggagttaaagaaaagaaaatgggtataagaggttcagctac gagtgaattaatatttgaggattgcagaatacctaaagaaaatttacttggaaaagaagg TABLE 10-continued Nucleotide sequences of pLogic031-nsrR-norB-butyrate construct tcaaggatttaagatagcaatgtctactcttgatggtggtagaattggtatagctgcaca
agctttaggtttagcacaaggtgctcttgatgaaactgttaaatatgtaaaagaaagagt
acaatttggtagaccattatcaaaattccaaaatacacaattccaattagctgatatgga
agttaaggtacaagcggctagacaccttgtatatcaagcagctataaataaagacttagg
aaaaccttatggagtagaagcagcaatggcaaaattatttgcagctgaaacagctatgga
agttactacaaaagctgtacaacttcatggaggatatggatacactcgtgactatccagt
agaaagaatgatgagagatgctaagataactgaaatatatgaaggaactagtgaagttca
aagaatggttatttcaggaaaactattaaaatagtaagaaggagatatacatatggagga
aggatttatgaatatagtcgtttgtataaaacaagttccagatacaacagaagttaaact
agatcctaatacaggtactttaattagagatggagtaccaagtataataaaccctgatga
taaagcaggtttagaagaagctataaaaattaaaagaagaaatgggtgctcatgtaactgt
tataacaatgggacctcctcaagcagatatggctttaaaagaagctttagcaatgggtgc
agatagaggtatattattaacagatagagcatttgcgggtgctgatacttgggcaacttc
atcagcattagcaggagcattaaaaaatatagattttgatattataatagctggaagaca
ggcgatagatggagatactgcacaagttggacctcaaatagctgaacatttaaatcttcc
atcaataacatatgctgaagaaataaaaactgaaggtgaatatgtattagtaaaaagaca
atttgaagattgttgccatgacttaaaagttaaaatgccatgccttataacaactcttaa
agatatgaacacaccaagatacatgaaagttggaagaatatatgatgctttcgaaaatga
tgtagtagaaacatggactgtaaaagatatagaagttgacccttctaatttaggtcttaa
aggttctccaactagtgtatttaaatcatttacaaaatcagttaaaccagctggtacaat
atacaatgaagatgcgaaaacatcagctggaattatcatagataaattaaaagagaagta
tatcatataataagaaggagatatacatatgggtaacgttttagtagtaatagaacaaag
agaaaatgtaattcaaactgtttctttagaattactaggaaaggctacagaaatagcaaa
agattatgatacaaaagtttctgcattacttttaggtagtaaggtagaaggtttaataga
tacattagcacactatggtgcagatgaggtaatagtagtagatgatgaagctttagcagt
gtatacaactgaaccatatacaaaagcagcttatgaagcaataaaagcagctgaccctat
agttgtattatttggtgcaacttcaataggtagagatttagcgcctagagtttctgctag
aatacatacaggtcttactgctgactgtacaggtcttgcagtagctgaagatacaaaatt
attattaatgacaagacctgcctttggtggaaatataatggcaacaatagtttgtaaaga
tttcagacctcaaatgtctacagttagaccaggggttatgaagaaaaatgaacctgatga
aactaaagaagctgtaattaaccgtttcaaggtagaatttaatgatgctgataaattagt
tcaagttgtacaagtaataaaagaagctaaaaaacaagttaaaatagaagatgctaagat
attagtttctgctggacgtggaatgggtggaaaagaaaacttagacatactttatgaatt
agctgaaattataggtggagaagtttctggttctcgtgccactatagatgcaggttggtt
agataaagcaagacaagttggtcaaactggtaaaactgtaagaccagacctttatatagc
atgtggtatatctggagcaatacaacatagctggtatggaagatgctgagtttatagt
tgctataaataaaaatccagaagctccaatatttaaatatgctgatgttggtatagttgg
agatgttcataaagtgcttccagaacttatcagtcagttaagtgttgcaaaagaaaagg
tgaagttttagctaactaataagaaggagatatacatatgagagaagtagtaattgccag TABLE 10-continued Nucleotide sequences of pLogic031-nsrR-norB-butyrate construct tgcagctagaacagcagtaggaagttttggaggagcatttaaatcagtttcagcggtaga gttaggggtaacagcagctaaagaagctataaaaagagctaacataactccagatatgat agatgaatctcttttagggggagtacttacagcaggtcttggacaaaatatagcaagaca aatagcattaggagcaggaataccagtagaaaaaccagctatgactataaatatagtttg tggttctggattaagatctgtttcaatggcatctcaacttatagcattaggtgatgctga tataatgttagttggtggagctgaaaacatgagtatgtctccttatttagtaccaagtgc gagatatggtgcaagaatgggtgatgctgcttttgttgattcaatgataaaagatggatt atcagacatatttaataactatcacatgggtattactgctgaaaacatagcagagcaatg gaatataactagagaagaacaagatgaattagctcttgcaagtcaaaataaagctgaaaa agctcaagctgaaggaaaatttgatgaagaaatagttcctgttgttataaaaggaagaaa aggtgacactgtagtagataaagatgaatatattaagcctggcactacaatggagaaact tgctaagttaagacctgcatttaaaaaagatggaacagttactgctggtaatgcatcagg aataaatgatggtgctgctatgttagtagtaatggctaaagaaaaagctgaagaactagg aatagagcctcttgcaactatagtttcttatggaacagctggtgttgaccctaaaataat gggatatggaccagttccagcaactaaaaaagctttagaagctgctaatatgactattga agatatagatttagttgaagctaatgaggcatttgctgcccaatctgtagctgtaataag agacttaaatatagatatgaataaagttaatgttaatggtggagcaatagctataggaca tccaataggatgctcaggagcaagaatacttactacacttttatatgaaatgaagagaag agatgctaaaactggtcttgctacactttgtataggcggtggaatgggaactactttaat agttaagagatagtaagaaggagatatacatatgaaattagctgtaataggtagtggaac tatgggaagtggtattgtacaaacttttgcaagttgtggacatgatgtatgtttaaagag tagaactcaaggtgctatagataaatgtttagctttattagataaaaatttaactaagtt agttactaagggaaaaatggatgaagctacaaaagcagaaatattaagtcatgttagttc aactactaattatgaagatttaaaagatatggatttaataatagaagcatctgtagaaga catgaatataaagaaagatgttttcaagttactagatgaattatgtaaagaagatactat cttggcaacaaatacttcatcattatctataacagaaatagcttcttctactaagcgccc agataaagttataggaatgcatttctttaatccagttcctatgatgaaattagttgaagt tataagtggtcagttaacatcaaaagttacttttgatacagtatttgaattatctaagag tatcaataaagtaccagtagatgtatctgaatctcctggatttgtagtaaatagaatact tatacctatgataaatgaagctgttggtatatatgcagatggtgttgcaagtaaagaaga aatagatgaagctatgaaattaggagcaaaccatccaatgggaccactagcattaggtga tttaatcggattagatgttgtttagctataatgaacgttttatatactgaatttggaga tactaaatatagacctcatccacttttagctaaaatggttagagctaatcaattaggaag aaaaactaagataggattctatgattataataaataataagaaggagatatacatatgag tacaagtgatgttaaagtttatgagaatgtagctgttgaagtagatggaaatatatgtac agtgaaaatgaatagacctaaagcccttaatgcaataaattcaaagactttagaagaact ttatgaagtatttgtagatattaataatgatgaaactattgatgttgtaatattgacagg ggaaggaaaggcatttgtagctggagcagatattgcatacatgaaagatttagatgctgt agctgctaaagattttagtatcttaggagcaaaagcttttggagaaatagaaaatagtaa TABLE 10-continued Nucleotide sequences of pLogic031-nsrR-norB-butyrate construct aaaagtagtgatagctgctgtaaacggatttgctttaggtggaggatgtgaacttgcaat ggcatgtgatataagaattgcatctgctaaagctaaatttggtcagccagaagtaactct tggataactccaggatatggaggaactcaaaggcttacaagattggttggaatggcaaa agcaaaagaattaatctttacaggtcaagttataaaagctgatgaagctgaaaaaatagg gctagtaaatagagtcgttgagccagacattttaatagaagaagttgagaaattagctaa gataatagctaaaaatgctcagcttgcagttagatactctaaagaagcaatacaacttgg tgctcaaactgatataaatactggaatagatatagaatctaatttatttggtctttgttt ttcaactaaagaccaaaaagaaggaatgtcagctttcgttgaaaagagagaagctaactt tataaagggtaataagaaggagatatacatatgagaagttttgaagaagtaattaagtt tgcaaaagaaagaggacctaaaactatatcagtagcatgttgccaagataaagaagtttt aatggcagttgaaatggctagaaaagaaaaaatagcaaatgccatttagtaggagatat agaaaagactaaagaaattgcaaaaagcatagacatggatatcgaaaattatgaactgat agatataaaagatttagcagaagcatctctaaaatctgttgaattagtttcacaaggaaa agccgacatggtaatgaaaggcttagtagacacatcaataatactaaaagcagttttaaa taaagaagtaggtcttagaactggaaatgtattaagtcacgtagcagtatttgatgtaga gggatatgatagattattttttcgtaactgacgcagctatgaacttagctcctgatacaaa tactaaaaagcaaatcatagaaaatgcttgcacagtagcacattcattagatataagtga accaaaagttgctgcaatatgcgcaaaagaaaaagtaaatccaaaaatgaaagatacagt tgaagctaaagaactagaagaaatgtatgaaagaggagaaatcaaaggttgtatggttgg tgggccttttgcaattgataatgcagtatctttagaagcagctaaacataaaggtataaa tcatcctgtagcaggacgagctgatatattattagccccagatattgaaggtggtaacat attatataaagctttggtattcttctcaaaatcaaaaaatgcaggagttatagttgggc taaagcaccaataatattaacttctagagcagacagtgaagaaactaaactaaactcaat agctttaggtgttttaatggcagcaaaggcataataagaaggagatatacatatgagcaa aatatttaaaatcttaacaataaatcctggttcgacatcaactaaaatagctgtatttga taatgaggatttagtatttgaaaaaactttaagacattcttcagaagaaataggaaaata tgagaaggtgtctgaccaatttgaatttcgtaaacaagtaatagaagaagctctaaaaga aggtggagtaaaaacatctgaattagatgctgtagtaggtagaggaggacttcttaaacc tataaaaggtggtacttattcagtaagtgctgctatgattgaagatttaaaagtgggagt tttaggagaacacgcttcaaacctaggtggaataatagcaaaacaataggtgaagaagt aaatgttccttcatacatagtagaccctgttgttgtagatgaattagaagatgttgctag aatttctggtatgcctgaaataagtagagcaagtgtagtacatgctttaaatcaaaaggc aatagcaagaagatatgctagagaaataaacaagaaatatgaagatataaatcttatagt tgcacacatgggtggaggagtttctgttggagctcataaaaatggtaaaatagtagatgt tgcaaacgcattagatggagaaggacctttctctccagaaagaagtggtggactaccagt aggtgcattagtaaaaatgtgctttagtggaaatatactcaagatgaaattaaaaagaa aataaaaggtaatggcggactagttgcatacttaaacactaatgatgctagagaagttga agaaagaattgaagctggtgatgaaaagctaaattagtatatgaagctatggcatatca aatctctaaagaaataggagctagtgctgcagttcttaagggagatgtaaaagcaatatt TABLE 10-continued Nucleotide sequences of pLogic031-nsrR-norB-butyrate construct attaactggtggaatcgcatattcaaaaatgtttacagaaatgattgcagatagagttaa atttatagcagatgtaaaagtttatccaggtgaagatgaaatgattgcattagctcaagg tggacttagagttttaactggtgaagaagaggctcaagtttatgataactaataa

TABLE 11

Nucleotide sequences of pLogic046-nsrR-norB-butyrate construct (SEQ ID NO: 68)
ttatta<u>tcgcaccgcaatcgggattttcgattcataaagcaggtcgtaggtcggcttgtt</u>

<u>gagcaggtcttgcagcgtgaaaccgtccagatacgtgaaaaacgacttcattgcaccgcc</u>

<u>gagtatgcccgtcagccggcaggacggcgtaatcaggcattcgttgttcgggcccataca</u>

<u>ctcgaccagctgcatcggttcgaggtggcggacgaccgcgccgatattgatgcgttcggg</u>

<u>cggcgcggccagcctcagcccgccgcctttcccgcgtacgctgtgcaagaacccgcctt</u>

<u>gaccagcgcggtaaccactttcatcaaatggcttttggaaatgccgtaggtcgaggcgat</u>

<u>ggtggcgatattgaccagcgcgtcgtcgttgacggcggtgtagatgaggacgcgcagccc</u>

<u>gtagtcggtatgttgggtcagatacat</u>acaacctccttagtacatgcaaaattatttcta gagcaacatacgagccggaagcataaagtgtaaagcctggggtgcctaatgagttgagtt gaggaattataacaggaagaaatattcctcatacgcttgtaattcctctatggttgttga caattaatcatcggctcgtataatg<span style="border:1px solid">tataacattcatattttgtgaatttttaaa</span>ctctag aaataattttgtttaactttaagaggagatatacatatgatcgtaaaacctatggtacg caacaatatctgcctgaacgcccatcctcagggctgcaagaagggagtggaagatcagat tgaatataccaagaaacgcattaccgcagaagtcaaagctggcgcaaaagctccaaaaaa cgttctggtgcttggctgctcaaatggttacggcctggcgagccgcattactgctgcgtt cggatacggggctgcgaccatcggcgtgtcctttgaaaaagcgggttcagaaaccaaata tggtacaccgggatggtacaataatttggcatttgatgaagcggcaaaacgcgagggtct ttatagcgtgacgatcgacggcgatgcgttttcagacgagatcaaggcccaggtaattga ggaagccaaaaaaaaggtatcaaatttgatctgatcgtatacagcttggccagcccagt acgtactgatcctgatacaggtatcatgcacaaaagcgttttgaaacccttggaaaaac gttcacaggcaaaacagtagatccgtttactggcgagctgaaggaaatctccgcggaacc agcaaatgacgaggaagcagccgccactgttaaagttatgggggtgaagattgggaacg ttggattaagcagctgtcgaaggaaggcctcttagaagaaggctgtattaccttggccta tagttatattggccctgaagctacccaagctttgtaccgtaaaggcacaatcggcaaggc caaagaacacctggaggccacagcacaccgtctcaacaaagagaacccgtcaatccgtgc cttcgtgagcgtgaataaaggcctggtaacccgcgcaagcgccgtaatcccggtaatccc tctgtatctcgccagcttgttcaaagtaatgaaagagaagggcaatcatgaaggttgtat tgaacagatcacgcgtctgtacgccgagcgcctgtaccgtaaagatggtacaattccagt tgatgaggaaaatcgcattcgcattgatgattgggagttagaagaagacgtccagaaagc ggtatccgcgttgatggagaaagtcacgggtgaaaacgcagaatctctcactgacttagc ggggtaccgccatgattcttagctagtaacggctttgatgtagaaggtattaattatga agcggaagttgaacgcttcgaccgtatctgataagaaggagatatacatatgagagaagt TABLE 11-continued Nucleotide sequences of pLogic046-nsrR-norB-butyrate construct agtaattgccagtgcagctagaacagcagtaggaagttttggaggagcatttaaatcagt ttcagcggtagagttaggggtaacagcagctaaagaagctataaaaagagctaacataac tccagatatgatagatgaatctcttttaggggagtacttacagcaggtcttggacaaaa tatagcaagacaaatagcattaggagcaggaataccagtagaaaaaccagctatgactat aaatatagtttgtggttctggattaagatctgtttcaatggcatctcaacttatagcatt aggtgatgctgatataatgttagttggtggagctgaaaacatgagtatgtctccttattt agtaccaagtgcgagatatggtgcaagaatgggtgatgctgcttttgttgattcaatgat aaaagatggattatcagacatatttaataactatcacatgggtattactgctgaaaacat agcagagcaatggaatataactagagaagaacaagatgaattagctcttgcaagtcaaaa taaagctgaaaaagctcaagctgaaggaaaatttgatgaagaaatagttcctgttgttat aaaaggaagaaaaggtgacactgtagtagataaagatgaatatattaagcctggcactac aatggagaaacttgctaagttaagacctgcatttaaaaaagatggaacagttactgctgg taatgcatcaggaataaatgatggtgctgctatgttagtagtaatggctaaagaaaaagc tgaagaactaggaatagagcctcttgcaactatagtttcttatggaacagctggtgttga ccctaaaataatgggatatggaccagttccagcaactaaaaaagctttagaagctgctaa tatgactattgaagatatagatttagttgaagctaatgaggcatttgctgcccaatctgt agctgtaataagagacttaaatatagatatgaataaagttaatgttaatggtggagcaat agctataggacatccaataggatgctcaggagcaagaatacttactacacttttatatga aatgaagagaagagatgctaaaactggtcttgctacactttgtataggcggtggaatggg aactactttaatagttaagagatagtaagaaggagatatacatatgaaattagctgtaat aggtagtggaactatgggaagtggtattgtacaaacttttgcaagttgtggacatgatgt atgtttaaagagtagaactcaaggtgctatagataaatgtttagctttattagataaaaa tttaactaagttagttactaagggaaaaatggatgaagctacaaaagcagaaatattaag tcatgttagttcaactactaattatgaagatttaaaagatatggatttaataatagaagc atctgtagaagacatgaatataaagaaagatgttttcaagttactagatgaattatgtaa agaagatactatcttggcaacaaatacttcatcattatctataacagaaatagcttcttc tactaagcgcccagataaagttataggaatgcatttctttaatccagttcctatgatgaa attagttgaagttataagtggtcagttaacatcaaaagttacttttgatacagtatttga attatctaagagtatcaataaagtaccagtagatgtatctgaatctcctggatttgtagt aaatagaatacttatacctatgataaatgaagctgttggtatatatgcagatggtgttgc aagtaaagaagaaatagatgaagctatgaaattaggagcaaaccatccaatgggaccact agcattaggtgatttaatcggattagatgttgttttagctataatgaacgttttatatac tgaatttggagatactaaatatagacctcatccacttttagctaaaatggttagagctaa tcaattaggaagaaaaactaagataggattctatgattataataaataataagaaggaga tatacatatgagtacaagtgatgttaaagtttatgagaatgtagctgttgaagtagatgg aaatatatgtacagtgaaaatgaatagacctaaagccccttaatgcaataaattcaaagac tttagaagaactttatgaagtatttgtagatattaataatgatgaaactattgatgttgt aatattgacaggggaaggaaaggcatttgtagctggagcagatattgcatacatgaaaga tttagatgctgtagctgctaaagattttagtatcttaggagcaaaagcttttggagaaat TABLE 11-continued Nucleotide sequences of pLogic046-nsrR-norB-butyrate construct agaaaatagtaaaaaagtagtgatagctgctgtaaacggatttgctttaggtggaggatg tgaacttgcaatggcatgtgatataagaattgcatctgctaaagctaaatttggtcagcc agaagtaactcttggaataactccaggatatggaggaactcaaaggcttacaagattggt tggaatggcaaaagcaaaagaattaatctttacaggtcaagttataaaagctgatgaagc tgaaaaaatagggctagtaaatagagtcgttgagccagacattttaatagaagaagttga gaaattagctaagataatagctaaaaatgctcagcttgcagttagatactctaaagaagc aatacaacttggtgctcaaactgatataaatactggaatagatatagaatctaatttatt tggtctttgtttttcaactaaagaccaaaaagaaggaatgtcagctttcgttgaaaagag agaagctaactttataaaagggtaataagaaggagatatacatatgagaagttttgaaga agtaattaagtttgcaaaagaaagaggacctaaaactatatcagtagcatgttgccaaga taaagaagttttaatggcagttgaaatggctagaaaagaaaaaatagcaaatgccatttt agtaggagatatagaaaagactaaagaaattgcaaaaagcatagacatggatatcgaaaa ttatgaactgatagatataaaagatttagcagaagcatctctaaaatctgttgaattagt ttcacaaggaaaagccgacatggtaatgaaaggcttagtagacacatcaataatactaaa agcagttttaaataaagaagtaggtcttagaactggaaatgtattaagtcacgtagcagt atttgatgtagagggatatgatagattatttttcgtaactgacgcagctatgaacttagc tcctgatacaaatactaaaaagcaaatcatagaaaatgcttgcacagtagcacattcatt agatataagtgaaccaaaagttgctgcaatatgcgcaaaagaaaaagtaaatccaaaaat gaaagatacagttgaagctaaagaactagaagaaatgtatgaaagaggagaaatcaaagg ttgtatggttggtgggccttttgcaattgataatgcagtatctttagaagcagctaaaca taaaggtataaatcatcctgtagcaggacgagctgatatattattagccccagatattga aggtggtaacatattatataaagctttggtattcttctcaaaatcaaaaaatgcaggagt tatagttggggctaaagcaccaataatattaacttctagagcagacagtgaagaaactaa actaaactcaatagctttaggtgtttaatggcagcaaaggcataataagaaggagatat acatatgagcaaaatatttaaaatcttaacaataaatcctggttcgacatcaactaaaat agctgtatttgataatgaggatttagtatttgaaaaaactttaagacattcttcagaaga aataggaaatatgagaaggtgtctgaccaatttgaatttcgtaaacaagtaatagaaga agctctaaaagaaggtggagtaaaaacatctgaattagatgctgtagtaggtagaggagg acttcttaaacctataaaaggtggtacttattcagtaagtgctgctatgattgaagattt aaaagtgggagttttaggagaacacgcttcaaacctaggtggaataatagcaaaacaaat aggtgaagaagtaaatgttccttcatacatagtagaccctgttgttgtagatgaattaga agatgttgctagaatttctggtatgcctgaaataagtagagcaagtgtagtacatgcttt aaatcaaaaggcaatagcaagaagatatgctagagaaataaacaagaaatatgaagatat aaatcttatagttgcacacatgggtggaggagtttctgttggagctcataaaaatggtaa aatagtagatgttgcaaacgcattagatggagaaggacctttctctccagaaagaagtgg tggactaccagtaggtgcattagtaaaaatgtgctttagtggaaaatatactcaagatga aattaaaagaaaataaaaggtaatggcggactagttgcatacttaaacactaatgatgc tagagaagttgaagaagaattgaagctggtgatgaaaaagctaaattagtatatgaagc tatggcatatcaaatctctaaagaaataggagctagtgctgcagttcttaagggagatgt TABLE 11-continued Nucleotide sequences of pLogic046-nsrR-norB-butyrate construct aaaagcaatattattaactggtggaatcgcatattcaaaaatgtttacagaaatgattgc agatagagttaaatttatagcagatgtaaaagtttatccaggtgaagatgaaatgattgc attagctcaaggtggacttagagttttaactggtgaagaagaggctcaagtttatgataa ctaataa

TABLE 12

Nucleotide sequences of pLogic031-tet-butyrate construct
(SEQ ID NO: 69)

```
   1 gtaaaacgac ggccagtgaa ttcgttaaga cccactttca catttaagtt gttttctaa
  61 tccgcatatg atcaattcaa ggccgaataa gaaggctggc tctgcacctt ggtgatcaaa
 121 taattcgata gcttgtcgta ataatggcgg catactatca gtagtaggtg tttccctttc
 181 ttctttagcg acttgatgct cttgatcttc caatacgcaa cctaaagtaa aatgccccac
 241 agcgctgagt gcatataatg cattctctag tgaaaaacct tgttggcata aaaaggctaa
 301 ttgattttcg agagtttcat actgttttct gtaggccgt gtacctaaat gtactttgc
 361 tccatcgcga tgacttagta aagcacatct aaaacttta gcgttattac gtaaaaaatc
 421 ttgccagctt tccccttcta aagggcaaaa gtgagtatgg tgcctatcta acatctcaat
 481 ggctaaggcg tcgagcaaag cccgcttatt ttttacatgc caatacaatg taggctgctc
 541 tacacctagc ttctgggcga gtttacgggt tgttaaacct tcgattccga cctcattaag
 601 cagctctaat gcgctgttaa tcactttact tttatctaat ctagacatca ttaattccta
 661 attttgttg acactctatc attgatagag ttattttacc actccctatc agtgatagag
 721 aaaagtgaac tctagaaata attttgttta actttaagaa ggagatatac atatggattt
 781 aaattctaaa aaatatcaga tgcttaaaga gctatatgta agcttcgctg aaaatgaagt
 841 taaaccttta gcaacagaac ttgatgaaga agaaagattt ccttatgaaa cagtggaaaa
 901 aatggcaaaa gcaggaatga tgggtatacc atatccaaaa gaatatggtg gagaaggtgg
 961 agacactgta ggatatataa tggcagttga agaattgtct agagtttgtg gtactacagg
1021 agttatatta tcagctcata catctcttgg ctcatggcct atatatcaat atggtaatga
1081 agaacaaaaa caaaaattct taagaccact agcaagtgga gaaaaattag gagcatttgg
1141 tcttactgag cctaatgctg gtacagatgc gtctggccaa caaacaactg ctgttttaga
1201 cggggatgaa tacatactta atggctcaaa atatttata caaacgcaa tagctggtga
1261 catatatgta gtaatggcaa tgactgataa atcaaggggg aacaaaggaa tatcagcatt
1321 tatagttgaa aaaggaactc ctgggtttag ctttggagtt aaagaaaaga aaatgggtat
1381 aagaggttca gctacgagtg aattaatatt tgaggattgc agaataccta agaaaattt
1441 acttggaaaa gaaggtcaag gatttaagat agcaatgtct actcttgatg gtggtagaat
1501 tggtatagct gcacaagctt taggtttagc acaaggtgct cttgatgaaa ctgttaaata
1561 tgtaaaagaa agagtacaat ttggtagacc attatcaaaa ttccaaaata cacaattcca
1621 attagctgat atggaagtta aggtacaagc ggctagacac cttgtatatc aagcagctat
1681 aaataaagac ttaggaaaac cttatgggagt agaagcagca atggcaaaat tatttgcagc
1741 tgaaacagct atggaagtta ctacaaaagc tgtacaactt catggaggat atggatacac
1801 tcgtgactat ccagtagaaa gaatgatgag agatgctaag ataactgaaa tatatgaagg
1861 aactagtgaa gttcaaagaa tggttatttc aggaaaacta ttaaaatagt aagaaggaga
```

TABLE 12-continued

Nucleotide sequences of pLogic031-tet-butyrate construct
(SEQ ID NO: 69)

```
1921 tatacatatg gaggaaggat ttatgaatat agtcgtttgt ataaaacaag ttccagatac 1981 aacagaagtt aaactagatc ctaatacagg tactttaatt agagatggag taccaagtat 2041 aataaaccct gatgataaag caggtttaga agaagctata aaattaaaag aagaaatggg 2101 tgctcatgta actgttataa caatgggacc tcctcaagca gatatggctt taaaagaagc 2161 tttagcaatg ggtgcagata gaggtatatt attaacagat agagcatttg cgggtgctga 2221 tacttgggca acttcatcag cattagcagg agcattaaaa aatatagatt ttgatattat 2281 aatagctgga agacaggcga tagatggaga tactgcacaa gttggacctc aaatagctga 2341 acatttaaat cttccatcaa taacatatgc tgaagaaata aaaactgaag gtgaatatgt 2401 attagtaaaa agacaatttg aagattgttg ccatgactta aaagttaaaa tgccatgcct 2461 tataacaact cttaaagata tgaacacacc aagatacatg aaagttggaa gaatatatga 2521 tgctttcgaa aatgatgtag tagaaacatg gactgtaaaa gatatagaag ttgacccttc 2581 taatttaggt cttaaaggtt ctccaactag tgtatttaaa tcatttacaa aatcagttaa 2641 accagctggt acaatataca atgaagatgc gaaaacatca gctggaatta tcatagataa 2701 attaaaagag aagtatatca tataataaga aggagatata catatgggta acgttttagt 2761 agtaatagaa caaagagaaa atgtaattca aactgtttct ttagaattac taggaaaggc 2821 tacagaaata gcaaaagatt atgatacaaa agtttctgca ttacttttag gtagtaaggt 2881 agaaggttta atagatacat tagcacacta tggtgcagat gaggtaatag tagtagatga 2941 tgaagcttta gcagtgtata caactgaacc atatacaaaa gcagcttatg aagcaataaa 3001 agcagctgac cctatagttg tattatttgg tgcaacttca ataggtagag atttagcgcc 3061 tagagtttct gctagaatac atacaggtct tactgctgac tgtacaggtc ttgcagtagc 3121 tgaagataca aaattattat taatgacaag acctgccttt ggtggaaata taatggcaac 3181 aatagtttgt aaagatttca gacctcaaat gtctacagtt agaccagggg ttatgaagaa 3241 aaatgaacct gatgaaacta agaagctgt aattaaccgt tcaaggtag aatttaatga 3301 tgctgataaa ttagttcaag ttgtacaagt aataaaagaa gctaaaaaac aagttaaaat 3361 agaagatgct aagatattag tttctgctgg acgtggaatg ggtggaaaag aaaacttaga 3421 catactttat gaattagctg aaattatagg tggagaagtt tctggttctc gtgccactat 3481 agatgcaggt tggttagata agcaagaca agttggtcaa actggtaaaa ctgtaagacc 3541 agcctttat atagcatgtg gtatatctgg agcaatacaa catatagctg gtatggaaga 3601 tgctgagttt atagttgcta taaataaaaa tccagaagct ccaatattta aatatgctga 3661 tgttggtata gttggagatg ttcataaagt gcttccagaa cttatcagtc agttaagtgt 3721 tgcaaaagaa aaaggtgaag ttttagctaa ctaataagaa ggagatatac atatgagaga 3781 agtagtaatt gccagtgcag ctagaacagc agtaggaagt tttggaggag catttaaatc 3841 agtttcagcg gtagagttag gggtaacagc agctaaagaa gctataaaaa gagctaacat 3901 aactccagat atgatagatg aatctctttt aggggagta cttacagcag gtcttggaca 3961 aaatatagca agacaaatag cattaggagc aggaatacca gtagaaaaac cagctatgac 4021 tataaatata gtttgtggtt ctggattaag atctgtttca atggcatctc aacttatagc 4081 attaggtgat gctgatataa tgttagttgg tggagctgaa acatgagta tgtctcctta 4141 tttagtacca agtgcgagat atggtgcaag aatgggtgat gctgcttttg ttgattcaat
```

TABLE 12-continued

Nucleotide sequences of pLogic031-tet-butyrate construct
(SEQ ID NO: 69)

```
4201 gataaaagat ggattatcag acatatttaa taactatcac atgggtatta ctgctgaaaa
4261 catagcagag caatggaata taactagaga agaacaagat gaattagctc ttgcaagtca
4321 aaataaagct gaaaaagctc aagctgaagg aaaatttgat gaagaaatag ttcctgttgt
4381 tataaaagga agaaaaggtg acactgtagt agataaagat gaatatatta agcctggcac
4441 tacaatggag aaacttgcta agttaagacc tgcatttaaa aaagatggaa cagttactgc
4501 tggtaatgca tcaggaataa atgatggtgc tgctatgtta gtagtaatgg ctaaagaaaa
4561 agctgaagaa ctaggaatag agcctcttgc aactatagtt tcttatggaa cagctggtgt
4621 tgaccctaaa ataatgggat atggaccagt tccagcaact aaaaaagctt tagaagctgc
4681 taatatgact attgaagata tagatttagt tgaagctaat gaggcatttg ctgcccaatc
4741 tgtagctgta ataagagact aaatataga tatgaataaa gttaatgtta atggtggagc
4801 aatagctata ggacatccaa taggatgctc aggagcaaga atacttacta cactttttata
4861 tgaaatgaag agaagagatg ctaaaactgg tcttgctaca ctttgtatag gcggtggaat
4921 gggaactact ttaatagtta agagatagta agaaggagat atacatatga aattagctgt
4981 aataggtagt ggaactatgg gaagtggtat tgtacaaact tttgcaagtt gtggacatga
5041 tgtatgttta aagagtagaa ctcaaggtgc tatagataaa tgtttagctt tattagataa
5101 aaatttaact aagttagtta ctaagggaaa aatggatgaa gctacaaaag cagaaatatt
5161 aagtcatgtt agttcaacta ctaattatga agatttaaaa gatatggatt taataataga
5221 agcatctgta gaagacatga atataaagaa agatgttttc aagttactag atgaattatg
5281 taaagaagat actatcttgg caacaaatac ttcatcatta tctataacag aaatagcttc
5341 ttctactaag cgcccagata agttataggg aatgcatttc tttaatccag ttcctatgat
5401 gaaattagtt gaagttataa gtggtcagtt aacatcaaaa gttacttttg atacagtatt
5461 tgaattatct aagagtatca ataaagtacc agtagatgta tctgaatctc ctggatttgt
5521 agtaaataga atacttatac ctatgataaa tgaagctgtt ggtatatatg cagatggtgt
5581 tgcaagtaaa gaagaaatag atgaagctat gaaattagga gcaaaccatc caatgggacc
5641 actagcatta ggtgatttaa tcggattaga tgttgtttta gctataatga acgtttata
5701 tactgaattt ggagatacta atatagacc tcatccactt ttagctaaaa tggttagagc
5761 taatcaatta ggaagaaaaa ctaagatagg attctatgat tataataaat aataagaagg
5821 agatatacat atgagtacaa gtgatgttaa agtttatgag aatgtagctg ttgaagtaga
5881 tggaaatata tgtacagtga aaatgaatag acctaaagcc cttaatgcaa taaattcaaa
5941 gactttagaa gaactttatg aagtatttgt agatattaat aatgatgaaa ctattgatgt
6001 tgtaatattg acaggggaag gaaaggcatt tgtagctgga gcagatattg catacatgaa
6061 agatttagat gctgtagctg ctaaagattt tagtatctta ggagcaaaag cttttggaga
6121 aatagaaaat agtaaaaaag tagtgatagc tgctgtaaac ggatttgctt taggtggagg
6181 atgtgaactt gcaatggcat gtgatataag aattgcatct gctaaagcta aatttggtca
6241 gccagaagta actcttggaa taactccagg atatggagga actcaaaggc ttacaagatt
6301 ggttggaatg gcaaaagcaa aagaattaat ctttacaggt caagttataa agctgatga
6361 agctgaaaaa ataggctag taaatagagt cgttgagcca gacattttaa tagaagaagt
6421 tgagaaatta gctaagataa tagctaaaaa tgctcagctt gcagttagat actctaaaga
6481 agcaatacaa cttggtgctc aaactgatat aaatactgga atagatatag aatctaattt
```

TABLE 12-continued

Nucleotide sequences of pLogic031-tet-butyrate construct
(SEQ ID NO: 69)

```
6541 atttggtctt tgtttttcaa ctaaagacca aaagaagga atgtcagctt tcgttgaaaa
6601 gagagaagct aactttataa aagggtaata agaaggagat atacatatga gaagttttga
6661 agaagtaatt aagtttgcaa agaaagagg acctaaaact atatcagtag catgttgcca
6721 agataaagaa gttttaatgg cagttgaaat ggctagaaaa gaaaaaatag caaatgccat
6781 tttagtagga gatatagaaa agactaaaga aattgcaaaa agcatagaca tggatatcga
6841 aaattatgaa ctgatagata taaaagattt agcagaagca tctctaaaat ctgttgaatt
6901 agtttcacaa ggaaaagccg acatggtaat gaaaggctta gtagacacat caataatact
6961 aaaagcagtt ttaaataaag aagtaggtct tagaactgga aatgtattaa gtcacgtagc
7021 agtatttgat gtagagggat atgatagatt attttttcgta actgacgcag ctatgaactt
7081 agctcctgat acaaatacta aaagcaaat catagaaaat gcttgcacag tagcacattc
7141 attagatata agtgaaccaa agttgctgc aatatgcgca aaagaaaaag taaatccaaa
7201 aatgaaagat acagttgaag ctaaagaact agaagaaatg tatgaaagag gagaaatcaa
7261 aggttgtatg gttggtgggc cttttgcaat tgataatgca gtatctttag aagcagctaa
7321 acataaaggt ataaatcatc ctgtagcagg acgagctgat atattattag ccccagatat
7381 tgaaggtggt aacatattat ataaagcttt ggtattcttc tcaaaatcaa aaaatgcagg
7441 agttatagtt ggggctaaag caccaataat attaacttct agagcagaca gtgaagaaac
7501 taaactaaac tcaatagctt taggtgtttt aatggcagca aaggcataat aagaaggaga
7561 tatacatatg agcaaaatat ttaaaatctt aacaataaat cctggttcga catcaactaa
7621 aatagctgta tttgataatg aggatttagt atttgaaaaa actttaagac attcttcaga
7681 agaaatagga aaatatgaga aggtgtctga ccaatttgaa tttcgtaaac aagtaataga
7741 agaagctcta aaagaaggtg gagtaaaaac atctgaatta gatgctgtag taggtagagg
7801 aggcttctt aaacctataa aaggtggtac ttattcagta agtgctgcta tgattgaaga
7861 tttaaagtg ggagttttag gagaacacgc ttcaaaccta ggtggaataa tagcaaaaca
7921 aataggtgaa gaagtaaatg ttccttcata catagtagac cctgttgttg tagatgaatt
7981 agaagatgtt gctagaattt ctggtatgcc tgaaataagt agagcaagtg tagtacatgc
8041 tttaaatcaa aaggcaatag caagaagata tgctagagaa ataaacaaga aatatgaaga
8101 tataaatctt atagttgcac acatgggtgg aggagtttct gttggagctc ataaaaatgg
8161 taaaatagta gatgttgcaa acgcattaga tggagaagga ccttctctc cagaaagaag
8221 tggtggacta ccagtaggtg cattagtaaa aatgtgcttt agtggaaaat atactcaaga
8281 tgaaattaaa agaaaaataa aaggtaatgg cggactagtt gcatacttaa acactaatga
8341 tgctagagaa gttgaagaaa gaattgaagc tggtgatgaa aaagctaaat tagtatatga
8401 agctatggca tatcaaatct ctaaagaaat aggagctagt gctgcagttc ttaagggaga
8461 tgtaaaagca atattattaa ctggtggaat cgcatattca aaaatgtttta cagaaatgat
8521 tgcagataga gttaaattta tagcagatgt aaagtttat ccaggtgaag atgaaatgat
8581 tgcattagct caaggtggac ttagagtttt aactggtgaa gagaggctc aagtttatga
8641 taactaataa
```

TABLE 13

Nucleotide sequences of pLogic046-tet-butyrate construct
(SEQ ID NO: 70)

```
   1 gtaaaacgac ggccagtgaa ttcgttaaga cccacttcca catttaagtt gtttttctaa
  61 tccgcatatg atcaattcaa ggccgaataa gaaggctggc tctgcacctt ggtgatcaaa
 121 taattcgata gcttgtcgta ataatggcgg catactatca gtagtaggtg tttccctttc
 181 ttctttagcg acttgatgct cttgatcttc aatacgcaa cctaaagtaa aatgccccac
 241 agcgctgagt gcatataatg cattctctag tgaaaaacct tgttggcata aaaaggctaa
 301 ttgattttcg agagtttcat actgtttttc tgtaggccgt gtacctaaat gtacttttgc
 361 tccatcgcga tgacttagta aagcacatct aaaacttta gcgttattac gtaaaaaatc
 421 ttgccagctt tccccttcta aagggcaaaa gtgagtatgg tgcctatcta acatctcaat
 481 ggctaaggcg tcgagcaaag cccgcttatt ttttacatgc aatacaatg taggctgctc
 541 tacacctagc ttctgggcga gtttacgggt tgttaaacct tcgattccga cctcattaag
 601 cagctctaat gcgctgttaa tcactttact tttatctaat ctagacatca ttaattccta
 661 attttt gttg acactctatc attgatagag ttattttacc actccctatc agtgatagag
 721 aa aagtgaac tctagaaata attttgttta actttaagaa ggagatatac atatgatcgt
 781 aaaacctatg gtacgcaaca atatctgcct gaacgcccat cctcagggct gcaagaaggg
 841 agtggaagat cagattgaat ataccaagaa acgcattacc gcagaagtca agctggcgc
 901 aaaagctcca aaaaacgttc tggtgcttgg ctgctcaaat ggttacgcc tggcgagccg
 961 cattactgct gcgttcggat acgggctgc gaccatcggc gtgtcctttg aaaaagcggg
1021 ttcagaaacc aaatatggta caccgggatg gtacaataat ttggcatttg atgaagcggc
1081 aaaacgcgag ggtctttata gcgtgacgat cgacggcgat gcgttttcag acgagatcaa
1141 ggcccaggta attgaggaag ccaaaaaaaa aggtatcaaa tttgatctga tcgtatacag
1201 cttggccagc ccagtacgta ctgatcctga tacaggtatc atgcacaaaa gcgttttgaa
1261 acccttgga aaaacgttca caggcaaaac agtagatccg tttactggcg agctgaagga
1321 aatctccgcg gaaccagcaa atgacgagga agcagccgcc actgttaaag ttatgggggg
1381 tgaagattgg aacgttgga ttaagcagct gtcgaaggaa ggcctcttag aagaaggctg
1441 tattaccttg gcctatagtt atattggccc tgaagctacc caagctttgt accgtaaagg
1501 cacaatcggc aaggccaaag aacacctgga ggccacagca caccgtctca acaaagagaa
1561 cccgtcaatc cgtgccttcg tgagcgtgaa taaaggcctg gtaacccgcg caagcgccgt
1621 aatcccggta atccctctgt atctcgccag cttgttcaaa gtaatgaaag agaagggcaa
1681 tcatgaaggt tgtattgaac agatcacgcg tctgtacgcc gagcgcctgt accgtaaaga
1741 tggtacaatt ccagttgatg aggaaaatcg cattcgcatt gatgattggg agttagaaga
1801 agacgtccag aaagcggtat ccgcgttgat ggagaaagtc acgggtgaaa acgcagaatc
1861 tctcactgac ttagcggggt accgccatga tttcttagct agtaacggct tgatgtaga
1921 aggtattaat tatgaagcgg aagttgaacg cttcgaccgt atctgataag aaggagatat
1981 acatatgaga gaagtagtaa ttgccagtgc agctagaaca gcagtaggaa gttttggagg
2041 agcatttaaa tcagtttcag cggtagagtt aggggtaaca gcagctaaag aagctataaa
2101 aagagctaac ataactccag atatgataga tgaatctctt ttaggggag tacttacagc
2161 aggtcttgga caaaatatag caagacaaat agcattagga gcaggaatac cagtagaaaa
2221 accagcatg actataaata gtttgtgg ttctggatta agatctgttt caatggcatc
2281 tcaacttata gcattaggtg atgctgatat aatgttagtt ggtggagctg aaaacatgag
```

TABLE 13-continued

Nucleotide sequences of pLogic046-tet-butyrate construct
(SEQ ID NO: 70)

```
2341 tatgtctcct tatttagtac caagtgcgag atatggtgca agaatgggtg atgctgcttt
2401 tgttgattca atgataaaag atggattatc agacatattt aataactatc acatgggtat
2461 tactgctgaa aacatagcag agcaatggaa tataactaga gaagaacaag atgaattagc
2521 tcttgcaagt caaaataaag ctgaaaaagc tcaagctgaa ggaaaatttg atgaagaaat
2581 agttcctgtt gttataaaag gaagaaaagg tgacactgta gtagataaag atgaatatat
2641 taagcctggc actacaatgg agaaacttgc taagttaaga cctgcattta aaaaagatgg
2701 aacagttact gctggtaatg catcaggaat aaatgatggt gctgctatgt tagtagtaat
2761 ggctaaagaa aaagctgaag aactaggaat agagcctctt gcaactatag tttcttatgg
2821 aacagctggt gttgacccta aaataatggg atatggacca gttccagcaa ctaaaaaagc
2881 tttagaagct gctaatatga ctattgaaga tatagattta gttgaagcta atgaggcatt
2941 tgctgcccaa tctgtagctg taataagaga cttaaatata gatatgaata agttaatgt
3001 taatggtgga gcaatagcta taggacatcc aataggatgc tcaggagcaa gaatacttac
3061 tacactttta tatgaaatga agagaagaga tgctaaaact ggtcttgcta cactttgtat
3121 aggcggtgga atgggaacta ctttaatagt taagagatag taagaaggag atatacatat
3181 gaaattagct gtaataggta gtggaactat gggaagtggt attgtacaaa cttttgcaag
3241 ttgtggacat gatgtatgtt taaagagtag aactcaaggt gctatagata aatgtttagc
3301 tttattagat aaaaatttaa ctaagttagt tactaaggga aaaatggatg aagctacaaa
3361 agcagaaata ttaagtcatg ttagttcaac tactaattat gaagatttaa agatatgga
3421 tttaataata gaagcatctg tagaagacat gaatataaag aaagatgttt tcaagttact
3481 agatgaatta tgtaaagaag atactatctt ggcaacaaat acttcatcat tatctataac
3541 agaaatagct tcttctacta agcgcccaga taaagttata ggaatgcatt tctttaatcc
3601 agttcctatg atgaaattag ttgaagttat aagtggtcag ttaacatcaa aagttacttt
3661 tgatacagta tttgaattat ctaagagtat caataaagta ccagtagatg tatctgaatc
3721 tcctggattt gtagtaaata gaatacttat acctatgata aatgaagctg ttggtatata
3781 tgcagatggt gttgcaagta aagaagaaat agatgaagct atgaaattag gagcaaacca
3841 tccaatggga ccactagcat taggtgattt aatcggatta gatgttgttt agctataat
3901 gaacgtttta tatactgaat ttggagatac taaatataga cctcatccac ttttagctaa
3961 aatggttaga gctaatcaat taggaagaaa aactaagata ggattctatg attataataa
4021 ataataagaa ggagatatac atatgagtac aagtgatgtt aaagtttatg agaatgtagc
4081 tgttgaagta gatggaaata tatgtacagt gaaaatgaat agacctaaag cccttaatgc
4141 aataaattca aagactttag aagaacttta tgaagtattt gtagatatta ataatgatga
4201 aactattgat gttgtaatat tgacagggga aggaaaggca tttgtagctg gagcagatat
4261 tgcatacatg aaagatttag atgctgtagc tgctaaagat tttagtatct taggagcaaa
4321 agcttttgga gaaatagaaa atagtaaaaa agtagtgata gctgctgtaa acggatttgc
4381 tttaggtgga ggatgtgaac ttgcaatggc atgtgatata agaattgcat ctgctaaagc
4441 taaatttggt cagccagaag taactcttgg aataactcca ggatatggag gaactcaaag
4501 gcttacaaga ttggttggaa tggcaaaagc aaaagaatta atctttacag gtcaagttat
4561 aaaagctgat gaagctgaaa aaatagggct agtaaataga gtcgttgagc cagacatttt
```

TABLE 13-continued

Nucleotide sequences of pLogic046-tet-butyrate construct
(SEQ ID NO: 70)

```
4621 aatagaagaa gttgagaaat tagctaagat aatagctaaa aatgctcagc ttgcagttag
4681 atactctaaa gaagcaatac aacttggtgc tcaaactgat ataaatactg gaatagatat
4741 agaatctaat ttatttggtc tttgtttttc aactaaagac caaaagaag gaatgtcagc
4801 tttcgttgaa aagagagaag ctaactttat aaaagggtaa taagaaggag atatacatat
4861 gagaagtttt gaagaagtaa ttaagtttgc aaaagaaaga ggacctaaaa ctatatcagt
4921 agcatgttgc caagataaag aagtttttaat ggcagttgaa atggctagaa aagaaaaaat
4981 agcaaatgcc attttagtag gagatataga aaagactaaa gaaattgcaa aaagcataga
5041 catggatatc gaaaattatg aactgataga tataaaagat ttagcagaag catctctaaa
5101 atctgttgaa ttagtttcac aaggaaaagc cgacatggta atgaaaggct tagtagacac
5161 atcaataata ctaaaagcag ttttaaataa agaagtaggt cttagaactg gaaatgtatt
5221 aagtcacgta gcagtatttg atgtagaggg atatgataga ttattttttcg taactgacgc
5281 agctatgaac ttagctcctg atacaaatac taaaaagcaa atcatagaaa atgcttgcac
5341 agtagcacat tcattagata taagtgaacc aaaagttgct gcaatatgcg caaaagaaaa
5401 agtaaatcca aaaatgaaag atacagttga agctaaagaa ctagaagaaa tgtatgaaag
5461 aggagaaatc aaaggttgta tggttggtgg gccttttgca attgataatg cagtatcttt
5521 agaagcagct aaacataaag gtataaatca tcctgtagca ggacgagctg atatattatt
5581 agccccagat attgaaggtg gtaacatatt atataaagct ttggtattct tctcaaaatc
5641 aaaaaatgca ggagttatag ttggggctaa agcaccaata atattaactt ctagagcaga
5701 cagtgaagaa actaaactaa actcaatagc tttaggtgtt ttaatggcag caaaggcata
5761 ataagaagga gatatacata tgagcaaaat atttaaaatc ttaacaataa atcctggttc
5821 gacatcaact aaaaatagctg tatttgataa tgaggattta gtatttgaaa aaactttaag
5881 acattcttca gaagaaatag gaaaatatga gaaggtgtct gaccaatttg aatttcgtaa
5941 acaagtaata gaagaagctc taaaagaagg tggagtaaaa acatctgaat tagatgctgt
6001 agtaggtaga ggaggacttc ttaaacctat aaaaggtggt acttattcag taagtgctgc
6061 tatgattgaa gatttaaaag tgggagtttt aggagaacac gcttcaaacc taggtggaat
6121 aatagcaaaa caaataggtg aagaagtaaa tgttccttca tacatagtag accctgttgt
6181 tgtagatgaa ttagaagatg ttgctagaat ttctggtatg cctgaaataa gtagagcaag
6241 tgtagtacat gctttaaatc aaaaggcaat agcaagaaga tatgctagag aaataaacaa
6301 gaaaatgaa gatataaatc ttatagttgc acacatgggt ggaggagttt ctgttggagc
6361 tcataaaaat ggtaaaatag tagatgttgc aaacgcatta gatggagaag gacctttctc
6421 tccagaaaga agtggtggac taccagtagg tgcattagta aaaatgtgct ttagtggaaa
6481 atatactcaa gatgaaatta aaagaaaat aaaaggtaat ggcggactag ttgcatactt
6541 aaacactaat gatgctagag aagttgaaga aagaattgaa gctggtgatg aaaaagctaa
6601 attagtatat gaagctatgg catatcaaat ctctaaagaa ataggagcta gtgctgcagt
6661 tcttaaggga gatgtaaaag caatattatt aactggtgga atcgcatatt caaaaatgtt
6721 tacagaaatg attgcagata gagttaaatt tatagcagat gtaaaagttt atccaggtga
6781 agatgaaatg attgcattag ctcaaggtgg acttagagtt ttaactggtg aagaagaggc
6841 tcaagtttat gataactaat aa
```

In some embodiments, the gene or gene cassette for producing the anti-inflammation and/or gut barrier function enhancer molecule is present on a plasmid and operably linked to a promoter that is induced by RNS. In some embodiments, the gene or gene cassette for producing the anti-inflammation and/or gut barrier function enhancer molecule is present in the chromosome and operably linked to a promoter that is induced by RNS. In some embodiments, the gene or gene cassette for producing the anti-inflammation and/or gut barrier function enhancer molecule is present on a chromosome and operably linked to a promoter that is induced by exposure to tetracycline. In some embodiments, the gene or gene cassette for producing the anti-inflammation and/or gut barrier function enhancer molecule is present on a plasmid and operably linked to a promoter that is induced by exposure to tetracycline. In some embodiments, expression is further optimized by methods known in the art, e.g., by optimizing ribosomal binding sites, manipulating transcriptional regulators, and/or increasing mRNA stability.

In some embodiments, the genetically engineered bacteria comprise a stably maintained plasmid or chromosome carrying the gene(s) or gene cassette(s) capable of producing an anti-inflammation and/or gut barrier function enhancer molecule, such that the gene(s) or gene cassette(s) can be expressed in the host cell, and the host cell is capable of survival and/or growth in vitro, e.g., in medium, and/or in vivo, e.g., in the gut. In some embodiments, a bacterium may comprise multiple copies of the gene or gene cassette for producing the anti-inflammation and/or gut barrier function enhance molecule. In some embodiments, gene or gene cassette is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, gene or gene cassette is expressed on a high-copy plasmid. In some embodiments, the high-copy plasmid may be useful for increasing gene or gene cassette expression. In some embodiments, gene or gene cassette is expressed on a chromosome.

In some embodiments, the genetically engineered bacteria may comprise multiple copies of the gene(s) or gene cassette(s) capable of producing an anti-inflammation and/or gut barrier function enhancer molecule. In some embodiments, the gene(s) or gene cassette(s) capable of producing an anti-inflammation and/or gut barrier function enhancer molecule is present on a plasmid and operatively linked to a RNS-responsive regulatory region. In some embodiments, the gene(s) or gene cassette(s) capable of producing an anti-inflammation and/or gut barrier function enhancer molecule is present in a chromosome and operatively linked to a RNS-responsive regulatory region.

In some embodiments, any of the gene(s) or gene cassette(s) of the present disclosure may be integrated into the bacterial chromosome at one or more integration sites. For example, one or more copies of the butyrogenic gene cassette may be integrated into the bacterial chromosome. Having multiple copies of the butyrogenic gene cassette integrated into the chromosome allows for greater production of the butyrate and also permits fine-tuning of the level of expression. Alternatively, different circuits described herein, such as any of the kill-switch circuits, in addition to the therapeutic gene(s) or gene cassette(s) could be integrated into the bacterial chromosome at one or more different integration sites to perform multiple different functions.

In some embodiments, the genetically engineered bacteria of the invention produce at least one anti-inflammation and/or gut barrier enhancer molecule in the presence of RNS to reduce local gut inflammation by at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold as compared to unmodified bacteria of the same subtype under the same conditions. Inflammation may be measured by methods known in the art, e.g., counting disease lesions using endoscopy; detecting T regulatory cell differentiation in peripheral blood, e.g., by fluorescence activated sorting; measuring T regulatory cell levels; measuring cytokine levels; measuring areas of mucosal damage; assaying inflammatory biomarkers, e.g., by qPCR; PCR arrays; transcription factor phosphorylation assays; immunoassays; and/or cytokine assay kits (Mesoscale, Cayman Chemical, Qiagen).

In some embodiments, the genetically engineered bacteria produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more of an anti-inflammation and/or gut barrier enhancer molecule in the presence of RNS than unmodified bacteria of the same subtype under the same conditions. Certain unmodified bacteria will not have detectable levels of the anti-inflammation and/or gut barrier enhancer molecule. In embodiments using genetically modified forms of these bacteria, the anti-inflammation and/or gut barrier enhancer molecule will be detectable in the presence of RNS.

In certain embodiments, the anti-inflammation and/or gut barrier enhancer molecule is butyrate. Methods of measuring butyrate levels, e.g., by mass spectrometry, gas chromatography, high-performance liquid chromatography (HPLC), are known in the art (see, e.g., Aboulnaga et al., 2013). In some embodiments, butyrate is measured as butyrate level/bacteria optical density (OD). In some embodiments, measuring the activity and/or expression of one or more gene products in the butyrogenic gene cassette serves as a proxy measurement for butyrate production. In some embodiments, the bacterial cells of the invention are harvested and lysed to measure butyrate production. In alternate embodiments, butyrate production is measured in the bacterial cell medium. In some embodiments, the genetically engineered bacteria produce at least about 1 nM/OD, at least about 10 nM/OD, at least about 100 nM/OD, at least about 500 nM/OD, at least about 1 µM/OD, at least about 10 µM/OD, at least about 100 µM/OD, at least about 500 µM/OD, at least about 1 mM/OD, at least about 2 mM/OD, at least about 3 mM/OD, at least about 5 mM/OD, at least about 10 mM/OD, at least about 20 mM/OD, at least about 30 mM/OD, or at least about 50 mM/OD of butyrate in the presence of RNS.

ROS-dependent Regulation

In some embodiments, the genetically engineered bacteria of the invention comprise a tunable regulatory region that is directly or indirectly controlled by a transcription factor that is capable of sensing at least one reactive oxygen species. The tunable regulatory region is operatively linked to a gene or gene cassette capable of directly or indirectly driving the expression of an anti-inflammation and/or gut barrier function enhancer molecule, thus controlling expression of the molecule relative to ROS levels. For example, the tunable regulatory region is a ROS-inducible regulatory region, and the molecule is butyrate; when ROS is present, e.g., in an inflamed tissue, a ROS-sensing transcription factor binds to and/or activates the regulatory region and drives expression of the butyrogenic gene cassette, thereby producing butyrate, which exerts anti-inflammation and/or gut barrier enhancing effects. Subsequently, when inflammation is ameliorated, ROS levels are reduced, and butyrate production is decreased or eliminated.

In some embodiments, the tunable regulatory region is a ROS-inducible regulatory region; in the presence of ROS, a transcription factor senses ROS and activates the ROS-inducible regulatory region, thereby driving expression of an operatively linked gene or gene cassette. In some embodiments, the transcription factor senses ROS and subsequently binds to the ROS-inducible regulatory region, thereby activating downstream gene expression. In alternate embodiments, the transcription factor is bound to the ROS-inducible regulatory region in the absence of ROS; when the transcription factor senses ROS, it undergoes a conformational change, thereby inducing downstream gene expression.

In some embodiments, the tunable regulatory region is a ROS-inducible regulatory region, and the transcription factor that senses ROS is OxyR. OxyR "functions primarily as a global regulator of the peroxide stress response" and is capable of regulating dozens of genes, e.g., "genes involved in $H_2O_2$ detoxification (katE, ahpCF), heme biosynthesis (hemH), reductant supply (grxA, gor, trxC), thiol-disulfide isomerization (dsbG), Fe-S center repair (sufA-E, sufS), iron binding (yaaA), repression of iron import systems (fur)" and "OxyS, a small regulatory RNA" (Dubbs et al., 2012). The genetically engineered bacteria of the invention may comprise any suitable ROS-responsive regulatory region from a gene that is activated by OxyR. Genes that are capable of being activated by OxyR are known in the art (see, e.g., Zheng et al., 2001; Dubbs et al., 2012; Table 1). In certain embodiments, the genetically engineered bacteria of the invention comprise a ROS-inducible regulatory region from oxyS that is operatively linked to a gene or gene cassette, e.g., a butyrogenic gene cassette. In the presence of ROS, e.g., $H_2O_2$, an OxyR transcription factor senses ROS and activates to the oxyS regulatory region, thereby driving expression of the operatively linked butyrogenic gene cassette and producing butyrate. In some embodiments, OxyR is encoded by an *E. coli* oxyR gene. In some embodiments, the oxyS regulatory region is an *E. coli* oxyS regulatory region. In some embodiments, the ROS-inducible regulatory region is selected from the regulatory region of katG, dps, and ahpC.

In alternate embodiments, the tunable regulatory region is a ROS-inducible regulatory region, and the corresponding transcription factor that senses ROS is SoxR. When SoxR is "activated by oxidation of its [2Fe-2S] cluster, it increases the synthesis of SoxS, which then activates its target gene expression" (Koo et al., 2003). "SoxR is known to respond primarily to superoxide and nitric oxide" (Koo et al., 2003), and is also capable of responding to $H_2O_2$. The genetically engineered bacteria of the invention may comprise any suitable ROS-responsive regulatory region from a gene that is activated by SoxR. Genes that are capable of being activated by SoxR are known in the art (see, e.g., Koo et al., 2003; Table 1). In certain embodiments, the genetically engineered bacteria of the invention comprise a ROS-inducible regulatory region from soxS that is operatively linked to a gene or gene cassette, e.g., a butyrogenic gene cassette. In the presence of ROS, the SoxR transcription factor senses ROS and activates the soxS regulatory region, thereby driving expression of the operatively linked butyrogenic gene cassette and producing butyrate.

In some embodiments, the tunable regulatory region is a ROS-derepressible regulatory region, and binding of a corresponding transcription factor represses downstream gene expression; in the presence of ROS, the transcription factor no longer binds to the regulatory region, thereby derepressing the operatively linked gene or gene cassette.

In some embodiments, the tunable regulatory region is a ROS-derepressible regulatory region, and the transcription factor that senses ROS is OhrR. OhrR "binds to a pair of inverted repeat DNA sequences overlapping the ohrA promoter site and thereby represses the transcription event," but oxidized OhrR is "unable to bind its DNA target" (Duarte et al., 2010). OhrR is a "transcriptional repressor [that] . . . senses both organic peroxides and NaOCl" (Dubbs et al., 2012) and is "weakly activated by $H_2O_2$ but it shows much higher reactivity for organic hydroperoxides" (Duarte et al., 2010). The genetically engineered bacteria of the invention may comprise any suitable ROS-responsive regulatory region from a gene that is repressed by OhrR. Genes that are capable of being repressed by OhrR are known in the art (see, e.g., Dubbs et al., 2012; Table 1). In certain embodiments, the genetically engineered bacteria of the invention comprise a ROS-derepressible regulatory region from ohrA that is operatively linked to a gene or gene cassette, e.g., a butyrogenic gene cassette. In the presence of ROS, e.g., NaOCl, an OhrR transcription factor senses ROS and no longer binds to the ohrA regulatory region, thereby derepressing the operatively linked butyrogenic gene cassette and producing butyrate.

OhrR is a member of the MarR family of ROS-responsive regulators. "Most members of the MarR family are transcriptional repressors and often bind to the −10 or -35 region in the promoter causing a steric inhibition of RNA polymerase binding" (Bussmann et al., 2010). Other members of this family are known in the art and include, but are not limited to, OspR, MgrA, RosR, and SarZ. In some embodiments, the transcription factor that senses ROS is OspR, MgRA, RosR, and/or SarZ, and the genetically engineered bacteria of the invention comprises one or more corresponding regulatory region sequences from a gene that is repressed by OspR, MgRA, RosR, and/or SarZ. Genes that are capable of being repressed by OspR, MgRA, RosR, and/or SarZ are known in the art (see, e.g., Dubbs et al., 2012).

In some embodiments, the tunable regulatory region is a ROS-derepressible regulatory region, and the corresponding transcription factor that senses ROS is RosR. RosR is "a MarR-type transcriptional regulator" that binds to an "18-bp inverted repeat with the consensus sequence TTGTTGAY-RYRTCAACWA" and is "reversibly inhibited by the oxidant $H_2O_2$" (Bussmann et al., 2010). RosR is capable of repressing numerous genes and putative genes, including but not limited to "a putative polyisoprenoid-binding protein (cg1322, gene upstream of and divergent from rosR), a sensory histidine kinase (cgtS9), a putative transcriptional regulator of the Crp/FNR family (cg3291), a protein of the glutathione S-transferase family (cg1426), two putative FMN reductases (cg1150 and cg1850), and four putative monooxygenases (cg0823, cg1848, cg2329, and cg3084)" (Bussmann et al., 2010). The genetically engineered bacteria of the invention may comprise any suitable ROS-responsive regulatory region from a gene that is repressed by RosR.

Genes that are capable of being repressed by RosR are known in the art (see, e.g., Bussmann et al., 2010; Table 1). In certain embodiments, the genetically engineered bacteria of the invention comprise a ROS-derepressible regulatory region from cgtS9 that is operatively linked to a gene or gene cassette, e.g., a butyrogenic gene cassette. In the presence of ROS, e.g., $H_2O_2$, a RosR transcription factor senses ROS and no longer binds to the cgtS9 regulatory region, thereby derepressing the operatively linked butyrogenic gene cassette and producing butyrate.

In some embodiments, it is advantageous for the genetically engineered bacteria to express a ROS-sensing transcription factor that does not regulate the expression of a significant number of native genes in the bacteria. In some embodiments, the genetically engineered bacterium of the invention expresses a ROS-sensing transcription factor from a different species, strain, or substrain of bacteria, wherein the transcription factor does not bind to regulatory sequences in the genetically engineered bacterium of the invention. In some embodiments, the genetically engineered bacterium of the invention is Escherichia coli, and the ROS-sensing transcription factor is RosR, e.g., from Corynebacterium glutamicum, wherein the Escherichia coli does not comprise binding sites for said RosR. In some embodiments, the heterologous transcription factor minimizes or eliminates off-target effects on endogenous regulatory regions and genes in the genetically engineered bacteria.

In some embodiments, the tunable regulatory region is a ROS-repressible regulatory region, and binding of a corresponding transcription factor represses downstream gene expression; in the presence of ROS, the transcription factor senses ROS and binds to the ROS-repressible regulatory region, thereby repressing expression of the operatively linked gene or gene cassette. In some embodiments, the ROS-sensing transcription factor is capable of binding to a regulatory region that overlaps with part of the promoter sequence. In alternate embodiments, the ROS-sensing transcription factor is capable of binding to a regulatory region that is upstream or downstream of the promoter sequence.

In some embodiments, the tunable regulatory region is a ROS-repressible regulatory region, and the transcription factor that senses ROS is PerR. In Bacillus subtilis, PerR "when bound to DNA, represses the genes coding for proteins involved in the oxidative stress response (katA, ahpC, and mrgA), metal homeostasis (hemAXCDBL, fur, and zoaA) and its own synthesis (perR)" (Marinho et al., 2014). PerR is a "global regulator that responds primarily to $H_2O_2$" (Dubbs et al., 2012) and "interacts with DNA at the per box, a specific palindromic consensus sequence (TTATAATNATTATAA) residing within and near the promoter sequences of PerR-controlled genes" (Marinho et al., 2014). PerR is capable of binding a regulatory region that "overlaps part of the promoter or is immediately downstream from it" (Dubbs et al., 2012). The genetically engineered bacteria of the invention may comprise any suitable ROS-responsive regulatory region from a gene that is repressed by PerR. Genes that are capable of being repressed by PerR are known in the art (see, e.g., Dubbs et al., 2012; Table 1).

In these embodiments, the genetically engineered bacteria may comprise a two repressor activation regulatory circuit, which is used to express an anti-inflammation and/or gut barrier function enhancer molecule. The two repressor activation regulatory circuit comprises a first ROS-sensing repressor, e.g., PerR, and a second repressor, e.g., TetR, which is operatively linked to a gene or gene cassette, e.g., a butyrogenic gene cassette. In one aspect of these embodiments, the ROS-sensing repressor inhibits transcription of the second repressor, which inhibits the transcription of the gene or gene cassette. Examples of second repressors useful in these embodiments include, but are not limited to, TetR, C1, and LexA. In some embodiments, the ROS-sensing repressor is PerR. In some embodiments, the second repressor is TetR. In this embodiment, a PerR-repressible regulatory region drives expression of TetR, and a TetR-repressible regulatory region drives expression of the gene or gene cassette, e.g., a butyrogenic gene cassette. In the absence of PerR binding (which occurs in the absence of ROS), tetR is transcribed, and TetR represses expression of the gene or gene cassette, e.g., a butyrogenic gene cassette. In the presence of PerR binding (which occurs in the presence of ROS), tetR expression is repressed, and the gene or gene cassette, e.g., a butyrogenic gene cassette, is expressed.

A ROS-responsive transcription factor may induce, derepress, or repress gene expression depending upon the regulatory region sequence used in the genetically engineered bacteria. For example, although "OxyR is primarily thought of as a transcriptional activator under oxidizing conditions . . . OxyR can function as either a repressor or activator under both oxidizing and reducing conditions" (Dubbs et al., 2012), and OxyR "has been shown to be a repressor of its own expression as well as that of fhuF (encoding a ferric ion reductase) and flu (encoding the antigen 43 outer membrane protein)" (Zheng et al., 2001). The genetically engineered bacteria of the invention may comprise any suitable ROS-responsive regulatory region from a gene that is repressed by OxyR. In some embodiments, OxyR is used in a two repressor activation regulatory circuit, as described above. Genes that are capable of being repressed by OxyR are known in the art (see, e.g., Zheng et al., 2001; Table 1). Or, for example, although RosR is capable of repressing a number of genes, it is also capable of activating certain genes, e.g., the narKGHJI operon. In some embodiments, the genetically engineered bacteria comprise any suitable ROS-responsive regulatory region from a gene that is activated by RosR. In addition, "PerR-mediated positive regulation has also been observed . . . and appears to involve PerR binding to distant upstream sites" (Dubbs et al., 2012). In some embodiments, the genetically engineered bacteria comprise any suitable ROS-responsive regulatory region from a gene that is activated by PerR.

One or more types of ROS-sensing transcription factors and corresponding regulatory region sequences may be present in genetically engineered bacteria. For example, "OhrR is found in both Gram-positive and Gram-negative bacteria and can coreside with either OxyR or PerR or both" (Dubbs et al., 2012). In some embodiments, the genetically engineered bacteria comprise one type of ROS-sensing transcription factor, e.g., OxyR, and one corresponding regulatory region sequence, e.g., from oxyS. In some embodiments, the genetically engineered bacteria comprise one type of ROS-sensing transcription factor, e.g., OxyR, and two or more different corresponding regulatory region sequences, e.g., from oxyS and katG. In some embodiments, the genetically engineered bacteria comprise two or more types of ROS-sensing transcription factors, e.g., OxyR and PerR, and two or more corresponding regulatory region sequences, e.g., from oxyS and katA, respectively. One ROS-responsive regulatory region may be capable of binding more than one transcription factor. In some embodiments, the genetically engineered bacteria comprise two or more types of ROS-sensing transcription factors and one corresponding regulatory region sequence.

Nucleic acid sequences of several exemplary OxyR-regulated regulatory regions are shown in Table 14. OxyR binding sites are underlined and bolded. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 71, 72, 73, or 74, or a functional fragment thereof.

TABLE 14

Nucleotide sequences of exemplary OxyR-regulated regulatory regions

| Regulatory sequence | 0123456789012345678901234567890123456789 |
|---|---|
| katG (SEQ ID NO: 71) | TGTGGCTTTTATGAAAATCACACAGTGATCACAAATTTTAAACAGAGCAC AAAATGCTGCCTCGAAATGAGGGCGGGAAAATAAGGTTATCAGCCTTGTT TTCTCCCTCATTACTTGAAGGATATGAAGCTAAAACCCTTTTTTATAAAG CATTTGTCCGAATTCGGACATAATCAAAAAAGCTTAATTAAGATCAATTT GATCTACATCTCTTTAACCAACAATATGTAAGATCTCAACTATCGCATCC GTGGATTAATTCAATTATAACTTCTCTCTAACGCTGTGTATCGTAACGGT AACACTGTAGAGGGGAGCACATTGATGCGAATTCATTAAAGAGGAGAAAG GTACC |
| dps (SEQ ID NO: 72) | TTCCGAAAATTCCTGGCGAGCAGATAAATAAGAATTGTTCTTATCAATAT ATCTAACTCATTGAATCTTTATTAGTTTTGTTTTTCACGCTTGTTACCAC TATTAGTGTGATAGGAACAGCCAGAATAGCGGAACACATAGCCGGTGCTA TACTTAATCTCGTTAATTACTGGGACATAACATCAAGAGGATATGAAATT CGAATTCATTAAAGAGGAGAAAGGTACC |
| ahpC (SEQ ID NO: 73) | GCTTAGATCAGGTGATTGCCCTTTGTTTATGAGGGTGTTGTAATCCATGT CGTTGTTGCATTTGTAAGGGCAACACCTCAGCCTGCAGGCAGGCACTGAA GATACCAAAGGGTAGTTCAGATTACACGGTCACCTGGAAAGGGGGCCATT TTACTTTTTATCGCCGCTGGCGGTGCAAAGTTCACAAAGTTGTCTTACGA AGGTTGTAAGGTAAAACTTATCGATTTGATAATGGAAACGCATTAGCCGA ATCGGCAAAAATTGGTTACCTTACATCTCATCGAAAACACGGAGGAAGTA TAGATGCGAATTCATTAAAGAGGAGAAAGGTACC |
| oxyS (SEQ ID NO: 74) | CTCGAGTTCATTATCCATCCTCCATCGCCACGATAGTTCATGGCGATAGG TAGAATAGCAATGAACGATTATCCCTATCAAGCATTCTGACTGATAATTG CTCACACGAATTCATTAAAGAGGAGAAAGGTACC |

In some embodiments, the genetically engineered bacteria of the invention comprise a gene encoding a ROS-sensing transcription factor, e.g., the oxyR gene, that is controlled by its native promoter, an inducible promoter, a promoter that is stronger than the native promoter, e.g., the GlnRS promoter or the P(Bla) promoter, or a constitutive promoter. In some instances, it may be advantageous to express the ROS-sensing transcription factor under the control of an inducible promoter in order to enhance expression stability. In some embodiments, expression of the ROS-sensing transcription factor is controlled by a different promoter than the promoter that controls expression of the therapeutic molecule. In some embodiments, expression of the ROS-sensing transcription factor is controlled by the same promoter that controls expression of the therapeutic molecule. In some embodiments, the ROS-sensing transcription factor and therapeutic molecule are divergently transcribed from a promoter region.

In some embodiments, the genetically engineered bacteria of the invention comprise a gene for a ROS-sensing transcription factor from a different species, strain, or substrain of bacteria. In some embodiments, the genetically engineered bacteria comprise a ROS-responsive regulatory region from a different species, strain, or substrain of bacteria. In some embodiments, the genetically engineered bacteria comprise a ROS-sensing transcription factor and corresponding ROS-responsive regulatory region from a different species, strain, or substrain of bacteria. The heterologous ROS-sensing transcription factor and regulatory region may increase the transcription of genes operatively linked to said regulatory region in the presence of ROS, as compared to the native transcription factor and regulatory region from bacteria of the same subtype under the same conditions.

In some embodiments, the genetically engineered bacteria comprise a ROS-sensing transcription factor, OxyR, and corresponding regulatory region, oxyS, from *Escherichia coli*. In some embodiments, the native ROS-sensing transcription factor, e.g., OxyR, is left intact and retains wild-type activity. In alternate embodiments, the native ROS-sensing transcription factor, e.g., OxyR, is deleted or mutated to reduce or eliminate wild-type activity.

In some embodiments, the genetically engineered bacteria of the invention comprise multiple copies of the endogenous gene encoding the ROS-sensing transcription factor, e.g., the oxyR gene. In some embodiments, the gene encoding the ROS-sensing transcription factor is present on a plasmid. In some embodiments, the gene encoding the ROS-sensing transcription factor and the gene or gene cassette for producing the therapeutic molecule are present on different plasmids. In some embodiments, the gene encoding the ROS-sensing transcription factor and the gene or gene cassette for producing the therapeutic molecule are present on the same. In some embodiments, the gene encoding the ROS-sensing transcription factor is present on a chromosome. In some embodiments, the gene encoding the ROS-sensing transcription factor and the gene or gene cassette for producing the therapeutic molecule are present on different chromosomes. In some embodiments, the gene encoding the ROS-sensing transcription factor and the gene or gene cassette for producing the therapeutic molecule are present on the same chromosome.

In some embodiments, the genetically engineered bacteria comprise a wild-type gene encoding a ROS-sensing transcription factor, e.g., the soxR gene, and a corresponding regulatory region, e.g., a soxS regulatory region, that is mutated relative to the wild-type regulatory region from bacteria of the same subtype. The mutated regulatory region increases the expression of the anti-inflammation and/or gut barrier enhancer molecule in the presence of ROS, as compared to the wild-type regulatory region under the same conditions. In some embodiments, the genetically engineered bacteria comprise a wild-type ROS-responsive regulatory region, e.g., the oxyS regulatory region, and a corresponding transcription factor, e.g., OxyR, that is mutated relative to the wild-type transcription factor from bacteria of the same subtype. The mutant transcription factor increases the expression of the anti-inflammation and/or gut barrier enhancer molecule in the presence of ROS, as compared to the wild-type transcription factor under the same conditions. In some embodiments, both the ROS-sensing transcription factor and corresponding regulatory region are mutated relative to the wild-type sequences from bacteria of the same subtype in order to increase expression of the anti-inflammation and/or gut barrier enhancer molecule in the presence of ROS.

Nucleic acid sequences of exemplary ROS-regulated constructs comprising an oxyS promoter are shown in Table 15 and Table 16. The nucleic acid sequence of an exemplary construct encoding OxyR is shown in Table 17. Nucleic acid sequences of tetracycline-regulated constructs comprising a tet promoter are shown in Table 18 and Table 19. Table 15 depicts the nucleic acid sequence of an exemplary ROS-regulated construct comprising an oxyS promoter and a butyrogenic gene cassette (pLogic031-oxyS-butyrate construct; SEQ ID NO: 75). Table 16 depicts the nucleic acid sequence of an exemplary ROS-regulated construct comprising an oxyS promoter and a butyrogenic gene cassette (pLogic046-oxyS-butyrate construct; SEQ ID NO: 76). Table 17 depicts the nucleic acid sequence of an exemplary construct encoding OxyR (pZA22-oxyR construct; SEQ ID NO: 77). Table 18 depicts the nucleic acid sequence of an exemplary tetracycline-regulated construct comprising a tet promoter and a butyrogenic gene cassette (pLogic031-tet-butyrate construct; SEQ ID NO: 78). The sequence encoding TetR is underlined, and the overlapping tetR/tetA promoters are boxed. Table 19 depicts the nucleic acid sequence of an exemplary tetracycline-regulated construct comprising a tet promoter and a butyrogenic gene cassette (pLogic046-tet-butyrate construct; SEQ ID NO: 79). The sequence encoding TetR is underlined, and the overlapping tetR/tetA promoters are boxed.

TABLE 15

Nucleotide sequences of pLogic031-oxyS-butyrate construct (SEQ ID NO: 75)

| | |
|---:|---|
| 1 | ctcgagttca ttatccatcc tccatcgcca cgatagttca tggcgatagg tagaatagca |
| 61 | atgaacgatt atccctatca agcattctga ctgataattg ctcacacgaa ttcattaaag |
| 121 | aggagaaagg taccatggat ttaaattcta aaaatatca gatgcttaaa gagctatatg |
| 181 | taagcttcgc tgaaaatgaa gttaaacctt tagcaacaga acttgatgaa gaagaaagat |
| 241 | ttccttatga aacagtggaa aaaatggcaa aagcaggaat gatgggtata ccatatccaa |
| 301 | aagaatatgg tggagaaggt ggagacactg taggatatat aatggcagtt gaagaattgt |
| 361 | ctagagtttg tggtactaca ggagttatat tatcagctca tacatctctt ggctcatggc |
| 421 | ctatatatca atatggtaat gaagaacaaa aacaaaaatt cttaagacca ctagcaagtg |
| 481 | gagaaaaatt aggagcattt ggtcttactg agcctaatgc tggtacagat gcgtctggcc |
| 541 | aacaaacaac tgctgtttta gacgggatg aatacatact taatggctca aaaatattta |
| 601 | taacaaacgc aatagctggt gacatatatg tagtaatggc aatgactgat aaatctaagg |
| 661 | ggaacaaagg aatatcagca tttatagttg aaaaaggaac tcctgggttt agctttggag |
| 721 | ttaaagaaaa gaaaatgggt ataagaggtt cagctacgag tgaattaata tttgaggatt |
| 781 | gcagaatacc taaagaaaat ttacttggaa aagaaggtca aggatttaag atagcaatgt |
| 841 | ctactcttga tggtggtaga attggtatag ctgcacaagc tttaggttta gcacaaggtg |
| 901 | ctcttgatga aactgttaaa tatgtaaaag aaagagtaca atttggtaga ccattatcaa |
| 961 | aattccaaaa tacacaattc caattagctg atatggaagt taaggtacaa gcggctagac |
| 1021 | accttgtata tcaagcagct ataaataaag acttaggaaa accttatgga gtagaagcag |
| 1081 | caatggcaaa attatttgca gctgaaacag ctatggaagt tactacaaaa gctgtacaac |
| 1141 | ttcatggagg atatgatac actcgtgact atccagtaga aagaatgatg agagatgcta |
| 1201 | agataactga aatatatgaa ggaactagtg aagttcaaag aatggttatt tcaggaaaac |
| 1261 | tattaaaata gtaagaagga gatatacata tggaggaagg atttatgaat atagtcgttt |
| 1321 | gtataaaaca agttccagat acaacagaag ttaaactaga tcctaataca ggtactttaa |

TABLE 15-continued

Nucleotide sequences of pLogic031-oxyS-butyrate construct(SEQ ID NO: 75)

```
1381  ttagagatgg agtaccaagt ataataaacc ctgatgataa agcaggttta gaagaagcta
1441  taaaattaaa agaagaaatg ggtgctcatg taactgttat aacaatggga cctcctcaag
1501  cagatatggc tttaaaagaa gctttagcaa tgggtgcaga tagaggtata ttattaacag
1561  atagagcatt tgcgggtgct gatacttggg caacttcatc agcattagca ggagcattaa
1621  aaaatataga ttttgatatt ataatagctg gaagacaggc gatagatgga gatactgcac
1681  aagttggacc tcaaatagct gaacatttaa atcttccatc aataacatat gctgaagaaa
1741  taaaaactga aggtgaatat gtattagtaa aaagacaatt tgaagattgt gccatgact
1801  taaaagttaa aatgccatgc cttataacaa ctcttaaaga tatgaacaca ccaagataca
1861  tgaaagttgg aagaatatat gatgctttcg aaaatgatgt agtagaaaca tggactgtaa
1921  aagatataga agttgaccct tctaatttag gtcttaaagg ttctccaact agtgtattta
1981  aatcatttac aaaatcagtt aaaccagctg gtacaatata caatgaagat gcgaaaacat
2041  cagctggaat tatcatagat aaattaaaag agaagtatat catataataa aaggagata
2101  tacatatggg taacgtttta gtagtaatag aacaaagaga aaatgtaatt caaactgttt
2161  ctttagaatt actaggaaag gctacagaaa tagcaaaaga ttatgataca aaagtttctg
2221  cattactttt aggtagtaag gtagaaggtt taatagatac attagcacac tatggtgcag
2281  atgaggtaat agtagtagat gatgaagctt tagcagtgta tacaactgaa ccatatacaa
2341  aagcagctta tgaagcaata aaagcagctg accctatagt tgtattattt ggtgcaactt
2401  caataggtag agatttagcg cctagagttt ctgctagaat acatacaggt cttactgctg
2461  actgtacagg tcttgcagta gctgaagata caaaattatt attaatgaca agacctgcct
2521  ttggtggaaa tataatggca acaatagttt gtaaagattt cagacctcaa atgtctacag
2581  ttagaccagg ggttatgaag aaaaatgaac ctgatgaaac taaagaagct gtaattaacc
2641  gtttcaaggt agaatttaat gatgctgata aattagttca agttgtacaa gtaataaaag
2701  aagctaaaaa acaagttaaa atagaagatg ctaagatatt agtttctgct ggacgtggaa
2761  tgggtggaaa agaaaactta gacatacttt atgaattagc tgaaattata ggtggagaag
2821  tttctggttc tcgtgccact atagatgcag gttggttaga taaagcaaga caagttggtc
2881  aaactggtaa aactgtaaga ccagaccttt atatagcatg tggtatatct ggagcaatac
2941  aacatatagc tggtatggaa gatgctgagt ttatagttgc tataaataaa aatccagaag
3001  ctccaatatt taaatatgct gatgttggta tagttggaga tgttcataaa gtgcttccag
3061  aacttatcag tcagttaagt gttgcaaaag aaaaggtga agttttagct aactaataag
3121  aaggagatat acatatgaga gaagtagtaa ttgccagtgc agctagaaca gcagtaggaa
3181  gttttggagg agcatttaaa tcagtttcag cggtagagtt aggggtaaca gcagctaaag
3241  aagctataaa aagagctaac ataactccag atatgataga tgaatctctt ttaggggag
3301  tacttacagc aggtcttgga caaaatatag caagacaaat agcattagga gcaggaatac
3361  cagtagaaaa accagctatg actataaata tagtttgtgg ttctggatta agatctgttt
3421  caatggcatc tcaacttata gcattaggtg atgctgatat aatgttagtt ggtggagctg
3481  aaaacatgag tatgtctcct tatttagtac caagtgcgag atatggtgca agaatgggtg
3541  atgctgcttt tgttgattca atgataaaag atggattatc agacatattt aataactatc
3601  acatgggtat tactgctgaa aacatagcag agcaatggaa tataactaga gaagaacaag
3661  atgaattagc tcttgcaagt caaaataaag ctgaaaaagc tcaagctgaa ggaaaatttg
```

TABLE 15-continued

Nucleotide sequences of pLogic031-oxyS-butyrate construct(SEQ ID NO: 75)

```
3721  atgaagaaat agttcctgtt gttataaaag gaagaaaagg tgacactgta gtagataaag
3781  atgaatatat taagcctggc actacaatgg agaaacttgc taagttaaga cctgcattta
3841  aaaaagatgg aacagttact gctggtaatg catcaggaat aaatgatggt gctgctatgt
3901  tagtagtaat ggctaaagaa aaagctgaag aactaggaat agagcctctt gcaactatag
3961  tttcttatgg aacagctggt gttgaccta aaataatggg atatggacca gttccagcaa
4021  ctaaaaaagc tttagaagct gctaatatga ctattgaaga tatagattta gttgaagcta
4081  atgaggcatt tgctgcccaa tctgtagctg taataagaga cttaaatata gatatgaata
4141  aagttaatgt taatggtgga gcaatagcta taggacatcc aataggatgc tcaggagcaa
4201  gaatacttac tacacttta tatgaaatga agagaagaga tgctaaaact ggtcttgcta
4261  cactttgtat aggcggtgga atgggaacta ctttaatagt taagagatag taagaaggag
4321  atatacatat gaaattagct gtaataggta gtggaactat gggaagtggt attgtacaaa
4381  cttttgcaag ttgtggacat gatgtatgtt taaagagtag aactcaaggt gctatagata
4441  aatgtttagc tttattagat aaaaatttaa ctaagttagt tactaaggga aaaatggatg
4501  aagctacaaa agcagaaata ttaagtcatg ttagttcaac tactaattat gaagatttaa
4561  aagatatgga tttaataata gaagcatctg tagaagacat gaatataaag aaagatgttt
4621  tcaagttact agatgaatta tgtaaagaag atactatctt ggcaacaaat acttcatcat
4681  tatctataac agaaatagct tcttctacta gcgcccaga taaagttata ggaatgcatt
4741  tctttaatcc agttcctatg atgaaattag ttgaagttat aagtggtcag ttaacatcaa
4801  aagttacttt tgatacagta tttgaattat ctaagagtat caataaagta ccagtagatg
4861  tatctgaatc tcctggattt gtagtaaata gaatacttat acctatgata aatgaagctg
4921  ttggtatata tgcagatggt gttgcaagta aagaagaaat agatgaagct atgaaattag
4981  gagcaaacca tccaatggga ccactagcat taggtgattt aatcggatta gatgttgttt
5041  tagctataat gaacgtttta tatactgaat ttggagatac taaatataga cctcatccac
5101  ttttagctaa aatggttaga gctaatcaat taggaagaaa aactaagata ggattctatg
5161  attataataa ataataagaa ggagatatac atatgagtac aagtgatgtt aaagtttatg
5221  agaatgtagc tgttgaagta gatggaaata tatgtacagt gaaaatgaat agacctaaag
5281  cccttaatgc aataaattca aagactttag aagaactta tgaagtattt gtagatatta
5341  ataatgatga aactattgat gttgtaatat tgacaggga aggaaaggca tttgtagctg
5401  gagcagatat tgcatacatg aaagatttag atgctgtagc tgctaaagat tttagtatct
5461  taggagcaaa agcttttgga gaaatagaaa atagtaaaaa agtagtgata gctgctgtaa
5521  acggatttgc tttaggtgga ggatgtgaac ttgcaatggc atgtgatata agaattgcat
5581  ctgctaaagc taaattggt cagccagaag taactcttgg aataactcca ggatatggag
5641  gaactcaaag gcttacaaga ttggttggaa tggcaaaagc aaaagaatta atctttacag
5701  gtcaagttat aaaagctgat gaagctgaaa aatagggct agtaaataga gtcgttgagc
5761  cagacatttt aatagaagaa gttgagaaat tagctaagat aatagctaaa aatgctcagc
5821  ttgcagttag atactctaaa gaagcaatac aacttggtgc tcaaactgat ataaatactg
5881  gaatagatat agaatctaat ttatttggtc tttgttttc aactaaagac caaaaagaag
5941  gaatgtcagc tttcgttgaa aagagagaag ctaactttat aaagggtaa taagaaggag
6001  atatacatat gagaagtttt gaagaagtaa ttaagtttgc aaaagaaaga ggacctaaaa
```

TABLE 15-continued

Nucleotide sequences of pLogic031-oxyS-butyrate construct(SEQ ID NO: 75)

```
6061  ctatatcagt agcatgttgc caagataaag aagttttaat ggcagttgaa atggctagaa
6121  aagaaaaaat agcaaatgcc attttagtag gagatataga aaagactaaa gaaattgcaa
6181  aaagcataga catggatatc gaaaattatg aactgataga tataaaagat ttagcagaag
6241  catctctaaa atctgttgaa ttagtttcac aaggaaaagc cgacatggta atgaaaggct
6301  tagtagacac atcaataata ctaaaagcag ttttaaataa agaagtaggg cttagaactg
6361  gaaatgtatt aagtcacgta gcagtatttg atgtagaggg atatgataga ttattttcg
6421  taactgacgc agctatgaac ttagctcctg atacaaatac taaaaagcaa atcatagaaa
6481  atgcttgcac agtagcacat tcattagata taagtgaacc aaaagttgct gcaatatgcg
6541  caaaagaaaa agtaaatcca aaaatgaaag atacagttga agctaaagaa ctagaagaaa
6601  tgtatgaaag aggagaaatc aaaggttgta tggttggtgg gccttttgca attgataatg
6661  cagtatcttt agaagcagct aaacataaag gtataaatca tcctgtagca ggacgagctg
6721  atatattatt agccccagat attgaaggtg gtaacatatt atataaagct ttggtattct
6781  tctcaaaatc aaaaaatgca ggagttatag ttggggctaa agcaccaata atattaactt
6841  ctagagcaga cagtgaagaa actaaactaa actcaatagc tttaggtgtt ttaatggcag
6901  caaaggcata ataagaagga gatatacata tgagcaaaat atttaaaatc ttaacaataa
6961  atcctggttc gacatcaact aaaatagctg tatttgataa tgaggattta gtatttgaaa
7021  aaactttaag acattcttca gaagaaatag gaaaatatga gaaggtgtct gaccaatttg
7081  aatttcgtaa acaagtaata gaagaagctc taaaagaagg tggagtaaaa acatctgaat
7141  tagatgctgt agtaggtaga ggaggacttc ttaaacctat aaaaggtggt acttattcag
7201  taagtgctgc tatgattgaa gatttaaaag tgggagtttt aggagaacac gcttcaaacc
7261  taggtggaat aatagcaaaa caataggtg aagaagtaaa tgttccttca tacatagtag
7321  accctgttgt tgtagatgaa ttagaagatg ttgctagaat ttctggtatg cctgaaataa
7381  gtagagcaag tgtagtacat gctttaaatc aaaggcaat agcaagaaga tatgctagag
7441  aaataaacaa gaaatatgaa gatataaatc ttatagttgc acacatgggt ggaggagttt
7501  ctgttggagc tcataaaaat ggtaaaatag tagatgttgc aaacgcatta gatggagaag
7561  gacctttctc tccagaaaga agtggtggac taccagtagg tgcattagta aaaatgtgct
7621  ttagtggaaa atatactcaa gatgaaatta aaagaaaat aaaaggtaat ggcggactag
7681  ttgcatactt aaacactaat gatgctagag aagttgaaga aagaattgaa gctggtgatg
7741  aaaaagctaa attagtatat gaagctatgg catatcaaat ctctaaagaa ataggagcta
7801  gtgctgcagt tcttaaggga gatgtaaaag caatattatt aactggtgga atcgcatatt
7861  caaaaatgtt tacagaaatg attgcagata gagttaaatt tatagcagat gtaaaagttt
7921  atccaggtga agatgaaatg attgcattag ctcaaggtgg acttagagtt ttaactggtg
7981  aagaagaggc tcaagtttat gataactaat aa
```

TABLE 16

Nucleotide sequences of pLogic046-oxyS-butyrate construct(SEQ ID NO: 76)

```
  1  ctcgagttca ttatccatcc tccatcgcca cgatagttca tggcgatagg tagaatagca
 61  atgaacgatt atccctatca agcattctga ctgataattg ctcacacgaa ttcattaaag
121  aggagaaagg taccatgatc gtaaaaccta tggtacgcaa caatatctgc ctgaacgccc
```

TABLE 16-continued

Nucleotide sequences of pLogic046-oxyS-butyrate construct(SEQ ID NO: 76)

```
 181   atcctcaggg ctgcaagaag ggagtggaag atcagattga atataccaag aaacgcatta
 241   ccgcagaagt caaagctggc gcaaaagctc caaaaaacgt tctggtgctt ggctgctcaa
 301   atggttacgg cctggcgagc cgcattactg ctgcgttcgg atacggggct gcgaccatcg
 361   gcgtgtcctt tgaaaaagcg ggttcagaaa ccaaatatgg tacaccggga tggtacaata
 421   atttggcatt tgatgaagcg gcaaaacgcg agggtcttta tagcgtgacg atcgacggcg
 481   atgcgttttc agacgagatc aaggcccagg taattgagga agccaaaaaa aaaggtatca
 541   aatttgatct gatcgtatac agcttggcca gcccagtacg tactgatcct gatacaggta
 601   tcatgcacaa aagcgttttg aaacccttg gaaaaacgtt cacaggcaaa acagtagatc
 661   cgtttactgg cgagctgaag gaaatctccg cggaaccagc aaatgacgag gaagcagccg
 721   ccactgttaa agttatgggg ggtgaagatt gggaacgttg gattaagcag ctgtcgaagg
 781   aaggcctctt agaagaaggc tgtattacct tggcctatag ttatattggc cctgaagcta
 841   cccaagcttt gtaccgtaaa ggcacaatcg gcaaggccaa agaacacctg gaggccacag
 901   cacaccgtct caacaaagag aacccgtcaa tccgtgcctt cgtgagcgtg aataaaggcc
 961   tggtaacccg cgcaagcgcc gtaatcccgg taatccctct gtatctcgcc agcttgttca
1021   aagtaatgaa agagaagggc aatcatgaag gttgtattga acagatcacg cgtctgtacg
1081   ccgagcgcct gtaccgtaaa gatggtacaa ttccagttga tgaggaaaat cgcattcgca
1141   ttgatgattg ggagttagaa gaagacgtcc agaaagcggt atccgcgttg atggagaaag
1201   tcacgggtga aaacgcagaa tctctcactg acttagcggg gtaccgccat gatttcttag
1261   ctagtaacgg ctttgatgta gaaggtatta attatgaagc ggaagttgaa cgcttcgacc
1321   gtatctgata agaaggagat atacatatga gagaagtagt aattgccagt gcagctagaa
1381   cagcagtagg aagttttgga ggagcattta aatcagtttc agcggtagag ttaggggtaa
1441   cagcagctaa agaagctata aaaagagcta acataactcc agatatgata gatgaatctc
1501   ttttaggggg agtacttaca gcaggtcttg acaaaaatat agcaagacaa atagcattag
1561   gagcaggaat accagtagaa aaaccagcta tgactataaa tatagtttgt ggttctggat
1621   taagatctgt ttcaatggca tctcaactta tagcattagg tgatgctgat ataatgttag
1681   ttggtggagc tgaaaacatg agtatgtctc cttatttagt accaagtgcg agatatggtg
1741   caagaatggg tgatgctgct tttgttgatt caatgataaa agatggatta tcagacatat
1801   ttaataacta tcacatgggt attactgctg aaaacatagc agagcaatgg aatataacta
1861   gagaagaaca agatgaatta gctcttgcaa gtcaaaataa agctgaaaaa gctcaagctg
1921   aaggaaaatt tgatgaagaa atagttcctg ttgttataaa aggaagaaaa ggtgacactg
1981   tagtagataa agatgaatat attaagcctg gcactacaat ggagaaactt gctaagttaa
2041   gacctgcatt taaaaagat ggaacagtta ctgctggtaa tgcatcagga ataaatgatg
2101   gtgctgctat gttagtagta atggctaaag aaaagctga agaactagga atagagcctc
2161   ttgcaactat agtttcttat ggaacagctg gtgttgaccc taaaataatg ggatatggac
2221   cagttccagc aactaaaaaa gctttagaag ctgctaatat gactattgaa gatatagatt
2281   tagttgaagc taatgaggca tttgctgccc aatctgtagc tgtaataaga gacttaaata
2341   tagatatgaa taaagttaat gttaatggtg gagcaatagc tataggacat ccaataggat
2401   gctcaggagc aagaatactt actacacttt tatatgaaat gaagagaaga gatgctaaaa
2461   ctggtcttgc tacactttgt ataggcggtg gaatgggaac tactttaata gttaagagat
```

TABLE 16-continued

Nucleotide sequences of pLogic046-oxyS-butyrate construct(SEQ ID NO: 76)

```
2521 agtaagaagg agatatacat atgaaattag ctgtaatagg tagtggaact atgggaagtg
2581 gtattgtaca aacttttgca agttgtggac atgatgtatg tttaaagagt agaactcaag
2641 gtgctataga taaatgttta gctttattag ataaaaattt aactaagtta gttactaagg
2701 gaaaaatgga tgaagctaca aaagcagaaa tattaagtca tgttagttca actactaatt
2761 atgaagattt aaaagatatg gatttaataa tagaagcatc tgtagaagac atgaatataa
2821 agaaagatgt tttcaagtta ctagatgaat tatgtaaaga agatactatc ttggcaacaa
2881 atacttcatc attatctata acagaaatag cttcttctac taagcgccca gataaagtta
2941 taggaatgca tttctttaat ccagttccta tgatgaaatt agttgaagtt ataagtggtc
3001 agttaacatc aaaagttact tttgatacag tatttgaatt atctaagagt atcaataaag
3061 taccagtaga tgtatctgaa tctcctggat ttgtagtaaa tagaatactt ataccttatga
3121 taaatgaagc tgttggtata tatgcagatg gtgttgcaag taaagaagaa atagatgaag
3181 ctatgaaatt aggagcaaac catccaatgg gaccactagc attaggtgat ttaatcggat
3241 tagatgttgt tttagctata atgaacgttt tatatactga atttggagat actaaatata
3301 gacctcatcc acttttagct aaaatggtta gagctaatca attaggaaga aaaactaaga
3361 taggattcta tgattataat aaataataag aaggagatat acatatgagt acaagtgatg
3421 ttaaagttta tgagaatgta gctgttgaag tagatggaaa tatatgtaca gtgaaaatga
3481 atagacctaa agcccttaat gcaataaatt caaagacttt agaagaactt tatgaagtat
3541 ttgtagatat taataatgat gaaactattg atgttgtaat attgacaggg gaaggaaagg
3601 catttgtagc tggagcagat attgcataca tgaaagattt agatgctgta gctgctaaag
3661 attttagtat cttaggagca aaagcttttg gagaaataga aaatagtaaa aaagtagtga
3721 tagctgctgt aaacggattt gctttaggtg gaggatgtga acttgcaatg gcatgtgata
3781 taagaattgc atctgctaaa gctaaatttg gtcagccaga agtaactctt ggaataactc
3841 caggatatgg aggaactcaa aggcttacaa gattggttgg aatggcaaaa gcaaaagaat
3901 taatctttac aggtcaagtt ataaaagctg atgaagctga aaaaataggg ctagtaaata
3961 gagtcgttga gccagacatt ttaatagaag aagttgagaa attagctaag ataatagcta
4021 aaaatgctca gcttgcagtt agatactcta aagaagcaat acaacttggt gctcaaactg
4081 atataaatac tggaatagat atagaatcta atttatttgg tctttgtttt tcaactaaag
4141 accaaaaaga aggaatgtca gctttcgttg aaaagagaga agctaacttt ataaaagggt
4201 aataagaagg agatatacat atgagaagtt ttgaagaagt aattaagttt gcaaaagaaa
4261 gaggacctaa aactatatca gtagcatgtt gccaagataa agaagtttta atggcagttg
4321 aaatggctag aaaagaaaaa atagcaaatg ccattttagt aggagatata gaaagactaa
4381 aagaaattgc aaaaagcata gacatggata tcgaaaatta tgaactgata gatataaaag
4441 atttagcaga agcatctcta aaatctgttg aattagtttc acaggaaaaa gccgacatgg
4501 taatgaaagg cttagtagac acatcaataa tactaaaagc agtttttaaat aaagaagtag
4561 gtcttagaac tggaaatgta ttaagtcacg tagcagtatt tgatgtagag ggatatgata
4621 gattattttt cgtaactgac gcagctatga acttagctcc tgatacaaat actaaaaagc
4681 aaatcataga aaatgcttgc acagtagcac attcattaga tataagtgaa ccaaaagttg
4741 ctgcaatatg cgcaaaagaa aaagtaaatc caaaaatgaa agatacagtt gaagctaaag
4801 aactagaaga aatgtatgaa agaggagaaa tcaaaggttg tatggttggt gggccttttg
```

TABLE 16-continued

Nucleotide sequences of pLogic046-oxyS-butyrate construct(SEQ ID NO: 76)

```
4861  caattgataa tgcagtatct ttagaagcag ctaaacataa aggtataaat catcctgtag
4921  caggacgagc tgatatatta ttagccccag atattgaagg tggtaacata ttatataaag
4981  ctttggtatt cttctcaaaa tcaaaaaatg caggagttat agttggggct aaagcaccaa
5041  taatattaac ttctagagca gacagtgaag aaactaaact aaactcaata gctttaggtg
5101  ttttaatggc agcaaaggca taataagaag gagatataca tatgagcaaa atatttaaaa
5161  tcttaacaat aaatcctggt tcgacatcaa ctaaaatagc tgtatttgat aatgaggatt
5221  tagtatttga aaaacttta agacattctt cagaagaaat aggaaaatat gagaaggtgt
5281  ctgaccaatt tgaatttcgt aaacaagtaa tagaagaagc tctaaaagaa ggtggagtaa
5341  aaacatctga attagatgct gtagtaggta gaggaggact tcttaaacct ataaaaggtg
5401  gtacttattc agtaagtgct gctatgattg aagatttaaa agtgggagtt ttaggagaac
5461  acgcttcaaa cctaggtgga ataatagcaa acaaatagg tgaagaagta aatgttcctt
5521  catacatagt agaccctgtt gttgtagatg aattagaaga tgttgctaga atttctggta
5581  tgcctgaaat aagtagagca agtgtagtac atgctttaaa tcaaaaggca atagcaagaa
5641  gatatgctag agaaataaac aagaaatatg aagatataaa tcttatagtt gcacacatgg
5701  gtggaggagt ttctgttgga gctcataaaa atggtaaaat agtagatgtt gcaaacgcat
5761  tagatggaga aggacctttc tctccagaaa gaagtggtgg actaccagta ggtgcattag
5821  taaaaatgtg ctttagtgga aaatatactc aagatgaaat taaaaagaaa ataaaaggta
5881  atggcggact agttgcatac ttaaacacta atgatgctag agaagttgaa gaaagaattg
5941  aagctggtga tgaaaaagct aaattagtat atgaagctat ggcatatcaa atctctaaag
6001  aaataggagc tagtgctgca gttcttaagg gagatgtaaa agcaatatta ttaactggtg
6061  gaatcgcata ttcaaaaatg tttacagaaa tgattgcaga tagagttaaa tttatagcag
6121  atgtaaaagt ttatccaggt gaagatgaaa tgattgcatt agctcaaggt ggacttagag
6181  ttttaactgg tgaagaagag gctcaagttt atgataacta ataa
```

TABLE 17

Nucleotide sequences of pZA22-oxyR constrcut(SEQ ID NO: 77)

```
  1  ctcgagatgc tagcaattgt gagcggataa caattgacat tgtgagcgga taacaagata
 61  ctgagcacat cagcaggacg cactgacctt aattaaaaga attcattaaa gaggagaaag
121  gtaccatgaa tattcgtgat cttgagtacc tggtggcatt ggctgaacac cgccattttc
181  ggcgtgcggc agattcctgc cacgttagcc agccgacgct tagcgggcaa attcgtaagc
241  tggaagatga gctgggcgtg atgttgctgg agcggaccag ccgtaaagtg ttgttcaccc
301  aggcgggaat gctgctggtg gatcaggcgc gtaccgtgct gcgtgaggtg aaagtcctta
361  aagagatggc aagccagcag ggcgagacga tgtccggacc gctgcacatt ggtttgattc
421  ccacagttgg accgtacctg ctaccgcata ttatccctat gctgcaccag acctttccaa
481  agctggaaat gtatctgcat gaagcacaga cccaccagtt actggcgcaa ctggacagcg
541  gcaaactcga ttgcgtgatc ctcgcgctgg tgaaagagag cgaagcattc attgaagtgc
601  cgttgtttga tgagccaatg ttgctggcta tctatgaaga tcacccgtgg gcgaaccgcg
661  aatgcgtacc gatggccgat ctggcagggg aaaaactgct gatgctggaa gatggtcact
```

TABLE 17-continued

| Nucleotide sequences of pZA22-oxyR constrcut(SEQ ID NO: 77) |
| --- |

```
 721  gtttgcgcga tcaggcaatg ggtttctgtt ttgaagccgg ggcggatgaa gatacacact
 781  tccgcgcgac cagcctggaa actctgcgca acatggtggc ggcaggtagc gggatcactt
 841  tactgccagc gctggctgtg ccgccggagc gcaaacgcga tggggttgtt tatctgccgt
 901  gcattaagcc ggaaccacgc cgcactattg gcctggttta tcgtcctggc tcaccgctgc
 961  gcagccgcta tgagcagctg gcagaggcca tccgcgcaag aatggatggc catttcgata
1021  aagttttaaa acaggcggtt taaggatccc atggtacgcg tgctagaggc atcaaataaa
1081  acgaaaggct cagtcgaaag actgggcctt tcgttttatc tgttgtttgt cggtgaacgc
1141  tctcctgagt aggacaaatc cgccgcccta gacctagggg atatattccg cttcctcgct
1201  cactgactcg ctacgctcgg tcgttcgact gcggcgagcg gaaatggctt acgaacgggg
1261  cggagatttc ctggaagatg ccaggaagat acttaacagg gaagtgagag ggccgcggca
1321  aagccgtttt tccataggct ccgccccct gacaagcatc acgaaatctg acgctcaaat
1381  cagtggtggc gaaacccgac aggactataa agataccagg cgtttccccc tggcggctcc
1441  ctcgtgcgct ctcctgttcc tgccttcgg tttaccggtg tcattccgct gttatggccg
1501  cgtttgtctc attccacgcc tgacactcag ttccgggtag gcagttcgct ccaagctgga
1561  ctgtatgcac gaacccccg ttcagtccga ccgctgcgcc ttatccggta actatcgtct
1621  tgagtccaac ccggaaagac atgcaaaagc accactggca gcagccactg gtaattgatt
1681  tagaggagtt agtcttgaag tcatgcgccg gttaaggcta aactgaaagg acaagttttg
1741  gtgactgcgc tcctccaagc cagttacctc ggttcaaaga gttggtagct cagagaacct
1801  tcgaaaaacc gccctgcaag gcggttttt cgttttcaga gcaagagatt acgcgcagac
1861  caaaacgatc tcaagaagat catcttatta atcagataaa atatttctag atttcagtgc
1921  aatttatctc ttcaaatgta gcacctgaag tcagccccat acgatataag ttgttactag
1981  tgcttggatt ctcaccaata aaaaacgccc ggcggcaacc gagcgttctg aacaaatcca
2041  gatggagttc tgaggtcatt actggatcta tcaacaggag tccaagcgag ctctcgaacc
2101  ccagagtccc gctcagaaga actcgtcaag aaggcgtag aaggcgatgc gctgcgaatc
2161  gggagcggcg ataccgtaaa gcacgaggaa gcggtcagcc cattcgccgc caagctcttc
2221  agcaatatca cgggtagcca acgctatgtc ctgatagcgg tccgccacac ccagccggcc
2281  acagtcgatg aatccagaaa agcggccatt ttccaccatg atattcggca agcaggcatc
2341  gccatgggtc acgacgagat cctcgccgtc gggcatgcgc gccttgagcc tggcgaacag
2401  ttcggctggc gcgagcccct gatgctcttc gtccagatca tcctgatcga caagaccggc
2461  ttccatccga gtacgtgctc gctcgatgcg atgtttcgct tggtggtcga atgggcaggt
2521  agccggatca agcgtatgca gccgccgcat tgcatcagcc atgatggata ctttctcggc
2581  aggagcaagg tgagatgaca ggagatcctg ccccggcact tcgcccaata gcagccagtc
2641  ccttcccgct tcagtgacaa cgtcgagcac agctgcgcaa ggaacgcccg tcgtggccag
2701  ccacgatagc cgcgctgcct cgtcctgcag ttcattcagg gcaccggaca ggtcggtctt
2761  gacaaaaaga accgggcgcc cctgcgctga cagccggaac acggcggcat cagagcagcc
2821  gattgtctgt tgtgcccagt catagccgaa tagcctctcc acccaagcgg ccggagaacc
2881  tgcgtgcaat ccatcttgtt caatcatgcg aaacgatcct catcctgtct cttgatcaga
2941  tcttgatccc ctgcgccatc agatccttgg cggcaagaaa gccatccagt ttactttgca
```

TABLE 17-continued

Nucleotide sequences of pZA22-oxyR constrcut(SEQ ID NO: 77)

```
3001  gggcttccca accttaccag agggcgcccc agctggcaat tccgacgtct aagaaaccat
3061  tattatcatg acattaacct ataaaaatag gcgtatcacg aggccctttc gtcttcac
```

TABLE 18

Nucleotide sequences of pLogic031-tet-butyrate construct
(SEQ ID NO: 78)

```
   1  gtaaaacgac ggccagtgaa ttcgttaaga cccactttca catttaagtt gtttttctaa
  61  tccgcatatg atcaattcaa ggccgaataa gaaggctggc tctgcaccct ggtgatcaaa
 121  taattcgata gcttgtcgta ataatggcgg catactatca gtagtaggtg tttcccttt c
 181  ttctttagcg acttgatgct cttgatcttc caatacgcaa cctaaagtaa aatgccccac
 241  agcgctgagt gcatataatg cattctctag tgaaaaacct tgttggcata aaaaggctaa
 301  ttgattttcg agagtttcat actgtttttc tgtaggccgt gtacctaaat gtactttttgc
 361  tccatcgcga tgacttagta aagcacatct aaaactttta gcgttattac gtaaaaaatc
 421  ttgccagctt tccccttcta aagggcaaaa gtgagtatgg tgcctatcta acatctcaat
 481  ggctaaggcg tcgagcaaag cccgcttatt ttttacatgc caatacaatg taggctgctc
 541  tacacctagc ttctgggcga gtttacgggt tgttaaacct tcgattccga cctcattaag
 601  cagctctaat gcgctgttaa tcactttact tttatctaat ctagacatca ttaattccta
 661  atttttgttg acactctatc attgatagag ttattttacc actccctatc agtgatagag
 721  aaaagtgaac tctagaaata attttgttta actttaagaa ggagatatac atatggattt
 781  aaattctaaa aaatatcaga tgcttaaaga gctatatgta agcttcgctg aaaatgaagt
 841  taaaccttta gcaacagaac ttgatgaaga agaaagattt ccttatgaaa cagtggaaaa
 901  aatggcaaaa gcaggaatga tgggtatacc atatccaaaa gaatatggtg gagaaggtgg
 961  agacactgta ggatatataa tggcagttga agaattgtct agagtttgtg gtactacagg
1021  agttatatta tcagctcata catctcttgg ctcatggcct atatatcaat atggtaatga
1081  agaacaaaaa caaaaattct aagaccact agcaagtgga gaaaaattag gagcatttgg
1141  tcttactgag cctaatgctg gtacagatgc gtctggccaa caaacaactg ctgttttaga
1201  cggggatgaa tacatactta atggctcaaa aatatttata acaaacgcaa tagctggtga
1261  catatatgta gtaatggcaa tgactgataa atctaagggg aacaaaggaa tatcagcatt
1321  tatagttgaa aaaggaactc ctgggtttag ctttggagtt aaagaaaaga aatgggtat
1381  aagaggttca gctacgagtg aattaatatt tgaggattgc agaataccta agaaaatt t
1441  acttggaaaa gaaggtcaag gatttaagat agcaatgtct actcttgatg gtggtagaat
1501  tggtatagct gcacaagctt taggtttagc acaaggtgct cttgatgaaa ctgttaaata
1561  tgtaaaagaa agagtacaat tggtagacc attatcaaaa ttccaaaata cacaattcca
1621  attagctgat atggaagtta aggtacaagc ggctagacac cttgtatatc aagcagctat
1681  aaataaagac ttaggaaaac cttatggagt agaagcagca atggcaaaat tatttgcagc
1741  tgaaacagct atggaagtta ctacaaaagc tgtacaactt catggaggat atggatacac
1801  tcgtgactat ccagtagaaa gaatgatgag agatgctaag ataactgaaa tatatgaagg
1861  aactagtgaa gttcaaagaa tggttatttc aggaaaacta ttaaaatagt aagaaggaga
1921  tatacatatg gaggaaggat ttatgaatat agtcgtttgt ataaaacaag ttccagatac
```

TABLE 18-continued

Nucleotide sequences of pLogic031-tet-butyrate construct
(SEQ ID NO: 78)

```
1981 aacagaagtt aaactagatc ctaatacagg tactttaatt agagatggag taccaagtat 2041 aataaaccct gatgataaag caggtttaga agaagctata aaattaaaag aagaaatggg 2101 tgctcatgta actgttataa caatgggacc tcctcaagca gatatggctt taaaagaagc 2161 tttagcaatg ggtgcagata gaggtatatt attaacagat agagcatttg cgggtgctga 2221 tacttgggca acttcatcag cattagcagg agcattaaaa aatatagatt ttgatattat 2281 aatagctgga agacaggcga tagatggaga tactgcacaa gttggacctc aaatagctga 2341 acatttaaat cttccatcaa taacatatgc tgaagaaata aaaactgaag gtgaatatgt 2401 attagtaaaa agacaatttg aagattgttg ccatgactta aaagttaaaa tgccatgcct 2461 tataacaact cttaaagata tgaacacacc aagatacatg aaagttggaa gaatatatga 2521 tgctttcgaa aatgatgtag tagaaacatg gactgtaaaa gatatagaag ttgacccttc 2581 taatttaggt cttaaaggtt ctccaactag tgtatttaaa tcatttacaa aatcagttaa 2641 accagctggt acaatataca atgaagatgc gaaaacatca gctggaatta tcatagataa 2701 attaaaagag aagtatatca tataataaga aggagatata catatgggta acgttttagt 2761 agtaatagaa caaagagaaa atgtaattca aactgtttct ttagaattac taggaaaggc 2821 tacagaaata gcaaaagatt atgatacaaa agtttctgca ttacttttag gtagtaaggt 2881 agaaggttta atagatacat tagcacacta tggtgcagat gaggtaatag tagtagatga 2941 tgaagcttta gcagtgtata caactgaacc atatacaaaa gcagcttatg aagcaataaa 3001 agcagctgac cctatagttg tattatttgg tgcaacttca ataggtagag atttagcgcc 3061 tagagtttct gctagaatac atacaggtct tactgctgac tgtacaggtc ttgcagtagc 3121 tgaagataca aaattattat taatgacaag acctgccttt ggtggaaata taatggcaac 3181 aatagtttgt aaagatttca gacctcaaat gtctacagtt agaccagggg ttatgaagaa 3241 aaatgaacct gatgaaacta agaagctgt aattaaccgt ttcaaggtag aatttaatga 3301 tgctgataaa ttagttcaag ttgtacaagt aataaaagaa gctaaaaaac aagttaaaat 3361 agaagatgct aagatattag tttctgctgg acgtggaatg ggtggaaaag aaaacttaga 3421 catactttat gaattagctg aaattatagg tggagaagtt tctggttctc gtgccactat 3481 agatgcaggt tggttagata agcaagaca agttggtcaa actggtaaaa ctgtaagacc 3541 agacctttat atagcatgtg gtatatctgg agcaatacaa catatagctg gtatggaaga 3601 tgctgagttt atagttgcta taaataaaaa tccagaagct ccaatattta aatatgctga 3661 tgttggtata gttggagatg ttcataaagt gcttccagaa cttatcagtc agttaagtgt 3721 tgcaaaagaa aaaggtgaag ttttagctaa ctaataagaa ggagatatac atatgagaga 3781 agtagtaatt gccagtgcag ctagaacagc agtaggaagt tttggaggag catttaaatc 3841 agtttcagcg gtagagttag ggtaacagc agctaaagaa gctataaaaa gagctaacat 3901 aactccagat atgatagatg aatctctttt aggggagta cttacagcag gtcttggaca 3961 aaatatagca agacaaatag cattaggagc aggaatacca gtagaaaaac cagctatgac 4021 tataaatata gtttgtggtt ctggattaag atctgtttca atggcatctc aacttatagc 4081 attaggtgat gctgatataa tgttagtgg tggagctgaa acatgagta tgtctcctta 4141 tttagtacca agtgcgagat atggtgcaag aatgggtgat gctgcttttg ttgattcaat 4201 gataaaagat ggattatcag acatatttaa taactatcac atgggtatta ctgctgaaaa 4261 catagcagag caatggaata taactagaga agaacaagat gaattagctc ttgcaagtca
```

TABLE 18-continued

Nucleotide sequences of pLogic031-tet-butyrate construct
(SEQ ID NO: 78)

```
4321 aaataaagct gaaaaagctc aagctgaagg aaatttgat gaagaaatag ttcctgttgt 4381 tataaaagga agaaaggtg acactgtagt agataaagat gaatatatta agcctggcac 4441 tacaatggag aaacttgcta agttaagacc tgcatttaaa aaagatggaa cagttactgc 4501 tggtaatgca tcaggaataa atgatggtgc tgctatgtta gtagtaatgg ctaaagaaaa 4561 agctgaagaa ctaggaatag agcctcttgc aactatagtt tcttatggaa cagctggtgt 4621 tgaccctaaa ataatgggat atggaccagt tccagcaact aaaaaagctt tagaagctgc 4681 taatatgact attgaagata tagatttagt tgaagctaat gaggcatttg ctgcccaatc 4741 tgtagctgta ataagagact taaatataga tatgaataaa gttaatgtta atggtggagc 4801 aatagctata ggacatccaa taggatgctc aggagcaaga atacttacta cacttttata 4861 tgaaatgaag agaagagatg ctaaaactgg tcttgctaca ctttgtatag gcggtggaat 4921 gggaactact ttaatagtta agagatagta agaaggagat atacatatga aattagctgt 4981 aataggtagt ggaactatgg gaagtggtat tgtacaaact tttgcaagtt gtggacatga 5041 tgtatgttta aagagtagaa ctcaaggtgc tatagataaa tgtttagctt tattagataa 5101 aaatttaact aagttagtta ctaagggaaa aatggatgaa gctacaaaag cagaaatatt 5161 aagtcatgtt agttcaacta ctaattatga agatttaaaa gatatggatt taataataga 5221 agcatctgta gaagacatga atataaagaa agatgttttc aagttactag atgaattatg 5281 taaagaagat actatcttgg caacaaatac ttcatcatta tctataacag aaatagcttc 5341 ttctactaag cgcccagata aagttatagg aatgcatttc tttaatccag ttcctatgat 5401 gaaattagtt gaagttataa gtggtcagtt aacatcaaaa gttactttg atacagtatt 5461 tgaattatct aagagtatca ataaagtacc agtagatgta tctgaatctc ctggatttgt 5521 agtaaataga atacttatac ctatgataaa tgaagctgtt ggtatatatg cagatggtgt 5581 tgcaagtaaa gaagaaatag atgaagctat gaaattagga gcaaaccatc caatgggacc 5641 actagcatta ggtgatttaa tcggattaga tgttgtttta gctataatga acgttttata 5701 tactgaattt ggagatacta aatatagacc tcatccactt ttagctaaaa tggttagagc 5761 taatcaatta ggaagaaaaa ctaagatagg attctatgat tataataaat aataagaagg 5821 agatatacat atgagtacaa gtgatgttaa agtttatgag aatgtagctg ttgaagtaga 5881 tggaaatata tgtacagtga aaatgaatag acctaaagcc cttaatgcaa taaattcaaa 5941 gactttagaa gaactttatg aagtatttgt agatattaat aatgatgaaa ctattgatgt 6001 tgtaatattg acaggggaag gaaaggcatt tgtagctgga gcagatattg catacatgaa 6061 agatttagat gctgtagctg ctaaagattt tagtatctta ggagcaaaag cttttggaga 6121 aatagaaaat agtaaaaaag tagtgatagc tgctgtaaac ggatttgctt taggtggagg 6181 atgtgaactt gcaatggcat gtgatataag aattgcatct gctaaagcta aatttggtca 6241 gccagaagta actcttggaa taactccagg atatggagga actcaaaggc ttacaagatt 6301 ggttggaatg gcaaaagcaa agaattaat ctttacaggt caagttataa aagctgatga 6361 agctgaaaaa atagggctag taaatagagt cgttgagcca gacatttaa tagaagaagt 6421 tgagaaatta gctaagataa tagctaaaaa tgctcagctt gcagttagat actctaaaga 6481 agcaatacaa cttggtgctc aaactgatat aaatactgga atagatatag aatctaatt 6541 atttggtctt tgtttttcaa ctaaagacca aaaagaagga atgtcagctt tcgttgaaaa
```

TABLE 18-continued

Nucleotide sequences of pLogic031-tet-butyrate construct
(SEQ ID NO: 78)

```
6601 gagagaagct aactttataa aagggtaata agaaggagat atacatatga gaagttttga 6661 agaagtaatt aagtttgcaa agaaagagg acctaaaact atatcagtag catgttgcca 6721 agataaagaa gttttaatgg cagttgaaat ggctagaaaa gaaaaaatag caaatgccat 6781 tttagtagga gatatagaaa agactaaaga aattgcaaaa agcatagaca tggatatcga 6841 aaattatgaa ctgatagata taaaagattt agcagaagca tctctaaaat ctgttgaatt 6901 agtttcacaa ggaaaagccg acatggtaat gaaaggctta gtagacacat caataatact 6961 aaaagcagtt ttaaataaag aagtaggtct tagaactgga aatgtattaa gtcacgtagc 7021 agtatttgat gtagagggat atgatagatt atttttcgta actgacgcag ctatgaactt 7081 agctcctgat acaaatacta aaagcaaat catagaaaat gcttgcacag tagcacattc 7141 attagatata agtgaaccaa agttgctgc aatatgcgca aaagaaaaag taaatccaaa 7201 aatgaaagat acagttgaag ctaaagaact agaagaaatg tatgaaagag gagaaatcaa 7261 aggttgtatg gttggtgggc cttttgcaat tgataatgca gtatctttag aagcagctaa 7321 acataaaggt ataaatcatc ctgtagcagg acgagctgat atattattag ccccagatat 7381 tgaaggtggt aacatattat ataaagcttt ggtattcttc tcaaaatcaa aaaatgcagg 7441 agttatagtt ggggctaaag caccaataat attaacttct agagcagaca gtgaagaaac 7501 taaactaaac tcaatagctt taggtgtttt aatggcagca aaggcataat aagaaggaga 7561 tatacatatg agcaaaatat ttaaaatctt aacaataaat cctggttcga catcaactaa 7621 aatagctgta tttgataatg aggatttagt atttgaaaaa actttaagac attcttcaga 7681 agaaatagga aaatatgaga aggtgtctga ccaatttgaa tttcgtaaac aagtaataga 7741 agaagctcta aaagaaggtg gagtaaaaac atctgaatta gatgctgtag taggtagagg 7801 aggacttctt aaacctataa aaggtggtac ttattcagta agtgctgcta tgattgaaga 7861 tttaaaagtg ggagttttag gagaacacgc ttcaaaccta ggtggaataa tagcaaaaca 7921 aataggtgaa gaagtaaatg ttccttcata catagtagac cctgttgttg tagatgaatt 7981 agaagatgtt gctagaattt ctggtatgcc tgaaataagt agagcaagtg tagtacatgc 8041 tttaaatcaa aaggcaatag caagaagata tgctagagaa ataacaaga aatatgaaga 8101 tataaatctt atagttgcac acatgggtgg aggagtttct gttggagctc ataaaaatgg 8161 taaaatagta gatgttgcaa acgcattaga tggagaagga cctttctctc cagaaagaag 8221 tggtggacta ccagtaggtg cattagtaaa aatgtgcttt agtggaaaat atactcaaga 8281 tgaaattaaa aagaaaataa aaggtaatgg cggactagtt gcatacttaa acactaatga 8341 tgctagagaa gttgaagaaa gaattgaagc tggtgatgaa aaagctaaat tagtatatga 8401 agctatggca tatcaaatct ctaaagaaat aggagctagt gctgcagttc ttaagggaga 8461 tgtaaaagca atattattaa ctggtggaat cgcatattca aaaatgttta cagaaatgat 8521 tgcagataga gttaaattta tagcagatgt aaaagtttat ccaggtgaag atgaaatgat 8581 tgcattagct caaggtggac ttagagtttt aactggtgaa gaagaggctc aagtttatga 8641 taactaataa
```

TABLE 19

Nucleotide sequences of pLogic046-tet-butyrate construct
(SEQ ID NO: 79)

```
   1 gtaaaacgac ggccagtgaa ttcgttaaga cccactttca catttaagtt gtttttctaa
  61 tccgcatatg atcaattcaa ggccgaataa gaaggctggc tctgcacctt ggtgatcaaa
 121 taattcgata gcttgtcgta ataatggcgg catactatca gtagtaggtg tttcccttc
 181 ttctttagcg acttgatgct cttgatcttc aatacgcaa cctaaagtaa aatgccccac
 241 agcgctgagt gcatataatg cattctctag tgaaaaacct tgttggcata aaaaggctaa
 301 ttgattttcg agagtttcat actgtttttc tgtaggccgt gtacctaaat gtacttttgc
 361 tccatcgcga tgacttagta aagcacatct aaaacttta gcgttattac gtaaaaaatc
 421 ttgccagctt tccccttcta aagggcaaaa gtgagtatgg tgcctatcta acatctcaat
 481 ggctaaggcg tcgagcaaag cccgcttatt ttttacatgc caatacaatg taggctgctc
 541 tacacctagc ttctgggcga gtttacgggt tgttaaacct tcgattccga cctcattaag
 601 cagctctaat gcgctgttaa tcactttact tttatctaat ctagacatca ttaattccta
 661 attttgttg acactctatc attgatagag ttattttacc actccctatc agtgatagag
 721 aaaagtgaac tctagaaata attttgttta actttaagaa ggagatatac atatgatcgt
 781 aaaacctatg gtacgcaaca atatctgcct gaacgcccat cctcagggct gcaagaaggg
 841 agtggaagat cagattgaat ataccaagaa acgcattacc gcagaagtca agctggcgc
 901 aaaagctcca aaaaacgttc tggtgcttgg ctgctcaaat ggttacgcc tggcgagccg
 961 cattactgct gcgttcggat acggggctgc gaccatcggc gtgtcctttg aaaaagcggg
1021 ttcagaaacc aaatatggta caccgggatg gtacaataat ttggcatttg atgaagcggc
1081 aaaacgcgag ggtctttata gcgtgacgat cgacggcgat gcgttttcag acgagatcaa
1141 ggcccaggta attgaggaag ccaaaaaaaa aggtatcaaa tttgatctga tcgtatacag
1201 cttggccagc ccagtacgta ctgatcctga tacaggtatc atgcacaaaa gcgttttgaa
1261 accctttgga aaaacgttca caggcaaaac agtagatccg tttactggcg agctgaagga
1321 aatctccgcg gaaccagcaa atgacgagga agcagccgcc actgttaaag ttatgggggg
1381 tgaagattgg gaacgttgga ttaagcagct gtcgaaggaa ggcctcttag aagaaggctg
1441 tattaccttg gcctatagtt atattggccc tgaagctacc caagctttgt accgtaaagg
1501 cacaatcggc aaggccaaag aacacctgga ggccacagca caccgtctca acaaagagaa
1561 cccgtcaatc cgtgccttcg tgagcgtgaa taaaggcctg gtaacccgcg caagcgccgt
1621 aatcccggta atccctctgt atctcgccag cttgttcaaa gtaatgaaag agaagggcaa
1681 tcatgaaggt tgtattgaac agatcacgcg tctgtacgcc gagcgcctgt accgtaaaga
1741 tggtacaatt ccagttgatg aggaaaatcg cattcgcatt gatgattggg agttagaaga
1801 agacgtccag aaagcggtat ccgcgttgat ggagaaagtc acgggtgaaa acgcagaatc
1861 tctcactgac ttagcggggt accgccatga tttcttagct agtaacggct tgatgtaga
1921 aggtattaat tatgaagcgg aagttgaacg cttcgaccgt atctgataag aaggagatat
1981 acatatgaga gaagtagtaa ttgccagtgc agctagaaca gcagtaggaa gttttggagg
2041 agcatttaaa tcagtttcag cggtagagtt aggggtaaca gcagctaaag aagctataaa
2101 aagagctaac ataactccag atatgataga tgaatctctt ttaggggag tacttacagc
2161 aggtcttgga caaaatatag caagacaaat agcattagga gcaggaatac cagtagaaaa
2221 accagcatat gactataaata tagtttgtgg ttctggatta agatctgttt caatggcatc
2281 tcaacttata gcattaggtg atgctgatat aatgttagtt ggtggagctg aaaacatgag
```

TABLE 19-continued

Nucleotide sequences of pLogic046-tet-butyrate construct
(SEQ ID NO: 79)

```
2341 tatgtctcct tatttagtac caagtgcgag atatggtgca agaatgggtg atgctgcttt
2401 tgttgattca atgataaaag atggattatc agacatattt aataactatc acatgggtat
2461 tactgctgaa acatagcag agcaatggaa tataactaga gaagaacaag atgaattagc
2521 tcttgcaagt caaaataaag ctgaaaaagc tcaagctgaa ggaaaatttg atgaagaaat
2581 agttcctgtt gttataaaag gaagaaaagg tgacactgta gtagataaag atgaatatat
2641 taagcctggc actacaatgg agaaacttgc taagttaaga cctgcattta aaaagatgg
2701 aacagttact gctggtaatg catcaggaat aaatgatggt gctgctatgt tagtagtaat
2761 ggctaaagaa aaagctgaag aactaggaat agagcctctt gcaactatag tttcttatgg
2821 aacagctggt gttgacccta aaataatggg atatggacca gttccagcaa ctaaaaaagc
2881 tttagaagct gctaatatga ctattgaaga tatagattta gttgaagcta atgaggcatt
2941 tgctgcccaa tctgtagctg taataagaga cttaaatata gatatgaata agttaatgt
3001 taatggtgga gcaatagcta taggacatcc aataggatgc tcaggagcaa gaatacttac
3061 tacactttta tatgaaatga agagaagaga tgctaaaact ggtcttgcta cactttgtat
3121 aggcggtgga atgggaacta ctttaatagt taagagatag taagaaggag atatacatat
3181 gaaattagct gtaataggta gtggaactat gggaagtggt attgtacaaa cttttgcaag
3241 ttgtggacat gatgtatgtt taagagtag aactcaaggt gctatagata atgtttagc
3301 tttattagat aaaaatttaa ctaagttagt tactaaggga aaaatggatg aagctacaaa
3361 agcagaaata ttaagtcatg ttagttcaac tactaattat gaagatttaa agatatgga
3421 tttaataata gaagcatctg tagaagacat gaatataaag aaagatgttt tcaagttact
3481 agatgaatta tgtaaagaag atactatctt ggcaacaaat acttcatcat tatctataac
3541 agaaatagct tcttctacta agcgcccaga taaagttata ggaatgcatt tctttaatcc
3601 agttcctatg atgaaattag ttgaagttat aagtggtcag ttaacatcaa aagttacttt
3661 tgatacagta tttgaattat ctaagagtat caataaagta ccagtagatg tatctgaatc
3721 tcctggattt gtagtaaata gaatacttat acctatgata aatgaagctg ttggtatata
3781 tgcagatggt gttgcaagta aagaagaaat agatgaagct atgaaattag gagcaaacca
3841 tccaatggga ccactagcat taggtgattt aatcggatta gatgttgttt tagctataat
3901 gaacgtttta tatactgaat ttggagatac taaatataga cctcatccac ttttagctaa
3961 aatggttaga gctaatcaat taggaagaaa aactaagata ggattctatg attataataa
4021 ataataagaa ggagatatac atatgagtac aagtgatgtt aaagtttatg agaatgtagc
4081 tgttgaagta gatggaaata tatgtacagt gaaaatgaat agacctaaag cccttaatgc
4141 aataaattca aagactttag aagaacttta tgaagtattt gtagatatta ataatgatga
4201 aactattgat gttgtaatat tgacagggga aggaaaggca tttgtagctg gagcagatat
4261 tgcatacatg aaagatttag atgctgtagc tgctaaagat tttagtatct taggagcaaa
4321 agcttttgga gaaatagaaa atagtaaaaa agtagtgata gctgctgtaa acggatttgc
4381 tttaggtgga ggatgtgaac ttgcaatggc atgtgatata agaattgcat ctgctaaagc
4441 taaatttggt cagccagaag taactcttgg aataactcca ggatatggag gaactcaaag
4501 gcttacaaga ttggttggaa tggcaaaagc aaaagaatta atctttacag gtcaagttat
4561 aaaagctgat gaagctgaaa aaatagggct agtaaataga gtcgttgagc cagacattt
```

TABLE 19-continued

Nucleotide sequences of pLogic046-tet-butyrate construct
(SEQ ID NO: 79)

```
4621 aatagaagaa gttgagaaat tagctaagat aatagctaaa aatgctcagc ttgcagttag 4681 atactctaaa gaagcaatac aacttggtgc tcaaactgat ataaatactg aatagatat 4741 agaatctaat ttatttggtc tttgttttc aactaaagac caaaagaag gaatgtcagc 4801 tttcgttgaa aagagagaag ctaactttat aaaagggtaa taagaaggag atatacatat 4861 gagaagtttt gaagaagtaa ttaagtttgc aaaagaaaga ggacctaaaa ctatatcagt 4921 agcatgttgc caagataaag aagtttaat ggcagttgaa atggctagaa aagaaaaat 4981 agcaaatgcc attttagtag gagatataga aaagactaaa gaaattgcaa aaagcataga 5041 catggatatc gaaaattatg aactgataga tataaaagat ttagcagaag catctctaaa 5101 atctgttgaa ttagtttcac aaggaaaagc cgacatggta atgaaaggct tagtagacac 5161 atcaataata ctaaaagcag ttttaaataa agaagtaggt cttagaactg gaaatgtatt 5221 aagtcacgta gcagtatttg atgtagaggg atatgataga ttattttcg taactgacgc 5281 agctatgaac ttagctcctg atacaaatac taaaaagcaa atcatagaaa atgcttgcac 5341 agtagcacat tcattagata taagtgaacc aaaagttgct gcaatatgcg caaaagaaaa 5401 agtaaatcca aaaatgaaag atacagttga agctaaagaa ctagaagaaa tgtatgaaag 5461 aggagaaatc aaaggttgta tggttggtgg gccttttgca attgataatg cagtatcttt 5521 agaagcagct aaacataaag gtataaatca tcctgtagca ggacgagctg atatattatt 5581 agccccagat attgaaggtg gtaacatatt atataaagct ttggtattct tctcaaaatc 5641 aaaaaatgca ggagttatag ttggggctaa agcaccaata atattaactt ctagagcaga 5701 cagtgaagaa actaaactaa actcaatagc tttaggtgtt ttaatggcag caaaggcata 5761 ataagaagga gatatacata tgagcaaaat atttaaaatc ttaacaataa atcctggttc 5821 gacatcaact aaaaatagctg tatttgataa tgaggattta gtatttgaaa aaactttaag 5881 acattcttca gaagaaatag gaaaatatga gaaggtgtct gaccaatttg aatttcgtaa 5941 acaagtaata gaagaagctc taaaagaagg tggagtaaaa acatctgaat tagatgctgt 6001 agtaggtaga ggaggacttc ttaaacctat aaaaggtggt acttattcag taagtgctgc 6061 tatgattgaa gatttaaaag tgggagtttt aggagaacac gcttcaaacc taggtggaat 6121 aatagcaaaa caaataggtg aagaagtaaa tgttccttca tacatagtag accctgttgt 6181 tgtagatgaa ttagaagatg ttgctagaat ttctggtatg cctgaaataa gtagagcaag 6241 tgtagtacat gctttaaatc aaaaggcaat agcaagaaga tatgctagag aaataaacaa 6301 gaaaatgaa gatataaatc ttatagttgc acacatgggt ggaggagttt ctgttggagc 6361 tcataaaaat ggtaaaatag tagatgttgc aaacgcatta gatggagaag gacctttctc 6421 tccagaaaga agtggtggac taccagtagg tgcattagta aaaatgtgct ttagtggaaa 6481 atatactcaa gatgaaatta aaagaaaat aaaaggtaat ggcggactag ttgcatactt 6541 aaacactaat gatgctagag aagttgaaga aagaattgaa gctggtgatg aaaaagctaa 6601 attagtatat gaagctatgg catatcaaat ctctaaagaa ataggagcta gtgctgcagt 6661 tcttaaggga gatgtaaaag caatattatt aactggtgga atcgcatatt caaaaatgtt 6721 tacagaaatg attgcagata gagttaaatt tatagcagat gtaaaagttt atccaggtga 6781 agatgaaatg attgcattag ctcaaggtgg acttagagtt ttaactggtg aagaagaggc 6841 tcaagtttat gataactaat aa
```

In some embodiments, the gene or gene cassette for producing the anti-inflammation and/or gut barrier function enhancer molecule is present on a plasmid and operably linked to a promoter that is induced by ROS. In some embodiments, the gene or gene cassette for producing the anti-inflammation and/or gut barrier function enhancer molecule is present in the chromosome and operably linked to a promoter that is induced by ROS. In some embodiments, the gene or gene cassette for producing the anti-inflammation and/or gut barrier function enhancer molecule is present on a chromosome and operably linked to a promoter that is induced by exposure to tetracycline. In some embodiments, the gene or gene cassette for producing the anti-inflammation and/or gut barrier function enhancer molecule is present on a plasmid and operably linked to a promoter that is induced by exposure to tetracycline. In some embodiments, expression is further optimized by methods known in the art, e.g., by optimizing ribosomal binding sites, manipulating transcriptional regulators, and/or increasing mRNA stability.

In some embodiments, the genetically engineered bacteria comprise a stably maintained plasmid or chromosome carrying the gene(s) or gene cassette(s) capable of producing an anti-inflammation and/or gut barrier function enhancer molecule, such that the gene(s) or gene cassette(s) can be expressed in the host cell, and the host cell is capable of survival and/or growth in vitro, e.g., in medium, and/or in vivo, e.g., in the gut. In some embodiments, a bacterium may comprise multiple copies of the gene or gene cassette for producing the anti-inflammation and/or gut barrier function enhance molecule. In some embodiments, gene or gene cassette is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, gene or gene cassette is expressed on a high-copy plasmid. In some embodiments, the high-copy plasmid may be useful for increasing gene or gene cassette expression. In some embodiments, gene or gene cassette is expressed on a chromosome.

In some embodiments, the genetically engineered bacteria may comprise multiple copies of the gene(s) or gene cassette(s) capable of producing an anti-inflammation and/or gut barrier function enhancer molecule. In some embodiments, the gene(s) or gene cassette(s) capable of producing an anti-inflammation and/or gut barrier function enhancer molecule is present on a plasmid and operatively linked to a ROS-responsive regulatory region. In some embodiments, the gene(s) or gene cassette(s) capable of producing an anti-inflammation and/or gut barrier function enhancer molecule is present in a chromosome and operatively linked to a ROS-responsive regulatory region.

In some embodiments, the genetically engineered bacteria of the invention produce at least one anti-inflammation and/or gut barrier enhancer molecule in the presence of ROS to reduce local gut inflammation by at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold as compared to unmodified bacteria of the same subtype under the same conditions. Inflammation may be measured by methods known in the art, e.g., counting disease lesions using endoscopy; detecting T regulatory cell differentiation in peripheral blood, e.g., by fluorescence activated sorting; measuring T regulatory cell levels; measuring cytokine levels; measuring areas of mucosal damage; assaying inflammatory biomarkers, e.g., by qPCR; PCR arrays; transcription factor phosphorylation assays; immunoassays; and/or cytokine assay kits (Mesoscale, Cayman Chemical, Qiagen).

In some embodiments, the genetically engineered bacteria produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more of an anti-inflammation and/or gut barrier enhancer molecule in the presence of ROS than unmodified bacteria of the same subtype under the same conditions. Certain unmodified bacteria will not have detectable levels of the anti-inflammation and/or gut barrier enhancer molecule. In embodiments using genetically modified forms of these bacteria, the anti-inflammation and/or gut barrier enhancer molecule will be detectable in the presence of ROS.

In certain embodiments, the anti-inflammation and/or gut barrier enhancer molecule is butyrate. Methods of measuring butyrate levels, e.g., by mass spectrometry, gas chromatography, high-performance liquid chromatography (HPLC), are known in the art (see, e.g., Aboulnaga et al., 2013). In some embodiments, butyrate is measured as butyrate level/bacteria optical density (OD). In some embodiments, measuring the activity and/or expression of one or more gene products in the butyrogenic gene cassette serves as a proxy measurement for butyrate production. In some embodiments, the bacterial cells of the invention are harvested and lysed to measure butyrate production. In alternate embodiments, butyrate production is measured in the bacterial cell medium. In some embodiments, the genetically engineered bacteria produce at least about 1 nM/OD, at least about 10 nM/OD, at least about 100 nM/OD, at least about 500 nM/OD, at least about 1 µM/OD, at least about 10 µM/OD, at least about 100 µM/OD, at least about 500 µM/OD, at least about 1 mM/OD, at least about 2 mM/OD, at least about 3 mM/OD, at least about 5 mM/OD, at least about 10 mM/OD, at least about 20 mM/OD, at least about 30 mM/OD, or at least about 50 mM/OD of butyrate in the presence of ROS.

Multiple Mechanisms of Action

In some embodiments, the bacteria are genetically engineered to include multiple mechanisms of action (MOAs), e.g., circuits producing multiple copies of the same product (e.g., to enhance copy number) or circuits performing multiple different functions. In some embodiments, the genetically engineered bacteria are capable of producing IL-2, IL-10, IL-22, IL-27, propionate, and butyrate. In some embodiments, the genetically engineered bacteria are capable of producing IL-10, IL-27, GLP-2, and butyrate. In some embodiments, the genetically engineered bacteria are capable of producing GLP-2, IL-10, IL-22, SOD, butyrate, and propionate. In some embodiments, the genetically engineered bacteria are capable of GLP-2, IL-2, IL-10, IL-22, IL-27, SOD, butyrate, and propionate. Any suitable combination of therapeutic molecules may be produced by the genetically engineered bacteria. Examples of insertion sites include, but are not limited to, malE/K, insB/I, araC/BAD, lacZ, dapA, cea, and other shown in FIG. 51. For example, the genetically engineered bacteria may include four copies of GLP-2 inserted at four different insertion sites, e.g., malE/K, insB/I, araC/BAD, and lacZ. Alternatively, the genetically engineered bacteria may include three copies of GLP-2 inserted at three different insertion sites, e.g., malE/K, insB/I, and/acZ, and three copies of a butyrate gene cassette inserted at three different insertion sites, e.g., dapA, cea, and araC/BAD.

Secretion

In some embodiments, the genetically engineered bacteria further comprise a native secretion mechanism (e.g., Gram-positive bacteria) or non-native secretion mechanism (e.g., Gram-negative bacteria) that is capable of secreting the the anti-inflammation and/or gut barrier enhancer molecule from the bacterial cytoplasm. Many bacteria have evolved sophisticated secretion systems to transport substrates across the bacterial cell envelope. Substrates, such as small molecules, proteins, and DNA, may be released into the extracellular space or periplasm (such as the gut lumen or other space), injected into a target cell, or associated with the bacterial membrane.

In Gram-negative bacteria, secretion machineries may span one or both of the inner and outer membranes. In some embodiments, the genetically engineered bacteria further comprise a non-native double membrane-spanning secretion system. Double membrane-spanning secretion systems include, but are not limited to, the type I secretion system (T1SS), the type II secretion system (T2SS), the type III secretion system (T3SS), the type IV secretion system (T4SS), the type VI secretion system (T6SS), and the resistance-nodulation-division (RND) family of multi-drug efflux pumps (Pugsley, 1993; Gerlach et al., 2007; Collinson et al., 2015; Costa et al., 2015; Reeves et al., 2015; WO2014138324A1, incorporated herein by reference). Examples of such secretion systems are shown in FIGS. 68-71. Mycobacteria, which have a Gram-negative-like cell envelope, may also encode a type VII secretion system (T7SS) (Stanley et al., 2003). With the exception of the T2SS, double membrane-spanning secretions generally transport substrates from the bacterial cytoplasm directly into the extracellular space or into the target cell. In contrast, the T2SS and secretion systems that span only the outer membrane may use a two-step mechanism, wherein substrates are first translocated to the periplasm by inner membrane-spanning transporters, and then transferred to the outer membrane or secreted into the extracellular space. Outer membrane-spanning secretion systems include, but are not limited to, the type V secretion or autotransporter system (T5SS), the curli secretion system, and the chaperone-usher pathway for pili assembly (Saier, 2006; Costa et al., 2015).

In some embodiments, the genetically engineered bacteria of the invention further comprise a type III or a type III-like secretion system (T3SS) from *Shigella, Salmonella, E. coli, Bivrio, Burkholderia, Yersinia, Chlamydia*, or *Pseudomonas*. The T3SS is capable of transporting a protein from the bacterial cytoplasm to the host cytoplasm through a needle complex. The T3SS may be modified to secrete the molecule from the bacterial cytoplasm, but not inject the molecule into the host cytoplasm. Thus, the molecule is secreted into the gut lumen or other extracellular space. In some embodiments, the genetically engineered bacteria comprise said modified T3SS and are capable of secreting the anti-inflammation and/or gut barrier enhancer molecule from the bacterial cytoplasm. In some embodiments, the secreted molecule comprises a type III secretion sequence that allows the molecule to be secreted from the bacteria.

In some embodiments, a flagellar type III secretion pathway is used to secrete the anti-inflammation and/or gut barrier enhancer molecule. In some embodiments, an incomplete flagellum is used to secrete a therapeutic molecule by recombinantly fusing the molecule to an N-terminal flagellar secretion signal of a native flagellar component. In this manner, the intracellularly expressed chimeric molecule can be mobilized across the inner and outer membranes into the surrounding host environment.

Figure 69:
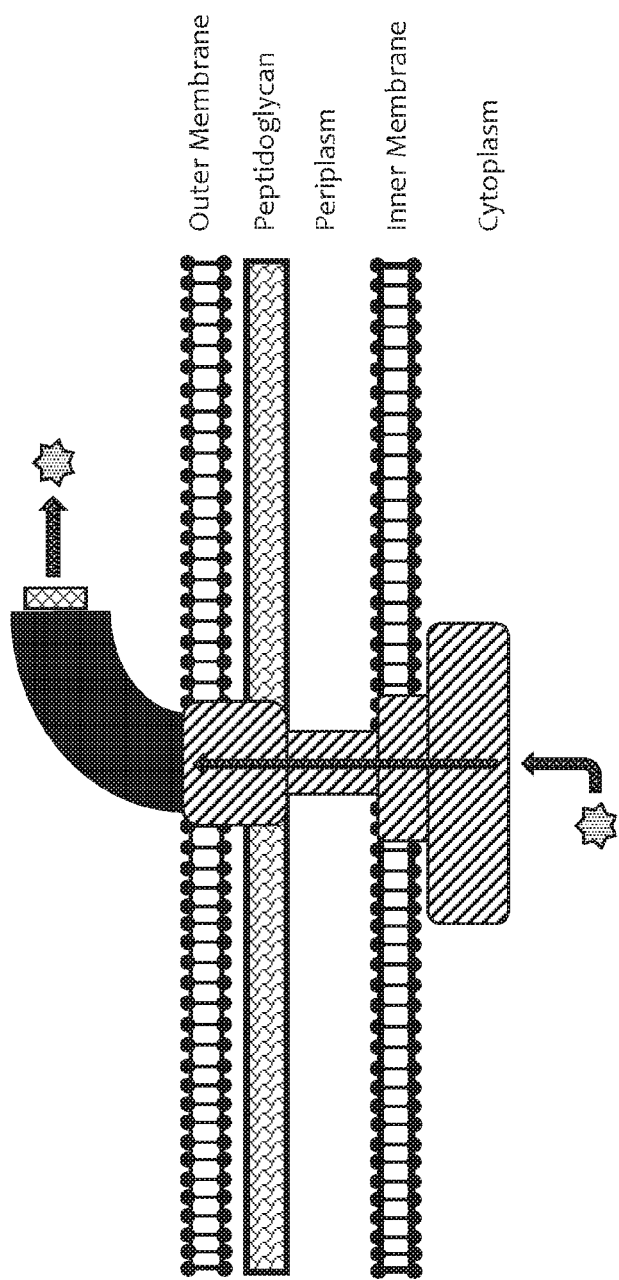
FIG. 69 depicts a schematic of a secretion system based on the flagellar type III secretion in which an incomplete flagellum is used to secrete a therapeutic peptide of interest (star) by recombinantly fusing the peptide to an N-terminal flagellar secretion signal of a native flagellar component so that the intracellularly expressed chimeric peptide can be mobilized across the inner and outer membranes into the surrounding host environment.
Figure 70:
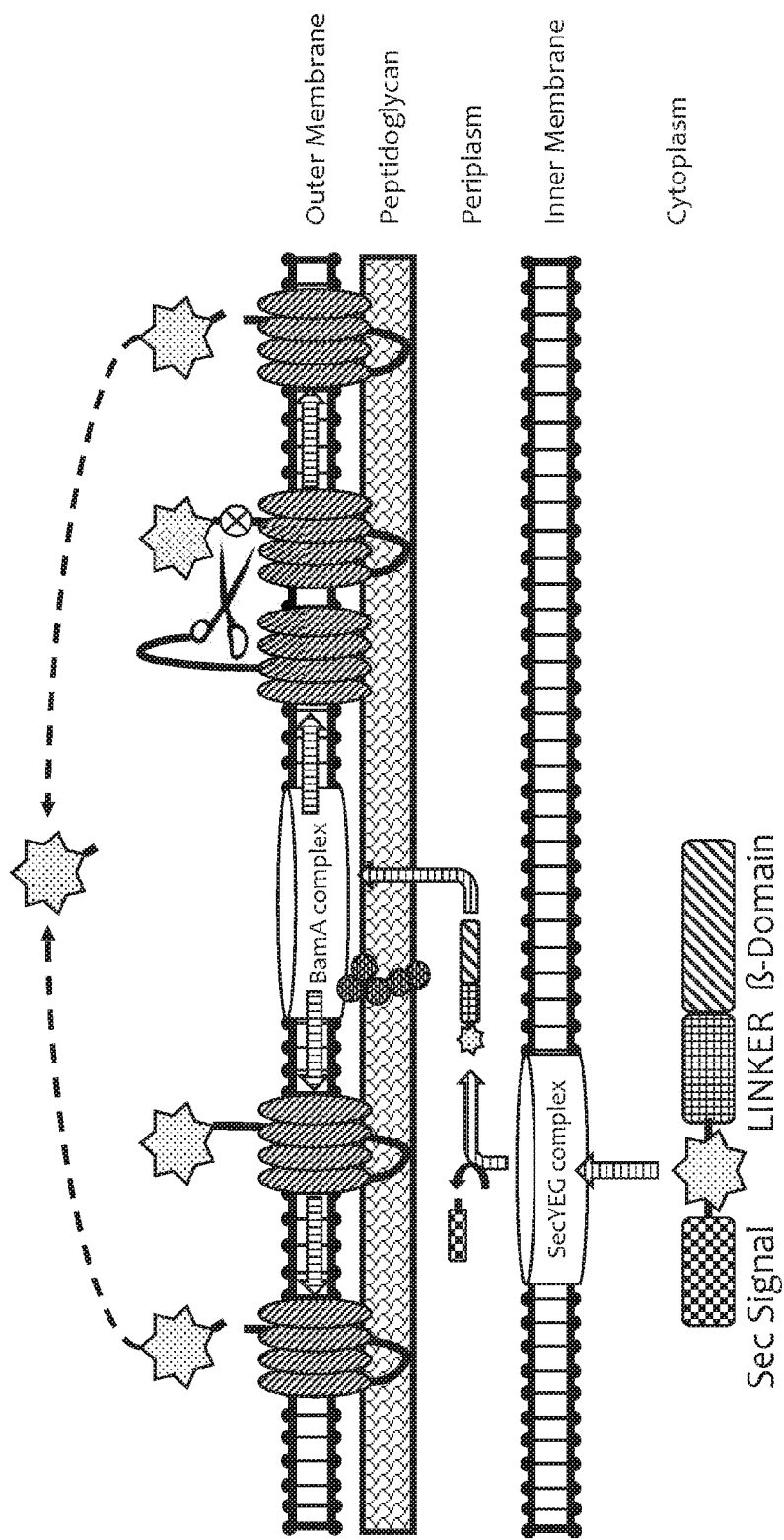
FIG. 70 depicts a schematic of a type V secretion system for the extracellular production of recombinant proteins in which a therapeutic peptide (star) can be fused to an N-terminal secretion signal, a linker and the beta-domain of an autotransporter. In this system, the N-terminal signal sequence directs the protein to the SecA-YEG machinery which moves the protein across the inner membrane into the periplasm, followed by subsequent cleavage of the signal sequence. The beta-domain is recruited to the Bam complex where the beta-domain is folded and inserted into the outer membrane as a beta-barrel structure. The therapeutic peptide is then thread through the hollow pore of the beta-barrel structure ahead of the linker sequence. The therapeutic peptide is freed from the linker system by an autocatalytic cleavage or by targeting of a membrane-associated peptidase (scissors) to a complementary protease cut site in the linker.

In some embodiments, a type V autotransporter secretion system is used to secrete the anti-inflammation and/or gut barrier enhancer molecule. Due to the simplicity of the machinery and capacity to handle relatively large protein fluxes, the type V secretion system is attractive for the extracellular production of recombinant proteins. As shown in FIG. 69, a therapeutic peptide (star) can be fused to an N-terminal secretion signal, a linker, and the beta-domain of an autotransporter. The N-terminal signal sequence directs the protein to the SecA-YEG machinery which moves the protein across the inner membrane into the periplasm, followed by subsequent cleavage of the signal sequence. The beta-domain is recruited to the Bam complex ('Beta-barrel assembly machinery') where the beta-domain is folded and inserted into the outer membrane as a beta-barrel structure. The therapeutic peptide is thread through the hollow pore of the beta-barrel structure ahead of the linker sequence. Once exposed to the extracellular environment, the therapeutic peptide can be freed from the linker system by an autocatalytic cleavage (left side of Bam complex) or by targeting of a membrane-associated peptidase (black scissors; right side of Bam complex) to a complimentary protease cut site in the linker. Thus, in some embodiments, the secreted molecule, such as a heterologous protein or peptide comprises an N-terminal secretion signal, a linker, and beta-domain of an autotransporter so as to allow the molecule to be secreted from the bacteria.

Figure 71:
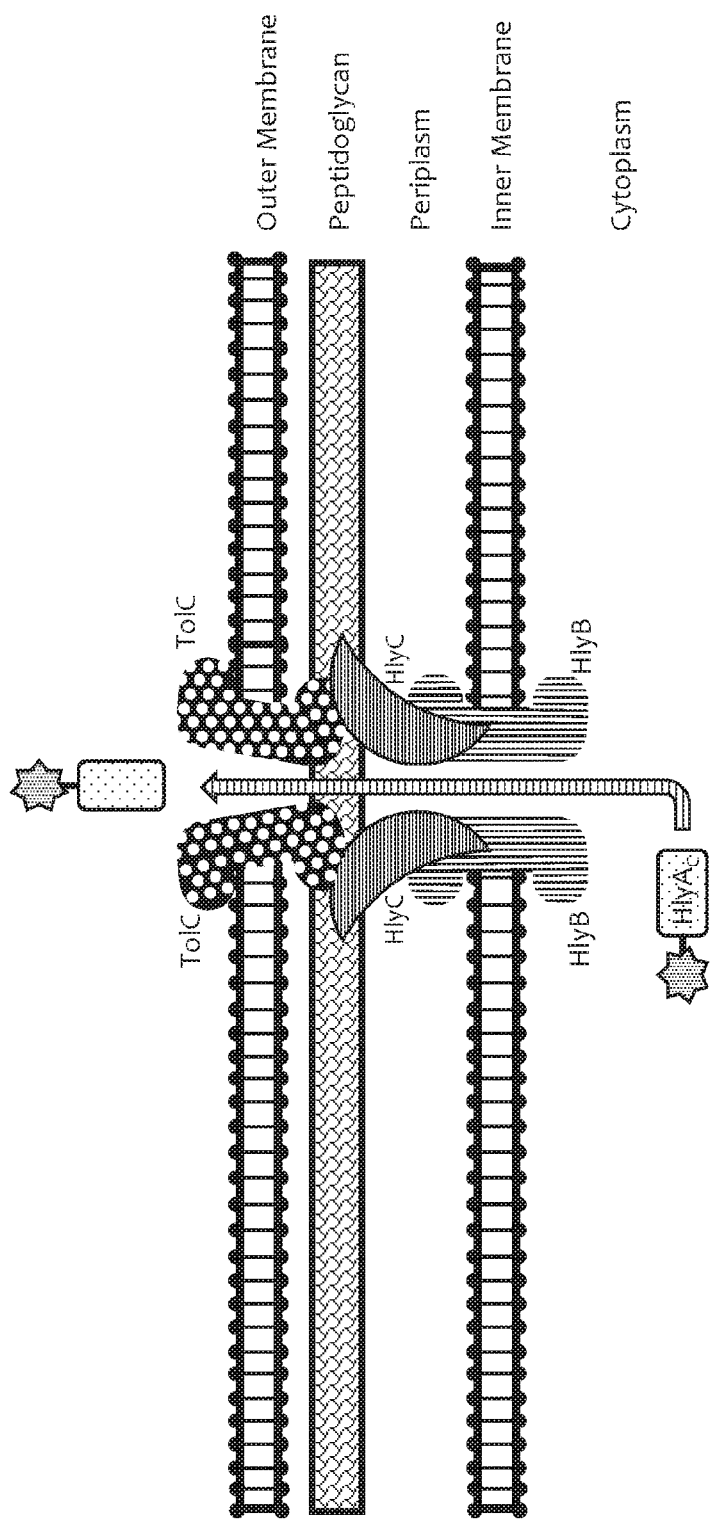
FIG. 71 depicts a schematic of a type I secretion system, which translocates a passenger peptide directly from the cytoplasm to the extracellular space using HlyB (an ATP-binding cassette transporter); HlyD (a membrane fusion protein); and TolC (an outer membrane protein) which form a channel through both the inner and outer membranes. The secretion signal-containing C-terminal portion of HlyA is fused to the C-terminal portion of a therapeutic peptide (star) to mediate secretion of this peptide.
Figure 72:
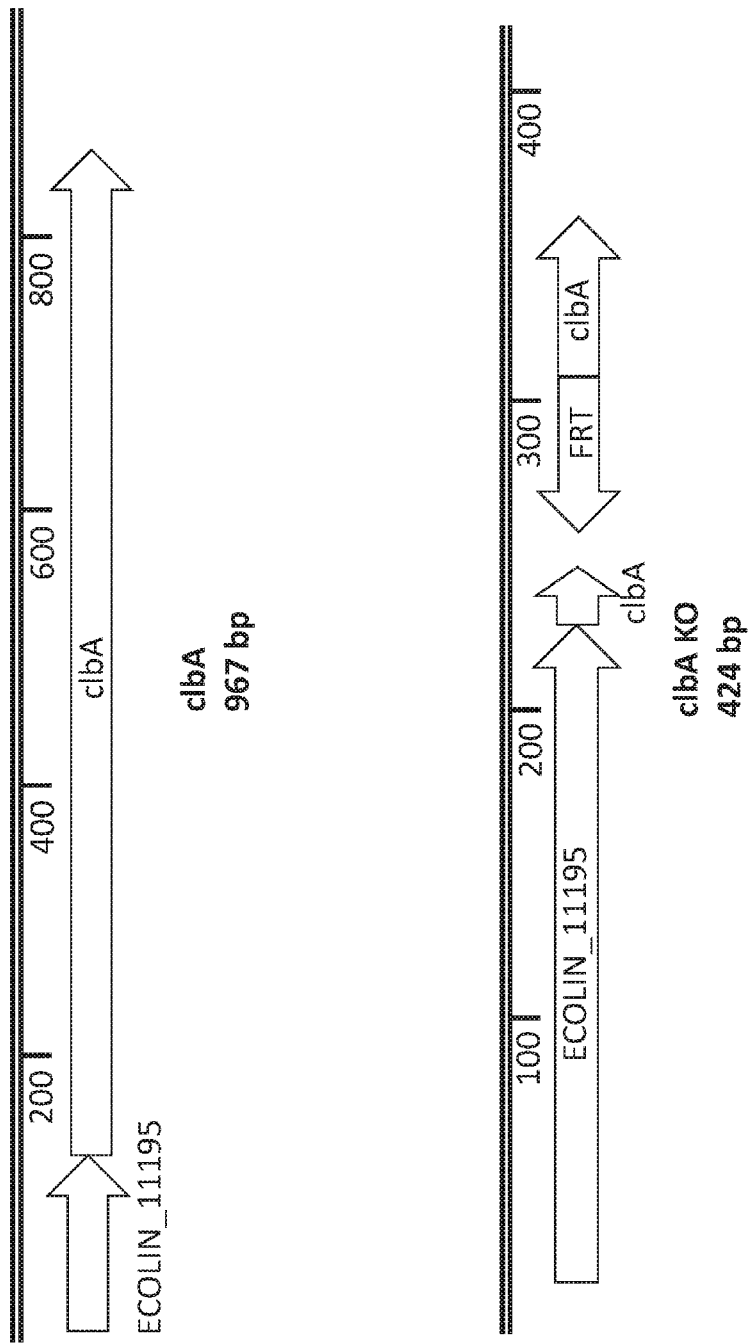
FIG. 72 depicts a schematic diagram of a wild-type clbA construct (upper panel) and a schematic diagram of a clbA knockout construct (lower panel).
Figure 74:
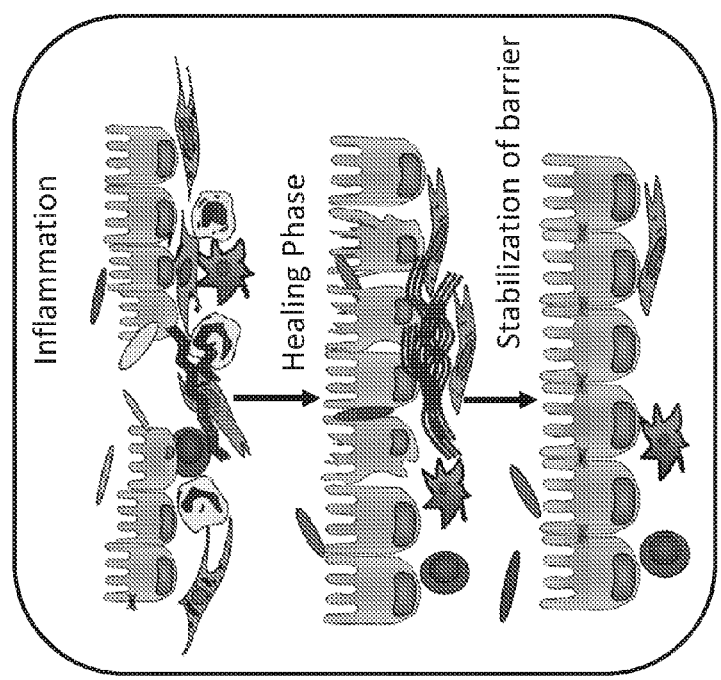
FIG. 74 depicts a schematic for inflammatory bowel disease (IBD) therapies that target pro-inflammatory neutrophils and macrophages and regulatory T cells (Treg), restore epithelial barrier integrity, and maintain mucosal barrier function. Decreasing the pro-inflammatory action of neutrophils and macrophages and increasing Treg restores epithelial barrier integrity and the mucosal barrier.
Figure 75:
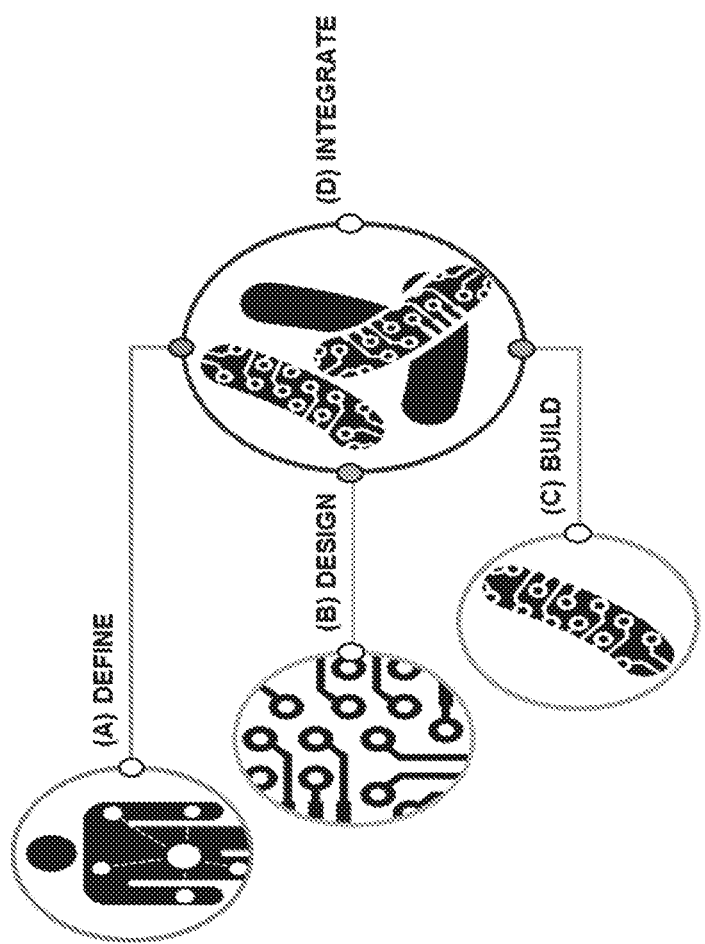
FIG. 75 depicts a schematic of non-limiting processes for designing and producing the genetically engineered bacteria of the present disclosure: identifying diverse candidate approaches based on microbial physiology and disease biology, using bioinformatics to determine candidate metabolic pathways, prospective tools to determine performance targets required of optimized engineered synthetic biotics (A); cutting-edge DNA assembly to enable combinatorial testing of pathway organization, mathematical models to predict pathway efficiency, internal stable of proprietary switches and parts to permit control and tuning of engineered circuits (B); building core structures ("chassies"), stably integrating engineered circuits into optimal chromosomal locations for efficient expression, employing unique functional assays to assess genetic circuit fidelity and activity (C); chromosomal markers enabling monitoring of synthetic biotic localization and transit times in animal models, expert microbiome network and bioinformatics support expanding understanding of how specific disease states affect GI microbial flora and the behaviors of synthetic biotics in that environment, activating process development research and optimization in-house during the discovery phase enables rapid and seamless transition of development candidates to pre-clinical progression, extensive experience in specialized disease animal model refinement supports prudent, high quality testing of candidate synthetic biotics (D).
Figure 76:
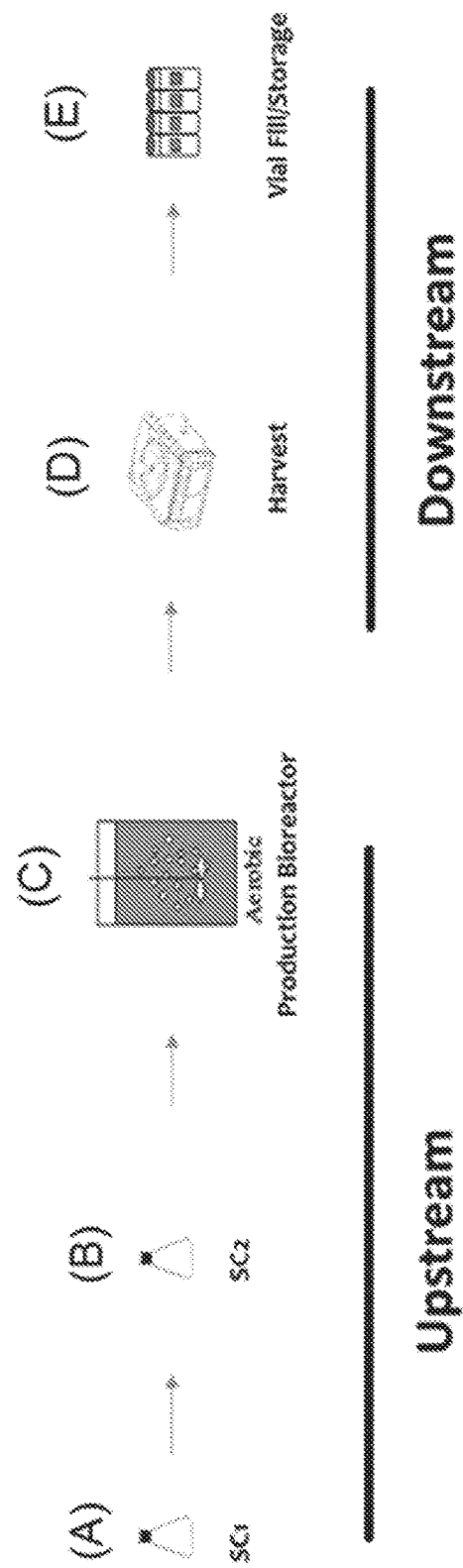
FIG. 76 depicts a schematic of non-limiting manufacturing processes for upstream and downstream production of the genetically engineered bacteria of the present disclosure. A depicts the parameters for starter culture 1 (SC1): loop full—glycerol stock, duration overnight, temperature 37° C., shaking at 250 rpm. B depicts the parameters for starter culture 2 (SC2): 1/100 dilution from SC1, duration 1.5 hours, temperature 37° C., shaking at 250 rpm. C depicts the parameters for the production bioreactor: inoculum—SC2, temperature 37° C., pH set point 7.00, pH dead band 0.05, dissolved oxygen set point 50%, dissolved oxygen cascade agitation/gas FLO, agitation limits 300-1200 rpm, gas FLO limits 0.5-20 standard liters per minute, duration 24 hours. D depicts the parameters for harvest: centrifugation at speed 4000 rpm and duration 30 minutes, wash 1×10% glycerol/PBS, centrifugation, re-suspension 10% glycerol/PBS. E depicts the parameters for vial fill/storage: 1-2 mL aliquots, −80° C.

In some embodiments, a hemolysin-based secretion system is used to secrete the anti-inflammation and/or gut barrier enhancer molecule. Type I secretion systems offer the advantage of translocating their passenger peptide directly from the cytoplasm to the extracellular space, obviating the two-step process of other secretion types. FIG. 71 shows the alpha-hemolysin (HlyA) of uropathogenic *Escherichia coli*. This pathway uses HlyB, an ATP-binding cassette transporter; HlyD, a membrane fusion protein; and TolC, an outer membrane protein. The assembly of these three proteins forms a channel through both the inner and outer membranes. Natively, this channel is used to secrete HlyA, however, to secrete the therapeutic molecule of the present disclosure, the secretion signal-containing C-terminal portion of HlyA is fused to the C-terminal portion of a therapeutic molecule (star) to mediate secretion of this molecule.

In alternate embodiments, the genetically engineered bacteria further comprise a non-native single membrane-spanning secretion system. Single membrane-spanning transporters may act as a component of a secretion system, or may export substrates independently. Such transporters include, but are not limited to, ATP-binding cassette translocases, flagellum/virulence-related translocases, conjugation-related translocases, the general secretory system (e.g., the SecYEG complex in *E. coli*), the accessory secretory system in mycobacteria and several types of Gram-positive bacteria (e.g., *Bacillus anthracis, Lactobacillus johnsonii, Corynebacterium glutamicum, Streptococcus gordonii, Staphylococcus aureus*), and the twin-arginine translocation (TAT) system (Saier, 2006; Rigel and Braunstein, 2008; Albiniak et al., 2013). It is known that the general secretory and TAT systems can both export substrates with cleavable N-terminal signal peptides into the periplasm, and have been explored in the context of biopharmaceutical production. The TAT system may offer particular advantages, however, in that it is able to transport folded substrates, thus eliminating the potential for premature or incorrect folding. In certain embodiments, the genetically engineered bacteria comprise a TAT or a TAT-like system and are capable of secreting the anti-inflammation and/or gut barrier enhancer molecule from the bacterial cytoplasm. One of ordinary skill in the art would appreciate that the secretion systems disclosed herein may be modified to act in different species, strains, and subtypes of bacteria, and/or adapted to deliver different effector molecules.

Essential Genes and Auxotrophs

As used herein, the term "essential gene" refers to a gene which is necessary to for cell growth and/or survival. Bacterial essential genes are well known to one of ordinary skill in the art, and can be identified by directed deletion of genes and/or random mutagenesis and screening (see, e.g., Zhang and Lin, 2009, DEG 5.0, a database of essential genes in both prokaryotes and eukaryotes, Nucl. Acids Res., 37:D455-D458 and Gerdes et al., Essential genes on metabolic maps, Curr. Opin. Biotechnol., 17(5):448-456, the entire contents of each of which are expressly incorporated herein by reference).

An "essential gene" may be dependent on the circumstances and environment in which an organism lives. For example, a mutation of, modification of, or excision of an essential gene may result in the genetically engineered bacteria of the disclosure becoming an auxotroph. An auxotrophic modification is intended to cause bacteria to die in the absence of an exogenously added nutrient essential for survival or growth because they lack the gene(s) necessary to produce that essential nutrient.

An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in a gene required for cell survival and/or growth. In one embodiment, the essential gene is a DNA synthesis gene, for example, thyA. In another embodiment, the essential gene is a cell wall synthesis gene, for example, dapA. In yet another embodiment, the essential gene is an amino acid gene, for example, serA or MetA. Any gene required for cell survival and/or growth may be targeted, including but not limited to, cysE, ginA, ilvD, leuB, lysA, serA, metA, giyA, hisB, ilvA, pheA, proA, thrC, trpC, tyrA, thyA, uraA, dapA, dapB, dapD, dapE, dapF, flhD, metB, metC, proAB, and thi1, as long as the corresponding wild-type gene product is not produced in the bacteria. For example, thymine is a nucleic acid that is required for bacterial cell growth; in its absence, bacteria undergo cell death. The thyA gene encodes thimidylate synthetase, an enzyme that catalyzes the first step in thymine synthesis by converting dUMP to dTMP (Sat et al., 2003). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the bacterial cell of the disclosure is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which the dapD gene is deleted and/or replaced with an unrelated gene. A dapD auxotroph can grow only when sufficient amounts of DAP are present, e.g., by adding DAP to growth media in vitro. Without sufficient amounts of DAP, the dapD auxotroph dies. In some embodiments, the auxotrophic modification is used to ensure that the bacterial cell does not survive in the absence of the auxotrophic gene product (e.g., outside of the gut).

In other embodiments, the genetically engineered bacterium of the present disclosure is a uraA auxotroph in which the uraA gene is deleted and/or replaced with an unrelated gene. The uraA gene codes for UraA, a membrane-bound transporter that facilitates the uptake and subsequent metabolism of the pyrimidine uracil (Andersen et al., 1995). An uraA auxotroph can grow only when sufficient amounts of uracil are present, e.g., by adding uracil to growth media in vitro. Without sufficient amounts of uracil, the uraA auxotroph dies. In some embodiments, auxotrophic modifications are used to ensure that the bacteria do not survive in the absence of the auxotrophic gene product (e.g., outside of the gut).

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria of the invention comprise a deletion or mutation in two or more genes required for cell survival and/or growth.

Other examples of essential genes include, but are not limited to yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, ftsB, eno, pyrG, chpR, lgt, fbaA, pgk, yqgD, metK, yqgF, plsC, ygiT, pare, ribB, cca, ygjD, tdcF, yraL, yihA, ftsN, murI, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, lspA, ispH, dapB, folA, imp, yabQ, ftsL, ftsI, murE, murF, mraY, murD, ftsW, murG, murC, ftsQ, ftsA, ftsZ, lpxC, secM, secA, can, folK, hemL, yadR, dapD, map, rpsB, infB, nusA, ftsH, obgE, rpmA, rplU, ispB, murA, yrbB, yrbK, yhbN, rpsI, rplM, degS, mreD, mreC, mreB, accB, accC, yrdC, def, fmt, rplQ, rpoA, rpsD, rpsK, rpsM, entD, mrdB, mrdA, nadD, hlepB, rpoE, pssA, yfiO, rplS, trmD, rpsP, ffh, grpE, yfjB, csrA, ispF, ispD, rplW, rplD, rplC, rpsI, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, rnpA, yidC, tnaB, glmS, glmU, wzyE, hemD, hemC, yigP, ubiB, ubiD, hemG, secY, rplO, rpmD, rpsE, rplR, rplF, rpsH, rpsN, rplE, rplX, rplN, rpsQ, rpmC, rplP, rpsC, rplV, rpsS, rplB, cdsA, yaeL, yaeT, lpxD, fabZ, lpxA, lpxB, dnaE, accA, tilS, proS, yafF, tsf, pyrH, olA, rlpB, leuS, lnt, glnS, fldA, cydA, infA, cydC, ftsK, lolA, serS, rpsA, msbA, lpxK, kdsB, mukF, mukE, mukB, asnS, fabA, mviN, rne, yceQ, fabD, fabG, acpP, tmk, holB, lolC, lolD, lolE, purB, ymfK, minE, mind, pth, rsA, ispE, lolB, hemA, prfA, prmC, kdsA, topA, ribA, fabI, racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson "Synthetic Auxotrophs with Ligand-Dependent Essential Genes for a BL21 (DE3) Biosafety Strain," ACS Synthetic Biology (2015) DOI: 10.1021/acssynbio.5b00085, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG, and adk. In some embodiments, the essential gene is dnaN comprising one or more of the following mutations: H191N, R240C, I317S, F319V, L340T, V347I, and S345C. In some embodiments, the essential gene is dnaN comprising the mutations H191N, R240C, I317S, F319V, L340T, V347I, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A, and F40G. In some embodiments, the essential gene is tyrS comprising the mutations L36V, C38A, and F40G. In some embodiments, the essential gene is metG comprising one or more of the following mutations: E45Q, N47R, I49G, and A51C. In some embodiments, the essential gene is metG comprising the mutations E45Q, N47R, I49G, and A51C. In some embodiments, the essential gene is adk comprising one or more of the following mutations: I4L, L51, and L6G. In some embodiments, the essential gene is adk comprising the mutations I4L, L51, and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, I49G, and A51C) are complemented by benzothiazole, indole, 2-aminobenzothiazole, indole-3-butyric acid, indole-3-acetic acid, or L-histidine methyl ester. Bacterial cells comprising mutations in dnaN (H191N, R240C, I317S, F319V, L340T, V347I, and S345C) are complemented by benzothiazole, indole or 2-aminobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L51, and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51C). In other embodiments, the bacterial cell comprises mutations in three essential genes. For example, in some embodiments, the bacterial cell comprises mutations in tyrS (L36V, C38A, and F40G), metG (E45Q, N47R, I49G, and A51C), and pheS (F125G, P183T, P184A, R186A, and I188L).

In some embodiments, the genetically engineered bacterium is a conditional auxotroph whose essential gene(s) is replaced using the arabinose system shown in FIGS. 57-61.

In some embodiments, the genetically engineered bacterium of the disclosure is an auxotroph and also comprises kill-switch circuitry, such as any of the kill-switch components and systems described herein. For example, the genetically engineered bacteria may comprise a deletion or mutation in an essential gene required for cell survival and/or growth, for example, in a DNA synthesis gene, for example, thyA, a cell wall synthesis gene, for example, dapA and/or an amino acid gene, for example, serA or MetA and may also comprise a toxin gene that is regulated by one or more transcriptional activators that are expressed in response to an environmental condition(s) and/or signal(s) (such as the described arabinose system) or regulated by one or more recombinases that are expressed upon sensing an exogenous environmental condition(s) and/or signal(s) (such as the recombinase systems described herein). Other embodiments are described in Wright et al., "GeneGuard: A Modular Plasmid System Designed for Biosafety," ACS Synthetic Biology (2015) 4: 307-316, the entire contents of which are expressly incorporated herein by reference). In some embodiments, the genetically engineered bacterium of the disclosure is an auxotroph and also comprises kill-switch circuitry, such as any of the kill-switch components and systems described herein, as well as another biosecurity system, such a conditional origin of replication (Wright et al., 2015). In other embodiments, auxotrophic modifications may also be used to screen for mutant bacteria that produce the anti-inflammation and/or gut barrier enhancer molecule. In some embodiments, the genetically engineered bacteria further comprise an antibiotic resistance gene.

Genetic Regulatory Circuits

In some embodiments, the genetically engineered bacteria comprise multi-layered genetic regulatory circuits for expressing the constructs described herein (see, e.g., U.S. Provisional Application No. 62/184,811, incorporated herein by reference in its entirety). The genetic regulatory circuits are useful to screen for mutant bacteria that produce an anti-inflammation and/or gut barrier enhancer molecule or rescue an auxotroph. In certain embodiments, the invention provides methods for selecting genetically engineered bacteria that produce one or more genes of interest.

In some embodiments, the invention provides genetically engineered bacteria comprising a gene or gene cassette for producing a therapeutic molecule (e.g., butyrate) and a T7 polymerase-regulated genetic regulatory circuit. For example, the genetically engineered bacteria comprise a first gene encoding a T7 polymerase, wherein the first gene is operably linked to a FNR-responsive promoter; a second gene or gene cassette for producing a therapeutic molecule (e.g., butyrate), wherein the second gene or gene cassette is operably linked to a T7 promoter that is induced by the T7 polymerase; and a third gene encoding an inhibitory factor, lysY, that is capable of inhibiting the T7 polymerase. In the presence of oxygen, FNR does not bind the FNR-responsive promoter, and the therapeutic molecule (e.g., butyrate) is not expressed. LysY is expressed constitutively (P-lac constitutive) and further inhibits T7 polymerase. In the absence of oxygen, FNR dimerizes and binds to the FNR-responsive promoter, T7 polymerase is expressed at a level sufficient to overcome lysY inhibition, and the therapeutic molecule (e.g., butyrate) is expressed. In some embodiments, the lysY gene is operably linked to an additional FNR binding site. In the absence of oxygen, FNR dimerizes to activate T7 polymerase expression as described above, and also inhibits lysY expression.

In some embodiments, the invention provides genetically engineered bacteria comprising a gene or gene cassette for producing a therapeutic molecule (e.g., butyrate) and a protease-regulated genetic regulatory circuit. For example, the genetically engineered bacteria comprise a first gene encoding an mf-Ion protease, wherein the first gene is operably linked to a FNR-responsive promoter; a second gene or gene cassette for producing a therapeutic molecule operably linked to a Tet regulatory region (TetO); and a third gene encoding an mf-Ion degradation signal linked to a Tet repressor (TetR), wherein the TetR is capable of binding to the Tet regulatory region and repressing expression of the second gene or gene cassette. The mf-Ion protease is capable of recognizing the mf-Ion degradation signal and degrading the TetR. In the presence of oxygen, FNR does not bind the FNR-responsive promoter, the repressor is not degraded, and the therapeutic molecule is not expressed. In the absence of oxygen, FNR dimerizes and binds the FNR-responsive promoter, thereby inducing expression of the mf-Ion protease. The mf-Ion protease recognizes the mf-Ion degradation signal and degrades the TetR, and the therapeutic molecule is expressed.

In some embodiments, the invention provides genetically engineered bacteria comprising a gene or gene cassette for producing a therapeutic molecule and a repressor-regulated genetic regulatory circuit. For example, the genetically engineered bacteria comprise a first gene encoding a first repressor, wherein the first gene is operably linked to a FNR-responsive promoter; a second gene or gene cassette for producing a therapeutic molecule operably linked to a first regulatory region comprising a constitutive promoter; and a third gene encoding a second repressor, wherein the second repressor is capable of binding to the first regulatory region and repressing expression of the second gene or gene cassette. The third gene is operably linked to a second regulatory region comprising a constitutive promoter, wherein the first repressor is capable of binding to the second regulatory region and inhibiting expression of the second repressor. In the presence of oxygen, FNR does not bind the FNR-responsive promoter, the first repressor is not expressed, the second repressor is expressed, and the therapeutic molecule is not expressed. In the absence of oxygen, FNR dimerizes and binds the FNR-responsive promoter, the first repressor is expressed, the second repressor is not expressed, and the therapeutic molecule is expressed.

Examples of repressors useful in these embodiments include, but are not limited to, ArgR, TetR, ArsR, AscG, LacI, CscR, DeoR, DgoR, FruR, GalR, GatR, Cl, LexA, RafR, QacR, and PtxS (US20030166191).

In some embodiments, the invention provides genetically engineered bacteria comprising a gene or gene cassette for producing a therapeutic molecule and a regulatory RNA-regulated genetic regulatory circuit. For example, the genetically engineered bacteria comprise a first gene encoding a regulatory RNA, wherein the first gene is operably linked to a FNR-responsive promoter, and a second gene or gene cassette for producing a therapeutic molecule. The second gene or gene cassette is operably linked to a constitutive promoter and further linked to a nucleotide sequence capable of producing an mRNA hairpin that inhibits translation of the therapeutic molecule. The regulatory RNA is capable of eliminating the mRNA hairpin and inducing translation via the ribosomal binding site. In the presence of oxygen, FNR does not bind the FNR-responsive promoter, the regulatory RNA is not expressed, and the mRNA hairpin prevents the therapeutic molecule from being translated. In the absence of oxygen, FNR dimerizes and binds the FNR-responsive promoter, the regulatory RNA is expressed, the mRNA hairpin is eliminated, and the therapeutic molecule is expressed.

In some embodiments, the invention provides genetically engineered bacteria comprising a gene or gene cassette for producing a therapeutic molecule and a CRISPR-regulated genetic regulatory circuit. For example, the genetically engineered bacteria comprise a Cas9 protein; a first gene encoding a CRISPR guide RNA, wherein the first gene is operably linked to a FNR-responsive promoter; a second gene or gene cassette for producing a therapeutic molecule, wherein the second gene or gene cassette is operably linked to a regulatory region comprising a constitutive promoter; and a third gene encoding a repressor operably linked to a constitutive promoter, wherein the repressor is capable of binding to the regulatory region and repressing expression of the second gene or gene cassette. The third gene is further linked to a CRISPR target sequence that is capable of binding to the CRISPR guide RNA, wherein said binding to the CRISPR guide RNA induces cleavage by the Cas9 protein and inhibits expression of the repressor. In the presence of oxygen, FNR does not bind the FNR-responsive promoter, the guide RNA is not expressed, the repressor is expressed, and the therapeutic molecule is not expressed. In the absence of oxygen, FNR dimerizes and binds the FNR-responsive promoter, the guide RNA is expressed, the repressor is not expressed, and the therapeutic molecule is expressed.

In some embodiments, the invention provides genetically engineered bacteria comprising a gene or gene cassette for producing a therapeutic molecule and a recombinase-regulated genetic regulatory circuit. For example, the genetically engineered bacteria comprise a first gene encoding a recombinase, wherein the first gene is operably linked to a FNR-responsive promoter, and a second gene or gene cassette for producing a therapeutic molecule operably linked to a constitutive promoter. The second gene or gene cassette is inverted in orientation (3' to 5') and flanked by recombinase binding sites, and the recombinase is capable of binding to the recombinase binding sites to induce expression of the second gene or gene cassette by reverting its orientation (5' to 3'). In the presence of oxygen, FNR does not bind the FNR-responsive promoter, the recombinase is not expressed, the gene or gene cassette remains in the 3' to 5' orientation, and no functional therapeutic molecule is produced. In the absence of oxygen, FNR dimerizes and binds the FNR-responsive promoter, the recombinase is expressed, the gene or gene cassette is reverted to the 5' to 3' orientation, and a functional therapeutic molecule is produced.

In some embodiments, the invention provides genetically engineered bacteria comprising a gene or gene cassette for producing a therapeutic molecule and a polymerase- and recombinase-regulated genetic regulatory circuit. For example, the genetically engineered bacteria comprise a first gene encoding a recombinase, wherein the first gene is operably linked to a FNR-responsive promoter; a second gene or gene cassette for producing a therapeutic molecule operably linked to a T7 promoter; a third gene encoding a T7 polymerase, wherein the T7 polymerase is capable of binding to the T7 promoter and inducing expression of the therapeutic molecule. The third gene encoding the T7 polymerase is inverted in orientation (3' to 5') and flanked by recombinase binding sites, and the recombinase is capable of binding to the recombinase binding sites to induce expression of the T7 polymerase gene by reverting its orientation (5' to 3'). In the presence of oxygen, FNR does not bind the FNR-responsive promoter, the recombinase is not expressed, the T7 polymerase gene remains in the 3' to 5' orientation, and the therapeutic molecule is not expressed. In the absence of oxygen, FNR dimerizes and binds the FNR-responsive promoter, the recombinase is expressed, the T7 polymerase gene is reverted to the 5' to 3' orientation, and the therapeutic molecule is expressed.

Synthetic gene circuits expressed on plasmids may function well in the short term but lose ability and/or function in the long term (Danino et al., 2015). In some embodiments, the genetically engineered bacteria comprise stable circuits for expressing genes of interest over prolonged periods. In some embodiments, the genetically engineered bacteria are capable of producing a therapeutic molecule and further comprise a toxin-anti-toxin system that simultaneously produces a toxin (hok) and a short-lived anti-toxin (sok), wherein loss of the plasmid causes the cell to be killed by the long-lived toxin (Danino et al., 2015). In some embodiments, the genetically engineered bacteria further comprise alp7 from *B. subtilis* plasmid pL20 and produces filaments that are capable of pushing plasmids to the poles of the cells in order to ensure equal segregation during cell division (Danino et al., 2015).

Host-plasmid Mutual Dependency

In some embodiments, the genetically engineered bacteria of the invention also comprise a plasmid that has been modified to create a host-plasmid mutual dependency. In certain embodiments, the mutually dependent host-plasmid platform is GeneGuard (Wright et al., 2015). In some embodiments, the GeneGuard plasmid comprises (i) a conditional origin of replication, in which the requisite replication initiator protein is provided in trans; (ii) an auxotrophic modification that is rescued by the host via genomic translocation and is also compatible for use in rich media; and/or (iii) a nucleic acid sequence which encodes a broad-spectrum toxin. The toxin gene may be used to select against plasmid spread by making the plasmid DNA itself disadvantageous for strains not expressing the anti-toxin (e.g., a wild-type bacterium). In some embodiments, the GeneGuard plasmid is stable for at least 100 generations without antibiotic selection. In some embodiments, the GeneGuard plasmid does not disrupt growth of the host. The GeneGuard plasmid is used to greatly reduce unintentional plasmid propagation in the genetically engineered bacteria of the invention.

The mutually dependent host-plasmid platform may be used alone or in combination with other biosafety mechanisms, such as those described herein (e.g., kill switches, auxotrophies). In some embodiments, the genetically engineered bacteria comprise a GeneGuard plasmid. In other embodiments, the genetically engineered bacteria comprise a GeneGuard plasmid and/or one or more kill switches. In other embodiments, the genetically engineered bacteria comprise a GeneGuard plasmid and/or one or more auxotrophies. In still other embodiments, the genetically engineered bacteria comprise a GeneGuard plasmid, one or more kill switches, and/or one or more auxotrophies.

Figure 66:
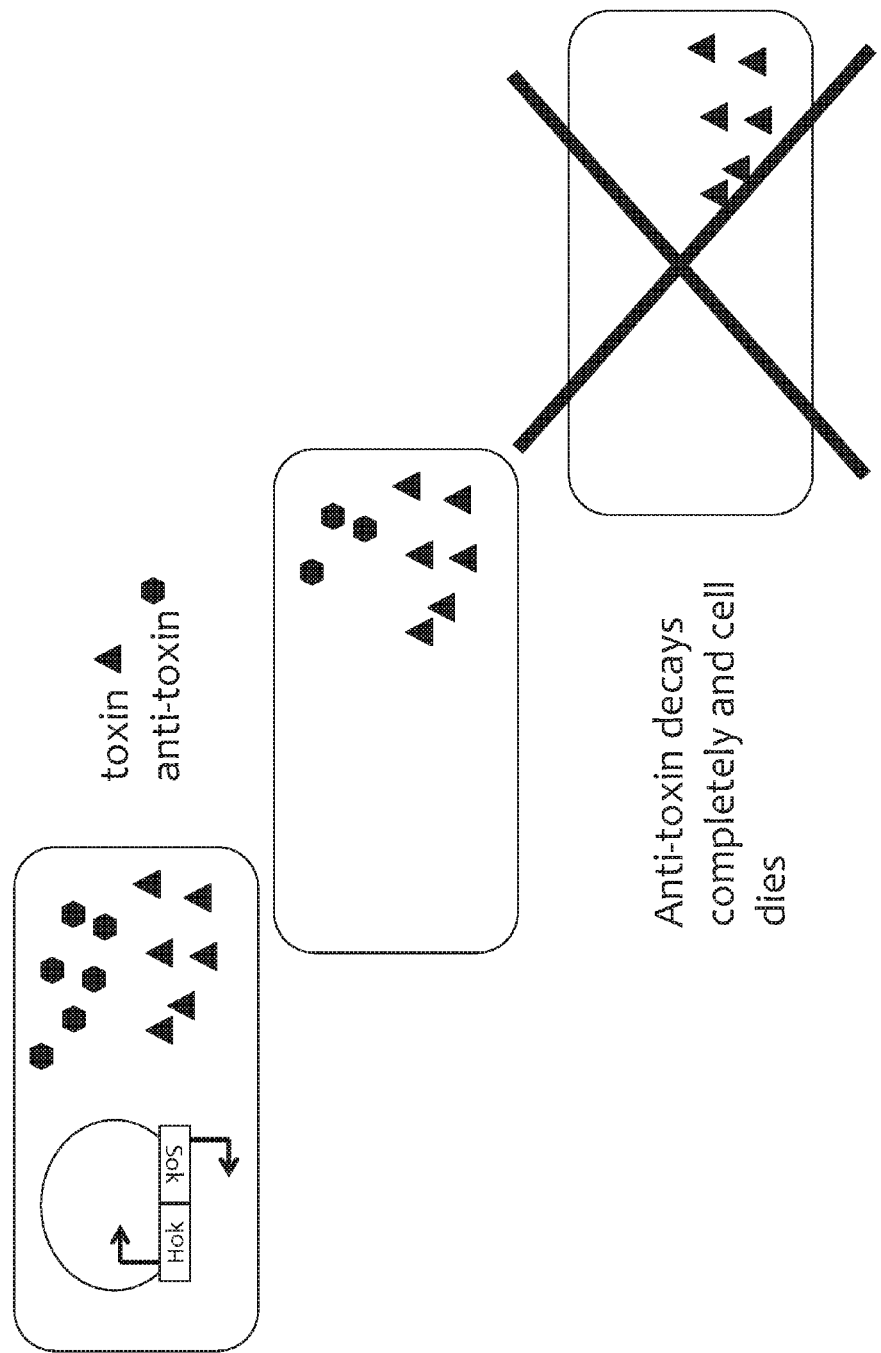
FIG. 66 depicts a one non-limiting embodiment of the disclosure, in which the genetically engineered bacteria produces equal amount of a Hok toxin and a short-lived Sok anti-toxin. When the cell loses the plasmid, the anti-toxin decays, and the cell dies. In the upper panel, the cell produces equal amounts of toxin and anti-toxin and is stable. In the center panel, the cell loses the plasmid and anti-toxin begins to decay. In the lower panel, the anti-toxin decays completely, and the cell dies.
Figure 67:
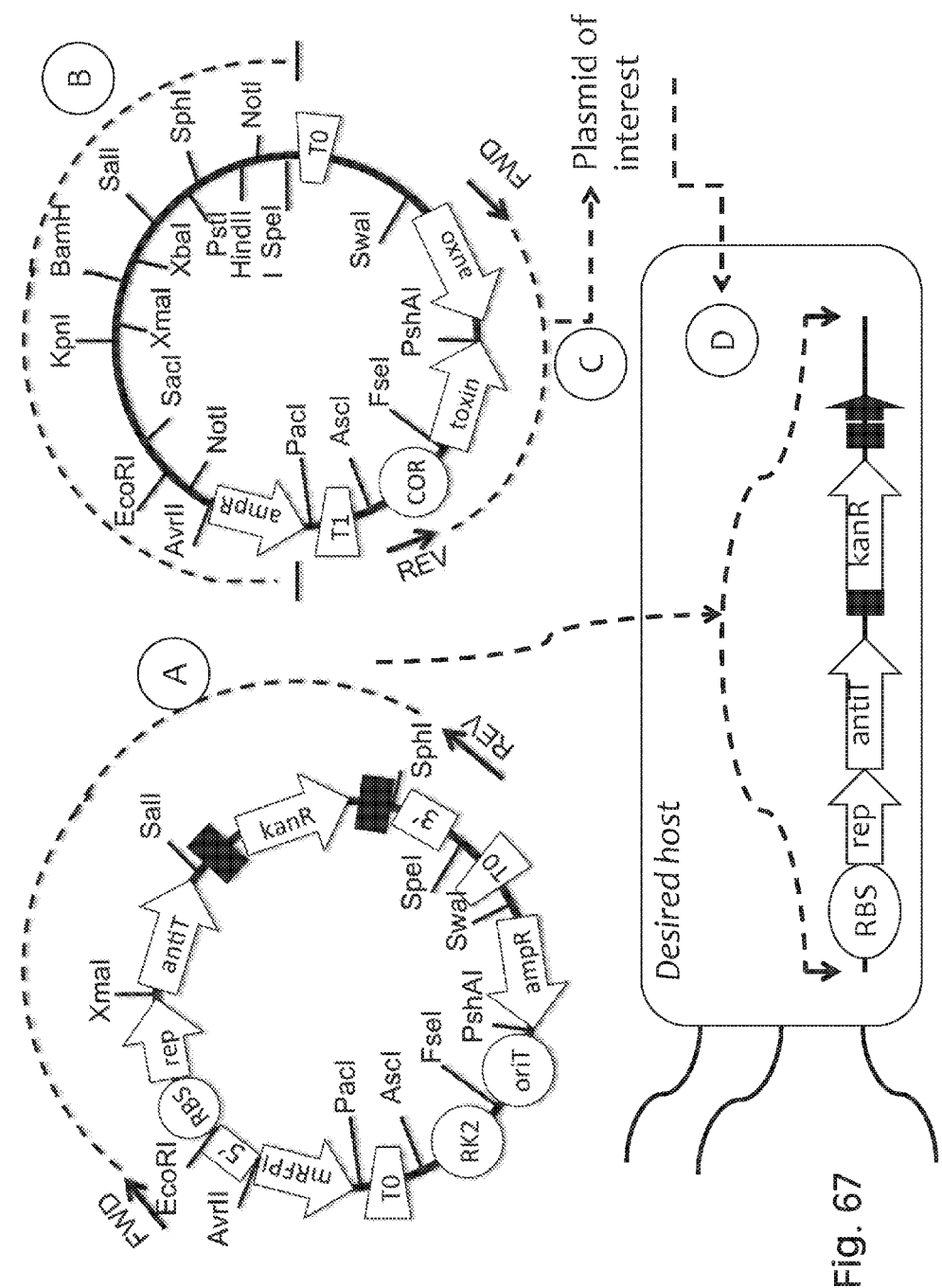
FIG. 67 depicts the use of GeneGuards as an engineered safety component. All engineered DNA is present on a plasmid which can be conditionally destroyed. See, e.g., Wright et al., 2015.
Figure 68:
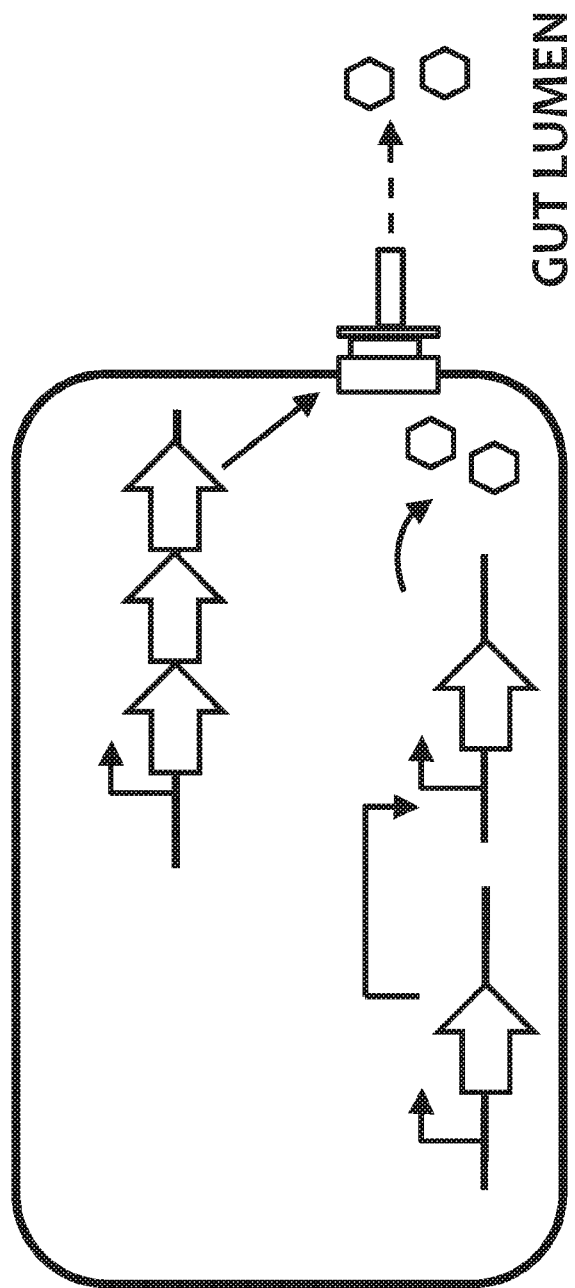
FIG. 68 depicts a modified type 3 secretion system (T3SS) to allow the bacteria to inject secreted therapeutic proteins into the gut lumen. An inducible promoter (small arrow, top), e.g. a FNR-responsive promoter, drives expression of the T3 secretion system gene cassette (3 large arrows, top) that produces the apparatus that secretes tagged peptides out of the cell. An inducible promoter (small arrow, bottom), e.g. a FNR-responsive promoter, drives expression of a regulatory factor, e.g. T7 polymerase, that then activates the expression of the tagged therapeutic peptide (hexagons).

Synthetic gene circuits express on plasmids may function well in the short term but lose ability and/or function in the long term (Danino et al., 2015). In some embodiments, the genetically engineered bacteria comprise stable circuits for expressing genes of interest over prolonged periods. In some embodiments, the genetically engineered bacteria are capable of producing an anti-inflammation and/or gut enhancer molecule and further comprise a toxin-anti-toxin system that simultaneously produces a toxin (hok) and a short-lived anti-toxin (sok), wherein loss of the plasmid causes the cell to be killed by the long-lived toxin (Danino et al., 2015; FIG. 66). In some embodiments, the genetically engineered bacteria further comprise alp7 from *B. subtilis* plasmid pL20 and produces filaments that are capable of pushing plasmids to the poles of the cells in order to ensure equal segregation during cell division (Danino et al., 2015).

Kill Switch

In some embodiments, the genetically engineered bacteria of the invention also comprise a kill switch (see, e.g., U.S. Provisional Application Nos. 62/183,935, 62/263,329, and 62/277,654, each of which is incorporated herein by reference in their entireties). The kill switch is intended to actively kill genetically engineered bacteria in response to external stimuli. As opposed to an auxotrophic mutation where bacteria die because they lack an essential nutrient for survival, the kill switch is triggered by a particular factor in the environment that induces the production of toxic molecules within the microbe that cause cell death.

Bacteria comprising kill switches have been engineered for in vitro research purposes, e.g., to limit the spread of a biofuel-producing microorganism outside of a laboratory environment. Bacteria engineered for in vivo administration to treat a disease may also be programmed to die at a specific time after the expression and delivery of a heterologous gene or genes, for example, an anti-inflammation and/or gut barrier enhancer molecule, or after the subject has experienced the therapeutic effect. For example, in some embodiments, the kill switch is activated to kill the bacteria after a period of time following expression of the anti-inflammation and/or gut barrier enhancer molecule, e.g., GLP-1. In some embodiments, the kill switch is activated in a delayed fashion following expression of the anti-inflammation and/or gut barrier enhancer molecule. Alternatively, the bacteria may be engineered to die after the bacterium has spread outside of a disease site. Specifically, it may be useful to prevent long-term colonization of subjects by the microorganism, spread of the microorganism outside the area of interest (for example, outside the gut) within the subject, or spread of the microorganism outside of the subject into the environment (for example, spread to the environment through the stool of the subject). Examples of such toxins that can be used in kill-switches include, but are not limited to, bacteriocins, lysins, and other molecules that cause cell death by lysing cell membranes, degrading cellular DNA, or other mechanisms. Such toxins can be used individually or in combination. The switches that control their production can be based on, for example, transcriptional activation (toggle switches; see, e.g., Gardner et al., 2000), translation (riboregulators), or DNA recombination (recombinase-based switches), and can sense environmental stimuli such as anaerobiosis or reactive oxygen species. These switches can be activated by a single environmental factor or may require several activators in AND, OR, NAND and NOR logic configurations to induce cell death. For example, an AND riboregulator switch is activated by tetracycline, isopropyl β-D-1-thiogalactopyranoside (IPTG), and arabinose to induce the expression of lysins, which permeabilize the cell membrane and kill the cell. IPTG induces the expression of the endolysin and holin mRNAs, which are then derepressed by the addition of arabinose and tetracycline. All three inducers must be present to cause cell death. Examples of kill switches are known in the art (Callura et al., 2010).

Kill-switches can be designed such that a toxin is produced in response to an environmental condition or external signal (e.g., the bacteria is killed in response to an external cue) or, alternatively designed such that a toxin is produced once an environmental condition no longer exists or an external signal is ceased.

Thus, in some embodiments, the genetically engineered bacteria of the disclosure are further programmed to die after sensing an exogenous environmental signal, for example, in low-oxygen conditions, in the presence of ROS, or in the presence of RNS. In some embodiments, the genetically engineered bacteria of the present disclosure comprise one or more genes encoding one or more recombinase(s), whose expression is induced in response to an environmental condition or signal and causes one or more recombination events that ultimately leads to the expression of a toxin which kills the cell. In some embodiments, the at least one recombination event is the flipping of an inverted heterologous gene encoding a bacterial toxin which is then constitutively expressed after it is flipped by the first recombinase. In one embodiment, constitutive expression of the bacterial toxin kills the genetically engineered bacterium. In these types of kill-switch systems once the engineered bacterial cell senses the exogenous environmental condition and expresses the heterologous gene of interest, the recombinant bacterial cell is no longer viable.

In another embodiment in which the genetically engineered bacteria of the present disclosure express one or more recombinase(s) in response to an environmental condition or signal causing at least one recombination event, the genetically engineered bacterium further expresses a heterologous gene encoding an anti-toxin in response to an exogenous environmental condition or signal. In one embodiment, the at least one recombination event is flipping of an inverted heterologous gene encoding a bacterial toxin by a first recombinase. In one embodiment, the inverted heterologous gene encoding the bacterial toxin is located between a first forward recombinase recognition sequence and a first reverse recombinase recognition sequence. In one embodiment, the heterologous gene encoding the bacterial toxin is constitutively expressed after it is flipped by the first recombinase. In one embodiment, the anti-toxin inhibits the activity of the toxin, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In another embodiment, the at least one recombination event is flipping of an inverted heterologous gene encoding a second recombinase by a first recombinase, followed by the flipping of an inverted heterologous gene encoding a bacterial toxin by the second recombinase. In one embodiment, the inverted heterologous gene encoding the second recombinase is located between a first forward recombinase recognition sequence and a first reverse recombinase recognition sequence. In one embodiment, the inverted heterologous gene encoding the bacterial toxin is located between a second forward recombinase recognition sequence and a second reverse recombinase recognition sequence. In one embodiment, the heterologous gene encoding the second recombinase is constitutively expressed after it is flipped by the first recombinase. In one embodiment, the heterologous gene encoding the bacterial toxin is constitutively expressed after it is flipped by the second recombinase. In one embodiment, the genetically engineered bacterium is killed by the bacterial toxin. In one embodiment, the genetically engineered bacterium further expresses a heterologous gene encoding an anti-toxin in response to the exogenous environmental condition. In one embodiment, the anti-toxin inhibits the activity of the toxin when the exogenous environmental condition is present, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In one embodiment, the at least one recombination event is flipping of an inverted heterologous gene encoding a second recombinase by a first recombinase, followed by flipping of an inverted heterologous gene encoding a third recombinase by the second recombinase, followed by flipping of an inverted heterologous gene encoding a bacterial toxin by the third recombinase.

In one embodiment, the at least one recombination event is flipping of an inverted heterologous gene encoding a first excision enzyme by a first recombinase. In one embodiment, the inverted heterologous gene encoding the first excision enzyme is located between a first forward recombinase recognition sequence and a first reverse recombinase recognition sequence. In one embodiment, the heterologous gene encoding the first excision enzyme is constitutively expressed after it is flipped by the first recombinase. In one embodiment, the first excision enzyme excises a first essential gene. In one embodiment, the programmed recombinant bacterial cell is not viable after the first essential gene is excised.

In one embodiment, the first recombinase further flips an inverted heterologous gene encoding a second excision enzyme. In one embodiment, the inverted heterologous gene encoding the second excision enzyme is located between a second forward recombinase recognition sequence and a second reverse recombinase recognition sequence. In one embodiment, the heterologous gene encoding the second excision enzyme is constitutively expressed after it is flipped by the first recombinase. In one embodiment, the genetically engineered bacterium dies or is no longer viable when the first essential gene and the second essential gene are both excised. In one embodiment, the genetically engineered bacterium dies or is no longer viable when either the first essential gene is excised or the second essential gene is excised by the first recombinase.

In one embodiment, the genetically engineered bacterium dies after the at least one recombination event occurs. In another embodiment, the genetically engineered bacterium is no longer viable after the at least one recombination event occurs.

In any of these embodiment, the recombinase can be a recombinase selected from the group consisting of: BxbI, PhiC31, TP901, BxbI, PhiC31, TP901, HK022, HP1, R4, Int1, Int3, Int3, Int4, Int5, Int6, Int7, Int8, Int9, Int10, Int11, Int12, Int13, Int14, Int15, Int16, Int17, Int18, Int19, Int20, Int21, Int22, Int23, Int24, Int25, Int26, Int27, Int28, Int29, Int30, Int31, Int32, Int33, and Int34, or a biologically active fragment thereof.

Figure 57:
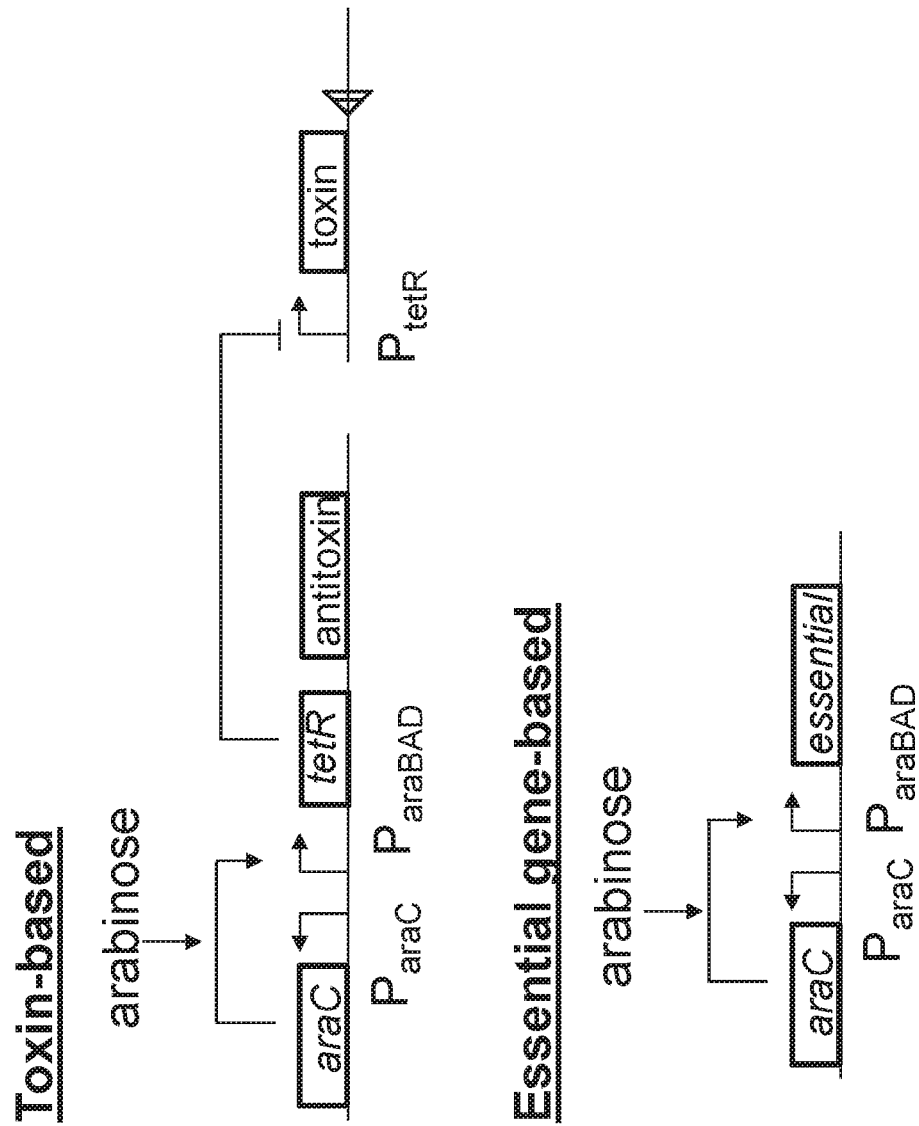
FIG. 57 depicts a schematic of a repression-based kill switch. In a toxin-based system, the AraC transcription factor is activated in the presence of arabinose and induces expression of TetR and an anti-toxin. TetR prevents the expression of the toxin. When arabinose is removed, TetR and the anti-toxin do not get made and the toxin is produced which kills the cell. In an essential gene-based system, the AraC transcription factor is activated in the presence of arabinose and induces expression of an essential gene.
Figure 58:
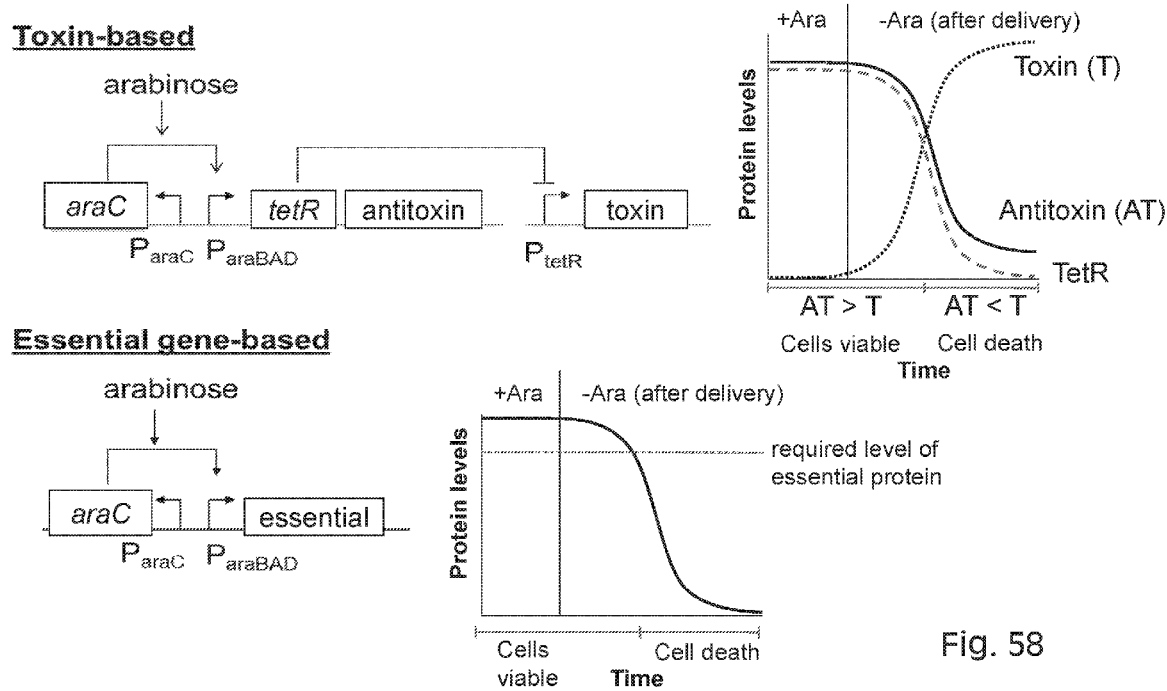
FIG. 58 depicts another non-limiting embodiment of the disclosure, wherein the expression of a heterologous gene is activated by an exogenous environmental signal, e.g., low-oxygen conditions. In the absence of arabinose, the AraC transcription factor adopts a conformation that represses transcription. In the presence of arabinose, the AraC transcription factor undergoes a conformational change that allows it to bind to and activate the araBAD promoter, which induces expression of TetR (tet repressor) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell.
Figure 59:
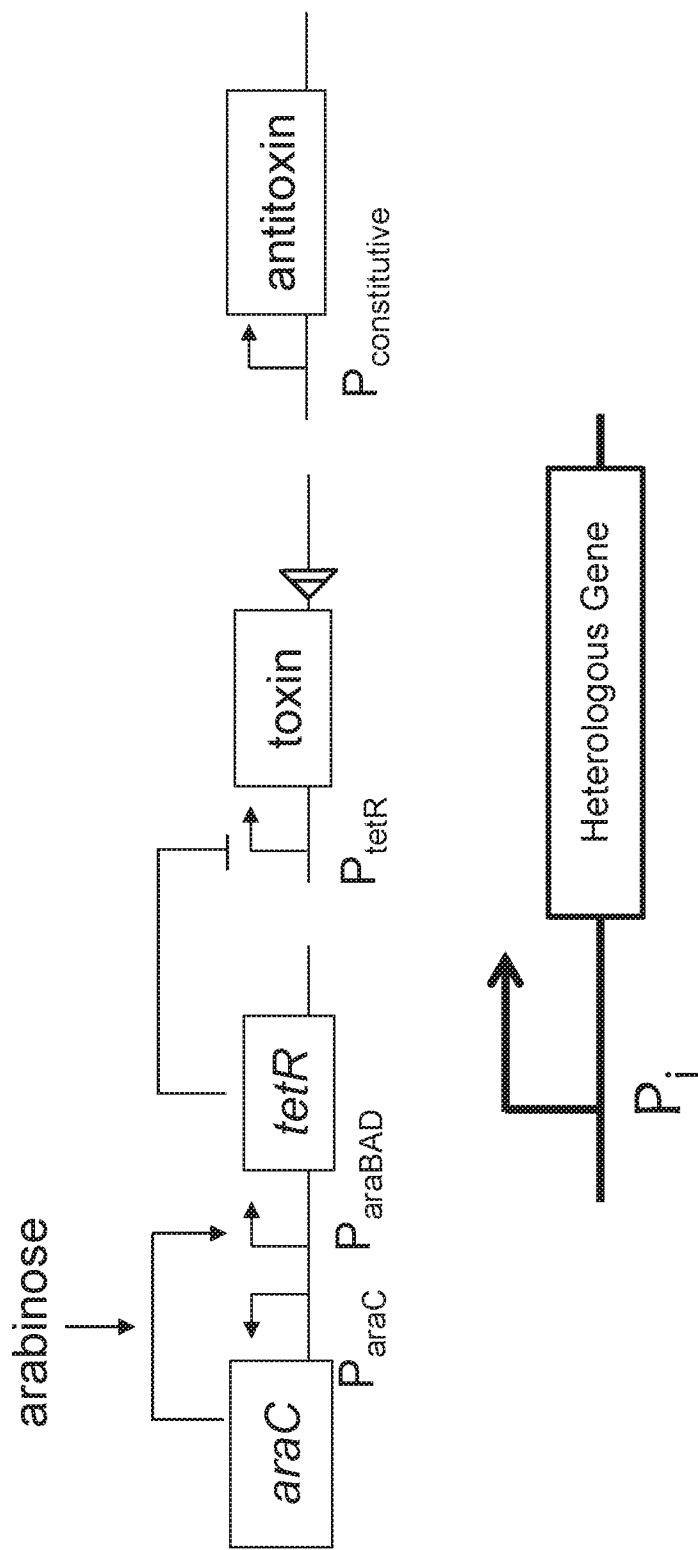
FIG. 59 depicts a non-limiting embodiment of the disclosure, where an anti-toxin is expressed from a constitutive promoter, and expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of TetR, thus preventing expression of a toxin. However, when arabinose is not present, TetR is not expressed, and the toxin is expressed, eventually overcoming the anti-toxin and killing the cell. The constitutive promoter regulating expression of the anti-toxin should be a weaker promoter than the promoter driving expression of the toxin. The araC gene is under the control of a constitutive promoter in this circuit.
Figure 60:
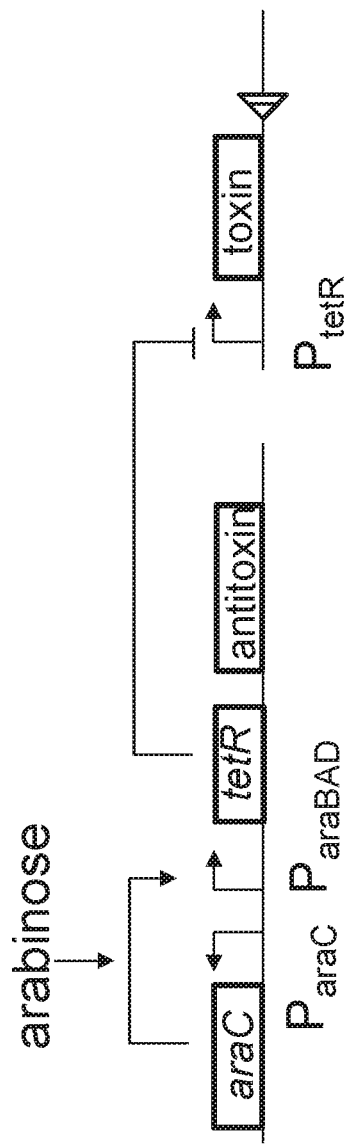
FIG. 60 depicts a schematic of a repression-based kill switch in which the AraC transcription factor is activated in the presence of arabinose and induces expression of TetR and an anti-toxin. TetR prevents the expression of the toxin. When arabinose is removed, TetR and the anti-toxin do not get made and the toxin is produced which kills the cell.
Figure 61:
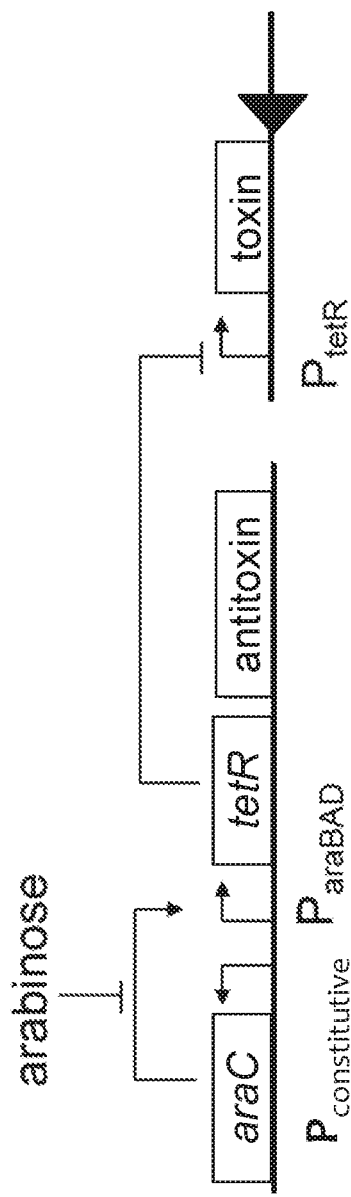
FIG. 61 depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of TetR (tet repressor) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell. The araC gene is under the control of a constitutive promoter in this circuit.
Figure 62:
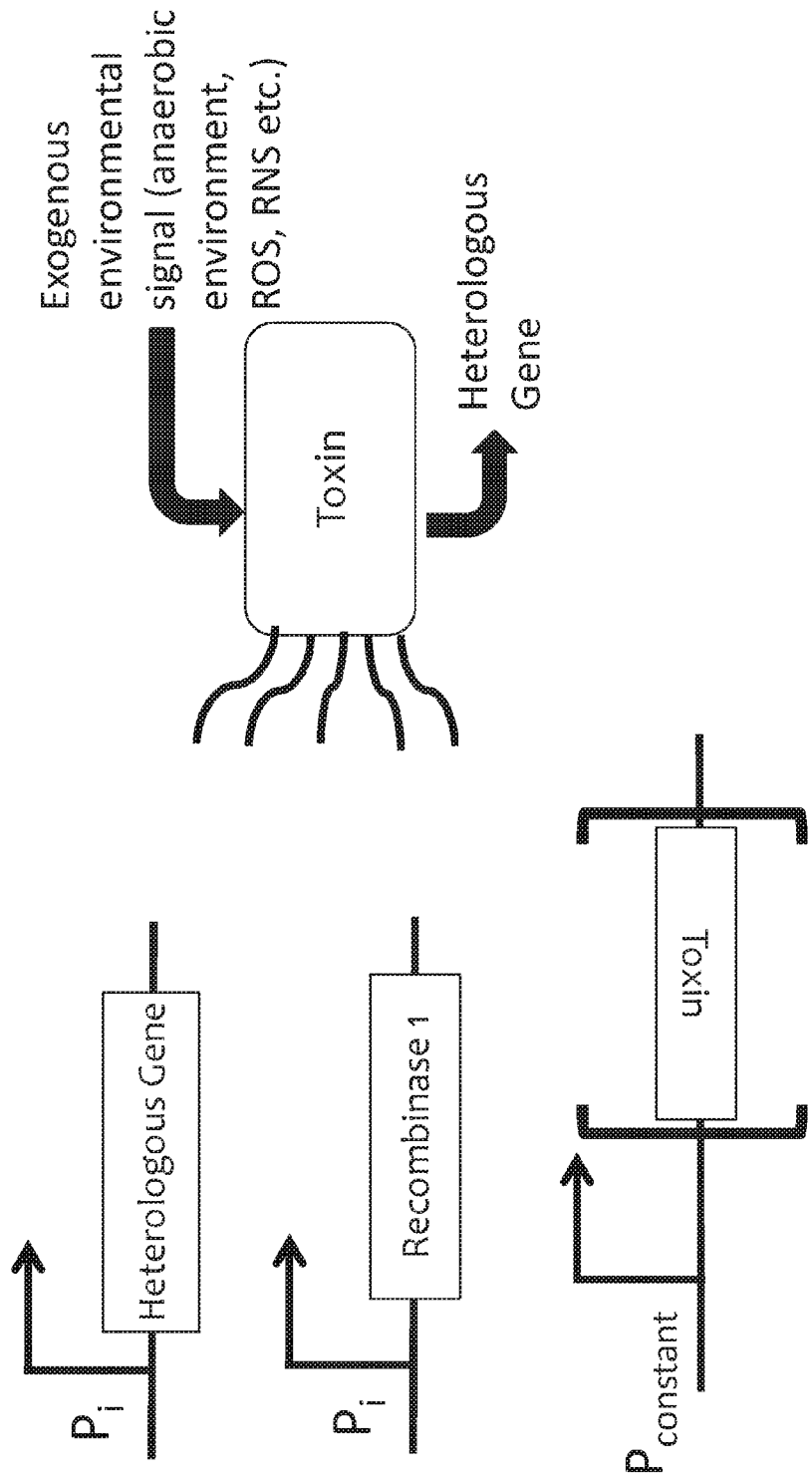
FIG. 62 depicts one non-limiting embodiment of the disclosure, where an exogenous environmental condition, e.g., low-oxygen conditions, or one or more environmental signals activates expression of a heterologous gene and at least one recombinase from an inducible promoter or inducible promoters. The recombinase then flips a toxin gene into an activated conformation, and the natural kinetics of the recombinase create a time delay in expression of the toxin, allowing the heterologous gene to be fully expressed. Once the toxin is expressed, it kills the cell.
Figure 63:
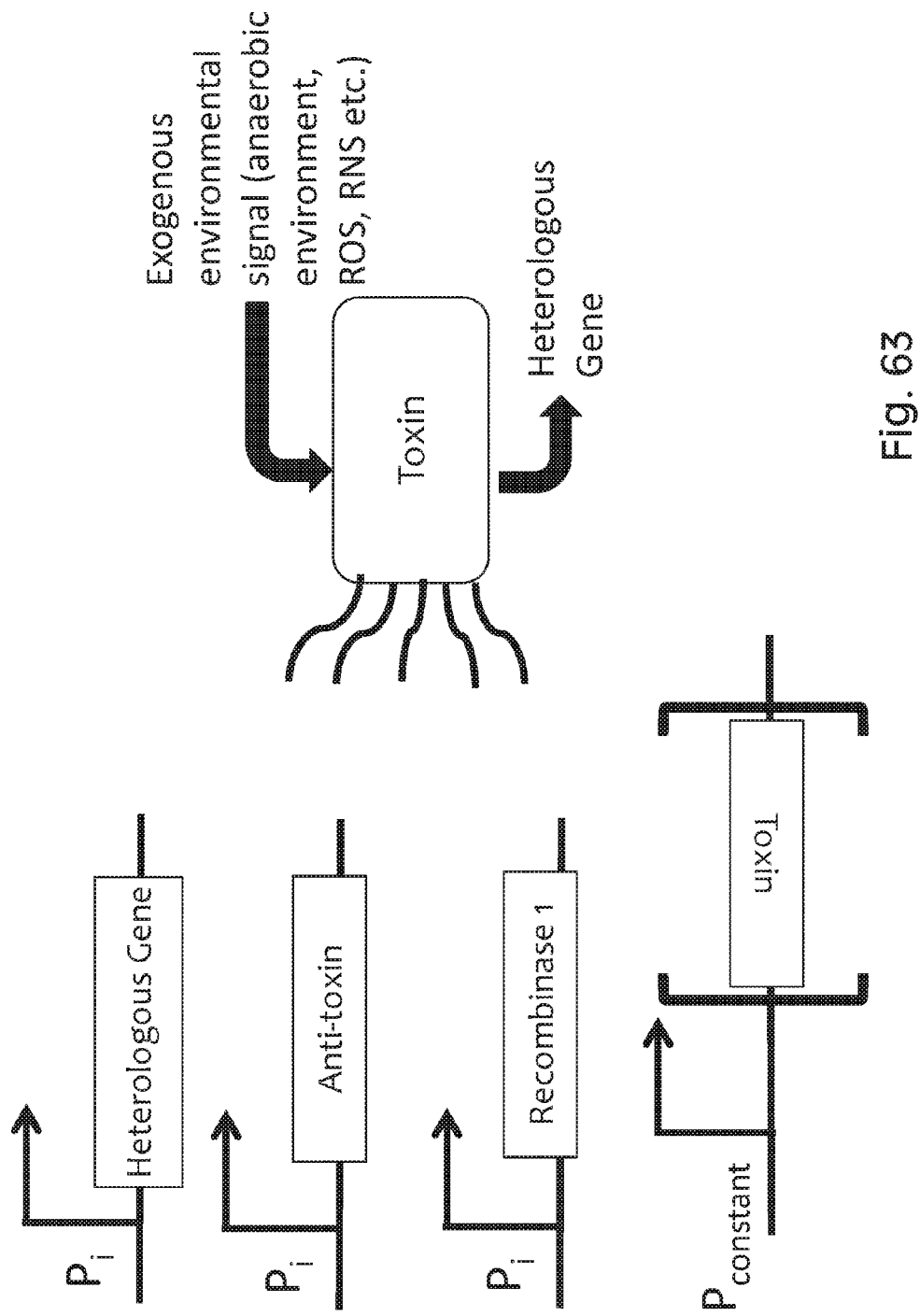
FIG. 63 depicts another non-limiting embodiment of the disclosure, where an exogenous environmental condition, e.g., low-oxygen conditions, or one or more environmental signals activates expression of a heterologous gene, an anti-toxin, and at least one recombinase from an inducible promoter or inducible promoters. The recombinase then flips a toxin gene into an activated conformation, but the presence of the accumulated anti-toxin suppresses the activity of the toxin. Once the exogenous environmental condition or cue(s) is no longer present, expression of the anti-toxin is turned off. The toxin is constitutively expressed, continues to accumulate, and kills the bacterial cell.
Figure 65:
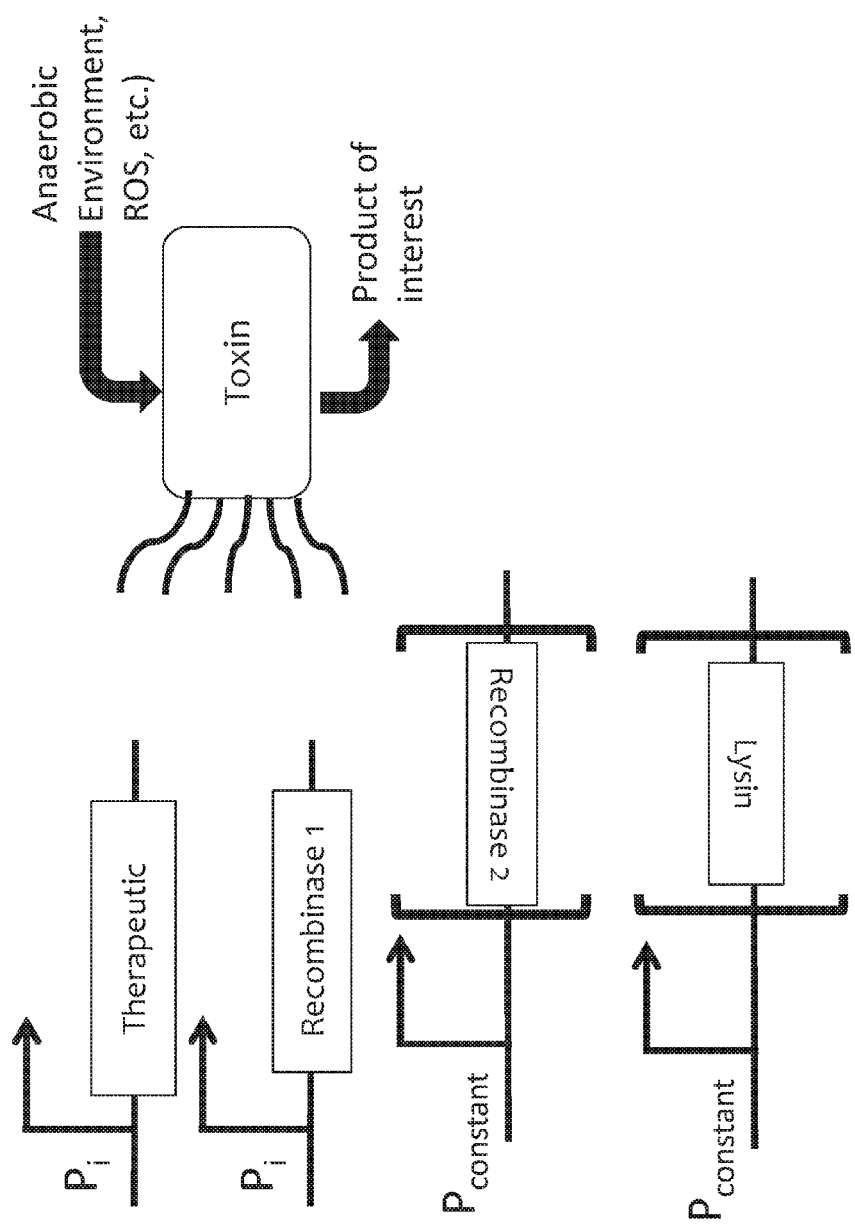
FIG. 65 depicts a schematic of an activation-based kill switch, in which $P_i$ is any inducible promoter, e.g., a FNR-responsive promoter. When the therapeutic is induced, the anti-toxin and recombinases are turned on, which results in the toxin being 'flipped' to the ON position after 4-6 hours, which results in a build-up of anti-toxin before the toxin is expressed. In absence of the inducing signal, only toxin is made and the cell dies.

In the above-described kill-switch circuits, a toxin is produced in the presence of an environmental factor or signal. In another aspect of kill-switch circuitry, a toxin may be repressed in the presence of an environmental factor (not produced) and then produced once the environmental condition or external signal is no longer present. Such kill switches are called repression-based kill switches and represent systems in which the bacterial cells are viable only in the presence of an external factor or signal, such as arabinose or other sugar. Exemplary kill switch designs in which the toxin is repressed in the presence of an external factor or signal (and activated once the external signal is removed) is shown in FIGS. 57, 60, 65. The disclosure provides recombinant bacterial cells which express one or more heterologous gene(s) upon sensing arabinose or other sugar in the exogenous environment. In this aspect, the recombinant bacterial cells contain the araC gene, which encodes the AraC transcription factor, as well as one or more genes under the control of the araBAD promoter. In the absence of arabinose, the AraC transcription factor adopts a conformation that represses transcription of genes under the control of the araBAD promoter. In the presence of arabinose, the AraC transcription factor undergoes a conformational change that allows it to bind to and activate the araBAD promoter, which induces expression of the desired gene, for example tetR, which represses expression of a toxin gene. In this embodiment, the toxin gene is repressed in the presence of arabinose or other sugar. In an environment where arabinose is not present, the tetR gene is not activated and the toxin is expressed, thereby killing the bacteria. The arabinose system can also be used to express an essential gene, in which the essential gene is only expressed in the presence of arabinose or other sugar and is not expressed when arabinose or other sugar is absent from the environment.

Thus, in some embodiments in which one or more heterologous gene(s) are expressed upon sensing arabinose in the exogenous environment, the one or more heterologous genes are directly or indirectly under the control of the araBAD promoter ($P_{araBAD}$). In some embodiments, the expressed heterologous gene is selected from one or more of the following: a heterologous therapeutic gene, a heterologous gene encoding an anti-toxin, a heterologous gene encoding a repressor protein or polypeptide, for example, a TetR repressor, a heterologous gene encoding an essential protein not found in the bacterial cell, and/or a heterologous encoding a regulatory protein or polypeptide.

Arabinose inducible promoters are known in the art, including $P_{ara}$, $P_{araB}$, $P_{araC}$, and $P_{araBAD}$. In one embodiment, the arabinose inducible promoter is from *E. coli*. In some embodiments, the $P_{araC}$ promoter and the $P_{araBAD}$ promoter operate as a bidirectional promoter, with the $P_{araBAD}$ promoter controlling expression of a heterologous gene(s) in one direction, and the $P_{araC}$ (in close proximity to, and on the opposite strand from the $P_{araBAD}$ promoter), controlling expression of a heterologous gene(s) in the other direction. In the presence of arabinose, transcription of both heterologous genes from both promoters is induced. However, in the absence of arabinose, transcription of both heterologous genes from both promoters is not induced.

In one exemplary embodiment of the disclosure, the genetically engineered bacteria of the present disclosure contains a kill-switch having at least the following sequences: a $P_{araBAD}$ promoter operably linked to a heterologous gene encoding a Tetracycline Repressor Protein (TetR), a $P_{araC}$ promoter operably linked to a heterologous gene encoding AraC transcription factor, and a heterologous gene encoding a bacterial toxin operably linked to a promoter which is repressed by the Tetracycline Repressor Protein ($P_{TetR}$). In the presence of arabinose, the AraC transcription factor activates the $P_{araBAD}$ promoter, which activates transcription of the TetR protein which, in turn, represses transcription of the toxin. In the absence of arabinose, however, AraC suppresses transcription from the $P_{araBAD}$ promoter and no TetR protein is expressed. In this case, expression of the heterologous toxin gene is activated, and the toxin is expressed. The toxin builds up in the recombinant bacterial cell, and the recombinant bacterial cell is killed. In one embodiment, the araC gene encoding the AraC transcription factor is under the control of a constitutive promoter and is therefore constitutively expressed.

In one embodiment of the disclosure, the genetically engineered bacterium further comprises an anti-toxin under the control of a constitutive promoter. In this situation, in the presence of arabinose, the toxin is not expressed due to repression by TetR protein, and the anti-toxin protein builds-up in the cell. However, in the absence of arabinose, TetR protein is not expressed, and expression of the toxin is induced. The toxin begins to build-up within the recombinant bacterial cell. The recombinant bacterial cell is no longer viable once the toxin protein is present at either equal or greater amounts than that of the anti-toxin protein in the cell, and the recombinant bacterial cell will be killed by the toxin.

In another embodiment of the disclosure, the genetically engineered bacterium further comprises an anti-toxin under the control of the $P_{araBAD}$ promoter. In this situation, in the presence of arabinose, TetR and the anti-toxin are expressed, the anti-toxin builds up in the cell, and the toxin is not expressed due to repression by TetR protein. However, in the absence of arabinose, both the TetR protein and the anti-toxin are not expressed, and expression of the toxin is induced. The toxin begins to build-up within the recombinant bacterial cell. The recombinant bacterial cell is no longer viable once the toxin protein is expressed, and the recombinant bacterial cell will be killed by the toxin.

In another exemplary embodiment of the disclosure, the genetically engineered bacteria of the present disclosure contains a kill-switch having at least the following sequences: a $P_{araBAD}$ promoter operably linked to a heterologous gene encoding an essential polypeptide not found in the recombinant bacterial cell (and required for survival), and a $P_{araC}$ promoter operably linked to a heterologous gene encoding AraC transcription factor. In the presence of arabinose, the AraC transcription factor activates the $P_{araBAD}$ promoter, which activates transcription of the heterologous gene encoding the essential polypeptide, allowing the recombinant bacterial cell to survive. In the absence of arabinose, however, AraC suppresses transcription from the $P_{araBAD}$ promoter and the essential protein required for survival is not expressed. In this case, the recombinant bacterial cell dies in the absence of arabinose. In some embodiments, the sequence of $P_{araBAD}$ promoter operably linked to a heterologous gene encoding an essential polypeptide not found in the recombinant bacterial cell can be present in the bacterial cell in conjunction with the TetR/toxin kill-switch system described directly above. In some embodiments, the sequence of $P_{araBAD}$ promoter operably linked to a heterologous gene encoding an essential polypeptide not found in the recombinant bacterial cell can be present in the bacterial cell in conjunction with the TetR/toxin/anti-toxin kill-switch system described directly above.

In yet other embodiments, the bacteria may comprise a plasmid stability system with a plasmid that produces both a short-lived anti-toxin and a long-lived toxin. In this system, the bacterial cell produces equal amounts of toxin and anti-toxin to neutralize the toxin. However, if/when the cell loses the plasmid, the short-lived anti-toxin begins to decay. When the anti-toxin decays completely the cell dies as a result of the longer-lived toxin killing it.

In some embodiments, the engineered bacteria of the present disclosure further comprise the gene(s) encoding the components of any of the above-described kill-switch circuits.

In any of the above-described embodiments, the bacterial toxin may be selected from the group consisting of a lysin, Hok, Fst, TisB, LdrD, Kid, SymE, MazF, FlmA, Ibs, XCV2162, dinJ, CcdB, MazF, ParE, YafO, Zeta, hicB, relB, yhaV, yoeB, chpBK, hipA, microcin B, microcin B17, microcin C, microcin C7-051, microcin J25, microcin ColV, microcin 24, microcin L, microcin D93, microcin L, microcin E492, microcin H47, microcin 147, microcin M, colicin A, colicin E1, colicin K, colicin N, colicin U, colicin B, colicin Ia, colicin Ib, colicin 5, colicin10, colicin S4, colicin Y, colicin E2, colicin E7, colicin E8, colicin E9, colicin E3, colicin E4, colicin E6, colicin E5, colicin D, colicin M, and cloacin DF13, or a biologically active fragment thereof.

In any of the above-described embodiments, the antitoxin may be selected from the group consisting of an anti-lysin, Sok, RNAII, IstR, RdlD, Kis, SymR, MazE, FlmB, Sib, ptaRNA1, yafQ, CcdA, MazE, ParD, yafN, Epsilon, HicA, relE, prlF, yefM, chpBI, hipB, MccE, MccE$^{CTD}$, MccF, Cai, ImmE1, Cki, Cni, Cui, Cbi, Iia, Imm, Cfi, Im10, Csi, Cyi, Im2, Im7, Im8, Im9, Im3, Im4, ImmE6, cloacin immunity protein (Cim), ImmE5, ImmD, and Cmi, or a biologically active fragment thereof.

In one embodiment, the bacterial toxin is bactericidal to the genetically engineered bacterium. In one embodiment, the bacterial toxin is bacteriostatic to the genetically engineered bacterium.

In some embodiments, the genetically engineered bacterium provided herein is an auxotroph. In one embodiment, the genetically engineered bacterium is an auxotroph selected from a cysE, ginA, ilvD, leuB, lysA, serA, metA, giyA, hisB, ilvA, pheA, proA, thrC, trpC, tyrA, thyA, uraA, dapA, dapB, dapD, dapE, dapF, flhD, metB, metC, proAB, and thi1 auxotroph. In some embodiments, the engineered bacteria have more than one auxotrophy, for example, they may be a ΔthyA and ΔdapA auxotroph.

In some embodiments, the genetically engineered bacterium provided herein further comprises a kill-switch circuit, such as any of the kill-switch circuits provided herein. For example, in some embodiments, the genetically engineered bacteria further comprise one or more genes encoding one or more recombinase(s) under the control of an inducible promoter and an inverted toxin sequence. In some embodiments, the genetically engineered bacteria further comprise one or more genes encoding an anti-toxin. In some embodiments, the engineered bacteria further comprise one or more genes encoding one or more recombinase(s) under the control of an inducible promoter and one or more inverted excision genes, wherein the excision gene(s) encode an enzyme that deletes an essential gene. In some embodiments, the genetically engineered bacteria further comprise one or more genes encoding an anti-toxin. In some embodiments, the engineered bacteria further comprise one or more genes encoding a toxin under the control of a promoter having a TetR repressor binding site and a gene encoding the TetR under the control of an inducible promoter that is induced by arabinose, such as P$_{araBAD}$. In some embodiments, the genetically engineered bacteria further comprise one or more genes encoding an anti-toxin.

In some embodiments, the genetically engineered bacterium is an auxotroph comprising a therapeutic payload and further comprises a kill-switch circuit, such as any of the kill-switch circuits described herein.

In some embodiments of the above described genetically engineered bacteria, the gene or gene cassette for producing the anti-inflammation and/or gut barrier enhancer molecule is present on a plasmid in the bacterium and operatively linked on the plasmid to the inducible promoter. In other embodiments, the gene or gene cassette for producing the anti-inflammation and/or gut barrier enhancermolecule is present in the bacterial chromosome and is operatively linked in the chromosome to the inducible promoter.

Mutagenesis

In some embodiments, the inducible promoter is operably linked to a detectable product, e.g., GFP, and can be used to screen for mutants. In some embodiments, the inducible promoter is mutagenized, and mutants are selected based upon the level of detectable product, e.g., by flow cytometry, fluorescence-activated cell sorting (FACS) when the detectable product fluoresces. In some embodiments, one or more transcription factor binding sites is mutagenized to increase or decrease binding. In alternate embodiments, the wild-type binding sites are left intact and the remainder of the regulatory region is subjected to mutagenesis. In some embodiments, the mutant promoter is inserted into the genetically engineered bacteria of the invention to increase expression of the anti-inflammation and/or gut barrier enhancer molecule under inducing conditions, as compared to unmutated bacteria of the same subtype under the same conditions. In some embodiments, the inducible promoter and/or corresponding transcription factor is a synthetic, non-naturally occurring sequence.

In some embodiments, the gene encoding an anti-inflammation and/or gut barrier enhancer molecule is mutated to increase expression and/or stability of said molecule under inducing conditions, as compared to unmutated bacteria of the same subtype under the same conditions. In some embodiments, one or more of the genes in a gene cassette for producing an anti-inflammation and/or gut barrier enhancer molecule is mutated to increase expression of said molecule under inducing conditions, as compared to unmutated bacteria of the same subtype under the same conditions.

Pharmaceutical Compositions and Formulations

Pharmaceutical compositions comprising the genetically engineered bacteria described herein may be used to inhibit inflammatory mechanisms in the gut, restore and tighten gut mucosal barrier function, and/or treat or prevent autoimmune disorders. Pharmaceutical compositions comprising one or more genetically engineered bacteria, alone or in combination with prophylactic agents, therapeutic agents, and/or pharmaceutically acceptable carriers are provided. In certain embodiments, the pharmaceutical composition comprises one species, strain, or subtype of bacteria that are engineered to comprise the genetic modifications described herein, e.g., to produce an anti-inflammation and/or gut barrier enhancer molecule. In alternate embodiments, the pharmaceutical composition comprises two or more species, strains, and/or subtypes of bacteria that are each engineered to comprise the genetic modifications described herein, e.g., to produce an anti-inflammation and/or gut barrier enhancer molecule.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered bacteria described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). Suitable dosage amounts for the genetically engineered bacteria may range from about $10^5$ to $10^{12}$ bacteria, e.g., approximately $10^5$ bacteria, approximately $10^6$ bacteria, approximately $10^2$ bacteria, approximately $10^8$ bacteria, approximately $10^9$ bacteria, approximately $10^{10}$ bacteria, approximately $10^{11}$ bacteria, or approximately $10^{11}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In one embodiment, the pharmaceutical composition is administered after the subject eats a meal.

The genetically engineered bacteria may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered bacteria disclosed herein may be administered topically and formulated in the form of an ointment, cream, transdermal patch, lotion, gel, shampoo, spray, aerosol, solution, emulsion, or other form well known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The genetically engineered bacteria disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, poly-acrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered bacteria are enterically coated for release into the gut or a particular region of the gut, for example, the large intestine. The typical pH profile from the stomach to the colon is about 1-4 (stomach), 5.5-6.0 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered bacteria described herein.

In one embodiment, the genetically engineered bacteria of the disclosure may be formulated in a composition suitable for administration to pediatric subjects. As is well known in the art, children differ from adults in many aspects, including different rates of gastric emptying, pH, gastrointestinal permeability, etc. (Ivanovska et al., *Pediatrics*, 134(2):361-372, 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the genetically engineered bacteria may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. For example, see U.S. 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered bacteria described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered bacteria may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see, e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, $LD_{50}$, $ED_{50}$, $EC_{50}$, and $IC_{50}$ may be determined, and the dose ratio between toxic and therapeutic effects ($LD_{50}/ED_{50}$) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

Methods of Treatment

Another aspect of the invention provides methods of treating autoimmune disorders, diarrheal diseases, IBD, related diseases, and other diseases that benefit from reduced gut inflammation and/or enhanced gut barrier function. In some embodiments, the invention provides for the use of at least one genetically engineered species, strain, or subtype of bacteria described herein for the manufacture of a medicament. In some embodiments, the invention provides for the use of at least one genetically engineered species, strain, or subtype of bacteria described herein for the manufacture of a medicament for treating autoimmune disorders, diarrheal diseases, IBD, related diseases, and other diseases that benefit from reduced gut inflammation and/or enhanced gut barrier function. In some embodiments, the invention provides at least one genetically engineered species, strain, or subtype of bacteria described herein for use in treating autoimmune disorders, diarrheal diseases, IBD, related diseases, and other diseases that benefit from reduced gut inflammation and/or enhanced gut barrier function.

In some embodiments, the diarrheal disease is selected from the group consisting of acute watery diarrhea, e.g., cholera, acute bloody diarrhea, e.g., dysentery, and persistent diarrhea. In some embodiments, the IBD or related disease is selected from the group consisting of Crohn's disease, ulcerative colitis, collagenous colitis, lymphocytic colitis, diversion colitis, Behcet's disease, intermediate colitis, short bowel syndrome, ulcerative proctitis, proctosigmoiditis, left-sided colitis, pancolitis, and fulminant colitis.

In some embodiments, the disease or condition is an autoimmune disorder selected from the group consisting of acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hemolytic anemia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, Castleman disease, celiac disease, Chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, Coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile idiopathic arthritis, juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (systemic lupus erythematosus), chronic Lyme disease, Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis *nodosa*, type I, II, & Ill autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, type 1 diabetes, asthma, ulcerative colitis, undifferentiated connective tissue disease (UCTD), uveitis, vasculitis, vesiculobullous dermatosis, vitiligo, and Wegener's granulomatosis. In some embodiments, the invention provides methods for reducing, ameliorating, or eliminating one or more symptom(s) associated with these diseases, including but not limited to diarrhea, bloody stool, mouth sores, perianal disease, abdominal pain, abdominal cramping, fever, fatigue, weight loss, iron deficiency, anemia, appetite loss, weight loss, anorexia, delayed growth, delayed pubertal development, and inflammation of the skin, eyes, joints, liver, and bile ducts. In some embodiments, the invention provides methods for reducing gut inflammation and/or enhancing gut barrier function, thereby ameliorating or preventing a systemic autoimmune disorder, e.g., asthma (Arrieta et al., 2015).

The method may comprise preparing a pharmaceutical composition with at least one genetically engineered species, strain, or subtype of bacteria described herein, and administering the pharmaceutical composition to a subject in a therapeutically effective amount. In some embodiments, the genetically engineered bacteria of the invention are administered orally in a liquid suspension. In some embodiments, the genetically engineered bacteria of the invention are lyophilized in a gel cap and administered orally. In some embodiments, the genetically engineered bacteria of the invention are administered via a feeding tube. In some embodiments, the genetically engineered bacteria of the invention are administered rectally, e.g., by enema. In some embodiments, the genetically engineered bacteria of the invention are administered topically, intraintestinally, intrajejunally, intraduodenally, intraileally, and/or intracolically.

In certain embodiments, the pharmaceutical composition described herein is administered to reduce gut inflammation, enhance gut barrier function, and/or treat or prevent an autoimmune disorder in a subject. In some embodiments, the methods of the present disclosure may reduce gut inflammation in a subject by at least about 10%, 20%, 25%, 30%, 40%, 50%, 60%, 70%, 75%, 80%, 85%, 90%, 95%, or more as compared to levels in an untreated or control subject. In some embodiments, the methods of the present disclosure may enhance gut barrier function in a subject by at least about 10%, 20%, 25%, 30%, 40%, 50%, 60%, 70%, 75%, 80%, 85%, 90%, 95%, or more as compared to levels in an untreated or control subject. In some embodiments, changes in inflammation and/or gut barrier function are measured by comparing a subject before and after administration of the pharmaceutical composition. In some embodiments, the method of treating or ameliorating the autoimmune disorder and/or the disease or condition associated with gut inflammation and/or compromised gut barrier function allows one or more symptoms of the disease or condition to improve by at least about 10%, 20%, 30%, 40%, 50%, 60%, 70%, 80%, 90%, 95%, or more.

Before, during, and after the administration of the pharmaceutical composition, gut inflammation and/or barrier function in the subject may be measured in a biological sample, such as blood, serum, plasma, urine, fecal matter, peritoneal fluid, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to enhance gut barrier function and/or to reduce gut inflammation to baseline levels, e.g., levels comparable to those of a healthy control, in a subject. In some embodiments, the methods may include administration of the compositions of the invention to reduce gut inflammation to undetectable levels in a subject, or to less than about 1%, 2%, 5%, 10%, 20%, 25%, 30%, 40%, 50%, 60%, 70%, 75%, or 80% of the subject's levels prior to treatment. In some embodiments, the methods may include administration of the compositions of the invention to enhance gut barrier function in a subject by about 1%, 2%, 5%, 10%, 20%, 25%, 30%, 40%, 50%, 60%, 70%, 75%, 80%, 90%, 100% or more of the subject's levels prior to treatment.

In certain embodiments, the genetically engineered bacteria are *E. coli* Nissle. The genetically engineered bacteria may be destroyed, e.g., by defense factors in the gut or blood serum (Sonnenborn et al., 2009) or by activation of a kill switch, several hours or days after administration. Thus, the pharmaceutical composition comprising the genetically engineered bacteria may be re-administered at a therapeutically effective dose and frequency. In alternate embodiments, the genetically engineered bacteria are not destroyed within hours or days after administration and may propagate and colonize the gut.

The pharmaceutical composition may be administered alone or in combination with one or more additional therapeutic agents, e.g., corticosteroids, aminosalicylates, anti-inflammatory agents. In some embodiments, the pharmaceutical composition is administered in conjunction with an anti-inflammatory drug (e.g., mesalazine, prednisolone, methylprednisolone, butesonide), an immunosuppressive drug (e.g., azathioprine, 6-mercaptopurine, methotrexate, cyclosporine, tacrolimus), an antibiotic (e.g., metronidazole, ornidazole, clarithromycin, rifaximin, ciprofloxacin, anti-TB), other probiotics, and/or biological agents (e.g., infliximab, adalimumab, certolizumab pegol) (Triantafillidis et al., 2011). An important consideration in the selection of the one or more additional therapeutic agents is that the agent(s) should be compatible with the genetically engineered bacteria of the invention, e.g., the agent(s) must not kill the bacteria. The dosage of the pharmaceutical composition and the frequency of administration may be selected based on the severity of the symptoms and the progression of the disorder. The appropriate therapeutically effective dose and/or frequency of administration can be selected by a treating clinician.

Treatment In Vivo

The genetically engineered bacteria of the invention may be evaluated in vivo, e.g., in an animal model. Any suitable animal model of a disease or condition associated with gut inflammation, compromised gut barrier function, and/or an autoimmune disorder may be used (see, e.g., Mizoguchi, 2012). The animal model may be a mouse model of IBD, e.g., a CD45RB$^{Hi}$ T cell transfer model or a dextran sodium sulfate (DSS) model. The animal model may be a mouse model of type 1 diabetes (T1D), and T1D may be induced by treatment with streptozotocin.

Colitis is characterized by inflammation of the inner lining of the colon, and is one form of IBD. In mice, modeling colitis often involves the aberrant expression of T cells and/or cytokines. One exemplary mouse model of IBD can be generated by sorting CD4+ T cells according to their levels of CD45RB expression, and adoptively transferring CD4+ T cells with high CD45RB expression from normal donor mice into immunodeficient mice. Non-limiting examples of immunodeficient mice that may be used for transfer include severe combined immunodeficient (SCID) mice (Morrissey et al., 1993; Powrie et al., 1993), and recombination activating gene 2 (RAG2)-deficient mice (Corazza et al., 1999). The transfer of CD45RB$^{Hi}$ T cells into immunodeficient mice, e.g., via intravenous or intraperitoneal injection, results in epithelial cell hyperplasia, tissue damage, and severe mononuclear cell infiltration within the colon (Byrne et al., 2005; Dohi et al., 2004; Wei et al., 2005). In some embodiments, the genetically engineered bacteria of the invention may be evaluated in a CD45RB$^{Hi}$ T cell transfer mouse model of IBD.

Another exemplary animal model of IBD can be generated by supplementing the drinking water of mice with dextran sodium sulfate (DSS) (Martinez et al., 2006; Okayasu et al., 1990; Whittem et al., 2010). Treatment with DSS results in epithelial damage and robust inflammation in the colon lasting several days. Single treatments may be used to model acute injury, or acute injury followed by repair. Mice treated acutely show signs of acute colitis, including bloody stool, rectal bleeding, diarrhea, and weight loss (Okayasu et al., 1990). In contrast, repeat administration cycles of DSS may be used to model chronic inflammatory disease. Mice that develop chronic colitis exhibit signs of colonic mucosal regeneration, such as dysplasia, lymphoid follicle formation, and shortening of the large intestine (Okayasu et al., 1990). In some embodiments, the genetically engineered bacteria of the invention may be evaluated in a DSS mouse model of IBD.

In some embodiments, the genetically engineered bacteria of the invention is administered to the animal, e.g., by oral gavage, and treatment efficacy is determined, e.g., by endoscopy, colon translucency, fibrin attachment, mucosal and vascular pathology, and/or stool characteristics. In some embodiments, the animal is sacrificed, and tissue samples are collected and analyzed, e.g., colonic sections are fixed and scored for inflammation and ulceration, and/or homogenized and analyzed for myeloperoxidase activity and cytokine levels (e.g., IL-1β, TNF-α, IL-6, IFN-γ and IL-10).

REFERENCES

Aboulnaga et al. Effect of an oxygen-tolerant bifurcating butyryl coenzyme A dehydrogenase/electron-transferring flavoprotein complex from *Clostridium difficile* on butyrate production in *Escherichia coli*. J Bact. 2013; 195(16):3704-13. PMID: 23772070.

Ahmad et al. scFv antibody: principles and clinical application. Clin Dev Immunol. 2012; 2012:980250. PMID: 22474489.

Alavi et al. Treatment of inflammatory bowel disease in a rodent model with the intestinal growth factor glucagon-like peptide-2. J Pediatr Surg. 2000 June; 35(6):847-51. PMID: 10873024.

Albiniak et al. High-level secretion of a recombinant protein to the culture medium with a *Bacillus subtilis* twin-arginine translocation system in *Escherichia coli*. FEBS J. 2013; 280(16):3810-21. PMID: 23745597.

Altenhoefer et al. The probiotic *Escherichia coli* strain Nissle 1917 interferes with invasion of human intestinal epithelial cells by different enteroinvasive bacterial pathogens. FEMS Immunol Med Microbiol. 2004 Apr. 9; 40(3):223-9. PMID: 15039098.

Alvarado et al. Targeting the Broadly Pathogenic Kynurenine Pathway. 2015. Sandeep, ed. Springer International Publishing: Switzerland.

Appleyard C B, Wallace J L. Reactivation of hapten-induced colitis and its prevention by anti-inflammatory drugs. Am J Physiol. 1995 July; 269(1 Pt 1):G119-25. PMID: 7631788.

Arai et al. Expression of the nir and nor genes for denitrification of *Pseudomonas aeruginosa* requires a novel CRP/FNR-related transcriptional regulator, DNR, in addition to ANR. FEBS Lett. 1995 Aug. 28; 371(1):73-6. PMID: 7664887.

Arrieta et al. Early infancy microbial and metabolic alterations affect risk of childhood asthma. Sci Transl Med. 2015 Sep. 30; 7(307):307ra152. PMID: 26424567.

Arthur et al. Intestinal inflammation targets cancer-inducing activity of the microbiota. Science. 2012 Oct. 5; 338 (6103):120-3. PMID: 22903521.

Atarashi et al. Induction of colonic regulatory T cells by indigenous *Clostridium* species. Science. 2011 Jan. 21; 331(6015):337-41. PMID: 21205640.

Boirivant et al. Oxazolone colitis: a murine model of T helper cell type 2 colitis treatable with antibodies to interleukin 4. J Exp Med. 1998 Nov. 16; 188(10):1929-39. PMID: 9815270.

Bramhall et al. Quality of methods reporting in animal models of colitis. Inflamm Bowel Dis. 2015 June; 21(6): 1248-59. PMID: 25989337.

Byrne et al. CD4+CD45RBHi T cell transfer induced colitis in mice is accompanied by osteopenia which is treatable with recombinant human osteoprotegerin. Gut. 2005 January; 54(1):78-86. PMID: 15591508.

Callura et al. Tracking, Tuning and terminating microbial physiology using synthetic riboregulators. Proc Natl Acad Sci. 2010; 27(36):15898-903. PMID: 20713708.

Castiglione et al. The transcription factor DNR from *Pseudomonas aeruginosa* specifically requires nitric oxide and haem for the activation of a target promoter in *Escherichia coli*. Microbiology. 2009 September; 155(Pt 9):2838-44. PMID: 19477902.

Chassaing et al. Dextran sulfate sodium (DSS)-induced colitis in mice. Curr Protoc Immunol. 2014 Feb. 4; 104:Unit 15.25. PMID: 24510619.

Chassaing et al. Fecal lipocalin 2, a sensitive and broadly dynamic non-invasive biomarker for intestinal inflammation. PLoS One. 2012; 7(9):e44328. PMID: 22957064.

Ciorba et al. Induction of IDO-1 by immunostimulatory DNA limits severity of experimental colitis. J Immunol. 2010 Apr. 1; 184(7):3907-16. PMID: 20181893.

Clarkson et al. Diaminopimelic acid and lysine auxotrophs of *Pseudomonas aeruginosa* 8602. J Gen Microbiol. 1971 May; 66(2):161-9. PMID: 4999073.

Cohen et al. Biologic therapies in inflammatory bowel disease. Transl Res. 2014 June; 163(6):533-56. PMID: 24467968.

Collinson et al. Channel crossing: how are proteins shipped across the bacterial plasma membrane? Philos Trans R Soc Lond B Biol Sci. 2015; 370: 20150025. PMID: 26370937.

Corazza et al. Nonlymphocyte-derived tumor necrosis factor is required for induction of colitis in recombination activating gene (RAG)2(−/−) mice upon transfer of CD4(+) CD45RB(hi) T cells. J Exp Med. 1999 Nov. 15; 190(10): 1479-92. PMID: 10562322.

Costa et al. Secretion systems in Gram-negative bacteria: structural and mechanistic insights. Nat Rev Microbiol. 2015; 13(6):343-59. PMID: 25978706.

Cuevas-Ramos et al. *Escherichia coli* induces DNA damage in vivo and triggers genomic instability in mammalian cells. Proc Natl Acad Sci USA. 2010 Jun. 22; 107(25): 11537-42. PMID: 20534522.

Cutting. *Bacillus* probiotics. Food Microbiol. 2011 April; 28(2):214-20. PMID: 21315976.

Danino et al. Programmable probiotics for detection of cancer in urine. Sci Transl Med. 2015 May 27; 7(289): 289ra84. PMID: 26019220.

Davis-Richardson et al. A model for the role of gut bacteria in the development of autoimmunity for type 1 diabetes. Diabetologia. 2015 July; 58(7):1386-93. PMID: 25957231.

Dinleyici et al. *Saccharomyces boulardii* CNCM I-745 in different clinical conditions. Expert Opin Biol Ther. 2014 November; 14(11):1593-609. PMID: 24995675.

Dohi et al. CD4+CD45RBHi interleukin-4 defective T cells elicit antral gastritis and duodenitis. Am J Pathol. 2004 October; 165(4):1257-68. PMID: 15466391.

Eiglmeier et al. Molecular genetic analysis of FNR-dependent promoters. Mol Microbiol. 1989 July; 3(7):869-78. PMID: 2677602.

Elson et al. The C3H/HeJBir mouse model: a high susceptibility phenotype for colitis. Int Rev Immunol. 2000; 19(1):63-75. PMID: 10723678.

El-Zaatari et al. Tryptophan catabolism restricts IFN-γ-expressing neutrophils and *Clostridium difficile* immunopathology. J Immunol. 2014 Jul. 15; 193(2):807-16. PMID: 24935925.

Erben et al. A guide to histomorphological evaluation of intestinal inflammation in mouse models. Int J Clin Exp Pathol. 2014 Jul. 15; 7(8):4557-76. PMID: 25197329.

Fasano A, Shea-Donohue T. Mechanisms of disease: the role of intestinal barrier function in the pathogenesis of gastrointestinal autoimmune diseases. Nat Clin Pract Gastroenterol Hepatol. 2005 September; 2(9):416-22. PMID: 16265432.

Fasano. Leaky gut and autoimmune diseases. Clin Rev Allergy Immunol. 2012 February; 42(1):71-8. PMID: 22109896.

Ferdinande et al. Inflamed intestinal mucosa features a specific epithelial expression pattern of indoleamine 2,3-dioxygenase. Int J Immunopathol Pharmacol. 2008 April-June; 21(2):289-95. PMID: 18547472.

Forrest et al. Levels of purine, kynurenine and lipid peroxidation products in patients with inflammatory bowel disease. In: Developments in Tryptophan and Serotonin Metabolism. 2003; 527:395-400. Allegri et al., ed. Springer Science+Business Media: New York.

Frenzel et al. Expression of recombinant antibodies. Front Immunol. 2013; 4:217. PMID: 23908655.

Furusawa et al. Commensal microbe-derived butyrate induces the differentiation of colonic regulatory T cells. Nature. 2013; 504:446-50. PMID: 24226770.

Galimand et al. Positive FNR-like control of anaerobic arginine degradation and nitrate respiration in *Pseudomonas aeruginosa*. J Bacteriol. 1991 March; 173(5):1598-606. PMID: 1900277.

Gardner et al. Construction of a genetic toggle switch in *Escherichia coli*. Nature. 2000; 403:339-42. PMID: 10659857.

Garrett et al. Communicable ulcerative colitis induced by T-bet deficiency in the innate immune system. Cell. 2007 Oct. 5; 131(1):33-45. PMID: 17923086.

Gerlach et al. Protein secretion systems and adhesins: the molecular armory of Gram-negative pathogens. Int J Med Microbiol. 2007; 297:401-15. PMID: 17482513.

Ghishan et al. Epithelial transport in inflammatory bowel diseases. Inflamm Bowel Dis. 2014 June; 20(6):1099-109. PMID: 24691115.

Gurtner et al. Inhibition of indoleamine 2,3-dioxygenase augments trinitrobenzene sulfonic acid colitis in mice. Gastroenterology. 2003 December; 125(6):1762-73. PMID: 14724829.

Hamer et al. Review article: the role of butyrate on colonic function. Aliment Pharmacol Ther. 2008 Jan. 15; 27(2): 104-19. PMID: 17973645.

Hammer et al. Spontaneous inflammatory disease in transgenic rats expressing HLA-B27 and human beta 2 m: an animal model of HLA-B27-associated human disorders. Cell. 1990 Nov. 30; 63(5):1099-112. PMID: 2257626.

Hasegawa et al. Activation of a consensus FNR-dependent promoter by DNR of *Pseudomonas aeruginosa* in response to nitrite. FEMS Microbiol Lett. 1998 Sep. 15; 166(2):213-7. PMID: 9770276.

Hermiston M L, Gordon J I. Inflammatory bowel disease and adenomas in mice expressing a dominant negative N-cadherin. Science. 1995 Nov. 17; 270(5239):1203-7. PMID: 7502046.

Hetzel et al. Acryloyl-CoA reductase from *Clostridium propionicum*. An enzyme complex of propionyl-CoA dehydrogenase and electron-transferring flavoprotein. EurJ Biochem. 2003 March; 270(5):902-10. PMID: 12603323.

Hillman. Simple, rapid method for determination of propionic acid and other short-chain fatty acids in serum. Clin Chem. 1978 May; 24(5):800-3. PMID: 647915.

Hoeren et al. Sequence and expression of the gene encoding the respiratory nitrous-oxide reductase from *Paracoccus denitrificans*. New and conserved structural and regulatory motifs. EurJ Biochem. 1993 Nov. 15; 218(1):49-57. PMID: 8243476.

Hristodorov et al. Recombinant H22(scFv) blocks CD64 and prevents the capture of anti-TNF monoclonal antibody. A potential strategy to enhance anti-TNF therapy. MAbs. 2014; 6(5):1283-9. PMID: 25517313.

Hsu et al. Differential mechanisms in the pathogenesis of autoimmune cholangitis versus inflammatory bowel disease in interleukin-2Ralpha(-/-) mice. Hepatology. 2009 January; 49(1):133-40. PMID: 19065673.

Ianiro et al. Fecal microbiota transplantation in inflammatory bowel disease: beyond the excitement. Medicine (Baltimore). 2014 October; 93(19):e97. PMID: 25340496.

Isabella et al. Deep sequencing-based analysis of the anaerobic stimulon in *Neisseria gonorrhoeae*. BMC Genomics. 2011 Jan. 20; 12:51. PMID: 21251255.

Iyer S S, Cheng G. Role of interleukin 10 transcriptional regulation in inflammation and autoimmune disease. Crit Rev Immunol. 2012; 32(1):23-63. PMID: 22428854.

Johansson et al. The inner of the two Muc2 mucin-dependent mucus layers in colon is devoid of bacteria. Proc Natl Acad Sci USA. 2008 Sep. 30; 105(39):15064-9. PMID: 18806221.

Kanai et al. A breakthrough in probiotics: *Clostridium butyricum* regulates gut homeostasis and anti-inflammatory response in inflammatory bowel disease. J Gastroenterol. 2015 September; 50(9):928-39. PMID: 25940150.

Keates et al. TransKingdom RNA interference: a bacterial approach to challenges in RNAi therapy and delivery. Biotechnol Genet Eng Rev. 2008; 25:113-27. PMID: 21412352.

Khor B, Gardet A, Xavier R J. Genetics and pathogenesis of inflammatory bowel disease. Nature. 2011 Jun. 15; 474 (7351):307-17. PMID: 21677747.

Kleman et al. Acetate metabolism by *Escherichia coli* in high-cell-density fermentation. Appl Environ Microbiol. 1994 November; 60(11):3952-8. PMID: 7993084.

Lerner et al. (a) Changes in intestinal tight junction permeability associated with industrial food additives explain the rising incidence of autoimmune disease. Autoimmun Rev. 2015 June; 14(6):479-89. PMID: 25676324.

Lerner et al. (b) Rheumatoid arthritis-celiac disease relationship: Joints get that gut feeling. Autoimmun Rev. 2015 November; 14(11):1038-47. PMID: 26190704.

Low et al. Animal models of ulcerative colitis and their application in drug research. Drug Des Devel Ther. 2013 Nov. 12; 7:1341-57. PMID: 24250223.

Lukovac et al. Differential modulation by Akkermansia muciniphila and *Faecalibacterium prausnitzii* of host peripheral lipid metabolism and histone acetylation in mouse gut organoids. MBio. 2014 Aug. 12; 5(4). pii: e01438-14. PMID: 25118238.

MacPherson B R, Pfeiffer C J. Experimental production of diffuse colitis in rats. Digestion. 1978; 17(2):135-50. PMID: 627326.

Martinez et al. Deletion of Mtgr1 sensitizes the colonic epithelium to dextran sodium sulfate-induced colitis. Gastroenterology. 2006 August; 131(2):579-88. PMID: 16890610.

Matteoli et al. Gut CD103+ dendritic cells express indoleamine 2,3-dioxygenase which influences T regulatory/T effector cell balance and oral tolerance induction. Gut. 2010 May; 59(5):595-604. PMID: 20427394.

Meadow et al. Biosynthesis of diaminopimelic acid and lysine in *Escherichia coli*. Biochem J. 1959 July; 72(3): 396-400. PMID: 16748796.

Mizoguchi. Animal models of inflammatory bowel disease. Prog Mol Biol Transl Sci. 2012; 105:263-320. PMID: 22137435.

Mombaerts et al. Spontaneous development of inflammatory bowel disease in T cell receptor mutant mice. Cell. 1993 Oct. 22; 75(2):274-82. PMID: 8104709.

Moolenbeek C, Ruitenberg E J. The "Swiss roll": a simple technique for histological studies of the rodent intestine. Lab Anim. 1981 January; 15(1):57-9. PMID: 7022018.

Moore et al. Regulation of FNR dimerization by subunit charge repulsion. J Biol Chem. 2006 Nov. 3; 281(44): 33268-75. PMID: 16959764.

Morrissey et al. CD4+ T cells that express high levels of CD45RB induce wasting disease when transferred into congenic severe combined immunodeficient mice. Disease development is prevented by cotransfer of purified CD4+ T cells. J Exp Med. 1993 Jul. 1; 178(1):237-44. PMID: 8100269.

Mourelle et al. Polyunsaturated phosphatidylcholine prevents stricture formation in a rat model of colitis. Gastroenterology. 1996 April; 110(4):1093-7. PMID: 8612998.

Nguyen et al. Lymphocyte-dependent and Th2 cytokine-associated colitis in mice deficient in Wiskott-Aldrich syndrome protein. Gastroenterology. 2007 October; 133 (4):1188-97. PMID: 17764675.

Nielsen. New strategies for treatment of inflammatory bowel disease. Front Med (Lausanne). 2014; 1:3. PMID: 25685754.

Nougayrede et al. *Escherichia coli* induces DNA double-strand breaks in eukaryotic cells. Science. 2006 Aug. 11; 313(5788):848-51. PMID: 16902142.

Ohman et al. Regression of Peyer's patches in G alpha i2 deficient mice prior to colitis is associated with reduced expression of Bcl-2 and increased apoptosis. Gut. 2002 September; 51(3):392-7. PMID: 12171962.

Okayasu et al. A novel method in the induction of reliable experimental acute and chronic ulcerative colitis in mice. Gastroenterology. 1990 March; 98(3):694-702. PMID: 1688816.

Olier et al. Genotoxicity of *Escherichia coli* Nissle 1917 strain cannot be dissociated from its probiotic activity. Gut Microbes. 2012 November-December; 3(6):501-9. PMID: 22895085.

Ostanin et al. T cell transfer model of chronic colitis: concepts, considerations, and tricks of the trade. Am J Physiol Gastrointest Liver Physiol. 2009 February; 296(2):G135-46. PMID: 19033538.

Paun et al. Immuno-ecology: how the microbiome regulates tolerance and autoimmunity. Curr Opin Immunol. 2015 Oct. 10; 37:34-9. PMID: 26460968.

Pizarro et al. SAMP1/YitFc mouse strain: a spontaneous model of Crohn's disease-like ileitis. Inflamm Bowel Dis. 2011 December; 17(12):2566-84. PMID: 21557393.

Powrie et al. Phenotypically distinct subsets of CD4+ T cells induce or protect from chronic intestinal inflammation in C. B-17 scid mice. Int Immunol. 1993 November; 5(11): 1461-71. PMID: 7903159.

Pugsley. The complete general secretory pathway in gram-negative bacteria. Microbiol Rev. 1993 March; 57(1):50-108. PMID: 8096622.

Purcell et al. Towards a whole-cell modeling approach for synthetic biology. Chaos. 2013 June; 23(2):025112. PMID: 23822510.

Ragsdale. Enzymology of the wood-Ljungdahl pathway of acetogenesis. Ann N Y Acad Sci. 2008 March; 1125:129-36. PMID: 18378591.

Ray et al. The effects of mutation of the anr gene on the aerobic respiratory chain of *Pseudomonas aeruginosa*. FEMS Microbiol Lett. 1997 Nov. 15; 156(2):227-32. PMID: 9513270.

Reeves et al. Engineering *Escherichia coli* into a protein delivery system for mammalian cells. ACS Synth Biol. 2015; 4(5):644-54. PMID: 25853840.

Reister et al. Complete genome sequence of the Gram-negative probiotic *Escherichia coli* strain Nissle 1917. J Biotechnol. 2014 Oct. 10; 187:106-7. PMID: 25093936.

Rembacken et al. Non-pathogenic *Escherichia coli* versus mesalazine for the treatment of ulcerative colitis: a randomised trial. Lancet. 1999 Aug. 21; 354(9179):635-9. PMID: 10466665.

Remington's Pharmaceutical Sciences, 22$^{nd}$ ed. Mack Publishing Co.

Rigel et al. A new twist on an old pathway—accessory Sec systems. Mol Microbiol. 2008 July; 69(2):291-302. PMID: 18544071.

Sabiu et al. Indomethacin-induced gastric ulceration in rats: Ameliorative roles of *Spondias mombin* and *Ficus exasperata*. Pharm Biol. 2016 January; 54(1):180-6. PMID: 25815713.

Saier. Protein secretion and membrane insertion systems in Gram-negative bacteria. J Membr Biol. 2006; 214(2):75-90. PMID: 17546510.

Salmon et al. Global gene expression profiling in *Escherichia coli* K12. The effects of oxygen availability and FNR. J Biol Chem. 2003 Aug. 8; 278(32):29837-55. PMID: 12754220.

Sanz et al. Microbiota, inflammation and obesity. Adv Exp Med Biol. 2014; 817:291-317. PMID: 24997040.

Sanz et al. Understanding the role of gut microbiome in metabolic disease risk. Pediatr Res. 2015 January; 77(1-2):236-44. PMID: 25314581.

Sat et al. The *Escherichia coli* mazEF suicide module mediates thymineless death. J Bacteriol. 2003 March; 185(6):1803-7. PMID: 12618443.

Satoh et al. New ulcerative colitis model induced by sulfhydryl blockers in rats and the effects of antiinflammatory drugs on the colitis. Jpn J Pharmacol. 1997 April; 73(4): 299-309. PMID: 9165366.

Sawers. Identification and molecular characterization of a transcriptional regulator from *Pseudomonas aeruginosa* PAO1 exhibiting structural and functional similarity to the FNR protein of *Escherichia coli*. Mol Microbiol. 1991 June; 5(6):1469-81. PMID: 1787797.

Schiel-Bengelsdorf et al. Pathway engineering and synthetic biology using acetogens. FEBS Lett. 2012 Jul. 16; 586(15):2191-8. PMID: 22710156.

Schultz. Clinical use of *E. coli* Nissle 1917 in inflammatory bowel disease. Inflamm Bowel Dis. 2008 July; 14(7): 1012-8. Review. PMID: 18240278.

Seguí et al. Superoxide dismutase ameliorates TNBS-induced colitis by reducing oxidative stress, adhesion molecule expression, and leukocyte recruitment into the inflamed intestine. J Leukoc Biol. 2004 September; 76(3): 537-44. PMID: 15197232.

Selmer et al. Propionate CoA-transferase from *Clostridium propionicum*. Cloning of gene and identification of glutamate 324 at the active site. Eur J Biochem. 2002 January; 269(1):372-80. PMID: 11784332.

Simpson et al. IBD: microbiota manipulation through diet and modified bacteria. Dig Dis. 2014; 32 Suppl 1:18-25. PMID: 25531349.

Smith et al. The microbial metabolites, short-chain fatty acids, regulate colonic Treg cell homeostasis. Science. 2013 Aug. 2; 341(6145):569-73. PMID: 23828891.

Sonnenborn et al. The non-pathogenic *Escherichia coli* strain Nissle 1917—features of a versatile probiotic. Microbial Ecology in Health and Disease. 2009; 21:122-58.

Stanley et al. Acute infection and macrophage subversion by *Mycobacterium tuberculosis* require a specialized secretion system. Proc Natl Acad Sci USA. 2003 October; 100(22):13001-6. PMID: 14557536.

Sugimoto et al. IL-22 ameliorates intestinal inflammation in a mouse model of ulcerative colitis. J Clin Invest. 2008 February; 118(2):534-44. PMID: 18172556.

Triantafillidis et al. Current and emerging drugs for the treatment of inflammatory bowel disease. Drug Des Devel Ther 5.5 (2011): 185-210.

Trunk et al. Anaerobic adaptation in *Pseudomonas aeruginosa*: definition of the Anr and Dnr regulons. Environ Microbiol. 2010 June; 12(6):1719-33. PMID: 20553552.

Tseng et al. Controlled biosynthesis of odd-chain fuels and chemicals via engineered modular metabolic pathways. Proc Natl Acad Sci USA. 2012 Oct. 30; 109(44):17925-30. PMID: 23071297.

Turski et al. Kynurenic Acid in the digestive system-new facts, new challenges. Int J Tryptophan Res. 2013 Sep. 4; 6:47-55. PMID: 24049450.

Ukena et al. Probiotic *Escherichia coli* Nissle 1917 inhibits leaky gut by enhancing mucosal integrity. PLoS One. 2007 Dec. 12; 2(12):e1308. PMID: 18074031.

Unden et al. Alternative respiratory pathways of *Escherichia coli*: energetics and transcriptional regulation in response to electron acceptors. Biochim Biophys Acta. 1997 Jul. 4; 1320(3):217-34. PMID: 9230919.

Varga et al. N-Methyl-D-aspartate receptor antagonism decreases motility and inflammatory activation in the early phase of acute experimental colitis in the rat. Neurogastroenterol Motil. 2010 February; 22(2):217-25. PMID: 19735360.

Wagner et al. Semisynthetic diet ameliorates Crohn's disease-like ileitis in TNFΔARE/WT mice through antigen-independent mechanisms of gluten. Inflamm Bowel Dis. 2013 May; 19(6):1285-94. PMID: 23567784.

Watanabe et al. Interleukin 7 transgenic mice develop chronic colitis with decreased interleukin 7 protein accumulation in the colonic mucosa. J Exp Med. 1998 Feb. 2; 187(3):389-402. PMID: 9449719.

Wei et al. Mesenteric B cells centrally inhibit CD4+ T cell colitis through interaction with regulatory T cell subsets. Proc Natl Acad Sci USA. 2005 Feb. 8; 102(6):2010-15. PMID: 15684084.

Wen et al. Innate immunity and intestinal microbiota in the development of Type 1 diabetes. Nature. 2008 Oct. 23; 455(7216):1109-13. PMID: 18806780.

Whittem et al. Murine colitis modeling using dextran sulfate sodium (DSS). J Vis Exp. 2010 Jan. 19; (35). PMID: 20087313.

Wilk et al. The mdr1a−/− mouse model of spontaneous colitis: a relevant and appropriate animal model to study inflammatory bowel disease. Immunol Res. 2005; 31(2): 151-9. PMID: 15778512.

Williams G T, Williams W J. Granulomatous inflammation—a review. J Clin Pathol. 1983 July; 36(7):723-733. PMID: 6345591.

Winteler et al. The homologous regulators ANR of Pseudomonas aeruginosa and FNR of Escherichia coli have overlapping but distinct specificities for anaerobically inducible promoters. Microbiology. 1996 March; 142 (Pt 3):685-93. PMID: 8868444.

Wolf et al. Overexpression of indoleamine 2,3-dioxygenase in human inflammatory bowel disease. Clin Immunol. 2004 October; 113(1):47-55. PMID: 15380529.

Wright et al. GeneGuard: A Modular Plasmid System Designed for Biosafety. ACS Synth Biol. 2015 Mar. 20; 4(3):307-16. PMID: 24847673.

Xiao et al. Nanoparticles with surface antibody against CD98 and carrying CD98 small interfering RNA reduce colitis in mice. Gastroenterology. 2014 May; 146(5): 1289-300. PMID: 24503126.

Yazbeck et al. Growth factor based therapies and intestinal disease: is glucagon-like peptide-2 the new way forward? Cytokine Growth Factor Rev. 2009 April; 20(2):175-84. PMID: 19324585.

Zhang et al. Deletion of interleukin-6 in mice with the dominant negative form of transforming growth factor beta receptor II improves colitis but exacerbates autoimmune cholangitis. Hepatology. 2010 July; 52(1):215-22. PMID: 20578264.

Zimmermann et al. Anaerobic growth and cyanide synthesis of Pseudomonas aeruginosa depend on anr, a regulatory gene homologous with fnr of Escherichia coli. Mol Microbiol. 1991 June; 5(6):1483-90. PMID: 1787798.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Examples

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Example 1

Construction of Vectors for Producing Therapeutic Molecules

Butyrate

To facilitate inducible production of butyrate in Escherichia coli Nissle, the eight genes of the butyrate production pathway from Peptoclostridium difficile 630 (bcd2, etfB3, etfA3, thiA1, hbd, crt2, pbt, and buk; NCBI; Table 4), as well as transcriptional and translational elements, are synthesized (Gen9, Cambridge, Mass.) and cloned into vector pBR322. In some embodiments, the butyrate gene cassette is placed under the control of a FNR regulatory region selected from SEQ ID NOs: 55-66 (Table 9). In certain constructs, the FNR-responsive promoter is further fused to a strong ribosome binding site sequence. For efficient translation of butyrate genes, each synthetic gene in the operon was separated by a 15 base pair ribosome binding site derived from the T7 promoter/translational start site. In certain constructs, the butyrate gene cassette is placed under the control of an RNS-responsive regulatory region, e.g., norB, and the bacteria further comprises a gene encoding a corresponding RNS-responsive transcription factor, e.g., nsrR (see, e.g., Tables 10 and 11). In certain constructs, the butyrate gene cassette is placed under the control of an ROS-responsive regulatory region, e.g., oxyS, and the bacteria further comprises a gene encoding a corresponding ROS-responsive transcription factor, e.g., oxyR (see, e.g., Tables 14-17). In certain constructs, the butyrate gene cassette is placed under the control of a tetracycline-inducible or constitutive promoter.

The gene products of the bcd2-etfA3-etfB3 genes form a complex that converts crotonyl-CoA to butyryl-CoA and may exhibit dependence on oxygen as a co-oxidant. Because the recombinant bacteria of the invention are designed to produce butyrate in an oxygen-limited environment (e.g. the mammalian gut), that dependence on oxygen could have a negative effect of butyrate production in the gut. It has been shown that a single gene from Treponema denticola, trans-2-enoynl-CoA reductase (ter, Table 4), can functionally replace this three gene complex in an oxygen-independent manner. Therefore, a second butyrate gene cassette in which the ter gene replaces the bcd2-etfA3-etfB3 genes of the first butyrate cassette is synthesized (Genewiz, Cambridge, Mass.). The ter gene is codon-optimized for E. coli codon usage using Integrated DNA Technologies online codon optimization tool (https://www.idtdna.com/CodonOpt). The second butyrate gene cassette, as well as transcriptional and translational elements, is synthesized (Gen9, Cambridge, Mass.) and cloned into vector pBR322. In certain constructs, the second butyrate gene cassette is placed under control of a FNR regulatory region as described above (Table 4). In certain constructs, the butyrate gene cassette is placed under the control of an RNS-responsive regulatory region, e.g., norB, and the bacteria further comprises a gene encoding a corresponding RNS-responsive transcription factor, e.g., nsrR (see, e.g., Tables 10 and 11). In certain constructs, the butyrate gene cassette is placed under the control of an ROS-responsive regulatory region, e.g., oxyS, and the bacteria further comprises a gene encoding a corresponding ROS-responsive transcription factor, e.g., oxyR (see, e.g., Tables 14-17). In certain constructs, the butyrate gene cassette is placed under the control of a tetracycline-inducible or constitutive promoter.

Figure 2:
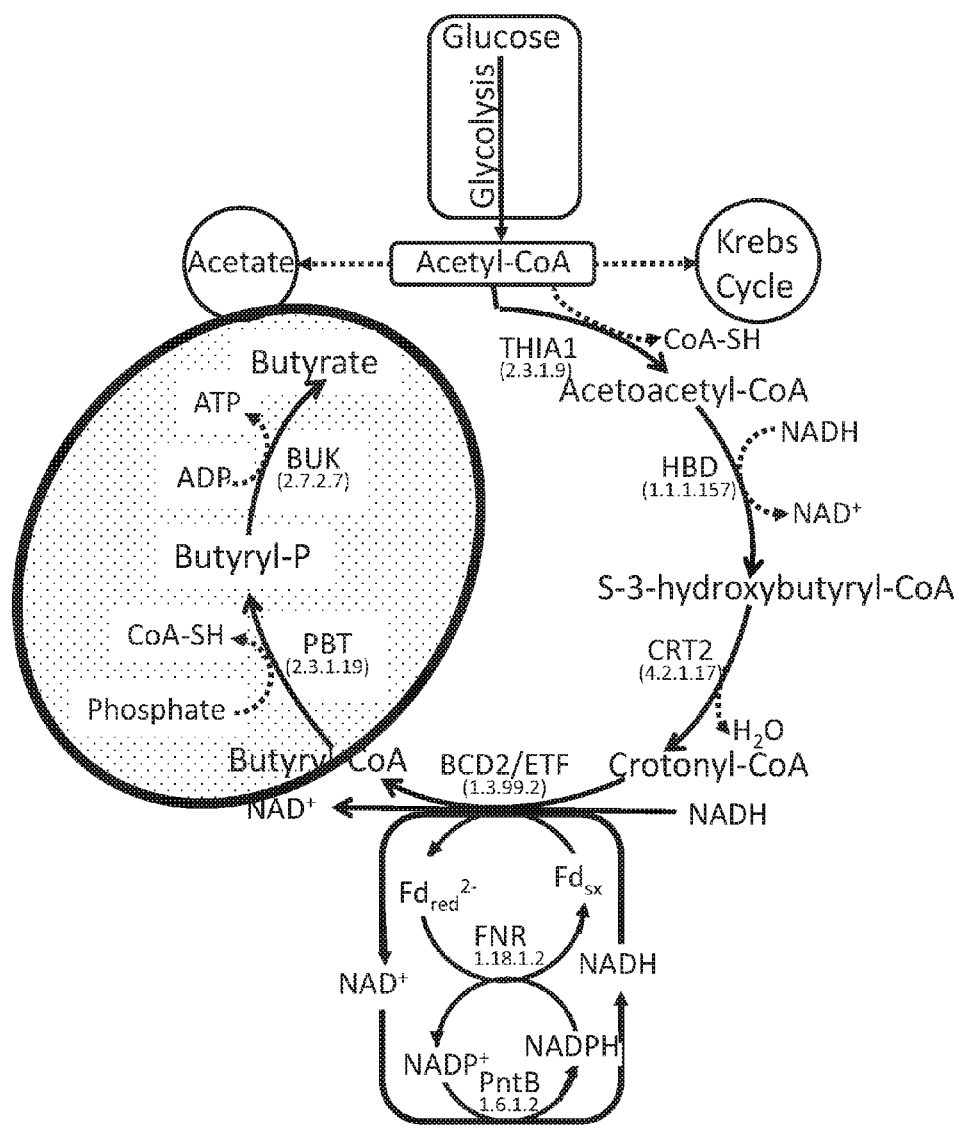
FIG. 2 depicts a schematic of a butyrate production pathway in which the circled genes (buk and pbt) may be deleted and replaced with tesB, which cleaves the CoA from butyryl-CoA.
Figure 3:
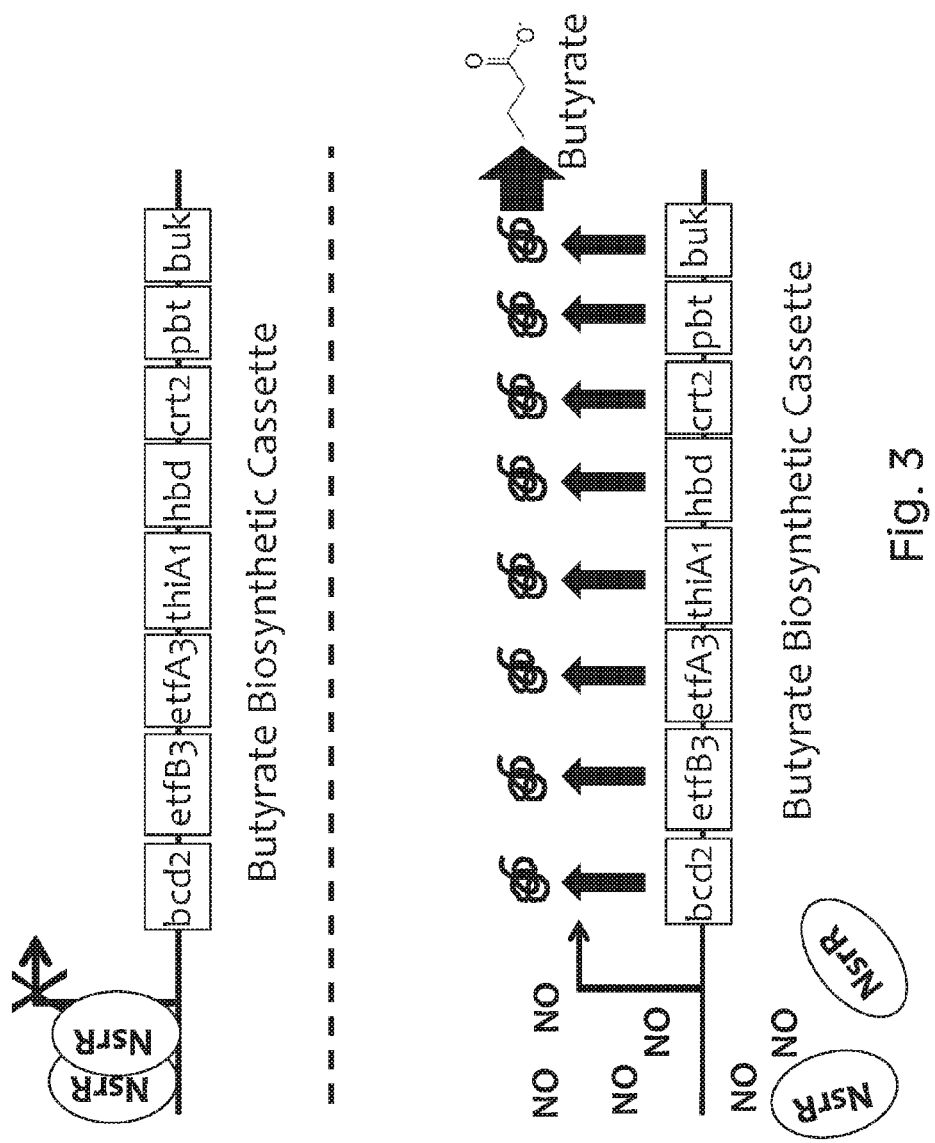
FIG. 3 depicts the gene organization of an exemplary recombinant bacterium of the invention and its derepression in the presence of nitric oxide (NO). In the upper panel, in the absence of NO, the NsrR transcription factor (gray circle, "NsrR") binds to and represses a corresponding regulatory region. Therefore, none of the butyrate biosynthesis enzymes (bcd2, etfB3, etfA3, thiA1, hbd, crt2, pbt, buk; black boxes) is expressed. In the lower panel, in the presence of NO, the NsrR transcription factor interacts with NO, and no longer binds to or represses the regulatory sequence. This leads to expression of the butyrate biosynthesis enzymes (indicated by gray arrows and black squiggles) and ultimately to the production of butyrate.
Figure 4:
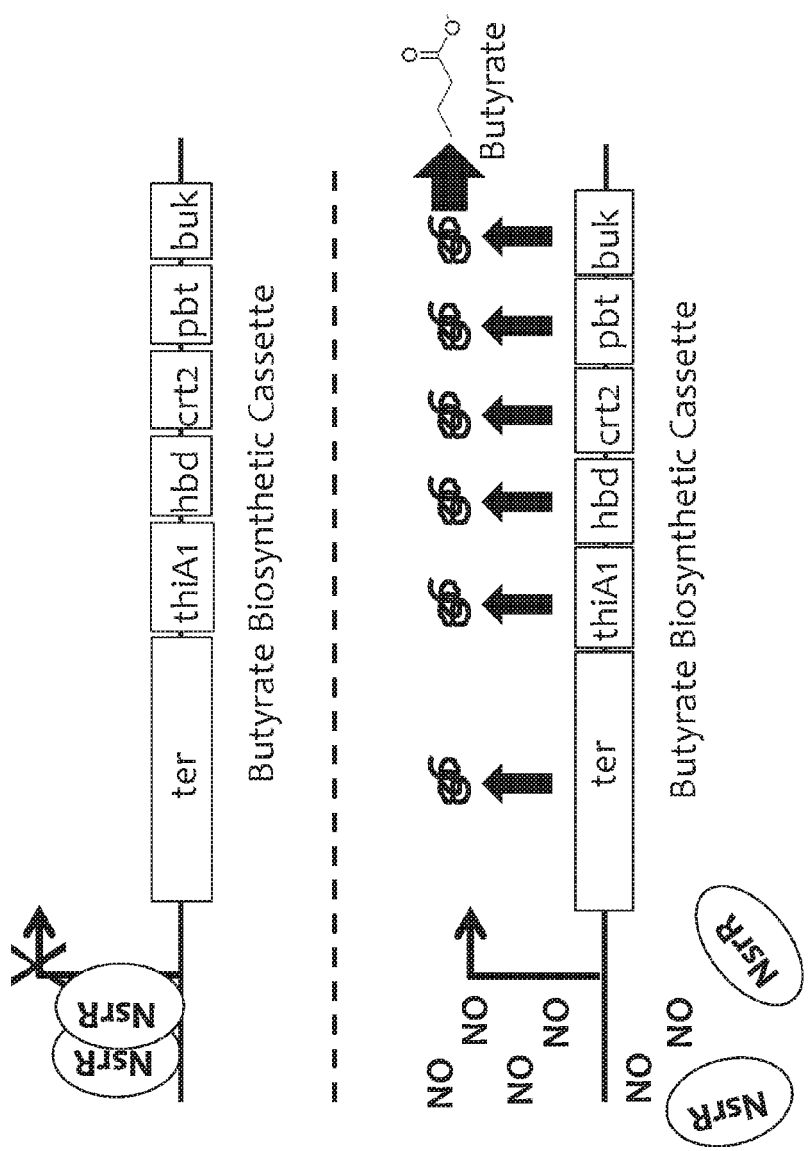
FIG. 4 depicts the gene organization of another exemplary recombinant bacterium of the invention and its derepression in the presence of NO. In the upper panel, in the absence of NO, the NsrR transcription factor (gray circle, "NsrR") binds to and represses a corresponding regulatory region. Therefore, none of the butyrate biosynthesis enzymes (ter, thiA1, hbd, crt2, pbt, buk; black boxes) is expressed. In the lower panel, in the presence of NO, the NsrR transcription factor interacts with NO, and no longer binds to or represses the regulatory sequence. This leads to expression of the butyrate biosynthesis enzymes (indicated by gray arrows and black squiggles) and ultimately to the production of butyrate.
Figure 5:
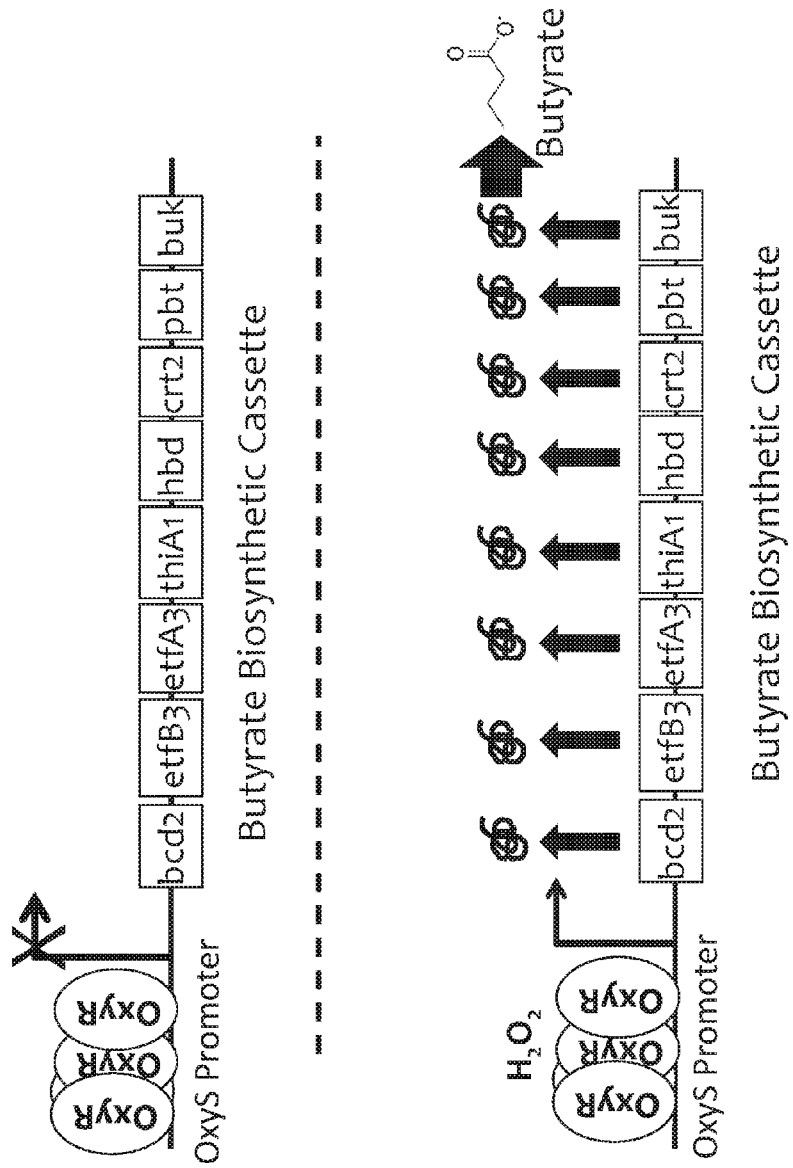
FIG. 5 depicts the gene organization of an exemplary recombinant bacterium of the invention and its induction in the presence of $H_2O_2$. In the upper panel, in the absence of $H_2O_2$, the OxyR transcription factor (gray circle, "OxyR") binds to, but does not induce, the oxyS promoter. Therefore, none of the butyrate biosynthesis enzymes (bcd2, etfB3, etfA3, thiA1, hbd, crt2, pbt, buk; black boxes) is expressed. In the lower panel, in the presence of $H_2O_2$, the OxyR transcription factor interacts with $H_2O_2$ and is then capable of inducing the oxyS promoter. This leads to expression of the butyrate biosynthesis enzymes (indicated by gray arrows and black squiggles) and ultimately to the production of butyrate.
Figure 6:
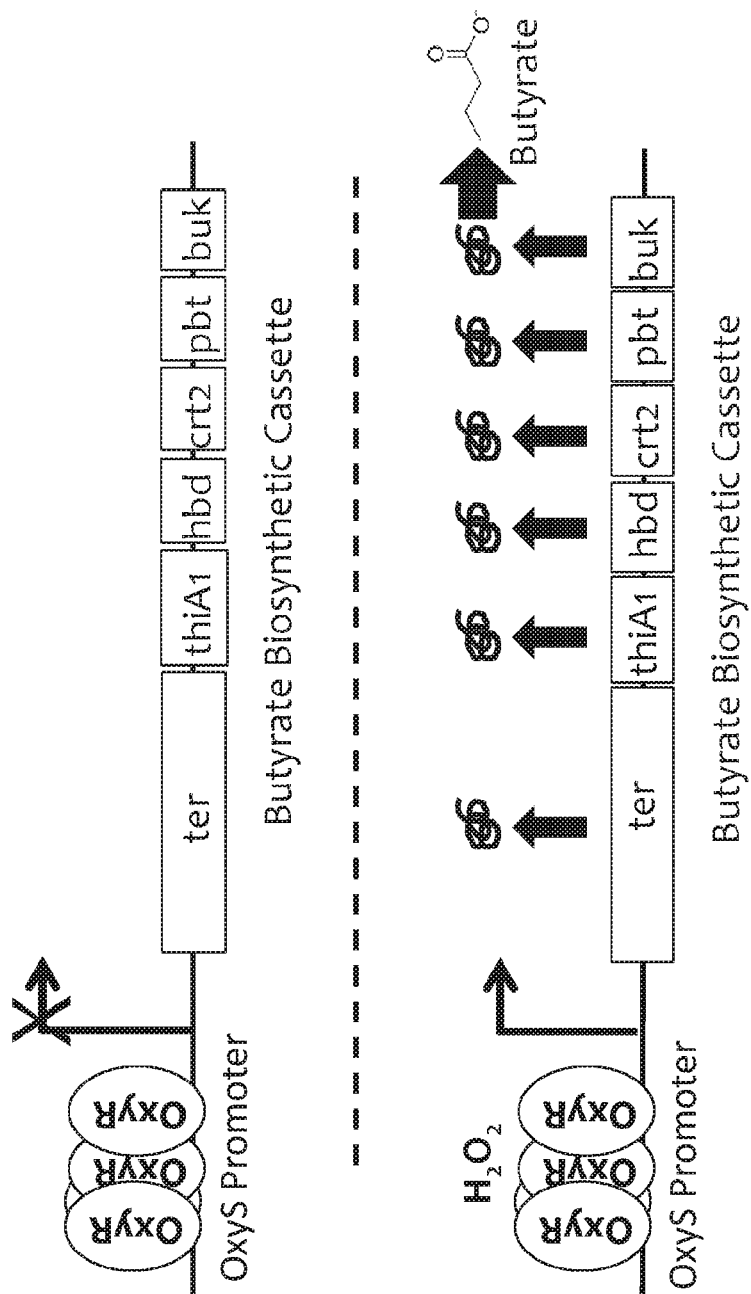
FIG. 6 depicts the gene organization of another exemplary recombinant bacterium of the invention and its induction in the presence of $H_2O_2$. In the upper panel, in the absence of $H_2O_2$, the OxyR transcription factor (gray circle, "OxyR") binds to, but does not induce, the oxyS promoter. Therefore, none of the butyrate biosynthesis enzymes (ter, thiA1, hbd, crt2, pbt, buk; black boxes) is expressed. In the lower panel, in the presence of $H_2O_2$, the OxyR transcription factor interacts with $H_2O_2$ and is then capable of inducing the oxyS promoter. This leads to expression of the butyrate biosynthesis enzymes (indicated by gray arrows and black squiggles) and ultimately to the production of butyrate.
Figure 7:
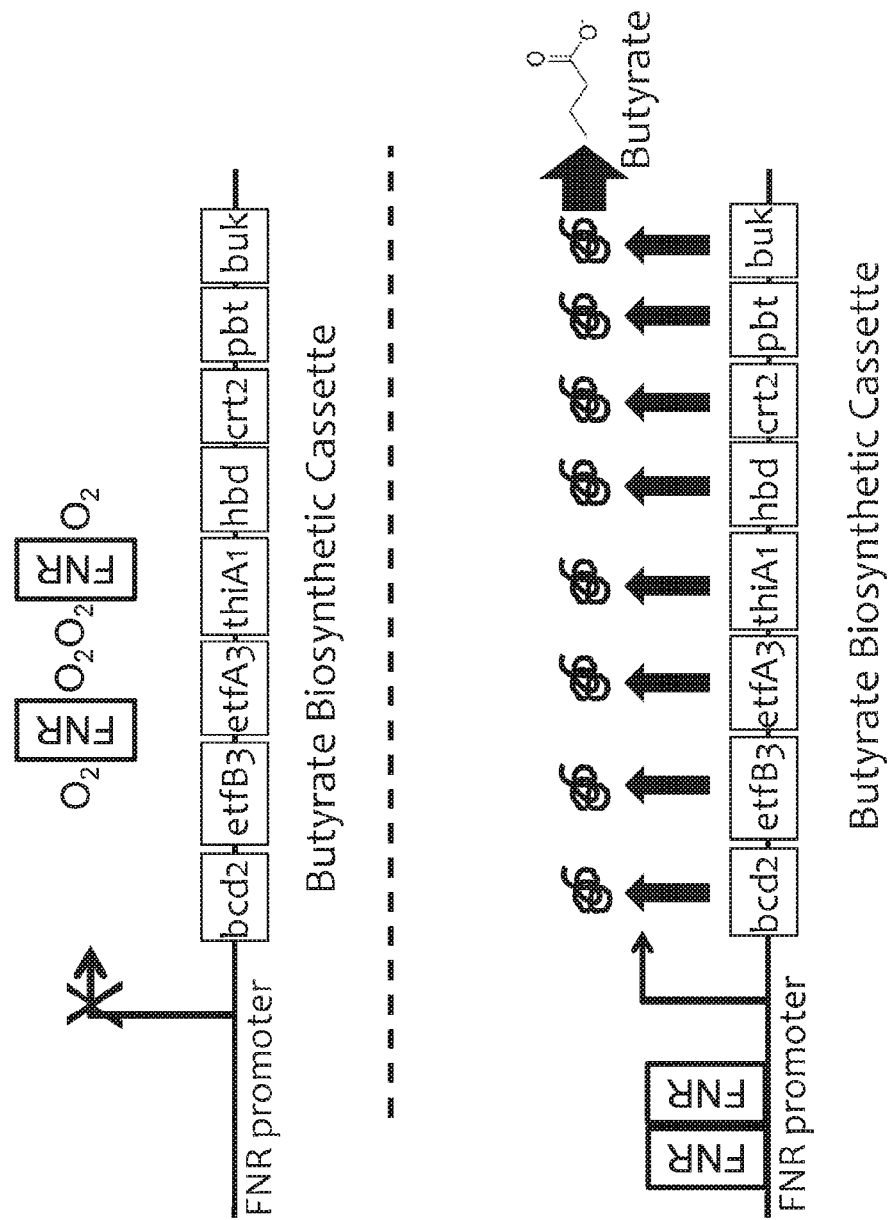
FIG. 7 depicts the gene organization of an exemplary recombinant bacterium of the invention and its induction under low-oxygen conditions. In the upper panel, relatively low butyrate production under aerobic conditions in which oxygen ($O_2$) prevents (indicated by "X") FNR (grey boxed "FNR") from dimerizing and activating the FNR-responsive promoter ("FNR promoter"). Therefore, none of the butyrate biosynthesis enzymes (bcd2, etfB3, etfA3, thiA1, hbd, crt2, pbt, and buk; black boxes) is expressed. In the lower panel, increased butyrate production under low-oxygen conditions due to FNR dimerizing (two grey boxed "FNR"s), binding to the FNR-responsive promoter, and inducing expression of the butyrate biosynthesis enzymes, which leads to the production of butyrate.
Figure 8:
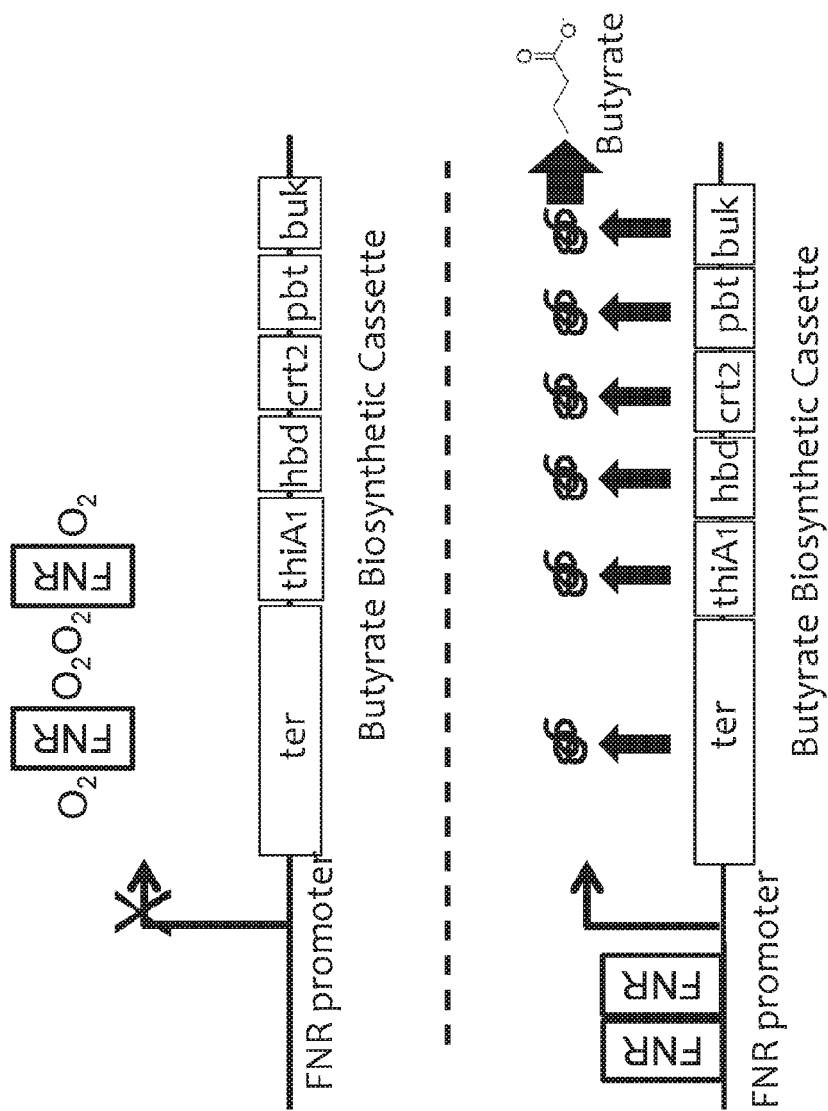
FIG. 8 depicts the gene organization of an exemplary recombinant bacterium of the invention and its induction under low-oxygen conditions. In the upper panel, relatively low butyrate production under aerobic conditions in which oxygen ($O_2$) prevents (indicated by "X") FNR (grey boxed "FNR") from dimerizing and activating the FNR-responsive promoter ("FNR promoter"). Therefore, none of the butyrate biosynthesis enzymes (ter, thiA1, hbd, crt2, pbt, and buk; black boxes) is expressed. In the lower panel, increased butyrate production under low-oxygen conditions due to FNR dimerizing (two grey boxed "FNR"s), binding to the FNR-responsive promoter, and inducing expression of the butyrate biosynthesis enzymes, which leads to the production of butyrate.

In a third butyrate gene cassette, the pbt and buk genes are replaced with tesB (SEQ ID NO: 10). TesB is a thioesterase found in *E. Coli* that cleaves off the butyrate from butyryl-coA, thus obviating the need for pbt-buk (see FIG. 2).

In one embodiment, tesB is placed under the control of a FNR regulatory region selected from SEQ ID NOs: 55-66 (Table 9) In an alternate embodiment, tesB is placed under the control of an RNS-responsive regulatory region, e.g., norB, and the bacteria further comprises a gene encoding a corresponding RNS-responsive transcription factor, e.g., nsrR (see, e.g., Tables 10 and 11). In yet another embodiment, tesB is placed under the control of an ROS-responsive regulatory region, e.g., oxyS, and the bacteria further comprises a gene encoding a corresponding ROS-responsive transcription factor, e.g., oxyR (see, e.g., Tables 14-17). In certain constructs, the different described butyrate gene cassettes are each placed under the control of a tetracycline-inducible or constitutive promoter. For example, genetically engineered Nissle are generated comprising a butyrate gene cassette in which the pbt and buk genes are replaced with tesB (SEQ ID NO: 10) expressed under the control of a nitric oxide-responsive regulatory (SEQ ID NO: 80). SEQ ID NO: 80 comprises a reverse complement of the nsrR repressor gene from *Neisseria gonorrhoeae* (underlined), intergenic region containing divergent promoters controlling nsrR and the butyrogenic gene cassette and their respective RBS (bold), and the butyrate genes (ter-thiA1-hbd-crt2-tesB) separated by RBS.

```
                                              SEQ ID NO: 80
ttatta tcgcaccgcaatcgggattttcgattcataaagcaggtcgt aggtcggcttgttgagcaggtcttgcagcgtgaaaccgtccagatac gtgaaaaacgacttcattgcaccgccgagtatgcccgtcagccggca ggacggcgtaatcaggcattcgttgttcgggcccatacactcgacca gctgcatcggttcgaggtggcggacgaccgcgccgatattgatgcgt tcgggcggcgcggccagcctcagcccgccgcctttcccgcgtacgct gtgcaagaacccgcctttgaccagcgcggtaaccactttcatcaaat ggcttttggaaatgccgtaggtcgaggcgatggtggcgatattgacc agcgcgtcgtcgttgacggcggtgtagatgaggacgcgcagcccgta gtcggtatgttgggtcagatacat acaacctccttagtacatgcaaa attatttctagagcaacatacgagccggaagcataaagtgtaaagcc tggggtgcctaatgagttgagttgaggaattataacaggaagaaata ttcctcatacgcttgtaattcctctatggttgttgacaattaatcat cggctcgtataatgtataacattcatattttgtgaattttaaactct agaaataattttgtttaactttaagaaggagatatacat atgatcgt
```

-continued
```
aaaacctatggtacgcaacaatatctgcctgaacgccatcctcagg gctgcaagaagggagtggaagatcagattgaatataccaagaaacgc attaccgcagaagtcaaagctggcgcaaaagctccaaaaaacgttct ggtgcttggctgctcaaatggttacggcctggcgagccgcattactg ctgcgttcggatacggggctgcgaccatcggcgtgtcctttgaaaaa gcgggttcagaaaccaaatatggtacaccgggatggtacaataattt ggcatttgatgaagcggcaaaacgcgagggtctttatagcgtgacga tcgacggcgatgcgttttcagacgagatcaaggcccaggtaattgag gaagccaaaaaaaaaggtatcaaatttgatctgatcgtatacagctt ggccagcccagtacgtactgatcctgatacaggtatcatgcacaaaa gcgttttgaaaccctttggaaaaacgttcacaggcaaaacagtagat ccgtttactggcgagctgaaggaaatctccgcggaaccagcaaatga cgaggaagcagccgccactgttaaagttatgggggggtgaagattggg aacgttggattaagcagctgtcgaaggaaggcctcttagaagaaggc tgtattaccttggcctatagttatattggccctgaagctacccaagc tttgtaccgtaaaggcacaatcggcaaggccaaagaacacctggagg ccacagcacaccgtctcaacaaagagaacccgtcaatccgtgccttc gtgagcgtgaataaaggcctggtaacccgcgcaagcgccgtaatccc ggtaatccctctgtatctcgccagcttgttcaaagtaatgaaagaga agggcaatcatgaaggttgtattgaacagatcacgcgtctgtacgcc gagcgcctgtaccgtaaagatggtacaattccagttgatgaggaaaa tcgcattcgcattgatgattgggagttagaagaagacgtccagaaag cggtatccgcgttgatggagaaagtcacgggtgaaaacgcagaatct ctcactgacttagcggggtaccgccatgatttcttagctagtaacgg ctttgatgtagaaggtattaattatgaagcggaagttgaacgcttcg accgtatctgataagaaggagatatacatatgagagaagtagtaatt gccagtgcagctagaacagcagtaggaagttttggaggagcatttaa atcagtttcagcggtagagttaggggtaacagcagctaaagaagcta taaaaagagctaacataactccagatatgatagatgaatctctttta ggggagtacttacagcaggtcttggacaaaatatagcaagacaaat agcattaggagcaggaataccagtagaaaaaccagctatgactataa atatagtttgtggttctggattaagatctgtttcaatggcatctcaa cttatagcattaggtgatgctgatataatgttagttggtggagctga aaacatgagtatgtctccttatttagtaccaagtgcgagatatggtg caagaatgggtgatgctgcttttgttgattcaatgataaaagatgga ttatcagacatatttaataactatcacatgggtattactgctgaaaa catagcagagcaatggaatataactagagaagaacaagatgaattag ctcttgcaagtcaaaataaagctgaaaaagctcaagctgaaggaaaa tttgatgaagaaatagttcctgttgttataaaaggaagaaaaggtga cactgtagtagataaagatgaatatattaagcctggcactacaatgg agaaacttgctaagttaagacctgcatttaaaaaagatggaacagtt
```

```
actgctggtaatgcatcaggaataaatgatggtgctgctatgttagt
agtaatggctaaagaaaaagctgaagaactaggaatagagcctcttg
caactatagtttcttatggaacagctggtgttgaccctaaaataatg
ggatatggaccagttccagcaactaaaaaagctttagaagctgctaa
tatgactattgaagatatagatttagttgaagctaatgaggcatttg
ctgcccaatctgtagctgtaataagagacttaaatatagatatgaat
aaagttaatgttaatggtggagcaatagctataggacatccaatagg
atgctcaggagcaagaatacttactacacttttatatgaaatgaaga
gaagagatgctaaaactggtcttgctacactttgtataggcggtgga
atgggaactactttaatagttaagagatagtaagaaggagatataca
tatgaaattagctgtaataggtagtggaactatgggaagtggtattg
tacaaacttttgcaagttgtggacatgatgtatgtttaaagagtaga
actcaaggtgctatagataaatgtttagctttattagataaaaattt
aactaagttagttactaagggaaaaatggatgaagctacaaaagcag
aaatattaagtcatgttagttcaactactaattatgaagatttaaaa
gatatggatttaataatagaagcatctgtagaagacatgaatataaa
gaaagatgttttcaagttactagatgaattatgtaaagaagatacta
tcttggcaacaaatacttcatcattatctataacagaaatagcttct
tctactaagcgcccagataaagttataggaatgcatttctttaatcc
agttcctatgatgaaattagttgaagttataagtggtcagttaacat
caaaagttacttttgatacagtatttgaattatctaagagtatcaat
aaagtaccagtagatgtatctgaatctcctggatttgtagtaaatag
aatacttatacctatgataaatgaagctgttggtatatatgcagatg
gtgttgcaagtaaagaagaaatagatgaagctatgaaattaggagca
aaccatccaatgggaccactagcattaggtgatttaatcggattaga
tgttgttttagctataatgaacgttttatatactgaatttggagata
ctaaatatagacctcatccacttttagctaaaatggttagagctaat
caattaggaagaaaaactaagataggattctatgattataataaata
ataagaggagatatacatatgagtacaagtgatgttaaagtttatg
agaatgtagctgttgaagtagatggaaatatatgtacagtgaaaatg
aatagacctaaagcccttaatgcaataaattcaaagactttagaaga
actttatgaagtatttgtagatattaataatgatgaaactattgatg
ttgtaatattgacaggggaaggaaaggcatttgtagctggagcagat
attgcatacatgaaagatttagatgctgtagctgctaaagattttag
tatcttaggagcaaaagcttttggagaaatagaaaatagtaaaaaag
tagtgatagctgctgtaaacggatttgctttaggtggaggatgtgaa
cttgcaatggcatgtgatataagaattgcatctgctaaagctaaatt
tggtcagccagaagtaactcttggaataactccaggatatggaggaa
ctcaaaggcttacaagattggttgaatggcaaaagcaaaagaatta
atctttacaggtcaagttataaaagctgatgaagctgaaaaaatagg
```

```
gctagtaaatagagtcgttgagccagacattttaatagaagaagttg
agaaattagctaagataatagctaaaaatgctcagcttgcagtttaga
tactctaaagaagcaatacaacttggtgctcaaactgatataaatac
tggaatagatatagaatctaatttatttggtctttgtttttcaacta
aagaccaaaaagaaggaatgtcagctttcgttgaaaagagagaagct
aactttataaaagggtaataagaaggagatatacatatgAGTCAGGC
GCTAAAAAATTTACTGACATTGTTAAATCTGGAAAAAATTGAGGAAG
GACTCTTTCGCGGCCAGAGTGAAGATTTAGGTTTACGCCAGGTGTTT
GGCGGCCAGGTCGTGGGTCAGGCCTTGTATGCTGCAAAAGAGACCGT
CCCTGAAGAGCGGCTGGTACATTCGTTTCACAGCTACTTTCTTCGCC
CTGGCGATAGTAAGAAGCCGATTATTTATGATGTCGAAACGCTGCGT
GACGGTAACAGCTTCAGCGCCCGCCGGGTTGCTGCTATTCAAAACGG
CAAACCGATTTTTTATATGACTGCCTCTTTCCAGGCACCAGAAGCGG
GTTTCGAACATCAAAAAACAATGCCGTCCGCGCCAGCGCCTGATGGC
CTCCCTTCGGAAACGCAAATCGCCCAATCGCTGGCGCACCTGCTGCC
GCCAGTGCTGAAAGATAAATTCATCTGCGATCGTCCGCTGGAAGTCC
GTCCGGTGGAGTTTCATAACCCACTGAAAGGTCACGTCGCAGAACCA
CATCGTCAGGTGTGGATCCGCGCAAATGGTAGCGTGCCGGATGACCT
GCGCGTTCATCAGTATCTGCTCGGTTACGCTTCTGATCTTAACTTCC
TGCCGGTAGCTCTACAGCCGCACGGCATCGGTTTTCTCGAACCGGGG
ATTCAGATTGCCACCATTGACCATTCCATGTGGTTCCATCGCCCGTT
TAATTTGAATGAATGGCTGCTGTATAGCGTGGAGAGCACCTCGGCGT
CCAGCGCACGTGGCTTTGTGCGCGGTGAGTTTTATACCCAAGACGGC
GTACTGGTTGCCTCGACCGTTCAGGAAGGGGTGATGCGTAATCACAA
Ttaa
```

Butyrate, IL-10, IL-22, GLP-2

In certain constructs, in addition to the butyrate production pathways described above, the *Escherichia coli* Nissle are further engineered to produce one or more molecules selected from IL-10, IL-2, IL-22, IL-27, SOD, kyurenine, kyurenic acid, and GLP-2 using the methods described above. In some embodiments, the bacteria comprise a gene cassette for producing butyrate as described above, and a gene encoding IL-10 (see, e.g., SEQ ID NO: 49). In some embodiments, the bacteria comprise a gene cassette for producing butyrate as described above, and a gene encoding IL-2 (see, e.g., 50). In some embodiments, the bacteria comprise a gene cassette for producing butyrate as described above, and a gene encoding IL-22 (see, e.g., 51). In some embodiments, the bacteria comprise a gene cassette for producing butyrate as described above, and a gene encoding IL-27 (see, e.g., SEQ ID NO: 52). In some embodiments, the bacteria comprise a gene cassette for producing butyrate as described above, and a gene encoding SOD (see, e.g., 53). In some embodiments, the bacteria comprise a gene cassette for producing butyrate as described above, and a gene encoding GLP-2 (see, e.g., SEQ ID NO: 54). In some embodiments, the bacteria comprise a gene cassette for producing butyrate as described above, and a gene or gene cassette for producing kyurenine or kyurenic acid. In some embodiments, the bacteria comprise a gene cassette for producing butyrate as described above, and a gene encoding IL-10, IL-22, and GLP-2. In one embodiment, each of the genes or gene cassettes is placed under the control of a FNR regulatory region selected from SEQ ID NOs: 55-66 (Table 9). In an alternate embodiment, each of the genes or gene cassettes is placed under the control of an RNS-responsive regulatory region, e.g., norB, and the bacteria further comprises a gene encoding a corresponding RNS-responsive transcription factor, e.g., nsrR (see, e.g., Tables 10 and 11). In yet another embodiment, each of the genes or gene cassettes is placed under the control of an ROS-responsive regulatory region, e.g., oxyS, and the bacteria further comprises a gene encoding a corresponding ROS-responsive transcription factor, e.g., oxyR (see, e.g., Tables 14-17). In certain constructs, one or more of the genes is placed under the control of a tetracycline-inducible or constitutive promoter.

Butyrate, Propionate, IL-10, IL-22, IL-2, IL-27

In certain constructs, in addition to the butyrate production pathways described above, the *Escherichia coli* Nissle are further engineered to produce propionate, and one or more molecules selected from IL-10, IL-2, IL-22, IL-27, SOD, kyurenine, kyurenic acid, and GLP-2 using the methods described above. In certain constructs, in addition to the butyrate production pathways described above, the *Escherichia coli* Nissle are further engineered to produce propionate, and one or more molecules selected from IL-10, IL-2, and IL-22. In certain constructs, in addition to the butyrate production pathways described above, the *Escherichia coli* Nissle are further engineered to produce propionate, and one or more molecules selected from IL-10, IL-2, and IL-27. In some embodiments, the genetically engineered bacteria further comprise acrylate pathway genes for propionate biosynthesis, pct, lcdA, lcdB, lcdC, etfA, acrB, and acrC. In an alternate embodiment, the genetically engineered bacteria comprise pyruvate pathway genes for propionate biosynthesis, thrA$^{fbr}$, thrB, thrC, ilvA$^{fbr}$, aceE, aceF, and lpd. In another alternate embodiment, the genetically engineered bacteria comprise thrA$^{fbr}$, thrB, thrC, ilvA$^{fbr}$, aceE, aceF, lpd, and tesB.

The bacteria comprise a gene cassette for producing butyrate as described above, a gene cassette for producing propionate as described above, a gene encoding IL-10 (see, e.g., 49), a gene encoding IL-27 (see, e.g., SEQ ID NO: 52), a gene encoding IL-22 (see, e.g., SEQ ID NO: 51), and a gene encoding IL-2 (see, e.g., SEQ ID NO: 50). In one embodiment, each of the genes or gene cassettes is placed under the control of a FNR regulatory region selected from SEQ ID NOs: 55-66 (Table 9). In an alternate embodiment, each of the genes or gene cassettes is placed under the control of an RNS-responsive regulatory region, e.g., norB, and the bacteria further comprises a gene encoding a corresponding RNS-responsive transcription factor, e.g., nsrR (see, e.g., Tables 10 and 11). In yet another embodiment, each of the genes or gene cassettes is placed under the control of an ROS-responsive regulatory region, e.g., oxyS, and the bacteria further comprises a gene encoding a corresponding ROS-responsive transcription factor, e.g., oxyR (see, e.g., Tables 14-17). In certain constructs, one or more of the genes is placed under the control of a tetracycline-inducible or constitutive promoter.

Butyrate, Propionate, IL-10, L-22, SOD, GLP-2, Kynurenine

In certain constructs, in addition to the butyrate production pathways described above, the *Escherichia coli* Nissle are further engineered to produce one or more molecules selected from IL-10, IL-22, SOD, GLP-2, and kynurenine using the methods described above. In certain constructs, in addition to the butyrate production pathways described above, the *Escherichia coli* Nissle are further engineered to produce propionate, and one or more molecules selected from IL-10, IL-22, SOD, GLP-2, and kynurenine using the methods described above. In certain constructs, in addition to the butyrate production pathways described above, the *Escherichia coli* Nissle are further engineered to produce IL-10, IL-27, IL-22, SOD, GLP-2, and kynurenine using the methods described above. In certain constructs, in addition to the butyrate production pathways described above, the *Escherichia coli* Nissle are further engineered to produce propionate, IL-10, IL-27, IL-22, SOD, GLP-2, and kynurenine using the methods described above. In some embodiments, the genetically engineered bacteria further comprise acrylate pathway genes for propionate biosynthesis, pct, lcdA, lcdB, lcdC, etfA, acrB, and acrC. In an alternate embodiment, the genetically engineered bacteria comprise pyruvate pathway genes for propionate biosynthesis, thrA$^{fbr}$, thrB, thrC, ilvA$^{fbr}$, aceE, aceF, and lpd. In another alternate embodiment, the genetically engineered bacteria comprise thrA$^{fbr}$, thrB, thrC, ilvA$^{fbr}$, aceE, aceF, lpd, and tesB.

The bacteria comprise a gene cassette for producing butyrate as described above, a gene cassette for producing propionate as described above, a gene encoding IL-10 (see, e.g., 49), a gene encoding IL-22 (see, e.g., SEQ ID NO: 51), a gene encoding SOD (see, e.g., SEQ ID NO: 53), a gene encoding GLP-2 (see, e.g., SEQ ID NO: 54), and a gene or gene cassette for producing kynurenine. In one embodiment, each of the genes or gene cassettes is placed under the control of a FNR regulatory region selected from SEQ ID NOs: 55-66 (Table 9). In an alternate embodiment, each of the genes or gene cassettes is placed under the control of an RNS-responsive regulatory region, e.g., norB, and the bacteria further comprises a gene encoding a corresponding RNS-responsive transcription factor, e.g., nsrR (see, e.g., Tables 10 and 11). In yet another embodiment, each of the genes or gene cassettes is placed under the control of an ROS-responsive regulatory region, e.g., oxyS, and the bacteria further comprises a gene encoding a corresponding ROS-responsive transcription factor, e.g., oxyR (see, e.g., Tables 14-17). In certain constructs, one or more of the genes is placed under the control of a tetracycline-inducible or constitutive promoter.

Butyrate, Propionate, IL-10, IL-27, IL-22, IL-2, SOD, GLP-2, Kynurenine

In certain constructs, in addition to the butyrate production pathways described above, the *Escherichia coli* Nissle are further engineered to produce one or more molecules selected from IL-10, IL-27, IL-22, IL-2, SOD, GLP-2, and kynurenine using the methods described above. In certain constructs, in addition to the butyrate production pathways described above, the *Escherichia coli* Nissle are further engineered to produce propionate and one or more molecules selected from IL-10, IL-27, IL-22, IL-2, SOD, GLP-2, and kynurenine using the methods described above. In certain constructs, in addition to the butyrate production pathways described above, the *Escherichia coli* Nissle are further engineered to produce IL-10, IL-27, IL-22, SOD, GLP-2, and kynurenine using the methods described above. In some embodiments, the genetically engineered bacteria further comprise acrylate pathway genes for propionate biosynthesis, pct, lcdA, lcdB, lcdC, etfA, acrB, and acrC. In an alternate embodiment, the genetically engineered bacteria comprise pyruvate pathway genes for propionate biosynthesis, thrA$^{fbr}$, thrB, thrC, ilvA$^{fbr}$, aceE, aceF, and lpd. In another alternate embodiment, the genetically engineered bacteria comprise thrA$^{fbr}$, thrB, thrC, ilvA$^{fbr}$, aceE, aceF, lpd, and tesB.

The bacteria comprise a gene cassette for producing butyrate as described above, a gene cassette for producing propionate as described above, a gene encoding IL-10 (see, e.g., 49), a gene encoding IL-27 (see, e.g., SEQ ID NO: 52), a gene encoding IL-22 (see, e.g., SEQ ID NO: 51), a gene encoding IL-2 (see, e.g., SEQ ID NO: 50), a gene encoding SOD (see, e.g., SEQ ID NO: 53), a gene encoding GLP-2 (see, e.g., SEQ ID NO: 54), and a gene or gene cassette for producing kynurenine. In one embodiment, each of the genes or gene cassettes is placed under the control of a FNR regulatory region selected from SEQ ID NOs: 55-66 (Table 9). In an alternate embodiment, each of the genes or gene cassettes is placed under the control of an RNS-responsive regulatory region, e.g., norB, and the bacteria further comprises a gene encoding a corresponding RNS-responsive transcription factor, e.g., nsrR (see, e.g., Tables 9 and 10). In yet another embodiment, each of the genes or gene cassettes is placed under the control of an ROS-responsive regulatory region, e.g., oxyS, and the bacteria further comprises a gene encoding a corresponding ROS-responsive transcription factor, e.g., oxyR (see, e.g., Tables 14-17). In certain constructs, one or more of the genes is placed under the control of a tetracycline-inducible or constitutive promoter.

In some embodiments, bacterial genes may be disrupted or deleted to produce an auxotrophic strain. These include, but are not limited to, genes required for oligonucleotide synthesis, amino acid synthesis, and cell wall synthesis, as shown below.

| Amino Acid | Oligonucleotide | Cell wall |
|---|---|---|
| cysE | thyA | dapA |
| glnA | uraA | dapB |
| ilvD |  | dapD |
| leuB |  | dapE |
| lysA |  | dapF |
| serA |  |  |
| metA |  |  |
| glyA |  |  |
| hisB |  |  |
| ilvA |  |  |
| pheA |  |  |
| proA |  |  |
| thrC |  |  |
| trpC |  |  |
| tyrA |  |  |

Example 2

Transforming *E. coli*

Each plasmid is transformed into *E. coli* Nissle or *E. coli* DH5a. All tubes, solutions, and cuvettes are pre-chilled to 4° C. An overnight culture of *E. coli* Nissle or *E. coli* DH5a is diluted 1:100 in 5 mL of lysogeny broth (LB) and grown until it reached an OD$_{600}$ of 0.4-0.6. The cell culture medium contains a selection marker, e.g., ampicillin, that is suitable for the plasmid. The *E. coli* cells are then centrifuged at 2,000 rpm for 5 min. at 4° C., the supernatant is removed, and the cells are resuspended in 1 mL of 4° C. water. The *E. coli* are again centrifuged at 2,000 rpm for 5 min. at 4° C., the supernatant is removed, and the cells are resuspended in 0.5 mL of 4° C. water. The *E. coli* are again centrifuged at 2,000 rpm for 5 min. at 4° C., the supernatant is removed, and the cells are finally resuspended in 0.1 mL of 4° C.

water. The electroporator is set to 2.5 kV. 0.5 µg of one of the above plasmids is added to the cells, mixed by pipetting, and pipetted into a sterile, chilled cuvette. The dry cuvette is placed into the sample chamber, and the electric pulse is applied. One mL of room-temperature SOC media is immediately added, and the mixture is transferred to a culture tube and incubated at 37° C. for 1 hr. The cells are spread out on an LB plate containing ampicillin and incubated overnight.

In alternate embodiments, the butyrate cassette can be inserted into the Nissle genome through homologous recombination (Genewiz, Cambridge, Mass.). Organization of the constructs and nucleotide sequences are provided herein. To create a vector capable of integrating the synthesized butyrate cassette construct into the chromosome, Gibson assembly was first used to add 1000 bp sequences of DNA homologous to the Nissle lacZ locus into the R6K origin plasmid pKD3. This targets DNA cloned between these homology arms to be integrated into the lacZ locus in the Nissle genome. Gibson assembly was used to clone the fragment between these arms. PCR was used to amplify the region from this plasmid containing the entire sequence of the homology arms, as well as the butyrate cassette between them. This PCR fragment was used to transform electrocompetent Nissle-pKD46, a strain that contains a temperature-sensitive plasmid encoding the lambda red recombinase genes. After transformation, cells were grown out for 2 hours before plating on chloramphenicol at 20 ug/mL at 37 degrees C. Growth at 37 degrees C. also cures the pKD46 plasmid. Transformants containing cassette were chloramphenicol resistant and lac-minus (lac-).

Example 3

Production of Butyrate in Recombinant *E. coli* Using Tet-inducible Promoter

Figure 18:
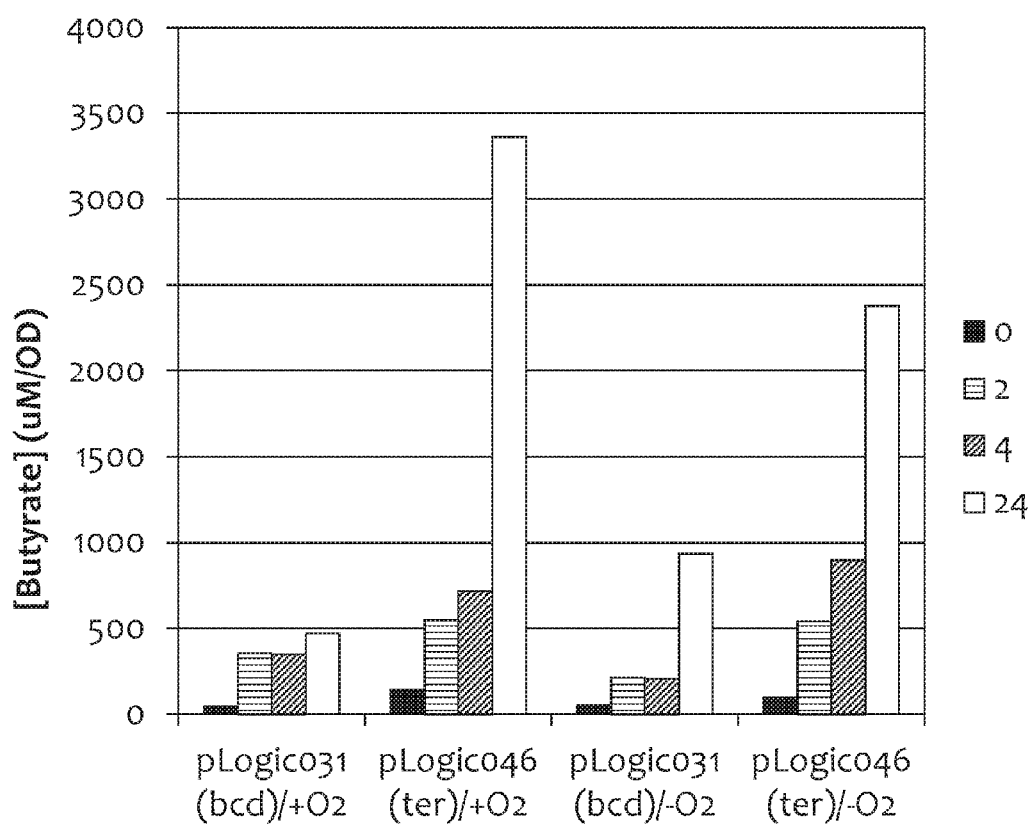
FIG. 18 depicts a graph of butyrate production. pLOGIC031 (bcd)/+O2 is Nissle containing plasmid pLOGIC031 grown aerobically. pLOGIC046 (ter)/+O2 is Nissle containing plasmid pLOGIC046 grown aerobically. pLOGIC031 (bcd)/−O2 is Nissle containing plasmid pLOGIC031 grown anaerobically. pLOGIC046 (ter)/−O2 is Nissle containing plasmid pLOGIC046 grown anaerobically. The ter construct results in higher butyrate production.

FIGS. 15-17, 20 and 21 show butyrate cassettes described above under the control of a tet-inducible promoter. Production of butyrate is assessed using the methods described below in Example 4. The tet-inducible cassettes tested include (1) tet-butyrate cassette comprising all eight genes (pLOGIC031); (2) tet-butyrate cassette in which the ter is substituted (pLOGIC046) and (3) tet-butyarte cassette in which tesB is substituted in place of pbt and buk genes. FIG. 18 shows butyrate production in strains pLOGIC031 and pLOGIC046 in the presence and absence of oxygen, in which there is no significant difference in butyrate production. Enhanced butyrate production was shown in Nissle in low copy plasmid expressing pLOGIC046 which contain a deletion of the final two genes (ptb-buk) and their replacement with the endogenous *E. Coli* tesB gene (a thioesterase that cleaves off the butyrate portion from butyryl CoA).

Figure 22:
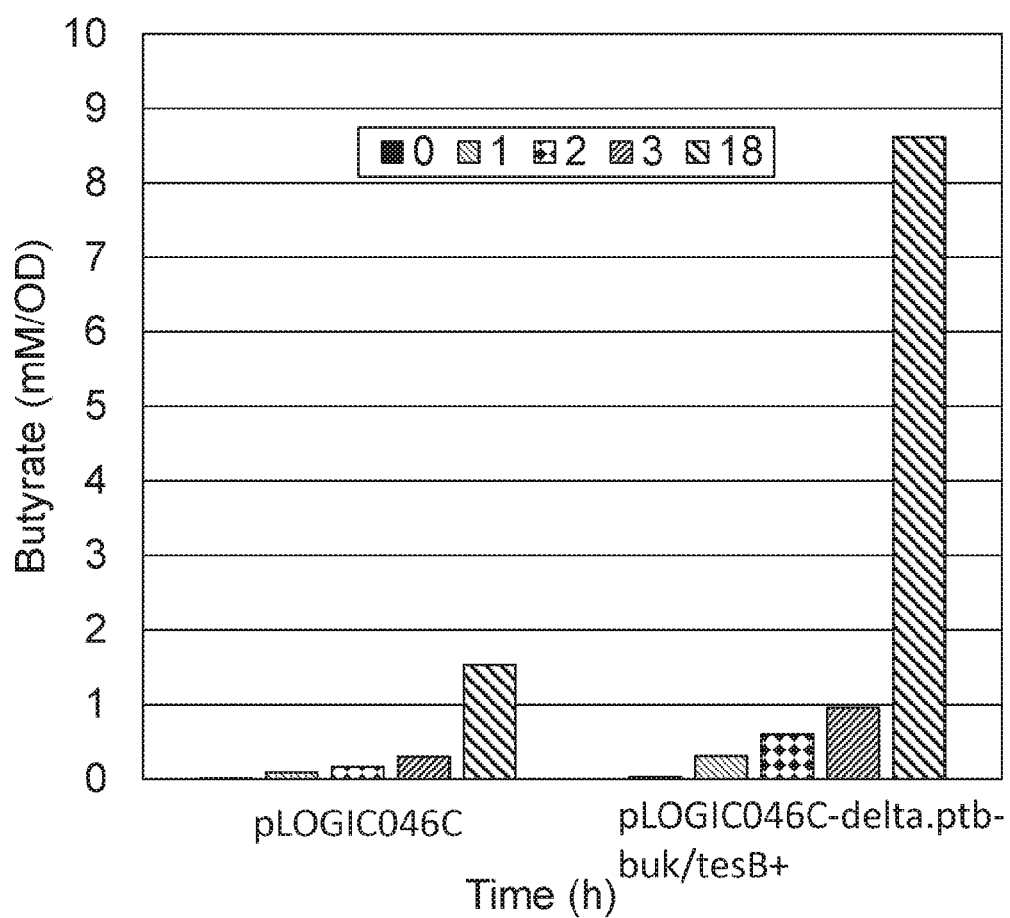
FIG. 22 depicts butyrate production using pLOGIC046 (a Nissle strain comprising plasmid pLOGIC046, an ATC-inducible ter-comprising butyrate construct) and pLOGIC046-delta.pbt-buk/tesB+(a Nissle strain comprising plasmid pLOGIC046-delta pbt.buk/tesB+, an ATC-inducible ter-comprising butyrate construct with a deletion in the pbt-buk genes and their replacement with the tesB gene). The tesB construct results in greater butyrate production.
Figure 23:
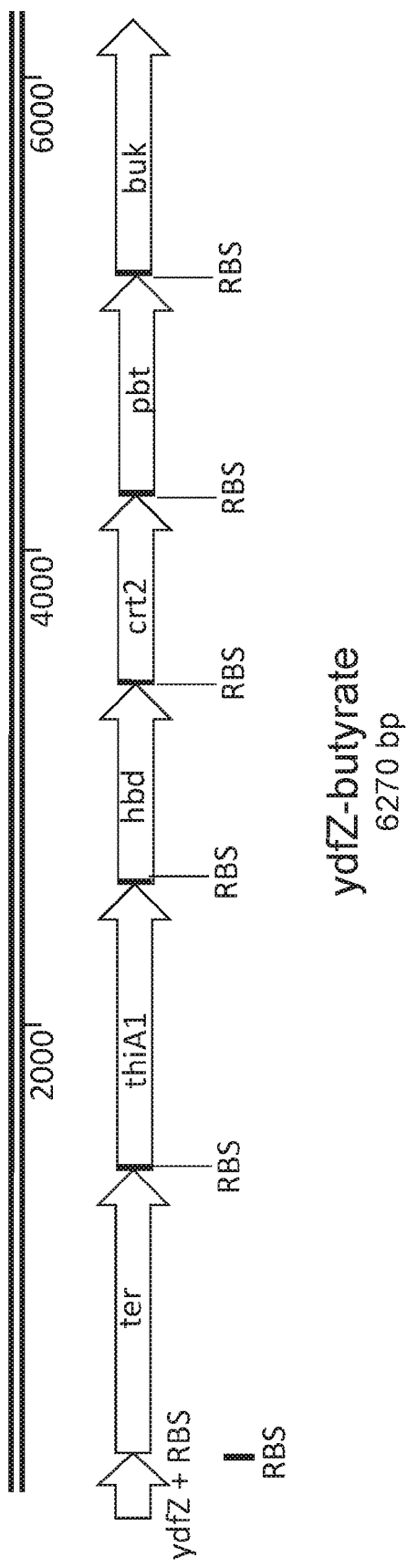
FIG. 23 depicts a schematic of a butyrate gene cassette, ydfZ-butyrate, comprising the ter substitution.

Overnight cultures of cells were diluted 1:100 in Lb and grown for 1.5 hours until early log phase was reached at which point anhydrous tet was added at a final concentration of 100 ng/ml to induce plasmid expression. After 2 hours induction, cells were washed and resuspended in M9 minimal media containing 0.5% glucose at OD600=0.5. Samples were removed at indicated times and cells spun down. The supernatant was tested for butyrate production using LC-MS. FIG. 22 shows butyrate production in strains comprising a tet-butyrate cassette having ter substitution (pLOGIC046) or the tesB substitution (ptb-buk deletion), demonstrating that the tesB substituted strain has greater butyrate production.

Figure 19:
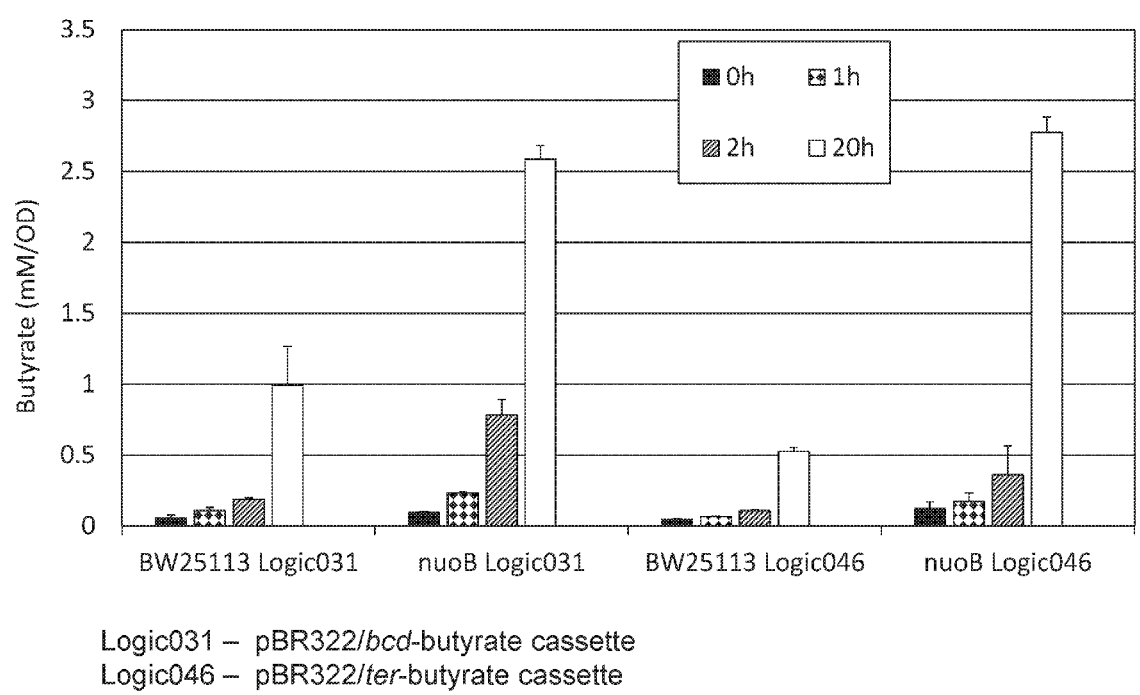
FIG. 19 depicts a graph of butyrate production using *E. coli* BW25113 butyrate-producing circuits comprising a nuoB gene deletion, which results in greater levels of butyrate production as compared to a wild-type parent control. nuoB is a main protein complex involved in the oxidation of NADH during respiratory growth. In some embodiments, preventing the coupling of NADH oxidation to electron transport increases the amount of NADH being used to support butyrate production.
Figure 20:
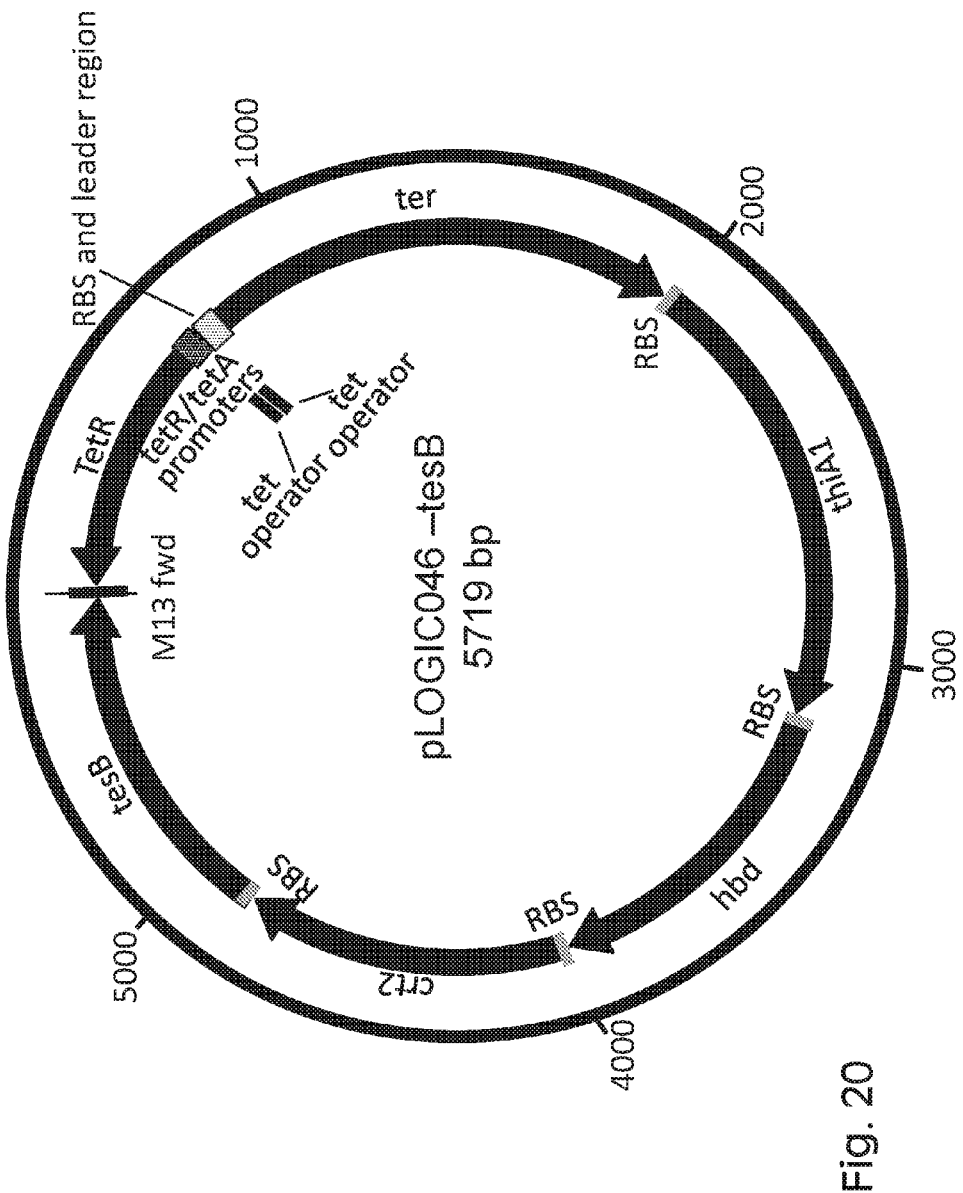
FIG. 20 depicts a schematic of pLogic046-tesB, in which buk and pbt are deleted and tesB substituted.
Figure 21:
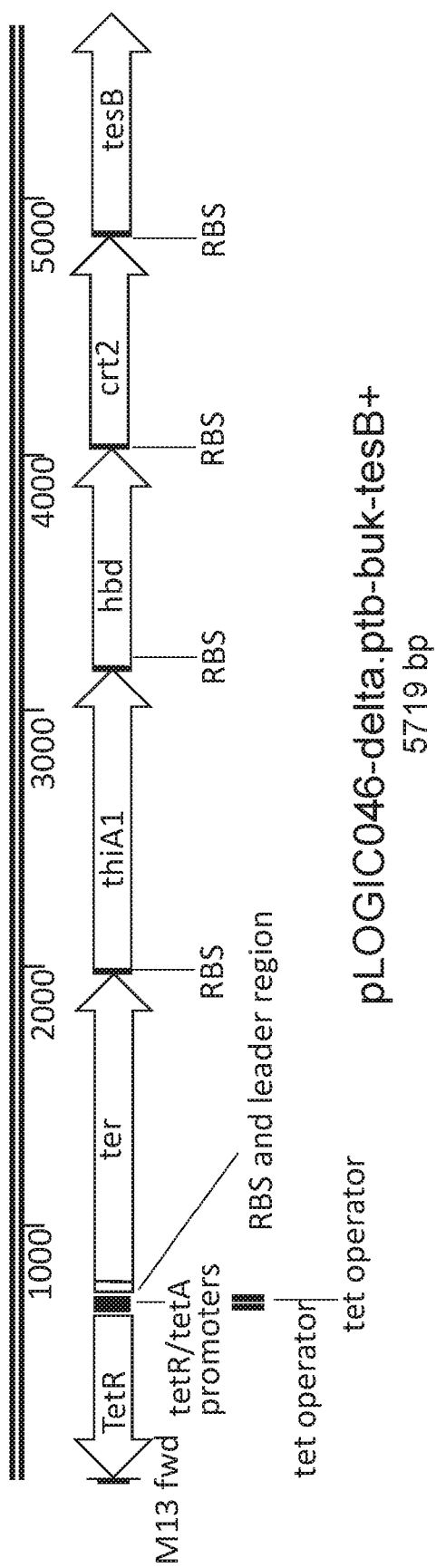
FIG. 21 depicts a linear schematic of a butyrate gene cassette, pLogic046-delta.ptb-buk-tesB+.

FIG. 19 shows the BW25113 strain of *E. Coli*, which is a common cloning strain and the background of the KEIO collection of *E. Coli* mutants. NuoB mutants having NuoB deletion were obtained. NuoB is a protein complex involved in the oxidation of NADH during respiratory growth (form of growth requiring electron transport). Preventing the coupling of NADH oxidation to electron transport allows an increase in the amount of NADH being used to support butyrate production. FIG. 19 shows that compared with wild-type Nissle, deletion of NuoB results in grater production of butyrate.

pLOGIC046-tesB-butyrate:
gtaaaacgacggccagtgaattcgttaagacccactttcacatttaa
gttgttttctaatccgcatatgatcaattcaaggccgaataagaag
gctggctctgcaccttggtgatcaaataattcgatagcttgtcgtaa
taatggcggcatactatcagtagtaggtgtttccctttcttctttag
cgacttgatgctcttgatcttccaatacgcaacctaaagtaaaatgc
cccacagcgctgagtgcatataatgcattctctagtgaaaaaccttg
ttggcataaaaaggctaattgattttcgagagtttcatactgttttt
ctgtaggccgtgtacctaaatgtacttttgctccatcgcgatgactt
agtaaagcacatctaaaacttttagcgttattacgtaaaaaatcttg
ccagctttccccttctaaagggcaaaagtgagtatggtgcctatcta
acatctcaatggctaaggcgtcgagcaaagcccgcttattttttaca
tgccaatacaatgtaggctgctctacacctagcttctgggcgagttt
acgggttgttaaaccttcgattccgacctcattaagcagctctaatg
cgctgttaatcactttacttttatctaatctagacatcattaattcc
taattttgttgacactctatcattgatagagttattttaccactcc
ctatcagtgatagagaaaagtgaactctagaaataattttgtttaac
tttaagaaggagatatacatatgatcgtaaaacctatggtacgcaac
aatatctgcctgaacgcccatcctcagggctgcaagaagggagtgga
agatcagattgaatataccaagaaacgcattaccgcagaagtcaaag
ctggcgcaaaagctccaaaaaacgttctggtgcttggctgctcaaat
ggttacggcctggcgagccgcattactgctgcgttcggatacgggc
tgcgaccatcggcgtgtcctttgaaaaagcgggttcagaaaccaaat
atggtacaccgggatggtacaataaatttggcatttgatgaagcgga
aaacgcgagggtctttatagcgtgacgatcgacggcgatgcgttttc
agacgagatcaaggcccaggtaattgaggaagccaaaaaaaaggta
tcaaatttgatctgatcgtatacagcttggccagcccagtacgtact
gatcctgatacaggtatcatgcacaaaagcgttttgaaacccttgg
aaaaacgttcacaggcaaaacagtagatccgtttactggcgagctga
aggaaatctccgcggaaccagcaaatgacgaggaagcagccgccact
gttaaagttatgggggtgaagattgggaacgttggattaagcagct
gtcgaaggaaggcctcttagaagaaggctgtattaccttggcctata
gttatattggccctgaagctacccaagctttgtaccgtaaaggcaca
atcggcaaggccaaagaacacctggaggccacagcacaccgtctcaa
caaagagaacccgtcaatccgtgccttcgtgagcgtgaataaaggcc tggtaacccgcgcaagcgccgtaatcccggtaatccctctgtatctc
gccagcttgttcaaagtaatgaaagagaagggcaatcatgaaggttg
tattgaacagatcacgcgtctgtacgccgagcgcctgtaccgtaaag
atggtacaattccagttgatgaggaaaatcgcattcgcattgatgat
tgggagttagaagaagacgtccagaaagcggtatccgcgttgatgga
gaaagtcacgggtgaaaacgcagaatctctcactgacttagcgggt
accgccatgatttcttagctagtaacggctttgatgtagaaggtatt
aattatgaagcggaagttgaacgcttcgaccgtatctgataagaagg
agatatacatatgagagaagtagtaattgccagtgcagctagaacag
cagtaggaagttttggaggagcatttaaatcagtttcagcggtagag
ttagggaaacagcagctaaagaagctataaaaagagctaacataac
tccagatatgatagatgaatctcttttaggggagtacttacagcag
gtcttggacaaaatatagcaagacaaatagcattaggagcaggaata
ccagtagaaaaccagctatgactataaatatagtttgtggttctgg
attaagatctgtttcaatggcatctcaacttatagcattaggtgatg
ctgatataatgttagttggtggagctgaaaacatgagtatgtctcct
tatttagtaccaagtgcgagatatggtgcaagaatgggtgatgctgc
ttttgttgattcaatgataaaagatggattatcagacatatttaata
actatcacatgggtattactgctgaaaacatagcagagcaatggaat
ataactagagaagaacaagatgaattagctcttgcaagtcaaaataa
agctgaaaaagctcaagctgaaggaaaatttgatgaagaaatagttc
ctgttgttataaaaggaagaaaaggtgacactgtagtagataaagat
gaatatattaagcctggcactacaatggagaaacttgctaagttaag
acctgcatttaaaaaagatggaacagttactgctggtaatgcatcag
gaataaatgatggtgctgctatgttagtagtaatggctaaagaaaaa
gctgaagaactaggaatagagcctcttgcaactatagtttcttatgg
aacagctggtgttgaccctaaaataatgggatatggaccagttccag
caactaaaaaagctttagaagctgctaatatgactattgaagatata
gatttagttgaagctaatgaggcatttgctgcccaatctgtagctgt
aataagagacttaaatatagatatgaataaagttaatgttaatggtg
gagcaatagctataggacatccaataggatgctcaggagcaagaata
cttactacacttttatatgaaatgaagagaagagatgctaaaactgg
tcttgctacactttgtataggcggtggaatgggaactactttaatag
ttaagagatagtaaggagatatacatatgaaattagctgtaata
ggtagtggaactatgggaagtggtattgtacaaacttttgcaagttg
tggacatgatgtatgtttaaagagtagaactcaaggtgctatagata
aatgtttagctttattagataaaaatttaactaagttagttactaag
ggaaaaatggatgaagctacaaaagcagaaatattaagtcatgttag
ttcaactactaattatgaagatttaaaagatatggatttaataatag
aagcatctgtagaagacatgaatataaagaaagatgttttcaagtta
ctagatgaattatgtaaagaagatactatcttggcaacaaatacttc -continued

```
atcattatctataacagaaatagcttcttctactaagcgcccagata aagttataggaatgcatttctttaatccagttcctatgatgaaatta gttgaagttataagtggtcagttaacatcaaaagttacttttgatac agtatttgaattatctaagagtatcaataaagtaccagtagatgtat ctgaatctcctggatttgtagtaaatagaatacttatacctatgata aatgaagctgttggtatatatgcagatggtgttgcaagtaaagaaga aatagatgaagctatgaaattaggagcaaaccatccaatgggaccac tagcattaggtgatttaatcggattagatgttgttttagctataatg aacgttttatatactgaatttggagatactaaatatagacctcatcc acttttagctaaaatggttagagctaatcaattaggaagaaaaacta agataggattctatgattataataaataataagaaggagatatacat atgagtacaagtgatgttaaagtttatgagaatgtagctgttgaagt agatggaaatatatgtacagtgaaaatgaatagacctaaagcccta atgcaataaattcaaagactttagaagaactttatgaagtatttgta gatattaataatgatgaaactattgatgttgtaatattgacagggga aggaaaggcatttgtagctggagcagatattgcatacatgaaagatt tagatgctgtagctgctaaagattttagtatcttaggagcaaaagct tttggagaaatagaaatagtaaaaaagtagtgatagctgctgtaaa cggatttgctttaggtggaggatgtgaacttgcaatggcatgtgata taagaattgcatctgctaaagctaaatttggtcagccagaagtaact cttggaataactccaggatggaggaactcaaaggcttacaagatt ggttggaatggcaaaagcaaaagaattaatctttacaggtcaagtta taaaagctgatgaagctgaaaaaatagggctagtaaatagagtcgtt gagccagacattttaatagaagaagttgagaaattagctaagataat agctaaaaatgctcagcttgcagttagatactctaaagaagcaatac aacttggtgctcaaactgatataaatactggaatagatatagaatct aatttatttggtctttgtttttcaactaaagaccaaaaagaaggaat gtcagctttcgttgaaaagagagaagctaactttataaaagggtaat aagaaggagatatacatatgAGTCAGGCGCTAAAAAATTTACTGACA

TTGTTAAATCTGGAAAAAATTGAGGAAGGACTCTTTCGCGGCCAGAG

TGAAGATTTAGGTTTACGCCAGGTGTTTGGCGGCCAGGTCGTGGGTC

AGGCCTTGTATGCTGCAAAAGAGACCGTCCCTGAAGAGCGGCTGGTA

CATTCGTTTCACAGCTACTTTCTTCGCCCTGGCGATAGTAAGAAGCC

GATTATTTATGATGTCGAAACGCTGCGTGACGGTAACAGCTTCAGCG

CCCGCCGGGTTGCTGCTATTCAAAACGGCAAACCGATTTTTTATATG

ACTGCCTCTTTCCAGGCACCAGAAGCGGGTTTCGAACATCAAAAAAC

AATGCCGTCCGCGCCAGCGCCTGATGCCTCCCTTCGGAAACGCAAA

TCGCCCAATCGCTGGCGCACCTGCTGCCGCCAGTGCTGAAAGATAAA

TTCATCTGCGATCGTCCGCTGGAAGTCCGTCCGGTGGAGTTTCATAA

CCCACTGAAAGGTCACGTCGCAGAACCACATCGTCAGGTGTGGATCC

GCGCAAATGGTAGCGTGCCGGATGACCTGCGCGTTCATCAGTATCTG

CTCGGTTACGCTTCTGATCTTAACTTCCTGCCGGTAGCTCTACAGCC

GCACGGCATCGGTTTTCTCGAACCGGGGATTCAGATTGCCACCATTG

ACCATTCCATGTGGTTCCATCGCCCGTTTAATTTGAATGAATGGCTG

CTGTATAGCGTGGAGAGCACCTCGGCGTCCAGCGCACGTGGCTTTGT

GCGCGGTGAGTTTTATACCCAAGACGGCGTACTGGTTGCCTCGACCG

TTCAGGAAGGGGTGATGCGTAATCACAATtaa
```

Example 4

Production of Butyrate in Recombinant *E. coli*

Production of butyrate is assessed in *E. coli* Nissle strains containing the butyrate cassettes described above in order to determine the effect of oxygen on butyrate production. All incubations are performed at 37° C. Cultures of *E. coli* strains DH5a and Nissle transformed with the butyrate cassettes are grown overnight in LB and then diluted 1:200 into 4 mL of M9 minimal medium containing 0.5% glucose. The cells are grown with shaking (250 rpm) for 4-6 h and incubated aerobically or anaerobically in a Coy anaerobic chamber (supplying 90% $N_2$, 5% $CO_2$, 5% $H_2$). One mL culture aliquots are prepared in 1.5 mL capped tubes and incubated in a stationary incubator to limit culture aeration. One tube is removed at each time point (0, 1, 2, 4, and 20 hours) and analyzed for butyrate concentration by LC-MS to confirm that butyrate production in these recombinant strains can be achieved in a low-oxygen environment.

In an alternate embodiment, overnight bacterial cultures were diluted 1:100 into fresh LB and grown for 1.5 hrs to allow entry into early log phase. At this point, long half-life nitric oxide donor (DETA-NO; diethylenetriamine-nitric oxide adduct) was added to cultures at a final concentration of 0.3 mM to induce expression from plasmid. After 2 hours of induction, cells were spun down, supernatant was discarded, and the cells were resuspended in M9 minimal media containing 0.5% glucose. Culture supernatant was then analyzed at indicated time points to assess levels of butyrate production. Genetically engineered Nissle comprising pLogic031-nsrR-norB-butyrate operon construct; SYN133) or (pLogic046-nsrR-norB-butyrate operon construct; SYN145) produce significantly more butyrate as compared to wild-type Nissle (SYN001).

Genetically engineered Nissle were generated comprising a butyrate gene cassette in which the pbt and buk genes are replaced with tesB (SEQ ID NO: 24) expressed under the control of a tetracycline promoter (pLOGIC046-tesB-butyrate; SEQ ID NO: 81). SEQ ID NO: 81 comprises a reverse complement of the tetR repressor (underlined), an intergenic region containing divergent promoters controlling tetR and the butyrate operon and their respective RBS (bold), and the butyrate genes (ter-thiA1-hbd-crt2-tesB) separated by RBS.

SEQ ID NO: 81 gtaaaacgacggccagtgaattcgttaagacccactttcacatttaa gttgttttctaatccgcatatgatcaattcaaggccgaataagaag gctggctctgcaccttggtgatcaaataattcgatagcttgtcgtaa -continued taatggcggcatactatcagtagtaggtgtttcccttttcttctttag
cgacttgatgctcttgatcttccaatacgcaacctaaagtaaaatgc
cccacagcgctgagtgcatataatgcattctctagtgaaaaaccttg
ttggcataaaaaggctaattgattttcgagagtttcatactgttttt
ctgtaggccgtgtacctaaatgtacttttgctccatcgcgatgactt
agtaaagcacatctaaaacttttagcgttattacgtaaaaaatcttg
ccagctttcccttctaaagggcaaaagtgagtatggtgcctatcta
acatctcaatggctaaggcgtcgagcaaagcccgcttattttttaca
tgccaatacaatgtaggctgctctacacctagattctgggcgagttt
acgggttgttaaaccttcgattccgacctcattaagcagctctaatg
cgctgttaatcactttacttttatctaatctagacat**cattaattcc
taattttgttgacactctatcattgatagagttattttaccactcc
ctatcagtgatagagaaaagtgaactctagaaataattttgtttaac
tttaagaaggagatatacat**atgatcgtaaaacctatggtacgcaac
aatatctgcctgaacgccatcctcagggctgcaagaagggagtgga
agatcagattgaatataccaagaaacgcattaccgcagaagtcaaag
ctggcgcaaaagctccaaaaaacgttctggtgcttggctgctcaaat
ggttacggcctggcgagccgcattactgctgcgttcggatacggggc
tgcgaccatcggcgtgtccttttgaaaaagcgggttcagaaaccaaat
atggtacaccgggatggtacaataaatttggcatttgatgaagcgga
aaacgcgagggtctttatagcgtgacgatcgacggcgatgcgttttc
agacgagatcaaggcccaggtaattgaggaagccaaaaaaaaggta
tcaaatttgatctgatcgtatacagcttggccagcccagtacgtact
gatcctgatacaggtatcatgcacaaaagcgttttgaaacccttggg
aaaaacgttcacaggcaaaacagtagatccgtttactggcgagctga
aggaaatctccgcggaaccagcaaatgacgaggaagcagccgccact
gttaaagttatggggggtgaagattgggaacgttggattaagcagct
gtcgaaggaaggcctcttagaagaaggctgtattaccttggcctata
gttatattggccctgaagctacccaagcttgtaccgtaaaggcaca
atcggcaaggccaaagaacacctggaggccacagcacaccgtctcaa
caaagagaacccgtcaatccgtgccttcgtgagcgtgaataaaggcc
tggtaacccgcgcaagcgccgtaatcccggtaatccctctgtatctc
gccagcttgttcaaagtaatgaaagagaagggcaatcatgaaggttg
tattgaacagatcacgcgtctgtacgccgagcgcctgtaccgtaaag
atggtacaattccagttgatgaggaaaatcgcattcgcattgatgat
tgggagttagaagaagacgtccagaaagcggtatccgcgttgatgga
gaaagtcacgggtgaaaacgcagaatctctcactgacttagcggggt
accgccatgattcttagctagtaacggctttgatgtagaaggtatt
aattatgaagcggaagttgaacgcttcgaccgtatctgataagaagg
agatatacatatgagagaagtagtaattgccagtgcagctagaacag
cagtaggaagttttggaggagcatttaaatcagtttcagcggtagag -continued ttaggggtaacagcagctaaagaagctataaaaagagctaacataac
tccagatatgatagatgaatctcttttaggggggagtacttacagcag
gtcttggacaaaatatagcaagacaaatagcattaggagcaggaata
ccagtagaaaaaccagctatgactataaatatagtttgtggttctgg
attaagatctgtttcaatggcatctcaacttatagcattaggtgatg
ctgatataatgttagttggtggagctgaaaacatgagtatgtctcct
tatttagtaccaagtgcgagatatggtgcaagaatgggtgatgctgc
ttttgttgattcaatgataaaagatggattatcagacatatttaata
actatcacatgggtattactgctgaaaacatagcagagcaatggaat
ataactagagaagaacaagatgaattagctcttgcaagtcaaaataa
agctgaaaaagctcaagctgaaggaaaatttgatgaagaaatagttc
ctgttgttataaaaggaagaaaaggtgacactgtagtagataaagat
gaatatattaagcctggcactacaatggagaaacttgctaagttaag
acctgcatttaaaaagatggaacagttactgctggtaatgcatcag
gaataaatgatggtgctgctatgttagtagtaatggctaaagaaaaa
gctgaagaactaggaatagagcctcttgcaactatagtttcttatgg
aacagctggtgttgaccctaaaataatgggatatggaccagttccag
caactaaaaaagctttagaagctgctaatatgactattgaagatata
gatttagttgaagctaatgaggcatttgctgcccaatctgtagctgt
aataagagacttaaatatagatatgaataaagttaatgttaatggtg
gagcaatagctataggacatccaataggatgctcaggagcaagaata
cttactacacttttatatgaaatgaagagaagagatgctaaaactgg
tcttgctacacttttgtataggcggtggaatgggaactactttaatag
ttaagagatagtaagaaggagatatacatatgaaattagctgtaata
ggtagtggaactatgggaagtggtattgtacaaacttttgcaagttg
tggacatgatgtatgtttaaagagtagaactcaaggtgctatagata
aatgtttagctttattagataaaaatttaactaagttagttactaag
ggaaaaatggatgaagctacaaaagcagaaatattaagtcatgttag
ttcaactactaattatgaagatttaaaagatatggatttaataatag
aagcatctgtagaagacatgaatataaagaaagatgttttcaagtta
ctagatgaattatgtaaagaagatactatcttggcaacaaatacttc
atcattatctataacagaaatagcttcttctactaagcgcccagata
aagttataggaatgcatttctttaatccagttcctatgatgaaatta
gttgaagttataagtggtcagttaacatcaaaagttacttttgatac
agtatttgaattatctaagagtatcaataaagtaccagtagatgtat
ctgaatctcctggatttgtagtaaatagaatacttataacctatgata
aatgaagctgttggtatatatgcagatggtgttgcaagtaaagaaga
aatagatgaagctatgaaattaggagcaaaaccatccaatgggaccac
tagcattaggtgatttaatcggattagatgttgttttagctataatg
aacgttttatatactgaatttggagatactaaatatagacctcatcc -continued
```
acttttagctaaaatggttagagctaatcaattaggaagaaaaacta agataggattctatgattataataaataataagaaggagatatacat atgagtacaagtgatgttaaagtttatgagaatgtagctgttgaagt agatggaaatatatgtacagtgaaaatgaatagacctaaagcccta atgcaataaattcaaagactttagaagaactttatgaagtatttgta gatattaataatgatgaaactattgatgttgtaatattgacaggga aggaaaggcatttgtagctggagcagatattgcatacatgaaagatt tagatgctgtagctgctaaagattttagtatcttaggagcaaaagct tttggagaaatagaaaatagtaaaaaagtagtgatagctgctgtaaa cggatttgctttaggtggaggatgtgaacttgcaatggcatgtgata taagaattgcatctgctaaagctaaatttggtcagccagaagtaact cttgaataactccaggatatggaggaactcaaaggcttacaagatt ggttggaatggcaaaagcaaaagaattaatctttacaggtcaagtta taaaagctgatgaagctgaaaaaatagggctagtaaatagagtcgtt gagccagacattttaatagaagaagttgagaaattagctaagataat agctaaaaatgctcagcttgcagttagatactctaaagaagcaatac aacttggtgctcaaactgatataaatactggaatagatatagaatct aatttatttggtctttgtttttcaactaaagaccaaaaagaaggaat gtcagctttcgttgaaaagagagaagctaactttataaaagggtaat aagaaggagatatacatatgAGTCAGGCGCTAAAAAATTTACTGACA

TTGTTAAATCTGGAAAAAATTGAGGAAGGACTCTTTCGCGGCCAGAG

TGAAGATTTAGGTTTACGCCAGGTGTTTGGCGGCCAGGTCGTGGGTC

AGGCCTTGTATGCTGCAAAAGAGACCGTCCCTGAAGAGCGGCTGGTA

CATTCGTTTCACAGCTACTTTCTTCGCCCTGGCGATAGTAAGAAGCC

GATTATTTATGATGTCGAAACGCTGCGTGACGGTAACAGCTTCAGCG

CCCGCCGGGTTGCTGCTATTCAAAACGGCAAACCGATTTTTTATATG

ACTGCCTCTTTCCAGGCACCAGAAGCGGGTTTCGAACATCAAAAAAC

AATGCCGTCCGCGCCAGCGCCTGATGGCCTCCCTTCGGAAACGCAAA

TCGCCCAATCGCTGGCGCACCTGCTGCCGCCAGTGCTGAAAGATAAA

TTCATCTGCGATCGTCCGCTGGAAGTCCGTCCGGTGGAGTTTCATAA

CCCACTGAAAGGTCACGTCGCAGAACCACATCGTCAGGTGTGGATCC

GCGCAAATGGTAGCGTGCCGGATGACCTGCGCGTTCATCAGTATCTG

CTCGGTTACGCTTCTGATCTTAACTTCCTGCCGGTAGCTCTACAGCC

GCACGGCATCGGTTTTCTCGAACCGGGGATTCAGATTGCCACCATTG

ACCATTCCATGTGGTTCCATCGCCCGTTTAATTTGAATGAATGGCTG

CTGTATAGCGTGGAGAGCACCTCGGCGTCCAGCGCACGTGGCTTTGT

GCGCGGTGAGTTTTATACCCAAGACGGCGTACTGGTTGCCTCGACCG

TTCAGGAAGGGGTGATGCGTAATCACAATtaa
```

Overnight bacterial cultures were diluted 1:100 into fresh LB and grown for 1.5 hrs to allow entry into early log phase. At this point, anhydrous tetracycline (ATC) was added to cultures at a final concentration of 100 ng/mL to induce expression of butyrate genes from plasmid. After 2 hours of induction, cells were spun down, supernatant was discarded, and the cells were resuspended in M9 minimal media containing 0.5% glucose. Culture supernatant was then analyzed at indicated time points to assess levels of butyrate production. Replacement of pbt and buk with tesB leads to greater levels of butyrate production.

Figure 24:
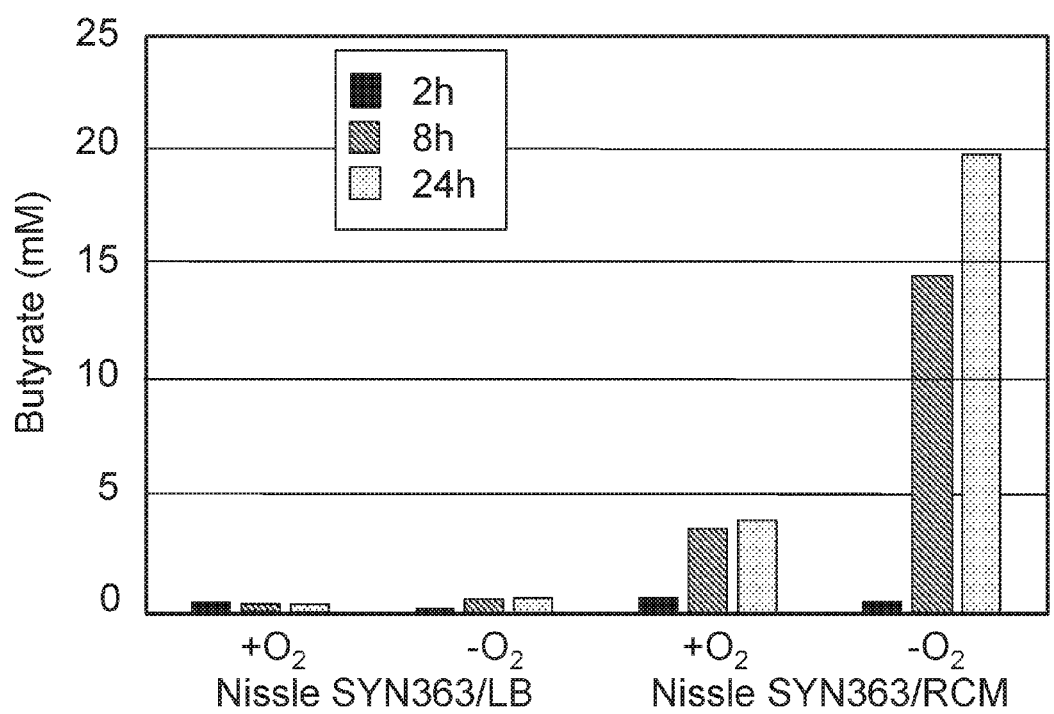
FIG. 24 depicts SYN363 in the presence and absence of glucose and oxygen in vitro. SYN363 comprises a butyrate gene cassette comprising the ter-thiA1-hbd-crt2-tesB genes under the control of a ydfZ promoter.
Figure 25:
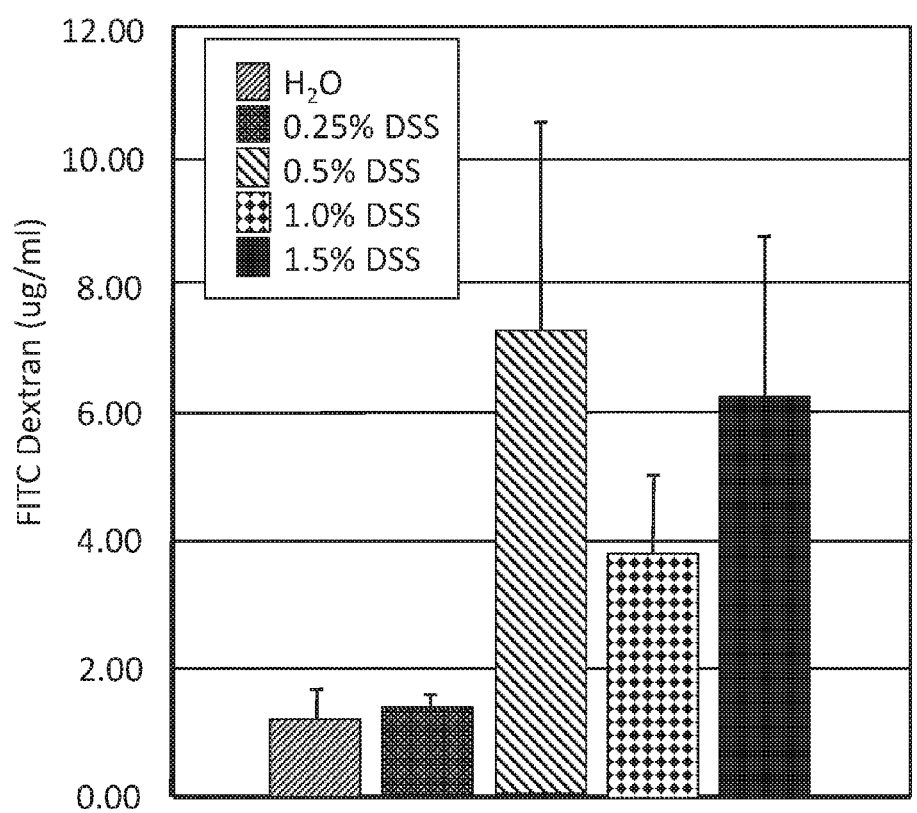
FIG. 25 depicts a graph measuring gut-barrier function in dextran sodium sulfate (DSS)-induced mouse models of IBD. The amount of FITC dextran found in the plasma of mice administered different concentrations of DSS was measured as an indicator of gut barrier function.
Figure 26:
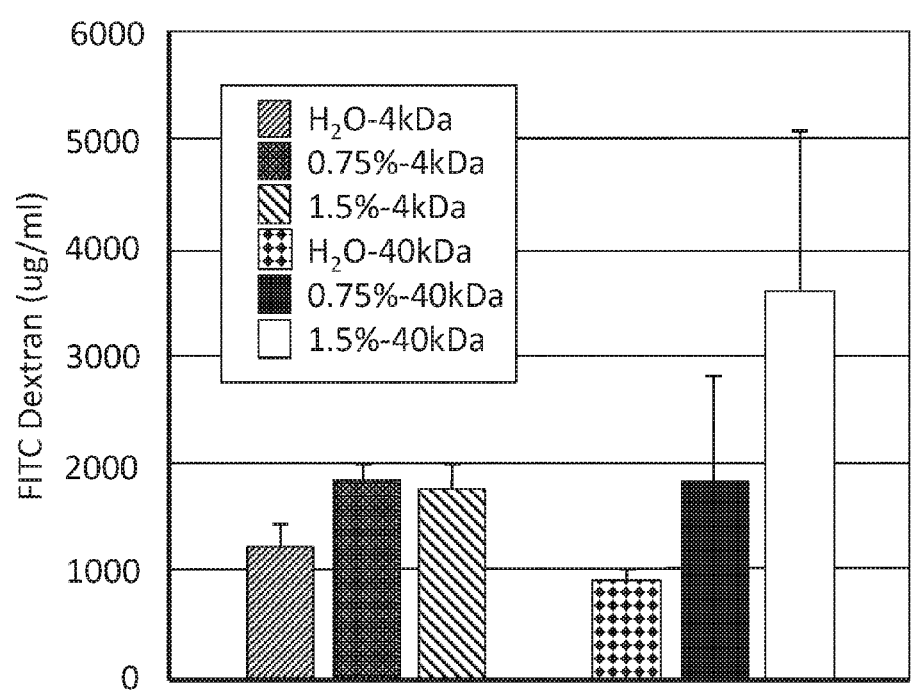
FIG. 26 depicts serum levels of FITC-dextran analyzed by spectrophotometry. FITC-dextran is a readout for gut barrier function in the DSS-induced mouse model of IBD.

FIG. 24 shows butyrate production in strains comprising an FNR-butyrate cassette syn 363 (having the ter substitution) in the presence/absence of glucose and oxygen. FIG. 24 Shows that bacteria need both glucose and anaerobic conditions for butyrate production from the FNR promoter. Cells were grown aerobically or anaerobically in media containg no glucose (LB) or in media containing glucose at 0.5% (RMC). Culture samples were taken at indicaed time pints and supernatant fractions were assessed for butyrate concentration using LC-MS. These data show that SYN 363 requires glucose for butyrate production and that in the presence of glucose butyrate production can be enhanced under anaerobic conditions when under the control of the anaerobic FNR-regulated ydfZ promoter.

Example 5

Efficacy of Butyrate-Expressing Bacteria in a Mouse Model of IBD

Bacteria harboring the butyrate cassettes described above are grown overnight in LB. Bacteria are then diluted 1:100 into LB containing a suitable selection marker, e.g., ampicillin, and grown to an optical density of 0.4-0.5 and then pelleted by centrifugation. Bacteria are resuspended in phosphate buffered saline and 100 microliters is administered by oral gavage to mice. IBD is induced in mice by supplementing drinking water with 3% dextran sodium sulfate for 7 days prior to bacterial gavage. Mice are treated daily for 1 week and bacteria in stool samples are detected by plating stool homogenate on agar plates supplemented with a suitable selection marker, e.g., ampicillin. After 5 days of bacterial treatment, colitis is scored in live mice using endoscopy. Endoscopic damage score is determined by assessing colon translucency, fibrin attachment, mucosal and vascular pathology, and/or stool characteristics. Mice are sacrificed and colonic tissues are isolated. Distal colonic sections are fixed and scored for inflammation and ulceration. Colonic tissue is homogenized and measurements are made for myeloperoxidase activity using an enzymatic assay kit and for cytokine levels (IL-1$\beta$, TNF-$\alpha$, IL-6, IFN-$\gamma$ and IL-10).

Example 6

Generating a DSS-Induced Mouse Model of IBD

The genetically engineered bacteria described in Example 1 can be tested in the dextran sodium sulfate (DSS)-induced mouse model of colitis. The administration of DSS to animals results in chemical injury to the intestinal epithelium, allowing proinflammatory intestinal contents (e.g., luminal antigens, enteric bacteria, bacterial products) to disseminate and trigger inflammation (Low et al., 2013). To prepare mice for DSS treatment, mice are labeled using ear punch, or any other suitable labeling method. Labeling individual mice allows the investigator to track disease progression in each mouse, since mice show differential susceptibilities and responsiveness to DSS induction. Mice are then weighed, and if required, the average group weight is equilibrated to eliminate any significant weight differences between groups. Stool is also collected prior to DSS administration, as a control for subsequent assays. Exemplary assays for fecal markers of inflammation (e.g., cytokine levels or myeloperoxidase activity) are described below.

For DSS administration, a 3% solution of DSS (MP Biomedicals, Santa Ana, Calif.; Cat. No. 160110) in autoclaved water is prepared. Cage water bottles are then filled with 100 mL of DSS water, and control mice are given the same amount of water without DSS supplementation. This amount is generally sufficient for 5 mice for 2-3 days. Although DSS is stable at room temperature, both types of water are changed every 2 days, or when turbidity in the bottles is observed.

Acute, chronic, and resolving models of intestinal inflammation are achieved by modifying the dosage of DSS (usually 1-5%) and the duration of DSS administration (Chassaing et al., 2014). For example, acute and resolving colitis may be achieved after a single continuous exposure to DSS over one week or less, whereas chronic colitis is typically induced by cyclical administration of DSS punctuated with recovery periods (e.g., four cycles of DSS treatment for 7 days, followed by 7-10 days of water).

FIG. 27 shows that butyrate produced in vivo in DSS mouse models under the control of an FNR promoter can be gut protective. LCN2 and calprotectin are both a measure of gut barrier disruption (measure by ELISA in this assay). FIG. 27 shows that Syn 363 (ter substitution) reduces inflammation and/or protects gut barrier as compared to Syn 94 (wildtype Nissle).

Example 7

Monitoring Disease Progression In Vivo

Following initial administration of DSS, stool is collected from each animal daily, by placing a single mouse in an empty cage (without bedding material) for 15-30 min. However, as DSS administration progresses and inflammation becomes more robust, the time period required for collection increases. Stool samples are collected using sterile forceps, and placed in a microfuge tube. A single pellet is used to monitor occult blood according to the following scoring system: 0, normal stool consistency with negative hemoccult; 1, soft stools with positive hemoccult; 2, very soft stools with traces of blood; and 3, watery stools with visible rectal bleeding. This scale is used for comparative analysis of intestinal bleeding. All remaining stool is reserved for the measurement of inflammatory markers, and frozen at −20° C.

The body weight of each animal is also measured daily. Body weights may increase slightly during the first three days following initial DSS administration, and then begin to decrease gradually upon initiation of bleeding. For mouse models of acute colitis, DSS is typically administered for 7 days. However, this length of time may be modified at the discretion of the investigator.

Example 8

In Vivo Efficacy of Genetically Engineered Bacteria Following DSS Induction

The genetically engineered bacteria described in Example 1 can be tested in DSS-induced animal models of IBD. Bacteria are grown overnight in LB supplemented with the appropriate antibiotic. Bacteria are then diluted 1:100 in fresh LB containing selective antibiotic, grown to an optical density of 0.4-0.5, and pelleted by centrifugation. Bacteria are then resuspended in phosphate buffered saline (PBS). IBD is induced in mice by supplementing drinking water with 3% DSS for 7 days prior to bacterial gavage. On day 7 of DSS treatment, 100 µL of bacteria (or vehicle) is administered to mice by oral gavage. Bacterial treatment is repeated once daily for 1 week, and bacteria in stool samples are detected by plating stool homogenate on selective agar plates.

After 5 days of bacterial treatment, colitis is scored in live mice using the Coloview system (Karl Storz Veterinary Endoscopy, Goleta, Calif.). In mice under 1.5-2.0% isoflurane anesthesia, colons are inflated with air and approximately 3 cm of the proximal colon can be visualized (Chassaing et al., 2014). Endoscopic damage is scored by assessing colon translucency (score 0-3), fibrin attachment to the bowel wall (score 0-3), mucosal granularity (score 0-3), vascular pathology (score 0-3), stool characteristics (normal to diarrhea; score 0-3), and the presence of blood in the lumen (score 0-3), to generate a maximum score of 18. Mice are sacrificed and colonic tissues are isolated using protocols described in Examples 8 and 9. Distal colonic sections are fixed and scored for inflammation and ulceration. Remaining colonic tissue is homogenized and cytokine levels (e.g., IL-1β, TNF-α, IL-6, IFN-γ, and IL-10), as well as myeloperoxidase activity, are measured using methods described below.

Example 9

Euthanasia Procedures for Rodent Models of IBD

Four and 24 hours prior to sacrifice, 5-bromo-2'-deooxyuridine (BrdU) (Invitrogen, Waltham, Mass.; Cat. No. B23151) may be intraperitoneally administered to mice, as recommended by the supplier. BrdU is used to monitor intestinal epithelial cell proliferation and/or migration via immunohistochemistry with standard anti-BrdU antibodies (Abcam, Cambridge, Mass.).

On the day of sacrifice, mice are deprived of food for 4 hours, and then gavaged with FITC-dextran tracer (4 kDa, 0.6 mg/g body weight). Fecal pellets are collected, and mice are euthanized 3 hours following FITC-dextran administration. Animals are then cardiac bled to collect hemolysis-free serum. Intestinal permeability correlates with fluorescence intensity of appropriately diluted serum (excitation, 488 nm; emission, 520 nm), and is measured using spectrophotometry. Serial dilutions of a known amount of FITC-dextran in mouse serum are used to prepare a standard curve.

Alternatively, intestinal inflammation is quantified according to levels of serum keratinocyte-derived chemokine (KC), lipocalin 2, calprotectin, and/or CRP-1. These proteins are reliable biomarkers of inflammatory disease activity, and are measured using DuoSet ELISA kits (R&D Systems, Minneapolis, Minn.) according to manufacturer's instructions. For these assays, control serum samples are diluted 1:2 or 1:4 for KC, and 1:200 for lipocalin 2. Samples from DSS-treated mice require a significantly higher dilution.

Example 10

Isolation and Preservation of Colonic Tissues

To isolate intestinal tissues from mice, each mouse is opened by ventral midline incision. The spleen is then removed and weighed. Increased spleen weights generally correlate with the degree of inflammation and/or anemia in the animal. Spleen lysates (100 mg/mL in PBS) plated on non-selective agar plates are also indicative of disseminated intestinal bacteria. The extent of bacterial dissemination should be consistent with any FITC-dextran permeability data.

Mesenteric lymph nodes are then isolated. These may be used to characterize immune cell populations and/or assay the translocation of gut bacteria. Lymph node enlargement is also a reliable indicator of DSS-induced pathology. Finally, the colon is removed by lifting the organ with forceps and carefully pulling until the cecum is visible. Colon dissection from severely inflamed DSS-treated mice is particularly difficult, since the inflammatory process causes colonic tissue to thin, shorten, and attach to extraintestinal tissues.

The colon and cecum are separated from the small intestine at the ileocecal junction, and from the anus at the distal end of the rectum. At this point, the mouse intestine (from cecum to rectum) may be imaged for gross analysis, and colonic length may be measured by straightening (but not stretching) the colon. The colon is then separated from the cecum at the ileocecal junction, and briefly flushed with cold PBS using a 5- or 10-mL syringe (with a feeding needle). Flushing removes any feces and/or blood. However, if histological staining for mucin layers or bacterial adhesion/translocation is ultimately anticipated, flushing the colon with PBS should be avoided. Instead, the colon is immersed in Carnoy's solution (60% ethanol, 30% chloroform, 10% glacial acetic acid; Johansson et al., 2008) to preserve mucosal architecture. The cecum can be discarded, as DSS-induced inflammation is generally not observed in this region.

After flushing, colon weights are measured. Inflamed colons exhibit reduced weights relative to normal colons due to tissue wasting, and reductions in colon weight correlate with the severity of acute inflammation. In contrast, in chronic models of colitis, inflammation is often associated with increased colon weight. Increased weight may be attributed to focal collections of macrophages, epithelioid cells, and multinucleated giant cells, and/or the accumulation of other cells, such as lymphocytes, fibroblasts, and plasma cells (Williams and Williams, 1983).

To obtain colon samples for later assays, colons are cut into the appropriate number of pieces. It is important to compare the same region of the colon from different groups of mice when performing any assay. For example, the proximal colon is frozen at −80° C. and saved for MPO analysis, the middle colon is stored in RNA later and saved for RNA isolation, and the rectal region is fixed in 10% formalin for histology. Alternatively, washed colons may be cultured ex vivo. Exemplary protocols for each of these assays are described below.

Example 11

Myeloperoxidase Activity Assay

Granulocyte infiltration in the rodent intestine correlates with inflammation, and is measured by the activity levels of myeloperoxidase, an enzyme abundantly expressed in neutrophil granulocytes. Myeloperoxidase (MPO) activity may be quantified using either o-dianisidine dihydrochloride (Sigma, St. Louis, Mo.; Cat. No. D3252) or 3,3',5,5'-tetramethylbenzidine (Sigma; Cat. No. T2885) as a substrate.

Briefly, clean, flushed samples of colonic tissue (50-100 mg) are removed from storage at −80° C. and immediately placed on ice. Samples are then homogenized in 0.5% hexadecyltrimethylammonium bromide (Sigma; Cat. No. H6269) in 50 mM phosphate buffer, pH 6.0. Homogenates are then disrupted for 30 sec by sonication, snap-frozen in dry ice, and thawed for a total of three freeze-thaw cycles before a final sonication for 30 sec.

For assays with o-dianisidine dihydrochloride, samples are centrifuged for 6 min at high speed (13,400 g) at 4° C. MPO in the supernatant is then assayed in a 96-well plate by adding 1 mg/mL of o-dianisidine dihydrochloride and 0.5× $10$-$4$% $H_2O_2$, and measuring optical density at 450 nm. A brownish yellow color develops slowly over a period of 10-20 min; however, if color development is too rapid, the assay is repeated after further diluting the samples. Human neutrophil MPO (Sigma; Cat. No. M6908) is used as a standard, with a range of 0.5-0.015 units/mL. One enzyme unit is defined as the amount of enzyme needed to degrade 1.0 μmol of peroxide per minute at 25° C. This assay is used to analyze MPO activity in rodent colonic samples, particularly in DSS-induced tissues.

For assays with 3,3',5,5'-tetramethylbenzidine (TMB), samples are incubated at 60° C. for 2 hours and then spun down at 4,000 g for 12 min. Enzymatic activity in the supernatant is quantified photometrically at 630 nm. The assay mixture consists of 20 mL supernatant, 10 mL TMB (final concentration, 1.6 mM) dissolved in dimethylsulfoxide, and 70 mL $H_2O_2$ (final concentration, 3.0 mM) diluted in 80 mM phosphate buffer, pH 5.4. One enzyme unit is defined as the amount of enzyme that produces an increase of one absorbance unit per minute. This assay is used to analyze MPO activity in rodent colonic samples, particularly in tissues induced by trinitrobenzene (TNBS) as described herein.

Example 12

RNA Isolation and Gene Expression Analysis

To gain further mechanistic insights into how the genetically engineered bacteria may reduce gut inflammation in vivo, gene expression is evaluated by semi-quantitative and/or real-time reverse transcription PCR.

For semi-quantitative analysis, total RNA is extracted from intestinal mucosal samples using the RNeasy isolation kit (Qiagen, Germantown, Md.; Cat. No. 74106). RNA concentration and purity are determined based on absorbency measurements at 260 and 280 nm. Subsequently, 1 μg of total RNA is reverse-transcribed, and cDNA is amplified for the following genes: tumor necrosis factor alpha (TNF-α), interferon-gamma (IFN-γ), interleukin-2 (IL-2), or any other gene associated with inflammation. Glyceraldehyde-3-phosphate dehydrogenase (GAPDH) is used as the internal standard. Polymerase chain reaction (PCR) reactions are performed with a 2-min melting step at 95° C., then 25 cycles of 30 sec at 94° C., 30 sec at 63° C., and 1 min at 75° C., followed by a final extension step of 5 min at 65° C. Reverse transcription (RT)-PCR products are separated by size on a 4% agarose gel and stained with ethidium bromide. Relative band intensities are analyzed using standard image analysis software.

For real-time, quantitative analysis, intestinal samples (50 mg) are stored in RNA later solution (Sigma; Cat. No. R0901) until RNA extraction. Samples should be kept frozen at −20° C. for long-term storage. On the day of RNA extraction, samples are thawed, or removed from RNA later, and total RNA is extracted using Trizol (Fisher Scientific, Waltham, Mass.; Cat. No. 15596026). Any suitable RNA extraction method may be used. When working with DSS-induced samples, it is necessary to remove all polysaccharides (including DSS) using the lithium chloride method (Chassaing et al., 2012). Traces of DSS in colonic tissues are known to interfere with PCR amplification in subsequent steps.

Primers are designed for various genes and cytokines associated with the immune response using Primer Express® software (Applied Biosystems, Foster City, Calif.). Following isolation of total RNA, reverse transcription is performed using random primers, dNTPs, and Superscripts® II enzyme (Invitrogen; Ser. No. 18/064,014). cDNA is then used for real-time PCR with SYBR Green PCR Master Mix (Applied Biosystems; 4309155) and the ABI PRISM 7000 Sequence Detection System (Applied Biosystems), although any suitable detection method may be used. PCR products are validated by melt analysis.

Example 13

Histology

Standard histological stains are used to evaluate intestinal inflammation at the microscopic level. Hematoxylin-eosin (H&E) stain allows visualization of the quality and dimension of cell infiltrates, epithelial changes, and mucosal architecture (Erben et al., 2014). Periodic Acid-Schiff (PAS) stain is used to stain for carbohydrate macromolecules (e.g., glycogen, glycoproteins, mucins). Goblet cells, for example, are PAS-positive due to the presence of mucin.

Swiss rolls are recommended for most histological stains, so that the entire length of the rodent intestine may be examined. This is a simple technique in which the intestine is divided into portions, opened longitudinally, and then rolled with the mucosa outwards (Moolenbeek and Ruitenberg, 1981). Briefly, individual pieces of colon are cut longitudinally, wrapped around a toothpick wetted with PBS, and placed in a cassette. Following fixation in 10% formalin for 24 hours, cassettes are stored in 70% ethanol until the day of staining. Formalin-fixed colonic tissue may be stained for BrdU using anti-BrdU antibodies (Abcam). Alternatively, Ki67 may be used to visualize epithelial cell proliferation. For stains using antibodies to more specific targets (e.g., immunohistochemistry, immunofluorescence), frozen sections are fixed in a cryoprotective embedding medium, such as Tissue-Tek® OCT (VWR, Radnor, Pa.; Cat. No. 25608-930).

For H&E staining, stained colonic tissues are analyzed by assigning each section four scores of 0-3 based on the extent of epithelial damage, as well as inflammatory infiltration into the mucosa, submucosa, and muscularis/serosa. Each of these scores is multiplied by: 1, if the change is focal; 2, if the change is patchy; and 3, if the change is diffuse. The four individual scores are then summed for each colon, resulting in a total scoring range of 0-36 per animal. Average scores for the control and affected groups are tabulated. Alternative scoring systems are detailed herein.

Example 14

Ex Vivo Culturing of Rodent Colons

Culturing colons ex vivo may provide information regarding the severity of intestinal inflammation. Longitudinally-cut colons (approximately 1.0 cm) are serially washed three times in Hanks' Balanced Salt Solution with 1.0% penicillin/streptomycin (Fisher; Cat. No. BP295950). Washed colons are then placed in the wells of a 24-well plate, each containing 1.0 mL of serum-free RPMI1640 medium (Fisher; Cat. No. 11875093) with 1.0% penicillin/streptomycin, and incubated at 37° C. with 5.0% $CO_2$ for 24 hours. Following incubation, supernatants are collected and centrifuged for 10 min at 4° C. Supernatants are stored at −80° C. prior to analysis for proinflammatory cytokines.

Example 15

In Vivo Efficacy of Genetically Engineered Bacteria Following TNBS Induction

Apart from DSS, the genetically engineered bacteria described in 1 can also be tested in other chemically induced animal models of IBD. Non-limiting example's include those induced by oxazolone (Boirivant et al., 1998), acetic acid (MacPherson and Pfeiffer, 1978), indomethacin (Sabiu et al., 2016), sulfhydryl inhibitors (Satoh et al., 1997), and trinitrobenzene sulfonic acid (TNBS) (Gurtner et al., 2003; Segui et al., 2004). To determine the efficacy of the genetically engineered bacteria in a TNBS-induced mouse model of colitis, bacteria are grown overnight in LB supplemented with the appropriate antibiotic. Bacteria are then diluted 1:100 in fresh LB containing selective antibiotic, grown to an optical density of 0.4-0.5, and pelleted by centrifugation. Bacteria are resuspended in PBS. IBD is induced in mice by intracolonic administration of 30 mg TNBS in 0.25 mL 50% (vol/vol) ethanol (Segui et al., 2004). Control mice are administered 0.25 mL saline. Four hours post-induction, 100 µL of bacteria (or vehicle) is administered to mice by oral gavage. Bacterial treatment is repeated once daily for 1 week. Animals are weighed daily.

After 7 days of bacterial treatment, mice are sacrificed via intraperitoneal administration of thiobutabarbital (100 mg/kg). Colonic tissues are isolated by blunt dissection, rinsed with saline, and weighed. Blood samples are collected by open cardiac puncture under aseptic conditions using a 1-mL syringe, placed in Eppendorf vials, and spun at 1,500 g for 10 min at 4° C. The supernatant serum is then pipetted into autoclaved Eppendorf vials and frozen at −80° C. for later assay of IL-6 levels using a quantitative, colorimetric commercial kit (R&D Systems).

Macroscopic damage is examined under a dissecting microscope by a blinded observer. An established scoring system is used to account for the presence/severity of intestinal adhesions (score 0-2), strictures (score 0-3), ulcers (score 0-3), and wall thickness (score 0-2) (Mourelle et al., 1996). Two colon samples (50 mg) are then excised, snap-frozen in liquid nitrogen, and stored at −80° C. for subsequent myeloperoxidase activity assay. If desired, additional samples are preserved in 10% formalin for histologic grading. Formalin-fixed colonic samples are then embedded in paraffin, and 5 µm sections are stained with H&E. Microscopic inflammation of the colon is assessed on a scale of 0 to 11, according to previously defined criteria (Appleyard and Wallace, 1995).

Example 16

Generating a Cell Transfer Mouse Model of IBD

The genetically engineered bacteria described in Example 1 can be tested in cell transfer animal models of IBD. One exemplary cell transfer model is the CD45RBHi T cell transfer model of colitis (Bramhall et al., 2015; Ostanin et al., 2009; Sugimoto et al., 2008). This model is generated by sorting CD4+ T cells according to their levels of CD45RB expression, and adoptively transferring CD4+ T cells with high CD45RB expression (referred to as CD45RBHi T cells) from normal donor mice into immunodeficient mice (e.g., SCID or RAG−/− mice). Specific protocols are described below.

Enrichment for CD4 T Cells

Following euthanization of C57BL/6 wild-type mice of either sex (Jackson Laboratories, Bar Harbor, Me.), mouse spleens are removed and placed on ice in a 100 mm Petri dish containing 10-15 mL of FACS buffer (1×PBS without Ca2+/Mg2+, supplemented with 4% fetal calf serum). Spleens are teased apart using two glass slides coated in FACS buffer, until no large pieces of tissue remain. The cell suspension is then withdrawn from the dish using a 10-mL syringe (no needle), and expelled out of the syringe (using a 26-gauge needle) into a 50-mL conical tube placed on ice. The Petri dish is washed with an additional 10 mL of FACS buffer, using the same needle technique, until the 50-mL conical tube is full. Cells are pelleted by centrifugation at 400 g for 10 min at 4° C. After the cell pellet is gently disrupted with a stream of FACS buffer, cells are counted. Cells used for counting are kept on ice and saved for single-color staining described in the next section. All other cells (i.e., those remaining in the 50-mL conical tube) are transferred to new 50-mL conical tubes. Each tube should contain a maximum of $25 \times 10^7$ cells.

To enrich for CD4+ T cells, the Dynal® Mouse CD4 Negative Isolation kit (Invitrogen; Cat. No. 114-15D) is used as per manufacturer's instructions. Any comparable CD4+ T cell enrichment method may be used. Following negative selection, CD4+ cells remain in the supernatant. Supernatant is carefully pipetted into a new 50-mL conical tube on ice, and cells are pelleted by centrifugation at 400 g for 10 min at 4° C. Cell pellets from all 50-mL tubes are then resuspended, pooled into a single 15-mL tube, and pelleted once more by centrifugation. Finally, cells are resuspended in 1 mL of fresh FACS buffer, and stained with anti-CD4-APC and anti-CD45RB-FITC antibodies.

Fluorescent Labeling of CD4+ T Cells

To label CD4+ T cells, an antibody cocktail containing appropriate dilutions of pre-titrated anti-CD4-APC and anti-CD45RB-FITC antibodies in FACS buffer (approximately 1 mL cocktail/5×107 cells) is added to a 1.5-mL Eppendorf tube, and the volume is adjusted to 1 mL with FACS buffer. Antibody cocktail is then combined with cells in a 15-mL tube. The tube is capped, gently inverted to ensure proper mixing, and incubated on a rocking platform for 15 min at 4° C.

During the incubation period, a 96-well round-bottom staining plate is prepared by transferring equal aliquots of counted cells (saved from the previous section) into each well of the plate that corresponds to single-color control staining. These wells are then filled to 200 µL with FACs buffer, and the cells are pelleted at 300 g for 3 min at 4° C. using a pre-cooled plate centrifuge. Following centrifugation, the supernatant is discarded using a 21-gauge needle attached to a vacuum line, and 100 µL of anti-CD16/32 antibody (Fc receptor-blocking) solution is added to each well to prevent non-specific binding. The plate is incubated on a rocking platform at 4° C. for 15 min. Cells are then washed with 200 µL FACS buffer and pelleted by centrifugation. Supernatant is aspirated, discarded, and 100 µL of the appropriate antibody (i.e., pre-titrated anti-CD4-APC or anti-CD45RB-FITC) is added to wells corresponding to each single-color control. Cells in unstained control wells are resuspended in 100 µL FACS buffer. The plate is incubated on a rocking platform at 4° C. for 15 min. After two washes, cells are resuspended in 200 µL of FACS buffer, transferred into twelve 75-mm flow tubes containing 150-200 µL of FACS buffer, and the tubes are placed on ice.

Following incubation, cells in the 15-mL tube containing antibody cocktail are pelleted by centrifugation at 400 g for 10 min at 4° C., and resuspended in FACS buffer to obtain a concentration of $25-50 \times 10^6$ cells/mL.

Purification of CD4+CD45RBHi T Cells

Cell sorting of CD45RBHi and CD45RBLow populations is performed using flow cytometry. Briefly, a sample of unstained cells is used to establish baseline autofluorescence, and for forward scatter vs. side scatter gating of lymphoid cells: Single-color controls are used to set the appropriate levels of compensation to apply to each fluorochrome. However, with FITC and APC fluorochromes, compensation is generally not required. A single-parameter histogram (gated on singlet lymphoid cells) is then used to gate CD4+(APC+) singlet cells, and a second singlet-parameter (gated on CD4+ singlet cells) is collected to establish sort gates. The CD45RBHi population is defined as the 40% of cells which exhibit the brightest CD45RB staining, whereas the CD45RBLow population is defined as the 15% of cells with the dimmest CD45RB expression. Each of these populations is sorted individually, and the CD45RBHi cells are used for adoptive transfer.

Adoptive Transfer

Purified populations of CD4+CD45RBHi cells are adoptively transferred into 6- to 8-week-old RAG−/− male mice. The collection tubes containing sorted cells are filled with FACS buffer, and the cells are pelleted by centrifugation. The supernatant is then discarded, and cells are resuspended in 500 µL PBS. Resuspended cells are transferred into an injection tube, with a maximum of 5×106 cells per tube, and diluted with cold PBS to a final concentration of 1×106 cells/mL. Injection tubes are kept on ice.

Prior to injection, recipient mice are weighed and injection tubes are gently inverted several times to mix the cells. Mixed cells (0.5 mL, ~0.5×106 cells) are carefully drawn into a 1-mL syringe with a 26G3/8 needle attached. Cells are then intraperitoneally injected into recipient mice.

Example 17

Efficacy of Genetically Engineered Bacteria in a CD45RBHi T Cell Transfer Model

To determine whether the genetically engineered bacteria of the disclosure are efficacious in CD45RBHi T cell transfer mice, disease progression following adoptive transfer is monitored by weighing each mouse on a weekly basis. Typically, modest weight increases are observed over the first 3 weeks post-transfer, followed by slow but progressive weight loss over the next 4-5 weeks. Weight loss is generally accompanied by the appearance of loose stools and diarrhea.

At weeks 4 or 5 post-transfer, as recipient mice begin to develop signs of disease, the genetically engineered bacteria described in Example 1 are grown overnight in LB supplemented with the appropriate antibiotic. Bacteria are then diluted 1:100 in fresh LB containing selective antibiotic, grown to an optical density of 0.4-0.5, and pelleted by centrifugation. Bacteria are resuspended in PBS and 100 µL of bacteria (or vehicle) is administered by oral gavage to CD45RBHi T cell transfer mite. Bacterial treatment is repeated once daily for 1-2 weeks before mice are euthanized. Murine colonic tissues are isolated and analyzed using the procedures described above.

Example 18

Efficacy of Genetically Engineered Bacteria in a Genetic Mouse Model of IBD

The genetically engineered bacteria described in Example 1 can be tested in genetic (including congenic and genetically modified) animal models of IBD. For example, IL-10 is an anti-inflammatory cytokine and the gene encoding IL-10 is a susceptibility gene for both Crohn's disease and ulcerative colitis (Khor et al., 2011). Functional impairment of IL-10, or its receptor, has been used to create several mouse models for the study of inflammation (Bramhall et al., 2015). IL10 knockout (IL-10−/−) mice housed under normal conditions develop chronic inflammation in the gut Oyer and Cheng, 2012).

To determine whether the genetically engineered bacteria of the disclosure are efficacious in IL-10−/− mice, bacteria are grown overnight in LB supplemented with the appropriate antibiotic. Bacteria are then diluted 1:100 in fresh LB containing selective antibiotic, grown to an optical density of 0.4-0.5, and pelleted by centrifugation. Bacteria are resuspended in PBS and 100 µL of bacteria (or vehicle) is administered by oral gavage to IL-10−/− mice. Bacterial treatment is repeated once daily for 1-2 weeks before mice are euthanized. Murine colonic tissues are isolated and analyzed using the procedures described above.

Protocols for testing the genetically engineered bacteria are similar for other genetic animal models of IBD. Such models include, but are not limited to, transgenic mouse models, e.g., SAMP1/YitFc (Pizarro et al., 2011), dominant negative N-cadherin mutant (NCAD delta; Hermiston and Gordon, 1995), TNFΔARE (Wagner et al., 2013), IL-7 (Watanabe et al., 1998), C3H/HeJBir (Elson et al., 2000), and dominant negative TGF-β receptor II mutant (Zhang et al., 2010); and knockout mouse models, e.g., TCRα−/− (Mombaerts et al., 1993; Sugimoto et al., 2008), WASP−/− (Nguyen et al., 2007), Mdr1a−/− (Wilk et al., 2005), IL-2 Rα−/− (Hsu et al., 2009), Gαi2−/− (Ohman et al., 2002), and TRUC (Tbet−/−Rag2−/−; Garrett et al., 2007).

Example 19

Efficacy of Genetically Engineered Bacteria in a Transgenic Rat Model of IBD

The genetically engineered bacteria described in Example 1 can be tested in non-murine animal models of IBD. The introduction of human leukocyte antigen B27 (HLA-B27) and the human β2-microglobulin gene into Fisher (F344) rats induces spontaneous, chronic inflammation in the GI tract (Alavi et al., 2000; Hammer et al., 1990). To investigate whether the genetically engineered bacteria of the invention are capable of ameliorating gut inflammation in this model, bacteria are grown overnight in LB supplemented with the appropriate antibiotic. Bacteria are then diluted 1:100 in fresh LB containing selective antibiotic, grown to an optical density of 0.4-0.5, and pelleted by centrifugation. Bacteria are resuspended in PBS and 100 µL of bacteria (or vehicle) is administered by oral gavage to transgenic F344-HLA-B27 rats. Bacterial treatment is repeated once daily for 2 weeks.

To determine whether bacterial treatment reduces the gross and histological intestinal lesions normally present in F344-HLA-B27 rats at 25 weeks of age, all animals are sacrificed at day 14 following the initial treatment. The GI tract is then resected from the ligament of Treitz to the rectum, opened along the antimesenteric border, and imaged using a flatbed scanner. Total mucosal damage, reported as a percent of the total surface area damaged, is quantified using standard image analysis software.

For microscopic analysis, samples (0.5-1.0 cm) are excised from both normal and diseased areas of the small and large intestine. Samples are fixed in formalin and embedded in paraffin before sections (5 µm) are processed for H&E staining. The stained sections are analyzed and scored as follows: 0, no inflammation; 1, mild inflammation extending into the submucosa; 2, moderate inflammation extending into the muscularis propria; and 3, severe inflammation. The scores are combined and reported as mean±standard error.

Example 19

Butyrate-Producing Bacterial Strain Reduces Gut Inflammation in a Low-Dose DSS-Induced Mouse Model of IBD At Day 0, 40 C57BL6 mice (8 weeks of age) were weighed and randomized into the following five treatment groups (n=8 per group): $H_2O$ control (group 1); 0.5% DSS control (group 2); 0.5% DSS+100 mM butyrate (group 3); 0.5% DSS+SYN94 (group 4); and 0.5% DSS+SYN363 (group 5). After randomization, the cage water for group 3 was changed to water supplemented with butyrate (100 mM), and groups 4 and 5 were administered 100 µL of SYN94 and SYN363 by oral gavage, respectively. At Day 1, groups 4 and 5 were gavaged with bacteria in the morning, weighed, and gavaged again in the evening. Groups 4 and 5 were also gavaged once per day for Day 2 and Day 3.

At Day 4, groups 4 and 5 were gavaged with bacteria, and then all mice were weighed. Cage water was changed to either H2O+0.5% DSS (groups 2, 4, and 5), or $H_2O$+0.5% DSS supplemented with 100 mM butyrate (group 3). Mice from groups 4 and 5 were gavaged again in the evening. On Days 5-7, groups 4 and 5 were gavaged with bacteria in the morning, weighed, and gavaged again in the evening.

At Day 8, all mice were fasted for 4 hours, and groups 4 and 5 were gavaged with bacteria immediately following the removal of food. All mice were then weighed, and gavaged with a single dose of FITC-dextran tracer (4 kDa, 0.6 mg/g body weight). Fecal pellets were collected; however, if colitis was severe enough to prevent feces collection, feces were harvested after euthanization. All mice were euthanized at exactly 3 hours following FITC-dextran administration. Animals were then cardiac bled and blood samples were processed to obtain serum. Levels of mouse lipocalin 2, calprotectin, and CRP-1 were quantified by ELISA, and serum levels of FITC-dextran were analyzed by spectrophotometry (see also Example 8).

FIG. 27 shows lipocalin 2 (LCN2) levels in all treatment groups, as demonstrated by ELISA, on. Day 8 of the study. Since LCN2 is a biomarker of inflammatory disease activity, these data suggest that SYN363 produces enough butyrate to significantly reduce LCN2 concentrations, as well as gut inflammation, in a low-dose DSS-induced mouse model of IBD.

Example 20

Nitric Oxide-inducible Reporter Constructs

Figure 28A:
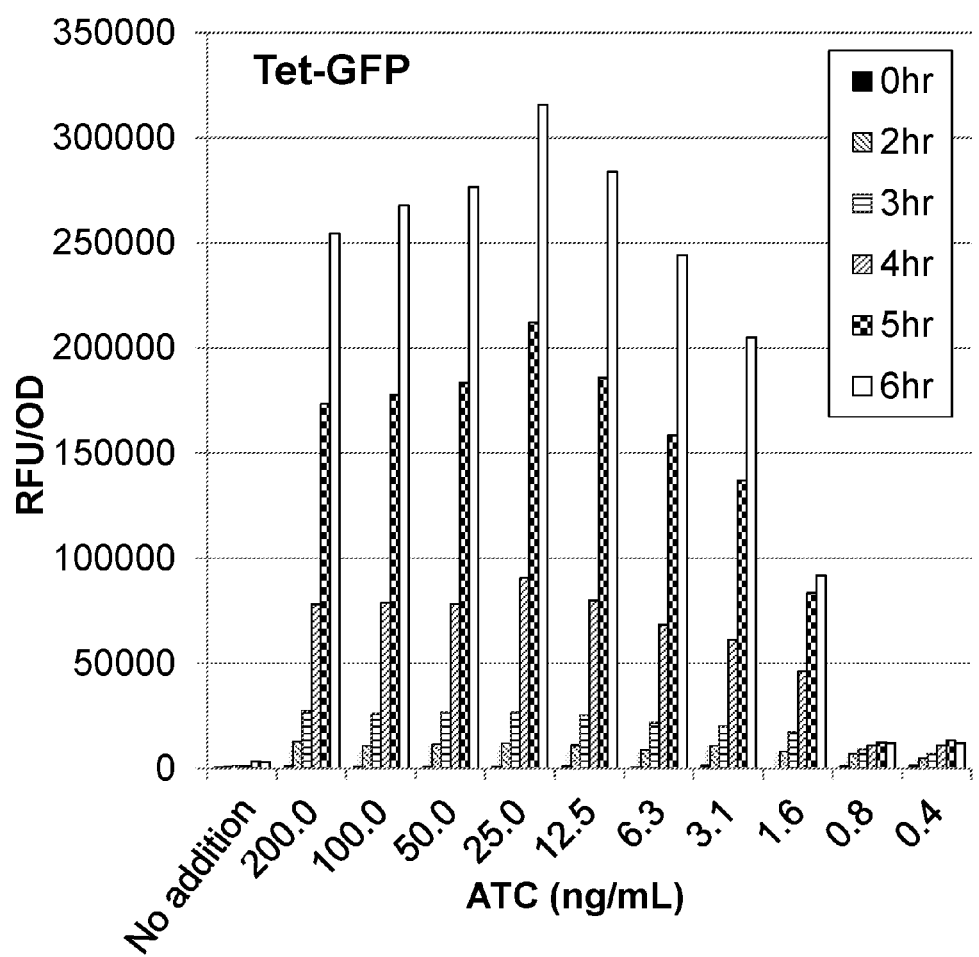
FIG. 28 depicts ATC or nitric oxide-inducible reporter constructs. These constructs, when induced by their cognate inducer, lead to expression of GFP. Nissle cells harboring plasmids with either the control, ATC-inducible $P_{tet}$-GFP reporter construct or the nitric oxide inducible $P_{nsrR}$-GFP reporter construct induced across a range of concentrations. Promoter activity is expressed as relative florescence units.
Figure 28B:
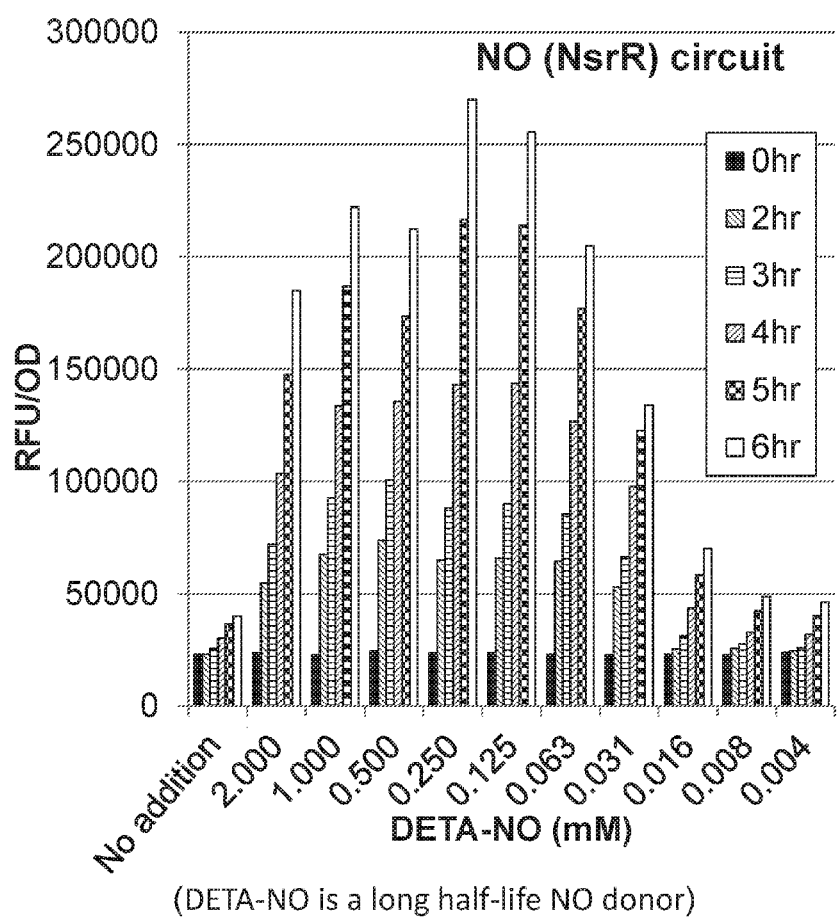
Figure 28C:
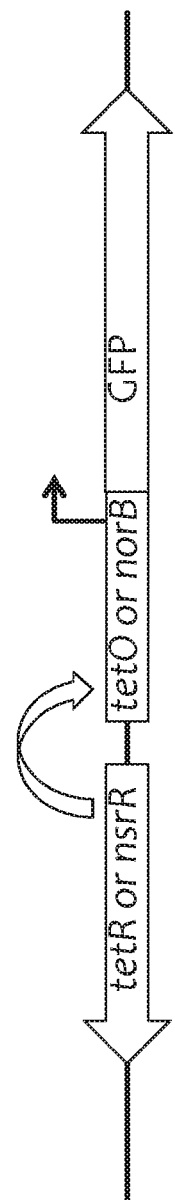

ATC and nitric oxide-inducible reporter constructs were synthesized (Genewiz, Cambridge, Mass.). When induced by their cognate inducers, these constructs express GFP, which is detected by monitoring fluorescence in a plate reader at an excitation/emission of 395/509 nm, respectively. Nissle cells harboring plasmids with either the control, ATC-inducible Ptet-GFP reporter construct, or the nitric oxide inducible PnsrR-GFP reporter construct were first grown to early log phase (OD600 of about 0.4-0.6), at which point they were transferred to 96-well microtiter plates containing LB and two-fold decreased inducer (ATC or the long half-life NO donor, DETA-NO (Sigma)). Both ATC and NO were able to induce the expression of GFP in their respective constructs across a range of concentrations (FIG. 28); promoter activity is expressed as relative florescence units. An exemplary sequence of a nitric oxide-inducible reporter construct is shown. The bsrR sequence is bolded. The gfp sequence is underlined. The PnsrR (NO regulated promoter and RBS) is italicized. The constitutive promoter and RBS are boxed.

These constructs, when induced by their cognate inducer, lead to high level expression of GFP, which is detected by monitoring fluorescence in a plate reader at an excitation/emission of 395/509 nm, respectively. Nissle cells harboring plasmids with either the ATC-inducible Ptet-GFP reporter construct or the nitric oxide inducible PnsrR-GFP reporter construct were first grown to early log phase (OD600=~0.4-0.6), at which point they were transferred to 96-well microtiter plates containing LB and 2-fold decreases in inducer (ATC or the long half-life NO donor, DETA-NO (Sigma)). It, was observed that both the ATC and NO were able to induce the expression of GFP in their respective construct across a wide range of concentrations. Promoter activity is expressed as relative florescence units.

Figure 29:
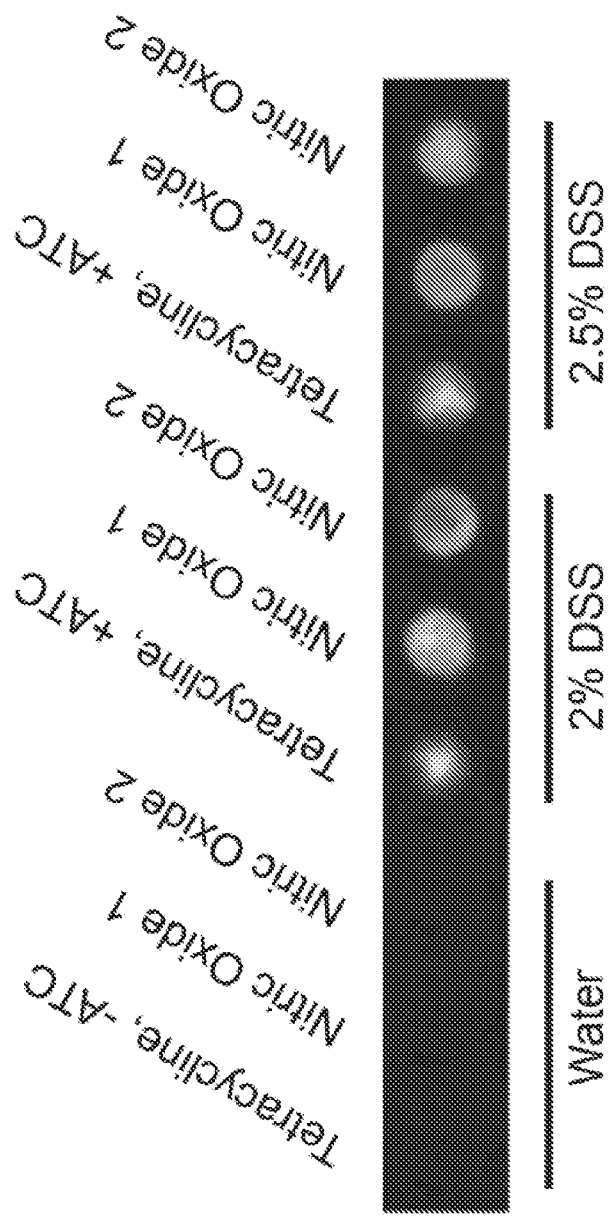
FIG. 29 depicts a dot blot of bacteria harboring a plasmid expressing NsrR under control of a constitutive promoter and the reporter gene gfp (green fluorescent protein) under control of an NsrR-inducible promoter. IBD is induced in mice by supplementing drinking water with 2-3% dextran sodium sulfate (DSS). Chemiluminescent is shown for NsrR-regulated promoters induced in DSS-treated mice.
Figure 30:
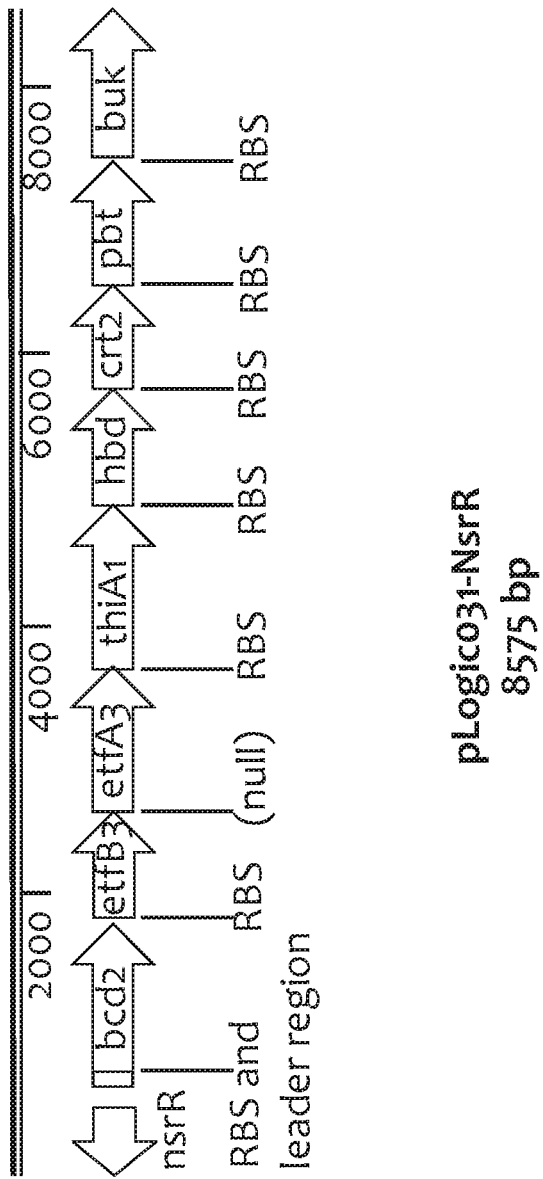
FIG. 30 depicts the construction and gene organization of an exemplary plasmid comprising a gene encoding NsrR, a regulatory sequence from norB, and a butyrogenic gene cassette (pLogic031-nsrR-norB-butyrate construct).
Figure 31:
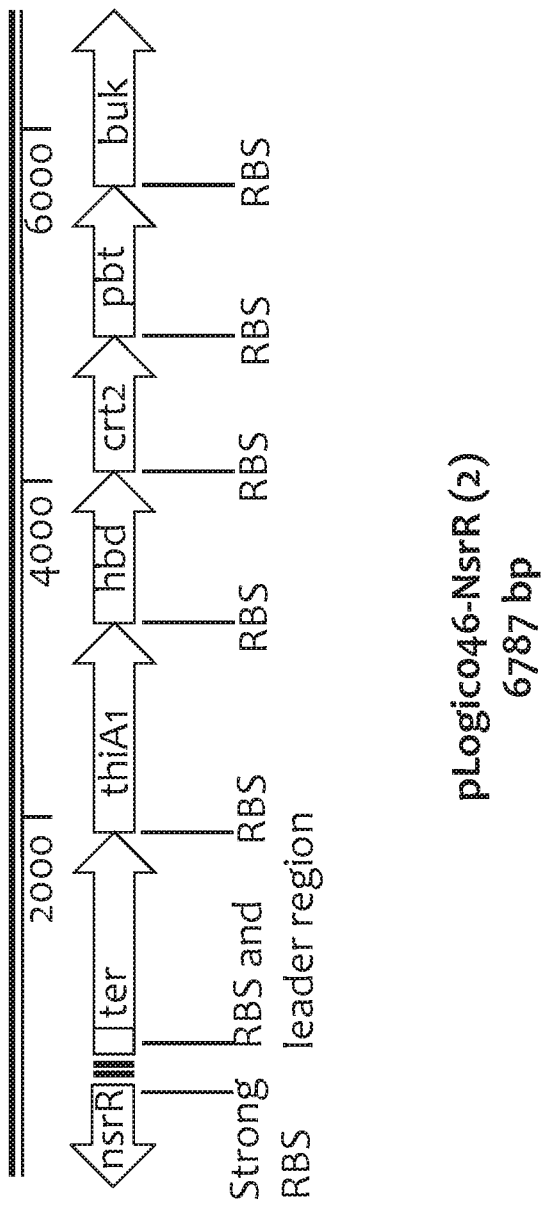
FIG. 31 depicts the construction and gene organization of another exemplary plasmid comprising a gene encoding NsrR, a regulatory sequence from norB, and a butyrogenic gene cassette (pLogic046-nsrR-norB-butyrogenic gene cassette).
Figure 32:
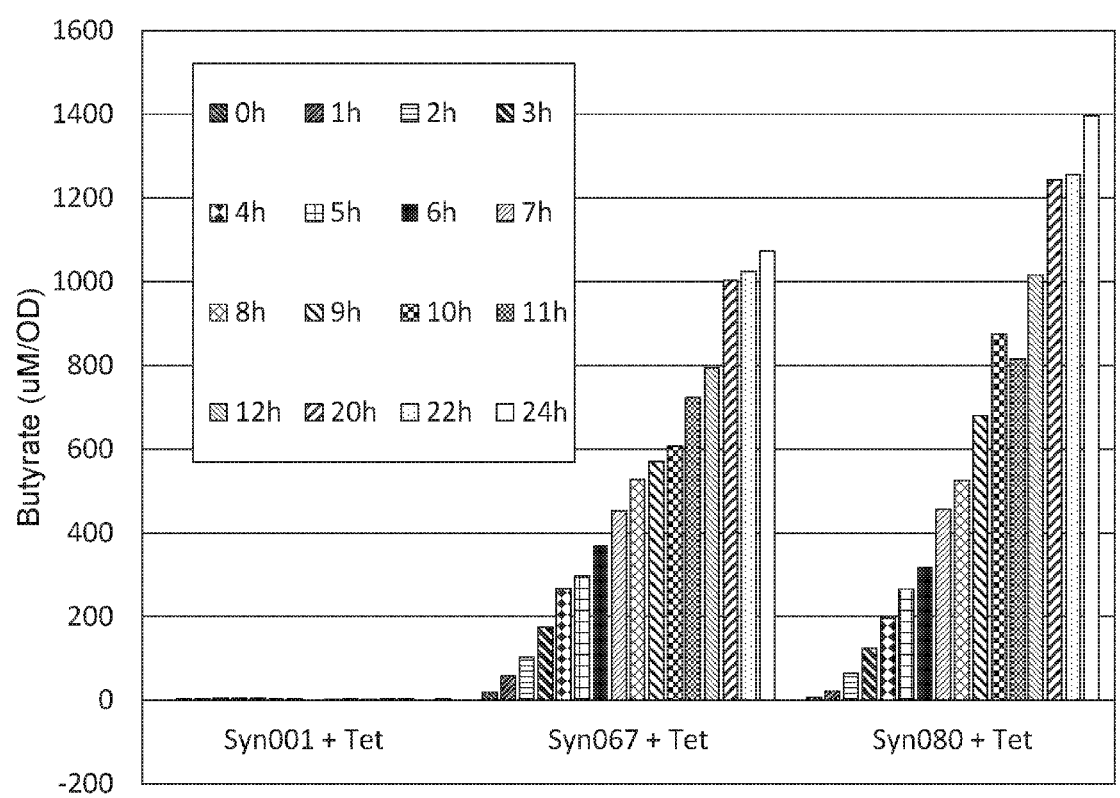
FIG. 32 depicts butyrate production using SYN001+tet (control wild-type Nissle comprising no plasmid), SYN067+tet (Nissle comprising the pLOGIC031 ATC-inducible butyrate plasmid), and SYN080+tet (Nissle comprising the pLOGIC046 ATC-inducible butyrate plasmid).
Figure 33:
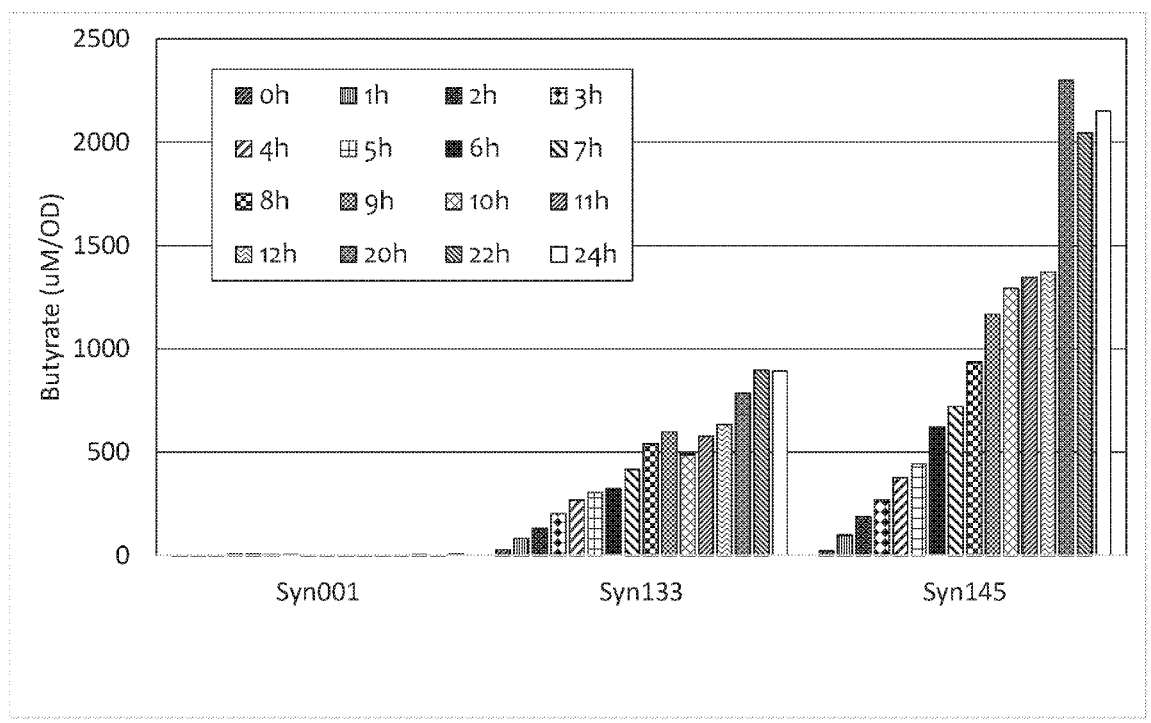
FIG. 33 depicts butyrate production by genetically engineered Nissle comprising the pLogic031-nsrR-norB-butyrate construct (SYN133) or the pLogic046-nsrR-norB-butyrate construct (SYN145), which produce more butyrate as compared to wild-type Nissle (SYN001).
Figure 34:
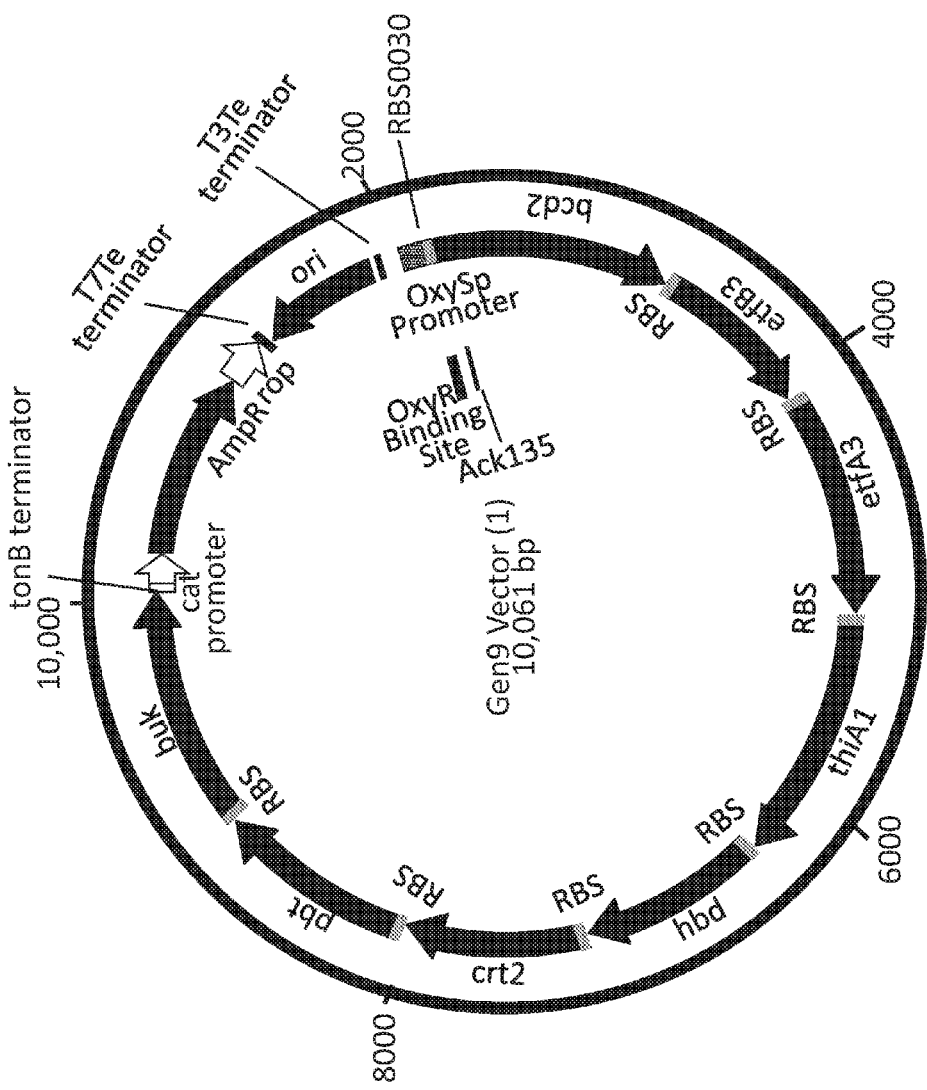
FIG. 34 depicts the construction and gene organization of an exemplary plasmid comprising an oxyS promoter and butyrogenic gene cassette (pLogic031-oxyS-butyrogenic gene cassette).
Figure 35:
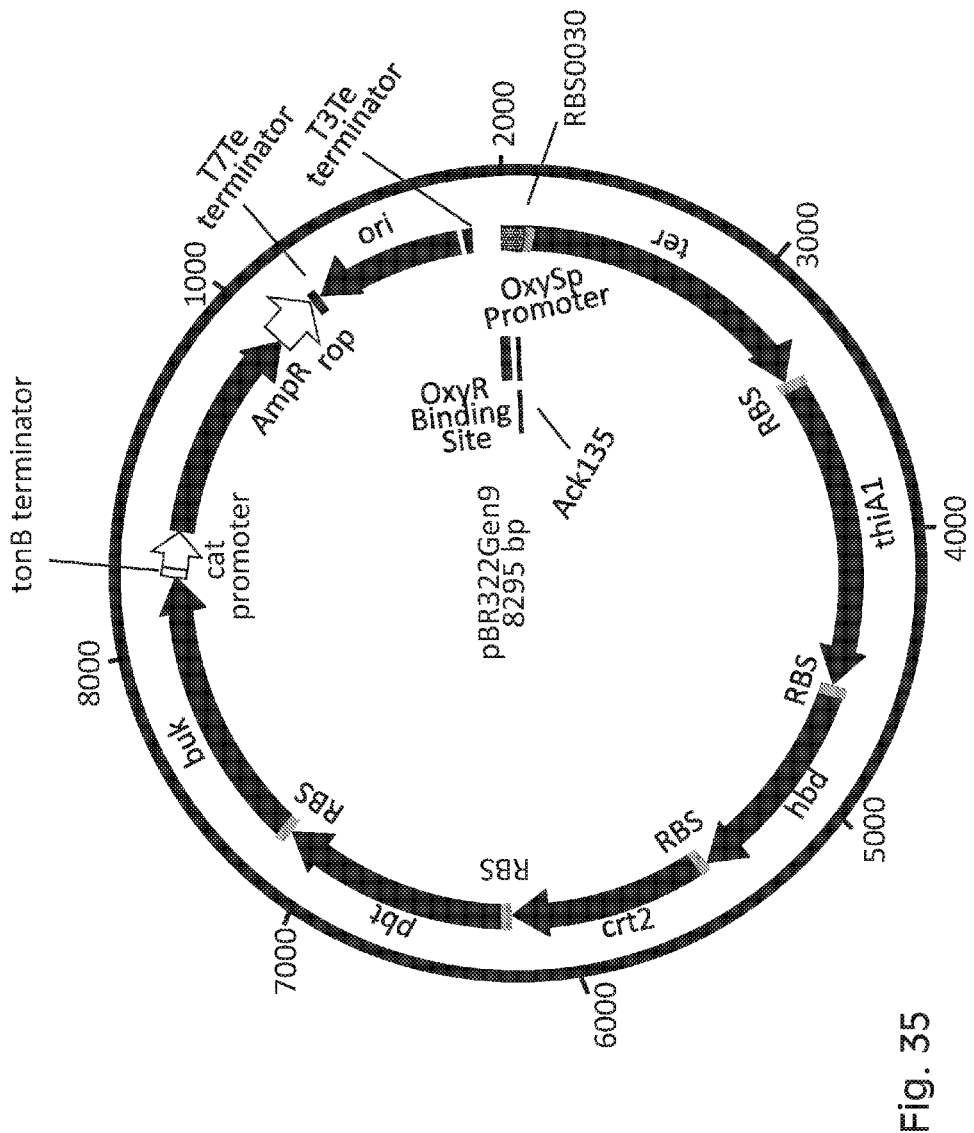
FIG. 35 depicts the construction and gene organization of another exemplary plasmid comprising an oxyS promoter and butyrogenic gene cassette (pLogic046-oxyS-butyrogenic gene cassette).
Figure 36:
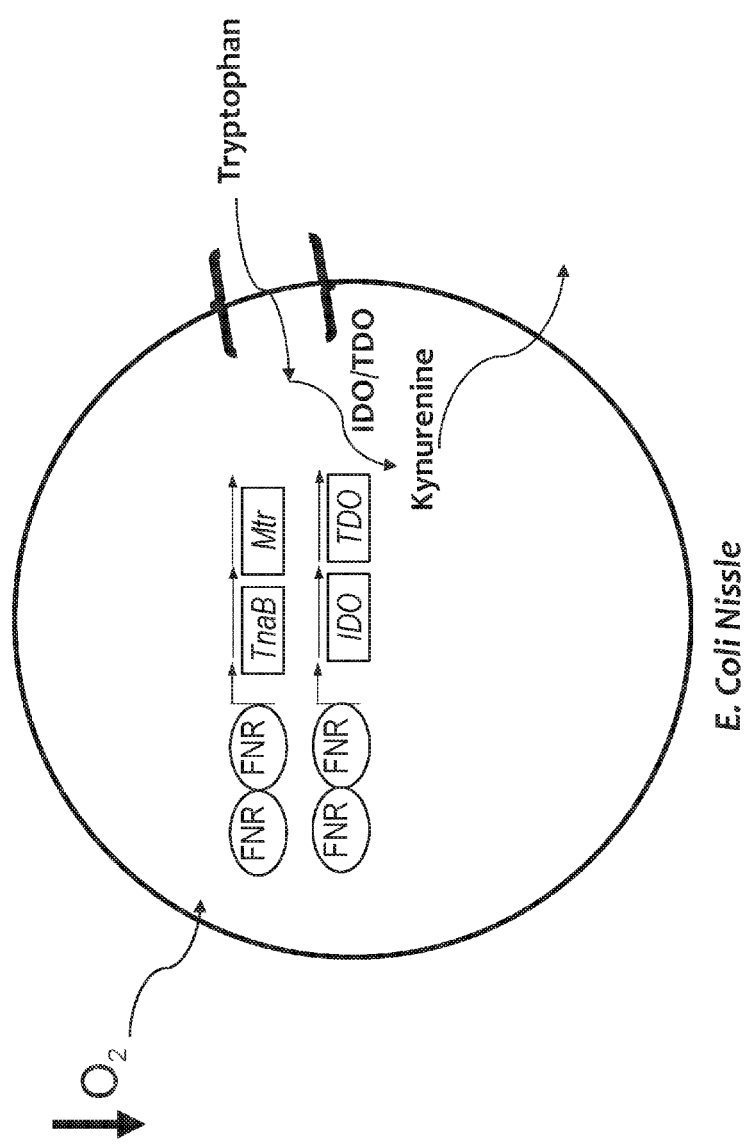
FIG. 36 depicts a schematic of an *E. coli* that is genetically engineered to express the essential gene tnaB, 5-methyltetrahydrofolate-homocysteine methyltransferase (mtr), tryptophan transporter, and the enzymes IDO and TDO to convert tryptophan into kynurenine.
Figure 37:
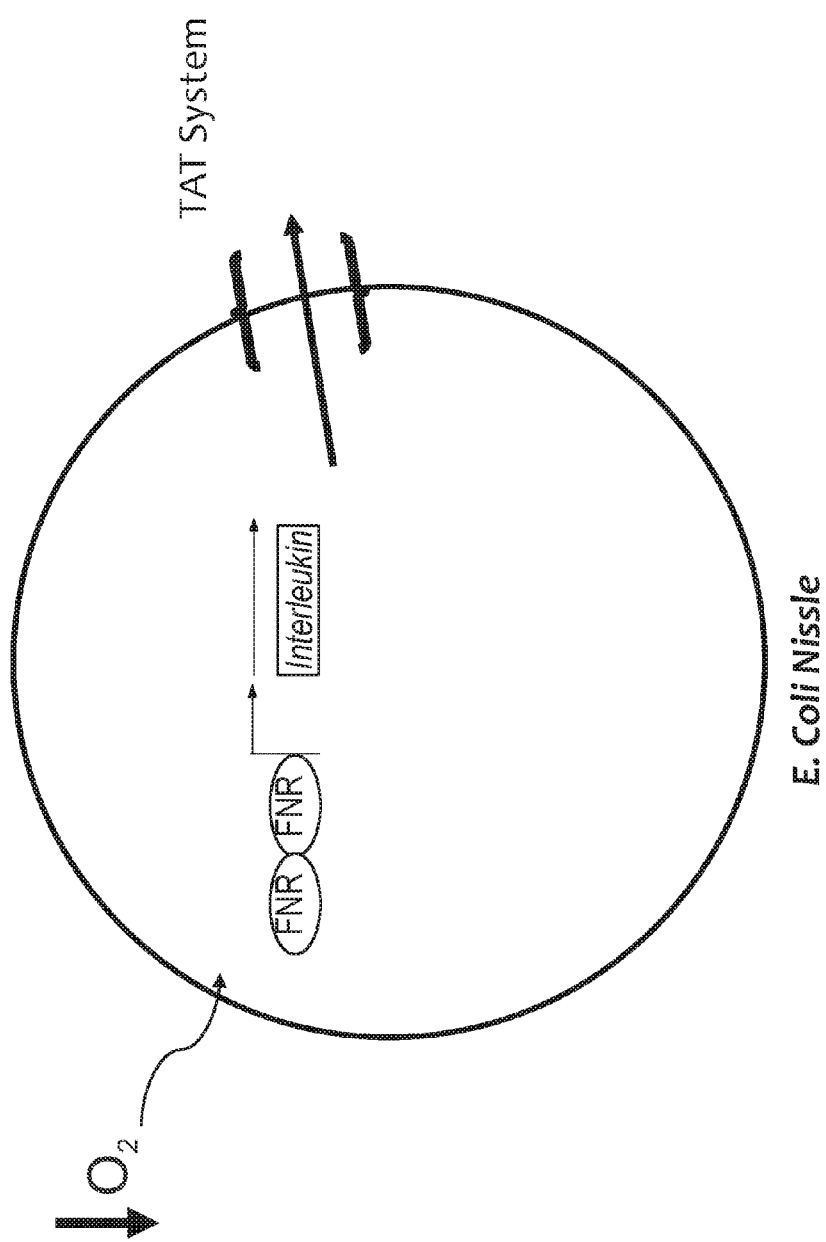
FIG. 37 depicts a schematic of an *E. coli* that is genetically engineered to express interleukin under the control of a FNR-responsive promoter and further comprising a TAT secretion system.
Figure 38:
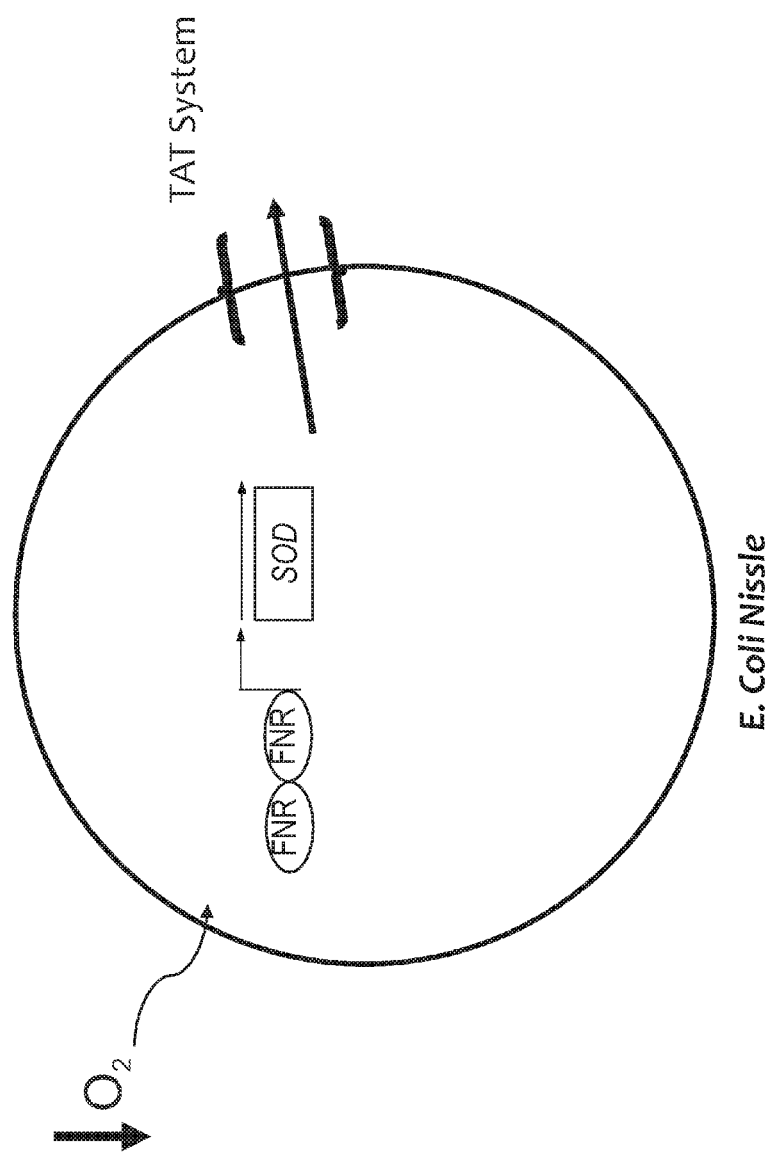
FIG. 38 depicts a schematic of an *E. coli* that is genetically engineered to express SOD under the control of a FNR-responsive promoter and further comprising a TAT secretion system.
Figure 39:
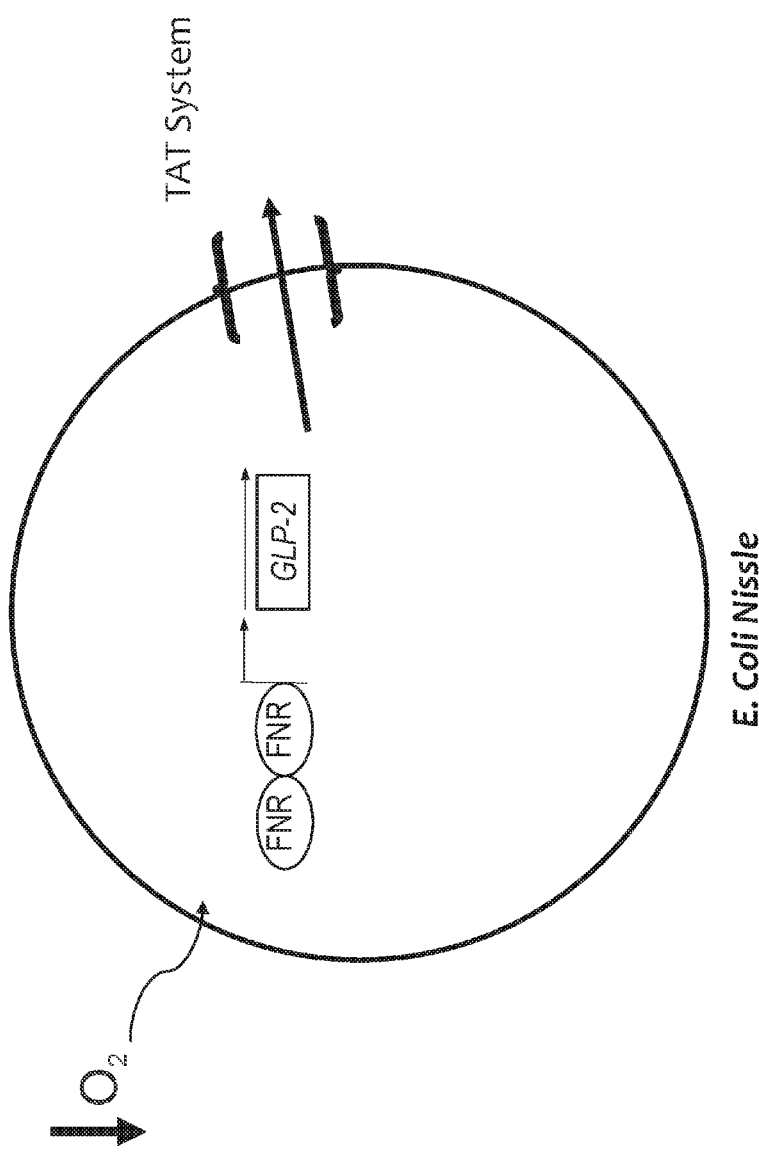
FIG. 39 depicts a schematic of an *E. coli* that is genetically engineered to express GLP-2 under the control of a FNR-responsive promoter and further comprising a TAT secretion system.
Figure 40:
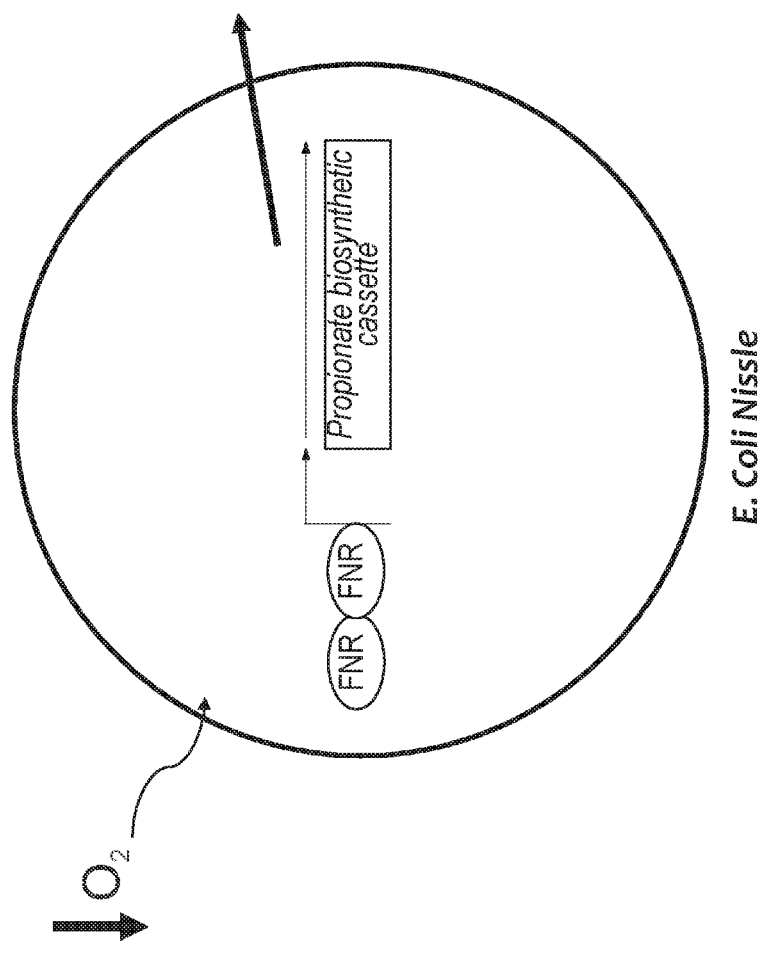
FIG. 40 depicts a schematic of an *E. coli* that is genetically engineered to express a propionate gene cassette under the control of a FNR-responsive promoter.
Figure 41:
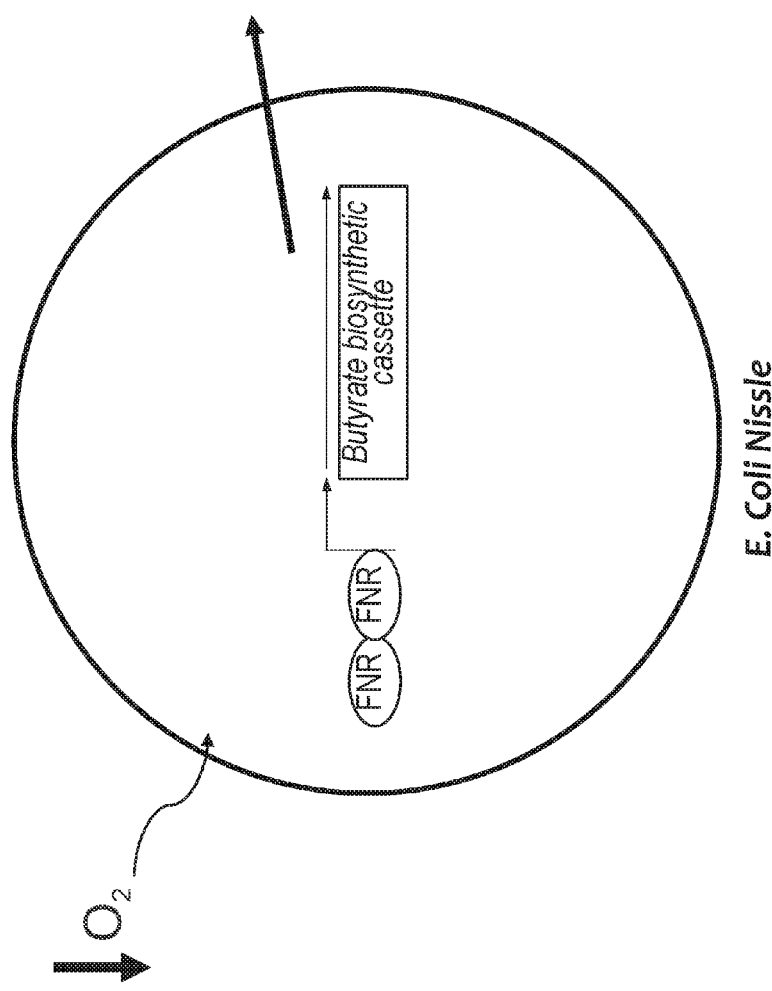
FIG. 41 depicts a schematic of an *E. coli* that is genetically engineered to express butyrate under the control of a FNR-responsive promoter.
Figure 42:
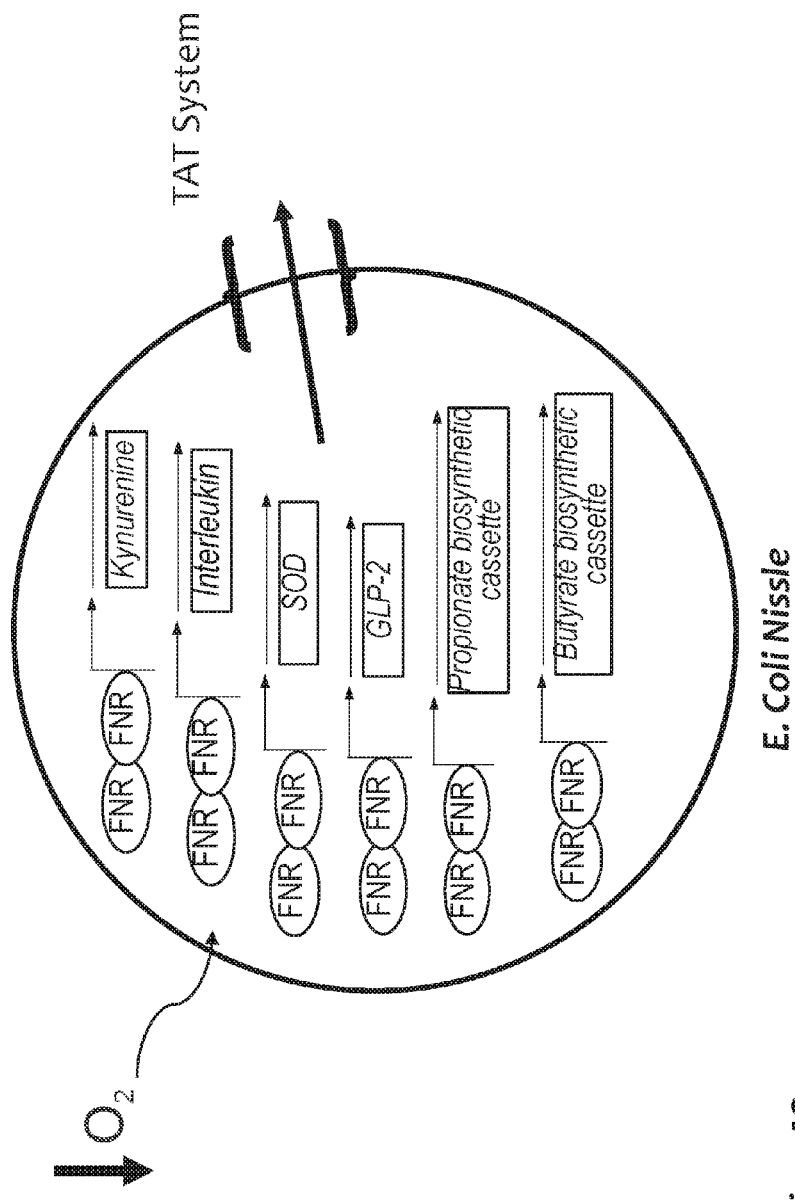
FIG. 42 depicts a schematic of an *E. coli* that is genetically engineered to express kynurenine, interleukin, SOD, GLP-2, a propionate gene cassette, and a butyrate gene cassette under the control of a FNR-responsive promoter and further comprising a TAT secretion system.
Figure 43:
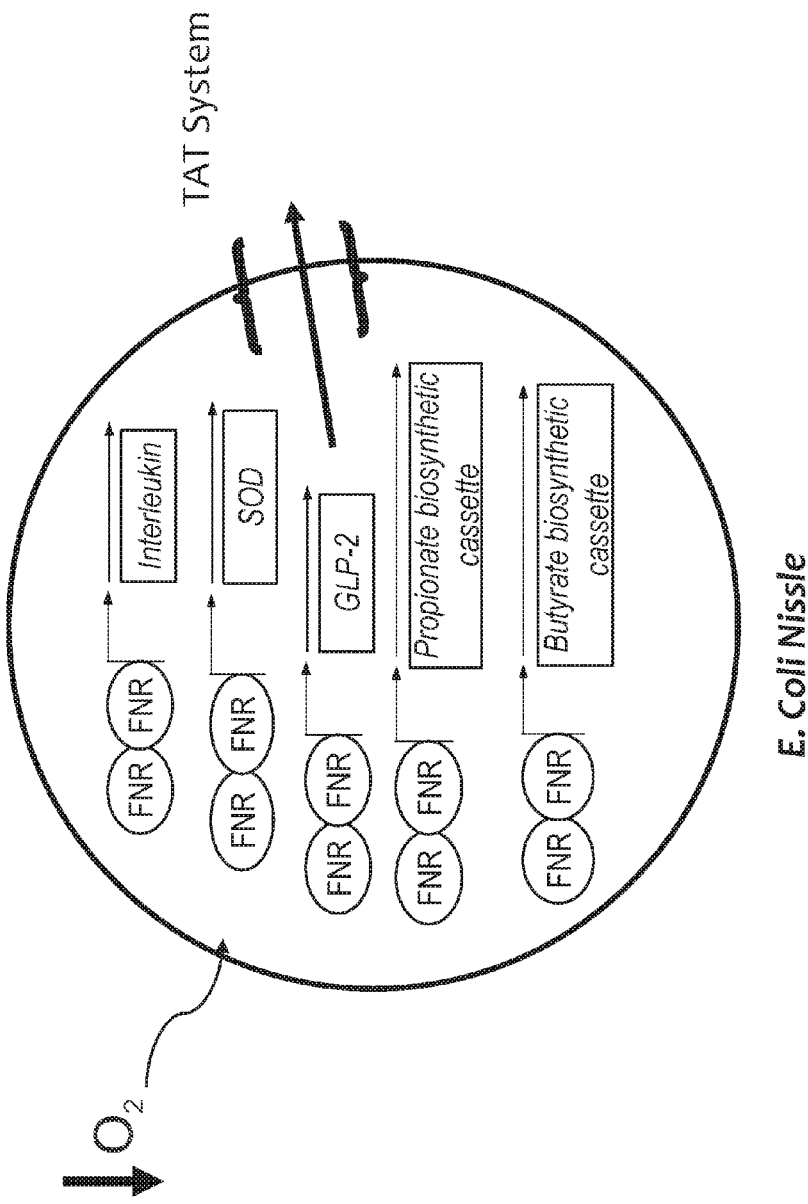
FIG. 43 depicts a schematic of an *E. coli* that is genetically engineered to express interleukin, OSD, GLP-2, a propionate gene cassette, and a butyrate gene cassette under the control of a FNR-responsive promoter and further comprising a TAT secretion system.
Figure 44:
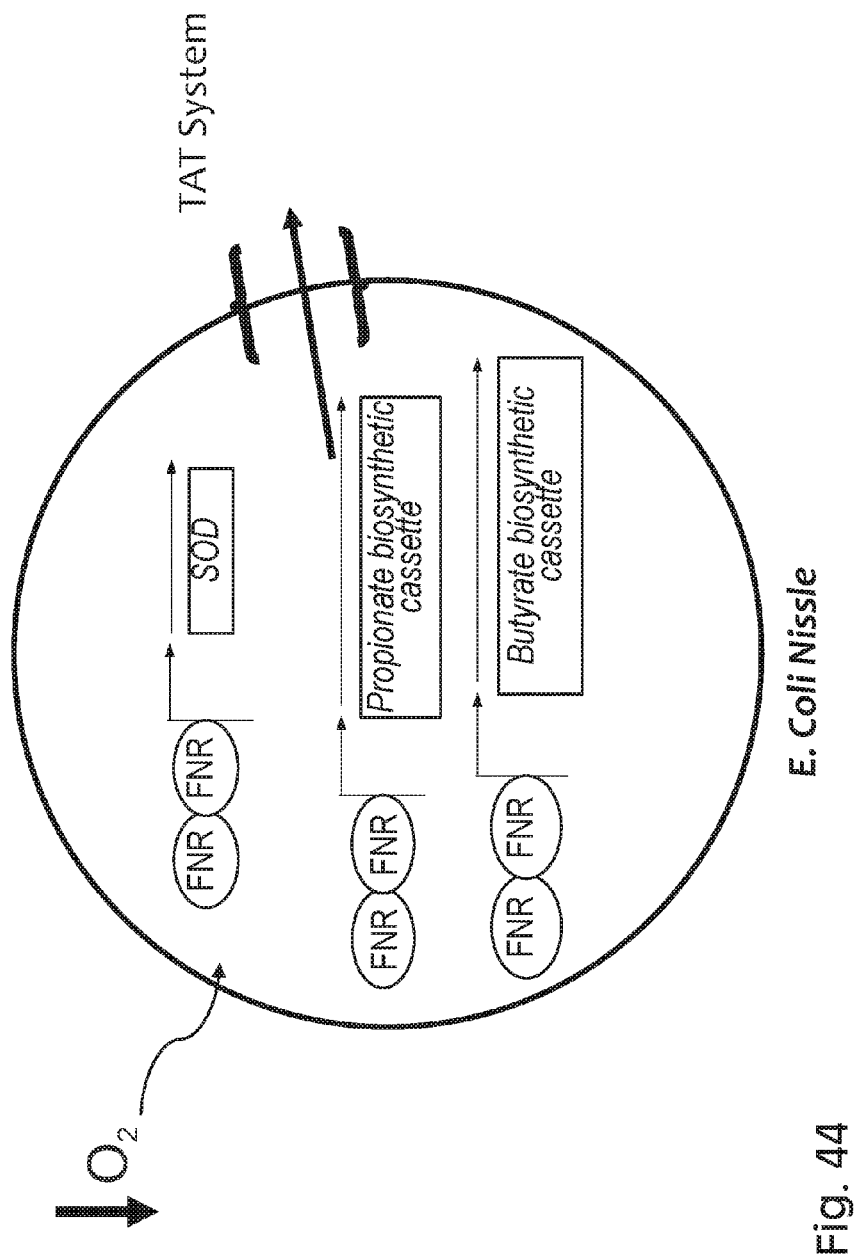
FIG. 44 depicts a schematic of an *E. coli* that is genetically engineered to express SOD, a propionate gene cassette, and a butyrate gene cassette under the control of a FNR-responsive promoter and further comprising a TAT secretion system.
Figure 45:
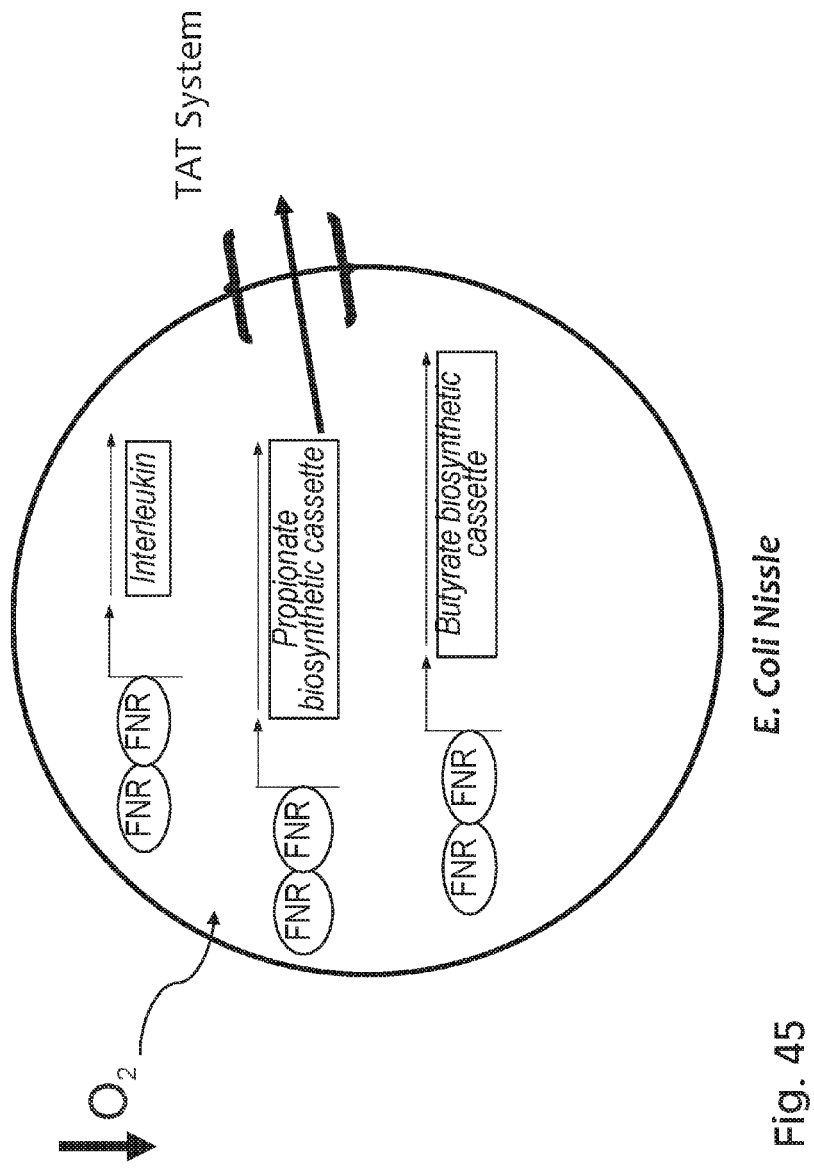
FIG. 45 depicts a schematic of an *E. coli* that is genetically engineered to express interleukin, a propionate gene cassette, and a butyrate gene cassette under the control of a FNR-responsive promoter and further comprising a TAT secretion system.
Figure 46:
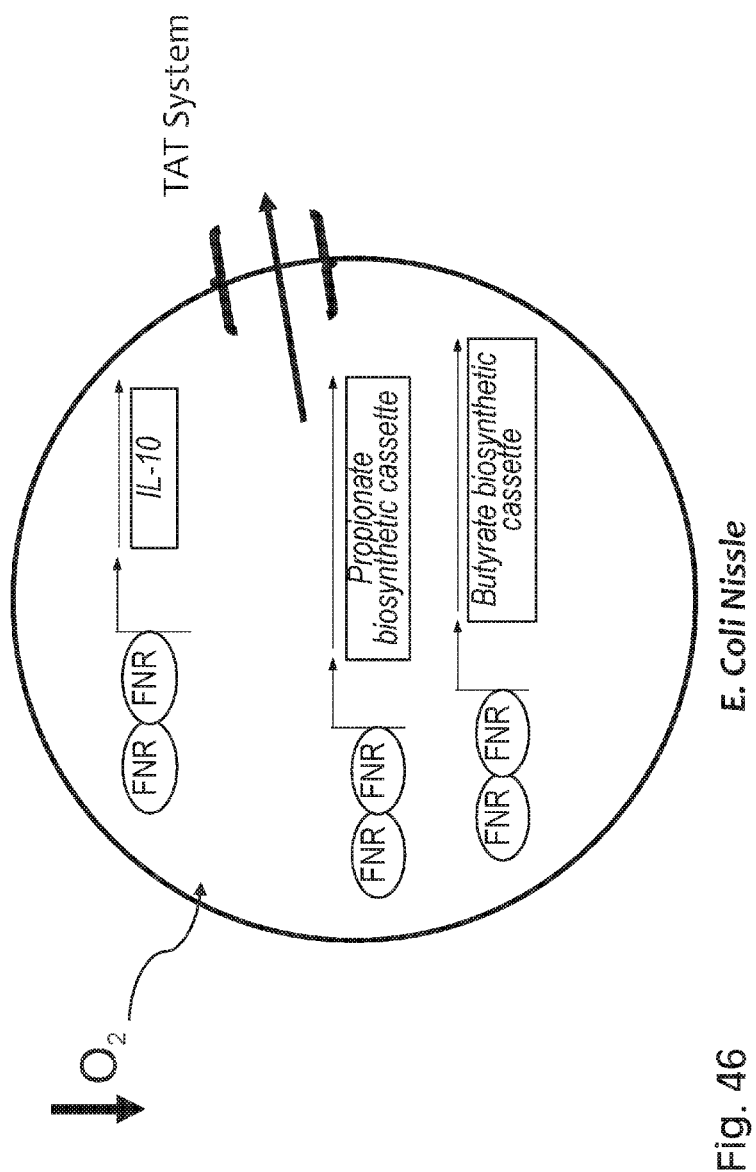
FIG. 46 depicts a schematic of an *E. coli* that is genetically engineered to express interleukin-10 (IL-10), a propionate gene cassette, and a butyrate gene cassette under the control of a FNR-responsive promoter and further comprising a TAT secretion system.
Figure 47:
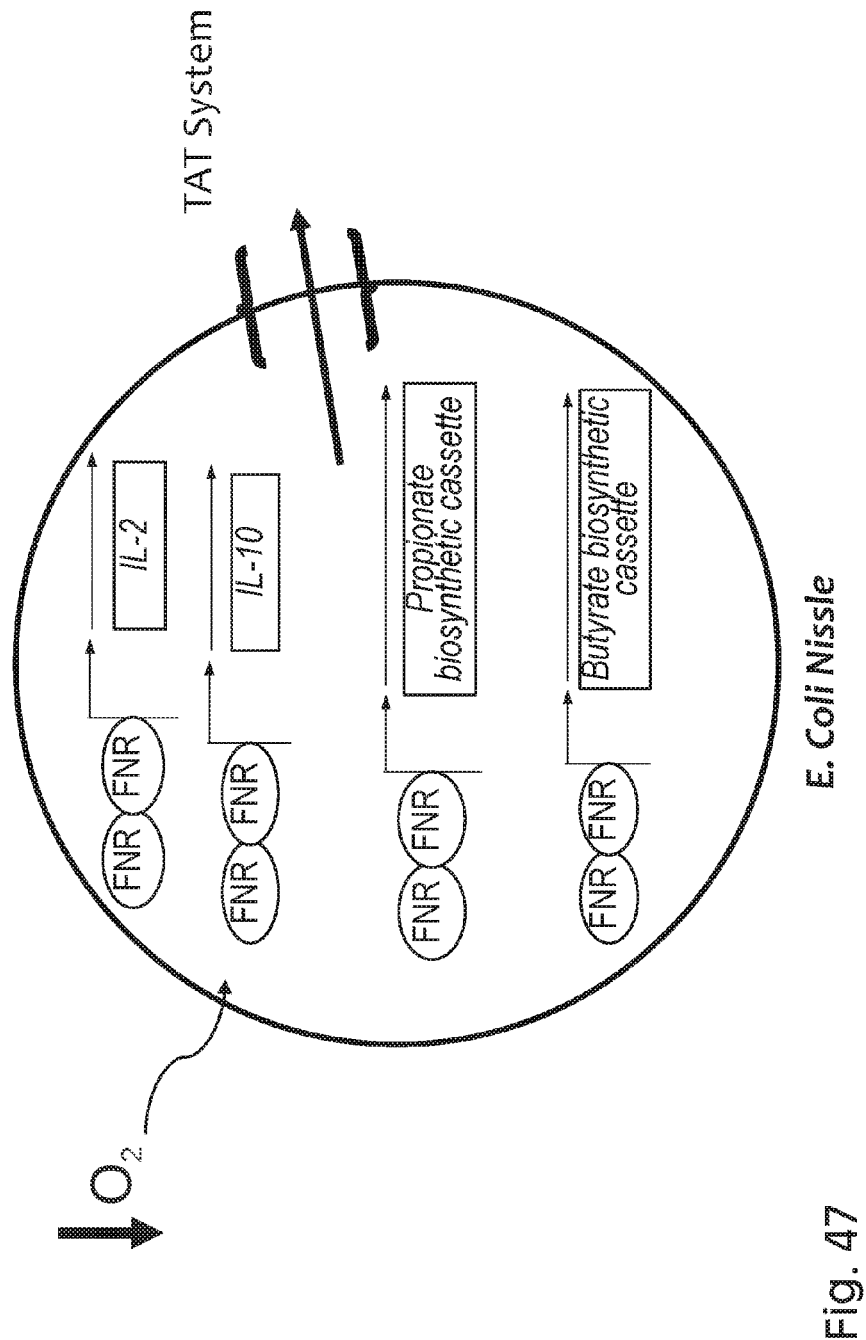
FIG. 47 depicts a schematic of an *E. coli* that is genetically engineered to express IL-2, IL-10, a propionate gene cassette, and a butyrate gene cassette under the control of a FNR-responsive promoter and further comprising a TAT secretion system.
Figure 48:
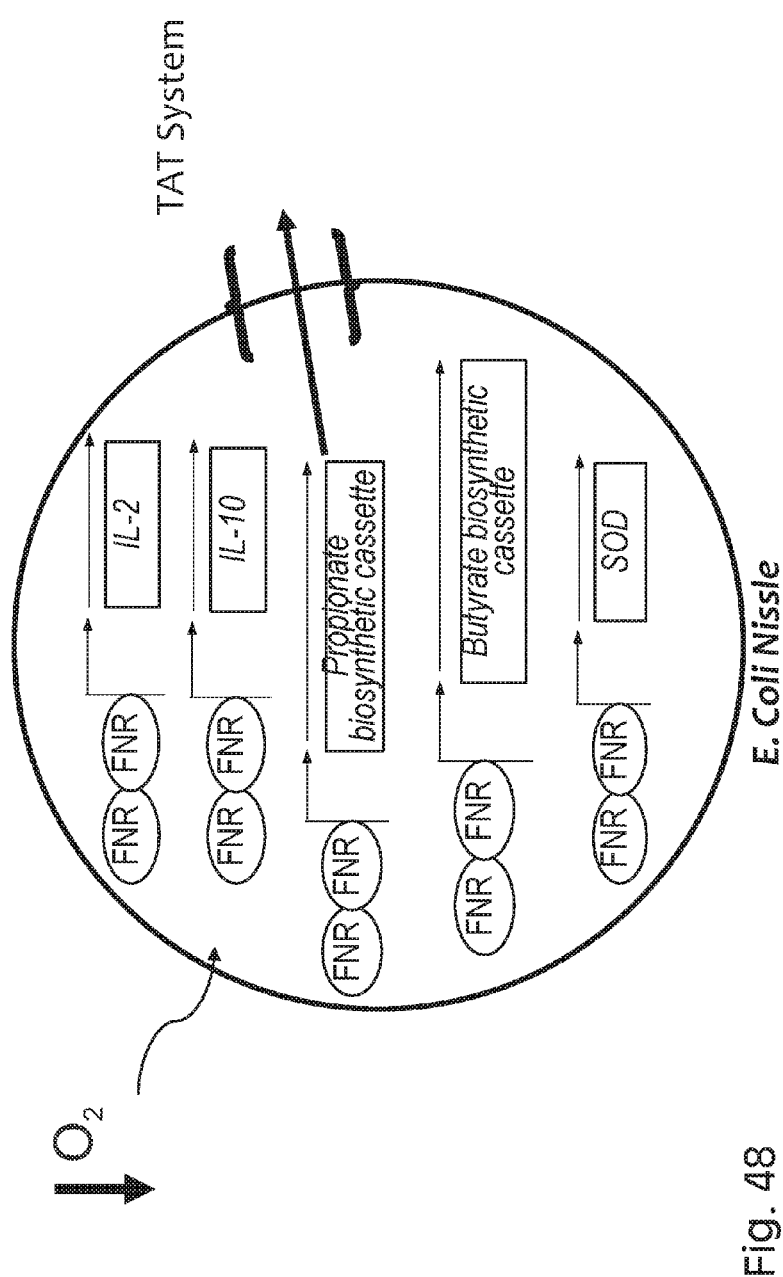
FIG. 48 depicts a schematic of an *E. coli* that is genetically engineered to express IL-2, IL-10, a propionate gene cassette, a butyrate gene cassette, and SOD under the control of a FNR-responsive promoter and further comprising a TAT secretion system.
Figure 49:
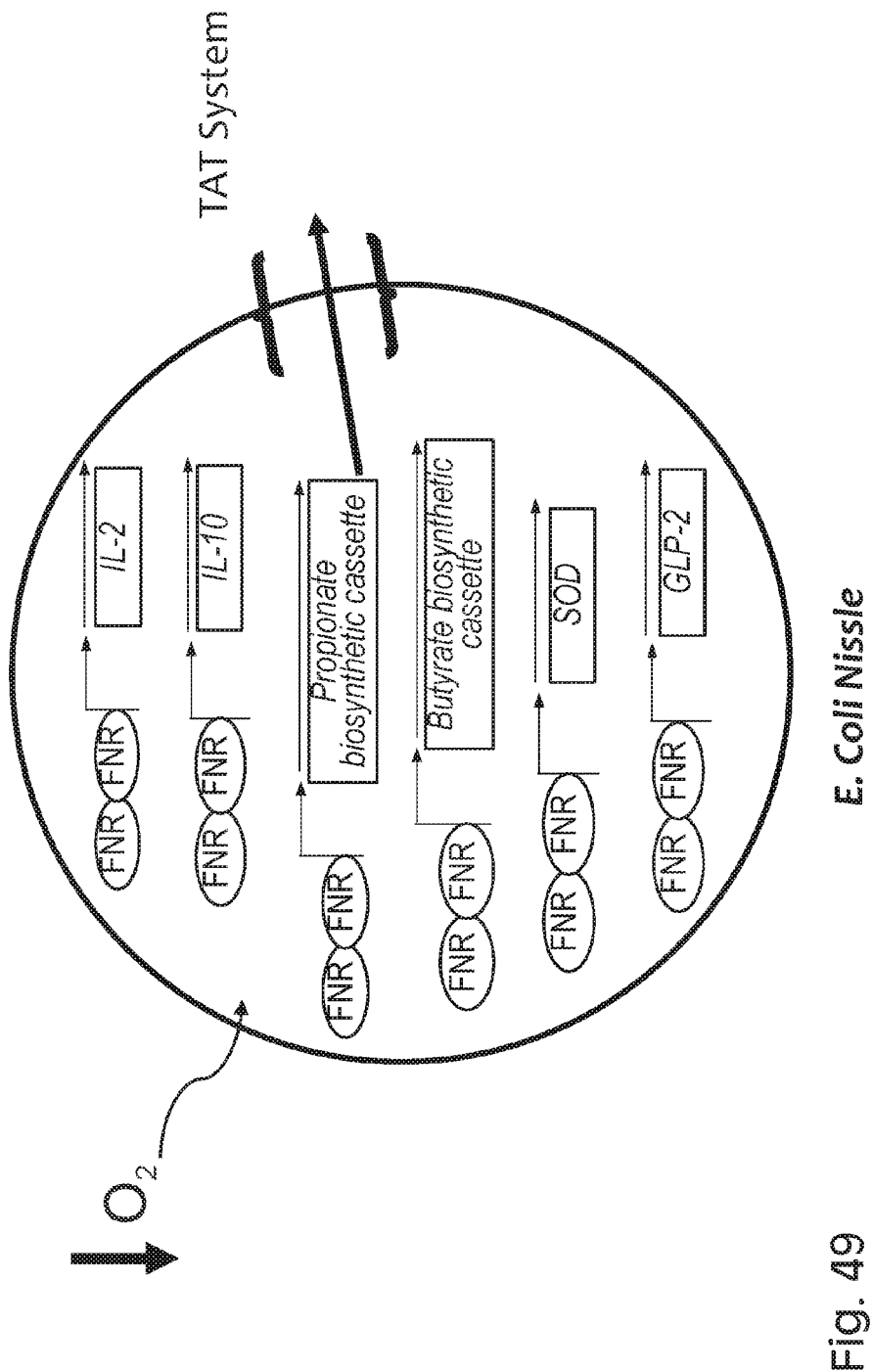
FIG. 49 depicts a schematic of an *E. coli* that is genetically engineered to express IL-2, IL-10, a propionate gene cassette, a butyrate gene cassette, SOD, and GLP-2 under the control of a FNR-responsive promoter and further comprising a TAT secretion system.
Figure 50:
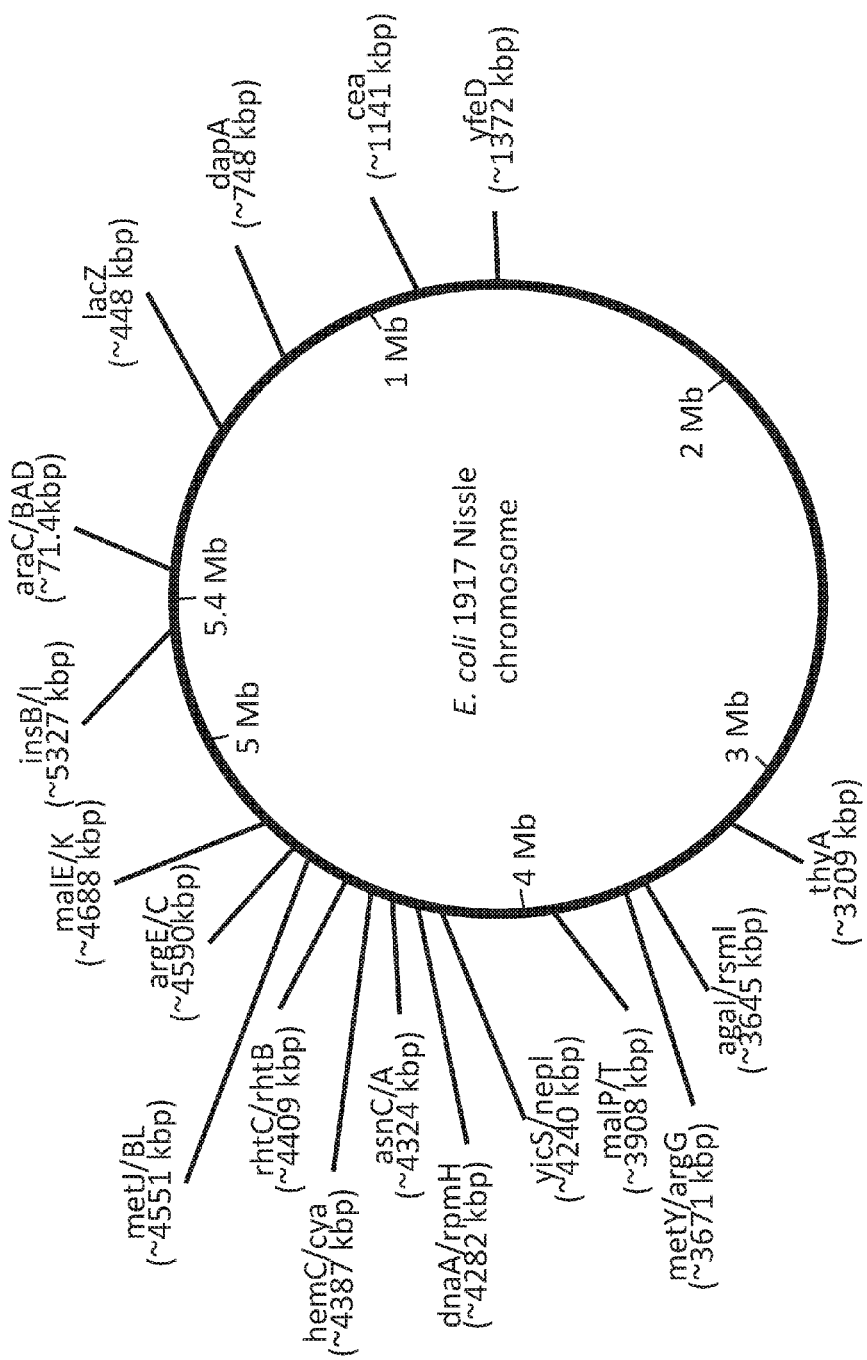
FIG. 50 depicts a map of exemplary integration sites within the *E. coli* 1917 Nissle chromosome. These sites indicate regions where circuit components may be inserted into the chromosome without interfering with essential gene expression. Backslashes (/) are used to show that the insertion will occur between divergently or convergently expressed genes. Insertions within biosynthetic genes, such as thyA, can be useful for creating nutrient auxotrophies. In some embodiments, an individual circuit component is inserted into more than one of the indicated sites.

FIG. 29 shows NO-GFP constructs (the dot blot) *E. coli* Nissle harboring the nitric oxide inducible NsrR-GFP reporter fusion were grown overnight in LB supplemented with kanamycin. Bacteria were then diluted 1:100 into LB containing kanamycin and grown to an optical density of 0.4-0.5 and then pelleted by centrifugation. Bacteria were resuspended in phosphate buffered saline and 100 microliters were administered by oral gavage to mice. IBD is induced in mice by supplementing drinking water with 2-3% dextran sodium sulfate for 7 days prior to bacterial gavage. At 4 hours post-gavage, mice were sacrificed and bacteria were recovered from colonic samples. Colonic contents were boiled in SOS, and the soluble fractions were used to perform a dot blot for GFP detection (induction of NsrR-regulated promoters). Detection of GFP was performed by binding of anti-GFP antibody conjugated to HRP (horse radish peroxidase). Detection was visualized using Pierce chemiluminescent detection kit. It is shown in the figure that NsrR-regulated promoters are induced in DSS-treated mice, but are not shown to be induced in untreated mice. This is consistent with the role of NsrR in response to NO, and thus inflammation.

Figure 15:
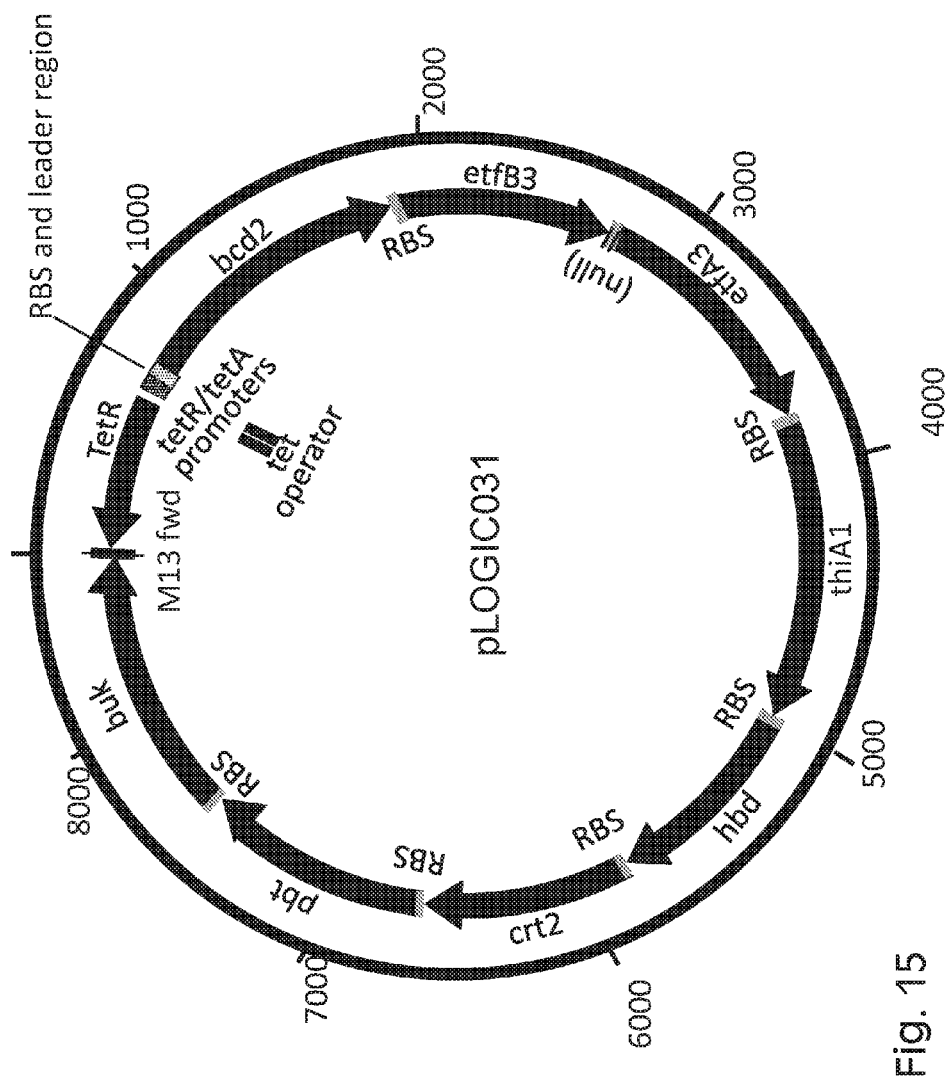
FIG. 15 depicts a schematic of a butyrate gene cassette, pLogic031 comprising the eight-gene butyrate cassette.
Figure 16:
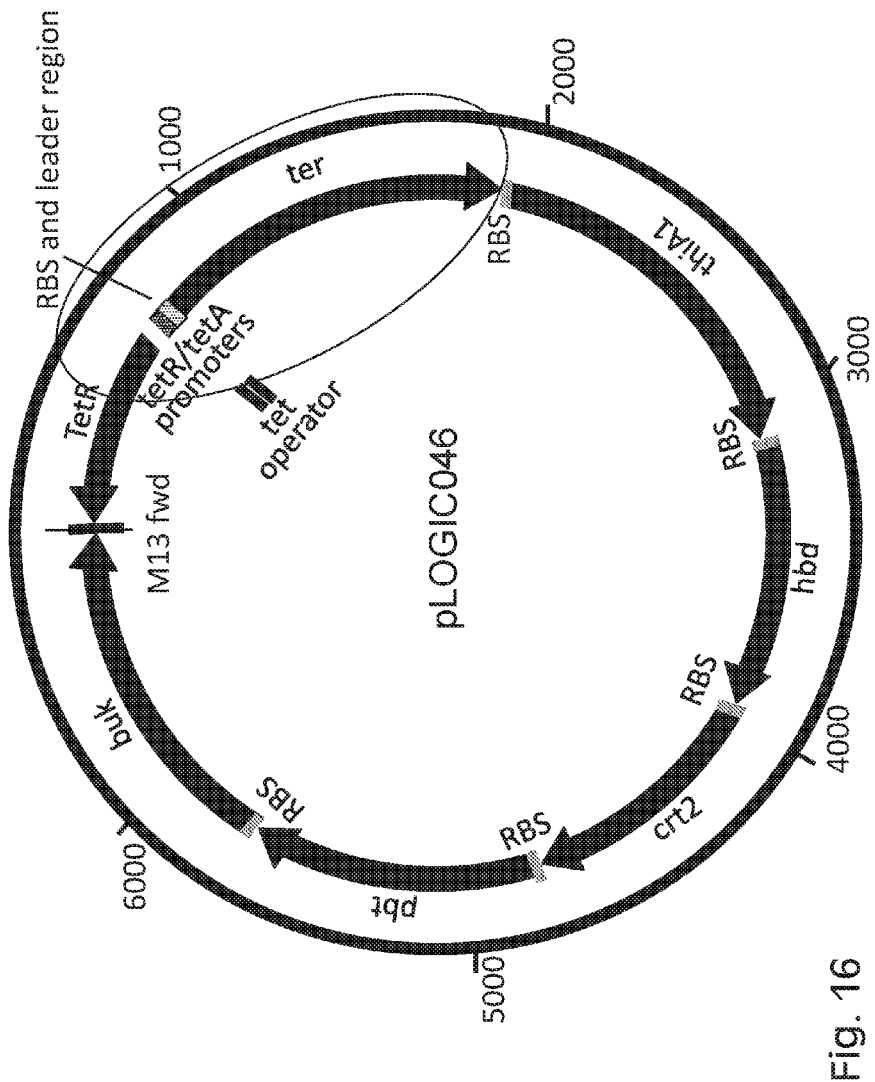
FIG. 16 depicts a schematic of a butyrate gene cassette, pLogic046 comprising the ter substitution (oval).
Figure 17:
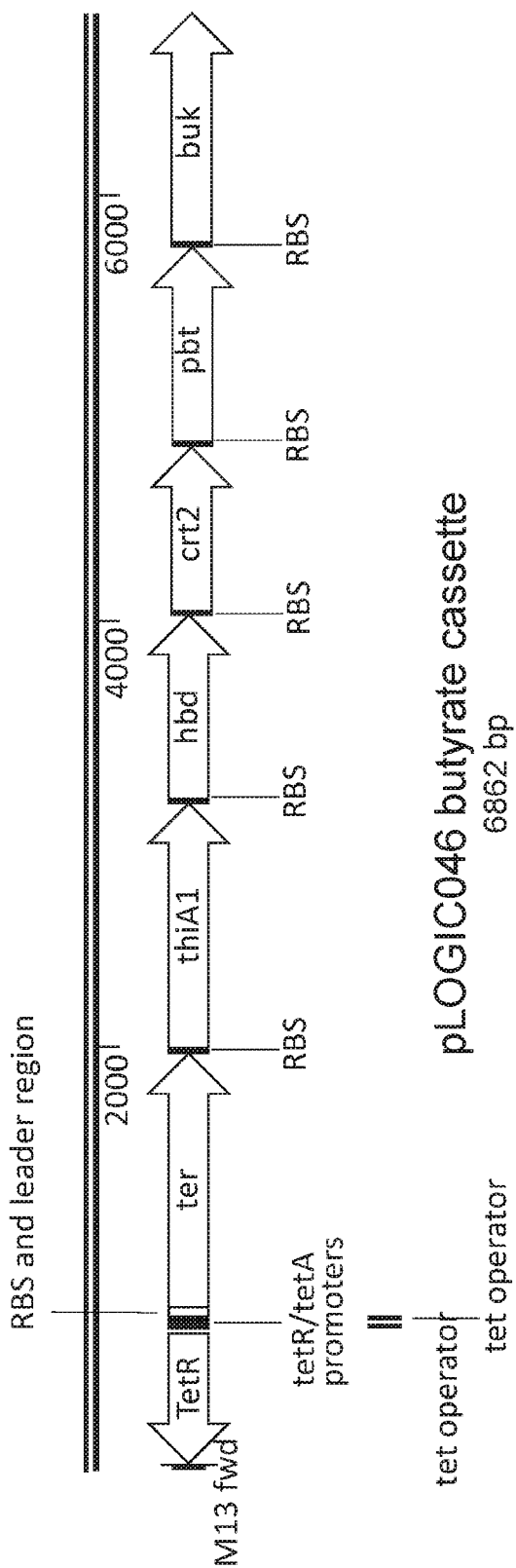
FIG. 17 depicts a linear schematic of a butyrate gene cassette, pLogic046.

Bacteria harboring a plasmid expressing NsrR under control of a constitutive promoter and the reporter gene gfp (green fluorescent protein) under control of an NsrR-inducible promoter were grown overnight in LB supplemented with kanamycin. Bacteria are then diluted 1:100 into LB containing kanamycin and grown to an optical density of about 0.4-0.5 and then pelleted by centrifugation. Bacteria are resuspended in phosphate buffered saline and 100 microliters were administered by oral gavage to mice. IBD is induced in mice by supplementing drinking water with 2-3% dextran sodium sulfate for 7 days prior to bacterial gavage. At 4 hours post-gavage, mice were sacrificed and bacteria were recovered from colonic samples. Colonic contents were boiled in SDS, and the soluble fractions were used to perform a dot blot for GFP detection (induction of NsrR-regulated promoters) Detection of GFP was performed by binding of anti-GFP antibody conjugated to HRP (horse radish peroxidase). Detection was visualized using Pierce chemiluminescent detection kit. FIG. 15 shows NsrR-regulated promoters are induced in DSS-treated mice, but not in untreated mice.

The invention claimed is:

1. A non-pathogenic bacterium comprising: a gene cassette encoding a biosynthetic pathway for producing butyrate, wherein the gene cassette is operably linked to a fumarate and nitrate reductase regulator (FNR)-responsive promoter, wherein the bacterium is *Escherichia coli* strain.

2. The bacterium of claim 1, wherein the bacterium is an auxotroph in diaminopimelic acid or an enzyme in the thymidine biosynthetic pathway.

3. A pharmaceutically acceptable composition comprising the bacterium of claim 2; and a pharmaceutically acceptable carrier.

4. The pharmaceutically acceptable composition of claim 3, formulated for oral or rectal administration.

5. The bacterium of claim 1, wherein the gene cassette is located on a chromosome in the bacterium.

6. The bacterium of claim 1, wherein the gene cassette is located on a plasmid in the bacterium.

* * * * *

UNITED STATES PATENT AND TRADEMARK OFFICE
CERTIFICATE OF CORRECTION

PATENT NO. : 10,273,489 B2
APPLICATION NO. : 15/301230
DATED : April 30, 2019
INVENTOR(S) : Dean Falb et al.

Page 1 of 1

It is certified that error appears in the above-identified patent and that said Letters Patent is hereby corrected as shown below:

In the Claims

Claim 1, Column 375, Line 60, "nitarate" should read --nitrate--.

Signed and Sealed this
Thirtieth Day of July, 2019

Andrei Iancu
*Director of the United States Patent and Trademark Office*

SEQUENCE LISTING

```
<160> NUMBER OF SEQ ID NOS: 86

<210> SEQ ID NO 1
<211> LENGTH: 1137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
atggatttaa attctaaaaa atatcagatg cttaaagagc tatatgtaag cttcgctgaa        60
aatgaagtta aacctttagc aacagaactt gatgaagaag aaagatttcc ttatgaaaca       120
gtggaaaaaa tggcaaaagc aggaatgatg ggtataccat atccaaaaga atatggtgga       180
gaaggtggag acactgtagg atatataatg gcagttgaag aattgtctag agtttgtggt       240
actacaggag ttatattatc agctcataca tctcttggct catggcctat atatcaatat       300
ggtaatgaag aacaaaaaca aaaattctta agaccactag caagtggaga aaaattagga       360
gcatttggtc ttactgagcc taatgctggt acagatgcgt ctggccaaca aacaactgct       420
gttttagacg gggatgaata catacttaat ggctcaaaaa tatttataac aaacgcaata       480
gctggtgaca tatatgtagt aatggcaatg actgataaat ctaaggggaa caaaggaata       540
```

```
tcagcattta tagttgaaaa aggaactcct gggtttagct ttggagttaa agaaaagaaa      600
atgggtataa gaggttcagc tacgagtgaa ttaatatttg aggattgcag aatacctaaa      660
gaaaatttac ttggaaaaga aggtcaagga tttaagatag caatgtctac tcttgatggt      720
ggtagaattg gtatagctgc acaagcttta ggtttagcac aaggtgctct tgatgaaact      780
gttaaatatg taaagaaag agtacaattt ggtagaccat tatcaaaatt ccaaaataca      840
caattccaat tagctgatat ggaagttaag gtacaagcgg ctagcacct tgtatatcaa       900 gcagctataa ataaagactt aggaaaacct tatggagtag aagcagcaat ggcaaaatta      960
tttgcagctg aaacagctat ggaagttact acaaaagctg tacaacttca tggaggatat     1020
ggatacactc gtgactatcc agtagaaaga atgatgagag atgctaagat aactgaaata     1080
tatgaaggaa ctagtgaagt tcaaagaatg gttatttcag gaaaactatt aaaatag       1137
```

<210> SEQ ID NO 2
<211> LENGTH: 783
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2

```
atgaatatag tcgtttgtat aaaacaagtt ccagatacaa cagaagttaa actagatcct       60
aatacaggta cttttaattag agatggagta ccaagtataa taaaccctga tgataaagca      120
ggtttagaag aagctataaa attaaaagaa gaaatgggtg ctcatgtaac tgttataaca      180
atgggacctc ctcaagcaga tatggcttta aagaagcttt agcaatggg tgcagataga       240 ggtatattat aacagatag agcatttgcg ggtgctgata cttgggcaac ttcatcagca       300
ttagcaggag cattaaaaaa tatagatttt gatattataa tagctggaag acaggcgata      360
gatggagata ctgcacaagt tggacctcaa atagctgaac atttaaatct tccatcaata      420
acatatgctg aagaaataaa aactgaaggt gaatatgtat tagtaaaaag acaatttgaa      480
gattgttgcc atgacttaaa agttaaaatg ccatgcctta taacaactct taagatatg      540 aacacaccaa gatacatgaa agttggaaga atatatgatg cttcgaaaaa tgatgtagta      600
gaaacatgga ctgtaaaaga tatagaagtt gaccttcta atttaggtct taaaggttct     660
ccaactagtg tatttaaatc atttacaaaa tcagttaaac cagctggtac aatatacaat      720
gaagatgcga aacatcagc tggaattatc atagataaat taaagagaa gtatatcata       780 taa                                                                    783
```

<210> SEQ ID NO 3
<211> LENGTH: 1011
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3

```
atgggtaacg ttttagtagt aatagaacaa agagaaatg taattcaaac tgtttctttta      60 gaattactag aaaggctac agaaatagca aaagattatg atacaaaagt ttctgcatta      120
cttttaggta gtaaggtaga aggtttaata gatacattag cacactatgg tgcagatgag      180
```

| | |
|---|---|
| gtaatagtag tagatgatga agctttagca gtgtatacaa ctgaaccata tacaaaagca | 240 |
| gcttatgaag caataaaagc agctgaccct atagttgtat tatttggtgc aacttcaata | 300 |
| ggtagagatt tagcgcctag agtttctgct agaatacata caggtcttac tgctgactgt | 360 |
| acaggtcttg cagtagctga agatacaaaa ttattattaa tgacaagacc tgcctttggt | 420 |
| ggaaatataa tggcaacaat agtttgtaaa gatttcagac ctcaaatgtc tacagttaga | 480 |
| ccagggggtta tgaagaaaaa tgaacctgat gaaactaaag aagctgtaat taaccgtttc | 540 |
| aaggtagaat ttaatgatgc tgataaatta gttcaagttg tacaagtaat aaaagaagct | 600 |
| aaaaaacaag ttaaaataga agatgctaag atattagttt ctgctggacg tggaatgggt | 660 |
| ggaaaagaaa acttagacat actttatgaa ttagctgaaa ttataggtgg agaagtttct | 720 |
| ggttctcgtg ccactataga tgcaggttgg ttagataaag caagacaagt tggtcaaact | 780 |
| ggtaaaactg taagaccaga cctttatata gcatgtggta tatctggagc aatacaacat | 840 |
| atagctggta tggaagatgc tgagtttata gttgctataa ataaaaatcc agaagctcca | 900 |
| atatttaaat atgctgatgt tggtatagtt ggagatgttc ataaagtgct tccagaactt | 960 |
| atcagtcagt taagtgttgc aaaagaaaaa ggtgaagttt tagctaacta a | 1011 |

<210> SEQ ID NO 4
<211> LENGTH: 1176
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 4

| | |
|---|---|
| atgagagaag tagtaattgc cagtgcagct agaacagcag taggaagttt tggaggagca | 60 |
| tttaaatcag tttcagcggt agagttaggg gtaacagcag ctaaagaagc tataaaaaga | 120 |
| gctaacataa ctccagatat gatagatgaa tctcttttag ggggagtact tacagcaggt | 180 |
| cttggacaaa atatagcaag acaaatagca ttaggagcag gaataccagt agaaaaacca | 240 |
| gctatgacta taaatatagt ttgtggttct ggattaagat ctgtttcaat ggcatctcaa | 300 |
| cttatagcat taggtgatgc tgatataatg ttagttggtg gagctgaaaa catgagtatg | 360 |
| tctccttatt tagtaccaag tgcgagatat ggtgcaagaa tgggtgatgc tgcttttgtt | 420 |
| gattcaatga taaagatgg attatcagac atatttaata actatcacat gggtattact | 480 |
| gctgaaaaca tagcagagca atggaatata actagagaag aacaagatga attagctctt | 540 |
| gcaagtcaaa ataaagctga aaaagctcaa gctgaaggaa atttgatga agaaatagtt | 600 |
| cctgttgtta taaaggaag aaaaggtgac actgtagtag ataaagatga atatattaag | 660 |
| cctggcacta caatggagaa acttgctaag ttaagacctg catttaaaaa agatggaaca | 720 |
| gttactgctg gtaatgcatc aggaataaat gatggtgctg ctatgttagt agtaatggct | 780 |
| aaagaaaaag ctgaagaact aggaatagag cctcttgcaa ctatagtttc ttatggaaca | 840 |
| gctggtgttg accctaaaat aatgggatat ggaccagttc cagcaactaa aaaagcttta | 900 |
| gaagctgcta atatgactat tgaagatata gatttagttg aagctaatga ggcatttgct | 960 |
| gcccaatctg tagctgtaat aagagactta aatatagata tgaataaagt taatgttaat | 1020 |
| ggtggagcaa tagctatagg acatccaata ggatgctcag gagcaagaat acttactaca | 1080 |
| cttttatatg aaatgaagag aagagatgct aaaactggtc ttgctacact ttgtataggc | 1140 |
| ggtggaatgg gaactacttt aatagttaag agatag | 1176 |

<210> SEQ ID NO 5
<211> LENGTH: 846
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5

| | | | | | |
|---|---|---|---|---|---|
| atgaaattag | ctgtaatagg | tagtggaact | atgggaagtg | gtattgtaca | aacttttgca | 60 |
| agttgtggac | atgatgtatg | tttaaagagt | agaactcaag | gtgctataga | taaatgttta | 120 |
| gctttattag | ataaaaattt | aactaagtta | gttactaagg | gaaaaatgga | tgaagctaca | 180 |
| aaagcagaaa | tattaagtca | tgttagttca | actactaatt | atgaagattt | aaaagatatg | 240 |
| gatttaataa | tagaagcatc | tgtagaagac | atgaatataa | agaaagatgt | tttcaagtta | 300 |
| ctagatgaat | tatgtaaaga | agatactatc | ttggcaacaa | atacttcatc | attatctata | 360 |
| acagaaatag | cttcttctac | taagcgccca | gataaagtta | taggaatgca | tttctttaat | 420 |
| ccagttccta | tgatgaaatt | agttgaagtt | ataagtggtc | agttaacatc | aaaagttact | 480 |
| tttgatacag | tatttgaatt | atctaagagt | atcaataaag | taccagtaga | tgtatctgaa | 540 |
| tctcctggat | tgtagtaaa | tagaatactt | atacctatga | taaatgaagc | tgttggtata | 600 |
| tatgcagatg | gtgttgcaag | taagaagaa | atagatgaag | ctatgaaatt | aggagcaaac | 660 |
| catccaatgg | gaccactagc | attaggtgat | ttaatcggat | tagatgttgt | tttagctata | 720 |
| atgaacgttt | tatatactga | atttggagat | actaaatata | gacctcatcc | acttttagct | 780 |
| aaaatggtta | gagctaatca | attaggaaga | aaaactaaga | taggattcta | tgattataat | 840 |
| aaataa | | | | | | 846 |

<210> SEQ ID NO 6
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

| | | | | | |
|---|---|---|---|---|---|
| atgagtacaa | gtgatgttaa | agtttatgag | aatgtagctg | ttgaagtaga | tggaaatata | 60 |
| tgtacagtga | aaatgaatag | acctaaagcc | cttaatgcaa | taaattcaaa | gactttagaa | 120 |
| gaactttatg | aagtatttgt | agatattaat | aatgatgaaa | ctattgatgt | tgtaatattg | 180 |
| acagggaag | gaaaggcatt | tgtagctgga | gcagatattg | catacatgaa | agatttagat | 240 |
| gctgtagctg | ctaaagattt | tagtatctta | ggagcaaaag | cttttggaga | aatagaaaat | 300 |
| agtaaaaaag | tagtgatagc | tgctgtaaac | ggatttgctt | taggtggagg | atgtgaactt | 360 |
| gcaatggcat | gtgatataag | aattgcatct | gctaaagcta | atttggtca | gccagaagta | 420 |
| actcttggaa | taactccagg | atatggagga | actcaaaggc | ttacaagatt | ggttggaatg | 480 |
| gcaaaagcaa | agaattaat | ctttacaggt | caagttataa | aagctgatga | agctgaaaaa | 540 |
| atagggctag | taaatagagt | cgttgagcca | gacattttaa | tagaagaagt | tgagaaatta | 600 |
| gctaagataa | tagctaaaaa | tgctcagctt | gcagttagat | actctaaaga | agcaatacaa | 660 |
| cttggtgctc | aaactgatat | aaatactgga | atagatatag | aatctaattt | atttggtctt | 720 |

| | |
|---|---|
| tgtttttcaa ctaaagacca aaaagaagga atgtcagctt tcgttgaaaa gagagaagct | 780 |
| aactttataa aagggtaa | 798 |

<210> SEQ ID NO 7
<211> LENGTH: 903
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7

| | |
|---|---|
| atgagaagtt ttgaagaagt aattaagttt gcaaagaaaa gaggacctaa aactatatca | 60 |
| gtagcatgtt gccaagataa agaagtttta atggcagttg aaatggctag aaaagaaaaa | 120 |
| atagcaaatg ccattttagt aggagatata gaaaagacta agaaattgc aaaaagcata | 180 |
| gacatggata tcgaaaatta tgaactgata gatataaaag atttagcaga agcatctcta | 240 |
| aaatctgttg aattagtttc acaaggaaaa gccgacatgg taatgaaagg cttagtagac | 300 |
| acatcaataa tactaaaagc agtttttaaat aaagaagtag gtcttagaac tggaaatgta | 360 |
| ttaagtcacg tagcagtatt tgatgtagag ggatatgata gattattttt cgtaactgac | 420 |
| gcagctatga acttagctcc tgatacaaat actaaaaagc aaatcataga aaatgcttgc | 480 |
| acagtagcac attcattaga tataagtgaa ccaaaagttg ctgcaatatg cgcaaaagaa | 540 |
| aaagtaaatc caaaaatgaa agatacagtt gaagctaaag aactagaaga atgtatgaa | 600 |
| agaggagaaa tcaaaggttg tatggttggt gggccttttg caattgataa tgcagtatct | 660 |
| ttagaagcag ctaaacataa aggtataaat catcctgtag caggacgagc tgatatatta | 720 |
| ttagccccag atattgaagg tggtaacata ttatataaag ctttggtatt cttctcaaaa | 780 |
| tcaaaaaatg caggagttat agttggggct aaagcaccaa taatattaac ttctagagca | 840 |
| gacagtgaag aaactaaact aaactcaata gctttaggtg ttttaatggc agcaaaggca | 900 |
| taa | 903 |

<210> SEQ ID NO 8
<211> LENGTH: 1080
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

| | |
|---|---|
| atgagcaaaa tatttaaaat cttaacaata aatcctggtt cgacatcaac taaaatagct | 60 |
| gtatttgata tgaggatttt agtatttgaa aaaactttaa gacattcttc agaagaaata | 120 |
| ggaaaatatg agaaggtgtc tgaccaattt gaatttcgta acaagtaat agaagaagct | 180 |
| ctaaaagaag gtggagtaaa aacatctgaa ttagatgctg tagtaggtag aggaggactt | 240 |
| cttaaaccta taaaaggtgg tacttattca gtaagtgctg ctatgattga agatttaaaa | 300 |
| gtgggagttt taggagaaca cgcttcaaac ctaggtggaa taatagcaaa acaaataggt | 360 |
| gaagaagtaa atgttccttc atacatagta gaccctgttg ttgtagatga attagaagat | 420 |
| gttgctagaa tttctggtat gcctgaaata agtagagcaa gtgtagtaca tgctttaaat | 480 |
| caaaaggcaa tagcaagaag atatgctaga gaaataaaca gaaatatga agatataaat | 540 |
| cttatagttg cacacatggg tggaggagtt tctgttggag ctcataaaaa tggtaaaata | 600 |

```
gtagatgttg caaacgcatt agatggagaa ggacctttct ctccagaaag aagtggtgga    660
ctaccagtag gtgcattagt aaaaatgtgc tttagtggaa aatatactca agatgaaatt    720
aaaaagaaaa taaaaggtaa tggcggacta gttgcatact aaacactaa tgatgctaga     780 gaagttgaag aaagaattga agctggtgat gaaaaagcta aattagtata tgaagctatg    840
gcatatcaaa tctctaaaga aataggagct agtgctgcag ttcttaaggg agatgtaaaa    900
gcaatattat taactggtgg aatcgcatat tcaaaaatgt ttacagaaat gattgcagat    960
agagttaaat ttatagcaga tgtaaaagtt tatccaggtg aagatgaaat gattgcatta   1020
gctcaaggtg gacttagagt tttaactggt gaagaagagg ctcaagttta tgataactaa   1080
```

<210> SEQ ID NO 9
<211> LENGTH: 1194
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9

```
atgatcgtaa aacctatggt acgcaacaat atctgcctga acgcccatcc tcagggctgc     60
aagaagggag tggaagatca gattgaatat accaagaaac gcattaccgc agaagtcaaa   120
gctggcgcaa aagctccaaa aaacgttctg gtgcttggct gctcaaatgg ttacggcctg    180
gcgagccgca ttactgctgc gttcggatac ggggctgcga ccatcggcgt gtcctttgaa    240
aaagcgggtt cagaaaccaa atatggtaca ccgggatggt acaataattt ggcatttgat    300
gaagcggcaa aacgcgaggg tctttatagc gtgacgatcg acggcgatgc gttttcagac    360
gagatcaagg cccaggtaat tgaggaagcc aaaaaaaag gtatcaaatt tgatctgatc     420
gtatacagct tggccagccc agtacgtact gatcctgata caggtatcat gcacaaaagc    480
gttttgaaac cctttggaaa aacgttcaca ggcaaaacag tagatccgtt tactggcgag    540
ctgaaggaaa tctccgcgga accagcaaat gacgaggaag cagccgccac tgttaaagtt    600 atgggggtg aagattggga acgttggatt aagcagctgt cgaaggaagg cctcttagaa    660
gaaggctgta ttaccttggc ctatagttat attggccctg aagctaccca agctttgtac    720
cgtaaaggca caatcggcaa ggccaaagaa cacctggagg ccacagcaca ccgtctcaac    780
aaagagaacc cgtcaatccg tgccttcgtg agcgtgaata aaggcctggt aacccgcgca    840
agcgccgtaa tcccggtaat ccctctgtat ctcgccagct tgttcaaagt aatgaaagag    900
aagggcaatc atgaaggttg tattgaacag atcacgcgtc tgtacgccga gcgcctgtac    960
cgtaaagatg gtacaattcc agttgatgag gaaaatcgca ttcgcattga tgattgggag   1020
ttagaagaag acgtccagaa agcggtatcc gcgttgatgg agaaagtcac gggtgaaaac   1080
gcagaatctc tcactgactt agcggggtac cgccatgatt tcttagctag taacggcttt   1140
gatgtagaag gtattaatta tgaagcggaa gttgaacgct tcgaccgtat ctga         1194
```

<210> SEQ ID NO 10
<211> LENGTH: 861
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10

```
atgagtcagg cgctaaaaaa tttactgaca ttgttaaatc tggaaaaaat tgaggaagga      60
ctctttcgcg gccagagtga agatttaggt ttacgccagg tgtttggcgg ccaggtcgtg     120
ggtcaggcct tgtatgctgc aaaagagacc gtccctgaag agcggctggt acattcgttt     180
cacagctact tcttcgccc tggcgatagt aagaagccga ttatttatga tgtcgaaacg     240
ctgcgtgacg gtaacagctt cagcgcccgc cgggttgctg ctattcaaaa cggcaaaccg     300
atttttata tgactgcctc tttccaggca ccagaagcgg gtttcgaaca tcaaaaaaca     360
atgccgtccg cgccagcgcc tgatggcctc ccttcggaaa cgcaaatcgc caatcgctg     420
gcgcacctgc tgccgccagt gctgaaagat aaattcatct gcgatcgtcc gctggaagtc     480
cgtccggtgg agtttcataa cccactgaaa ggtcacgtcg cagaaccaca tcgtcaggtg     540
tggatccgcg caaatggtag cgtgccggat gacctgcgcg ttcatcagta tctgctcggt     600
tacgcttctg atcttaactt cctgccggta gctctacagc cgcacggcat cggttttctc     660
gaaccgggga ttcagattgc caccattgac cattccatgt ggttccatcg cccgtttaat     720
ttgaatgaat ggctgctgta tagcgtggag agcacctcgg cgtccagcgc acgtggcttt     780
gtgcgcggtg agtttatac ccaagacggc gtactggttg cctcgaccgt tcaggaaggg     840
gtgatgcgta atcacaatta a                                                861
```

<210> SEQ ID NO 11
<211> LENGTH: 378
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Met Asp Leu Asn Ser Lys Lys Tyr Gln Met Leu Lys Glu Leu Tyr Val
1               5                   10                  15

Ser Phe Ala Glu Asn Glu Val Lys Pro Leu Ala Thr Glu Leu Asp Glu
            20                  25                  30

Glu Glu Arg Phe Pro Tyr Glu Thr Val Glu Lys Met Ala Lys Ala Gly
        35                  40                  45

Met Met Gly Ile Pro Tyr Pro Lys Glu Tyr Gly Gly Glu Gly Gly Asp
    50                  55                  60

Thr Val Gly Tyr Ile Met Ala Val Glu Glu Leu Ser Arg Val Cys Gly
65                  70                  75                  80

Thr Thr Gly Val Ile Leu Ser Ala His Thr Ser Leu Gly Ser Trp Pro
                85                  90                  95

Ile Tyr Gln Tyr Gly Asn Glu Glu Gln Lys Gln Lys Phe Leu Arg Pro
            100                 105                 110

Leu Ala Ser Gly Glu Lys Leu Gly Ala Phe Gly Leu Thr Glu Pro Asn
        115                 120                 125

Ala Gly Thr Asp Ala Ser Gly Gln Gln Thr Thr Ala Val Leu Asp Gly
    130                 135                 140

Asp Glu Tyr Ile Leu Asn Gly Ser Lys Ile Phe Ile Thr Asn Ala Ile
145                 150                 155                 160

Ala Gly Asp Ile Tyr Val Val Met Ala Met Thr Asp Lys Ser Lys Gly
                165                 170                 175

Asn Lys Gly Ile Ser Ala Phe Ile Val Glu Lys Gly Thr Pro Gly Phe
            180                 185                 190
```

```
Ser Phe Gly Val Lys Glu Lys Met Gly Ile Arg Gly Ser Ala Thr
        195                 200                 205

Ser Glu Leu Ile Phe Glu Asp Cys Arg Ile Pro Lys Glu Asn Leu Leu
210                 215                 220

Gly Lys Glu Gly Gln Gly Phe Lys Ile Ala Met Ser Thr Leu Asp Gly
225                 230                 235                 240

Gly Arg Ile Gly Ile Ala Ala Gln Ala Leu Gly Leu Ala Gln Gly Ala
                245                 250                 255

Leu Asp Glu Thr Val Lys Tyr Val Lys Glu Arg Val Gln Phe Gly Arg
                260                 265                 270

Pro Leu Ser Lys Phe Gln Asn Thr Gln Phe Gln Leu Ala Asp Met Glu
                275                 280                 285

Val Lys Val Gln Ala Ala Arg His Leu Val Tyr Gln Ala Ala Ile Asn
                290                 295                 300

Lys Asp Leu Gly Lys Pro Tyr Gly Val Glu Ala Ala Met Ala Lys Leu
305                 310                 315                 320

Phe Ala Ala Glu Thr Ala Met Glu Val Thr Thr Lys Ala Val Gln Leu
                325                 330                 335

His Gly Gly Tyr Gly Tyr Thr Arg Asp Tyr Pro Val Glu Arg Met Met
                340                 345                 350

Arg Asp Ala Lys Ile Thr Glu Ile Tyr Glu Gly Thr Ser Glu Val Gln
                355                 360                 365

Arg Met Val Ile Ser Gly Lys Leu Leu Lys
                370                 375

<210> SEQ ID NO 12
<211> LENGTH: 260
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Asn Ile Val Val Cys Ile Lys Gln Val Pro Asp Thr Thr Glu Val
1               5                   10                  15

Lys Leu Asp Pro Asn Thr Gly Thr Leu Ile Arg Asp Gly Val Pro Ser
                20                  25                  30

Ile Ile Asn Pro Asp Asp Lys Ala Gly Leu Glu Glu Ala Ile Lys Leu
                35                  40                  45

Lys Glu Glu Met Gly Ala His Val Thr Val Ile Thr Met Gly Pro Pro
50                  55                  60

Gln Ala Asp Met Ala Leu Lys Glu Ala Leu Ala Met Gly Ala Asp Arg
65                  70                  75                  80

Gly Ile Leu Leu Thr Asp Arg Ala Phe Ala Gly Ala Asp Thr Trp Ala
                85                  90                  95

Thr Ser Ser Ala Leu Ala Gly Ala Leu Lys Asn Ile Asp Phe Asp Ile
                100                 105                 110

Ile Ile Ala Gly Arg Gln Ala Ile Asp Gly Asp Thr Ala Gln Val Gly
                115                 120                 125

Pro Gln Ile Ala Glu His Leu Asn Leu Pro Ser Ile Thr Tyr Ala Glu
                130                 135                 140

Glu Ile Lys Thr Glu Gly Glu Tyr Val Leu Val Lys Arg Gln Phe Glu
145                 150                 155                 160
```

```
Asp Cys Cys His Asp Leu Lys Val Lys Met Pro Cys Leu Ile Thr Thr
            165                 170                 175

Leu Lys Asp Met Asn Thr Pro Arg Tyr Met Lys Val Gly Arg Ile Tyr
        180                 185                 190

Asp Ala Phe Glu Asn Asp Val Val Glu Thr Trp Thr Val Lys Asp Ile
        195                 200                 205

Glu Val Asp Pro Ser Asn Leu Gly Leu Lys Gly Ser Pro Thr Ser Val
    210                 215                 220

Phe Lys Ser Phe Thr Lys Ser Val Lys Pro Ala Gly Thr Ile Tyr Asn
225                 230                 235                 240

Glu Asp Ala Lys Thr Ser Ala Gly Ile Ile Asp Lys Leu Lys Glu
                245                 250                 255

Lys Tyr Ile Ile
            260

<210> SEQ ID NO 13
<211> LENGTH: 336
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Gly Asn Val Leu Val Val Ile Glu Gln Arg Glu Asn Val Ile Gln
1               5                   10                  15

Thr Val Ser Leu Glu Leu Leu Gly Lys Ala Thr Glu Ile Ala Lys Asp
            20                  25                  30

Tyr Asp Thr Lys Val Ser Ala Leu Leu Gly Ser Lys Val Glu Gly
        35                  40                  45

Leu Ile Asp Thr Leu Ala His Tyr Gly Ala Asp Glu Val Ile Val Val
    50                  55                  60

Asp Asp Glu Ala Leu Ala Val Tyr Thr Thr Glu Pro Tyr Thr Lys Ala
65                  70                  75                  80

Ala Tyr Glu Ala Ile Lys Ala Ala Asp Pro Ile Val Val Leu Phe Gly
                85                  90                  95

Ala Thr Ser Ile Gly Arg Asp Leu Ala Pro Arg Val Ser Ala Arg Ile
            100                 105                 110

His Thr Gly Leu Thr Ala Asp Cys Thr Gly Leu Ala Val Ala Glu Asp
        115                 120                 125

Thr Lys Leu Leu Leu Met Thr Arg Pro Ala Phe Gly Gly Asn Ile Met
    130                 135                 140

Ala Thr Ile Val Cys Lys Asp Phe Arg Pro Gln Met Ser Thr Val Arg
145                 150                 155                 160

Pro Gly Val Met Lys Lys Asn Glu Pro Asp Glu Thr Lys Glu Ala Val
                165                 170                 175

Ile Asn Arg Phe Lys Val Glu Phe Asn Asp Ala Asp Lys Leu Val Gln
            180                 185                 190

Val Val Gln Val Ile Lys Glu Ala Lys Gln Val Lys Ile Glu Asp
        195                 200                 205

Ala Lys Ile Leu Val Ser Ala Gly Arg Gly Met Gly Gly Lys Glu Asn
    210                 215                 220

Leu Asp Ile Leu Tyr Glu Leu Ala Glu Ile Ile Gly Gly Glu Val Ser
225                 230                 235                 240

Gly Ser Arg Ala Thr Ile Asp Ala Gly Trp Leu Asp Lys Ala Arg Gln
```

```
            245                 250                 255
Val Gly Gln Thr Gly Lys Thr Val Arg Pro Asp Leu Tyr Ile Ala Cys
            260                 265                 270

Gly Ile Ser Gly Ala Ile Gln His Ile Ala Gly Met Glu Asp Ala Glu
            275                 280                 285

Phe Ile Val Ala Ile Asn Lys Asn Pro Glu Ala Pro Ile Phe Lys Tyr
            290                 295                 300

Ala Asp Val Gly Ile Val Gly Asp Val His Lys Val Leu Pro Glu Leu
305                 310                 315                 320

Ile Ser Gln Leu Ser Val Ala Lys Glu Lys Gly Glu Val Leu Ala Asn
            325                 330                 335

<210> SEQ ID NO 14
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Arg Glu Val Val Ile Ala Ser Ala Ala Arg Thr Ala Val Gly Ser
1               5                   10                  15

Phe Gly Gly Ala Phe Lys Ser Val Ser Ala Val Glu Leu Gly Val Thr
            20                  25                  30

Ala Ala Lys Glu Ala Ile Lys Arg Ala Asn Ile Thr Pro Asp Met Ile
            35                  40                  45

Asp Glu Ser Leu Leu Gly Gly Val Leu Thr Ala Gly Leu Gly Gln Asn
50                  55                  60

Ile Ala Arg Gln Ile Ala Leu Gly Ala Gly Ile Pro Val Glu Lys Pro
65                  70                  75                  80

Ala Met Thr Ile Asn Ile Val Cys Gly Ser Gly Leu Arg Ser Val Ser
            85                  90                  95

Met Ala Ser Gln Leu Ile Ala Leu Gly Asp Ala Asp Ile Met Leu Val
            100                 105                 110

Gly Gly Ala Glu Asn Met Ser Met Ser Pro Tyr Leu Val Pro Ser Ala
            115                 120                 125

Arg Tyr Gly Ala Arg Met Gly Asp Ala Ala Phe Val Asp Ser Met Ile
            130                 135                 140

Lys Asp Gly Leu Ser Asp Ile Phe Asn Asn Tyr His Met Gly Ile Thr
145                 150                 155                 160

Ala Glu Asn Ile Ala Glu Gln Trp Asn Ile Thr Arg Glu Glu Gln Asp
            165                 170                 175

Glu Leu Ala Leu Ala Ser Gln Asn Lys Ala Glu Lys Ala Gln Ala Glu
            180                 185                 190

Gly Lys Phe Asp Glu Glu Ile Val Pro Val Val Ile Lys Gly Arg Lys
            195                 200                 205

Gly Asp Thr Val Val Asp Lys Asp Glu Tyr Ile Lys Pro Gly Thr Thr
            210                 215                 220

Met Glu Lys Leu Ala Lys Leu Arg Pro Ala Phe Lys Lys Asp Gly Thr
225                 230                 235                 240

Val Thr Ala Gly Asn Ala Ser Gly Ile Asn Asp Gly Ala Ala Met Leu
            245                 250                 255

Val Val Met Ala Lys Glu Lys Ala Glu Glu Leu Gly Ile Glu Pro Leu
            260                 265                 270
```

```
Ala Thr Ile Val Ser Tyr Gly Thr Ala Gly Val Asp Pro Lys Ile Met
            275                 280                 285

Gly Tyr Gly Pro Val Pro Ala Thr Lys Lys Ala Leu Glu Ala Ala Asn
        290                 295                 300

Met Thr Ile Glu Asp Ile Asp Leu Val Glu Ala Asn Glu Ala Phe Ala
305                 310                 315                 320

Ala Gln Ser Val Ala Val Ile Arg Asp Leu Asn Ile Asp Met Asn Lys
                325                 330                 335

Val Asn Val Asn Gly Gly Ala Ile Ala Ile Gly His Pro Ile Gly Cys
            340                 345                 350

Ser Gly Ala Arg Ile Leu Thr Thr Leu Leu Tyr Glu Met Lys Arg Arg
            355                 360                 365

Asp Ala Lys Thr Gly Leu Ala Thr Leu Cys Ile Gly Gly Gly Met Gly
            370                 375                 380

Thr Thr Leu Ile Val Lys Arg
385                 390

<210> SEQ ID NO 15
<211> LENGTH: 281
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Met Lys Leu Ala Val Ile Gly Ser Gly Thr Met Gly Ser Gly Ile Val
1               5                   10                  15

Gln Thr Phe Ala Ser Cys Gly His Asp Val Cys Leu Lys Ser Arg Thr
            20                  25                  30

Gln Gly Ala Ile Asp Lys Cys Leu Ala Leu Leu Asp Lys Asn Leu Thr
        35                  40                  45

Lys Leu Val Thr Lys Gly Lys Met Asp Glu Ala Thr Lys Ala Glu Ile
    50                  55                  60

Leu Ser His Val Ser Ser Thr Thr Asn Tyr Glu Asp Leu Lys Asp Met
65                  70                  75                  80

Asp Leu Ile Ile Glu Ala Ser Val Glu Asp Met Asn Ile Lys Lys Asp
                85                  90                  95

Val Phe Lys Leu Leu Asp Glu Leu Cys Lys Glu Asp Thr Ile Leu Ala
            100                 105                 110

Thr Asn Thr Ser Ser Leu Ser Ile Thr Glu Ile Ala Ser Ser Thr Lys
        115                 120                 125

Arg Pro Asp Lys Val Ile Gly Met His Phe Phe Asn Pro Val Pro Met
    130                 135                 140

Met Lys Leu Val Glu Val Ile Ser Gly Gln Leu Thr Ser Lys Val Thr
145                 150                 155                 160

Phe Asp Thr Val Phe Glu Leu Ser Lys Ser Ile Asn Lys Val Pro Val
                165                 170                 175

Asp Val Ser Glu Ser Pro Gly Phe Val Val Asn Arg Ile Leu Ile Pro
            180                 185                 190

Met Ile Asn Glu Ala Val Gly Ile Tyr Ala Asp Gly Val Ala Ser Lys
        195                 200                 205

Glu Glu Ile Asp Glu Ala Met Lys Leu Gly Ala Asn His Pro Met Gly
    210                 215                 220
```

```
Pro Leu Ala Leu Gly Asp Leu Ile Gly Leu Asp Val Val Leu Ala Ile
225                 230                 235                 240

Met Asn Val Leu Tyr Thr Glu Phe Gly Asp Thr Lys Tyr Arg Pro His
            245                 250                 255

Pro Leu Leu Ala Lys Met Val Arg Ala Asn Gln Leu Gly Arg Lys Thr
        260                 265                 270

Lys Ile Gly Phe Tyr Asp Tyr Asn Lys
    275                 280
```

```
<210> SEQ ID NO 16
<211> LENGTH: 265
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Ser Thr Ser Asp Val Lys Val Tyr Glu Asn Val Ala Val Glu Val
1               5                   10                  15

Asp Gly Asn Ile Cys Thr Val Lys Met Asn Arg Pro Lys Ala Leu Asn
            20                  25                  30

Ala Ile Asn Ser Lys Thr Leu Glu Glu Leu Tyr Glu Val Phe Val Asp
        35                  40                  45

Ile Asn Asn Asp Glu Thr Ile Asp Val Val Ile Leu Thr Gly Glu Gly
    50                  55                  60

Lys Ala Phe Val Ala Gly Ala Asp Ile Ala Tyr Met Lys Asp Leu Asp
65                  70                  75                  80

Ala Val Ala Ala Lys Asp Phe Ser Ile Leu Gly Ala Lys Ala Phe Gly
                85                  90                  95

Glu Ile Glu Asn Ser Lys Lys Val Val Ile Ala Ala Val Asn Gly Phe
            100                 105                 110

Ala Leu Gly Gly Gly Cys Glu Leu Ala Met Ala Cys Asp Ile Arg Ile
        115                 120                 125

Ala Ser Ala Lys Ala Lys Phe Gly Gln Pro Glu Val Thr Leu Gly Ile
    130                 135                 140

Thr Pro Gly Tyr Gly Gly Thr Gln Arg Leu Thr Arg Leu Val Gly Met
145                 150                 155                 160

Ala Lys Ala Lys Glu Leu Ile Phe Thr Gly Gln Val Ile Lys Ala Asp
                165                 170                 175

Glu Ala Glu Lys Ile Gly Leu Val Asn Arg Val Val Gly Pro Asp Ile
            180                 185                 190

Leu Ile Glu Glu Val Glu Lys Leu Ala Lys Ile Ile Ala Lys Asn Ala
        195                 200                 205

Gln Leu Ala Val Arg Tyr Ser Lys Glu Ala Ile Gln Leu Gly Ala Gln
    210                 215                 220

Thr Asp Ile Asn Thr Gly Ile Asp Ile Glu Ser Asn Leu Phe Gly Leu
225                 230                 235                 240

Cys Phe Ser Thr Lys Asp Gln Lys Glu Gly Met Ser Ala Phe Val Glu
                245                 250                 255

Lys Arg Glu Ala Asn Phe Ile Lys Gly
            260                 265
```

```
<210> SEQ ID NO 17
<211> LENGTH: 300
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

Met Arg Ser Phe Glu Glu Val Ile Lys Phe Ala Lys Glu Arg Gly Pro
1               5                   10                  15

Lys Thr Ile Ser Val Ala Cys Cys Gln Asp Lys Glu Val Leu Met Ala
            20                  25                  30

Val Glu Met Ala Arg Lys Glu Lys Ile Ala Asn Ala Ile Leu Val Gly
        35                  40                  45

Asp Ile Glu Lys Thr Lys Glu Ile Ala Lys Ser Ile Asp Met Asp Ile
    50                  55                  60

Glu Asn Tyr Glu Leu Ile Asp Ile Lys Asp Leu Ala Glu Ala Ser Leu
65                  70                  75                  80

Lys Ser Val Glu Leu Val Ser Gln Gly Lys Ala Asp Met Val Met Lys
                85                  90                  95

Gly Leu Val Asp Thr Ser Ile Ile Leu Lys Ala Val Leu Asn Lys Glu
            100                 105                 110

Val Gly Leu Arg Thr Gly Asn Val Leu Ser His Val Ala Val Phe Asp
        115                 120                 125

Val Glu Gly Tyr Asp Arg Leu Phe Phe Val Thr Asp Ala Ala Met Asn
    130                 135                 140

Leu Ala Pro Asp Thr Asn Thr Lys Lys Gln Ile Ile Glu Asn Ala Cys
145                 150                 155                 160

Thr Val Ala His Ser Leu Asp Ile Ser Glu Pro Lys Val Ala Ala Ile
                165                 170                 175

Cys Ala Lys Glu Lys Val Asn Pro Lys Met Lys Asp Thr Val Glu Ala
            180                 185                 190

Lys Glu Leu Glu Glu Met Tyr Glu Arg Gly Glu Ile Lys Gly Cys Met
        195                 200                 205

Val Gly Gly Pro Phe Ala Ile Asp Asn Ala Val Ser Leu Glu Ala Ala
    210                 215                 220

Lys His Lys Gly Ile Asn His Pro Val Ala Gly Arg Ala Asp Ile Leu
225                 230                 235                 240

Leu Ala Pro Asp Ile Glu Gly Gly Asn Ile Leu Tyr Lys Ala Leu Val
                245                 250                 255

Phe Phe Ser Lys Ser Lys Asn Ala Gly Val Ile Val Gly Ala Lys Ala
            260                 265                 270

Pro Ile Ile Leu Thr Ser Arg Ala Asp Ser Glu Glu Thr Lys Leu Asn
        275                 280                 285

Ser Ile Ala Leu Gly Val Leu Met Ala Ala Lys Ala
    290                 295                 300

<210> SEQ ID NO 18
<211> LENGTH: 359
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

Met Ser Lys Ile Phe Lys Ile Leu Thr Ile Asn Pro Gly Ser Thr Ser
1               5                   10                  15

Thr Lys Ile Ala Val Phe Asp Asn Glu Asp Leu Val Phe Glu Lys Thr
            20                  25                  30

Leu Arg His Ser Ser Glu Ile Gly Lys Tyr Glu Lys Val Ser Asp
        35                  40                  45

Gln Phe Glu Phe Arg Lys Gln Val Ile Glu Ala Leu Lys Glu Gly
 50                  55                  60

Gly Val Lys Thr Ser Glu Leu Asp Ala Val Val Gly Arg Gly Gly Leu
65                  70                  75                  80

Leu Lys Pro Ile Lys Gly Gly Thr Tyr Ser Val Ser Ala Ala Met Ile
                85                  90                  95

Glu Asp Leu Lys Val Gly Val Leu Gly Glu His Ala Ser Asn Leu Gly
            100                 105                 110

Gly Ile Ile Ala Lys Gln Ile Gly Glu Glu Val Asn Val Pro Ser Tyr
        115                 120                 125

Ile Val Asp Pro Val Val Val Asp Glu Leu Glu Asp Val Ala Arg Ile
130                 135                 140

Ser Gly Met Pro Glu Ile Ser Arg Ala Ser Val Val His Ala Leu Asn
145                 150                 155                 160

Gln Lys Ala Ile Ala Arg Arg Tyr Ala Arg Glu Ile Asn Lys Lys Tyr
                165                 170                 175

Glu Asp Ile Asn Leu Ile Val Ala His Met Gly Gly Gly Val Ser Val
            180                 185                 190

Gly Ala His Lys Asn Gly Lys Ile Val Asp Val Ala Asn Ala Leu Asp
        195                 200                 205

Gly Glu Gly Pro Phe Ser Pro Glu Arg Ser Gly Gly Leu Pro Val Gly
    210                 215                 220

Ala Leu Val Lys Met Cys Phe Ser Gly Lys Tyr Thr Gln Asp Glu Ile
225                 230                 235                 240

Lys Lys Lys Ile Lys Gly Asn Gly Gly Leu Val Ala Tyr Leu Asn Thr
                245                 250                 255

Asn Asp Ala Arg Glu Val Glu Glu Arg Ile Glu Ala Gly Asp Glu Lys
            260                 265                 270

Ala Lys Leu Val Tyr Glu Ala Met Ala Tyr Gln Ile Ser Lys Glu Ile
        275                 280                 285

Gly Ala Ser Ala Ala Val Leu Lys Gly Asp Val Lys Ala Ile Leu Leu
    290                 295                 300

Thr Gly Gly Ile Ala Tyr Ser Lys Met Phe Thr Glu Met Ile Ala Asp
305                 310                 315                 320

Arg Val Lys Phe Ile Ala Asp Val Lys Val Tyr Pro Gly Glu Asp Glu
                325                 330                 335

Met Ile Ala Leu Ala Gln Gly Gly Leu Arg Val Leu Thr Gly Glu Glu
            340                 345                 350

Glu Ala Gln Val Tyr Asp Asn
        355

<210> SEQ ID NO 19
<211> LENGTH: 397
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

```
Met Ile Val Lys Pro Met Val Arg Asn Asn Ile Cys Leu Asn Ala His
1               5                   10                  15

Pro Gln Gly Cys Lys Lys Gly Val Glu Asp Gln Ile Glu Tyr Thr Lys
            20                  25                  30

Lys Arg Ile Thr Ala Glu Val Lys Ala Gly Ala Lys Ala Pro Lys Asn
        35                  40                  45

Val Leu Val Leu Gly Cys Ser Asn Gly Tyr Gly Leu Ala Ser Arg Ile
50                  55                  60

Thr Ala Ala Phe Gly Tyr Gly Ala Ala Thr Ile Gly Val Ser Phe Glu
65                  70                  75                  80

Lys Ala Gly Ser Glu Thr Lys Tyr Gly Thr Pro Gly Trp Tyr Asn Asn
            85                  90                  95

Leu Ala Phe Asp Glu Ala Ala Lys Arg Glu Gly Leu Tyr Ser Val Thr
            100                 105                 110

Ile Asp Gly Asp Ala Phe Ser Asp Glu Ile Lys Ala Gln Val Ile Glu
        115                 120                 125

Glu Ala Lys Lys Lys Gly Ile Lys Phe Asp Leu Ile Val Tyr Ser Leu
130                 135                 140

Ala Ser Pro Val Arg Thr Asp Pro Asp Thr Gly Ile Met His Lys Ser
145                 150                 155                 160

Val Leu Lys Pro Phe Gly Lys Thr Phe Thr Gly Lys Thr Val Asp Pro
            165                 170                 175

Phe Thr Gly Glu Leu Lys Glu Ile Ser Ala Glu Pro Ala Asn Asp Glu
            180                 185                 190

Glu Ala Ala Ala Thr Val Lys Val Met Gly Gly Glu Asp Trp Glu Arg
            195                 200                 205

Trp Ile Lys Gln Leu Ser Lys Glu Gly Leu Leu Glu Glu Gly Cys Ile
        210                 215                 220

Thr Leu Ala Tyr Ser Tyr Ile Gly Pro Glu Ala Thr Gln Ala Leu Tyr
225                 230                 235                 240

Arg Lys Gly Thr Ile Gly Lys Ala Lys Glu His Leu Glu Ala Thr Ala
            245                 250                 255

His Arg Leu Asn Lys Glu Asn Pro Ser Ile Arg Ala Phe Val Ser Val
            260                 265                 270

Asn Lys Gly Leu Val Thr Arg Ala Ser Ala Val Ile Pro Val Ile Pro
        275                 280                 285

Leu Tyr Leu Ala Ser Leu Phe Lys Val Met Lys Glu Lys Gly Asn His
        290                 295                 300

Glu Gly Cys Ile Glu Gln Ile Thr Arg Leu Tyr Ala Glu Arg Leu Tyr
305                 310                 315                 320

Arg Lys Asp Gly Thr Ile Pro Val Asp Glu Glu Asn Arg Ile Arg Ile
            325                 330                 335

Asp Asp Trp Glu Leu Glu Glu Asp Val Gln Lys Ala Val Ser Ala Leu
            340                 345                 350

Met Glu Lys Val Thr Gly Glu Asn Ala Glu Ser Leu Thr Asp Leu Ala
            355                 360                 365

Gly Tyr Arg His Asp Phe Leu Ala Ser Asn Gly Phe Asp Val Glu Gly
            370                 375                 380

Ile Asn Tyr Glu Ala Glu Val Glu Arg Phe Asp Arg Ile
385                 390                 395

<210> SEQ ID NO 20
<211> LENGTH: 286
<212> TYPE: PRT
```

<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 20

```
Met Ser Gln Ala Leu Lys Asn Leu Leu Thr Leu Leu Asn Leu Glu Lys
1               5                   10                  15
Ile Glu Glu Gly Leu Phe Arg Gly Gln Ser Glu Asp Leu Gly Leu Arg
            20                  25                  30
Gln Val Phe Gly Gly Gln Val Val Gly Gln Ala Leu Tyr Ala Ala Lys
        35                  40                  45
Glu Thr Val Pro Glu Glu Arg Leu Val His Ser Phe His Ser Tyr Phe
    50                  55                  60
Leu Arg Pro Gly Asp Ser Lys Lys Pro Ile Ile Tyr Asp Val Glu Thr
65                  70                  75                  80
Leu Arg Asp Gly Asn Ser Phe Ser Ala Arg Arg Val Ala Ala Ile Gln
                85                  90                  95
Asn Gly Lys Pro Ile Phe Tyr Met Thr Ala Ser Phe Gln Ala Pro Glu
            100                 105                 110
Ala Gly Phe Glu His Gln Lys Thr Met Pro Ser Ala Pro Ala Pro Asp
        115                 120                 125
Gly Leu Pro Ser Glu Thr Gln Ile Ala Gln Ser Leu Ala His Leu Leu
    130                 135                 140
Pro Pro Val Leu Lys Asp Lys Phe Ile Cys Asp Arg Pro Leu Glu Val
145                 150                 155                 160
Arg Pro Val Glu Phe His Asn Pro Leu Lys Gly His Val Ala Glu Pro
                165                 170                 175
His Arg Gln Val Trp Ile Arg Ala Asn Gly Ser Val Pro Asp Asp Leu
            180                 185                 190
Arg Val His Gln Tyr Leu Leu Gly Tyr Ala Ser Asp Leu Asn Phe Leu
        195                 200                 205
Pro Val Ala Leu Gln Pro His Gly Ile Gly Phe Leu Glu Pro Gly Ile
    210                 215                 220
Gln Ile Ala Thr Ile Asp His Ser Met Trp Phe His Arg Pro Phe Asn
225                 230                 235                 240
Leu Asn Glu Trp Leu Leu Tyr Ser Val Glu Ser Thr Ser Ala Ser Ser
                245                 250                 255
Ala Arg Gly Phe Val Arg Gly Glu Phe Tyr Thr Gln Asp Gly Val Leu
            260                 265                 270
Val Ala Ser Thr Val Gln Glu Gly Val Met Arg Asn His Asn
        275                 280                 285
```

<210> SEQ ID NO 21
<211> LENGTH: 1575
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 21

| | | | | | |
|---|---|---|---|---|---|
| atgcgcaaag | tgccgattat | cacggctgac | gaggccgcaa | aactgatcaa | ggacggcgac | 60 |
| accgtgacaa | ctagcggctt | tgtgggtaac | gcgatccctg | aggcccttga | ccgtgcagtc | 120 |
| gaaaagcgtt | tcctggaaac | gggcgaaccg | aagaacatta | cttatgtata | ttgcggcagt | 180 |

```
cagggcaatc gcgacggtcg tggcgcagaa catttcgcgc atgaaggcct gctgaaacgt    240
tatatcgctg gccattgggc gaccgtcccg gcgttaggga aaatggccat ggagaataaa    300
atggaggcct acaatgtctc tcagggcgcc ttgtgtcatc tctttcgcga tattgcgagc    360
cataaaccgg gtgtgttcac gaaagtagga atcggcacct tcattgatcc acgtaacggt    420
ggtgggaagg tcaacgatat taccaaggaa gatatcgtag aactggtgga attaaaggg    480 caggaatacc tgttttatcc ggcgttcccg atccatgtcg cgctgattcg tggcacctat    540
gcggacgaga gtggtaacat cacctttgaa aaagaggtag cgcctttgga agggacttct    600
gtctgtcaag cggtgaagaa ctcgggtggc attgtcgtgg ttcaggttga gcgtgtcgtc    660
aaagcaggca cgctggatcc gcgccatgtg aaagttccgg gtatctatgt agattacgta    720
gtcgtcgcgg atccggagga ccatcaacag tcccttgact gcgaatatga tcctgccctt    780
agtggagagc accgtcgtcc ggaggtggtg ggtgaaccac tgcctttatc cgcgaagaaa    840
gtcatcggcc gccgtggcgc gattgagctc gagaaagacg ttgcagtgaa ccttggggta    900
ggtgcacctg agtatgtggc ctccgtggcc gatgaagaag gcattgtgga ttttatgact    960
ctcacagcgg agtccggcgc tatcggtggc gttccagccg gcggtgttcg ctttggggcg   1020
agctacaatg ctgacgcctt gatcgaccag ggctaccaat ttgattatta cgacggtggg   1080
ggtctggatc tttgttacct gggtttagct gaatgcgacg aaaagggtaa tatcaatgtt   1140
agccgcttcg gtcctcgtat cgctgggtgc ggcggattca ttaacattac ccaaaacacg   1200
ccgaaagtct tcttttgtgg gacctttaca gccggggggc tgaaagtgaa aattgaagat   1260
ggtaaggtga ttatcgttca ggaagggaaa cagaagaaat tccttaaggc agtggagcaa   1320 atcacctta atgagacgt ggccttagcg aacaagcaac aagttaccta catcacggag   1380
cgttgcgtct tcctcctcaa agaagacggt ttacaccttt cggaaatcgc gccaggcatc   1440
gatctgcaga cccagatttt ggatgttatg gactttgccc cgatcattga tcgtgacgca   1500
aacgggcaga ttaaactgat ggacgcggcg ttattcgcag aagggctgat gggcttgaaa   1560
gaaatgaagt cttaa                                                    1575
```

<210> SEQ ID NO 22
<211> LENGTH: 1269
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
atgagcttaa cccaaggcat gaaagctaaa caactgttag catactttca gggtaaagcc     60
gatcaggatg cacgtgaagc gaaagcccgc ggtgagctgg tctgctggtc ggcgtcagtc    120
gcgccgccgg aattttgcgt aacaatgggc attgccatga tctacccgga gactcatgca    180
gcgggcatcg gtgcccgcaa aggtgcgatg gacatgctgg aagttgcgga ccgcaaaggc    240
tacaacgtgg attgttgttc ctacggccgt gtaaatatgg ttacatggaa atgttaaaa    300 gaagccgcca tcacgggcgt caagccggaa gttttggtta attcccctgc tgctgacgtt    360
ccgcttcccg atttggtgat tacgtgtaat aatatctgta acacgctgct gaaatggtac    420
gaaaacttag cagcagaact cgatattcct tgcatcgtga tcgacgtacc gtttaatcat    480
accatgccga ttccggaata tgccaaggcc tacatcgcgg accagttccg caatgcaatt    540
```

```
tctcagctgg aagttatttg tggccgtccg ttcgattgga agaaatttaa ggaggtcaaa    600
gatcagaccc agcgtagcgt ataccactgg aaccgcattg ccgagatggc gaaatacaag    660
cctagcccgc tgaacggctt cgatctgttc aattacatgg cgttaatcgt ggcgtgccgc    720
agcctggatt atgcagaaat tacctttaaa gcgttcgcgg acgaattaga agagaatttg    780
aaggcgggta tctacgcctt taaaggtgcg gaaaaaacgc gctttcaatg ggaaggtatc    840
gcggtgtggc cacatttagg tcacacgttt aaatctatga agaatctgaa ttcgattatg    900
accggtacgg catacccccgc cctttgggac ctgcactatg acgctaacga cgaatctatg    960
cactctatgg ctgaagcgta cacccgtatt tatattaata cttgtctgca gaacaaagta   1020
gaggtcctgc ttgggatcat ggaaaaaggc caggtggatg gtaccgtata tcatctgaat   1080
cgcagctgca aactgatgag tttcctgaac gtggaaacgg ctgaaattat aaagagaag    1140 aacggtcttc cttacgtctc cattgatggc gatcagaccg atcctcgcgt tttttctccg   1200
gcccagtttg ataccgtgt tcaggccctg gttgagatga tggaggccaa tatggcggca   1260
gcggaataa                                                          1269
```

<210> SEQ ID NO 23
<211> LENGTH: 1125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
atgtcacgcg tggaggcaat cctgtcgcag ctgaaagatg tcgccgcgaa tccgaaaaaa     60
gccatggatg actataaagc tgaaacaggt aagggcgcgg ttggtatcat gccgatctac    120
agccccgaag aaatggtaca cgccgctggc tatttgccga tgggaatctg ggcgcccag    180 ggcaaaacga ttagtaaagc gcgcaccttat ctgcctgctt ttgcctgcag cgtaatgcag    240
caggttatgg aattacagtg cgagggcgcg tatgatgacc tgtccgcagt tattttttagc    300 gtaccgtgcg acactctcaa atgtcttagc cagaaatgga aagtacgtc cccagtgatt    360 gtatttacgc atccgcagaa ccgcggatta gaagcggcga ccaattctt ggttaccgag    420 tatgaactgg taaaagcaca actggaatca gttctgggtg tgaaaatttc aaacgccgcc    480
ctggaaaatt cgattgcaat ttataacgag aatcgtgccg tgatgcgtga ttcgtgaaa    540 gtggcagcgg actatcctca agtcattgac gcagtgagcc gccacgcggt ttttaaagcg    600
cgccagttta tgcttaagga aaaacatacc gcacttgtga agaactgat cgctgagatt    660 aaagcaacgc cagtccagcc gtgggacgga aaaaaggttg tagtgacggg cattctgttg    720
gaaccgaatg agttattaga tatctttaat gagtttaaga tcgcgattgt tgatgatgat    780
ttagcgcagg aaagccgtca gatcgtgttt gacgttctgg acggagaagg cggaccgctc    840
taccgtatgg ctaaagcgtg gcagcaaatg tatggctgct cgctggcaac cgacaccaag    900
aagggtcgcg gccgtatgtt aattaacaaa acgattcaga ccggtgcgga cgctatcgta    960
gttgcaatga tgaagttttg cgacccagaa gaatgggatt atccggtaat gtaccgtgaa   1020
tttgaagaaa aaggggtcaa atcacttatg attgaggtgg atcaggaagt atcgtctttc   1080
gaacagatta aaacccgtct gcagtcattc gtcgaaatgc tttaa                  1125
```

<210> SEQ ID NO 24
<211> LENGTH: 779

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

```
atgtatacct tggggattga tgtcggttct gcctctagta aagcggtgat tctgaaagat    60
ggaaaagata ttgtcgctgc cgaggttgtc caagtcggta ccggctcctc gggtccccaa   120
cgcgcactgg acaaagcctt tgaagtctct ggcttaaaaa aggaagacat cagctacaca   180
gtagctacgg gctatgggcg cttcaatttt agcgacgcgg ataaacagat ttcggaaatt   240
agctgtcatg ccaaaggcat ttatttctta gtaccaactg cgcgcactat tattgacatt   300
ggcggccaag atgcgaaagc catccgcctg gacgacaagg ggggtattaa gcaattcttc   360
atgaatgata aatgcgcggc gggcacgggg cgtttcctgg aagtcatggc tcgcgtactt   420
gaaaccaccc tggatgaaat ggctgaactg gatgaacagg cgactgacac cgctcccatt   480
tcaagcacct gcacggtttt cgccgaaagc gaagtaatta gccaattgag caatggtgtc   540
tcacgcaaca acatcattaa aggtgtccat ctgagcgttg cgtcacgtgc gtgtggtctg   600
gcgtatcgcg gcggtttgga gaaagatgtt gttatgacag gtggcgtggc aaaaaatgca   660
ggggtggtgc gcgcggtggc gggcgttctg aagaccgatg ttatcgttgc tccgaatcct   720
cagacgaccg gtgcactggg ggcagcgctg tatgcttatg aggccgccca aagaagta   779
```

<210> SEQ ID NO 25
<211> LENGTH: 1104
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

```
atggccttca atagcgcaga tattaattct ttccgcgata tttgggtgtt ttgtgaacag    60
cgtgagggca aactgattaa caccgatttc gaattaatta gcgaaggtcg taaactggct   120
gacgaacgcg gaagcaaact ggttggaatt ttgctggggc acgaagttga agaaatcgca   180
aaagaattag gcggctatgg tgcggacaag gtaattgtgt gcgatcatcc ggaacttaaa   240
ttttacacta cggatgctta tgccaaagtt ttatgtgacg tcgtgatgga agagaaaccg   300
gaggtaattt tgatcggtgc caccaacatt ggccgtgatc tcggaccgcg ttgtgctgca   360
cgcttgcaca cggggctgac ggctgattgc acgcacctgg atattgatat gaataaatat   420
gtggactttc ttagcaccag tagcaccttg gatatctcgt cgatgacttt ccctatggaa   480
gatacaaacc ttaaaatgac gcgccctgca tttggcggac atctgatggc aacgatcatt   540
tgtccacgct tccgtccctg tatgagcaca gtgcgcccccg gagtgatgaa gaaagcggag   600
ttctcgcagg agatggcgca agcatgtcaa gtagtgaccc gtcacgtaaa tttgtcggat   660
gaagacctta aaactaaagt aattaatatc gtgaaggaaa cgaaaaagat tgtggatctg   720
atcggcgcag aaattattgt gtcagttggt cgtggtatct cgaaagatgt ccaaggtgga   780
attgcactgg ctgaaaaaact tgcggacgca tttggtaacg gtgtcgtggg cggctcgcgc   840
gcagtgattg attccggctg gttacctgcg gatcatcagg ttggacaaaac cggtaagacc   900
gtgcacccga aagtctacgt ggcgctgggt attagtgggg ctatccagca taaggctggg   960
```

```
atgcaagact ctgaactgat cattgccgtc aacaagacg aaacggcgcc tatcttcgac       1020
tgcgccgatt atggcatcac cggtgattta tttaaaatcg taccgatgat gatcgacgcg      1080
atcaaagagg gtaaaaacgc atga                                              1104
```

<210> SEQ ID NO 26
<211> LENGTH: 804
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
atgcgcatct atgtgtgtgt gaaacaagtc ccagatacga gcggcaaggt ggccgttaac        60
cctgatggga cccttaaccg tgcctcaatg gcagcgatta ttaacccgga cgatatgtcc       120
gcgatcgaac aggcattaaa actgaaagat gaaaccggat gccaggttac ggcgcttacg       180
atgggtcctc ctcctgccga gggcatgttg cgcgaaatta ttgcaatggg ggccgacgat       240
ggtgtgctga tttcggcccg tgaatttggg gggtccgata ccttcgcaac cagtcaaatt       300
attagcgcgg caatccataa attaggctta agcaatgaag acatgatctt ttgcggtcgt       360
caggccattg acggtgatac ggcccaagtc ggccctcaaa ttgccgaaaa actgagcatc       420
ccacaggtaa cctatggcgc aggaatcaaa aaatctggtg atttagtgct ggtgaagcgt       480
atgttggagg atggttatat gatgatcgaa gtcgaaactc catgtctgat tacctgcatt       540
caggataaag cggtaaaacc acgttacatg actctcaacg gtattatgga atgctactcc       600
aagccgctcc tcgttctcga ttacgaagca ctgaaagatg aaccgctgat cgaacttgat       660
accattgggc ttaaaggctc cccgacgaat atctttaaat cgtttacgcc gcctcagaaa       720
ggcgttggtg tcatgctcca aggcaccgat aaggaaaaag tcgaggatct ggtggataag       780
ctgatgcaga aacatgtcat ctaa                                              804
```

<210> SEQ ID NO 27
<211> LENGTH: 1185
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27

```
atgttcttac tgaagattaa aaaagaacgt atgaaacgca tggactttag tttaacgcgt        60
gaacaggaga tgttaaaaaa actggcgcgt cagtttgctg agatcgagct ggaaccggtg       120
gccgaagaga ttgatcgtga gcacgttttt cctgcagaaa actttaagaa gatggcggaa       180
attggcttaa ccggcattgg tatcccgaaa gaatttggtg ctccggtgg aggcaccctg       240 gagaaggtca ttgccgtgtc agaattcggc aaaaagtgta tggcctcagc ttccatttta      300
agcattcatc ttatcgcgcc gcaggcaatc tacaaatatg ggaccaaaga acagaaagag       360
acgtacctgc cgcgtcttac caaaggtggt gaactgggcg cctttgcgct gacagaacca       420
aacgccggaa gcgatgccgg cgcggtaaaa acgaccgcga ttctggacag ccagacaaac       480
gagtacgtgc tgaatggcac caaatgcttt atcagcgggg gcgggcgcgc gggtgttctt       540 gtaattttg cgcttactga accgaaaaaa ggtctgaaag gatgagcgc gattatcgtg       600 gagaaaggga ccccgggctt cagcatcggc aaggtggaga gcaagatggg gatcgcaggt       660
```

| | |
|---|---|
| tcggaaaccg cggaacttat cttcgaagat tgtcgcgttc cggctgccaa ccttttaggt | 720 |
| aaagaaggca aaggctttaa aattgctatg gaagccctgg atggcgcccg tattggcgtg | 780 |
| ggcgctcaag caatcggaat tgccgagggg gcgatcgacc tgagtgtgaa gtacgttcac | 840 |
| gagcgcattc aatttggtaa accgatcgcg aatctgcagg gaattcaatg gtatatcgcg | 900 |
| gatatggcga ccaaaaccgc cgcggcacgc gcacttgttg agtttgcagc gtatcttgaa | 960 |
| gacgcgggta aaccgttcac aaaggaatct gctatgtgca agctgaacgc ctccgaaaac | 1020 |
| gcgcgttttg tgacaaattt agctctgcag attcacgggg gttacggtta tatgaaagat | 1080 |
| tatccgttag agcgtatgta tcgcgatgct aagattacgg aaatttacga ggggacatca | 1140 |
| gaaatccata aggtggtgat tgcgcgtgaa gtaatgaaac gctaa | 1185 |

<210> SEQ ID NO 28
<211> LENGTH: 2463
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

| | |
|---|---|
| atgcgagtgt tgaagttcgg cggtacatca gtggcaaatg cagaacgttt tctgcgtgtt | 60 |
| gccgatattc tggaaagcaa tgccaggcag gggcaggtgg ccaccgtcct ctctgccccc | 120 |
| gccaaaatca ccaaccacct ggtggcgatg attgaaaaaa ccattagcgg ccaggatgct | 180 |
| ttacccaata tcagcgatgc cgaacgtatt tttgccgaac ttttgacggg actcgccgcc | 240 |
| gcccagccgg ggttcccgct ggcgcaattg aaaactttcg tcgatcagga atttgcccaa | 300 |
| ataaaacatg tcctgcatgg cattagtttg ttggggcagt gcccggatag catcaacgct | 360 |
| gcgctgattt gccgtggcga gaaaatgtcg atcgccatta tggccggcgt attagaagcg | 420 |
| cgcggtcaca acgttactgt tatcgatccg gtcgaaaaac tgctggcagt ggggcattac | 480 |
| ctcgaatcta ccgtcgatat tgctgagtcc acccgccgta ttgcggcaag ccgcattccg | 540 |
| gctgatcaca tggtgctgat ggcaggtttc accgccggta atgaaaaagg cgaactggtg | 600 |
| gtgcttggac gcaacggttc cgactactct gctgcggtgc tggctgcctg tttacgcgcc | 660 |
| gattgttgcg agatttggac ggacgttgac ggggtctata cctgcgaccc gcgtcaggtg | 720 |
| cccgatgcga ggttgttgaa gtcgatgtcc taccaggaag cgatggagct ttcctacttc | 780 |
| ggcgctaaag ttcttcaccc ccgcaccatt accccgcatcg cccagttcca gatcccttgc | 840 |
| ctgattaaaa ataccggaaa tcctcaagca ccaggtacgc tcattggtgc cagccgtgat | 900 |
| gaagacgaat taccggtcaa gggcatttcc aatctgaata acatggcaat gttcagcgtt | 960 |
| tctggtccgg ggatgaaagg gatggtcggc atggcggcgc gcgtctttgc agcgatgtca | 1020 |
| cgcgcccgta tttccgtggt gctgattacg caatcatctt ccgaatacag catcagtttc | 1080 |
| tgcgttccac aaagcgactg tgtgcgagct gaacgggcaa tgcaggaaga gttctacctg | 1140 |
| gaactgaaag aaggcttact ggagccgctg gcagtgacgg aacggctggc cattatctcg | 1200 |
| gtggtaggtg atggtatgcg cacccttcgt gggatctcgg cgaaattctt tgccgcactg | 1260 |
| gcccgcgcca atatcaacat tgtcgccatt gctcagagat cttctgaacg ctcaatctct | 1320 |
| gtcgtggtaa ataacgatga tgcgaccact ggcgtgcgcg ttactcatca gatgctgttc | 1380 |
| aataccgatc aggttatcga agtgtttgtg attggcgtcg gtggcgttgg cggtgcgctg | 1440 |

```
ctggagcaac tgaagcgtca gcaaagctgg ctgaagaata acatatcga cttacgtgtc    1500 tgcggtgttg ccaactcgaa ggctctgctc accaatgtac atggccttaa tctggaaaac    1560
tggcaggaag aactggcgca agccaaagag ccgtttaatc tcgggcgctt aattcgcctc    1620
gtgaaagaat atcatctgct gaacccggtc attgttgact gcacttccag ccaggcagtg    1680
gcggatcaat atgccgactt cctgcgcgaa ggtttccacg ttgtcacgcc gaacaaaaag    1740
gccaacacct cgtcgatgga ttactaccat cagttgcgtt atgcggcgga aaaatcgcgg    1800
cgtaaattcc tctatgacac caacgttggg gctggattac cggttattga aacctgcaa     1860 aatctgctca atgcaggtga tgaattgatg aagttctccg gcattctttc tggttcgctt    1920
tcttatatct tcggcaagtt agacgaaggc atgagtttct ccgaggcgac cacgctggcg    1980
cgggaaatgg gttataccga accggacccg cgagatgatc tttctggtat ggatgtggcg    2040
cgtaaactat tgattctcgc tcgtgaaacg ggacgtgaac tggagctggc ggatattgaa    2100
attgaacctg tgctgcccgc agagtttaac gccgagggtg atgttgccgc ttttatggcg    2160
aatctgtcac aactcgacga tctctttgcc gcgcgcgtgg cgaaggcccg tgatgaagga    2220
aaagttttgc gctatgttgg caatattgat gaagatggcg tctgccgcgt gaagattgcc    2280
gaagtggatg gtaatgatcc gctgttcaaa gtgaaaaatg gcgaaaacgc cctggccttc    2340
tatagccact attatcagcc gctgccgttg gtactgcgcg gatatggtgc gggcaatgac    2400
gttacagctg ccggtgtctt tgctgatctg ctacgtaccc tctcatggaa gttaggagtc    2460
tga                                                                 2463
```

<210> SEQ ID NO 29
<211> LENGTH: 933
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 29

```
atggttaaag tttatgcccc ggcttccagt gccaatatga gcgtcgggtt tgatgtgctc      60
ggggcggcgg tgacacctgt tgatggtgca ttgctcggag atgtagtcac ggttgaggcg    120
gcagagacat tcagtctcaa caacctcgga cgctttgccg ataagctgcc gtcagaacca    180
cgggaaaata tcgttttatca gtgctgggag cgttttttgcc aggaactggg taagcaaatt    240
ccagtggcga tgaccctgga aaagaatatg ccgatcggtt cgggcttagg ctccagtgcc    300
tgttcggtgg tcgcggcgct gatggcgatg aatgaacact gcggcaagcc gcttaatgac    360
actcgtttgc tggctttgat gggcgagctg gaaggccgta tctccggcag cattcattac    420
gacaacgtgg caccgtgttt tctcggtggt atgcagttga tgatcgaaga aaacgacatc    480
atcagccagc aagtgccagg gtttgatgag tggctgtggg tgctggcgta tccggggatt    540
aaagtctcga cggcagaagc cagggctatt ttaccggcgc agtatcgccg ccaggattgc    600
attgcgcacg gcgacatct ggcaggcttc attcacgcct gctattcccg tcagcctgag    660
cttgccgcga agctgatgaa agatgttatc gctgaaccct accgtgaacg gttactgcca    720
ggcttccggc aggcgcggca ggcggtcgcg gaaatcggcg cggtagcgag cggtatctcc    780
ggctccggcc cgaccttgtt cgctctgtgt gacaagccgg aaaccgccca gcgcgttgcc    840
gactggttgg gtaagaacta cctgcaaaat caggaaggtt tgttcatat tgccggctg     900 gatacggcgg gcgcacgagt actggaaaac taa                                933
```

<210> SEQ ID NO 30
<211> LENGTH: 1287
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30

```
atgaaactct acaatctgaa agatcacaac gagcaggtca gctttgcgca agccgtaacc      60
caggggttgg gcaaaaatca ggggctgttt tttccgcacg acctgccgga attcagcctg     120
actgaaattg atgagatgct gaagctggat tttgtcaccc gcagtgcgaa gatcctctcg     180
gcgtttattg gtgatgaaat cccacaggaa atcctggaag agcgcgtgcg cgcggcgttt     240
gccttcccgg ctccggtcgc caatgttgaa agcgatgtcg gttgtctgga attgttccac     300
gggccaacgc tggcatttaa agatttcggc ggtcgcttta tggcacaaat gctgacccat     360
attgcgggtg ataagccagt gaccattctg accgcgacct ccggtgatac cggagcggca     420
gtggctcatg ctttctacgg tttaccgaat gtgaaagtgg ttatcctcta tccacgaggc     480
aaaatcagtc cactgcaaga aaaactgttc tgtacattgg gcggcaatat cgaaactgtt     540
gccatcgacg gcgatttcga tgcctgtcag gcgctggtga agcaggcgtt tgatgatgaa     600
gaactgaaag tggcgctagg gttaaactcg gctaactcga ttaacatcag ccgtttgctg     660
gcgcagattt gctactactt tgaagctgtt gcgcagctgc gcaggagac gcgcaaccag     720 ctggttgtct cggtgccaag cggaaacttc ggcgatttga cggcgggtct gctggcgaag     780
tcactcggtc tgccggtgaa acgtttatt gctgcgacca acgtgaacga taccgtgcca     840
cgtttcctgc acgacggtca gtggtcaccc aaagcgactc aggcgacgtt atccaacgcg     900
atggacgtga gtcagccgaa caactggccg cgtgtggaag agttgttccg ccgcaaaatc     960
tggcaactga aagagctggg ttatgcagcc gtggatgatg aaaccacgca acagacaatg    1020
cgtgagttaa aagaactggg ctacacttcg gagccgcacg ctgccgtagc ttatcgtgcg    1080
ctgcgtgatc agttgaatcc aggcgaatat ggcttgttcc tcggcaccgc gcatccggcg    1140
aaatttaaag agagcgtgga agcgattctc ggtgaaacgt tggatctgcc aaaagagctg    1200
gcagaacgtg ctgatttacc cttgctttca cataatctgc ccgccgattt tgctgcgttg    1260
cgtaaattga tgatgaatca tcagtaa                                       1287
```

<210> SEQ ID NO 31
<211> LENGTH: 1311
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

```
atgagtgaaa catacgtgtc tgagaaaagt ccaggagtga tggctagcgg agcggagctg      60
attcgtgccg ccgacattca aacggcgcag gcacgaattt cctccgtcat tgcaccaact     120
ccattgcagt attgccctcg tctttctgag gaaaccggag cggaaatcta ccttaagcgt     180
gaggatctgc aggatgttcg ttcctacaag atccgcggtg cgctgaactc tggagcgcag     240
ctcacccaag agcagcgcga tgcaggtatc gttgccgcat ctgcaggtaa ccatgcccag     300
```

| | |
|---|---|
| ggcgtggcct atgtgtgcaa gtccttgggc gttcagggac gcatctatgt tcctgtgcag | 360 |
| actccaaagc aaaagcgtga ccgcatcatg gttcacggcg gagagtttgt ctccttggtg | 420 |
| gtcactggca ataacttcga cgaagcatcg gctgcagcgc atgaagatgc agagcgcacc | 480 |
| ggcgcaacgc tgatcgagcc tttcgatgct cgcaacaccg tcatcggtca gggcaccgtg | 540 |
| gctgctgaga tcttgtcgca gctgacttcc atgggcaaga gtgcagatca cgtgatggtt | 600 |
| ccagtcggcg gtggcggact tcttgcaggt gtggtcagct acatggctga tatggcacct | 660 |
| cgcactgcga tcgttggtat cgaaccagcg ggagcagcat ccatgcaggc tgcattgcac | 720 |
| aatggtggac caatcacttt ggagactgtt gatcccttg tggacggcgc agcagtcaaa | 780 |
| cgtgtcggag atctcaacta caccatcgtg gagaagaacc agggtcgcgt gcacatgatg | 840 |
| agcgcgaccg agggcgctgt gtgtactgag atgctcgatc tttaccaaaa cgaaggcatc | 900 |
| atcgcggagc ctgctggcgc gctgtctatc gctgggttga aggaaatgtc ctttgcacct | 960 |
| ggttctgcag tggtgtgcat catctctggt ggcaacaacg atgtgctgcg ttatgcggaa | 1020 |
| atcgctgagc gctccttggt gcaccgcggt ttgaagcact acttcttggt gaacttcccg | 1080 |
| caaaagcctg gtcagttgcg tcacttcctg gaagatatcc tgggaccgga tgatgacatc | 1140 |
| acgctgtttg agtacctcaa cgcaacaac cgtgagaccg gtactgcgtt ggtgggtatt | 1200 |
| cacttgagtg aagcatcagg attggattct ttgctggaac gtatggagga atcggcaatt | 1260 |
| gattcccgtc gcctcgagcc gggcacccct gagtacgaat acttgaccta a | 1311 |

<210> SEQ ID NO 32
<211> LENGTH: 2664
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 32

| | |
|---|---|
| atgtcagaac gtttcccaaa tgacgtggat ccgatcgaaa ctcgcgactg gctccaggcg | 60 |
| atcgaatcgg tcatccgtga agaaggtgtt gagcgtgctc agtatctgat cgaccaactg | 120 |
| cttgctgaag cccgcaaagg cggtgtaaac gtagccgcag gcacaggtat cagcaactac | 180 |
| atcaacacca tccccgttga agaacaaccg gagtatccgg gtaatctgga actggaacgc | 240 |
| cgtattcgtt cagctatccg ctggaacgcc atcatgacgg tgctgcgtgc gtcgaaaaaa | 300 |
| gacctcgaac tgggcggcca tatggcgtcc ttccagtctt ccgcaaccat ttatgatgtg | 360 |
| tgctttaacc acttcttccg tgcacgcaac gagcaggatg gcggcgacct ggtttacttc | 420 |
| cagggccaca tctccccggg cgtgtacgct cgtgctttcc tggaaggtcg tctgactcag | 480 |
| gagcagctgg ataacttccg tcaggaagtt cacggcaatg gcctctcttc ctatccgcac | 540 |
| ccgaaactga tgccggaatt ctggcagttc ccgaccgtat ctatgggtct gggtccgatt | 600 |
| ggtgctattt accaggctaa attcctgaaa tatctggaac ccgtggcct gaaagatacc | 660 |
| tctaaacaaa ccgtttacgc gttcctcggt gacggtgaaa tggacgaacc ggaatccaaa | 720 |
| ggtgcgatca ccatcgctac ccgtgaaaaa ctggataacc tggtcttcgt tatcaactgt | 780 |
| aacctgcagc gtcttgacgg cccggtcacc ggtaacggca agatcatcaa cgaactggaa | 840 |
| ggcatcttcg aaggtgctgg ctggaacgtg atcaaagtga tgtggggtag ccgttgggat | 900 |
| gaactgctgc gtaaggatac cagcggtaaa ctgatccagc tgatgaacga aaccgttgac | 960 |
| ggcgactacc agaccttcaa atcgaaagat ggtgcgtacg ttcgtgaaca cttcttcggt | 1020 |

-continued

| | |
|---|---|
| aaatatcctg aaaccgcagc actggttgca gactggactg acgagcagat ctgggcactg | 1080 |
| aaccgtggtg gtcacgatcc gaagaaaatc tacgctgcat tcaagaaagc gcaggaaacc | 1140 |
| aaaggcaaag cgacagtaat ccttgctcat accattaaag gttacggcat gggcgacgcg | 1200 |
| gctgaaggta aaacatcgc gcaccaggtt aagaaaatga acatggacgg tgtgcgtcat | 1260 |
| atccgcgacc gtttcaatgt gccggtgtct gatgcagata tcgaaaaact gccgtacatc | 1320 |
| accttcccgg aaggttctga agagcatacc tatctgcacg ctcagcgtca gaaactgcac | 1380 |
| ggttatctgc caagccgtca gccgaacttc accgagaagc ttgagctgcc gagcctgcaa | 1440 |
| gacttcggcg cgctgttgga agagcagagc aaagagatct ctaccactat cgctttcgtt | 1500 |
| cgtgctctga acgtgatgct gaagaacaag tcgatcaaag atcgtctggt accgatcatc | 1560 |
| gccgacgaag cgcgtacttt cggtatggaa ggtctgttcc gtcagattgg tatttacagc | 1620 |
| ccgaacggtc agcagtacac cccgcaggac cgcgagcagg ttgcttacta taagaagac | 1680 |
| gagaaaggtc agattctgca ggaagggatc aacgagctgg cgcaggttg ttcctggctg | 1740 |
| gcagcggcga cctcttacag caccaacaat ctgccgatga tcccgttcta catctattac | 1800 |
| tcgatgttcg gcttccagcg tattggcgat ctgtgctggg cggctggcga ccagcaagcg | 1860 |
| cgtggcttcc tgatcggcgg tacttccggt cgtaccaccc tgaacggcga aggtctgcag | 1920 |
| cacgaagatg gtcacagcca cattcagtcg ctgactatcc cgaactgtat ctcttacgac | 1980 |
| ccggcttacg cttacgaagt tgctgtcatc atgcatgacg gtctggagcg tatgtacggt | 2040 |
| gaaaaacaag agaacgttta ctactacatc actacgctga acgaaaacta ccacatgccg | 2100 |
| gcaatgccgg aaggtgctga ggaaggtatc cgtaaaggta tctacaaact cgaaactatt | 2160 |
| gaaggtagca aagtaaagt tcagctgctc ggctccggtt ctatcctgcg tcacgtccgt | 2220 |
| gaagcagctg agatcctggc gaaagattac ggcgtaggtt ctgacgttta tagcgtgacc | 2280 |
| tccttcaccg agctggcgcg tgatggtcag gattgtgaac gctggaacat gctgcacccg | 2340 |
| ctggaaactc cgcgcgttcc gtatatcgct caggtgatga cgacgctcc ggcagtggca | 2400 |
| tctaccgact atatgaaact gttcgctgag caggtccgta cttacgtacc ggctgacgac | 2460 |
| taccgcgtac tgggtactga tggcttcggt cgttccgaca gccgtgagaa cctgcgtcac | 2520 |
| cacttcgaag ttgatgcttc ttatgtcgtg gttgcggcgc tgggcgaact ggctaaacgt | 2580 |
| ggcgaaatcg ataagaaagt ggttgctgac gcaatcgcca aattcaacat cgatgcagat | 2640 |
| aaagttaacc cgcgtctggc gtaa | 2664 |

<210> SEQ ID NO 33
<211> LENGTH: 1893
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 33

| | |
|---|---|
| atggctatcg aaatcaaagt accggacatc ggggctgatg aagttgaaat caccgagatc | 60 |
| ctggtcaaag tgggcgacaa agttgaagcc gaacagtcgc tgatcaccgt agaaggcgac | 120 |
| aaagcctcta tggaagttcc gtctccgcag gcgggtatcg ttaagagat caaagtctct | 180 |
| gttggcgata aaacccagac cggcgcactg attatgattt tcgattccgc cgacggtgca | 240 |
| gcagacgctg cacctgctca ggcagaagag aagaaagaag cagctccggc agcagcacca | 300 |

```
gcggctgcgg cggcaaaaga cgttaacgtt ccggatatcg gcagcgacga agttgaagtg      360
accgaaatcc tggtgaaagt tggcgataaa gttgaagctg aacagtcgct gatcaccgta      420
gaaggcgaca aggcttctat ggaagttccg gctccgtttg ctggcaccgt gaaagagatc      480
aaagtgaacg tgggtgacaa agtgtctacc ggctcgctga ttatggtctt cgaagtcgcg      540
ggtgaagcag gcgcggcagc tccggccgct aaacaggaag cagctccggc agcggcccct      600
gcaccagcgg ctggcgtgaa agaagttaac gttccggata tcggcggtga cgaagttgaa      660
gtgactgaag tgatggtgaa agtgggcgac aaagttgccg ctgaacagtc actgatcacc      720
gtagaaggcg acaaagcttc tatggaagtt ccggcgccgt ttgcaggcgt cgtgaaggaa      780
ctgaaagtca cgttggcga taaagtgaaa actggctcgc tgattatgat cttcgaagtt      840
gaaggcgcag cgcctgcggc agctcctgcg aaacaggaag cggcagcgcc ggcaccggca      900
gcaaaagctg aagccccggc agcagcacca gctgcgaaag cggaaggcaa atctgaattt      960
gctgaaaacg acgcttatgt tcacgcgact ccgctgatcc gccgtctggc acgcgagttt     1020
ggtgttaacc ttgcgaaagt gaagggcact ggccgtaaag gtcgtatcct gcgcgaagac     1080
gttcaggctt acgtgaaaga agctatcaaa cgtgcagaag cagctccggc agcgactggc     1140
ggtggtatcc ctggcatgct gccgtggccg aaggtggact tcagcaagtt tggtgaaatc     1200
gaagaagtgg aactgggccg catccagaaa atctctggtg cgaacctgag ccgtaactgg     1260
gtaatgatcc cgcatgttac tcacttcgac aaaaccgata tcaccgagtt ggaagcgttc     1320
cgtaaacagc agaacgaaga agcggcgaaa cgtaagctgg atgtgaagat caccccggtt     1380
gtcttcatca tgaaagccgt tgctgcagct cttgagcaga tgcctcgctt caatagttcg     1440
ctgtcggaag acggtcagcg tctgacccctg aagaaataca tcaacatcgg tgtggcggtg     1500 gatacccccga acggtctggt tgttccggta ttcaaagacg tcaacaagaa aggcatcatc     1560
gagctgtctc gcgagctgat gactatttct aagaaagcgc gtgacggtaa gctgactgcg     1620
ggcgaaatgc agggcggttg cttcaccatc tccagcatcg gcggcctggg tactaccccac     1680 ttcgcgccga ttgtgaacgc gccggaagtg gctatcctcg gcgtttccaa gtccgcgatg     1740
gagccggtgt ggaatggtaa agagttcgtg ccgcgtctga tgctgccgat ttctctctcc     1800
ttcgaccacc gcgtgatcga cggtgctgat ggtgcccgtt tcattaccat cattaacaac     1860
acgctgtctg acattcgccg tctggtgatg taa                                 1893
```

<210> SEQ ID NO 34
<211> LENGTH: 1425
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34

```
atgagtactg aaatcaaaac tcaggtcgtg gtacttgggg caggcccccgc aggttactcc       60 gctgccttcc gttgcgctga tttaggtctg gaaaccgtaa tcgtagaacg ttacaacacc      120
cttggcggta tttgcctgaa cgtcggctgt atcccttcta aagcactgct gcacgtagca      180
aaagttatcg aagaagccaa agcgctggct gaacacggta tcgtcttcgg cgaaccgaaa      240
accgatatcg acaagattcg tacctggaaa gagaaagtga tcaatcagct gaccggtggt      300
ctggctggta tggcgaaagg ccgcaaagtc aaagtggtca cggtctgggg taaattcacc      360
ggggctaaca ccctggaagt tgaaggtgag aacggcaaaa ccgtgatcaa cttcgacaac      420
```

```
gcgatcattg cagcgggttc tcgcccgatc caactgccgt ttattccgca tgaagatccg      480
cgtatctggg actccactga cgcgctggaa ctgaaagaag taccagaacg cctgctggta      540
atgggtggcg gtatcatcgg tctggaaatg ggcaccgttt accacgcgct gggttcacag      600
attgacgtgg ttgaaatgtt cgaccaggtt atcccggcag ctgacaaaga catcgttaaa      660
gtcttcacca agcgtatcag caagaaattc aacctgatgc tggaaaccaa agttaccgcc      720
gttgaagcga aagaagacgg catttatgtg acgatggaag gcaaaaaagc acccgctgaa      780
ccgcagcgtt acgacgccgt gctggtagcg attggtcgtg tgccgaacgg taaaaacctc      840
gacgcaggca aagcaggcgt ggaagttgac gaccgtggtt tcatccgcgt tgacaaacag      900
ctgcgtacca acgtaccgca catctttgct atcggcgata tcgtcggtca accgatgctg      960
gcacacaaag gtgttcacga aggtcacgtt gccgctgaag ttatcgccgg taagaaacac     1020
tacttcgatc cgaaagttat cccgtccatc gcctatacca accagaagt tgcatgggtg     1080
ggtctgactg agaagaagc gaaagagaaa ggcatcagct atgaaaccgc caccttcccg     1140
tgggctgctt ctggtcgtgc tatcgcttcc gactgcgcag acggtatgac caagctgatt     1200
ttcgacaaag aatctcaccg tgtgatcggt ggtgcgattg tcggtactaa cggcggcgag     1260
ctgctgggtg aaatcggcct ggcaatcgaa atgggttgtg atgctgaaga catcgcactg     1320
accatccacg cgcaccccga ctctgcacga tctgtgggcc tggcggcaga agtgttcgaa     1380
ggtagcatta ccgacctgcc gaacccgaaa gcgaagaaga agtaa                    1425
```

<210> SEQ ID NO 35
<211> LENGTH: 524
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

```
Met Arg Lys Val Pro Ile Ile Thr Ala Asp Glu Ala Ala Lys Leu Ile
1               5                   10                  15

Lys Asp Gly Asp Thr Val Thr Thr Ser Gly Phe Val Gly Asn Ala Ile
            20                  25                  30

Pro Glu Ala Leu Asp Arg Ala Val Glu Lys Arg Phe Leu Glu Thr Gly
        35                  40                  45

Glu Pro Lys Asn Ile Thr Tyr Val Tyr Cys Gly Ser Gln Gly Asn Arg
    50                  55                  60

Asp Gly Arg Gly Ala Glu His Phe Ala His Glu Gly Leu Leu Lys Arg
65                  70                  75                  80

Tyr Ile Ala Gly His Trp Ala Thr Val Pro Ala Leu Gly Lys Met Ala
                85                  90                  95

Met Glu Asn Lys Met Glu Ala Tyr Asn Val Ser Gln Gly Ala Leu Cys
            100                 105                 110

His Leu Phe Arg Asp Ile Ala Ser His Lys Pro Gly Val Phe Thr Lys
        115                 120                 125

Val Gly Ile Gly Thr Phe Ile Asp Pro Arg Asn Gly Gly Gly Lys Val
    130                 135                 140

Asn Asp Ile Thr Lys Glu Asp Ile Val Glu Leu Val Glu Ile Lys Gly
145                 150                 155                 160

Gln Glu Tyr Leu Phe Tyr Pro Ala Phe Pro Ile His Val Ala Leu Ile
                165                 170                 175
```

```
Arg Gly Thr Tyr Ala Asp Glu Ser Gly Asn Ile Thr Phe Glu Lys Glu
            180                 185                 190

Val Ala Pro Leu Glu Gly Thr Ser Val Cys Gln Ala Val Lys Asn Ser
        195                 200                 205

Gly Gly Ile Val Val Gln Val Glu Arg Val Val Lys Ala Gly Thr
210                 215                 220

Leu Asp Pro Arg His Val Lys Val Pro Gly Ile Tyr Val Asp Tyr Val
225                 230                 235                 240

Val Val Ala Asp Pro Glu Asp His Gln Gln Ser Leu Asp Cys Glu Tyr
                245                 250                 255

Asp Pro Ala Leu Ser Gly Glu His Arg Arg Pro Glu Val Val Gly Glu
            260                 265                 270

Pro Leu Pro Leu Ser Ala Lys Lys Val Ile Gly Arg Arg Gly Ala Ile
        275                 280                 285

Glu Leu Glu Lys Asp Val Ala Val Asn Leu Gly Val Gly Ala Pro Glu
290                 295                 300

Tyr Val Ala Ser Val Ala Asp Glu Glu Gly Ile Val Asp Phe Met Thr
305                 310                 315                 320

Leu Thr Ala Glu Ser Gly Ala Ile Gly Gly Val Pro Ala Gly Gly Val
                325                 330                 335

Arg Phe Gly Ala Ser Tyr Asn Ala Asp Ala Leu Ile Asp Gln Gly Tyr
            340                 345                 350

Gln Phe Asp Tyr Tyr Asp Gly Gly Gly Leu Asp Leu Cys Tyr Leu Gly
        355                 360                 365

Leu Ala Glu Cys Asp Glu Lys Gly Asn Ile Asn Val Ser Arg Phe Gly
370                 375                 380

Pro Arg Ile Ala Gly Cys Gly Gly Phe Ile Asn Ile Thr Gln Asn Thr
385                 390                 395                 400

Pro Lys Val Phe Phe Cys Gly Thr Phe Thr Ala Gly Gly Leu Lys Val
                405                 410                 415

Lys Ile Glu Asp Gly Lys Val Ile Ile Val Gln Glu Gly Lys Gln Lys
            420                 425                 430

Lys Phe Leu Lys Ala Val Glu Gln Ile Thr Phe Asn Gly Asp Val Ala
        435                 440                 445

Leu Ala Asn Lys Gln Gln Val Thr Tyr Ile Thr Glu Arg Cys Val Phe
450                 455                 460

Leu Leu Lys Glu Asp Gly Leu His Leu Ser Glu Ile Ala Pro Gly Ile
465                 470                 475                 480

Asp Leu Gln Thr Gln Ile Leu Asp Val Met Asp Phe Ala Pro Ile Ile
                485                 490                 495

Asp Arg Asp Ala Asn Gly Gln Ile Lys Leu Met Asp Ala Ala Leu Phe
            500                 505                 510

Ala Glu Gly Leu Met Gly Leu Lys Glu Met Lys Ser
        515                 520

<210> SEQ ID NO 36
<211> LENGTH: 422
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36
```

```
Met Ser Leu Thr Gln Gly Met Lys Ala Lys Gln Leu Leu Ala Tyr Phe
1               5                   10                  15
Gln Gly Lys Ala Asp Gln Asp Ala Arg Glu Ala Lys Ala Arg Gly Glu
                20                  25                  30
Leu Val Cys Trp Ser Ala Ser Val Ala Pro Pro Glu Phe Cys Val Thr
            35                  40                  45
Met Gly Ile Ala Met Ile Tyr Pro Glu Thr His Ala Ala Gly Ile Gly
50                  55                  60
Ala Arg Lys Gly Ala Met Asp Met Leu Glu Val Ala Asp Arg Lys Gly
65                      70                  75                  80
Tyr Asn Val Asp Cys Cys Ser Tyr Gly Arg Val Asn Met Gly Tyr Met
                    85                  90                  95
Glu Cys Leu Lys Glu Ala Ala Ile Thr Gly Val Lys Pro Glu Val Leu
                100                 105                 110
Val Asn Ser Pro Ala Ala Asp Val Pro Leu Pro Asp Leu Val Ile Thr
            115                 120                 125
Cys Asn Asn Ile Cys Asn Thr Leu Leu Lys Trp Tyr Glu Asn Leu Ala
130                 135                 140
Ala Glu Leu Asp Ile Pro Cys Ile Val Ile Asp Val Pro Phe Asn His
145                 150                 155                 160
Thr Met Pro Ile Pro Glu Tyr Ala Lys Ala Tyr Ile Ala Asp Gln Phe
                165                 170                 175
Arg Asn Ala Ile Ser Gln Leu Glu Val Ile Cys Gly Arg Pro Phe Asp
                180                 185                 190
Trp Lys Lys Phe Lys Glu Val Lys Asp Gln Thr Gln Arg Ser Val Tyr
                195                 200                 205
His Trp Asn Arg Ile Ala Glu Met Ala Lys Tyr Lys Pro Ser Pro Leu
210                 215                 220
Asn Gly Phe Asp Leu Phe Asn Tyr Met Ala Leu Ile Val Ala Cys Arg
225                 230                 235                 240
Ser Leu Asp Tyr Ala Glu Ile Thr Phe Lys Ala Phe Ala Asp Glu Leu
                245                 250                 255
Glu Glu Asn Leu Lys Ala Gly Ile Tyr Ala Phe Lys Gly Ala Glu Lys
                260                 265                 270
Thr Arg Phe Gln Trp Glu Gly Ile Ala Val Trp Pro His Leu Gly His
                275                 280                 285
Thr Phe Lys Ser Met Lys Asn Leu Asn Ser Ile Met Thr Gly Thr Ala
                290                 295                 300
Tyr Pro Ala Leu Trp Asp Leu His Tyr Asp Ala Asn Asp Glu Ser Met
305                 310                 315                 320
His Ser Met Ala Glu Ala Tyr Thr Arg Ile Tyr Ile Asn Thr Cys Leu
                325                 330                 335
Gln Asn Lys Val Glu Val Leu Leu Gly Ile Met Glu Lys Gly Gln Val
                340                 345                 350
Asp Gly Thr Val Tyr His Leu Asn Arg Ser Cys Lys Leu Met Ser Phe
                355                 360                 365
Leu Asn Val Glu Thr Ala Glu Ile Ile Lys Glu Lys Asn Gly Leu Pro
370                 375                 380
Tyr Val Ser Ile Asp Gly Asp Gln Thr Asp Pro Arg Val Phe Ser Pro
385                 390                 395                 400
Ala Gln Phe Asp Thr Arg Val Gln Ala Leu Val Glu Met Met Glu Ala
                405                 410                 415
Asn Met Ala Ala Ala Glu
```

-continued

420

<210> SEQ ID NO 37
<211> LENGTH: 374
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

Met Ser Arg Val Glu Ala Ile Leu Ser Gln Leu Lys Asp Val Ala Ala
1               5                   10                  15

Asn Pro Lys Lys Ala Met Asp Asp Tyr Lys Ala Glu Thr Gly Lys Gly
                20                  25                  30

Ala Val Gly Ile Met Pro Ile Tyr Ser Pro Glu Glu Met Val His Ala
            35                  40                  45

Ala Gly Tyr Leu Pro Met Gly Ile Trp Gly Ala Gln Gly Lys Thr Ile
        50                  55                  60

Ser Lys Ala Arg Thr Tyr Leu Pro Ala Phe Ala Cys Ser Val Met Gln
65                  70                  75                  80

Gln Val Met Glu Leu Gln Cys Glu Gly Ala Tyr Asp Asp Leu Ser Ala
                85                  90                  95

Val Ile Phe Ser Val Pro Cys Asp Thr Leu Lys Cys Leu Ser Gln Lys
            100                 105                 110

Trp Lys Gly Thr Ser Pro Val Ile Val Phe Thr His Pro Gln Asn Arg
        115                 120                 125

Gly Leu Glu Ala Ala Asn Gln Phe Leu Val Thr Glu Tyr Glu Leu Val
    130                 135                 140

Lys Ala Gln Leu Glu Ser Val Leu Gly Val Lys Ile Ser Asn Ala Ala
145                 150                 155                 160

Leu Glu Asn Ser Ile Ala Ile Tyr Asn Glu Asn Arg Ala Val Met Arg
                165                 170                 175

Glu Phe Val Lys Val Ala Ala Asp Tyr Pro Gln Val Ile Asp Ala Val
            180                 185                 190

Ser Arg His Ala Val Phe Lys Ala Arg Gln Phe Met Leu Lys Glu Lys
        195                 200                 205

His Thr Ala Leu Val Lys Glu Leu Ile Ala Glu Ile Lys Ala Thr Pro
    210                 215                 220

Val Gln Pro Trp Asp Gly Lys Lys Val Val Thr Gly Ile Leu Leu
225                 230                 235                 240

Glu Pro Asn Glu Leu Leu Asp Ile Phe Asn Glu Phe Lys Ile Ala Ile
                245                 250                 255

Val Asp Asp Asp Leu Ala Gln Glu Ser Arg Gln Ile Arg Val Asp Val
            260                 265                 270

Leu Asp Gly Glu Gly Gly Pro Leu Tyr Arg Met Ala Lys Ala Trp Gln
        275                 280                 285

Gln Met Tyr Gly Cys Ser Leu Ala Thr Asp Thr Lys Lys Gly Arg Gly
    290                 295                 300

Arg Met Leu Ile Asn Lys Thr Ile Gln Thr Gly Ala Asp Ala Ile Val
305                 310                 315                 320

Val Ala Met Met Lys Phe Cys Asp Pro Glu Glu Trp Asp Tyr Pro Val
                325                 330                 335

Met Tyr Arg Glu Phe Glu Glu Lys Gly Val Lys Ser Leu Met Ile Glu
            340                 345                 350

Val Asp Gln Glu Val Ser Ser Phe Glu Gln Ile Lys Thr Arg Leu Gln
        355                 360                 365

Ser Phe Val Glu Met Leu
    370

<210> SEQ ID NO 38
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Tyr Thr Leu Gly Ile Asp Val Gly Ser Ala Ser Ser Lys Ala Val
1               5                   10                  15

Ile Leu Lys Asp Gly Lys Asp Ile Val Ala Ala Glu Val Val Gln Val
                20                  25                  30

Gly Thr Gly Ser Ser Gly Pro Gln Arg Ala Leu Asp Lys Ala Phe Glu
            35                  40                  45

Val Ser Gly Leu Lys Lys Glu Asp Ile Ser Tyr Thr Val Ala Thr Gly
    50                  55                  60

Tyr Gly Arg Phe Asn Phe Ser Asp Ala Asp Lys Gln Ile Ser Glu Ile
65                  70                  75                  80

Ser Cys His Ala Lys Gly Ile Tyr Phe Leu Val Pro Thr Ala Arg Thr
                85                  90                  95

Ile Ile Asp Ile Gly Gly Gln Asp Ala Lys Ala Ile Arg Leu Asp Asp
            100                 105                 110

Lys Gly Gly Ile Lys Gln Phe Phe Met Asn Asp Lys Cys Ala Ala Gly
        115                 120                 125

Thr Gly Arg Phe Leu Glu Val Met Ala Arg Val Leu Glu Thr Thr Leu
130                 135                 140

Asp Glu Met Ala Glu Leu Asp Glu Gln Ala Thr Asp Thr Ala Pro Ile
145                 150                 155                 160

Ser Ser Thr Cys Thr Val Phe Ala Glu Ser Glu Val Ile Ser Gln Leu
                165                 170                 175

Ser Asn Gly Val Ser Arg Asn Asn Ile Ile Lys Gly Val His Leu Ser
            180                 185                 190

Val Ala Ser Arg Ala Cys Gly Leu Ala Tyr Arg Gly Gly Leu Glu Lys
        195                 200                 205

Asp Val Val Met Thr Gly Gly Val Ala Lys Asn Ala Gly Val Val Arg
    210                 215                 220

Ala Val Ala Gly Val Leu Lys Thr Asp Val Ile Val Ala Pro Asn Pro
225                 230                 235                 240

Gln Thr Thr Gly Ala Leu Gly Ala Ala Leu Tyr Ala Tyr Glu Ala Ala
                245                 250                 255

Gln Lys Lys

<210> SEQ ID NO 39
<211> LENGTH: 367
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Ala Phe Asn Ser Ala Asp Ile Asn Ser Phe Arg Asp Ile Trp Val
1               5                   10                  15

Phe Cys Glu Gln Arg Glu Gly Lys Leu Ile Asn Thr Asp Phe Glu Leu
            20                  25                  30

Ile Ser Glu Gly Arg Lys Leu Ala Asp Glu Arg Gly Ser Lys Leu Val
        35                  40                  45

Gly Ile Leu Leu Gly His Glu Val Glu Ile Ala Lys Glu Leu Gly
    50                  55                  60

Gly Tyr Gly Ala Asp Lys Val Ile Val Cys Asp His Pro Glu Leu Lys
65                  70                  75                  80

Phe Tyr Thr Thr Asp Ala Tyr Ala Lys Val Leu Cys Asp Val Val Met
                85                  90                  95

Glu Glu Lys Pro Glu Val Ile Leu Ile Gly Ala Thr Asn Ile Gly Arg
            100                 105                 110

Asp Leu Gly Pro Arg Cys Ala Ala Arg Leu His Thr Gly Leu Thr Ala
        115                 120                 125

Asp Cys Thr His Leu Asp Ile Asp Met Asn Lys Tyr Val Asp Phe Leu
    130                 135                 140

Ser Thr Ser Ser Thr Leu Asp Ile Ser Ser Met Thr Phe Pro Met Glu
145                 150                 155                 160

Asp Thr Asn Leu Lys Met Thr Arg Pro Ala Phe Gly His Leu Met
                165                 170                 175

Ala Thr Ile Ile Cys Pro Arg Phe Arg Pro Cys Met Ser Thr Val Arg
            180                 185                 190

Pro Gly Val Met Lys Lys Ala Glu Phe Ser Gln Glu Met Ala Gln Ala
        195                 200                 205

Cys Gln Val Val Thr Arg His Val Asn Leu Ser Asp Glu Asp Leu Lys
    210                 215                 220

Thr Lys Val Ile Asn Ile Val Lys Glu Thr Lys Lys Ile Val Asp Leu
225                 230                 235                 240

Ile Gly Ala Glu Ile Ile Val Ser Val Gly Arg Gly Ile Ser Lys Asp
                245                 250                 255

Val Gln Gly Gly Ile Ala Leu Ala Glu Lys Leu Ala Asp Ala Phe Gly
            260                 265                 270

Asn Gly Val Val Gly Gly Ser Arg Ala Val Ile Asp Ser Gly Trp Leu
        275                 280                 285

Pro Ala Asp His Gln Val Gly Gln Thr Gly Lys Thr Val His Pro Lys
    290                 295                 300

Val Tyr Val Ala Leu Gly Ile Ser Gly Ala Ile Gln His Lys Ala Gly
305                 310                 315                 320

Met Gln Asp Ser Glu Leu Ile Ile Ala Val Asn Lys Asp Glu Thr Ala
                325                 330                 335

Pro Ile Phe Asp Cys Ala Asp Tyr Gly Ile Thr Gly Asp Leu Phe Lys
            340                 345                 350

Ile Val Pro Met Met Ile Asp Ala Ile Lys Glu Gly Lys Asn Ala
        355                 360                 365

<210> SEQ ID NO 40
<211> LENGTH: 267
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 40

Met Arg Ile Tyr Val Cys Val Lys Gln Val Pro Asp Thr Ser Gly Lys
1               5                   10                  15

Val Ala Val Asn Pro Asp Gly Thr Leu Asn Arg Ala Ser Met Ala Ala
            20                  25                  30

Ile Ile Asn Pro Asp Asp Met Ser Ala Ile Glu Gln Ala Leu Lys Leu
        35                  40                  45

Lys Asp Glu Thr Gly Cys Gln Val Thr Ala Leu Thr Met Gly Pro Pro
    50                  55                  60

Pro Ala Glu Gly Met Leu Arg Glu Ile Ile Ala Met Gly Ala Asp Asp
65                  70                  75                  80

Gly Val Leu Ile Ser Ala Arg Glu Phe Gly Gly Ser Asp Thr Phe Ala
                85                  90                  95

Thr Ser Gln Ile Ile Ser Ala Ala Ile His Lys Leu Gly Leu Ser Asn
            100                 105                 110

Glu Asp Met Ile Phe Cys Gly Arg Gln Ala Ile Asp Gly Asp Thr Ala
        115                 120                 125

Gln Val Gly Pro Gln Ile Ala Glu Lys Leu Ser Ile Pro Gln Val Thr
    130                 135                 140

Tyr Gly Ala Gly Ile Lys Lys Ser Gly Asp Leu Val Leu Val Lys Arg
145                 150                 155                 160

Met Leu Glu Asp Gly Tyr Met Met Ile Glu Val Thr Pro Cys Leu
                165                 170                 175

Ile Thr Cys Ile Gln Asp Lys Ala Val Lys Pro Arg Tyr Met Thr Leu
            180                 185                 190

Asn Gly Ile Met Glu Cys Tyr Ser Lys Pro Leu Leu Val Leu Asp Tyr
        195                 200                 205

Glu Ala Leu Lys Asp Glu Pro Leu Ile Glu Leu Asp Thr Ile Gly Leu
    210                 215                 220

Lys Gly Ser Pro Thr Asn Ile Phe Lys Ser Phe Thr Pro Pro Gln Lys
225                 230                 235                 240

Gly Val Gly Val Met Leu Gln Gly Thr Asp Lys Glu Lys Val Glu Asp
                245                 250                 255

Leu Val Asp Lys Leu Met Gln Lys His Val Ile
            260                 265

<210> SEQ ID NO 41
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 41

Met Phe Leu Leu Lys Ile Lys Lys Glu Arg Met Lys Arg Met Asp Phe
1               5                   10                  15

Ser Leu Thr Arg Glu Gln Glu Met Leu Lys Lys Leu Ala Arg Gln Phe
            20                  25                  30

Ala Glu Ile Glu Leu Glu Pro Val Ala Glu Ile Asp Arg Glu His
        35                  40                  45

Val Phe Pro Ala Glu Asn Phe Lys Met Ala Glu Ile Gly Leu Thr
    50                  55                  60

```
Gly Ile Gly Ile Pro Lys Glu Phe Gly Ser Gly Gly Gly Thr Leu
 65                  70                  75                  80

Glu Lys Val Ile Ala Val Ser Glu Phe Gly Lys Lys Cys Met Ala Ser
             85                  90                  95

Ala Ser Ile Leu Ser Ile His Leu Ile Ala Pro Gln Ala Ile Tyr Lys
            100                 105                 110

Tyr Gly Thr Lys Glu Gln Lys Glu Thr Tyr Leu Pro Arg Leu Thr Lys
        115                 120                 125

Gly Gly Glu Leu Gly Ala Phe Ala Leu Thr Glu Pro Asn Ala Gly Ser
    130                 135                 140

Asp Ala Gly Ala Val Lys Thr Thr Ala Ile Leu Asp Ser Gln Thr Asn
145                 150                 155                 160

Glu Tyr Val Leu Asn Gly Thr Lys Cys Phe Ile Ser Gly Gly Arg
                165                 170                 175

Ala Gly Val Leu Val Ile Phe Ala Leu Thr Glu Pro Lys Lys Gly Leu
                180                 185                 190

Lys Gly Met Ser Ala Ile Ile Val Glu Lys Gly Thr Pro Gly Phe Ser
            195                 200                 205

Ile Gly Lys Val Glu Ser Lys Met Gly Ile Ala Gly Ser Glu Thr Ala
        210                 215                 220

Glu Leu Ile Phe Glu Asp Cys Arg Val Pro Ala Ala Asn Leu Leu Gly
225                 230                 235                 240

Lys Glu Gly Lys Gly Phe Lys Ile Ala Met Glu Ala Leu Asp Gly Ala
                245                 250                 255

Arg Ile Gly Val Gly Ala Gln Ala Ile Gly Ile Ala Glu Gly Ala Ile
                260                 265                 270

Asp Leu Ser Val Lys Tyr Val His Glu Arg Ile Gln Phe Gly Lys Pro
            275                 280                 285

Ile Ala Asn Leu Gln Gly Ile Gln Trp Tyr Ile Ala Asp Met Ala Thr
        290                 295                 300

Lys Thr Ala Ala Ala Arg Ala Leu Val Glu Phe Ala Ala Tyr Leu Glu
305                 310                 315                 320

Asp Ala Gly Lys Pro Phe Thr Lys Glu Ser Ala Met Cys Lys Leu Asn
                325                 330                 335

Ala Ser Glu Asn Ala Arg Phe Val Thr Asn Leu Ala Leu Gln Ile His
            340                 345                 350

Gly Gly Tyr Gly Tyr Met Lys Asp Tyr Pro Leu Glu Arg Met Tyr Arg
        355                 360                 365

Asp Ala Lys Ile Thr Glu Ile Tyr Glu Gly Thr Ser Glu Ile His Lys
370                 375                 380

Val Val Ile Ala Arg Glu Val Met Lys Arg
385                 390

<210> SEQ ID NO 42
<211> LENGTH: 820
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
```

```
            20                  25                  30
Val Ala Thr Val Leu Ser Ala Pro Ala Lys Ile Thr Asn His Leu Val
            35                  40                  45

Ala Met Ile Glu Lys Thr Ile Ser Gly Gln Asp Ala Leu Pro Asn Ile
        50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                    85                  90                  95

Glu Phe Ala Gln Ile Lys His Val Leu His Gly Ile Ser Leu Leu Gly
                100                 105                 110

Gln Cys Pro Asp Ser Ile Asn Ala Ala Leu Ile Cys Arg Gly Glu Lys
            115                 120                 125

Met Ser Ile Ala Ile Met Ala Gly Val Leu Glu Ala Arg Gly His Asn
        130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                    165                 170                 175

Ser Arg Ile Pro Ala Asp His Met Val Leu Met Ala Gly Phe Thr Ala
                180                 185                 190

Gly Asn Glu Lys Gly Glu Leu Val Val Leu Gly Arg Asn Gly Ser Asp
            195                 200                 205

Tyr Ser Ala Ala Val Leu Ala Ala Cys Leu Arg Ala Asp Cys Cys Glu
        210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                    245                 250                 255

Leu Ser Tyr Phe Gly Ala Lys Val Leu His Pro Arg Thr Ile Thr Pro
                260                 265                 270

Ile Ala Gln Phe Gln Ile Pro Cys Leu Ile Lys Asn Thr Gly Asn Pro
            275                 280                 285

Gln Ala Pro Gly Thr Leu Ile Gly Ala Ser Arg Asp Glu Asp Glu Leu
        290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                    325                 330                 335

Ala Ala Met Ser Arg Ala Arg Ile Ser Val Val Leu Ile Thr Gln Ser
                340                 345                 350

Ser Ser Glu Tyr Ser Ile Ser Phe Cys Val Pro Gln Ser Asp Cys Val
            355                 360                 365

Arg Ala Glu Arg Ala Met Gln Glu Glu Phe Tyr Leu Glu Leu Lys Glu
        370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                    405                 410                 415

Phe Ala Ala Leu Ala Arg Ala Asn Ile Asn Ile Val Ala Ile Ala Gln
                420                 425                 430

Arg Ser Ser Glu Arg Ser Ile Ser Val Val Val Asn Asn Asp Asp Ala
            435                 440                 445
```

```
Thr Thr Gly Val Arg Val Thr His Gln Met Leu Phe Asn Thr Asp Gln
    450                 455                 460

Val Ile Glu Val Phe Val Ile Gly Val Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Leu Ala Gln Ala
        515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Thr
                565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
        595                 600                 605

Val Gly Ala Gly Leu Pro Val Ile Glu Asn Leu Gln Asn Leu Leu Asn
    610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
        675                 680                 685

Glu Thr Gly Arg Glu Leu Glu Leu Ala Asp Ile Glu Ile Glu Pro Val
    690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
                725                 730                 735

Arg Asp Glu Gly Lys Val Leu Arg Tyr Val Gly Asn Ile Asp Glu Asp
            740                 745                 750

Gly Val Cys Arg Val Lys Ile Ala Glu Val Asp Gly Asn Asp Pro Leu
        755                 760                 765

Phe Lys Val Lys Asn Gly Glu Asn Ala Leu Ala Phe Tyr Ser His Tyr
    770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
                805                 810                 815

Lys Leu Gly Val
            820

<210> SEQ ID NO 43
<211> LENGTH: 310
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic polypeptide"

<400> SEQUENCE: 43

Met Val Lys Val Tyr Ala Pro Ala Ser Ser Ala Asn Met Ser Val Gly
1               5                   10                  15

Phe Asp Val Leu Gly Ala Ala Val Thr Pro Val Asp Gly Ala Leu Leu
            20                  25                  30

Gly Asp Val Thr Val Glu Ala Ala Glu Thr Phe Ser Leu Asn Asn
        35                  40                  45

Leu Gly Arg Phe Ala Asp Lys Leu Pro Ser Glu Pro Arg Glu Asn Ile
50                  55                  60

Val Tyr Gln Cys Trp Glu Arg Phe Cys Gln Glu Leu Gly Lys Gln Ile
65                  70                  75                  80

Pro Val Ala Met Thr Leu Glu Lys Asn Met Pro Ile Gly Ser Gly Leu
                85                  90                  95

Gly Ser Ser Ala Cys Ser Val Val Ala Ala Leu Met Ala Met Asn Glu
            100                 105                 110

His Cys Gly Lys Pro Leu Asn Asp Thr Arg Leu Leu Ala Leu Met Gly
        115                 120                 125

Glu Leu Glu Gly Arg Ile Ser Gly Ser Ile His Tyr Asp Asn Val Ala
130                 135                 140

Pro Cys Phe Leu Gly Gly Met Gln Leu Met Ile Glu Glu Asn Asp Ile
145                 150                 155                 160

Ile Ser Gln Gln Val Pro Gly Phe Asp Glu Trp Leu Trp Val Leu Ala
                165                 170                 175

Tyr Pro Gly Ile Lys Val Ser Thr Ala Glu Ala Arg Ala Ile Leu Pro
            180                 185                 190

Ala Gln Tyr Arg Arg Gln Asp Cys Ile Ala His Gly Arg His Leu Ala
        195                 200                 205

Gly Phe Ile His Ala Cys Tyr Ser Arg Gln Pro Glu Leu Ala Ala Lys
210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
            260                 265                 270

Pro Glu Thr Ala Gln Arg Val Ala Asp Trp Leu Gly Lys Asn Tyr Leu
        275                 280                 285

Gln Asn Gln Glu Gly Phe Val His Ile Cys Arg Leu Asp Thr Ala Gly
290                 295                 300

Ala Arg Val Leu Glu Asn
305                 310

<210> SEQ ID NO 44
<211> LENGTH: 428
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

Met Lys Leu Tyr Asn Leu Lys Asp His Asn Glu Gln Val Ser Phe Ala

-continued

```
1               5                   10                  15
Gln Ala Val Thr Gln Gly Leu Gly Lys Asn Gln Gly Leu Phe Phe Pro
                20                  25                  30
His Asp Leu Pro Glu Phe Ser Leu Thr Glu Ile Asp Glu Met Leu Lys
                35                  40                  45
Leu Asp Phe Val Thr Arg Ser Ala Lys Ile Leu Ser Ala Phe Ile Gly
50                  55                  60
Asp Glu Ile Pro Gln Glu Ile Leu Glu Glu Arg Val Arg Ala Ala Phe
65                  70                  75                  80
Ala Phe Pro Ala Pro Val Ala Asn Val Glu Ser Asp Val Gly Cys Leu
                85                  90                  95
Glu Leu Phe His Gly Pro Thr Leu Ala Phe Lys Asp Phe Gly Gly Arg
                100                 105                 110
Phe Met Ala Gln Met Leu Thr His Ile Ala Gly Asp Lys Pro Val Thr
                115                 120                 125
Ile Leu Thr Ala Thr Ser Gly Asp Thr Gly Ala Ala Val Ala His Ala
130                 135                 140
Phe Tyr Gly Leu Pro Asn Val Lys Val Val Ile Leu Tyr Pro Arg Gly
145                 150                 155                 160
Lys Ile Ser Pro Leu Gln Glu Lys Leu Phe Cys Thr Leu Gly Gly Asn
                165                 170                 175
Ile Glu Thr Val Ala Ile Asp Gly Asp Phe Asp Ala Cys Gln Ala Leu
                180                 185                 190
Val Lys Gln Ala Phe Asp Asp Glu Glu Leu Lys Val Ala Leu Gly Leu
                195                 200                 205
Asn Ser Ala Asn Ser Ile Asn Ile Ser Arg Leu Leu Ala Gln Ile Cys
210                 215                 220
Tyr Tyr Phe Glu Ala Val Ala Gln Leu Pro Gln Glu Thr Arg Asn Gln
225                 230                 235                 240
Leu Val Val Ser Val Pro Ser Gly Asn Phe Gly Asp Leu Thr Ala Gly
                245                 250                 255
Leu Leu Ala Lys Ser Leu Gly Leu Pro Val Lys Arg Phe Ile Ala Ala
                260                 265                 270
Thr Asn Val Asn Asp Thr Val Pro Arg Phe Leu His Asp Gly Gln Trp
                275                 280                 285
Ser Pro Lys Ala Thr Gln Ala Thr Leu Ser Asn Ala Met Asp Val Ser
                290                 295                 300
Gln Pro Asn Asn Trp Pro Arg Val Glu Glu Leu Phe Arg Arg Lys Ile
305                 310                 315                 320
Trp Gln Leu Lys Glu Leu Gly Tyr Ala Ala Val Asp Asp Glu Thr Thr
                325                 330                 335
Gln Gln Thr Met Arg Glu Leu Lys Leu Gly Tyr Thr Ser Glu Pro
                340                 345                 350
His Ala Ala Val Ala Tyr Arg Ala Leu Arg Asp Gln Leu Asn Pro Gly
                355                 360                 365
Glu Tyr Gly Leu Phe Leu Gly Thr Ala His Pro Ala Lys Phe Lys Glu
                370                 375                 380
Ser Val Glu Ala Ile Leu Gly Glu Thr Leu Asp Leu Pro Lys Glu Leu
385                 390                 395                 400
Ala Glu Arg Ala Asp Leu Pro Leu Leu Ser His Asn Leu Pro Ala Asp
                405                 410                 415
Phe Ala Ala Leu Arg Lys Leu Met Met Asn His Gln
                420                 425
```

<210> SEQ ID NO 45
<211> LENGTH: 436
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Met Ser Glu Thr Tyr Val Ser Glu Lys Ser Pro Gly Val Met Ala Ser
1               5                   10                  15

Gly Ala Glu Leu Ile Arg Ala Ala Asp Ile Gln Thr Ala Gln Ala Arg
            20                  25                  30

Ile Ser Ser Val Ile Ala Pro Thr Pro Leu Gln Tyr Cys Pro Arg Leu
        35                  40                  45

Ser Glu Glu Thr Gly Ala Glu Ile Tyr Leu Lys Arg Glu Asp Leu Gln
    50                  55                  60

Asp Val Arg Ser Tyr Lys Ile Arg Gly Ala Leu Asn Ser Gly Ala Gln
65              70                  75                  80

Leu Thr Gln Glu Gln Arg Asp Ala Gly Ile Val Ala Ala Ser Ala Gly
            85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Ala Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Ala Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
            340                 345                 350
```

```
His Tyr Phe Leu Val Asn Phe Pro Gln Lys Pro Gly Gln Leu Arg His
            355                 360                 365

Phe Leu Glu Asp Ile Leu Gly Pro Asp Asp Ile Thr Leu Phe Glu
370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
            405                 410                 415

Glu Ser Ala Ile Asp Ser Arg Arg Leu Glu Pro Gly Thr Pro Glu Tyr
            420                 425                 430

Glu Tyr Leu Thr
            435

<210> SEQ ID NO 46
<211> LENGTH: 887
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Met Ser Glu Arg Phe Pro Asn Asp Val Asp Pro Ile Glu Thr Arg Asp
1               5                   10                  15

Trp Leu Gln Ala Ile Glu Ser Val Ile Arg Glu Gly Val Glu Arg
            20                  25                  30

Ala Gln Tyr Leu Ile Asp Gln Leu Leu Ala Glu Ala Arg Lys Gly Gly
            35                  40                  45

Val Asn Val Ala Ala Gly Thr Gly Ile Ser Asn Tyr Ile Asn Thr Ile
50                  55                  60

Pro Val Glu Glu Gln Pro Glu Tyr Pro Gly Asn Leu Glu Leu Glu Arg
65                  70                  75                  80

Arg Ile Arg Ser Ala Ile Arg Trp Asn Ala Ile Met Thr Val Leu Arg
            85                  90                  95

Ala Ser Lys Lys Asp Leu Glu Leu Gly Gly His Met Ala Ser Phe Gln
            100                 105                 110

Ser Ser Ala Thr Ile Tyr Asp Val Cys Phe Asn His Phe Arg Ala
            115                 120                 125

Arg Asn Glu Gln Asp Gly Gly Asp Leu Val Tyr Phe Gln Gly His Ile
            130                 135                 140

Ser Pro Gly Val Tyr Ala Arg Ala Phe Leu Glu Gly Arg Leu Thr Gln
145                 150                 155                 160

Glu Gln Leu Asp Asn Phe Arg Gln Glu Val His Gly Asn Gly Leu Ser
                165                 170                 175

Ser Tyr Pro His Pro Lys Leu Met Pro Glu Phe Trp Gln Phe Pro Thr
            180                 185                 190

Val Ser Met Gly Leu Gly Pro Ile Gly Ala Ile Tyr Gln Ala Lys Phe
            195                 200                 205

Leu Lys Tyr Leu Glu His Arg Gly Leu Lys Asp Thr Ser Lys Gln Thr
            210                 215                 220

Val Tyr Ala Phe Leu Gly Asp Gly Glu Met Asp Glu Pro Glu Ser Lys
225                 230                 235                 240

Gly Ala Ile Thr Ile Ala Thr Arg Glu Lys Leu Asp Asn Leu Val Phe
                245                 250                 255

Val Ile Asn Cys Asn Leu Gln Arg Leu Asp Gly Pro Val Thr Gly Asn
```

-continued

```
            260                 265                 270
Gly Lys Ile Ile Asn Glu Leu Glu Gly Ile Phe Glu Gly Ala Gly Trp
            275                 280                 285

Asn Val Ile Lys Val Met Trp Gly Ser Arg Trp Asp Glu Leu Leu Arg
290                 295                 300

Lys Asp Thr Ser Gly Lys Leu Ile Gln Leu Met Asn Glu Thr Val Asp
305                 310                 315                 320

Gly Asp Tyr Gln Thr Phe Lys Ser Lys Asp Gly Ala Tyr Val Arg Glu
                    325                 330                 335

His Phe Phe Gly Lys Tyr Pro Glu Thr Ala Ala Leu Val Ala Asp Trp
                    340                 345                 350

Thr Asp Glu Gln Ile Trp Ala Leu Asn Arg Gly Gly His Asp Pro Lys
            355                 360                 365

Lys Ile Tyr Ala Ala Phe Lys Lys Ala Gln Glu Thr Lys Gly Lys Ala
            370                 375                 380

Thr Val Ile Leu Ala His Thr Ile Lys Gly Tyr Gly Met Gly Asp Ala
385                 390                 395                 400

Ala Glu Gly Lys Asn Ile Ala His Gln Val Lys Lys Met Asn Met Asp
                    405                 410                 415

Gly Val Arg His Ile Arg Asp Arg Phe Asn Val Pro Val Ser Asp Ala
                    420                 425                 430

Asp Ile Glu Lys Leu Pro Tyr Ile Thr Phe Pro Glu Gly Ser Glu Glu
            435                 440                 445

His Thr Tyr Leu His Ala Gln Arg Gln Lys Leu His Gly Tyr Leu Pro
            450                 455                 460

Ser Arg Gln Pro Asn Phe Thr Glu Lys Leu Glu Leu Pro Ser Leu Gln
465                 470                 475                 480

Asp Phe Gly Ala Leu Leu Glu Glu Gln Ser Lys Glu Ile Ser Thr Thr
                    485                 490                 495

Ile Ala Phe Val Arg Ala Leu Asn Val Met Leu Lys Asn Lys Ser Ile
                    500                 505                 510

Lys Asp Arg Leu Val Pro Ile Ile Ala Asp Glu Ala Arg Thr Phe Gly
            515                 520                 525

Met Glu Gly Leu Phe Arg Gln Ile Gly Ile Tyr Ser Pro Asn Gly Gln
            530                 535                 540

Gln Tyr Thr Pro Gln Asp Arg Glu Gln Val Ala Tyr Tyr Lys Glu Asp
545                 550                 555                 560

Glu Lys Gly Gln Ile Leu Gln Glu Gly Ile Asn Glu Leu Gly Ala Gly
                    565                 570                 575

Cys Ser Trp Leu Ala Ala Ala Thr Ser Tyr Ser Thr Asn Asn Leu Pro
                    580                 585                 590

Met Ile Pro Phe Tyr Ile Tyr Tyr Ser Met Phe Gly Phe Gln Arg Ile
            595                 600                 605

Gly Asp Leu Cys Trp Ala Ala Gly Asp Gln Gln Ala Arg Gly Phe Leu
            610                 615                 620

Ile Gly Gly Thr Ser Gly Arg Thr Thr Leu Asn Gly Glu Gly Leu Gln
625                 630                 635                 640

His Glu Asp Gly His Ser His Ile Gln Ser Leu Thr Ile Pro Asn Cys
                    645                 650                 655

Ile Ser Tyr Asp Pro Ala Tyr Ala Tyr Glu Val Ala Val Ile Met His
                    660                 665                 670

Asp Gly Leu Glu Arg Met Tyr Gly Glu Lys Gln Glu Asn Val Tyr Tyr
            675                 680                 685
```

```
Tyr Ile Thr Thr Leu Asn Glu Asn Tyr His Met Pro Ala Met Pro Glu
            690                 695                 700

Gly Ala Glu Glu Gly Ile Arg Lys Gly Ile Tyr Lys Leu Glu Thr Ile
705                 710                 715                 720

Glu Gly Ser Lys Gly Lys Val Gln Leu Leu Gly Ser Gly Ser Ile Leu
                725                 730                 735

Arg His Val Arg Glu Ala Ala Glu Ile Leu Ala Lys Asp Tyr Gly Val
            740                 745                 750

Gly Ser Asp Val Tyr Ser Val Thr Ser Phe Thr Glu Leu Ala Arg Asp
        755                 760                 765

Gly Gln Asp Cys Glu Arg Trp Asn Met Leu His Pro Leu Glu Thr Pro
        770                 775                 780

Arg Val Pro Tyr Ile Ala Gln Val Met Asn Asp Ala Pro Ala Val Ala
785                 790                 795                 800

Ser Thr Asp Tyr Met Lys Leu Phe Ala Glu Gln Val Arg Thr Tyr Val
                805                 810                 815

Pro Ala Asp Asp Tyr Arg Val Leu Gly Thr Asp Gly Phe Gly Arg Ser
            820                 825                 830

Asp Ser Arg Glu Asn Leu Arg His His Phe Glu Val Ala Ser Tyr
        835                 840                 845

Val Val Val Ala Ala Leu Gly Glu Leu Ala Lys Arg Gly Glu Ile Asp
850                 855                 860

Lys Lys Val Val Ala Asp Ala Ile Ala Lys Phe Asn Ile Asp Ala Asp
865                 870                 875                 880

Lys Val Asn Pro Arg Leu Ala
                885

<210> SEQ ID NO 47
<211> LENGTH: 630
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Met Ala Ile Glu Ile Lys Val Pro Asp Ile Gly Ala Asp Glu Val Glu
1               5                   10                  15

Ile Thr Glu Ile Leu Val Lys Val Gly Asp Lys Val Glu Ala Glu Gln
            20                  25                  30

Ser Leu Ile Thr Val Glu Gly Asp Lys Ala Ser Met Glu Val Pro Ser
        35                  40                  45

Pro Gln Ala Gly Ile Val Lys Glu Ile Lys Val Ser Val Gly Asp Lys
    50                  55                  60

Thr Gln Thr Gly Ala Leu Ile Met Ile Phe Ser Ala Asp Gly Ala
65                  70                  75                  80

Ala Asp Ala Ala Pro Ala Gln Ala Glu Glu Lys Lys Glu Ala Ala Pro
                85                  90                  95

Ala Ala Ala Pro Ala Ala Ala Ala Lys Asp Val Asn Val Pro Asp
            100                 105                 110

Ile Gly Ser Asp Glu Val Glu Val Thr Glu Ile Leu Val Lys Val Gly
        115                 120                 125

Asp Lys Val Glu Ala Glu Gln Ser Leu Ile Thr Val Glu Gly Asp Lys
    130                 135                 140
```

```
Ala Ser Met Glu Val Pro Ala Pro Phe Ala Gly Thr Val Lys Glu Ile
145                 150                 155                 160

Lys Val Asn Val Gly Asp Lys Val Ser Thr Gly Ser Leu Ile Met Val
            165                 170                 175

Phe Glu Val Ala Gly Glu Ala Gly Ala Ala Pro Ala Ala Lys Gln
            180                 185                 190

Glu Ala Ala Pro Ala Ala Ala Pro Ala Pro Ala Ala Gly Val Lys Glu
            195                 200                 205

Val Asn Val Pro Asp Ile Gly Gly Asp Glu Val Glu Val Thr Glu Val
    210                 215                 220

Met Val Lys Val Gly Asp Lys Val Ala Ala Glu Gln Ser Leu Ile Thr
225                 230                 235                 240

Val Glu Gly Asp Lys Ala Ser Met Glu Val Pro Ala Pro Phe Ala Gly
            245                 250                 255

Val Val Lys Glu Leu Lys Val Asn Val Gly Asp Lys Val Lys Thr Gly
            260                 265                 270

Ser Leu Ile Met Ile Phe Glu Val Glu Gly Ala Ala Pro Ala Ala Ala
            275                 280                 285

Pro Ala Lys Gln Glu Ala Ala Pro Ala Pro Ala Ala Lys Ala Glu
290                 295                 300

Ala Pro Ala Ala Ala Pro Ala Ala Lys Ala Glu Gly Lys Ser Glu Phe
305                 310                 315                 320

Ala Glu Asn Asp Ala Tyr Val His Ala Thr Pro Leu Ile Arg Arg Leu
            325                 330                 335

Ala Arg Glu Phe Gly Val Asn Leu Ala Lys Val Lys Gly Thr Gly Arg
            340                 345                 350

Lys Gly Arg Ile Leu Arg Glu Asp Val Gln Ala Tyr Val Lys Glu Ala
            355                 360                 365

Ile Lys Arg Ala Glu Ala Ala Pro Ala Ala Thr Gly Gly Gly Ile Pro
            370                 375                 380

Gly Met Leu Pro Trp Pro Lys Val Asp Phe Ser Lys Phe Gly Glu Ile
385                 390                 395                 400

Glu Glu Val Glu Leu Gly Arg Ile Gln Lys Ile Ser Gly Ala Asn Leu
            405                 410                 415

Ser Arg Asn Trp Val Met Ile Pro His Val Thr His Phe Asp Lys Thr
            420                 425                 430

Asp Ile Thr Glu Leu Glu Ala Phe Arg Lys Gln Gln Asn Glu Glu Ala
            435                 440                 445

Ala Lys Arg Lys Leu Asp Val Lys Ile Thr Pro Val Val Phe Ile Met
450                 455                 460

Lys Ala Val Ala Ala Ala Leu Glu Gln Met Pro Arg Phe Asn Ser Ser
465                 470                 475                 480

Leu Ser Glu Asp Gly Gln Arg Leu Thr Leu Lys Lys Tyr Ile Asn Ile
            485                 490                 495

Gly Val Ala Val Asp Thr Pro Asn Gly Leu Val Val Pro Val Phe Lys
            500                 505                 510

Asp Val Asn Lys Lys Gly Ile Ile Glu Leu Ser Arg Glu Leu Met Thr
            515                 520                 525

Ile Ser Lys Lys Ala Arg Asp Gly Lys Leu Thr Ala Gly Glu Met Gln
            530                 535                 540

Gly Gly Cys Phe Thr Ile Ser Ser Ile Gly Gly Leu Gly Thr Thr His
545                 550                 555                 560

Phe Ala Pro Ile Val Asn Ala Pro Glu Val Ala Ile Leu Gly Val Ser
```

```
                    565                 570                 575

Lys Ser Ala Met Glu Pro Val Trp Asn Gly Lys Glu Phe Val Pro Arg
                580                 585                 590

Leu Met Leu Pro Ile Ser Leu Ser Phe Asp His Arg Val Ile Asp Gly
            595                 600                 605

Ala Asp Gly Ala Arg Phe Ile Thr Ile Ile Asn Asn Thr Leu Ser Asp
610                 615                 620

Ile Arg Arg Leu Val Met
625                 630

<210> SEQ ID NO 48
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
                20                  25                  30

Val Ile Val Glu Arg Tyr Asn Thr Leu Gly Gly Val Cys Leu Asn Val
            35                  40                  45

Gly Cys Ile Pro Ser Lys Ala Leu Leu His Val Ala Lys Val Ile Glu
        50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285
```

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
                340                 345                 350

Thr Lys Pro Glu Val Ala Trp Val Gly Leu Thr Glu Lys Glu Ala Lys
            355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
                420                 425                 430

Cys Asp Ala Glu Asp Ile Ala Leu Thr Ile His Ala His Pro Thr Leu
            435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 49
<211> LENGTH: 483
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49
atgagccccg acagggaac tcaaagcgag aacagctgca cacattttcc aggtaatctt      60
ccaaatatgc ttcgtgactt gcgtgacgct ttctctcgcg tgaaaacctt ttttcagatg     120
aaggatcagt tagataatct gctgctgaaa gaatcgcttc ttgaggactt caagggatat    180
ctgggatgtc aggcgttatc tgagatgatt cagtttattt tggaagaagt tatgccccag    240
gctgagaatc aagaccctga catcaaagcg catgtgaata gcctgggcga gaatctgaag    300
acactgcgcc tgcgtcttcg ccgctgtcac cgttttctgc cttgcgaaaa taagagtaag    360
gccgttgagc aagtgaaaaa tgctttcaac aagttacaag aaaaagggat ttacaaagct    420
atgtctgagt ttgacatttt cattaattac attgaggcct acatgactat gaagattcgc    480
aat                                                                  483

<210> SEQ ID NO 50
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Met Ala Pro Thr Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
                20                  25                  30

Lys Asn Pro Lys Leu Thr Arg Met Leu Thr Phe Lys Phe Tyr Met Pro
            35                  40                  45

Lys Lys Ala Thr Glu Leu Lys His Leu Gln Cys Leu Glu Glu Glu Leu
50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
            115                 120                 125

Ile Ile Ser Thr Leu Thr
        130

<210> SEQ ID NO 51
<211> LENGTH: 179
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
                20                  25                  30

Ala Ala Pro Ile Ser Ser His Cys Arg Leu Asp Lys Ser Asn Phe Gln
            35                  40                  45

Gln Pro Tyr Ile Thr Asn Arg Thr Phe Met Leu Ala Lys Glu Ala Ser
50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
            115                 120                 125

Leu Ser Thr Cys His Ile Glu Gly Asp Asp Leu His Ile Gln Arg Asn
            130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 52
<211> LENGTH: 243
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 52

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
210                 215                 220

Ser Lys Ala Gly His Ser Val Trp Pro Leu Gly Phe Pro Thr Leu Ser
225                 230                 235                 240

Pro Gln Pro

<210> SEQ ID NO 53
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
        50                  55                  60

Phe Asn Pro Leu Ser Arg Lys His Gly Gly Pro Lys Asp Glu Glu Arg
```

His Val Gly Asp Leu Gly Asn Val Thr Ala Asp Lys Asp Gly Val Ala
65                  70                  75                  80

Asp Val Ser Ile Glu Asp Ser Val Ile Ser Leu Ser Gly Asp His Cys
            85                  90                  95

Ile Ile Gly Arg Thr Leu Val Val His Glu Lys Ala Asp Asp Leu Gly
            100                 105                 110

Lys Gly Gly Asn Glu Glu Ser Thr Lys Thr Gly Asn Ala Gly Ser Arg
        115                 120                 125

Leu Ala Cys Gly Val Ile Gly Ile Ala Gln
130                 135                 140

145                 150

<210> SEQ ID NO 54
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 55
<211> LENGTH: 117
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
atccccatca ctcttgatgg agatcaattc cccaagctgc tagagcgtta ccttgccctt      60
aaacattagc aatgtcgatt tatcagaggg ccgacaggct cccacaggag aaaaccg       117

<210> SEQ ID NO 56
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
ctcttgatcg ttatcaattc ccacgctgtt tcagagcgtt accttgccct taaacattag      60
caatgtcgat ttatcagagg gccgacaggc tcccacagga gaaaaccg                 108

<210> SEQ ID NO 57
<211> LENGTH: 290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 57
gtcagcataa caccctgacc tctcattaat tgttcatgcc gggcggcact atcgtcgtcc      60
ggccttttcc tctcttactc tgctacgtac atctatttct ataaatccgt tcaatttgtc     120
tgttttttgc acaaacatga aatatcagac aattccgtga cttaagaaaa tttatacaaa     180
tcagcaatat accccttaag gagtatataa aggtgaattt gatttacatc aataagcggg     240
gttgctgaat cgttaaggta ggcggtaata gaaaagaaat cgaggcaaaa                 290

<210> SEQ ID NO 58
<211> LENGTH: 433
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58
cggcccgatc gttgaacata gcggtccgca ggcggcactg cttacagcaa acggtctgta      60
cgctgtcgtc tttgtgatgt gcttcctgtt aggtttcgtc agccgtcacc gtcagcataa     120
caccctgacc tctcattaat tgctcatgcc ggacggcact atcgtcgtcc ggccttttcc     180
tctcttcccc cgctacgtgc atctatttct ataaacccgc tcattttgtc tattttttgc     240
acaaacatga aatatcagac aattccgtga cttaagaaaa tttatacaaa tcagcaatat     300
acccattaag gagtatataa aggtgaattt gatttacatc aataagcggg gttgctgaat     360
cgttaaggta ggcggtaata gaaaagaaat cgaggcaaaa atgtttgttt aactttaaga     420
aggagatata cat                                                         433

<210> SEQ ID NO 59
<211> LENGTH: 290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
gtcagcataa caccctgacc tctcattaat tgctcatgcc ggacggcact atcgtcgtcc      60
ggccttttcc tctcttcccc cgctacgtgc atctatttct ataaacccgc tcattttgtc     120
tattttttgc acaaacatga aatatcagac aattccgtga cttaagaaaa tttatacaaa     180
tcagcaatat acccattaag gagtatataa aggtgaattt gatttacatc aataagcggg     240
gttgctgaat cgttaaggta ggcggtaata gaaaagaaat cgaggcaaaa                 290

<210> SEQ ID NO 60
<211> LENGTH: 173
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60
atttcctctc atcccatccg gggtgagagt cttttccccc gactatggc tcatgcatgc       60 atcaaaaaag atgtgagctt gatcaaaaac aaaaatatt tcactcgaca ggagtattta     120
tattgcgccc gttacgtggg cttcgactgt aaatcagaaa ggagaaaaca cct            173
```

<210> SEQ ID NO 61
<211> LENGTH: 305
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61
gtcagcataa caccctgacc tctcattaat tgttcatgcc gggcggcact atcgtcgtcc    60
ggccttttcc tctcttactc tgctacgtac atctatttct ataaatccgt tcaatttgtc   120 tgtttttgc acaaacatga aatatcagac aattccgtga cttaagaaaa tttatacaaa    180
tcagcaatat accccttaag gagtatataa aggtgaattt gatttacatc aataagcggg   240
gttgctgaat cgttaaggat ccctctagaa ataattttgt ttaactttaa gaaggagata   300
tacat                                                              305

<210> SEQ ID NO 62
<211> LENGTH: 180
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62
catttcctct catcccatcc ggggtgagag tctttccccc cgacttatgg ctcatgcatg    60
catcaaaaaa gatgtgagct tgatcaaaaa caaaaaatat ttcactcgac aggagtattt   120
atattgcgcc cggatccctc tagaaataat tttgtttaac tttaagaagg agatatacat   180

<210> SEQ ID NO 63
<211> LENGTH: 199
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63
agttgttctt attggtggtg ttgctttatg gttgcatcgt agtaaatggt tgtaacaaaa    60 gcaattttc cggctgtctg tatacaaaaa cgccgtaaag tttgagcgaa gtcaataaac    120
tctctaccca ttcagggcaa tatctctctt ggatccctct agaaataatt tgtttaact   180 ttaagaagga gatatacat                                                199

<210> SEQ ID NO 64
<211> LENGTH: 207
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64
agttgttctt attggtggtg ttgctttatg gttgcatcgt agtaaatggt tgtaacaaaa    60 gcaattttc cggctgtctg tatacaaaaa cgccgcaaag tttgagcgaa gtcaataaac    120
tctctaccca ttcagggcaa tatctctctt ggatccaaag tgaactctag aaataatttt    180
gtttaacttt aagaaggaga tatacat                                        207

<210> SEQ ID NO 65
<211> LENGTH: 390
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
tcgtctttgt gatgtgcttc ctgttaggtt tcgtcagccg tcaccgtcag cataacaccc     60
tgacctctca ttaattgctc atgccggacg gcactatcgt cgtccggcct tttcctctct   120
tcccccgcta cgtgcatcta tttctataaa cccgctcatt ttgtctattt tttgcacaaa   180
catgaaatat cagacaattc cgtgacttaa gaaaatttat acaaatcagc aatatacccca  240 ttaaggagta tataaaggtg aatttgattt acatcaataa gcggggttgc tgaatcgtta   300
aggtagaaat gtgatctagt tcacatttgc ggtaatagaa aagaaatcga ggcaaaaatg   360
tttgtttaac tttaagaagg agatatacat                                    390

<210> SEQ ID NO 66
<211> LENGTH: 200
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66
agttgttctt attggtggtg ttgctttatg gttgcatcgt agtaaatggt tgtaacaaaa     60
gcaatttttc cggctgtctg tatacaaaaa cgccgcaaag tttgagcgaa gtcaataaac   120
tctctaccca ttcagggcaa tatctctcaa atgtgatcta gttcacattt tttgtttaac   180
tttaagaagg agatatacat                                               200

<210> SEQ ID NO 67
<211> LENGTH: 8575
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
ttattatcgc accgcaatcg ggattttcga ttcataaagc aggtcgtagg tcggcttgtt     60
gagcaggtct tgcagcgtga aaccgtccag atacgtgaaa aacgacttca ttgcaccgcc   120
gagtatgccc gtcagccggc aggacggcgt aatcaggcat tcgttgttcg ggcccataca   180
ctcgaccagc tgcatcggtt cgaggtggcg gacgaccgcg ccgatattga tgcgttcggg   240
cggcgcggcc agcctcagcc cgccgccttt cccgcgtacg ctgtgcaaga acccgccttt   300
gaccagcgcg gtaaccactt tcatcaaatg gcttttggaa atgccgtagg tcgaggcgat   360
ggtggcgata ttgaccagcg cgtcgtcgtt gacggcggtg tagatgagga cgcgcagccc   420
gtagtcggta tgttgggtca gatacataca acctccttag tacatgcaaa attatttcta   480
gagcaacata cgagccggaa gcataaagtg taaagcctgg ggtgcctaat gagttgagtt   540

```
gaggaattat aacaggaaga aatattcctc atacgcttgt aattcctcta tggttgttga    600
caattaatca tcggctcgta taatgtataa cattcatatt ttgtgaattt taaactctag    660
aaataatttt gtttaacttt aagaaggaga tatacatatg gatttaaatt ctaaaaaata    720
tcagatgctt aaagagctat atgtaagctt cgctgaaaat gaagttaaac ctttagcaac    780
agaacttgat gaagaagaaa gatttcctta tgaaacagtg gaaaaaatgg caaaagcagg    840
aatgatgggt ataccatatc aaaagaata tggtggagaa ggtggagaca ctgtaggata    900
tataatggca gttgaagaat tgtctagagt ttgtggtact acaggagtta tattatcagc    960
tcatacatct cttggctcat ggcctatata tcaatatggt aatgaagaac aaaaacaaaa   1020
attcttaaga ccactagcaa gtggagaaaa attaggagca tttggtctta ctgagcctaa   1080
tgctggtaca gatgcgtctg gccaacaaac aactgctgtt ttagacgggg atgaatacat   1140
acttaatggc tcaaaaatat ttataacaaa cgcaatagct ggtgacatat atgtagtaat   1200
ggcaatgact gataaatcta aggggaacaa aggaatatca gcatttatag ttgaaaaagg   1260
aactcctggg tttagctttg gagttaaaga aagaaaatg ggtataagag gttcagctac   1320
gagtgaatta atatttgagg attgcagaat acctaaagaa aatttacttg gaaaagaagg   1380
tcaaggattt aagatagcaa tgtctactct tgatggtggt agaattggta tagctgcaca   1440
agctttaggt ttagcacaag gtgctcttga tgaaactgtt aaatatgtaa agaaagagt   1500
acaatttggt agaccattat caaaattcca aaatacacaa ttccaattag ctgatatgga   1560
agttaaggta caagcggcta gacaccttgt atatcaagca gctataaata aagacttagg   1620
aaaaccttat ggagtagaag cagcaatggc aaaattattt gcagctgaaa cagctatgga   1680
agttactaca aaagctgtac aacttcatgg aggatatgga tacactcgtg actatccagt   1740
agaaagaatg atgagagatg ctaagataac tgaaatatat gaaggaacta gtgaagttca   1800
aagaatggtt atttcaggaa aactattaaa atagtaagaa ggagatatac atatggagga   1860
aggatttatg aatatagtcg tttgtataaa acaagttcca gatacaacag aagttaaact   1920
agatcctaat acaggtactt taattagaga tggagtacca agtataataa accctgatga   1980
taaagcaggt ttagaagaag ctataaaatt aaaagaagaa atgggtgctc atgtaactgt   2040
tataacaatg ggacctcctc aagcagatat ggctttaaaa gaagctttag caatgggtgc   2100
agatagaggt atattattaa cagatagagc atttgcgggt gctgatactt gggcaacttc   2160
atcagcatta gcaggagcat taaaaatat agattttgat attataatag ctggaagaca   2220
ggcgatagat ggagatactg cacaagttgg acctcaaata gctgaacatt taaatcttcc   2280
atcaataaca tatgctgaag aaataaaaac tgaaggtgaa tatgtattag taaaaagaca   2340
atttgaagat tgttgccatg acttaaaagt taaaatgcca tgccttataa caactcttaa   2400
agatatgaac acaccaagat acatgaaagt tggaagaata tatgatgctt cgaaaatga   2460
tgtagtagaa acatggactg taaaagatat agaagttgac ccttctaatt taggtcttaa   2520
aggttctcca actagtgtat ttaaatcatt tacaaaatca gttaaaccag ctggtacaat   2580
atacaatgaa gatgcgaaaa catcagctgg aattatcata gataaattaa aagagaagta   2640
tatcatataa taagaaggag atatacatat gggtaacgtt ttagtagtaa tagaacaaag   2700
agaaaatgta attcaaactg tttctttaga attactagga aaggctacag aaatagcaaa   2760
agattatgat acaaaagttt ctgcattact tttaggtagt aaggtagaag gtttaataga   2820
tacattagca cactatggtg cagatgaggt aatagtagta gatgatgaag ctttagcagt   2880
```

```
gtatacaact gaaccatata caaaagcagc ttatgaagca ataaaagcag ctgaccctat    2940
agttgtatta tttggtgcaa cttcaatagg tagagattta gcgcctagag tttctgctag    3000
aatacataca ggtcttactg ctgactgtac aggtcttgca gtagctgaag atacaaaatt    3060
attattaatg acaagacctg cctttggtgg aaatataatg gcaacaatag tttgtaaaga    3120
tttcagacct caaatgtcta cagttagacc aggggttatg aagaaaaatg aacctgatga    3180
aactaaagaa gctgtaatta accgtttcaa ggtagaattt aatgatgctg ataaattagt    3240
tcaagttgta caagtaataa agaagctaaa aaacaagtt aaaatagaag atgctaagat    3300
attagtttct gctggacgtg gaatgggtgg aaaagaaaac ttagacatac tttatgaatt    3360
agctgaaatt ataggtggag aagtttctgg ttctcgtgcc actatagatg caggttggtt    3420
agataaagca agacaagttg gtcaaactgg taaaactgta agaccagacc tttatatagc    3480
atgtggtata tctggagcaa tacaacatat agctggtatg gaagatgctg agtttatagt    3540
tgctataaat aaaaatccag aagctccaat atttaaatat gctgatgttg gtatagttgg    3600
agatgttcat aaagtgcttc cagaacttat cagtcagtta agtgttgcaa aagaaaaagg    3660
tgaagtttta gctaactaat aagaaggaga tatacatatg agagaagtag taattgccag    3720
tgcagctaga acagcagtag gaagttttgg aggagcattt aaatcagttt cagcggtaga    3780
gttaggggta acagcagcta aagaagctat aaaaagagct aacataactc cagatatgat    3840
agatgaatct cttttagggg gagtacttac agcaggtctt ggacaaaata tagcaagaca    3900
aatagcatta ggagcaggaa taccagtaga aaaaccagct atgactataa atatagtttg    3960
tggttctgga ttaagatctg tttcaatggc atctcaactt atagcattag gtgatgctga    4020
tataatgtta gttggtggag ctgaaaacat gagtatgtct ccttatttag taccaagtgc    4080
gagatatggt gcaagaatgg gtgatgctgc ttttgttgat tcaatgataa agatggatt    4140 atcagacata tttaataact atcacatggg tattactgct gaaaacatag cagagcaatg    4200
gaatataact agagaagaac aagatgaatt agctcttgca agtcaaaata agctgaaaa    4260 agctcaagct gaaggaaaat ttgatgaaga aatagttcct gttgttataa aaggaagaaa    4320
aggtgacact gtagtagata agatgaata tattaagcct ggcactacaa tggagaaact    4380
tgctaagtta agacctgcat ttaaaaaaga tggaacagtt actgctggta atgcatcagg    4440
aataaatgat ggtgctgcta tgttagtagt aatggctaaa gaaaagctg aagaactagg    4500 aatagagcct cttgcaacta tagtttctta tggaacagct ggtgttgacc ctaaaataat    4560
gggatatgga ccagttccag caactaaaaa agctttagaa gctgctaata tgactattga    4620
agatatagat ttagttgaag ctaatgaggc atttgctgcc caatctgtag ctgtaataag    4680
agacttaaat atagatatga ataaagttaa tgttaatggt ggagcaatag ctataggaca    4740
tccaatagga tgctcaggag caagaatact tactacactt ttatatgaaa tgaagagaag    4800
agatgctaaa actggtcttg ctacactttg tataggcggt ggaatgggaa ctactttaat    4860
agttaagaga tagtaagaag gagatataca tatgaaatta gctgtaatag gtagtggaac    4920
tatgggaagt ggtattgtac aaactttttg caagttgtgga catgatgtat gtttaaagag    4980
tagaactcaa ggtgctatag ataaatgttt agctttatta gataaaaatt taactaagtt    5040
agttactaag ggaaaaatgg atgaagctac aaaagcagaa atattaagtc atgttagttc    5100
aactactaat tatgaagatt taaaagatat ggatttaata atagaagcat ctgtagaaga    5160
catgaatata aagaaagatg tttttcaagtt actagatgaa ttatgtaaag aagatactat    5220
cttggcaaca aatacttcat cattatctat aacagaaata gcttcttcta ctaagcgccc    5280
```

```
agataaagtt ataggaatgc atttctttaa tccagttcct atgatgaaat tagttgaagt    5340
tataagtggt cagttaacat caaaagttac ttttgataca gtatttgaat tatctaagag    5400
tatcaataaa gtaccagtag atgtatctga atctcctgga tttgtagtaa atagaatact    5460
tatacctatg ataaatgaag ctgttggtat atatgcagat ggtgttgcaa gtaaagaaga    5520
aatagatgaa gctatgaaat taggagcaaa ccatccaatg ggaccactag cattaggtga    5580
tttaatcgga ttagatgttg ttttagctat aatgaacgtt ttatatactg aatttggaga    5640
tactaaatat agacctcatc cacttttagc taaaatggtt agagctaatc aattaggaag    5700
aaaaactaag ataggattct atgattataa taaataataa gaaggagata tacatatgag    5760
tacaagtgat gttaaagttt atgagaatgt agctgttgaa gtagatggaa atatatgtac    5820
agtgaaaatg aatagaccta agcccttaa tgcaataaat tcaaagactt tagaagaact    5880
ttatgaagta tttgtagata ttaataatga tgaaactatt gatgttgtaa tattgacagg    5940
ggaaggaaag gcatttgtag ctggagcaga tattgcatac atgaaagatt tagatgctgt    6000
agctgctaaa gattttagta tcttaggagc aaaagctttt ggagaaatag aaaatagtaa    6060
aaaagtagtg atagctgctg taaacggatt tgctttaggt ggaggatgtg aacttgcaat    6120
ggcatgtgat ataagaattg catctgctaa agctaaattt ggtcagccag aagtaactct    6180
tggaataact ccaggatatg gaggaactca aaggcttaca agattggttg gaatggcaaa    6240
agcaaaagaa ttaatctttta caggtcaagt tataaaagct gatgaagctg aaaaaatagg    6300
gctagtaaat agagtcgttg agccagacat tttaatagaa gaagttgaga aattagctaa    6360
gataatagct aaaaatgctc agcttgcagt tagatactct aaagaagcaa tacaacttgg    6420
tgctcaaact gatataaata ctggaataga tatagaatct aatttatttg gtctttgttt    6480
ttcaactaaa gaccaaaaag aaggaatgtc agctttcgtt gaaaagagag aagctaactt    6540
tataaaaggg taataagaag gagatataca tatgagaagt tttgaagaag taattaagtt    6600
tgcaaaagaa agaggaccta aaactatatc agtagcatgt tgccaagata agaagttttt    6660
aatggcagtt gaaatggcta gaaaagaaaa aatagcaaat gccattttag taggagatat    6720
agaaaagact aaagaaattg caaaaagcat agacatggat atcgaaaatt atgaactgat    6780
agatataaaa gatttagcag aagcatctct aaaatctgtt gaattagttt cacaaggaaa    6840
agccgacatg gtaatgaaag cttagtagaa cacatcaata atactaaaag cagttttaaa    6900
taaagaagta ggtcttagaa ctggaaatgt attaagtcac gtagcagtat ttgatgtaga    6960
gggatatgat agattatttt tcgtaactga cgcagctatg aacttagctc ctgatacaaa    7020
tactaaaaag caaatcatag aaaatgcttg cacagtagca cattcattag ataaagtga    7080 accaaaagtt gctgcaatat gcgcaaaaga aaaagtaaat ccaaaaatga agatacagt    7140 tgaagctaaa gaactagaag aaatgtatga agaggagaa atcaaaggtt gtatggttgg    7200
tgggcctttt gcaattgata atgcagtatc tttagaagca gctaaacata aaggtataaa    7260
tcatcctgta gcaggacgag ctgatatatt attagcccca gatattgaag gtggtaacat    7320
attatataaa gctttggtat tcttctcaaa atcaaaaaat gcaggagtta tagttggggc    7380
taaagcacca ataatattaa cttctagagc agacagtgaa gaaactaaac taaactcaat    7440
agctttaggt gttttaatgg cagcaaaggc ataataagaa ggagatatac atatgagcaa    7500
aatatttaaa atcttaacaa taaatcctgg ttcgacatca actaaaatag ctgtatttga    7560
taatgaggat ttagtatttg aaaaaactt aagcattct tcagaagaaa taggaaaata    7620
```

```
tgagaaggtg tctgaccaat ttgaatttcg taaacaagta atagaagaag ctctaaaaga      7680
aggtggagta aaaacatctg aattagatgc tgtagtaggt agaggaggac ttcttaaacc      7740
tataaaaggt ggtacttatt cagtaagtgc tgctatgatt gaagatttaa aagtgggagt      7800
tttaggagaa cacgcttcaa acctaggtgg aataatagca aaacaaatag gtgaagaagt      7860
aaatgttcct tcatacatag tagaccctgt tgttgtagat gaattagaag atgttgctag      7920
aatttctggt atgcctgaaa taagtagagc aagtgtagta catgctttaa atcaaaaggc      7980
aatagcaaga agatatgcta gagaaataaa caagaaatat gaagatataa atcttatagt      8040
tgcacacatg ggtggaggag tttctgttgg agctcataaa aatggtaaaa tagtagatgt      8100
tgcaaacgca ttagatggag aaggacccttt ctctccagaa agaagtggtg gactaccagt      8160
aggtgcatta gtaaaaatgt gctttagtgg aaaatatact caagatgaaa ttaaaaagaa      8220
aataaaaggt aatggcggac tagttgcata cttaaacact aatgatgcta gagaagttga      8280
agaaagaatt gaagctggtg atgaaaaagc taaattagta tatgaagcta tggcatatca      8340
aatctctaaa gaaataggag ctagtgctgc agttcttaag ggagatgtaa aagcaatatt      8400
attaactggt ggaatcgcat attcaaaaat gtttacagaa atgattgcag atagagttaa      8460
atttatagca gatgtaaaag tttatccagg tgaagatgaa atgattgcat agctcaagg      8520 tggacttaga gttttaactg gtgaagaaga ggctcaagtt tatgataact aataa         8575
```

<210> SEQ ID NO 68
<211> LENGTH: 6787
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68

```
ttattatcgc accgcaatcg ggattttcga ttcataaagc aggtcgtagg tcggcttgtt        60
gagcaggtct tgcagcgtga aaccgtccag atacgtgaaa aacgacttca ttgcaccgcc       120
gagtatgccc gtcagccggc aggacggcgt aatcaggcat tcgttgttcg ggcccataca       180
ctcgaccagc tgcatcggtt cgaggtggcg gacgaccgcg ccgatattga tgcgttcggg       240
cggcgcggcc agcctcagcc cgccgccttt cccgcgtacg ctgtgcaaga acccgccttt       300
gaccagcgcg gtaaccactt tcatcaaatg gcttttggaa atgccgtagg tcgaggcgat       360
ggtggcgata ttgaccagcg cgtcgtcgtt gacggcggtg tagatgagga cgcgcagccc       420
gtagtcggta tgttgggtca gatacataca acctccttag tacatgcaaa attatttcta       480
gagcaacata cgagccggaa gcataaagtg taaagcctgg ggtgcctaat gagttgagtt       540
gaggaattat aacaggaaga atattcctc atacgcttgt aattcctcta tggttgttga       600
caattaatca tcggctcgta taatgtataa cattcatatt ttgtgaattt taaactctag       660
aaataatttt gtttaacttt aagaaggaga tatacatatg atcgtaaaac ctatggtacg       720
caacaatatc tgcctgaacg cccatcctca gggctgcaag aagggagtgg aagatcagat       780
tgaatatacc aagaaacgca ttaccgcaga agtcaaagct ggcgcaaaag ctccaaaaaa       840
cgttctggtg cttggctgct caaatggtta cggcctggcg agccgcatta ctgctgcgtt       900
cggatacggg gctgcgacca tcggcgtgtc ctttgaaaaa gcgggttcag aaaccaaata       960
tggtacaccg ggatggtaca ataatttggc atttgatgaa gcggcaaaac gcgagggtct      1020
ttatagcgtg acgatcgacg gcgatgcgtt ttcagacgag atcaaggccc aggtaattga      1080
```

```
ggaagccaaa aaaaaaggta tcaaatttga tctgatcgta tacagcttgg ccagcccagt    1140
acgtactgat cctgatacag gtatcatgca caaaagcgtt ttgaaaccct ttggaaaaac    1200
gttcacaggc aaaacagtag atccgtttac tggcgagctg aaggaaatct ccgcggaacc    1260
agcaaatgac gaggaagcag ccgccactgt taaagttatg gggggtgaag attgggaacg    1320
ttggattaag cagctgtcga aggaaggcct cttagaagaa ggctgtatta ccttggccta    1380
tagttatatt ggccctgaag ctacccaagc tttgtaccgt aaaggcacaa tcggcaaggc    1440
caaagaacac ctggaggcca agcacaccg tctcaacaaa gagaacccgt caatccgtgc    1500
cttcgtgagc gtgaataaag gcctggtaac ccgcgcaagc gccgtaatcc cggtaatccc    1560
tctgtatctc gccagcttgt tcaaagtaat gaaagagaag ggcaatcatg aaggttgtat    1620
tgaacagatc acgcgtctgt acgccgagcg cctgtaccgt aaagatggta caattccagt    1680
tgatgaggaa aatcgcattc gcattgatga ttgggagtta aagaagacg tccagaaagc    1740 ggtatccgcg ttgatggaga aagtcacggg tgaaaacgca gaatctctca ctgacttagc    1800
ggggtaccgc catgatttct tagctagtaa cggctttgat gtagaaggta ttaattatga    1860
agcggaagtt gaacgcttcg accgtatctg ataagaagga gatatacata tgagagaagt    1920
agtaattgcc agtgcagcta gaacagcagt aggaagtttt ggaggagcat ttaaatcagt    1980
ttcagcggta gagttagggg taacagcagc taaagaagct ataaaaagag ctaacataac    2040
tccagatatg atagatgaat ctcttttagg gggagtactt acagcaggtc ttggacaaaa    2100
tatagcaaga caaatagcat taggagcagg aataccagta gaaaaaccag ctatgactat    2160
aaatatagtt tgtggttctg gattaagatc tgtttcaatg gcatctcaac ttatagcatt    2220
aggtgatgct gatataatgt tagttggtgg agctgaaaac atgagtatgt ctccttattt    2280
agtaccaagt gcgagatatg gtgcaagaat gggtgatgct gcttttgttg attcaatgat    2340
aaaagatgga ttatcagaca tatttaataa ctatcacatg gtattactg ctgaaaacat    2400 agcagagcaa tggaatataa ctagagaaga acaagatgaa ttagctcttg caagtcaaaa    2460
taaagctgaa aaagctcaag ctgaaggaaa atttgatgaa gaaatagttc tgttgttat    2520 aaaaggaaga aaaggtgaca ctgtagtaga taaagatgaa tatattaagc ctggcactac    2580
aatggagaaa cttgctaagt taagacctgc atttaaaaaa gatggaacag ttactgctgg    2640
taatgcatca ggaataaatg atggtgctgc tatgttagta gtaatggcta aagaaaaagc    2700
tgaagaacta ggaatagagc ctcttgcaac tatagtttct tatggaacag ctggtgttga    2760
ccctaaaata atgggatatg gaccagttcc agcaactaaa aaagctttag aagctgctaa    2820
tatgactatt gaagatatag atttagttga agctaatgag gcatttgctg cccaatctgt    2880
agctgtaata agagacttaa atatagatat gaataaagtt aatgttaatg gtggagcaat    2940
agctatagga catccaatag gatgctcagg agcaagaata cttactacac tttatatga    3000 aatgaagaga agagatgcta aaactggtct tgctacactt tgtataggcg gtggaatggg    3060
aactacttta atagttaaga gatagtaaga aggagatata catatgaaat agctgtaat    3120 aggtagtgga actatgggaa gtggtattgt acaaactttt gcaagttgtg gacatgatgt    3180
atgtttaaag agtagaactc aaggtgctat agataaatgt ttagctttat tagataaaaa    3240
tttaactaag ttagttacta agggaaaaat ggatgaagct acaaaagcag aaatattaag    3300
tcatgttagt tcaactacta attatgaaga tttaaaagat atggatttaa taatagaagc    3360
atctgtagaa gacatgaata taaagaaaga tgttttcaag ttactagatg aattatgtaa    3420
```

```
agaagatact atcttggcaa caaatacttc atcattatct ataacagaaa tagcttcttc    3480
tactaagcgc ccagataaag ttataggaat gcatttcttt aatccagttc ctatgatgaa    3540
attagttgaa gttataagtg gtcagttaac atcaaaagtt acttttgata cagtatttga    3600
attatctaag agtatcaata aagtaccagt agatgtatct gaatctcctg gatttgtagt    3660
aaatagaata cttataccta tgataaatga agctgttggt atatatgcag atggtgttgc    3720
aagtaaagaa gaaatagatg aagctatgaa attaggagca aaccatccaa tgggaccact    3780
agcattaggt gatttaatcg gattagatgt tgttttagct ataatgaacg ttttatatac    3840
tgaatttgga gatactaaat atagacctca tccactttta gctaaaatgg ttagagctaa    3900
tcaattagga agaaaaacta agataggatt ctatgattat aataaataat aagaaggaga    3960
tatacatatg agtacaagtg atgttaaagt ttatgagaat gtagctgttg aagtagatgg    4020
aaatatatgt acagtgaaaa tgaatagacc taaagcccct aatgcaataa attcaaagac    4080
tttagaagaa cttatgaag tatttgtaga tattaataat gatgaaacta ttgatgttgt    4140
aatattgaca ggggaaggaa aggcatttgt agctggagca gatattgcat acatgaaaga    4200
tttagatgct gtagctgcta aagattttag tatcttagga gcaaaagctt ttggagaaat    4260
agaaaatagt aaaaaagtag tgatagctgc tgtaaacgga tttgctttag gtggaggatg    4320
tgaacttgca atggcatgtg atataagaat tgcatctgct aaagctaaat ttggtcagcc    4380
agaagtaact cttggaataa ctccaggata tggaggaact caaaggctta caagattggt    4440
tggaatggca aaagcaaaag aattaatctt tacaggtcaa gttataaaag ctgatgaagc    4500
tgaaaaaata gggctagtaa atagagtcgt tgagccagac atttaatag aagaagttga    4560 gaaattagct aagataatag ctaaaaatgc tcagcttgca gttagatact ctaaagaagc    4620
aatcaaactt ggtgctcaaa ctgatataaa tactggaata gatatagaat ctaatttatt    4680
tggtctttgt ttttcaacta agaccaaaa agaaggaatg tcagctttcg ttgaaaagag    4740
agaagctaac tttataaaag ggtaataaga aggagatata catatgagaa gttttgaaga    4800
agtaattaag tttgcaaaag aaagaggacc taaaactata tcagtagcat gttgccaaga    4860
taaagaagtt ttaatggcag ttgaaatggc tagaaaagaa aaaatagcaa atgccatttt    4920
agtaggagat atagaaaaga ctaaagaaat tgcaaaaagc atagacatgg atatcgaaaa    4980
ttatgaactg atagatataa aagatttagc agaagcatct ctaaaatctg ttgaattagt    5040
ttcacaagga aaagccgaca tggtaatgaa aggcttagta gacacatcaa taatactaaa    5100
agcagtttta aataaagaag taggtcttag aactggaaat gtattaagtc acgtagcagt    5160
atttgatgta gagggatatg atagattatt tttcgtaact gacgcagcta tgaacttagc    5220
tcctgataca aatactaaaa agcaaatcat agaaaatgct tgcacagtag cacattcatt    5280
agatataagt gaaccaaaag ttgctgcaat atgcgcaaaa gaaaaagtaa atccaaaaat    5340
gaaagataca gttgaagcta aagaactaga gaaatgtat gaaagaggag aaatcaaagg    5400
ttgtatggtt ggtgggcctt ttgcaattga taatgcagta tctttagaag cagctaaaca    5460
taaaggtata aatcatcctg tagcaggacg agctgatata ttattagccc cagatattga    5520
aggtggtaac atattatata aagctttggt attcttctca aaatcaaaaa atgcaggagt    5580
tatagttggg gctaaagcac caataatatt aacttctaga gcagacagtg aagaaactaa    5640
actaaactca atagctttag gtgtttttaat ggcagcaaag gcataataag aaggagatat    5700
acatatgagc aaaatattta aaatcttaac aataaatcct ggttcgacat caactaaaat    5760
agctgtattt gataatgagg atttagtatt tgaaaaaact ttaagacatt cttcagaaga    5820
```

-continued

| | |
|---|---|
| aataggaaaa tatgagaagg tgtctgacca atttgaattt cgtaaacaag taatagaaga | 5880 |
| agctctaaaa gaaggtggag taaaaacatc tgaattagat gctgtagtag gtagaggagg | 5940 |
| acttcttaaa cctataaaag gtggtactta ttcagtaagt gctgctatga ttgaagattt | 6000 |
| aaaagtggga gttttaggag aacacgcttc aaacctaggt ggaataatag caaaacaaat | 6060 |
| aggtgaagaa gtaaatgttc cttcatacat agtagaccct gttgttgtag atgaattaga | 6120 |
| agatgttgct agaatttctg gtatgcctga aataagtaga gcaagtgtag tacatgcttt | 6180 |
| aaatcaaaag gcaatagcaa gaagatatgc tagagaaata aacaagaaat atgaagatat | 6240 |
| aaatcttata gttgcacaca tgggtggagg agtttctgtt ggagctcata aaaatggtaa | 6300 |
| aatagtagat gttgcaaacg cattagatgg agaaggacct ttctctccag aaagaagtgg | 6360 |
| tggactacca gtaggtgcat tagtaaaaat gtgctttagt ggaaaatata ctcaagatga | 6420 |
| aattaaaaag aaaataaaag gtaatggcgg actagttgca tacttaaaca ctaatgatgc | 6480 |
| tagagaagtt gaagaaagaa ttgaagctgg tgatgaaaaa gctaaattag tatatgaagc | 6540 |
| tatggcatat caaatctcta agaaatagg agctagtgct gcagttctta agggagatgt | 6600 |
| aaaagcaata ttattaactg gtggaatcgc atattcaaaa atgtttacag aaatgattgc | 6660 |
| agatagagtt aaatttatag cagatgtaaa agtttatcca ggtgaagatg aaatgattgc | 6720 |
| attagctcaa ggtggactta gagttttaac tggtgaagaa gaggctcaag tttatgataa | 6780 |
| ctaataa | 6787 |

<210> SEQ ID NO 69
<211> LENGTH: 8650
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

| | |
|---|---|
| gtaaaacgac ggccagtgaa ttcgttaaga cccactttca catttaagtt gttttctaa | 60 |
| tccgcatatg atcaattcaa ggccgaataa gaaggctggc tctgcacctt ggtgatcaaa | 120 |
| taattcgata gcttgtcgta ataatggcgg catactatca gtagtaggtg tttcccttc | 180 |
| ttctttagcg acttgatgct cttgatcttc caatacgcaa cctaaagtaa aatgccccac | 240 |
| agcgctgagt gcatataatg cattctctag tgaaaaacct tgttggcata aaaaggctaa | 300 |
| ttgattttcg agagtttcat actgtttttc tgtaggccgt gtacctaaat gtactttttgc | 360 |
| tccatcgcga tgacttagta aagcacatct aaaacttta gcgttattac gtaaaaaatc | 420 |
| ttgccagctt tccccttcta aagggcaaaa gtgagtatgg tgcctatcta acatctcaat | 480 |
| ggctaaggcg tcgagcaaag cccgcttatt ttttacatgc caatacaatg taggctgctc | 540 |
| tacacctagc ttctgggcga gtttacgggt tgttaaacct tcgattccga cctcattaag | 600 |
| cagctctaat gcgctgttaa tcactttact tttatctaat ctagacatca ttaattccta | 660 |
| atttttgttg acactctatc attgatagag ttattttacc actccctatc agtgatagag | 720 |
| aaaagtgaac tctagaaata attttgttta actttaagaa ggagatatac atatggattt | 780 |
| aaattctaaa aaatatcaga tgcttaaaga gctatatgta agcttcgctg aaaatgaagt | 840 |
| taaaccttta gcaacagaac ttgatgaaga agaaagattt ccttatgaaa cagtggaaaa | 900 |
| aatggcaaaa gcaggaatga tgggtatacc atatccaaaa gaatatggtg gagaaggtgg | 960 |

```
agacactgta ggatatataa tggcagttga agaattgtct agagtttgtg gtactacagg    1020
agttatatta tcagctcata catctcttgg ctcatggcct atatatcaat atggtaatga    1080
agaacaaaaa caaaaattct taagaccact agcaagtgga gaaaaattag gagcatttgg    1140
tcttactgag cctaatgctg gtacagatgc gtctggccaa caaacaactg ctgttttaga    1200
cggggatgaa tacatactta atggctcaaa aatatttata acaaacgcaa tagctggtga    1260
catatatgta gtaatggcaa tgactgataa atctaagggg aacaaaggaa tatcagcatt    1320
tatagttgaa aaaggaactc ctgggtttag ctttggagtt aaagaaaaga aaatgggtat    1380
aagaggttca gctacgagtg aattaatatt tgaggattgc agaataccta agaaaaattt    1440
acttggaaaa gaaggtcaag gatttaagat agcaatgtct actcttgatg gtggtagaat    1500
tggtatagct gcacaagctt taggtttagc acaaggtgct cttgatgaaa ctgttaaata    1560
tgtaaaagaa agagtacaat ttggtagacc attatcaaaa ttccaaaata cacaattcca    1620
attagctgat atggaagtta aggtacaagc ggctagacac cttgtatatc aagcagctat    1680
aaataaagac ttaggaaaac cttatggagt agaagcagca atggcaaaat tatttgcagc    1740
tgaaacagct atggaagtta ctacaaaagc tgtacaactt catggaggat atggatacac    1800
tcgtgactat ccagtagaaa gaatgatgag agatgctaag ataactgaaa tatatgaagg    1860
aactagtgaa gttcaaagaa tggttatttc aggaaaacta ttaaaatagt aagaaggaga    1920
tatacatatg gaggaaggat ttatgaatat agtcgtttgt ataaaacaag ttccagatac    1980
aacagaagtt aaactagatc ctaatacagg tactttaatt agagatggag taccaagtat    2040
aataaaccct gatgataaag caggtttaga agaagctata aaattaaaag aagaaatggg    2100
tgctcatgta actgttataa caatgggacc tcctcaagca gatatggctt taaaagaagc    2160
tttagcaatg ggtgcagata gaggtatatt attaacagat agagcatttg cgggtgctga    2220
tacttgggca acttcatcag cattagcagg agcattaaaa aatatagatt ttgatattat    2280
aatagctgga agacaggcga tagatggaga tactgcacaa gttggacctc aaatagctga    2340
acatttaaat cttccatcaa taacatatgc tgaagaaata aaaactgaag gtgaatatgt    2400
attagtaaaa agacaatttg aagattgttg ccatgactta aaagtaaaaa tgccatgcct    2460
tataacaact cttaaagata tgaacacacc aagatacatg aaagttggaa gaatatatga    2520
tgctttcgaa aatgatgtag tagaaacatg gactgtaaaa gatatagaag ttgacccttc    2580
taatttaggt cttaaaggtt ctccaactag tgtatttaaa tcatttacaa aatcagttaa    2640
accagctggt acaatataca atgaagatgc gaaaacatca gctggaatta tcatagataa    2700
attaaaagag aagtatatca tataataaga aggagatata catatgggta acgtttttagt    2760 agtaatagaa caaagagaaa atgtaattca aactgtttct ttagaattac taggaaaggc    2820
tacagaaata gcaaaagatt atgatacaaa agtttctgca ttactttag gtagtaaggt    2880 agaaggttta atagatacat tagcacacta tggtgcagat gaggtaatag tagtagatga    2940
tgaagcttta gcagtgtata caactgaacc atatacaaaa gcagcttatg aagcaataaa    3000
agcagctgac cctatagttg tattatttgg tgcaacttca ataggtagag atttagcgcc    3060 tagagttttct gctagaatac atacaggtct tactgctgac tgtacaggtc ttgcagtagc    3120
tgaagataca aaattattat taatgacaag acctgccttt ggtggaaata taatggcaac    3180 aatagttttgt aaagatttca gacctcaaat gtctacagtt agaccagggg ttatgaagaa    3240
aaatgaacct gatgaaacta agaagcttgt aattaaccgt ttcaaggtag aatttaatga    3300
tgctgataaa ttagttcaag ttgtacaagt aataaaagaa gctaaaaaac aagttaaaat    3360
```

```
agaagatgct aagatattag tttctgctgg acgtggaatg ggtggaaaag aaaacttaga    3420
catactttat gaattagctg aaattatagg tggagaagtt tctggttctc gtgccactat    3480
agatgcaggt tggttagata aagcaagaca agttggtcaa actggtaaaa ctgtaagacc    3540
agacctttat atagcatgtg gtatatctgg agcaatacaa catatagctg gtatggaaga    3600
tgctgagttt atagttgcta taaataaaaa tccagaagct ccaatattta aatatgctga    3660
tgttggtata gttggagatg ttcataaagt gcttccagaa cttatcagtc agttaagtgt    3720
tgcaaaagaa aaaggtgaag ttttagctaa ctaataagaa ggagatatac atatgagaga    3780
agtagtaatt gccagtgcag ctagaacagc agtaggaagt tttggaggag catttaaatc    3840
agtttcagcg gtagagttag gggtaacagc agctaaagaa gctataaaaa gagctaacat    3900
aactccagat atgatagatg aatctctttt aggggagta cttacagcag gtcttggaca    3960
aaatatagca agacaaatag cattaggagc aggaatacca gtagaaaaac cagctatgac    4020
tataaatata gtttgtggtt ctggattaag atctgtttca atggcatctc aacttatagc    4080
attaggtgat gctgatataa tgttagttgg tggagctgaa acatgagta tgtctcctta    4140 tttagtacca agtgcgagat atggtgcaag aatgggtgat gctgcttttg ttgattcaat    4200
gataaaagat ggattatcag acatatttaa taactatcac atgggtatta ctgctgaaaa    4260
catagcagag caatggaata taactagaga agaacaagag gaattagctc ttgcaagtca    4320
aaataaagct gaaaagctc aagctgaagg aaaatttgat gaagaaatag ttcctgttgt    4380
tataaaagga gaaaaggtg acactgtagt agataaagat gaatatatta gcctggcac    4440 tacaatggag aaacttgcta agttaagacc tgcatttaaa aaagatggaa cagttactgc    4500
tggtaatgca tcaggaataa atgatggtgc tgctatgtta gtagtaatgg ctaaagaaaa    4560
agctgaagaa ctaggaatag agcctcttgc aactatagtt tcttatggaa cagctggtgt    4620
tgaccctaaa ataatgggat atggaccagt tccagcaact aaaaaagctt agaagctgc    4680 taatatgact attgaagata tagatttagt tgaagctaat gaggcatttg ctgcccaatc    4740
tgtagctgta ataagagact aaaatataga tatgaataaa gttaatgtta atggtggagc    4800
aatagctata ggacatccaa taggatgctc aggagcaaga atacttacta cacttttata    4860
tgaaatgaag agaagagatg ctaaaactgg tcttgctaca cttttgtatag gcggtggaat    4920 gggaactact ttaatagtta agagatagta agaaggagat atacatatga aattagctgt    4980
aataggtagt ggaactatgg gaagtggtat tgtacaaact tttgcaagtt gtggacatga    5040
tgtatgttta aagagtagaa ctcaaggtgc tatagataaa tgtttagctt attagataaa    5100
aaatttaact aagttagtta ctaagggaaa aatggatgaa gctacaaaag cagaaatatt    5160
aagtcatgtt agttcaacta ctaattatga agatttaaaa gatatggatt taataataga    5220
agcatctgta gaagacatga atataaagaa agatgttttc aagttactag atgaattatg    5280
taaagaagat actatcttgg caacaaatac ttcatcatta tctataacag aaatagcttc    5340
ttctactaag cgcccagata agttatatagg aatgcatttc tttaatccag ttcctatgat    5400
gaaattagtt gaagttataa gtggtcagtt aacatcaaaa gttacttttg atacagtatt    5460
tgaattatct aagagtatca ataaagtacc agtgatgta tctgaatctc ctggatttgt    5520
agtaaataga atacttatac ctatgataaa tgaagctgtt ggtatatatg cagatggtgt    5580
tgcaagtaaa gaagaaatag atgaagctat gaaattagga gcaaaccatc caatgggacc    5640
actagcatta ggtgatttaa tcggattaga tgttgtttta gctataatga acgttttata    5700
```

```
tactgaattt ggagatacta atatagacc  tcatccactt ttagctaaaa tggttagagc   5760
taatcaatta ggaagaaaaa ctaagatagg attctatgat tataataaat aataagaagg   5820
agatatacat atgagtacaa gtgatgttaa agtttatgag aatgtagctg ttgaagtaga   5880
tggaaatata tgtacagtga aaatgaatag acctaaagcc cttaatgcaa taaattcaaa   5940
gactttagaa gaactttatg aagtatttgt agatattaat aatgatgaaa ctattgatgt   6000
tgtaatattg acaggggaag gaaaggcatt tgtagctgga gcagatattg catacatgaa   6060
agatttagat gctgtagctg ctaaagattt tagtatctta ggagcaaaag cttttggaga   6120
aatagaaaat agtaaaaaag tagtgatagc tgctgtaaac ggatttgctt taggtggagg   6180
atgtgaactt gcaatggcat gtgatataag aattgcatct gctaaagcta aatttggtca   6240
gccagaagta actcttggaa taactccagg atatggagga actcaaaggc ttacaagatt   6300
ggttggaatg gcaaaagcaa aagaattaat ctttacaggt caagttataa aagctgatga   6360
agctgaaaaa atagggctag taaatagagt cgttgagcca gacattttaa tagaagaagt   6420
tgagaaatta gctaagataa tagctaaaaa tgctcagctt gcagttagat actctaaaga   6480
agcaatacaa cttggtgctc aaactgatat aaatactgga atagatatag aatctaatttt  6540 atttggtctt tgttttttcaa ctaaagacca aaaagaagga atgtcagctt tcgttgaaaa   6600
gagagaagct aactttataa aagggtaata agaaggagat atacatatga aagttttga    6660 agaagtaatt aagtttgcaa aagaaagagg acctaaaact atatcagtag catgttgcca   6720
agataaagaa gttttaatgg cagttgaaat ggctagaaaa gaaaaaatag caaatgccat   6780
tttagtagga gatatagaaa agactaaaga aattgcaaaa agcatagaca tggatatcga   6840
aaattatgaa ctgatagata taaaagattt agcagaagca tctctaaaat ctgttgaatt   6900
agtttcacaa ggaaaagccg acatggtaat gaaaggctta gtagacacat caataatact   6960
aaaagcagtt ttaaataaag aagtaggtct tagaactgga aatgtattaa gtcacgtagc   7020
agtatttgat gtagagggat atgatagatt atttttcgta actgacgcag ctatgaactt   7080
agctcctgat acaaatacta aaagcaaat  catagaaaat gcttgcacag tagcacattc   7140
attagatata agtgaaccaa aagttgctgc aatatgcgca aaagaaaaag taaatccaaa   7200
aatgaaagat acagttgaag ctaaagaact agaagaaatg tatgaaagag gagaaatcaa   7260
aggttgtatg gttggtgggc cttttgcaat tgataatgca gtatctttag aagcagctaa   7320
acataaaggt ataaatcatc ctgtagcagg acgagctgat atattattag ccccagatat   7380
tgaaggtggt aacatattat ataaagctttt ggtattcttc tcaaaatcaa aaaatgcagg   7440
agttatagtt ggggctaaag caccaataat attaacttct agagcagaca gtgaagaaac   7500
taaactaaac tcaatagctt taggtgtttt aatggcagca aaggcataat aagaaggaga   7560
tatacatatg agcaaaatat ttaaaatctt aacaataaat cctggttcga catcaactaa   7620
aatagctgta tttgataatg aggatttagt atttgaaaaa actttaagac attcttcaga   7680
agaaatagga aaatatgaga aggtgtctga ccaatttgaa tttcgtaaac aagtaataga   7740
agaagctcta aagaaggtg  gagtaaaaac atctgaatta gatgctgtag taggtagagg   7800
aggacttctt aaacctataa aaggtggtac ttattcagta agtgctgcta tgattgaaga   7860
tttaaaagtg ggagttttag gagaacacgc ttcaaaccta ggtggaataa tagcaaaaca   7920
aataggtgaa gaagtaaatg ttccttcata catagtagac cctgttgttg tagatgaatt   7980
agaagatgtt gctagaattt ctggtatgcc tgaaataagt agagcaagtg tagtacatgc   8040
tttaaatcaa aaggcaatag caagaagata tgctagagaa ataaacaaga aatatgaaga   8100
```

```
tataaatctt atagttgcac acatgggtgg aggagtttct gttggagctc ataaaaatgg    8160
taaaatagta gatgttgcaa acgcattaga tggagaagga cctttctctc cagaaagaag    8220
tggtggacta ccagtaggtg cattagtaaa aatgtgcttt agtggaaaat atactcaaga    8280
tgaaattaaa aagaaaataa aaggtaatgg cggactagtt gcatacttaa acactaatga    8340
tgctagagaa gttgaagaaa gaattgaagc tggtgatgaa aaagctaaat tagtatatga    8400
agctatggca tatcaaatct ctaaagaaat aggagctagt gctgcagttc ttaagggaga    8460
tgtaaaagca atattattaa ctggtggaat cgcatattca aaaatgttta cagaaatgat    8520
tgcagataga gttaaattta tagcagatgt aaaagtttat ccaggtgaag atgaaatgat    8580
tgcattagct caaggtggac ttagagtttt aactggtgaa gaagaggctc aagtttatga    8640
taactaataa                                                          8650
```

<210> SEQ ID NO 70
<211> LENGTH: 6862
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70

```
gtaaaacgac ggccagtgaa ttcgttaaga cccactttca catttaagtt gttttctaa      60 tccgcatatg atcaattcaa ggccgaataa gaaggctggc tctgcacctt ggtgatcaaa    120
taattcgata gcttgtcgta ataatggcgg catactatca gtagtaggtg tttccctttc    180
ttctttagcg acttgatgct cttgatcttc caatacgcaa cctaaagtaa aatgccccac    240
agcgctgagt gcatataatg cattctctag tgaaaaacct tgttggcata aaaaggctaa    300
ttgattttcg agagtttcat actgttttc tgtaggccgt gtacctaaat gtacttttgc    360
tccatcgcga tgacttagta aagcacatct aaaacttta gcgttattac gtaaaaaatc    420
ttgccagctt tccccttcta aagggcaaaa gtgagtatgg tgcctatcta acatctcaat    480
ggctaaggcg tcgagcaaag cccgcttatt ttttacatgc caatacaatg taggctgctc    540
tacacctagc ttctgggcga gtttacgggt tgttaaacct tcgattccga cctcattaag    600
cagctctaat gcgctgttaa tcactttact tttatctaat ctagacatca ttaattccta    660 attttgttg acactctatc attgatagag ttatttacc actccctatc agtgatagag    720
aaaagtgaac tctagaaata atttgttta actttaagaa ggagatatac atatgatcgt    780
aaaacctatg gtacgcaaca atatctgcct gaacgcccat cctcagggct gcaagaaggg    840
agtggaagat cagattgaat ataccaagaa acgcattacc gcagaagtca agctggcgc    900 aaaagctcca aaaaacgttc tggtgcttgg ctgctcaaat ggttacggcc tggcgagccg    960
cattactgct gcgttcggat acgggctgc gaccatcggc gtgtcctttg aaaaagcggg   1020
ttcagaaacc aaatatggta caccgggatg gtacaataat ttggcatttg atgaagcggc   1080
aaaacgcgag ggtctttata gcgtgacgat cgacggcgat gcgttttcag acgagatcaa   1140
ggcccaggta attgaggaag ccaaaaaaaa aggtatcaaa tttgatctga tcgtatacag   1200
cttggccagc ccagtacgta ctgatcctga tacaggtatc atgcacaaaa gcgttttgaa   1260
accctttgga aaaacgttca caggcaaaac agtagatccg tttactgcg agctgaagga   1320 aatctccgcg gaaccagcaa atgacgagga agcagccgcc actgttaaag ttatgggggg   1380
```

```
tgaagattgg gaacgttgga ttaagcagct gtcgaaggaa ggcctcttag aagaaggctg    1440
tattaccttg gcctatagtt atattggccc tgaagctacc caagctttgt accgtaaagg    1500
cacaatcggc aaggccaaag aacacctgga ggccacagca caccgtctca acaaagagaa    1560
cccgtcaatc cgtgccttcg tgagcgtgaa taaaggcctg gtaacccgcg caagcgccgt    1620
aatcccggta atccctctgt atctcgccag cttgttcaaa gtaatgaaag agaagggcaa    1680
tcatgaaggt tgtattgaac agatcacgcg tctgtacgcc gagcgcctgt accgtaaaga    1740
tggtacaatt ccagttgatg aggaaaatcg cattcgcatt gatgattggg agttagaaga    1800
agacgtccag aaagcggtat ccgcgttgat ggagaaagtc acgggtgaaa acgcagaatc    1860
tctcactgac ttagcggggt accgccatga tttcttagct agtaacggct tgatgtaga    1920 aggtattaat tatgaagcgg aagttgaacg cttcgaccgt atctgataag aaggagatat    1980
acatatgaga gaagtagtaa ttgccagtgc agctagaaca gcagtaggaa gttttggagg    2040
agcatttaaa tcagtttcag cggtagagtt agggtaaca gcagctaaag aagctataaa     2100
aagagctaac ataactccag atatgataga tgaatctctt ttaggggag tacttacagc      2160 aggtcttgga caaaatatag caagacaaat agcattagga gcaggaatac cagtagaaaa    2220
accagctatg actataaata tagtttgtgg ttctggatta agatctgttt caatggcatc    2280
tcaacttata gcattaggtg atgctgatat aatgttagtt ggtggagctg aaaacatgag    2340
tatgtctcct tatttagtac caagtgcgag atatggtgca agaatgggtg atgctgcttt    2400
tgttgattca atgataaaag atggattatc agacatattt aataactatc acatgggtat    2460
tactgctgaa aacatagcag agcaatggaa tataactaga gaagaacaag atgaattagc    2520
tcttgcaagt caaaataaag ctgaaaaagc tcaagctgaa ggaaaatttg atgaagaaat    2580
agttcctgtt gttataaaag gaagaaaagg tgacactgta gtagataaag atgaatatat    2640
taagcctggc actacaatgg agaaacttgc taagttaaga cctgcattta aaaaagatgg    2700
aacagttact gctggtaatg catcaggaat aaatgatggt gctgctatgt tagtagtaat    2760
ggctaaagaa aaagctgaag aactaggaat agagcctctt gcaactatag tttcttatgg    2820
aacagctggt gttgaccta aaataatggg atatggacca gttccagcaa ctaaaaaagc    2880
tttagaagct gctaatatga ctattgaaga tatagattta gttgaagcta atgaggcatt    2940
tgctgcccaa tctgtagctg taataagaga cttaaatata gatatgaata agttaatgt    3000 taatggtgga gcaatagcta taggacatcc aataggatgc tcaggagcaa gaatacttac    3060
tacactttta tatgaaatga gagaagaga tgctaaaact ggtcttgcta cactttgtat    3120
aggcggtgga atgggaacta ctttaatagt taagagatag taagaaggag atatacatat    3180
gaaattagct gtaataggta gtggaactat gggaagtggt attgtacaaa cttttgcaag    3240
ttgtggacat gatgtatgtt taagagtag aactcaaggt gctatagata atgtttagc     3300 tttattagat aaaaatttaa ctaagttagt tactaaggga aaaatggatg aagctacaaa    3360
agcagaaata ttaagtcatg ttagttcaac tactaattat gaagatttaa agatatgga    3420 tttaataata gaagcatctg tagaagacat gaatataaag aaagatgttt tcaagttact    3480
agatgaatta tgtaaagaag atactatctt ggcaacaaat acttcatcat tatctataac    3540
agaaatagct tcttctacta gcgcccaga taaagttata ggaatgcatt tctttaatcc    3600
agttcctatg atgaaattag ttgaagttat aagtggtcag ttaacatcaa aagttacttt    3660
tgatacagta tttgaattat ctaagagtat caataaagta ccagtagatg tatctgaatc    3720
tcctggattt gtagtaaata gaatacttat acctatgata aatgaagctg ttggtatata    3780
```

```
tgcagatggt gttgcaagta aagaagaaat agatgaagct atgaaattag gagcaaacca    3840
tccaatggga ccactagcat taggtgattt aatcggatta gatgttgttt tagctataat    3900
gaacgtttta tatactgaat ttggagatac taaatataga cctcatccac ttttagctaa    3960
aatggttaga gctaatcaat taggaagaaa aactaagata ggattctatg attataataa    4020
ataataagaa ggagatatac atatgagtac aagtgatgtt aaagtttatg agaatgtagc    4080
tgttgaagta gatggaaata tatgtacagt gaaaatgaat agacctaaag cccttaatgc    4140
aataaattca aagactttag aagaacttta tgaagtattt gtagatatta ataatgatga    4200
aactattgat gttgtaatat tgacagggga aggaaaggca tttgtagctg gagcagatat    4260
tgcatacatg aaagatttag atgctgtagc tgctaaagat tttagtatct taggagcaaa    4320
agcttttgga gaaatagaaa atagtaaaaa agtagtgata gctgctgtaa acggatttgc    4380
tttaggtgga ggatgtgaac ttgcaatggc atgtgatata agaattgcat ctgctaaagc    4440
taaatttggt cagccagaag taactcttgg aataactcca ggatatggag gaactcaaag    4500
gcttacaaga ttggttggaa tggcaaaagc aaaagaatta atctttacag gtcaagttat    4560
aaaagctgat gaagctgaaa aaatagggct agtaaaataga gtcgttgagc cagacatttt    4620
aatagaagaa gttgagaaat tagctaagat aatagctaaa aatgctcagc ttgcagttag    4680
atactctaaa gaagcaatac aacttggtgc tcaaactgat ataaatactg aatagatat    4740 agaatctaat ttatttggtc tttgtttttc aactaaagac caaaagaag gaatgtcagc    4800 tttcgttgaa aagagagaag ctaactttat aaaagggtaa taagaaggag atatacatat    4860
gagaagtttt gaagaagtaa ttaagtttgc aaaagaaaga ggacctaaaa ctatatcagt    4920
agcatgttgc caagataaag aagttttaat ggcagttgaa atggctagaa aagaaaaaat    4980
agcaaatgcc attttagtag gagatatata aaagactaaa gaaattgcaa aaagcataga    5040
catggatatc gaaaattatg aactgataga tataaaagat ttagcagaag catctctaaa    5100
atctgttgaa ttagttttcac aaggaaaagc cgacatggta atgaaaggct tagtagacac    5160
atcaataata ctaaaagcag ttttaaataa agaagtaggt cttagaactg gaaatgtatt    5220
aagtcacgta gcagtatttg atgtagaggg atatgataga ttattttttcg taactgacgc    5280 agctatgaac ttagctcctg atacaaatac taaaaagcaa atcatagaaa atgcttgcac    5340
agtagcacat tcattagata taagtgaacc aaaagttgct gcaatatgcg caaaagaaaa    5400
agtaaatcca aaaatgaaag atacagttga agctaaagaa ctagaagaaa tgtatgaaag    5460
aggagaaatc aaaggttgta tggttggtgg gccttttgca attgataatg cagtatcttt    5520
agaagcagct aaacataaag gtataaatca tcctgtagca ggacgagctg atatattatt    5580
agccccagat attgaaggtg gtaacatatt atataaagct ttggtattct tctcaaaatc    5640
aaaaaatgca ggagttatag ttggggctaa agcaccaata atattaactt ctagagcaga    5700
cagtgaagaa actaaactaa actcaatagc tttaggtgtt ttaatggcag caaaggcata    5760
ataagaagga gatatacata tgagcaaaat atttaaaatc ttaacaataa atcctggttc    5820
gacatcaact aaaatagctg tatttgataa tgaggattta gtatttgaaa aaactttaag    5880
acattcttca gaagaaatag gaaaatatga gaaggtgtct gaccaatttg aatttcgtaa    5940
acaagtaata gaagaagctc taaaagaagg tggagtaaaa acatctgaat tagatgctgt    6000
agtaggtaga ggaggacttc ttaaacctat aaaaggtggt acttattcag taagtgctgc    6060
tatgattgaa gatttaaaag tgggagttttt aggagaacac gcttcaaacc taggtggaat    6120
```

```
aatagcaaaa caaataggtg aagaagtaaa tgttccttca tacatagtag accctgttgt    6180
tgtagatgaa ttagaagatg ttgctagaat ttctggtatg cctgaaataa gtagagcaag    6240
tgtagtacat gctttaaatc aaaaggcaat agcaagaaga tatgctagag aaataaacaa    6300
gaaatatgaa gatataaatc ttatagttgc acacatgggt ggaggagttt ctgttggagc    6360
tcataaaaat ggtaaaatag tagatgttgc aaacgcatta gatggagaag gacctttctc    6420
tccagaaaga agtggtggac taccagtagg tgcattagta aaaatgtgct ttagtggaaa    6480
atatactcaa gatgaaatta aaagaaaat aaaggtaat ggcggactag ttgcatactt      6540
aaacactaat gatgctagag aagttgaaga aagaattgaa gctggtgatg aaaaagctaa    6600
attagtatat gaagctatgg catatcaaat ctctaaagaa ataggagcta gtgctgcagt    6660
tcttaaggga gatgtaaaag caatattatt aactggtgga atcgcatatt caaaaatgtt    6720
tacagaaatg attgcagata gagttaaatt tatagcagat gtaaaagttt atccaggtga    6780
agatgaaatg attgcattag ctcaaggtgg acttagagtt ttaactggtg aagaagaggc    6840
tcaagtttat gataactaat aa                                             6862

<210> SEQ ID NO 71
<211> LENGTH: 355
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
tgtggctttt atgaaaatca cacagtgatc acaaatttta aacagagcac aaaatgctgc      60
ctcgaaatga gggcgggaaa ataaggttat cagccttgtt ttctccctca ttacttgaag     120
gatatgaagc taaaacccctt ttttataaag catttgtccg aattcggaca taatcaaaaa    180
agcttaatta agatcaattt gatctacatc tctttaacca acaatatgta agatctcaac     240
tatcgcatcc gtggattaat tcaattataa cttctctcta acgctgtgta tcgtaacggt     300
aacactgtag aggggagcac attgatgcga attcattaaa gaggagaaag gtacc          355

<210> SEQ ID NO 72
<211> LENGTH: 228
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72
ttccgaaaat tcctggcgag cagataaata agaattgttc ttatcaatat atctaactca      60
ttgaatcttt attagttttg tttttcacgc ttgttaccac tattagtgtg ataggaacag     120
ccagaatagc ggaacacata gccggtgcta tacttaatct cgttaattac tgggacataa     180
catcaagagg atatgaaatt cgaattcatt aaagaggaga aaggtacc                  228

<210> SEQ ID NO 73
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 73

```
gcttagatca ggtgattgcc ctttgtttat gagggtgttg taatccatgt cgttgttgca    60
tttgtaaggg caacacctca gcctgcaggc aggcactgaa gataccaaag ggtagttcag   120
attacacggt cacctggaaa gggggccatt ttacttttta tcgccgctgg cggtgcaaag   180
ttcacaaagt tgtcttacga aggttgtaag gtaaaactta tcgatttgat aatggaaacg   240
cattagccga atcggcaaaa attggttacc ttacatctca tcgaaaacac ggaggaagta   300
tagatgcgaa ttcattaaag aggagaaagg tacc                               334
```

<210> SEQ ID NO 74
<211> LENGTH: 134
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 74

```
ctcgagttca ttatccatcc tccatcgcca cgatagttca tggcgatagg tagaatagca    60
atgaacgatt atccctatca agcattctga ctgataattg ctcacacgaa ttcattaaag   120
aggagaaagg tacc                                                      134
```

<210> SEQ ID NO 75
<211> LENGTH: 8012
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

```
ctcgagttca ttatccatcc tccatcgcca cgatagttca tggcgatagg tagaatagca    60
atgaacgatt atccctatca agcattctga ctgataattg ctcacacgaa ttcattaaag   120
aggagaaagg taccatggat ttaaattcta aaaaatatca gatgcttaaa gagctatatg   180
taagcttcgc tgaaaatgaa gttaaacctt tagcaacaga acttgatgaa gaagaaagat   240
ttccttatga aacagtggaa aaaatggcaa agcaggaat gatgggtata ccatatccaa   300
aagaatatgg tggagaaggt ggagacactg taggatatat aatggcagtt gaagaattgt   360
ctagagttg tggtactaca ggagttatat tatcagctca tacatctctt ggctcatggc   420
ctatatatca atatggtaat gaagaacaaa acaaaaaatt cttaagacca ctagcaagtg   480
gagaaaaatt aggagcattt ggtcttactg agcctaatgc tggtacagat gcgtctggcc   540
aacaaacaac tgctgtttta gacggggatg aatacatact taatggctca aaaatattta   600
taacaaacgc aatagctggt gacatatatg tagtaatggc aatgactgat aaatctaagg   660
ggaacaaagg aatatcagca tttatagttg aaaaaggaac tcctgggttt agctttggag   720
ttaaagaaaa gaaaatgggt ataagaggtt cagctacgag tgaattaata tttgaggatt   780
gcagaatacc taaagaaaat ttacttggaa agaaggtca aggatttaag atagcaatgt   840
ctactcttga tggtggtaga attggtatag ctgcacaagc tttaggttta gcacaaggtg   900
ctcttgatga aactgttaaa tatgtaaaag aagagtaca atttggtaga ccattatcaa   960
aattccaaaa tacacaattc caattagctg atatggaagt taagtacaa gcggctagac  1020
```

```
accttgtata tcaagcagct ataaataaag acttaggaaa accttatgga gtagaagcag    1080
caatggcaaa attatttgca gctgaaacag ctatggaagt tactacaaaa gctgtacaac    1140
ttcatggagg atatggatac actcgtgact atccagtaga aagaatgatg agagatgcta    1200
agataactga atatatgaa ggaactagtg aagttcaaag aatggttatt tcaggaaaac     1260
tattaaaata gtaagaagga gatatacata tggaggaagg atttatgaat atagtcgttt    1320
gtataaaaca agttccagat acaacagaag ttaaactaga tcctaataca ggtactttaa    1380
ttagagatgg agtaccaagt ataataaacc ctgatgataa agcaggttta gaagaagcta    1440
taaaattaaa agaagaaatg ggtgctcatg taactgttat aacaatggga cctcctcaag    1500
cagatatggc tttaaaagaa gctttagcaa tgggtgcaga tagaggtata ttattaacag    1560
atagagcatt tgcgggtgct gatacttggg caacttcatc agcattagca ggagcattaa    1620
aaaatataga ttttgatatt ataatagctg aagacaggc gatagatgga gatactgcac     1680
aagttggacc tcaaatagct gaacatttaa atcttccatc aataacatat gctgaagaaa    1740
taaaaactga aggtgaatat gtattagtaa aaagacaatt tgaagattgt tgccatgact    1800
taaaagttaa aatgccatgc cttataacaa ctcttaaaga tatgaacaca ccaagataca    1860
tgaaagttgg aagaatatat gatgctttcg aaaatgatgt agtagaaaca tggactgtaa    1920
aagatataga agttgaccct tctaatttag gtcttaaagg ttctccaact agtgtattta    1980
aatcatttac aaaatcagtt aaaccagctg gtacaatata caatgaagat gcgaaaacat    2040
cagctggaat tatcatagat aaattaaaag agaagtatat catataataa gaaggagata    2100
tacatatggg taacgtttta gtagtaatag aacaaagaga aaatgtaatt caaactgttt    2160
ctttagaatt actaggaaag gctacagaaa tagcaaaaga ttatgataca aaagtttctg    2220
cattactttt aggtagtaag gtagaaggtt aatagatac attagcacac tatggtgcag    2280
atgaggtaat agtagtagat gatgaagctt tagcagtgta tacaactgaa ccatatacaa    2340
aagcagctta tgaagcaata aaagcagctg accctatagt tgtattattt ggtgcaactt    2400
caataggtag agatttagcg cctagagttt ctgctagaat acatacaggt cttactgctg    2460
actgtacagg tcttgcagta gctgaagata caaaattatt attaatgaca agacctgcct    2520
ttggtggaaa tataatggca acaatagttt gtaaagattt cagacctcaa atgtctacag    2580
ttagaccagg ggttatgaag aaaaatgaac ctgatgaaac taaagaagct gtaattaacc    2640
gtttcaaggt agaatttaat gatgctgata aattagttca agttgtacaa gtaataaaag    2700
aagctaaaaa acaagttaaa atagaagatg ctaagatatt agtttctgct ggacgtggaa    2760
tgggtggaaa agaaaactta gacatacttt atgaattagc tgaaattata ggtggagaag    2820
tttctggttc tcgtgccact atagatgcag gttggttaga taaagcaaga caagttggtc    2880
aaactggtaa aactgtaaga ccagacctt atatagcatg tggtatatct ggagcaatac     2940
aacatatagc tggtatggaa gatgctgagt ttatagttgc tataaataaa atccagaag     3000 ctccaatatt taaatatgct gatgttggta tagttggaga tgttcataaa gtgcttccag    3060
aacttatcag tcagttaagt gttgcaaaag aaaaggtga agttttagct aactaataag     3120
aaggagatat acatatgaga gaagtagtaa ttgccagtgc agctagaaca gcagtaggaa    3180
gttttggagg agcatttaaa tcagtttcag cggtagagtt aggggtaaca gcagctaaag    3240
aagctataaa aagagctaac ataactccag atatgataga tgaatctctt ttaggggag     3300 tacttacagc aggtcttgga caaaatatag caagacaaat agcattagga gcaggaatac    3360
cagtagaaaa accagctatg actataaata tagtttgtgg ttctggatta agatctgttt    3420
```

```
caatggcatc tcaacttata gcattaggtg atgctgatat aatgttagtt ggtggagctg    3480
aaaacatgag tatgtctcct tatttagtac caagtgcgag atatggtgca agaatgggtg    3540
atgctgcttt tgttgattca atgataaaag atggattatc agacatattt aataactatc    3600
acatgggtat tactgctgaa aacatagcag agcaatggaa tataactaga gaagaacaag    3660
atgaattagc tcttgcaagt caaaataaag ctgaaaaagc tcaagctgaa ggaaaatttg    3720
atgaagaaat agttcctgtt gttataaaag gaagaaaagg tgacactgta gtagataaag    3780
atgaatatat taagcctggc actacaatgg agaaacttgc taagttaaga cctgcattta    3840
aaaaagatgg aacagttact gctggtaatg catcaggaat aaatgatggt gctgctatgt    3900
tagtagtaat ggctaaagaa aaagctgaag aactaggaat agagcctctt gcaactatag    3960
tttcttatgg aacagctggt gttgaccctaaaataatggg atatggacca gttccagcaa    4020
```

```
caatggcatc tcaacttata gcattaggtg atgctgatat aatgttagtt ggtggagctg    3480
aaaacatgag tatgtctcct tatttagtac caagtgcgag atatggtgca agaatgggtg    3540
atgctgcttt tgttgattca atgataaaag atggattatc agacatattt aataactatc    3600
acatgggtat tactgctgaa aacatagcag agcaatggaa tataactaga gaagaacaag    3660
atgaattagc tcttgcaagt caaaataaag ctgaaaaagc tcaagctgaa ggaaaatttg    3720
atgaagaaat agttcctgtt gttataaaag gaagaaaagg tgacactgta gtagataaag    3780
atgaatatat taagcctggc actacaatgg agaaacttgc taagttaaga cctgcattta    3840
aaaaagatgg aacagttact gctggtaatg catcaggaat aaatgatggt gctgctatgt    3900
tagtagtaat ggctaaagaa aaagctgaag aactaggaat agagcctctt gcaactatag    3960
tttcttatgg aacagctggt gttgacccta aaataatggg atatggacca gttccagcaa    4020
ctaaaaaagc tttagaagct gctaatatga ctattgaaga tatagattta gttgaagcta    4080
atgaggcatt tgctgcccaa tctgtagctg taataagaga cttaaatata gatatgaata    4140
aagttaatgt taatggtgga gcaatagcta taggacatcc aataggatgc tcaggagcaa    4200
gaatacttac tacacttttta tatgaaatga agagaagaga tgctaaaaact ggtcttgcta    4260
cactttgtat aggcggtgga atgggaacta ctttaatagt taagagatag taagaaggag    4320
atatacatat gaaattagct gtaataggta gtggaactat gggaagtggt attgtacaaa    4380
cttttgcaag ttgtggacat gatgtatgtt taaagagtag aactcaaggt gctatagata    4440
aatgtttagc tttattagat aaaaatttaa ctaagttagt tactaaggga aaaatggatg    4500
aagctacaaa agcagaaata ttaagtcatg ttagttcaac tactaattat gaagatttaa    4560
aagatatgga tttaataata gaagcatctg tagaagacat gaatataaag aaagatgttt    4620
tcaagttact agatgaatta tgtaaagaag atactatctt ggcaacaaat acttcatcat    4680
tatctataac agaaatagct tcttctacta agcgcccaga taaagttata ggaatgcatt    4740
tctttaatcc agttcctatg atgaaattag ttgaagttat aagtggtcag ttaacatcaa    4800
aagttacttt tgatacagta tttgaattat ctaagagtat caataaagta ccagtagatg    4860
tatctgaatc tcctggattt gtagtaaata gaatacttat acctatgata aatgaagctg    4920
ttggtatata tgcagatggt gttgcaagta aagaagaaat agatgaagct atgaaattag    4980
gagcaaacca tccaatggga ccactagcat taggtgattt aatcggatta gatgttgttt    5040
tagctataat gaacgtttta tatactgaat ttggagatac taaatataga cctcatccac    5100
ttttagctaa aatggttaga gctaatcaat taggaagaaa aactaagata ggattctatg    5160
attataataa ataataagaa ggagatatac atatgagtac aagtgatgtt aaagtttatg    5220
agaatgtagc tgttgaagta gatggaaata tatgtacagt gaaaatgaat agacctaaag    5280
ccccttaatgc aataaattca aagactttag aagaacttta tgaagtattt gtagatatta    5340
ataatgatga aactattgat gttgtaatat tgacagggga aggaaaggca tttgtagctg    5400
gagcagatat tgcatacatg aaagatttag atgctgtagc tgctaaagat tttagtatct    5460
taggagcaaa agcttttgga gaaatagaaa atagtaaaaa agtagtgata gctgctgtaa    5520
acggatttgc tttaggtgga ggatgtgaac ttgcaatggc atgtgatata agaattgcat    5580
ctgctaaagc taaatttggt cagccagaag taactcttgg aataactcca ggatatggag    5640
gaactcaaag gcttacaaga ttggttggaa tggcaaaagc aaaagaatta atctttacag    5700
gtcaagttat aaaagctgat gaagctgaaa aaatagggct agtaaataga gtcgttgagc    5760
```

```
cagacatttt aatagaagaa gttgagaaat tagctaagat aatagctaaa aatgctcagc    5820
ttgcagttag atactctaaa gaagcaatac aacttggtgc tcaaactgat ataaatactg    5880
gaatagatat agaatctaat ttatttggtc tttgttttc aactaaagac caaaagaag     5940 gaatgtcagc tttcgttgaa aagagagaag ctaactttat aaaagggtaa taagaaggag   6000
atatacatat gagaagtttt gaagaagtaa ttaagtttgc aaaagaaaga ggacctaaaa   6060
ctatatcagt agcatgttgc caagataaag aagtttaat ggcagttgaa atggctagaa    6120
aagaaaaaat agcaaatgcc attttagtag agatataga aaagactaaa gaaattgcaa    6180
aaagcataga catggatatc gaaaattatg aactgataga tataaaagat ttagcagaag   6240
catctctaaa atctgttgaa ttagtttcac aaggaaaagc cgacatggta atgaaaggct   6300
tagtagacac atcaataata ctaaaagcag ttttaaataa agaagtaggt cttagaactg   6360
gaaatgtatt aagtcacgta gcagtatttg atgtagaggg atatgataga ttattttcg    6420 taactgacgc agctatgaac ttagctcctg atacaaatac taaaaagcaa atcatagaaa   6480
atgcttgcac agtagcacat tcattagata taagtgaacc aaaagttgct gcaatatgcg   6540
caaaagaaaa agtaaatcca aaaatgaaag atacagttga agctaaagaa ctagaagaaa   6600
tgtatgaaag aggagaaatc aaaggttgta tggttggtgg gccttttgca attgataatg   6660
cagtatcttt agaagcagct aaacataaag gtataaatca tcctgtagca ggacgagctg   6720
atatattatt agcccagat attgaaggtg gtaacatatt atataaagct ttggtattct    6780
tctcaaaatc aaaaaatgca ggagttatag ttggggctaa agcaccaata atattaactt   6840
ctagagcaga cagtgaagaa actaaactaa actcaatagc tttaggtgtt ttaatggcag   6900
caaaggcata ataagaagga gatatacata tgagcaaaat atttaaaatc ttaacaataa   6960
atcctggttc gacatcaact aaaatagctg tatttgataa tgaggattta gtatttgaaa   7020
aaactttaag acattcttca gaagaaatag gaaatatga aaggtgtct gaccaatttg     7080 aatttcgtaa acaagtaata gaagaagctc taaagaagg tggagtaaaa acatctgaat    7140
tagatgctgt agtaggtaga ggaggacttc ttaaacctat aaaaggtggt acttattcag   7200
taagtgctgc tatgattgaa gatttaaaag tgggagtttt aggagaacac gcttcaaacc   7260
taggtggaat aatagcaaaa caaataggtg aagaagtaaa tgttccttca tacatagtag   7320
accctgttgt tgtagatgaa ttagaagatg ttgctagaat ttctggtatg cctgaaataa   7380
gtagagcaag tgtagtacat gctttaaatc aaaaggcaat agcaagaaga tatgctagag   7440
aaataaacaa gaaatatgaa gatataaatc ttatagttgc acacatgggt ggaggagttt   7500
ctgttggagc tcataaaaat ggtaaaatag tagatgttgc aaacgcatta gatggagaag   7560
gacctttctc tccagaaaga agtggtggac taccagtagg tgcattagta aaaatgtgct   7620
ttagtggaaa atatactcaa gatgaaatta aaaagaaaat aaaaggtaat ggcggactag   7680
ttgcatactt aaacactaat gatgctgag aagttgaaga aagaattgaa gctggtgatg    7740
aaaaagctaa attagtatat gaagctatgg catatcaaat ctctaaagaa ataggagcta   7800
gtgctgcagt tcttaaggga gatgtaaaag caatattatt aactggtgga atcgcatatt   7860
caaaaatgtt tacagaaatg attgcagata gagttaaatt tatagcagat gtaaaagttt   7920
atccaggtga agatgaaatg attgcattag ctcaaggtgg acttagagtt ttaactggtg   7980
aagaagaggc tcaagtttat gataactaat aa                                 8012
```

<210> SEQ ID NO 76
<211> LENGTH: 6224

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 76

```
ctcgagttca ttatccatcc tccatcgcca cgatagttca tggcgatagg tagaatagca      60
atgaacgatt atccctatca agcattctga ctgataattg ctcacacgaa ttcattaaag     120
aggagaaagg taccatgatc gtaaaaccta tggtacgcaa caatatctgc ctgaacgccc     180
atcctcaggg ctgcaagaag ggagtggaag atcagattga atataccaag aaacgcatta     240
ccgcagaagt caaagctggc gcaaaagctc caaaaaacgt tctggtgctt ggctgctcaa     300
atggttacgg cctggcgagc cgcattactg ctgcgttcgg atacggggct gcgaccatcg     360
gcgtgtcctt tgaaaaagcg ggttcagaaa ccaaatatgg tacaccggga tggtacaata     420
atttggcatt tgatgaagcg gcaaaacgcg agggtcttta tagcgtgacg atcgacggcg     480
atgcgttttc agacgagatc aaggcccagg taattgagga agccaaaaaa aaaggtatca     540
aatttgatct gatcgtatac agcttggcca gcccagtacg tactgatcct gatacaggta     600
tcatgcacaa aagcgttttg aaacccttg gaaaaacgtt cacaggcaaa acagtagatc     660
cgtttactgg cgagctgaag gaaatctccg cggaaccagc aaatgacgag gaagcagccg     720
ccactgttaa agttatgggg ggtgaagatt gggaacgttg gattaagcag ctgtcgaagg     780
aaggcctctt agaagaaggc tgtattacct tggcctatag ttatattggc cctgaagcta     840
cccaagcttt gtaccgtaaa ggcacaatcg gcaaggccaa agaacacctg gaggccacag     900
cacaccgtct caacaaagag aacccgtcaa tccgtgcctt cgtgagcgtg aataaaggcc     960
tggtaacccg cgcaagcgcc gtaatcccgg taatccctct gtatctcgcc agcttgttca    1020
aagtaatgaa agagaagggc aatcatgaag gttgtattga acagatcacg cgtctgtacg    1080
ccgagcgcct gtaccgtaaa gatggtacaa ttccagttga tgaggaaaat cgcattcgca    1140
ttgatgattg ggagttagaa gaagacgtcc agaaagcggt atccgcgttg atggagaaag    1200
tcacgggtga aaacgcagaa tctctcactg acttagcggg gtaccgccat gatttcttag    1260
ctagtaacgg ctttgatgta gaaggtatta attatgaagc ggaagttgaa cgcttcgacc    1320
gtatctgata gaaggagat atacatgat gagaagtagt aattgccagt gcagctagaa    1380
cagcagtagg aagttttgga ggagcattta atcagtttc agcggtagag ttaggggtaa    1440
cagcagctaa agaagctata aaagagctat acataactcc agatatgata gatgaatctc    1500
ttttagggg agtacttaca gcaggtcttg gacaaaatat agcaagacaa atagcattag    1560
gagcaggaat accagtagaa aaaccagcta tgactataaa tatagtttgt ggttctggat    1620
taagatctgt ttcaatggca tctcaactta tagcattagg tgatgctgat ataatgttag    1680
ttggtggagc tgaaaacatg agtatgtctc cttatttagt accaagtgcg agatatggtg    1740
caagaatggg tgatgctgct tttgttgatt caatgataaa agatggatta tcagacatat    1800
ttaataacta tcacatgggt attactgctg aaaacatagc agagcaatgg aatataacta    1860
gagaagaaca agatgaatta gctcttgcaa gtcaaaataa agctgaaaaa gctcaagctg    1920
aaggaaaatt tgatgaagaa atagttcctg ttgttataaa aggaagaaaa ggtgacactg    1980
tagtagataa agatgaatat attaagcctg cactacaat ggagaaactt gctaagttaa    2040
gacctgcatt taaaaaagat ggaacagtta ctgctggtaa tgcatcagga ataaatgatg    2100
```

```
gtgctgctat gttagtagta atggctaaag aaaaagctga agaactagga atagagcctc  2160
ttgcaactat agtttcttat ggaacagctg gtgttgaccc taaaataatg ggatatggac  2220
cagttccagc aactaaaaaa gctttagaag ctgctaatat gactattgaa gatatagatt  2280
tagttgaagc taatgaggca tttgctgccc aatctgtagc tgtaataaga gacttaaata  2340
tagatatgaa taaagttaat gttaatggtg gagcaatagc tataggacat ccaataggat  2400
gctcaggagc aagaatactt actacacttt tatatgaaat gaagagaaga gatgctaaaa  2460
ctggtcttgc tacactttgt ataggcggtg gaatgggaac tactttaata gttaagagat  2520
agtaagaagg agatatacat atgaaattag ctgtaatagg tagtggaact atgggaagtg  2580
gtattgtaca aactttttgca agttgtggac atgatgtatg tttaaagagt agaactcaag  2640
gtgctataga taaatgttta gctttattag ataaaaattt aactaagtta gttactaagg  2700
gaaaaatgga tgaagctaca aaagcagaaa tattaagtca tgttagttca actactaatt  2760
atgaagattt aaaagatatg gatttaataa tagaagcatc tgtagaagac atgaatataa  2820
agaaagatgt tttcaagtta ctagatgaat tatgtaaaga agatactatc ttggcaacaa  2880
atacttcatc attatctata acagaaatag cttcttctac taagcgccca gataaagtta  2940
taggaatgca tttctttaat ccagttccta tgatgaaatt agttgaagtt ataagtggtc  3000
agttaacatc aaaagttact tttgatacag tatttgaatt atctaagagt atcaataaag  3060
taccagtaga tgtatctgaa tctcctggat ttgtagtaaa tagaatactt atacctatga  3120
taaatgaagc tgttggtata tatgcagatg gtgttgcaag taaagaagaa atagatgaag  3180
ctatgaaatt aggagcaaac catccaatgg gaccactagc attaggtgat ttaatcggat  3240
tagatgttgt tttagctata atgaacgttt tatatactga atttggagat actaaatata  3300
gacctcatcc acttttagct aaaatggtta gagctaatca attaggaaga aaaactaaga  3360
taggattcta tgattataat aaataataag aaggagatat acatatgagt acaagtgatg  3420
ttaaagttta tgagaatgta gctgttgaag tagatgggaaa tatatgtaca gtgaaaatga  3480
atagacctaa agcccttaat gcaataaatt caaagacttt agaagaactt tatgaagtat  3540
ttgtagatat taataatgat gaaactattg atgttgtaat attgacaggg gaaggaaagg  3600
catttgtagc tggagcagat attgcataca tgaaagattt agatgctgta gctgctaaag  3660
attttagtat cttaggagca aaagcttttg gagaaataga aatagtaaaa aagtagtga  3720 tagctgctgt aaacggattt gctttaggtg gaggatgtga acttgcaatg gcatgtgata  3780
taagaattgc atctgctaaa gctaaatttg gtcagccaga agtaactctt ggaataactc  3840
caggatatgg aggaactcaa aggcttacaa gattggttgg aatggcaaaa gcaaaagaat  3900
taatctttac aggtcaagtt ataaaagctg atgaagctga aaaaataggg ctagtaaata  3960
gagtcgttga gccagacatt ttaatagaag aagttgagaa attagctaag ataatagcta  4020
aaaatgctca gcttgcagtt agatactcta agaagcaat acaacttggt gctcaaactg  4080
atataaatac tggaatagat atagaatcta atttatttgg tctttgtttt tcaactaaag  4140
accaaaaaga aggaatgtca gctttcgttg aaaagagaga agctaacttt ataaagggt  4200 aataagaagg agatatacat atgagaagtt ttgaagaagt aattaagttt gcaaaagaaa  4260
gaggacctaa aactatatca gtagcatgtt gccaagataa agaagttttta atggcagttg  4320 aaatggctag aaaagaaaaa atagcaaatg ccatttttagt aggagatata gaaagagaca  4380
aagaaattgc aaaagcata gacatggata tcgaaaatta tgaactgata gatataaag  4440 atttagcaga agcatctcta aaatctgttg aattagtttc acaaggaaaa gccgacatgg  4500
```

```
taatgaaagg cttagtagac acatcaataa tactaaaagc agttttaaat aaagaagtag    4560
gtcttagaac tggaaatgta ttaagtcacg tagcagtatt tgatgtagag ggatatgata    4620
gattattttt cgtaactgac gcagctatga acttagctcc tgatacaaat actaaaaagc    4680
aaatcataga aaatgcttgc acagtagcac attcattaga tataagtgaa ccaaaagttg    4740
ctgcaatatg cgcaaaagaa aaagtaaatc aaaaatgaa agatacagtt gaagctaaag    4800
aactagaaga aatgtatgaa agaggagaaa tcaaaggttg tatggttggt gggccttttg    4860
caattgataa tgcagtatct ttagaagcag ctaaacataa aggtataaat catcctgtag    4920
caggacgagc tgatatatta ttagccccag atattgaagg tggtaacata ttatataaag    4980
ctttggtatt cttctcaaaa tcaaaaaatg caggagttat agttggggct aaagcaccaa    5040
taatattaac ttctagagca gacagtgaag aaactaaact aaactcaata gctttaggtg    5100
ttttaatggc agcaaaggca taataagaag gagatataca tatgagcaaa atatttaaaa    5160
tcttaacaat aaatcctggt tcgacatcaa ctaaaatagc tgtatttgat aatgaggatt    5220
tagtatttga aaaaacttta agacattctt cagaagaaat aggaaaatat gagaaggtgt    5280
ctgaccaatt tgaatttcgt aaacaagtaa tagaagaagc tctaaaagaa ggtggagtaa    5340
aaacatctga attagatgct gtagtaggta gaggaggact tcttaaacct ataaaaggtg    5400
gtacttattc agtaagtgct gctatgattg aagatttaaa agtgggagtt ttaggagaac    5460
acgcttcaaa cctaggtgga ataatagcaa aacaaatagg tgaagaagta aatgttcctt    5520
catacatagt agaccctgtt gttgtagatg aattagaaga tgttgctaga atttctggta    5580
tgcctgaaat aagtagagca agtgtagtac atgctttaaa tcaaaaggca atagcaagaa    5640
gatatgctag agaaataaac aagaaatatg aagtataaaa tcttatagtt gcacacatgg    5700
gtggaggagt ttctgttgga gctcataaaa atggtaaaat agtagatgtt gcaaacgcat    5760
tagatggaga aggaccttc tctccagaaa gaagtggtgg actaccagta ggtgcattag    5820
taaaaatgtg ctttagtgga aaatatactc aagatgaaat taaaagaaa ataaaaggta    5880 atggcggact agttgcatac ttaaacacta atgatgctag agaagttgaa gaaagaattg    5940
aagctggtga tgaaaaagct aaattagtat atgaagctat ggcatatcaa atctctaaag    6000
aaataggagc tagtgctgca gttcttaagg gagatgtaaa agcaatatta ttaactggtg    6060
gaatcgcata ttcaaaaatg tttacagaaa tgattgcaga tagagttaaa tttatagcag    6120
atgtaaaagt ttatccaggt gaagatgaaa tgattgcatt agctcaaggt ggacttagag    6180
ttttaactgg tgaagaagag gctcaagttt atgataacta ataa                     6224
```

<210> SEQ ID NO 77
<211> LENGTH: 3118
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77

```
ctcgagatgc tagcaattgt gagcggataa caattgacat tgtgagcgga taacaagata     60
ctgagcacat cagcaggacg cactgacctt aattaaaaga attcattaaa gaggagaaag    120
gtaccatgaa tattcgtgat cttgagtacc tggtggcatt ggctgaacac cgccattttc    180
ggcgtgcggc agattcctgc cacgttagcc agccgacgct tagcgggcaa attcgtaagc    240
```

```
tggaagatga gctgggcgtg atgttgctgg agcggaccag ccgtaaagtg ttgttcaccc    300
aggcgggaat gctgctggtg gatcaggcgc gtaccgtgct gcgtgaggtg aaagtcctta    360
aagagatggc aagccagcag ggcgagacga tgtccggacc gctgcacatt ggtttgattc    420
ccacagttgg accgtacctg ctaccgcata ttatccctat gctgcaccag acctttccaa    480
agctggaaat gtatctgcat gaagcacaga cccaccagtt actggcgcaa ctggacagcg    540
gcaaactcga ttgcgtgatc ctcgcgctgg tgaaagagag cgaagcattc attgaagtgc    600
cgttgtttga tgagccaatg ttgctggcta tctatgaaga tcacccgtgg gcgaaccgcg    660
aatgcgtacc gatggccgat ctggcagggg aaaaactgct gatgctggaa gatggtcact    720
gtttgcgcga tcaggcaatg ggtttctgtt ttgaagccgg ggcggatgaa gatacacact    780
tccgcgcgac cagcctggaa actctgcgca acatggtggc ggcaggtagc gggatcactt    840
tactgccagc gctggctgtg ccgccggagc gcaaacgcga tggggttgtt tatctgccgt    900
gcattaagcc ggaaccacgc cgcactattg gcctggttta tcgtcctggc tcaccgctgc    960
gcagccgcta tgagcagctg gcagaggcca tccgcgcaag aatggatggc catttcgata   1020
aagttttaaa acaggcggtt taaggatccc atggtacgcg tgctagaggc atcaaataaa   1080
acgaaaggct cagtcgaaag actgggcctt tcgttttatc tgttgtttgt cggtgaacgc   1140
tctcctgagt aggacaaatc cgccgcccta gacctagggg atatattccg cttcctcgct   1200
cactgactcg ctacgctcgg tcgttcgact gcggcgagcg gaaatggctt acgaacgggg   1260
cggagatttc ctggaagatg ccaggaagat acttaacagg gaagtgagag gccgcggca    1320 aagccgtttt tccataggct ccgccccct gacaagcatc acgaaatctg acgctcaaat   1380
cagtggtggc gaaacccgac aggactataa agataccagg cgtttccccc tggcggctcc   1440
ctcgtgcgct ctcctgttcc tgcctttcgg tttaccggtg tcattccgct gttatggccg   1500
cgtttgtctc attccacgcc tgacactcag ttccgggtag gcagttcgct ccaagctgga   1560
ctgtatgcac gaaccccccg ttcagtccga ccgctgcgcc ttatccggta actatcgtct   1620
tgagtccaac ccggaaagac atgcaaaagc accactggca gcagccactg gtaattgatt   1680
tagaggagtt agtcttgaag tcatgcgccg gttaaggcta aactgaaagg acaagttttg   1740
gtgactgcgc tcctccaagc cagttacctc ggttcaaaga gttggtagct cagagaacct   1800
tcgaaaaacc gccctgcaag gcggttttt cgttttcaga gcaagagatt acgcgcagac   1860
caaaacgatc tcaagaagat catcttatta atcagataaa atatttctag atttcagtgc   1920
aatttatctc ttcaaatgta gcacctgaag tcagccccat acgatataag ttgttactag   1980
tgcttggatt ctcaccaata aaaaacgccc ggcggcaacc gagcgttctg aacaaatcca   2040
gatggagttc tgaggtcatt actggatcta tcaacaggag tccaagcgag ctctcgaacc   2100
ccagagtccc gctcagaaga actcgtcaag aaggcgatag aaggcgatgc gctgcgaatc   2160
gggagcggcg ataccgtaaa gcacgaggaa gcggtcagcc cattcgccgc caagctcttc   2220
agcaatatca cgggtagcca acgctatgtc ctgatagcgg tccgccacac ccagccggcc   2280
acagtcgatg aatccagaaa agcggccatt ttccaccatg atattcggca agcaggcatc   2340
gccatgggtc acgacgagat cctcgccgtc gggcatgcgc gccttgagcc tggcgaacag   2400
ttcggctggc gcgagcccct gatgctcttc gtccagatca tcctgatcga caagaccggc   2460
ttccatccga gtacgtgctc gctcgatgcg atgtttcgct tggtggtcga atgggcaggt   2520
agccggatca agcgtatgca gccgccgcat tgcatcagcc atgatggata ctttctcggc   2580
aggagcaagg tgagatgaca ggagatcctg ccccggcact cgcccaata gcagccagtc   2640
```

```
ccttcccgct tcagtgacaa cgtcgagcac agctgcgcaa ggaacgcccg tcgtggccag    2700
ccacgatagc cgcgctgcct cgtcctgcag ttcattcagg gcaccggaca ggtcggtctt    2760
gacaaaaaga accgggcgcc cctgcgctga cagccggaac acggcggcat cagagcagcc    2820
gattgtctgt tgtgcccagt catagccgaa tagcctctcc acccaagcgg ccggagaacc    2880
tgcgtgcaat ccatcttgtt caatcatgcg aaacgatcct catcctgtct cttgatcaga    2940
tcttgatccc ctgcgccatc agatccttgg cggcaagaaa gccatccagt ttactttgca    3000
gggcttccca accttaccag agggcgcccc agctggcaat tccgacgtct aagaaaccat    3060
tattatcatg acattaacct ataaaaatag gcgtatcacg aggccctttc gtcttcac     3118

<210> SEQ ID NO 78
<211> LENGTH: 8650
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
gtaaaacgac ggccagtgaa ttcgttaaga cccactttca catttaagtt gttttttctaa   60 tccgcatatg atcaattcaa ggccgaataa gaaggctggc tctgcacctt ggtgatcaaa    120
taattcgata gcttgtcgta ataatggcgg catactatca gtagtaggtg tttccctttc    180
ttctttagcg acttgatgct cttgatcttc aatacgcaa cctaaagtaa aatgccccac     240
agcgctgagt gcatataatg cattctctag tgaaaaacct tgttggcata aaaaggctaa    300
ttgattttcg agagtttcat actgtttttc tgtaggccgt gtacctaaat gtactttgc    360 tccatcgcga tgacttagta aagcacatct aaaacttta gcgttattac gtaaaaaatc    420
ttgccagctt tccccttcta aagggcaaaa gtgagtatgg tgcctatcta acatctcaat    480
ggctaaggcg tcgagcaaag cccgcttatt ttttacatgc caatacaatg taggctgctc    540
tacacctagc ttctgggcga gtttacgggt tgttaaacct tcgattccga cctcattaag    600
cagctctaat gcgctgttaa tcactttact tttatctaat ctagacatca ttaattccta    660 attttttgttg acactctatc attgatagag ttatttttacc actccctatc agtgatagag   720
aaaagtgaac tctagaaata attttgttta actttaagaa ggagatatac atatggattt    780
aaattctaaa aaatatcaga tgcttaaaga gctatatgta agcttcgctg aaaatgaagt    840
taaaccttta gcaacagaac ttgatgaaga agaaagattt ccttatgaaa cagtggaaaa    900
aatggcaaaa gcaggaatga tgggtatacc atatccaaaa gaatatggtg gagaaggtgg    960
agacactgta ggatatataa tggcagttga agaattgtct agagtttgtg gtactacagg   1020
agttatatta tcagctcata catctcttgg ctcatggcct atatatcaat atggtaatga   1080
agaacaaaaa caaaaattct taagaccact agcaagtgga gaaaaattag gagcatttgg   1140
tcttactgag cctaatgctg gtacagatgc gtctggccaa caaacaactg ctgttttaga   1200 cgggggatgaa tacatactta atggctcaaa aatatttata acaaacgcaa tagctggtga   1260
catatatgta gtaatggcaa tgactgataa atcctaagggg aacaaggaa tatcagcatt   1320 tatagttgaa aaaggaactc ctgggtttag cttttggagtt aaagaaaaga aatgggtat   1380 aagaggttca gctacgagtg aattaatatt tgaggattgc agaataccta agaaaattt    1440 acttggaaaa gaaggtcaag gatttaagat agcaatgtct actcttgatg gtggtagaat   1500
```

```
tggtatagct gcacaagctt taggtttagc acaaggtgct cttgatgaaa ctgttaaata    1560
tgtaaaagaa agagtacaat ttggtagacc attatcaaaa ttccaaaata cacaattcca    1620
attagctgat atggaagtta aggtacaagc ggctagacac cttgtatatc aagcagctat    1680
aaataaagac ttaggaaaac cttatggagt agaagcagca atggcaaaat tatttgcagc    1740
tgaaacagct atggaagtta ctacaaaagc tgtacaactt catggaggat atggatacac    1800
tcgtgactat ccagtagaaa gaatgatgag agatgctaag ataactgaaa tatatgaagg    1860
aactagtgaa gttcaaagaa tggttatttc aggaaaacta ttaaaatagt aagaaggaga    1920
tatacatatg gaggaaggat ttatgaatat agtcgtttgt ataaaacaag ttccagatac    1980
aacagaagtt aaactagatc ctaatacagg tactttaatt agagatggag taccaagtat    2040
aataaaccct gatgataaag caggtttaga agaagctata aaattaaaag aagaaatggg    2100
tgctcatgta actgttataa caatgggacc tcctcaagca gatatggctt taaaagaagc    2160
tttagcaatg ggtgcagata gaggtatatt attaacagat agagcatttg cgggtgctga    2220
tacttgggca acttcatcag cattagcagg agcattaaaa aatatagatt ttgatattat    2280
aatagctgga agacaggcga tagatggaga tactgcacaa gttggaccte aaatagctga    2340 acatttaaat cttccatcaa taacatatgc tgaagaaata aaaactgaag gtgaatatgt    2400
attagtaaaa agacaatttg aagattgttg ccatgactta aaagttaaaa tgccatgcct    2460
tataacaact cttaaagata tgaacacacc aagatacatg aaagttggaa gaatatatga    2520
tgctttcgaa aatgatgtag tagaaacatg gactgtaaaa gatatagaag ttgacccttc    2580
taatttaggt cttaaaggtt ctccaactag tgtatttaaa tcatttacaa aatcagttaa    2640
accagctggt acaatataca atgaagatgc gaaaacatca gctggaatta tcatagataa    2700
attaaaagag aagtatatca tataataaga aggagatata catatgggta acgttttagt    2760
agtaatagaa caaagagaaa atgtaattca aactgtttct ttagaattac taggaaaggc    2820
tacagaaata gcaaaagatt atgatacaaa agtttctgca ttactttag gtagtaaggt    2880 agaaggttta atagatacat tagcacacta tggtgcagat gaggtaatag tagtagatga    2940
tgaagcttta gcagtgtata caactgaacc atatacaaaa gcagcttatg aagcaataaa    3000
agcagctgac cctatagttg tattatttgg tgcaacttca ataggtagag atttagcgcc    3060 tagagttttct gctagaatac atacaggtct tactgctgac tgtacaggtc ttgcagtagc    3120
tgaagataca aaattattat taatgacaag acctgccttt ggtggaaata atggcaac    3180 aatagtttgt aaagatttca gacctcaaat gtctacagtt agaccagggg ttatgaagaa    3240
aaatgaacct gatgaaacta agaagctgt aattaaccgt ttcaaggtag aatttaatga    3300
tgctgataaa ttagttcaag ttgtacaagt aataaaagaa gctaaaaac aagttaaaat    3360 agaagatgct aagatattag tttctgctgg acgtggaatg ggtggaaaag aaaacttaga    3420
catactttat gaattagctg aaattatagg tggagaagtt tctggttctc gtgccactat    3480
agatgcaggt tggttagata aagcaagaca agttggtcaa actggtaaaa ctgtaagacc    3540
agacctttat atagcatgtg gtatatctgg agcaatacaa catatagctg gtatggaaga    3600
tgctgagttt atagttgcta taaataaaaa tccagaagct ccaatattta aatatgctga    3660
tgttggtata gttggagatg ttcataaagt gcttccagaa cttatcagtc agttaagtgt    3720
tgcaaaagaa aaaggtgaag ttttagctaa ctaataagaa ggagatatac atatgagaga    3780
agtagtaatt gccagtgcag ctagaacagc agtaggaagt tttggaggag catttaaatc    3840
agtttcagcg gtagagttag gggtaacagc agctaaagaa gctataaaaa gagctaacat    3900
```

```
aactccagat atgatagatg aatctctttt aggggagta cttacagcag gtcttggaca    3960
aaatatagca agacaaatag cattaggagc aggaatacca gtagaaaaac cagctatgac    4020
tataaatata gtttgtggtt ctggattaag atctgtttca atggcatctc aacttatagc    4080
attaggtgat gctgatataa tgttagttgg tggagctgaa acatgagta tgtctcctta     4140 tttagtacca agtgcgagat atggtgcaag aatgggtgat gctgcttttg ttgattcaat    4200
gataaaagat ggattatcag acatatttaa taactatcac atgggtatta ctgctgaaaa    4260
catagcagag caatggaata taactagaga agaacaagat gaattagctc ttgcaagtca    4320
aaataaagct gaaaaagctc aagctgaagg aaaatttgat gaagaaatag ttcctgttgt    4380
tataaaagga agaaaaggtg acactgtagt agataaagat gaatatatta agcctggcac    4440
tacaatggag aaacttgcta agttaagacc tgcatttaaa aaagatggaa cagttactgc    4500
tggtaatgca tcaggaataa atgatggtgc tgctatgtta gtagtaatgg ctaaagaaaa    4560
agctgaagaa ctaggaatag agcctcttgc aactatagtt tcttatggaa cagctggtgt    4620
tgaccctaaa ataatgggat atggaccagt tccagcaact aaaaaagctt tagaagctgc    4680
taatatgact attgaagata tagatttagt tgaagctaat gaggcatttg ctgcccaatc    4740
tgtagctgta ataagagact taaatataga tatgaataaa gttaatgtta atggtggagc    4800
aatagctata ggacatccaa taggatgctc aggagcaaga atacttacta cacttttata    4860
tgaaatgaag agaagagatg ctaaaactgg tcttgctaca ctttgtatag gcggtggaat    4920
gggaactact ttaatagtta agagatagta agaaggagat atacatatga aattagctgt    4980
aataggtagt ggaactatgg gaagtggtat tgtacaaact tttgcaagtt gtggacatga    5040
tgtatgttta aagagtagaa ctcaaggtgc tatagataaa tgtttagctt tattagataa    5100
aaatttaact aagttagtta ctaagggaaa aatggatgaa gctacaaaag cagaaatatt    5160
aagtcatgtt agttcaacta ctaattatga agatttaaaa gatatggatt taataataga    5220
agcatctgta gaagacatga atataaagaa agatgttttc aagttactag atgaattatg    5280
taaagaagat actatcttgg caacaaatac ttcatcatta tctataacag aaatagcttc    5340
ttctactaag cgcccagata aagttatagg aatgcatttc tttaatccag ttcctatgat    5400
gaaattagtt gaagttataa gtggtcagtt aacatcaaaa gttacttttg atacagtatt    5460
tgaattatct aagagtatca ataaagtacc agtagatgta tctgaatctc ctggatttgt    5520
agtaaataga atacttatac ctatgataaa tgaagctgtt ggtatatatg cagatggtgt    5580
tgcaagtaaa gaagaaatag atgaagctat gaaattagga gcaaaccatc caatgggacc    5640
actagcatta ggtgatttaa tcggattaga tgttgtttta gctataatga acgttttata    5700
tactgaattt ggagatacta aatatagacc tcatccactt ttagctaaaa tggttagagc    5760
taatcaatta ggaagaaaaa ctaagatagg attctatgat tataataaat aataagaagg    5820
agatatacat atgagtacaa gtgatgttaa agtttatgag aatgtagctg ttgaagtaga    5880
tggaaatata tgtacagtga aaatgaatag acctaaagcc cttaatgcaa taaattcaaa    5940
gactttagaa gaactttatg aagtatttgt agatattaat aatgatgaaa ctattgatgt    6000
tgtaatattg acaggggaag gaaaggcatt tgtagctgga gcagatattg catacatgaa    6060
agatttagat gctgtagctg ctaaagattt tagtatctta ggagcaaaag cttttggaga    6120
aatagaaaat agtaaaaaag tagtgatagc tgctgtaaac ggatttgctt taggtggagg    6180
atgtgaactt gcaatggcat gtgatataag aattgcatct gctaaagcta aatttggtca    6240
```

-continued

```
gccagaagta actcttggaa taactccagg atatggagga actcaaaggc ttacaagatt    6300
ggttggaatg gcaaaagcaa agaattaat ctttacaggt caagttataa aagctgatga    6360
agctgaaaaa atagggctag taaatagagt cgttgagcca gacattttaa tagaagaagt    6420
tgagaaatta gctaagataa tagctaaaaa tgctcagctt gcagttagat actctaaaga    6480
agcaatacaa cttggtgctc aaactgatat aaatactgga atagatatag aatctaatttt   6540 atttggtctt tgtttttcaa ctaaagacca aaaagaagga atgtcagctt tcgttgaaaa    6600
gagagaagct aactttataa aagggtaata agaaggagat atacatatga aagttttga    6660 agaagtaatt aagtttgcaa agaaagagg acctaaaact atatcagtag catgttgcca    6720
agataaagaa gttttaatgg cagttgaaat ggctagaaaa gaaaaaatag caaatgccat    6780
tttagtagga gatatagaaa agactaaaga aattgcaaaa agcatagaca tggatatcga    6840
aaattatgaa ctgatagata taaagatttt agcagaagca tctctaaaat ctgttgaatt    6900
agtttcacaa ggaaaagccg acatggtaat gaaaggctta gtagacacat caataatact    6960
aaaagcagtt ttaaataaag aagtaggtct tagaactgga aatgtattaa gtcacgtagc    7020
agtatttgat gtagagggat atgatagatt attttttcgta actgacgcag ctatgaactt    7080
agctcctgat acaaatacta aaaagcaaat catagaaaat gcttgcacag tagcacattc    7140
attagatata agtgaaccaa aagttgctgc aatatgcgca aaagaaaaag taaatccaaa    7200
aatgaaagat acagttgaag ctaaagaact agaagaaatg tatgaaagag gagaaatcaa    7260
aggttgtatg gttggtgggc cttttgcaat tgataatgca gtatctttag aagcagctaa    7320
acataaaggt ataaatcatc ctgtagcagg acgagctgat atattattag ccccagatat    7380
tgaaggtggt aacatattat ataaagcttt ggtattcttc tcaaaatcaa aaaatgcagg    7440
agttatagtt ggggctaaag caccaataat attaacttct agagcagaca gtgaagaaac    7500
taaactaaac tcaatagctt taggtgtttt aatggcagca aaggcataat aagaaggaga    7560
tatacatatg agcaaaatat ttaaaatctt aacaataaat cctggttcga catcaactaa    7620
aatagctgta tttgataatg aggatttagt atttgaaaaa actttaagac attcttcaga    7680
agaaatagga aaatatgaga aggtgtctga ccaatttgaa tttcgtaaac aagtaataga    7740
agaagctcta aaagaaggtg gagtaaaaac atctgaatta gatgctgtag taggtagagg    7800
aggacttctt aaacctataa aaggtggtac ttattcagta agtgctgcta tgattgaaga    7860
tttaaaagtg ggagttttag agaacacgc ttcaaaccta ggtggaataa tagcaaaaca    7920
aataggtgaa gaagtaaatg ttccttcata catagtagac cctgttgttg tagatgaatt    7980
agaagatgtt gctagaattt ctggtatgcc tgaaataagt agagcaagtg tagtacatgc    8040
tttaaatcaa aaggcaatag caagaagata tgctagagaa ataaacaaga atatgaagaa    8100
tataaatctt atagttgcac acatgggtgg aggagtttct gttggagctc ataaaaatgg    8160
taaaatagta gatgttgcaa acgcattaga tggagaagga cctttctctc cagaagaag    8220 tggtggacta ccagtaggtg cattagtaaa aatgtgcttt agtggaaaat atactcaaga    8280
tgaaattaaa aagaaaataa aaggtaatgg cggactagtt gcatacttaa acactaatga    8340
tgctagagaa gttgaagaaa gaattgaagc tggtgatgaa aaagctaaat tagtatatga    8400
agctatggca tatcaaatct ctaaagaaat aggagctagt gctgcagttc ttaagggaga    8460
tgtaaaagca atattattaa ctggtggaat cgcatattca aaaatgttta cagaaatgat    8520
tgcagataga gttaaatttta tagcagatgt aaaagtttat ccaggtgaag atgaaatgat    8580
tgcattagct caaggtggac ttagagtttt aactggtgaa gaagaggctc aagtttatga    8640
```

-continued

| | |
|---|---|
| taactaataa | 8650 |

<210> SEQ ID NO 79
<211> LENGTH: 6862
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 79

| | |
|---|---|
| gtaaaacgac ggccagtgaa ttcgttaaga cccactttca catttaagtt gttttctaa | 60 |
| tccgcatatg atcaattcaa ggccgaataa gaaggctggc tctgcacctt ggtgatcaaa | 120 |
| taattcgata gcttgtcgta ataatggcgg catactatca gtagtaggtg tttccctttc | 180 |
| ttctttagcg acttgatgct cttgatcttc caatacgcaa cctaaagtaa aatgccccac | 240 |
| agcgctgagt gcatataatg cattctctag tgaaaaacct tgttggcata aaaaggctaa | 300 |
| ttgattttcg agagtttcat actgtttttc tgtaggccgt gtacctaaat gtacttttgc | 360 |
| tccatcgcga tgacttagta aagcacatct aaaactttta gcgttattac gtaaaaaatc | 420 |
| ttgccagctt tccccttcta aagggcaaaa gtgagtatgg tgcctatcta acatctcaat | 480 |
| ggctaaggcg tcgagcaaag cccgcttatt ttttacatgc caatacaatg taggctgctc | 540 |
| tacacctagc ttctgggcga gtttacgggt tgttaaacct tcgattccga cctcattaag | 600 |
| cagctctaat gcgctgttaa tcactttact tttatctaat ctagacatca ttaattccta | 660 |
| attttttgttg acactctatc attgatagag ttattttacc actccctatc agtgatagag | 720 |
| aaaagtgaac tctagaaaata attttgttta actttaagaa ggagatatac atatgatcgt | 780 |
| aaaacctatg gtacgcaaca atatctgcct gaacgcccat cctcagggct gcaagaaggg | 840 |
| agtggaagat cagattgaat ataccaagaa acgcattacc gcagaagtca aagctggcgc | 900 |
| aaaagctcca aaaacgttc tggtgcttgg ctgctcaaat ggttacggcc tggcgagccg | 960 |
| cattactgct gcgttcggat acggggctgc gaccatcggc gtgtcctttg aaaaagcggg | 1020 |
| ttcagaaacc aaatatggta caccgggatg gtacaataat ttggcatttg atgaagcggc | 1080 |
| aaaacgcgag ggtctcttata gcgtgacgat cgacggcgat gcgttttcag acgagatcaa | 1140 |
| ggcccaggta attgaggaag ccaaaaaaaa aggtatcaaa tttgatctga tcgtatacag | 1200 |
| cttggccagc ccagtacgta ctgatcctga tacaggtatc atgcacaaaa gcgttttgaa | 1260 |
| accctttgga aaaacgttca caggcaaaac agtagatccg tttactggcg agctgaagga | 1320 |
| aatctccgcg gaaccagcaa atgacgagga agcagccgcc actgttaaag ttatgggggg | 1380 |
| tgaagattgg gaacgttgga ttaagcagct gtcgaaggaa ggcctcttag aagaggctg | 1440 |
| tattaccttg gcctatagtt atattggccc tgaagctacc caagctttgt accgtaaagg | 1500 |
| cacaatcggc aaggccaaag aacacctgga ggccacagca caccgtctca acaaagagaa | 1560 |
| cccgtcaatc cgtgccttcg tgagcgtgaa taaaggcctg gtaacccgcg caagcgccgt | 1620 |
| aatcccggta atccctctgt atctcgccag cttgttcaaa gtaatgaaag agaagggcaa | 1680 |
| tcatgaaggt tgtattgaac agatcacgcg tctgtacgcc gagcgcctgt accgtaaaga | 1740 |
| tggtacaatt ccagttgatg aggaaaatcg cattcgcatt gatgattggg agttagaaga | 1800 |
| agacgtccag aaagcggtat ccgcgttgat ggagaaagtc acgggtgaaa acgcagaatc | 1860 |
| tctcactgac ttagcggggt accgccatga tttcttagct agtaacggct tgatgtaga | 1920 |

```
aggtattaat tatgaagcgg aagttgaacg cttcgaccgt atctgataag aaggagatat    1980
acatatgaga gaagtagtaa ttgccagtgc agctagaaca gcagtaggaa gttttggagg    2040
agcatttaaa tcagtttcag cggtagagtt aggggtaaca gcagctaaag aagctataaa    2100
aagagctaac ataactccag atatgataga tgaatctctt ttaggggag tacttacagc     2160 aggtcttgga caaaatatag caagacaaat agcattagga gcaggaatac cagtagaaaa    2220
accagctatg actataaata tagttttgtgg ttctggatta agatctgttt caatggcatc   2280
tcaacttata gcattaggtg atgctgatat aatgttagtt ggtggagctg aaaacatgag    2340
tatgtctcct tatttagtac caagtgcgag atatggtgca agaatgggtg atgctgcttt    2400
tgttgattca atgataaaag atggattatc agacatattt aataactatc acatgggtat    2460
tactgctgaa acatagcag agcaatggaa tataactaga gaagaacaag atgaattagc     2520
tcttgcaagt caaaataaag ctgaaaaagc tcaagctgaa ggaaaatttg atgaagaaat    2580
agttcctgtt gttataaaag gaagaaaagg tgacactgta gtagataaag atgaatatat    2640
taagcctggc actacaatgg agaaacttgc taagttaaga cctgcattta aaaagatgg     2700 aacagttact gctggtaatg catcaggaat aaatgatggt gctgctatgt tagtagtaat    2760
ggctaaagaa aaagctgaag aactaggaat agagcctctt gcaactatag tttcttatgg    2820
aacagctggt gttgacccta aaataatggg atatggacca gttccagcaa ctaaaaaagc    2880
tttagaagct gctaatatga ctattgaaga tatagattta gttgaagcta atgaggcatt    2940
tgctgcccaa tctgtagctg taataagaga cttaaatata gatatgaata agttaatgt     3000 taatggtgga gcaatagcta taggacatcc aataggatgc tcaggagcaa gaatacttac    3060
tacactttta tatgaaatga agagaagaga tgctaaaact ggtcttgcta cactttgtat    3120
aggcggtgga atgggaacta ctttaatagt taagagatag taagaaggag atatacatat    3180
gaaattagct gtaataggta gtggaactat gggaagtggt attgtacaaa cttttgcaag    3240
ttgtggacat gatgtatgtt taaagagtag aactcaaggt gctatagata atgtttagc     3300 tttattagat aaaaatttaa ctaagttagt tactaaggga aaaatggatg aagctacaaa    3360
agcagaaata ttaagtcatg ttagttcaac tactaattat gaagatttaa agatatgga    3420 tttaataata gaagcatctg tagaagacat gaatataaag aaagatgttt tcaagttact    3480
agatgaatta tgtaaagaag atactatctt ggcaacaaat acttcatcat tatctataac    3540
agaaatagct tcttctacta agcgcccaga taaagttata ggaatgcatt tctttaatcc    3600
agttcctatg atgaaattag ttgaagttat aagtggtcag ttaacatcaa aagttacttt    3660
tgatacagta tttgaattat ctaagagtat caataaagta ccagtagatg tatctgaatc    3720 tcctggatt gtagtaaata gaatacttat acctatgata aatgaagctg ttggtatata    3780
tgcagatggt gttgcaagta aagaagaaat agatgaagct atgaaattag gagcaaacca    3840
tccaatggga ccactagcat taggtgattt aatcggatta gatgttgttt tagctataat    3900 gaacgttta tatactgaat ttggagatac taaaatataga cctcatccac ttttagctaa   3960
aatggttaga gctaatcaat taggaagaaa aactaagata ggattctatg attataataa    4020
ataataagaa ggagatatac atatgagtac aagtgatgtt aaagtttatg agaatgtagc    4080
tgttgaagta gatggaaata tatgtacagt gaaaatgaat agacctaaag cccttaatgc    4140
aataaattca aagactttag aagaacttta tgaagtattt gtagatatta ataatgatga    4200
aactattgat gttgtaatat tgacaggga aggaaaggca tttgtagctg agcagatat     4260 tgcatacatg aaagatttag atgctgtagc tgctaaagat tttagtatct taggagcaaa    4320
```

```
agcttttgga gaaatagaaa atagtaaaaa agtagtgata gctgctgtaa acggatttgc    4380
tttaggtgga ggatgtgaac ttgcaatggc atgtgatata agaattgcat ctgctaaagc    4440
taaatttggt cagccagaag taactcttgg aataactcca ggatatggag gaactcaaag    4500
gcttacaaga ttggttggaa tggcaaaagc aaaagaatta atctttacag gtcaagttat    4560
aaaagctgat gaagctgaaa aaatagggct agtaaataga gtcgttgagc cagacatttt    4620
aatagaagaa gttgagaaat tagctaagat aatagctaaa aatgctcagc ttgcagttag    4680
atactctaaa gaagcaatac aacttggtgc tcaaactgat ataaatactg aatagatat    4740 agaatcaat ttatttggtc tttgttttc aactaaagac caaaagaag gaatgtcagc    4800 tttcgttgaa aagagagaag ctaactttat aaagggtaa taagaaggag atatacatat    4860
gagaagtttt gaagaagtaa ttaagtttgc aaaagaaaga ggacctaaaa ctatatcagt    4920
agcatgttgc caagataaag aagtttaat ggcagttgaa atggctagaa agaaaaaat    4980 agcaaatgcc attttagtag gagatataga aaagactaaa gaaattgcaa aaagcataga    5040
catggatatc gaaaattatg aactgataga tataaaagat ttagcagaag catctctaaa    5100
atctgttgaa ttagttttcac aaggaaaagc cgacatggta atgaaaggct tagtagacac    5160
atcaataata ctaaaagcag ttttaaataa agaagtaggt cttagaactg gaaatgtatt    5220
aagtcacgta gcagtatttg atgtagaggg atatgataga ttattttcg taactgacgc    5280 agctatgaac ttagctcctg atacaaatac taaaaagcaa atcatagaaa atgcttgcac    5340
agtagcacat tcattagata taagtgaacc aaaagttgct gcaatatgcg caaaagaaaa    5400
agtaaatcca aaaatgaaag atacagttga agctaaagaa ctagaagaaa tgtatgaaag    5460
aggagaaatc aaaggttgta tggttggtgg gccttttgca attgataatg cagtatcttt    5520
agaagcagct aaacataaag gtataaatca tcctgtagca ggacgagctg atatattatt    5580
agccccagat attgaaggtg gtaacatatt atataaagct ttggtattct tctcaaaatc    5640
aaaaaatgca ggagttatag ttggggctaa agcaccaata atattaactt ctagagcaga    5700
cagtgaagaa actaaactaa actcaatagc tttaggtgtt ttaatggcag caaaggcata    5760
ataagaagga gatatacata tgagcaaaat atttaaaatc ttaacaataa atcctggttc    5820
gacatcaact aaaatagctg tatttgataa tgaggattta gtatttgaaa aaactttaag    5880
acattcttca gaagaaatag gaaaatatga gaaggtgtct gaccaatttg aatttcgtaa    5940
acaagtaata gaagaagctc taaaagaagg tggagtaaaa acatctgaat tagatgctgt    6000
agtaggtaga ggaggacttc ttaaacctat aaaaggtggt acttattcag taagtgctgc    6060
tatgattgaa gatttaaaag tgggagtttt aggagaacac gcttcaaacc taggtggaat    6120
aatagcaaaa caaataggtg aagaagtaaa tgttccttca tacatagtag accctgttgt    6180
tgtagatgaa ttagaagatg ttgctagaat ttctggtatg cctgaaataa gtagagcaag    6240
tgtagtacat gctttaaatc aaaaggcaat agcaagaaga tatgctagag aaataaacaa    6300
gaaatatgaa gatataaatc ttatagttgc acacatgggt ggaggagttt ctgttggagc    6360
tcataaaaat ggtaaaatag tagatgttgc aaacgcatta gatggagaag gacctttctc    6420
tccagaaaga agtggtggac taccagtagg tgcattagta aaaatgtgct ttagtggaaa    6480
atatactcaa gatgaaatta aaagaaaat aaaggtaat ggcggactag ttgcatactt    6540
aaacactaat gatgctagag aagttgaaga aagaattgaa gctggtgatg aaaaagctaa    6600
attagtatat gaagctatgg catatcaaat ctctaaagaa ataggagcta gtgctgcagt    6660
```

```
tcttaaggga gatgtaaaag caatattatt aactggtgga atcgcatatt caaaaatgtt      6720
tacagaaatg attgcagata gagttaaatt tatagcagat gtaaaagttt atccaggtga      6780
agatgaaatg attgcattag ctcaaggtgg acttagagtt ttaactggtg aagaagaggc      6840
tcaagtttat gataactaat aa                                              6862
```

<210> SEQ ID NO 80
<211> LENGTH: 5644
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80

```
ttattatcgc accgcaatcg ggattttcga ttcataaagc aggtcgtagg tcggcttgtt        60
gagcaggtct tgcagcgtga aaccgtccag atacgtgaaa aacgacttca ttgcaccgcc       120
gagtatgccc gtcagccggc aggacggcgt aatcaggcat tcgttgttcg ggcccataca       180
ctcgaccagc tgcatcggtt cgaggtggcg gacgaccgcg ccgatattga tgcgttcggg       240
cggcgcggcc agcctcagcc cgccgccttt cccgcgtacg ctgtgcaaga acccgccttt       300
gaccagcgcg gtaaccactt tcatcaaatg gcttttggaa atgccgtagg tcgaggcgat       360
ggtggcgata ttgaccagcg cgtcgtcgtt gacggcggtg tagatgagga cgcgcagccc       420
gtagtcggta tgttgggtca gatacataca acctccttag tacatgcaaa attatttcta       480
gagcaacata cgagccggaa gcataaagtg taaagcctgg ggtgcctaat gagttgagtt       540
gaggaattat aacaggaaga atattcctc atacgcttgt aattcctcta tggttgttga       600
caattaatca tcggctcgta taatgtataa cattcatatt ttgtgaattt taaactctag       660
aaataatttt gtttaacttt aagaaggaga tatacatatg atcgtaaaac ctatggtacg       720
caacaatatc tgcctgaacg cccatcctca gggctgcaag aagggagtgg aagatcagat       780
tgaatatacc aagaaacgca ttaccgcaga agtcaaagct ggcgcaaaag ctccaaaaaa       840
cgttctggtg cttggctgct caaatggtta cggcctggcg agccgcatta ctgctgcgtt       900
cggatacggg gctgcgacca tcggcgtgtc ctttgaaaaa gcgggttcag aaaccaaata       960
tggtacaccg ggatggtaca ataatttggc atttgatgaa gcggcaaaac gcagagggtct      1020 ttatagcgtg acgatcgacg gcgatgcgtt ttcagacgag atcaaggccc aggtaattga      1080
ggaagccaaa aaaaaggta tcaaatttga tctgatcgta tacagcttgg ccagcccagt       1140
acgtactgat cctgatacag gtatcatgca caaaagcgtt ttgaaaccct ttggaaaaac      1200
gttcacaggc aaaacagtag atccgttac tggcgagctg aaggaaatct ccgcggaacc      1260
agcaaatgac gaggaagcag ccgccactgt taaagttatg ggggtgaag attgggaacg       1320 ttggattaag cagctgtcga aggaaggcct cttagaagaa ggctgtatta ccttggccta      1380
tagttatatt ggccctgaag ctacccaagc tttgtaccgt aaaggcacaa tcggcaaggc      1440
caaagaacac ctggaggcca cagcacaccg tctcaacaaa gagaacccgt caatccgtgc      1500
cttcgtgagc gtgaataaag gcctggtaac ccgcgcaagc gccgtaatcc cggtaatccc      1560
tctgtatctc gccagcttgt tcaaagtaat gaaagagaag ggcaatcatg aaggttgtat      1620
tgaacagatc acgcgtctgt acgccgagcg cctgtaccgt aaagatggta caattccagt      1680
tgatgaggaa aatcgcattc gcattgatga ttggagtta gaagaacgtc cagaaagc         1740 ggtatccgcg ttgatggaga aagtcacggg tgaaaacgca gaatctctca ctgacttagc      1800
```

```
ggggtaccgc catgatttct tagctagtaa cggctttgat gtagaaggta ttaattatga    1860
agcggaagtt gaacgcttcg accgtatctg ataagaagga gatatacata tgagagaagt    1920
agtaattgcc agtgcagcta gaacagcagt aggaagtttt ggaggagcat ttaaatcagt    1980
ttcagcggta gagttagggg taacagcagc taaagaagct ataaaaagag ctaacataac    2040
tccagatatg atagatgaat ctcttttagg gggagtactt acagcaggtc ttggacaaaa    2100
tatagcaaga caaatagcat taggagcagg aataccagta gaaaaaccag ctatgactat    2160
aaatatagtt tgtggttctg gattaagatc tgtttcaatg gcatctcaac ttatagcatt    2220
aggtgatgct gatataatgt tagttggtgg agctgaaaac atgagtatgt ctccttattt    2280
agtaccaagt gcgagatatg gtgcaagaat gggtgatgct gcttttgttg attcaatgat    2340
aaaagatgga ttatcagaca tatttaataa ctatcacatg gtattactg ctgaaaacat    2400 agcagagcaa tggaatataa ctagagaaga acaagatgaa ttagctcttg caagtcaaaa    2460
taaagctgaa aaagctcaag ctgaaggaaa atttgatgaa gaaatagttc ctgttgttat    2520
aaaaggaaga aaaggtgaca ctgtagtaga taaagatgaa tatattaagc ctggcactac    2580
aatggagaaa cttgctaagt taagacctgc atttaaaaaa gatggaacag ttactgctgg    2640
taatgcatca ggaataaatg atggtgctgc tatgttagta gtaatggcta agaaaaaagc    2700
tgaagaacta ggaatagagc ctcttgcaac tatagtttct tatggaacag ctggtgttga    2760
ccctaaaata atgggatatg gaccagttcc agcaactaaa aaagctttag aagctgctaa    2820
tatgactatt gaagatatag atttagttga agctaatgag gcatttgctg cccaatctgt    2880
agctgtaata agagacttaa atatagatat gaataaagtt aatgttaatg gtggagcaat    2940
agctatagga catccaatag gatgctcagg agcaagaata cttactacac ttttatatga    3000
aatgaagaga agagatgcta aaactggtct tgctacactt tgtataggcg gtggaatggg    3060
aactacttta atagttaaga gatagtaaga aggagatata catatgaaat tagctgtaat    3120
aggtagtgga actatgggaa gtggtattgt acaaactttt gcaagttgtg gacatgatgt    3180
atgtttaaag agtagaactc aaggtgctat agataaatgt ttagctttat tagataaaaa    3240
tttaactaag ttagttacta agggaaaaat ggatgaagct acaaaagcag aaatattaag    3300
tcatgttagt tcaactacta attatgaaga tttaaaagat atggatttaa taatagaagc    3360
atctgtagaa gacatgaata taagaaagaa tgttttcaag ttactagatg aattatgtaa    3420
agaagatact atcttggcaa caaatacttc atcattatct ataacagaaa tagcttcttc    3480
tactaagcgc ccagataaag ttataggaat gcatttcttt aatccagttc ctatgatgaa    3540
attagttgaa gttataagtg gtcagttaac atcaaaagtt acttttgata cagtatttga    3600
attatctaag agtatcaata aagtaccagt agatgtatct gaatctcctg gatttgtagt    3660
aaatagaata cttataccta tgataaatga agctgttggt atatatgcag atggtgttgc    3720
aagtaaagaa gaaatagatg aagctatgaa attaggagca aaccatccaa tgggaccact    3780
agcattaggt gatttaatcg gattagatgt tgttttagct ataatgaacg ttttatatac    3840
tgaatttgga gatactaaat atagacctca tccacttttta gctaaaatgg ttagagctaa    3900
tcaattagga agaaaaacta agataggatt ctatgattat aataaataat aagaaggaga    3960
tatacatatg agtacaagtg atgttaaagt ttatgagaat gtagctgttg aagtagatgg    4020
aaatatatgt acagtgaaaa tgaatagacc taaagcccctt aatgcaataa attcaaagac    4080
tttagaagaa ctttatgaag tatttgtaga tattaataat gatgaaacta ttgatgttgt    4140
```

| | |
|---|---|
| aatattgaca ggggaaggaa aggcatttgt agctggagca gatattgcat acatgaaaga | 4200 |
| tttagatgct gtagctgcta aagattttag tatcttagga gcaaaagctt ttggagaaat | 4260 |
| agaaaatagt aaaaaagtag tgatagctgc tgtaaacgga tttgctttag gtggaggatg | 4320 |
| tgaacttgca atggcatgtg atataagaat tgcatctgct aaagctaaat ttggtcagcc | 4380 |
| agaagtaact cttggaataa ctccaggata tggaggaact caaaggctta caagattggt | 4440 |
| tggaatggca aaagcaaaag aattaatctt tacaggtcaa gttataaaag ctgatgaagc | 4500 |
| tgaaaaaata gggctagtaa atagagtcgt tgagccagac attttaatag aagaagttga | 4560 |
| gaaattagct aagataatag ctaaaaatgc tcagcttgca gttagatact ctaaagaagc | 4620 |
| aatacaactt ggtgctcaaa ctgatataaa tactggaata gatatagaat ctaatttatt | 4680 |
| tggtctttgt ttttcaacta aagaccaaaa agaaggaatg tcagctttcg ttgaaaagag | 4740 |
| agaagctaac tttataaaag ggtaataaga aggagatata catatgagtc aggcgctaaa | 4800 |
| aaatttactg acattgttaa atctggaaaa aattgaggaa ggactctttc gcggccagag | 4860 |
| tgaagattta ggtttacgcc aggtgtttgg cggccaggtc gtgggtcagg ccttgtatgc | 4920 |
| tgcaaaagag accgtccctg aagagcggct ggtacattcg tttcacagct actttcttcg | 4980 |
| ccctggcgat agtaagaagc cgattattta tgatgtcgaa acgctgcgtg acggtaacag | 5040 |
| cttcagcgcc cgccgggttg ctgctattca aaacggcaaa ccgattttt atatgactgc | 5100 |
| ctcttttccag gcaccagaag cgggtttcga acatcaaaaa acaatgccgt ccgcgccagc | 5160 |
| gcctgatggc ctcccttcgg aaacgcaaat cgcccaatcg ctggcgcacc tgctgccgcc | 5220 |
| agtgctgaaa gataaattca tctgcgatcg tccgctggaa gtccgtccgg tggagtttca | 5280 |
| taacccactg aaaggtcacg tcgcagaacc acatcgtcag gtgtggatcc gcgcaaatgg | 5340 |
| tagcgtgccg gatgacctgc gcgttcatca gtatctgctc ggttacgctt ctgatcttaa | 5400 |
| cttcctgccg gtagctctac agccgcacgg catcggtttt ctcgaaccgg ggattcagat | 5460 |
| tgccaccatt gaccattcca tgtggttcca tcgcccgttt aatttgaatg aatggctgct | 5520 |
| gtatagcgtg gagagcacct cggcgtccag cgcacgtggc tttgtgcgcg tgagtttta | 5580 |
| tacccaagac ggcgtactgg ttgcctcgac cgttcaggaa ggggtgatgc gtaatcacaa | 5640 |
| ttaa | 5644 |

<210> SEQ ID NO 81
<211> LENGTH: 5719
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

| | |
|---|---|
| gtaaaacgac ggccagtgaa ttcgttaaga cccactttca catttaagtt gttttctaa | 60 |
| tccgcatatg atcaattcaa ggccgaataa gaaggctggc tctgcacctt ggtgatcaaa | 120 |
| taattcgata gcttgtcgta ataatggcgg catactatca gtagtaggtg tttccctttc | 180 |
| ttctttagcg acttgatgct cttgatcttc caatacgcaa cctaaagtaa aatgccccac | 240 |
| agcgctgagt gcatataatg cattctctag tgaaaaacct tgttggcata aaaaggctaa | 300 |
| ttgattttcg agagtttcat actgtttttc tgtaggccgt gtacctaaat gtactttgc | 360 |
| tccatcgcga tgacttagta aagcacatct aaaactttta gcgttattac gtaaaaaatc | 420 |
| ttgccagctt tccccttcta aagggcaaaa gtgagtatgg tgcctatcta acatctcaat | 480 |

```
ggctaaggcg tcgagcaaag cccgcttatt ttttacatgc aatacaatg taggctgctc      540 tacacctagc ttctgggcga gtttacgggt tgttaaacct tcgattccga cctcattaag    600
cagctctaat gcgctgttaa tcactttact tttatctaat ctagacatca ttaattccta    660
atttttgttg acactctatc attgatagag ttattttacc actccctatc agtgatagag    720
aaaagtgaac tctagaaata attttgttta actttaagaa ggagatatac atatgatcgt    780 aaacctatg gtacgcaaca atatctgcct gaacgcccat cctcagggct gcaagaaggg     840
agtggaagat cagattgaat ataccaagaa acgcattacc gcagaagtca agctggcgc     900 aaaagctcca aaaacgttc tggtgcttgg ctgctcaaat ggttacggcc tggcgagccg     960
cattactgct gcgttcggat acggggctgc gaccatcggc gtgtcctttg aaaaagcggg    1020
ttcagaaacc aaatatggta caccgggatg gtacaataat ttggcatttg atgaagcggc    1080
aaaacgcgag ggtctttata gcgtgacgat cgacggcgat gcgttttcag acgagatcaa    1140
ggcccaggta attgaggaag ccaaaaaaaa aggtatcaaa tttgatctga tcgtatacag    1200
cttggccagc ccagtacgta ctgatcctga tacaggtatc atgcacaaaa gcgttttgaa    1260 acccttgga aaaacgttca caggcaaaac agtagatccg tttactggcg agctgaagga    1320
aatctccgcg gaaccagcaa atgacgagga agcagccgcc actgttaaag ttatgggggg    1380
tgaagattgg gaacgttgga ttaagcagct gtcgaaggaa ggcctcttag aagaaggctg    1440
tattaccttg gcctatagtt atattggccc tgaagctacc caagctttgt accgtaaagg    1500
cacaatcggc aaggccaaag aacacctgga ggccacagca caccgtctca acaaagagaa    1560
cccgtcaatc cgtgccttcg tgagcgtgaa taaaggcctg gtaacccgcg caagcgccgt    1620
aatcccggta atccctctgt atctcgccag cttgttcaaa gtaatgaaag agaagggcaa    1680
tcatgaaggt tgtattgaac agatcacgcg tctgtacgcc gagcgcctgt accgtaaaga    1740
tggtacaatt ccagttgatg aggaaaatcg cattcgcatt gatgattggg agttagaaga    1800
agacgtccag aaagcggtat ccgcgttgat ggagaaagtc acgggtgaaa acgcagaatc    1860
tctcactgac ttagcggggt accgccatga tttcttagct agtaacggct ttgatgtaga    1920
aggtattaat tatgaagcgg aagttgaacg cttcgaccgt atctgataag aaggagatat    1980
acatatgaga gaagtagtaa ttgccagtgc agctagaaca gcagtaggaa gttttggagg    2040
agcatttaaa tcagtttcag cggtagagtt aggggtaaca gcagctaaag aagctataaa    2100
aagagctaac ataactccag atatgataga tgaatctctt ttaggggag tacttacagc     2160 aggtcttgga caaaatatag caagacaaat agcattagga gcaggaatac cagtagaaaa    2220
accagctatg actataaata tagtttgtgg ttctggatta agatctgttt caatggcatc    2280
tcaacttata gcattaggtg atgctgatat aatgttagtt ggtggagctg aaaacatgag    2340
tatgtctcct tatttagtac caagtgcgag atatggtgca agaatgggtg atgctgcttt    2400
tgttgattca atgataaaag atggattatc agacatattt aataactatc acatgggtat    2460
tactgctgaa acatagcag agcaatggaa tataactaga gaagaacaag atgaattagc    2520
tcttgcaagt caaaataaag ctgaaaaagc tcaagctgaa ggaaaatttg atgaagaaat    2580
agttcctgtt gttataaaag gaagaaaagg tgacactgta gtagataaag atgaatatat    2640
taagcctggc actacaatgg agaaacttgc taagttaaga cctgcattta aaaagatgg     2700 aacagttact gctggtaatg catcaggaat aaatgatggt gctgctatgt tagtagtaat    2760
ggctaaagaa aaagctgaag aactaggaat agagcctctt gcaactatag tttcttatgg    2820
```

-continued

```
aacagctggt gttgacccta aaataatggg atatggacca gttccagcaa ctaaaaaagc    2880
tttagaagct gctaatatga ctattgaaga tatagattta gttgaagcta atgaggcatt    2940
tgctgcccaa tctgtagctg taataagaga cttaaatata gatatgaata agttaatgt     3000 taatggtgga gcaatagcta taggacatcc aataggatgc tcaggagcaa gaatacttac    3060
tacactttta tatgaaatga agagaagaga tgctaaaact ggtcttgcta cactttgtat    3120
aggcggtgga atgggaacta ctttaatagt taagagatag taagaaggag atatacatat    3180
gaaattagct gtaataggta gtggaactat gggaagtggt attgtacaaa cttttgcaag    3240
ttgtggacat gatgtatgtt taaagagtag aactcaaggt gctatagata atgtttagc     3300 tttattagat aaaaatttaa ctaagttagt tactaaggga aaaatggatg aagctacaaa    3360
agcagaaata ttaagtcatg ttagttcaac tactaattat gaagatttaa agatatgga     3420 tttaataata gaagcatctg tagaagacat gaatataaag aaagatgttt tcaagttact    3480
agatgaatta tgtaaagaag atactatctt ggcaacaaat acttcatcat tatctataac    3540
agaaatagct tcttctacta agcgcccaga taaagttata ggaatgcatt tctttaatcc    3600
agttcctatg atgaaattag ttgaagttat aagtggtcag ttaacatcaa aagttacttt    3660
tgatacagta tttgaattat ctaagagtat caataaagta ccagtagatg tatctgaatc    3720
tcctggattt gtagtaaata gaatacttat acctatgata atgaagctg ttggtatata     3780 tgcagatggt gttgcaagta aagaagaaat agatgaagct atgaaattag gagcaaacca    3840
tccaatggga ccactagcat taggtgattt aatcggatta gatgttgttt tagctataat    3900
gaacgtttta tatactgaat ttggagatac taaaatataga cctcatccac ttttagctaa    3960
aatggttaga gctaatcaat taggaagaaa aactaagata ggattctatg attataataa    4020
ataataagaa ggagatatac atatgagtac aagtgatgtt aaagtttatg agaatgtagc    4080
tgttgaagta gatggaaata tatgtacagt gaaaatgaat agacctaaag cccttaatgc    4140
aataaattca aagactttag aagaacttta tgaagtattt gtagatatta ataatgatga    4200
aactattgat gttgtaatat tgacaggga aggaaaggca tttgtagctg gagcagatat     4260
tgcatacatg aaagatttag atgctgtagc tgctaaagat tttagtatct taggagcaaa    4320
agcttttgga gaaatagaaa atagtaaaaa agtagtgata gctgctgtaa acggatttgc    4380
tttaggtgga ggatgtgaac ttgcaatggc atgtgatata agaattgcat ctgctaaagc    4440
taaatttggt cagccagaag taactcttgg aataactcca ggatatggag gaactcaaag    4500
gcttacaaga ttggttggaa tggcaaaagc aaaagaatta atctttacag gtcaagttat    4560
aaaagctgat gaagctgaaa aaatagggct agtaaataga gtcgttgagc cagacatttt    4620
aatagaagaa gttgagaaat tagctaagat aatagctaaa aatgctcagc ttgcagttag    4680
atactctaaa gaagcaatac aacttggtgc tcaaactgat ataaatactg gaatagatat    4740 agaatcaat ttatttggtc tttgtttttc aactaaagac caaaaagaag gaatgtcagc     4800
tttcgttgaa aagagagaag ctaactttat aaaagggtaa taagaaggag atatacatat    4860
gagtcaggcg ctaaaaaatt tactgacatt gttaaatctg gaaaaaattg aggaaggact    4920
ctttcgcggc cagagtgaag atttaggttt acgccaggtg tttggcggcc aggtcgtggg    4980
tcaggccttg tatgctgcaa agagaccgt ccctgaagag cggctggtac attcgtttca     5040
cagctacttt cttcgccctg gcgatagtaa gaagccgatt attttatgatg tcgaacgct    5100 gcgtgacggt aacagcttca gcgcccgccg ggttgctgct attcaaaacg gcaaccgat    5160 ttttatatg actgcctctt tccaggcacc agaagcgggt ttcgaacatc aaaaaacaat    5220
```

```
gccgtccgcg ccagcgcctg atggcctccc ttcggaaacg caaatcgccc aatcgctggc    5280
gcacctgctg ccgccagtgc tgaaagataa attcatctgc gatcgtccgc tggaagtccg    5340
tccggtggag tttcataacc cactgaaagg tcacgtcgca gaaccacatc gtcaggtgtg    5400
gatccgcgca aatggtagcg tgccggatga cctgcgcgtt catcagtatc tgctcggtta    5460
cgcttctgat cttaacttcc tgccggtagc tctacagccg cacggcatcg gttttctcga    5520 accgggatt cagattgcca ccattgacca ttccatgtgg ttccatcgcc cgtttaattt     5580
gaatgaatgg ctgctgtata gcgtggagag cacctcggcg tccagcgcac gtggctttgt    5640
gcgcggtgag ttttataccc aagacggcgt actggttgcc tcgaccgttc aggaaggggt    5700
gatgcgtaat cacaattaa                                                 5719
```

```
<210> SEQ ID NO 82
<211> LENGTH: 967
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82
caaatatcac ataatcttaa catatcaata aacacagtaa agtttcatgt gaaaaacatc      60
aaacataaaa tacaagctcg gaatacgaat cacgctatac acattgctaa caggaatgag    120
attatctaaa tgaggattga tatattaatt ggacatacta gttttttttca tcaaaccagt    180 agagataact tccttcacta tctcaatgag gaagaaataa aacgctatga tcagtttcat    240
tttgtgagtg ataaagaact ctatatttta agccgtatcc tgctcaaaac agcactaaaa    300
agatatcaac ctgatgtctc attacaatca tggcaattta gtacgtgcaa atatggcaaa    360
ccatttatag ttttttcctca gttggcaaaa aagattttttt ttaacctttc ccatactata    420
gatacagtag ccgttgctat tagttctcac tgcgagcttg gtgtcgatat tgaacaaata    480
agagatttag acaactctta tctgaatatc agtcagcatt ttttttactcc acaggaagct    540 actaacatag tttcacttcc tcgttatgaa ggtcaattac tttttttggaa aatgtggacg    600 ctcaaagaag cttacatcaa atatcgaggt aaaggcctat ctttaggact ggattgtatt    660
gaatttcatt taacaaataa aaaactaact tcaaaatata gaggttcacc tgtttatttc    720
tctcaatgga aaatatgtaa ctcatttctc gcattagcct ctccactcat caccccctaaa   780 ataactattg agctatttcc tatgcagtcc caactttatc accacgacta tcagctaatt    840
cattcgtcaa atgggcagaa ttgaatcgcc acggataatc tagacacttc tgagccgtcg    900
ataatattga ttttcatatt ccgtcggtgg tgtaagtatc ccgcataatc gtgccattca    960
catttag                                                              967
```

```
<210> SEQ ID NO 83
<211> LENGTH: 424
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
ggatgggggg aaacatggat aagttcaaag aaaaaaaccc gttatctctg cgtgaaagac      60
```

-continued

```
aagtattgcg catgctggca caaggtgatg agtactctca aatatcacat aatcttaaca    120
tatcaataaa cacagtaaag tttcatgtga aaaacatcaa acataaaata caagctcgga    180
atacgaatca cgctatacac attgctaaca ggaatgagat tatctaaatg aggattgatg    240
tgtaggctgg agctgcttcg aagttcctat actttctaga gaataggaac ttcggaatag    300
gaacttcgga ataggaacta aggaggatat tcatatgtcg tcaaatgggc agaattgaat    360
cgccacggat aatctagaca cttctgagcc gtcgataata ttgattttca tattccgtcg    420
gtgg                                                                 424
```

<210> SEQ ID NO 84
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic consensus sequence"
<220> FEATURE:
<221> NAME/KEY: modified_base
<222> LOCATION: (6)..(9)
<223> OTHER INFORMATION: a, c, t, g, unknown or other

<400> SEQUENCE: 84
ttgatnnnna tcaa    14

<210> SEQ ID NO 85
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic consensus sequence"

<400> SEQUENCE: 85
ttgttgayry rtcaacwa    18

<210> SEQ ID NO 86
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic consensus sequence"
<220> FEATURE:
<221> NAME/KEY: modified_base
<222> LOCATION: (8)..(8)
<223> OTHER INFORMATION: a, c, t, g, unknown or other

<400> SEQUENCE: 86
ttataatnat tataa    15